US011192865B2

(12) United States Patent
Konradi et al.

(10) Patent No.: US 11,192,865 B2
(45) Date of Patent: Dec. 7, 2021

(54) BENZOSULFONYL COMPOUNDS

(71) Applicant: Vivace Therapeutics, Inc., San Mateo, CA (US)

(72) Inventors: Andrei W. Konradi, Burlingame, CA (US); Tracy Tzu-Ling Tang Lin, Redwood City, CA (US)

(73) Assignee: VIVACE THERAPEUTICS, INC., San Mateo, CA (US)

(*) Notice: Subject to any disclaimer, the term of this patent is extended or adjusted under 35 U.S.C. 154(b) by 0 days.

(21) Appl. No.: 16/640,557

(22) PCT Filed: Aug. 20, 2018

(86) PCT No.: PCT/US2018/047112
§ 371 (c)(1),
(2) Date: Feb. 20, 2020

(87) PCT Pub. No.: WO2019/040380
PCT Pub. Date: Feb. 28, 2019

(65) Prior Publication Data
US 2020/0354325 A1 Nov. 12, 2020

Related U.S. Application Data

(60) Provisional application No. 62/548,037, filed on Aug. 21, 2017.

(51) Int. Cl.
C07D 257/04 (2006.01)
A61P 35/00 (2006.01)
C07D 213/38 (2006.01)
C07D 231/12 (2006.01)
C07D 233/58 (2006.01)
C07D 235/00 (2006.01)
C07D 239/26 (2006.01)
C07D 249/06 (2006.01)
C07D 249/08 (2006.01)
C07D 271/06 (2006.01)
C07D 271/10 (2006.01)
C07D 401/04 (2006.01)
C07D 401/06 (2006.01)

(52) U.S. Cl.
CPC ............ C07D 257/04 (2013.01); A61P 35/00 (2018.01); C07D 213/38 (2013.01); C07D 231/12 (2013.01); C07D 233/58 (2013.01); C07D 235/00 (2013.01); C07D 239/26 (2013.01); C07D 249/06 (2013.01); C07D 249/08 (2013.01); C07D 271/06 (2013.01); C07D 271/10 (2013.01); C07D 401/04 (2013.01); C07D 401/06 (2013.01)

(58) Field of Classification Search
CPC .. C07D 257/04; C07D 213/38; C07D 231/12; C07D 233/58; C07D 235/00; C07D 239/26; C07D 249/06; C07D 249/08; C07D 271/06; C07D 271/10; C07D 401/04; C07D 401/06; A61P 35/00
See application file for complete search history.

(56) References Cited

U.S. PATENT DOCUMENTS

| 3,895,027 | A | 7/1975 | Katner |
| 3,903,106 | A | 9/1975 | Katner et al. |
| 4,010,273 | A | 3/1977 | Bormann et al. |
| 4,492,710 | A * | 1/1985 | Merkel ............... C07D 213/65 514/428 |
| 4,962,119 | A | 10/1990 | Boschelli et al. |
| 5,017,467 | A | 5/1991 | Masukawa et al. |
| 5,066,668 | A | 11/1991 | Boschelli et al. |
| 5,114,958 | A | 5/1992 | Boschelli et al. |
| 5,462,952 | A | 10/1995 | Boschelli et al. |
| 5,670,526 | A | 9/1997 | Dodd et al. |
| 6,211,209 | B1 | 4/2001 | Baragi et al. |
| 6,545,030 | B1 | 4/2003 | Barrett et al. |
| 6,972,287 | B1 | 12/2005 | Augelli-Szafran et al. |
| 7,019,033 | B2 | 3/2006 | Barrett et al. |
| 7,956,191 | B2 | 6/2011 | Abel et al. |
| 8,076,486 | B2 | 12/2011 | Goutopoulos et al. |
| 8,198,457 | B2 | 6/2012 | Abel et al. |
| 8,524,911 | B2 | 9/2013 | Abel et al. |
| 8,841,459 | B2 | 9/2014 | Deppe et al. |
| 9,790,229 | B2 | 10/2017 | Bui et al. |
| 2003/0004193 | A1 | 1/2003 | Barrett et al. |
| 2005/0004186 | A1 | 1/2005 | Barrett et al. |
| 2007/0259051 | A1 | 11/2007 | Feinmark et al. |
| 2009/0048301 | A1 | 2/2009 | Chen et al. |
| 2009/0318438 | A1 | 12/2009 | Chen et al. |
| 2015/0111885 | A1 * | 4/2015 | Bennett ............... C07D 213/70 514/230.5 |
| 2016/0289171 | A1 | 10/2016 | Balog et al. |
| 2017/0137428 | A1 | 5/2017 | Spangenberg |
| 2020/0062721 | A1 | 2/2020 | Konradi et al. |

FOREIGN PATENT DOCUMENTS

| WO | WO-0042029 A1 | 7/2000 |
| WO | WO-0105391 A2 | 1/2001 |
| WO | WO-03045912 A1 | 6/2003 |
| WO | WO-2004056789 A1 | 7/2004 |
| WO | WO-2005004818 A2 | 1/2005 |
| WO | WO-2007123936 A1 | 11/2007 |
| WO | WO-2009086163 A2 | 7/2009 |
| WO | WO-2013188138 A1 | 12/2013 |

(Continued)

OTHER PUBLICATIONS

Sebio; Clin Cancer Res 2015, 21, 5002-5007. DOI: 10.1158/1078-0432.CCR-15-0411 (Year: 2015).*

(Continued)

Primary Examiner — Daniel R Carcanague
(74) Attorney, Agent, or Firm — Wilson Sonsini Goodrich & Rosati

(57) ABSTRACT

Provided herein are compounds and pharmaceutical compositions comprising said compounds that are useful for treating cancers. Specific cancers include those that are mediated by YAP/TAZ or those that are modulated by the interaction between YAP/TAZ and TEAD.

19 Claims, 2 Drawing Sheets

(56) References Cited

FOREIGN PATENT DOCUMENTS

| WO | WO-2016161269 A1 | 10/2016 |
| WO | WO-2016161279 A1 | 10/2016 |
| WO | WO-2016161286 A1 | 10/2016 |
| WO | WO-2017058716 A1 | 4/2017 |
| WO | WO-2018204532 A1 | 11/2018 |
| WO | WO-2019040380 A1 | 2/2019 |
| WO | WO-2019113236 A1 | 6/2019 |
| WO | WO-2019222431 A1 | 11/2019 |

OTHER PUBLICATIONS

Fleisher et al. Improved oral drug delivery: solubility limitations overcome by the use of prodrugs. Advanced Drug Delivery Reviews 19:115-130 (1996).

Pobbati et al. Targeting the Central Pocket in Human Transcription Factor TEAD as a Potential Cancer Therapeutic Strategy. Structure 23:2076-2086 (2015).

PUBCHEM Substance record for SID 274578875, available date: Dec. 18, 2015 (retrieved on Jun. 22, 2018). Retrieved from https://pubchem.ncbi.nlm.nih.gov/substance/274578875.

Science IP Report 2017 (1079 pgs).

Berge et al. Pharmaceutical Salts. Journal of Pharmaceutical Sciences 66(1):1-19 (Jan. 1977).

Bundgaard et al. Design of Prodrugs pp. 7-9, 21-24 (1985).

Holmes et al., Discovery and structure-activity relationships of novel sulfonamides as potent PTP1B inhibitors.Bioorganic and Medicinal Chemistry Letters. 15:4336-4341. (2005).

PCT/US2018/047112 International Search Report and Written Opinion dated Oct. 30, 2018.

Pubchem Compound Summary CID 68170056 deposited Nov. 30, 2012.

Yokokawa et al., Discovery of potent non-nucleoside inhibitors of dengue viral RNA-dependent RNA polymerase from a fragment hit using structure-based drug design. Journal of Medicinal Chemistry59(8):3935-3952 (2016).

Manbeck et al. Photoluminescent Copper(I) Complexes with Amido-Triazolato Ligands. Inorganic Chemistry 50(8):3431-3441 (2011).

\* cited by examiner

BENZOSULFONYL COMPOUNDS

CROSS-REFERENCE

This application is a § 371 U.S. National Stage Application of International Application No. PCT/US2018/047112, filed Aug. 20, 2018, which claims benefit of U.S. Provisional Patent Application No. 62/548,037 filed on Aug. 21, 2017, all of which are incorporated herein by reference in their entirety.

BACKGROUND OF THE DISCLOSURE

YAP and TAZ are transcriptional co-activators of the Hippo pathway network and regulate cell proliferation, migration, and apoptosis. Inhibition of the Hippo pathway promotes YAP/TAZ translocation to the nucleus, wherein YAP/TAZ interact with transcriptional enhancer associate domain (TEAD) transcription factors and coactivate the expression of target genes and promote cell proliferation. Hyperactivation of YAP and TAZ and/or mutations in one or more members of the Hippo pathway network have been implicated in numerous cancers. Described herein are inhibitors associated with one or more members of the Hippo pathway network, such as inhibitors of YAP/TAZ or inhibitors that modulate the interaction between YAP/TAZ and TEAD.

SUMMARY OF THE DISCLOSURE

Provided herein are benzosulfonyl compounds and pharmaceutical compositions comprising said compounds. In some embodiments, the subject compounds are useful for the treatment of cancer.

Provided in one aspect is a compound of Formula (I) or a pharmaceutically acceptable salt thereof:

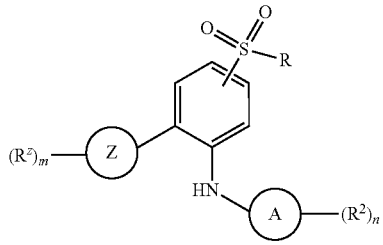

Formula (I)

wherein,

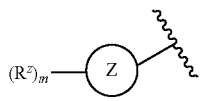

is a substituted or unsubstituted monocyclic 5-membered heterocyclic ring containing at least one N atom or a substituted or unsubstituted monocyclic 6-membered heteroaryl ring containing at least one N atom;

each $R^z$ is independently H, halogen, —CN, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, -$L^1$-$Y^1$, or -$L^2$-$L^3$-$Y^2$;

m is 0, 1, 2, 3, 4, or 5;

$L^1$ is substituted or unsubstituted $C_1$-$C_6$alkylene, substituted or unsubstituted $C_2$-$C_{10}$cyclolkylene, or substituted or unsubstituted $C_2$-$C_{10}$heterocycloalkylene;

$Y^1$ is substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;

$L^2$ is absent, substituted or unsubstituted $C_1$-$C_6$alkylene, substituted or unsubstituted $C_2$-$C_{10}$cyclolkylene, or substituted or unsubstituted $C_2$-$C_{10}$heterocycloalkylene;

$L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —O—NR$^3$(C=O)—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(C=O)—NR$^3$(SO$_2$)—, —(SO$_2$)NR$^3$—(C=O)O—, —O(C=O)—NR$^3$(SO$_2$)—, —NR$^3$(SO$_2$)NR$^3$—(C=O)—, —(C=O)—NR$^3$(SO$_2$)NR$^3$—, —O(C=O)—NR$^3$(SO$_2$)—NR$^3$—, or —NR$^3$(SO$_2$)NR$^3$—(C=O)O—;

each $R^3$ is independently H or substituted or unsubstituted $C_1$-$C_6$alkyl;

$Y^2$ is H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;

or $R^3$ and $Y^2$ on the same N atom are taken together with the N atom to which they are attached to form a substituted or unsubstituted N-containing heterocycle;

R is NHR$^1$ or R$^1$;

R$^1$ is substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

is substituted or unsubstituted phenyl or substituted or unsubstituted cyclohexyl;

each $R^2$ is independently H, halogen, —N$_3$, —CN, —OR$^4$, —SR$^4$, —(SO$_2$)R$^4$, —N(R$^4$)$_2$, —CO$_2$R$^4$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, or

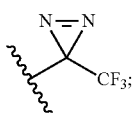

n is 0, 1, 2, 3, 4, or 5; and
each $R^4$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments,

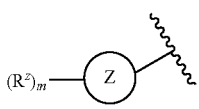

is a substituted or unsubstituted monocyclic 5-membered heterocyclic ring containing at least one N atom.

In some embodiments,

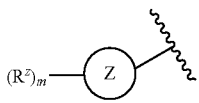

is a substituted or unsubstituted monocyclic 5-membered heterocyclic ring containing 1-4 N atoms, 0-2 O atoms, and 0-2 S atoms.

In some embodiments,

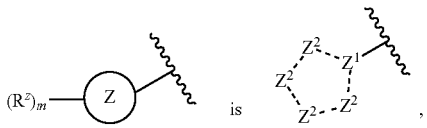

$Z^1$ is —N—, —CH—, or —C—;
each $Z^2$ is independently —$CR^z$, —$CHR^z$—, —$C(R^z)_2$—, —$NR^z$—, —N—, —O—, or —S—,
each —— is independently a single or double bond; and with the provision that the 5-membered heterocyclic ring contains at least one N atom.

In some embodiments,

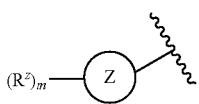

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazolidinyl, substituted or unsubstituted thiazolidinyl, or substituted or unsubstituted isothiazolidinyl.

In some embodiments,

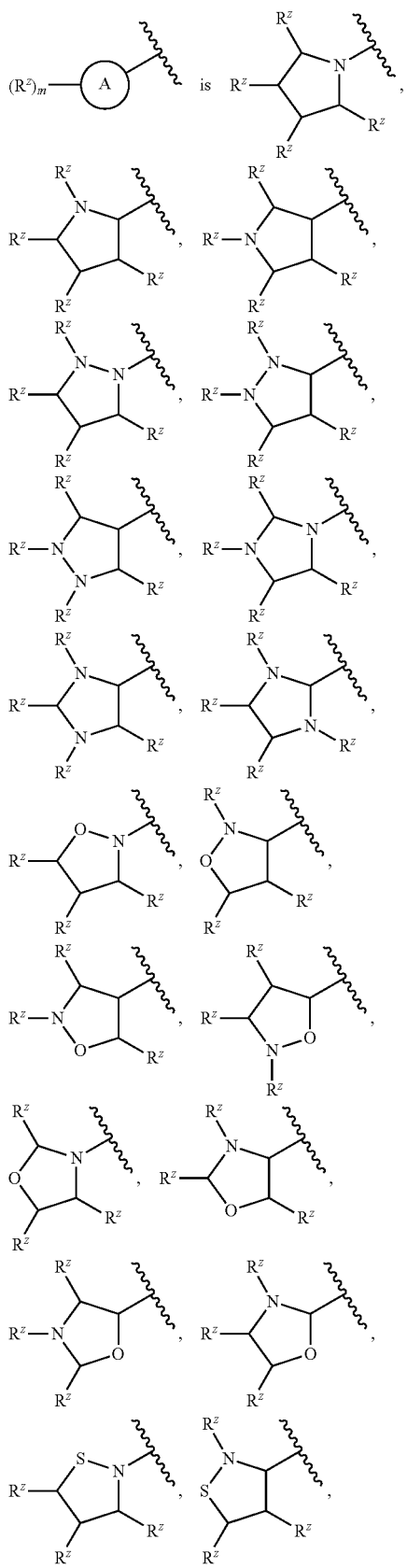

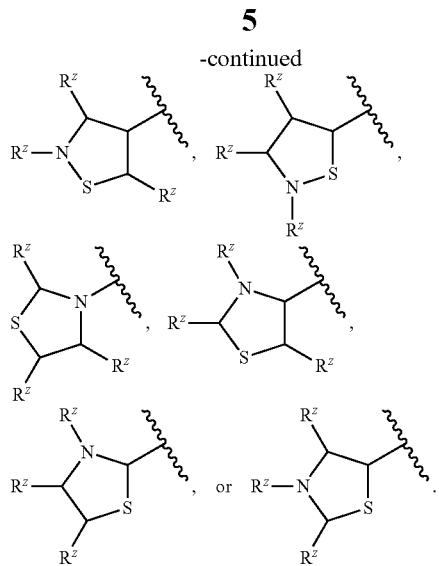

In some embodiments,

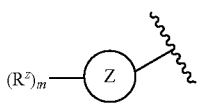

is substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazoyl, substituted or unsubstituted tetrazoyl, substituted or unsubstituted oxadiazolyl, substituted or unsubstituted thiadiazolyl, or substituted or unsubstituted dithiazolyl.

In some embodiments,

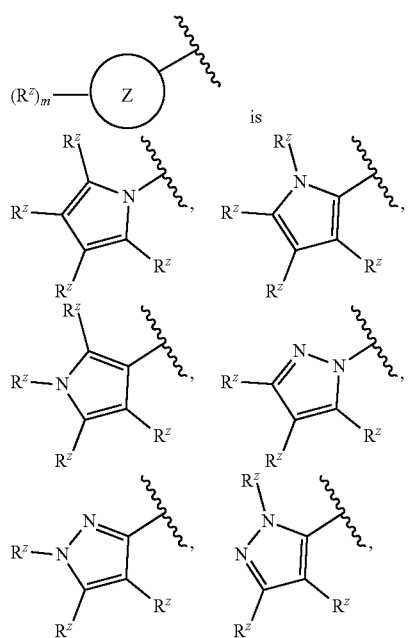

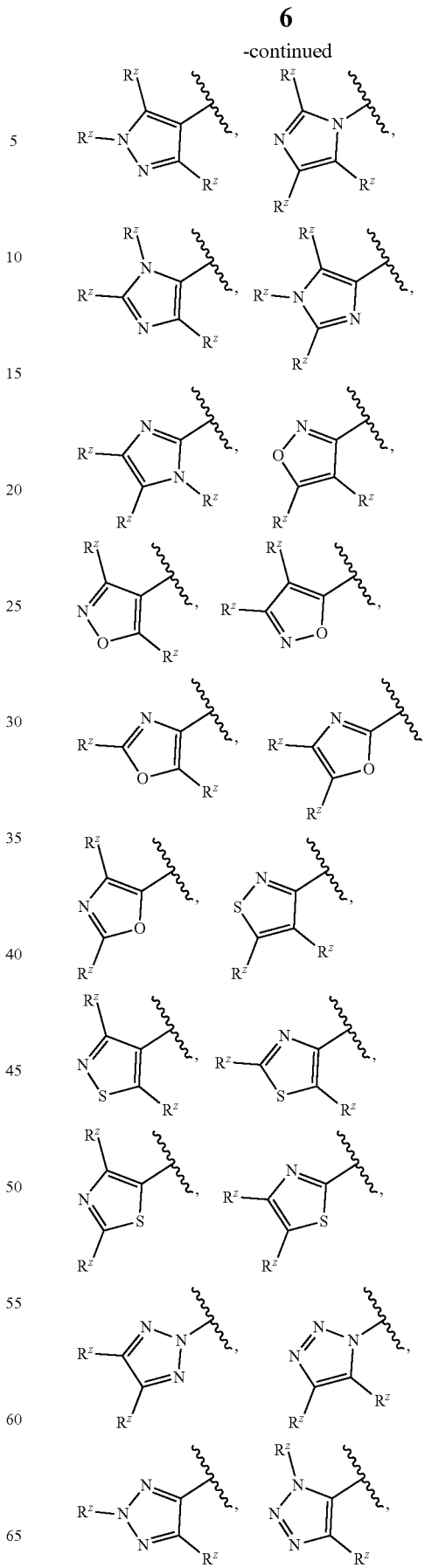

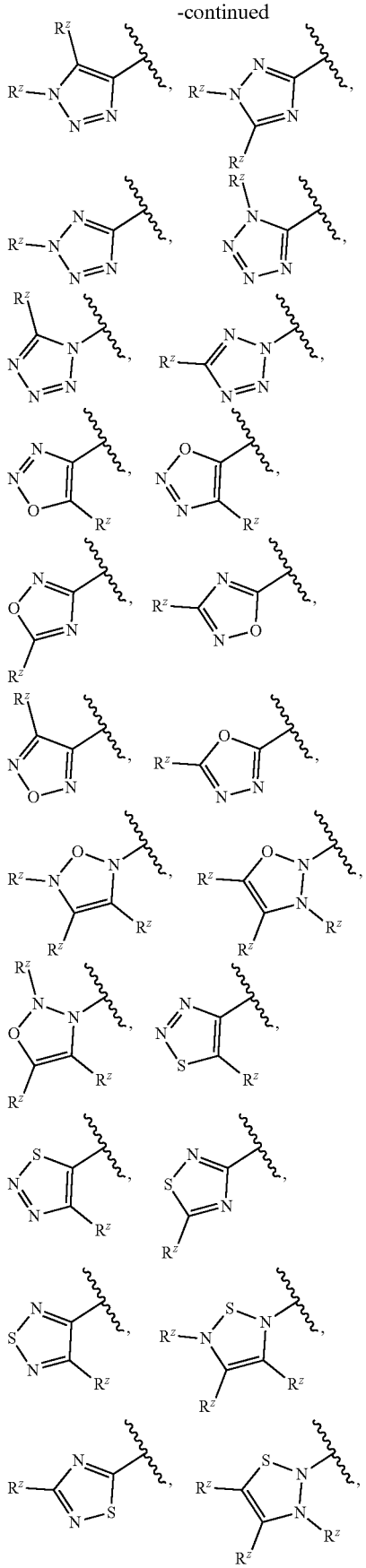

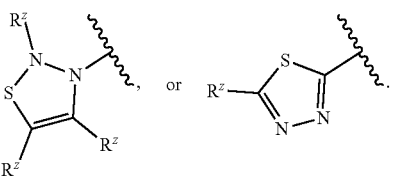

In some embodiments,

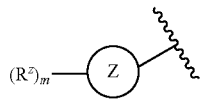

is a substituted or unsubstituted monocyclic 6-membered heteroaryl ring containing at least one N atom.

In some embodiments,

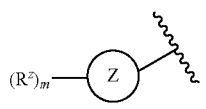

is a substituted or unsubstituted monocyclic 6-membered heteroaryl ring containing 1 or 2 N atoms.

In some embodiments,

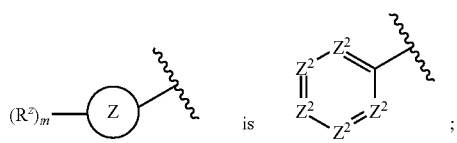

each $Z^2$ is independently $CR^z$ or N; and
at least one $Z^2$ is N.

In some embodiments,

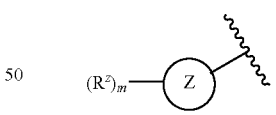

is substituted or unsubstituted pyridinyl, substituted or unsubstituted pyrazinyl, substituted or unsubstituted pyrimidinyl, or substituted or unsubstituted pyridazinyl.

In some embodiments,

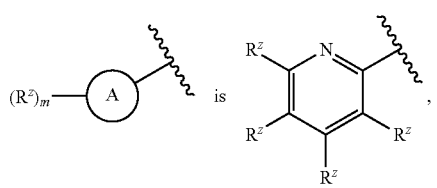

-continued

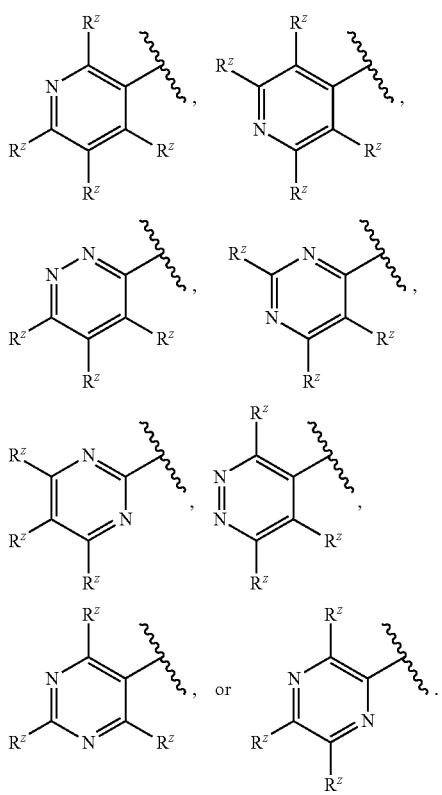

In some embodiments, the compound has the structure of Formula (Ia), or a pharmaceutically acceptable salt thereof:

Formula (Ia)

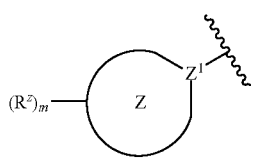

wherein
$Z^1$ is —N—, —CH—, or —C—.

In some embodiments,

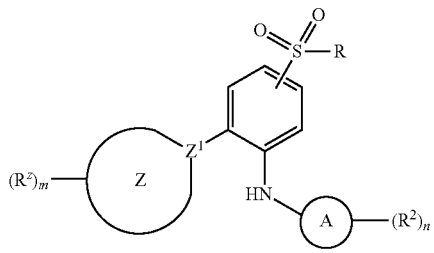

is a substituted or unsubstituted monocyclic 5-membered heterocyclic ring containing at least one N atom, and the at least one N atom is adjacent to $Z^1$.

In some embodiments,

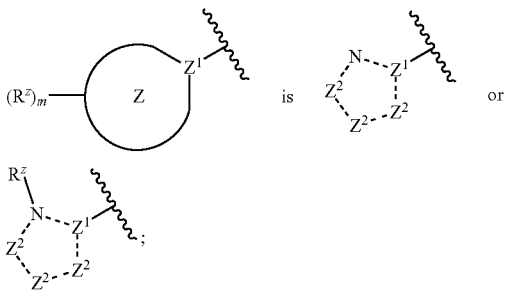

each $Z^2$ is independently CR, NR, N, O, or S;
each —— is independently a single or double bond; and
with the provision that the 5-membered heterocyclic ring contains at least one N atom.

In some embodiments,

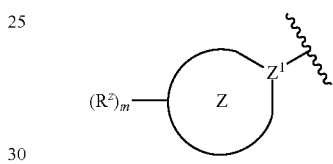

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazolidinyl, substituted or unsubstituted thiazolidinyl, or substituted or unsubstituted isothiazolidinyl.

In some embodiments,

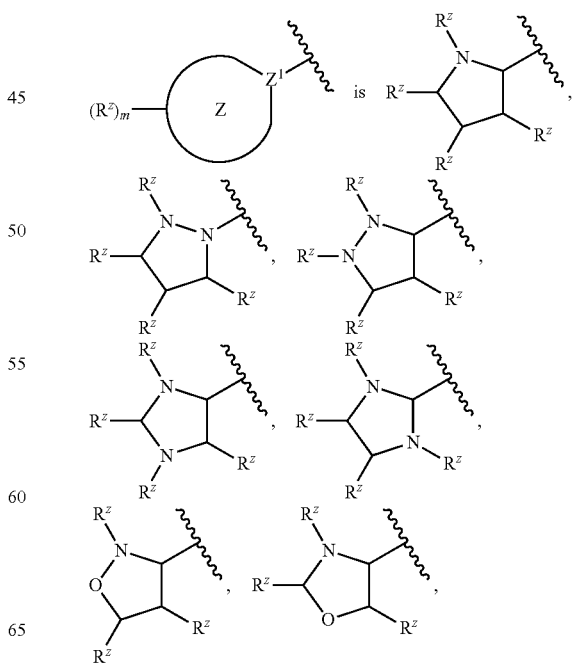

-continued

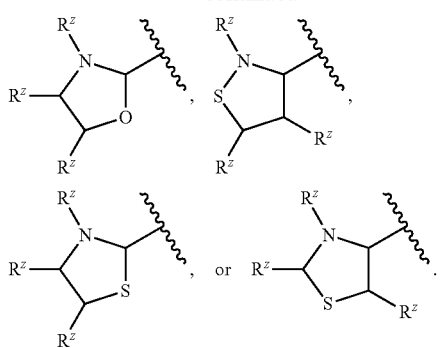

In some embodiments,

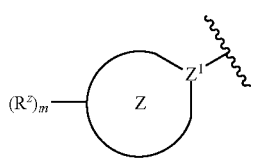

is substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazoyl, substituted or unsubstituted tetrazoyl, substituted or unsubstituted oxadiazolyl, substituted or unsubstituted thiadiazolyl, or substituted or unsubstituted dithiazolyl.

In some embodiments,

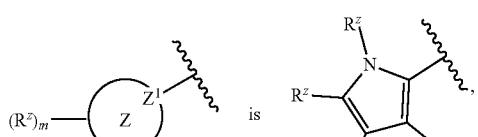

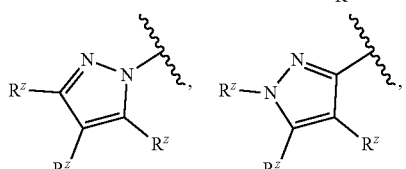

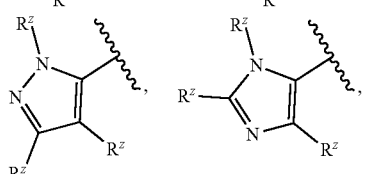

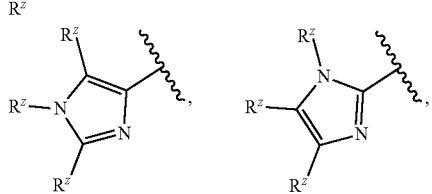

-continued

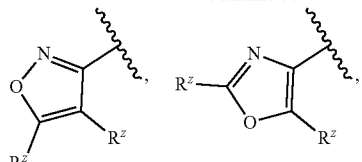

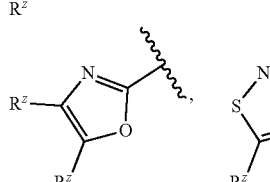

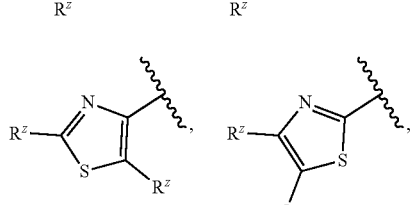

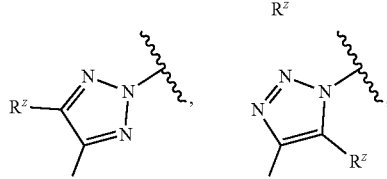

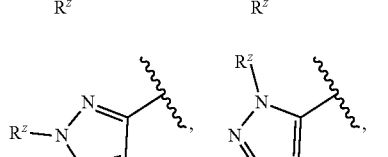

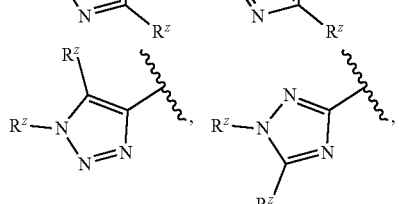

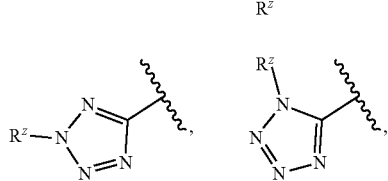

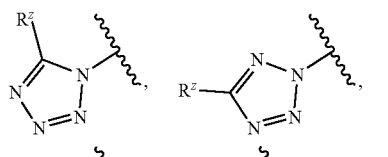

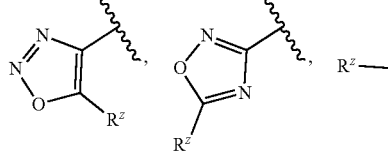

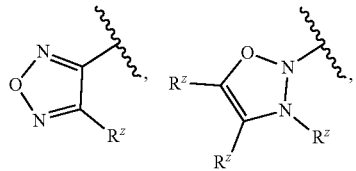

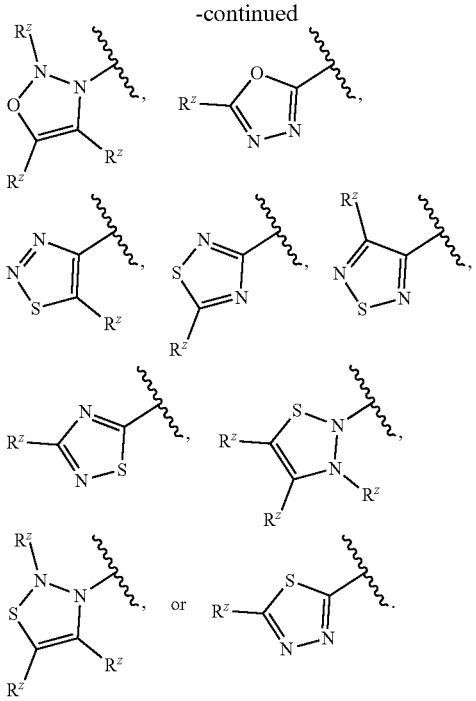

In some embodiments,

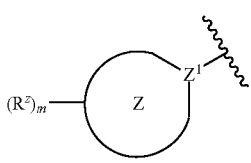

is a substituted or unsubstituted monocyclic 6-membered heteroaryl ring containing at least one N atom, and wherein the at least one N atom is adjacent to $Z^1$.

In some embodiments,

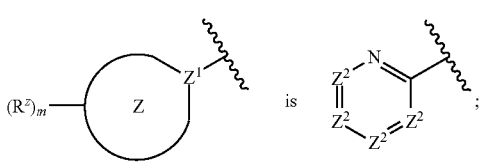

and each $Z^2$ is independently $CR^z$ or N.

In some embodiments,

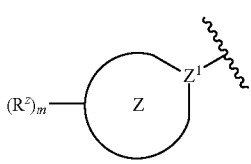

is substituted or unsubstituted pyridinyl, substituted or unsubstituted pyrazinyl, substituted or unsubstituted pyrimidinyl, or substituted or unsubstituted pyridazinyl.

In some embodiments,

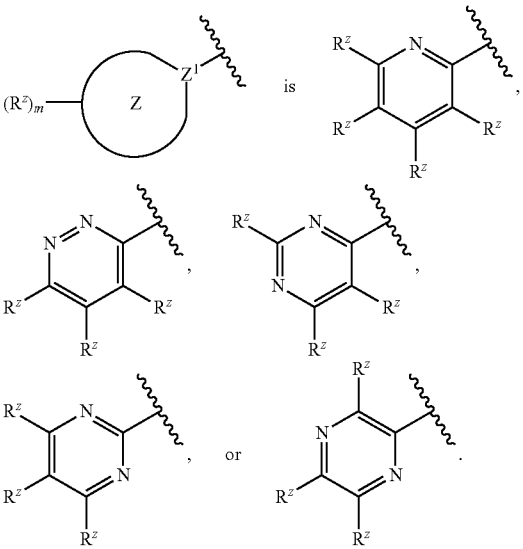

In some embodiments, each $R^z$ is independently H, halogen, —CN, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl. In some embodiments, each $R^z$ is independently H, halogen, substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl. In some embodiments, each $R^z$ is independently H, —F, —Cl, —Br, —I, methyl, ethyl, n-propyl, iso-propyl, n-butyl, iso-butyl, tert-butyl, cyclopropyl, cyclobutyl, cyclopentyl, cyclohexyl, or phenyl.

In some embodiments, each $R^z$ is -$L^1$-Y. In some embodiments, $L^1$ is substituted or unsubstituted $C_1$-$C_4$alkylene; and $Y^1$ is substituted or unsubstituted $C_3$-$C_{10}$cycloalkyl, substituted or unsubstituted $C_2$-$C_{10}$ heterocycloalkyl, substituted or unsubstituted aryl, or substituted or unsubstituted heteroaryl.

In some embodiments, each R is -$L^2$-$L^3$-$Y^2$. In some embodiments, $L^2$ is substituted or unsubstituted $C_1$-$C_6$alkylene; $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(SO$_2$)NR$^3$—(C=O)O—, —NR$^3$(SO$_2$)NR$^3$—(C=O)—, or —NR$^3$(SO$_2$)NR$^3$—(C=O)O—; each $R^3$ is independently H or substituted or unsubstituted $C_1$-$C_6$alkyl; and $Y^2$ is H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl.

In some embodiments, $L^2$ is absent; $L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$O—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(SO$_2$)NR$^3$—(C=O)O—, —NR$^3$(SO$_2$)NR$^3$—(C=O)—, or —NR$^3$(SO$_2$)NR$^3$—(C=O)O—; each $R^3$ is independently H or substituted or unsubstituted $C_1$-$C_6$alkyl; and $Y^2$ is H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl.

In some embodiments,

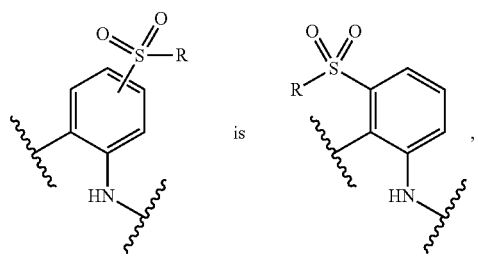

In some embodiments,

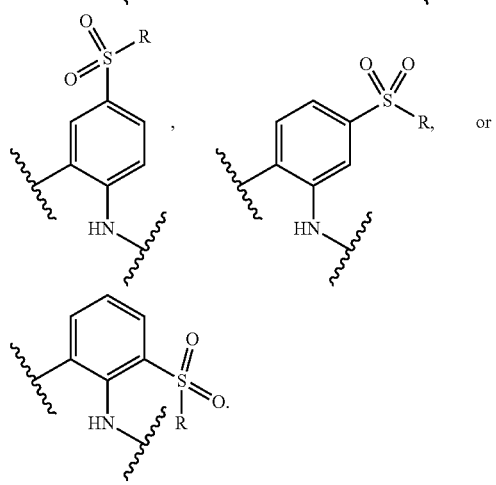

In some embodiments,

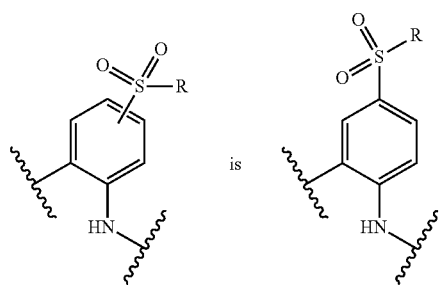

In some embodiments, R is NHR$^1$; and R is substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments, R is methyl, ethyl, n-propyl, iso-propyl, n-butyl, iso-butyl, tert-butyl, cyclopropyl, cyclobutyl, cyclopentyl, cyclohexyl, or phenyl.

In some embodiments, R is R$^1$; and R is substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments, R is methyl, ethyl, n-propyl, iso-propyl, n-butyl, iso-butyl, tert-butyl, cyclopropyl, cyclobutyl, cyclopentyl, cyclohexyl, or phenyl.

In some embodiments, is

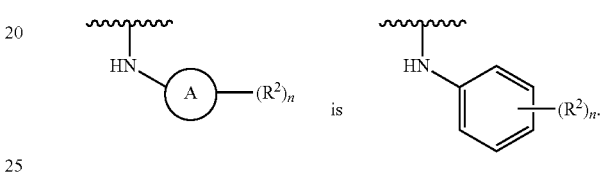

In some embodiments, the compound has the structure of Formula (Ib), or a pharmaceutically acceptable salt thereof:

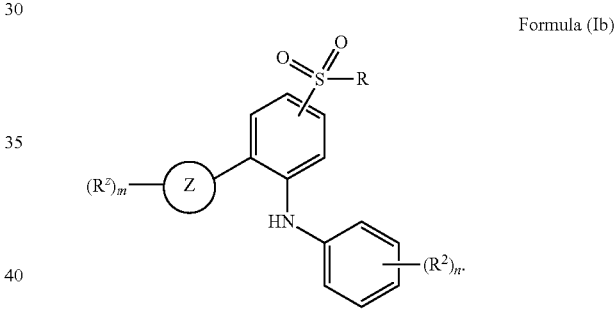

Formula (Ib)

In some embodiments,

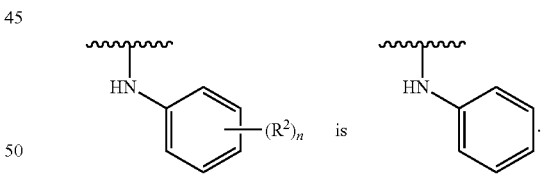

In some embodiments,

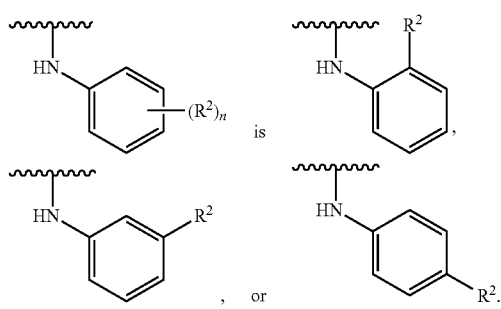

In some embodiments,

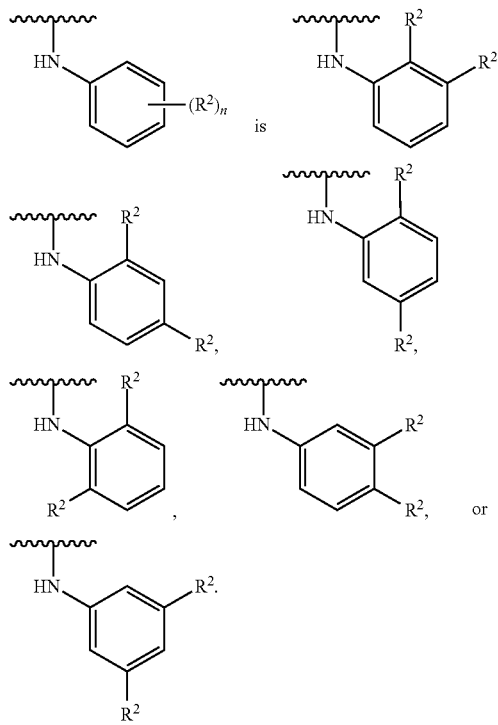

In some embodiments, is

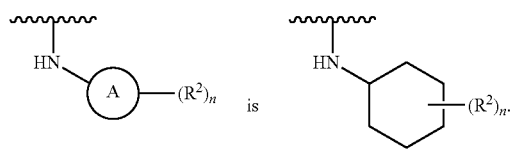

In some embodiments, the compound has the structure of Formula (Ic), or a pharmaceutically acceptable salt thereof:

Formula (Ic)

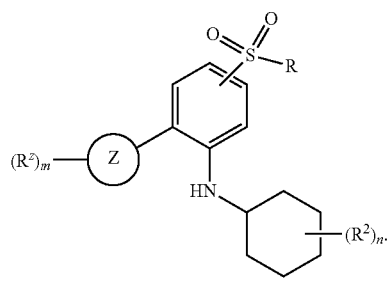

In some embodiments,

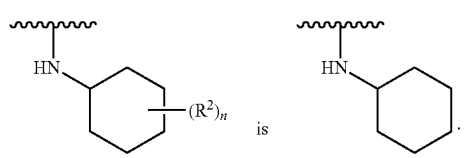

In some embodiments,

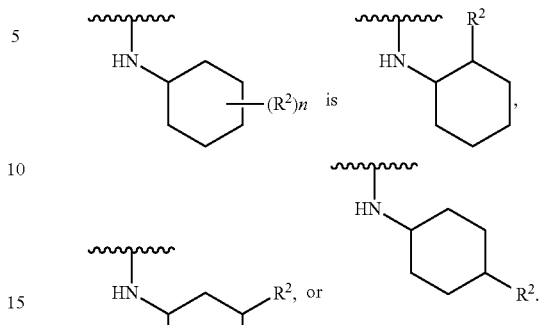

In some embodiments,

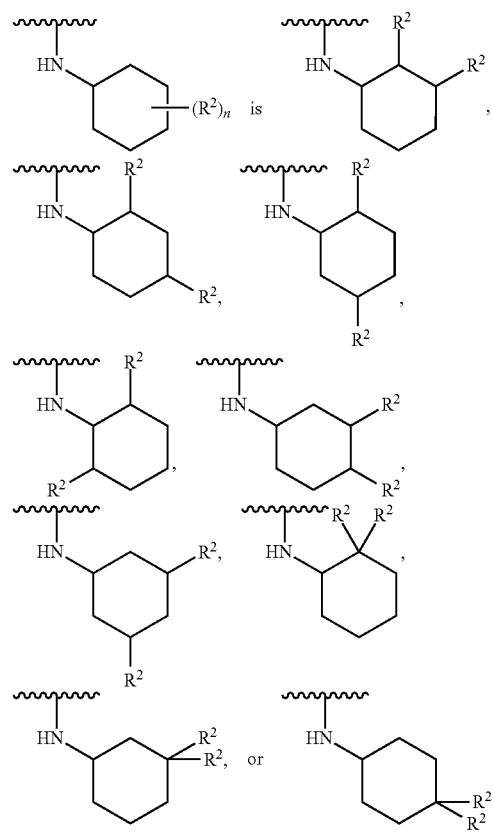

In some embodiments, each $R^2$ is independently H, halogen, $-N_3$, $-CN$, $-OR^4$, $-SR^4$, $-(SO_2)R^4$, $-N(R^4)_2$, $-CO_2R^4$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments, the compound has the structure of Formula (Id), or a pharmaceutically acceptable salt thereof:

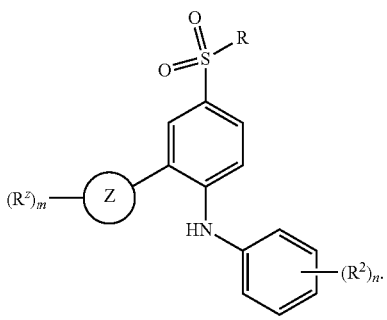

Formula (Id)

In some embodiments, the compound has the structure of Formula (Ie), or a pharmaceutically acceptable salt thereof:

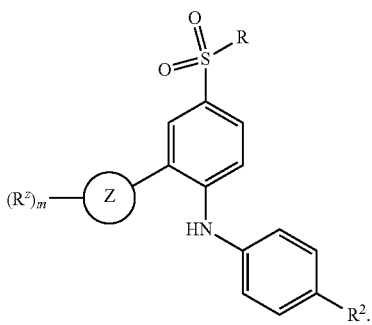

Formula (Ie)

In some embodiments, the compound has the structure of Formula (If), or a pharmaceutically acceptable salt thereof:

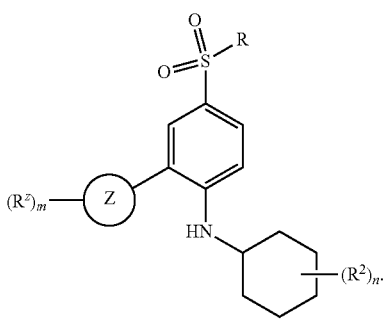

Formula (If)

In some embodiments, the compound has the structure of Formula (Ig), or a pharmaceutically acceptable salt thereof:

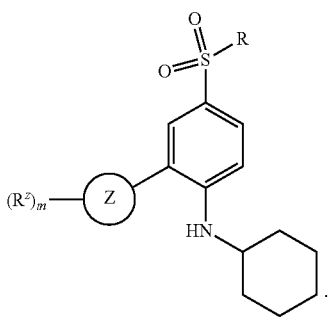

Formula (Ig)

In some embodiments, the compound exhibits an $IC_{50}$ of no more than about 3.000 μM.

Provided in another aspect is a compound, or pharmaceutically acceptable salt thereof, wherein the compound is a compound from Table 1, or a pharmaceutically acceptable salt thereof.

Provided in another aspect is a pharmaceutical composition comprising a pharmaceutically acceptable excipient and any one of the compounds disclosed herein or a pharmaceutically acceptable salt thereof.

Provided herein is a method for treating a cancer in a subject in need thereof comprising administering a therapeutically effective amount of a compound of any one of the compounds disclosed herein or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Certain Terminology

Figure 1:
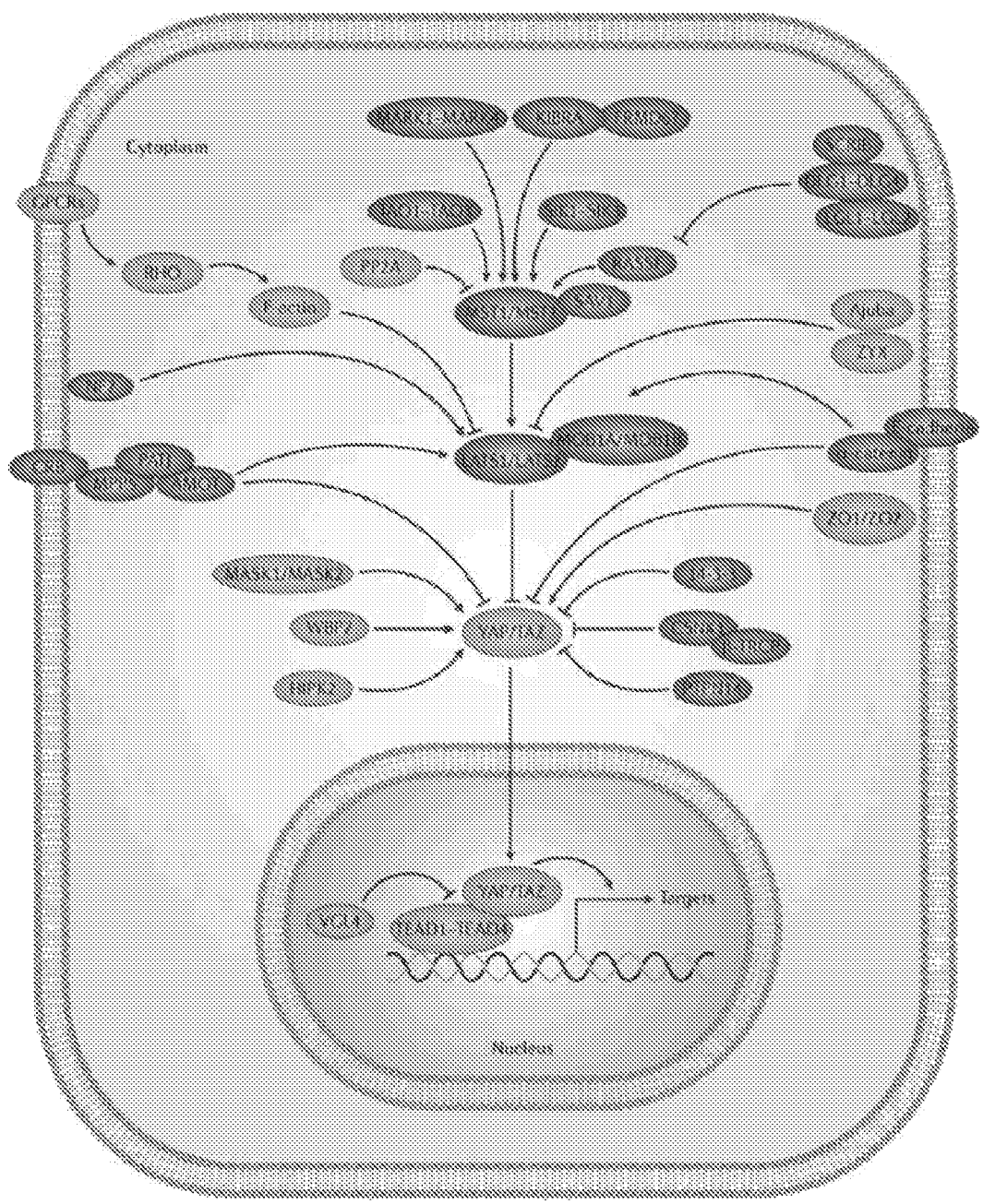
FIG. 1 illustrates a schematic representation of the Hippo signaling network. Hippo pathway components shaded in dark gray indicate components that inhibit YAP/TAZ activity. Hippo pathway components shaded in light gray indicate components that promote YAP/TAZ activity. Pointed and blunt arrowheads indicate activating and inhibitory interactions, respectively. Abbreviations: α-CAT (α-Catenin), AJUB (Ajuba), AMOT (Angiomotin), β-TRCP (β-transducing repeat containing protein), CK1 (Casein Kinase 1), CRB (Crumbs), E-CAD (E-cadherin), EX (Expanded), GPCR (G-protein coupled receptor), HIPK (Homeodomain interacting protein kinase), KIBRA (Kidney brain), LATS (Large tumor suppressor), LGL (Lethal giant larvae), MASK (Multiple ankyrin single KH), MER (Merlin), MOB (Mps one binder), MST (Mammalian sterile 20 like), PALS (Protein Associated with Lin-7), PATJ (Pals-associated tight junction protein), PP2A (Protein phosphatase 2A), PTPN14 (Protein tyrosine phosphatase non-receptor type 14), RASSF (Ras associated factor), SAV (Salvador), SCRIB (Scribble), SIK (Salt inducible kinase), TAO (Thousand and one amino acid protein), TAZ (transcriptional coactivator with PDZ-binding motif), TEAD (TEA domain protein), VGL4 (Vestigial-like 4), WBP2 (WW domain binding protein 2), YAP (Yes associated protein), ZO (Zonula occludens), ZYX (Zyxin).

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, in some embodiments, ranges and amounts are expressed as "about" a particular value or range. About also includes the exact amount. Hence "about 5 µL" means "about 5 µL" and also "5 µL." Generally, the term "about" includes an amount that is expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly, or a hospice worker).

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2), and —S(O)$_t$N(R$^a$)$_2$ (where t is 1 or 2), where each R$^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each R is independently alkyl, fluoroalkyl, carbocyclyl, carbocyclylalkyl, aryl, aralkyl, heterocyclyl, heterocyclylalkyl, heteroaryl, or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2), and —S(O)$_t$N(R$^a$)$_2$ (where t is 1 or 2), where each R$^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2), and —S(O)$_t$N(R$^a$)$_2$ (where t is 1 or 2), where each R$^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. In some embodiments, the points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_5$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2), and —S(O)$_t$N(R$^a$)$_2$ (where t is 1 or 2), where each R$^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin, and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—CN, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2), and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl, or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aryloxy" refers to a radical bonded through an oxygen atom of the formula —O-aryl, where aryl is as defined above.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, and in some embodiments, include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. In some embodiments, the carbocyclyl is saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$—C cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —CN, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2), and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where R is an alkylene chain as defined above. The alkylene chain and the carbocyclyl radical are optionally substituted as defined above.

"Halo" or "halogen" refers to bromo, chloro, fluoro, or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" or "heterocycle" refers to a stable 3- to 18-membered non-aromatic ring radical that comprises two to twelve carbon atoms and from one to six heteroatoms selected from nitrogen, oxygen, and sulfur. Unless stated otherwise specifically in the specification, the heterocyclyl radical is a monocyclic, bicyclic, tricyclic, or tetracyclic ring system, which include fused or bridged ring systems in some embodiments. The heteroatoms in the heterocyclyl radical are optionally oxidized. One or more nitrogen atoms, if present, are optionally quaternized. The heterocyclyl radical is partially or fully saturated. In some embodiments, the heterocyclyl is attached to the rest of the molecule through any atom of the ring(s). In some embodiments, the heterocyclyl is saturated, (i.e., containing single bonds only) or unsaturated (i.e., containing one or more double bonds or triple bonds.) A fully saturated heterocyclyl radical is also referred to as "heterocycloalkyl." Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —CN, —$R^b$—CN, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2), and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl. In some embodiments, the alkyl part of the heteroalkyl radical is optionally substituted as defined for an alkyl group.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen, and sulfur. As used herein, in some embodiments, the heteroaryl radical is a monocyclic, bicyclic, tricyclic, or tetracyclic ring system, wherein at least one of the rings in the ring system is fully unsaturated, i.e., it contains a cyclic, delocalized (4n+2) π-electron system in accordance with the Hackel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-TH-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —R—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2), and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

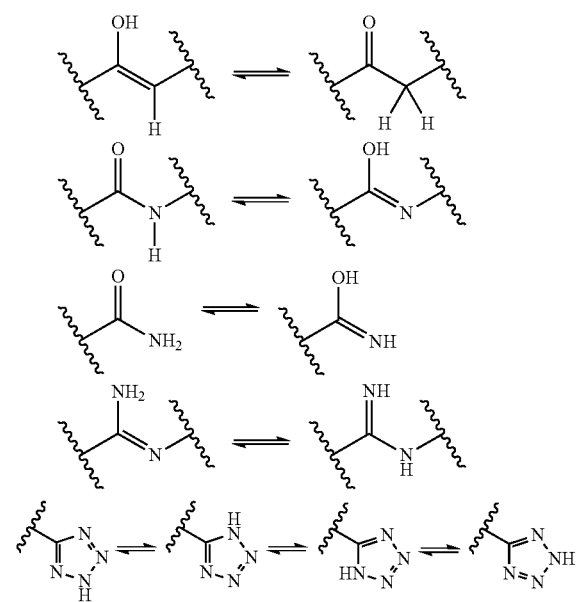

-continued

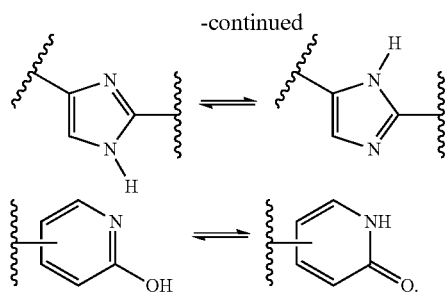

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the compounds described herein is intended to encompass any and all pharmaceutically suitable salt forms. Pharmaceutically acceptable salts of the compounds described herein are optionally pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). In some embodiments, acid addition salts of basic compounds are prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines, and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including, but not limited to, therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is afflicted with the underlying disorder in some embodiments. For prophylactic benefit, in some embodiments, the compositions are administered to a patient at risk of developing a particular disease, or to a patient reporting one or more of the physiological symptoms of a disease, even though a diagnosis of this disease has not been made.

"Prodrug" is meant to indicate a compound that is converted under physiological conditions or by solvolysis to a biologically active compound described herein. Thus, the term "prodrug" refers to a precursor of a biologically active compound that is pharmaceutically acceptable. In some embodiments, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. In some embodiments, prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino, or mercapto group is bonded to any group that, when the prodrug of the active compound is administered to a mammalian subject, cleaves to form a free hydroxy, free amino, or free mercapto group, respectively. Examples of prodrugs include, but are not limited to, acetate, formate, and benzoate derivatives of alcohol or amine functional groups in the active compounds and the like.

Compounds

In some embodiments, the compounds disclosed herein are benzosulfonyl compounds.

Provided in one aspect is a compound of Formula (I) or a pharmaceutically acceptable salt thereof:

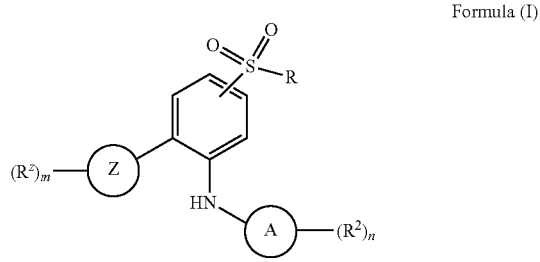

Formula (I)

wherein

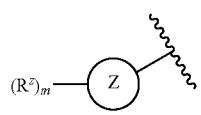

is a substituted or unsubstituted monocyclic 5-membered heterocyclic ring containing at least one N atom or a substituted or unsubstituted monocyclic 6-membered heteroaryl ring containing at least one N atom;

each $R^z$ is independently H, halogen, —CN, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, -$L^1$-$Y^1$, or -$L^2$-$L^3$-$Y^2$;

m is 0, 1, 2, 3, 4, or 5;

L is substituted or unsubstituted $C_1$-$C_6$alkylene, substituted or unsubstituted $C_2$-$C_{10}$cyclolkylene, or substituted or unsubstituted $C_2$-$C_{10}$heterocycloalkylene;

$Y^1$ is substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;

$L^2$ is absent, substituted or unsubstituted $C_1$-$C_6$alkylene, substituted or unsubstituted $C_2$-$C_{10}$cyclolkylene, or substituted or unsubstituted $C_2$-$C_{10}$heterocycloalkylene;

$L^3$ is —O—, —S—, —(S=O)—, —(SO$_2$)—, —NR$^3$—, —(C=O)—, —(C=O)O—, —O(C=O)—, —(C=O)NR$^3$—, —(C=O)NR$^3$—O—, —O—NR$^3$(C=O)—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(C=O)—NR$^3$(SO$_2$)—, —(SO$_2$)NR$^3$—(C=O)O—, —O(C=O)—NR$^3$(SO$_2$)—, —NR$^3$(SO$_2$)NR$^3$—(C=O)—, —(C=O)—NR$^3$(SO$_2$)NR$^3$—, —O(C=O)—NR$^3$(SO$_2$)—NR$^3$—, or —NR$^3$(SO$_2$)NR$^3$—(C=O)O—;

each $R^3$ is independently H or substituted or unsubstituted $C_1$-$C_6$alkyl;

$Y^2$ is H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;

or $R^3$ and $Y^2$ on the same N atom are taken together with the N atom to which they are attached to form a substituted or unsubstituted N-containing heterocycle;

R is NHR$^1$ or R$^1$;

R$^1$ is substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

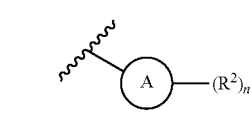

is substituted or unsubstituted phenyl or substituted or unsubstituted cyclohexyl;

each $R^2$ is independently H, halogen, —N$_3$, —CN, —OR$^4$, —SR$^4$, —(SO$_2$)R$^4$, —N(R$^4$)$_2$, —CO$_2$R$^4$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, or

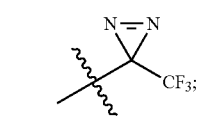 [SMILES: *C1(C(F)(F)F)N=N1]

n is 0, 1, 2, 3, 4, or 5; and each $R^4$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments,

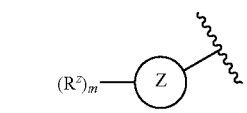

is a substituted or unsubstituted monocyclic 5-membered heterocyclic ring containing at least one N atom.

In some embodiments,

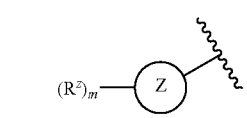

is a substituted or unsubstituted monocyclic 5-membered heterocyclic ring containing 1-4 N atoms, 0-2 O atoms, and 0-2 S atoms.

In some embodiments,

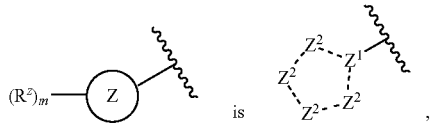 is $Z^1$ is —N—, —CH—, or —C—;
each $Z^2$ is independently —CR$^z$, —CHR$^z$—, —C(R$^z$)$_2$—, —NR$^z$—, —N—, —O—, or —S—,
each ⎯⎯ is independently a single or double bond; and with the provision that the 5-membered heterocyclic ring contains at least one N atom.

In some embodiments,

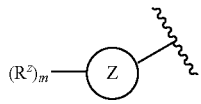

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazolidinyl, substituted or unsubstituted thiazolidinyl, or substituted or unsubstituted isothiazolidinyl.

In some embodiments,

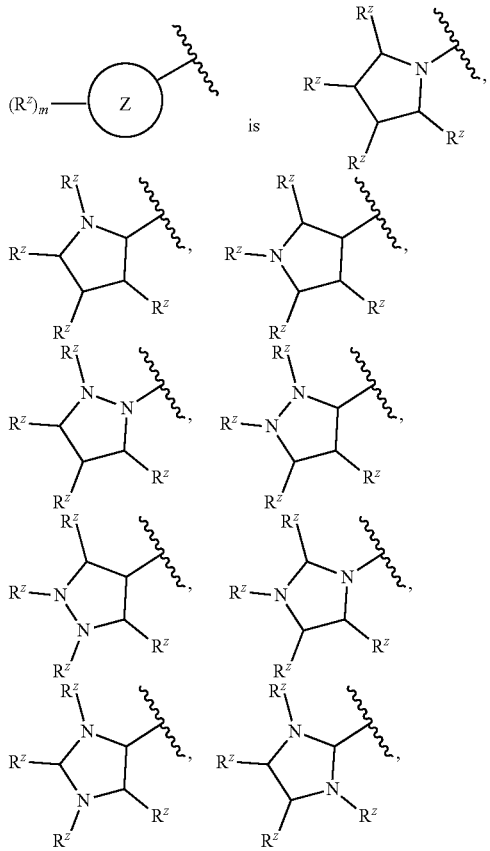

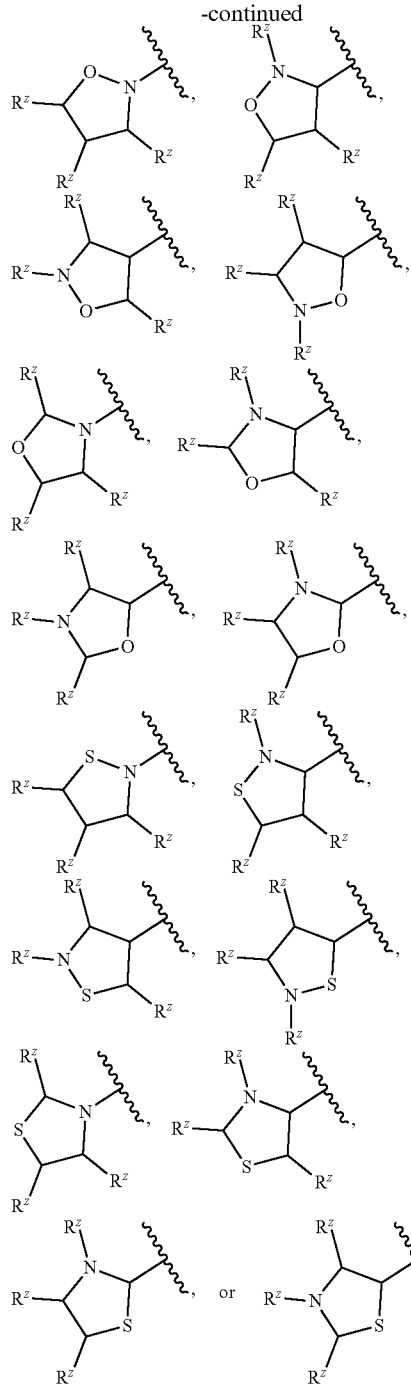

In some embodiments,

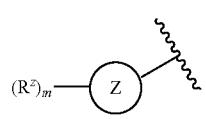

is substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazoyl, substituted or unsubstituted tetrazoyl, substituted or unsubstituted oxadiazolyl, substituted or unsubstituted thiadiazolyl, or substituted or unsubstituted dithiazolyl.
In some embodiments,
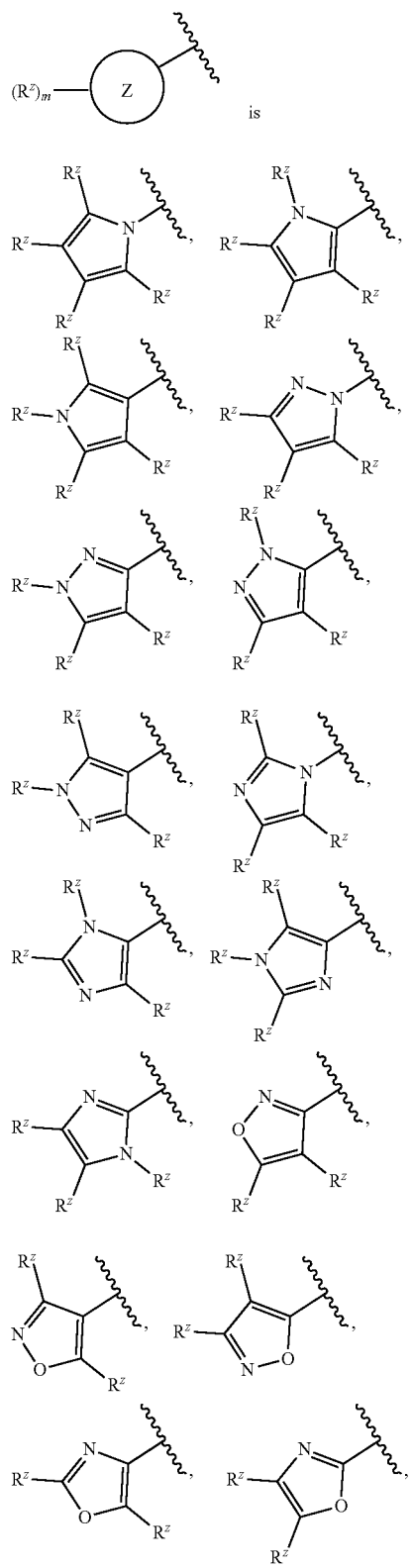
is
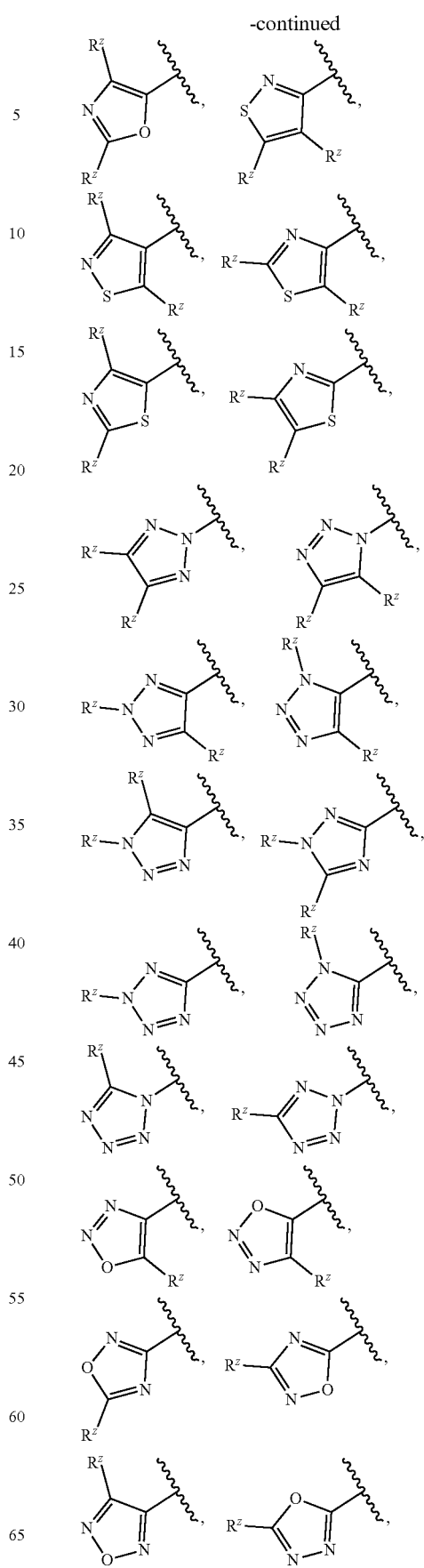

-continued

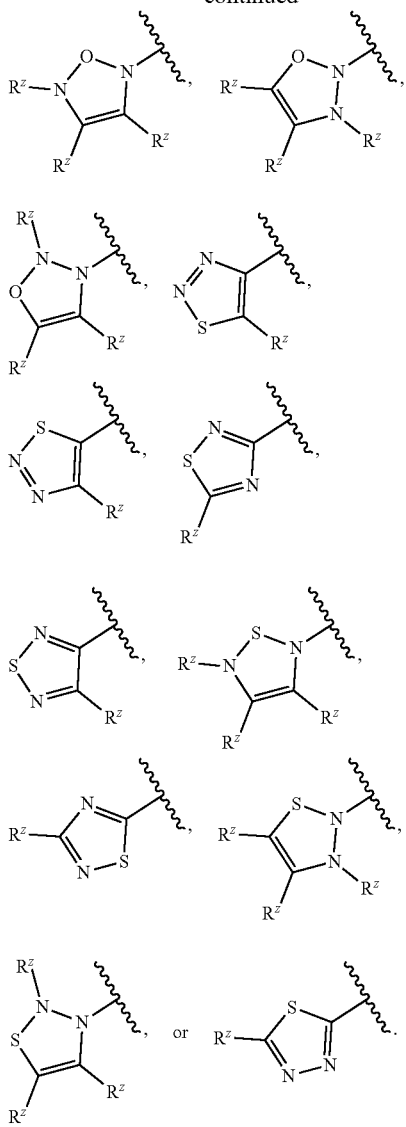

In some embodiments,

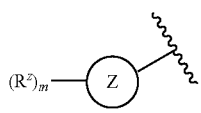

is a substituted or unsubstituted monocyclic 6-membered heteroaryl ring containing at least one N atom.

In some embodiments,

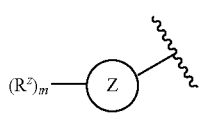

is a substituted or unsubstituted monocyclic 6-membered heteroaryl ring containing 1 or 2 N atoms.

In some embodiments,

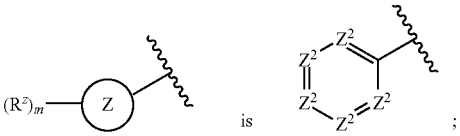

each $Z^2$ is independently $CR^z$ or N; and at least one $Z^2$ is N.

In some embodiments,

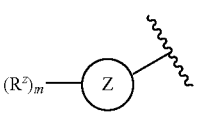

is substituted or unsubstituted pyridinyl, substituted or unsubstituted pyrazinyl, substituted or unsubstituted pyrimidinyl, or substituted or unsubstituted pyridazinyl.

In some embodiments,

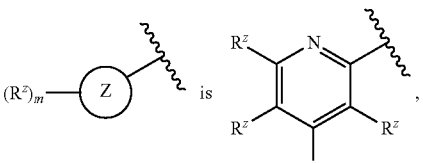

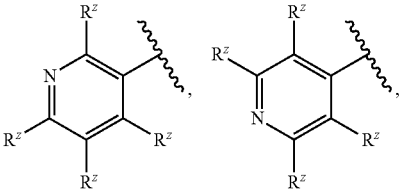

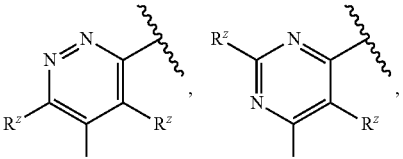

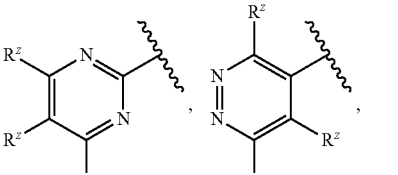

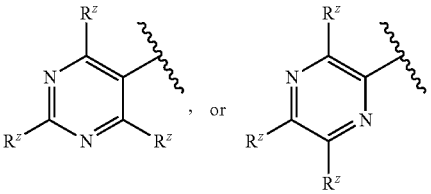

In some embodiments, the compound has the structure of Formula (Ia), or a pharmaceutically acceptable salt thereof:

Formula (Ia)

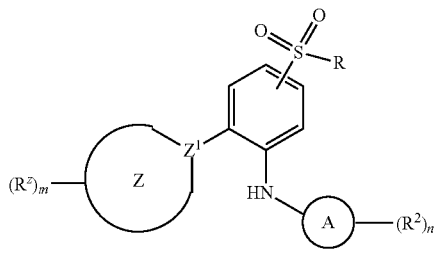

wherein $Z^1$ is —N—, —CH—, or —C—.

In some embodiments,

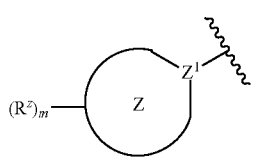

is a substituted or unsubstituted monocyclic 5-membered heterocyclic ring containing at least one N atom, and the at least one N atom is adjacent to $Z^1$.

In some embodiments,

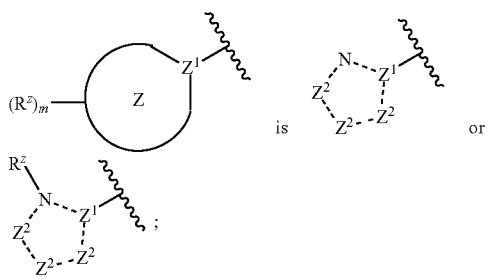

each $Z^2$ is independently CR, NR, N, O, or S;
each —— is independently a single or double bond; and
with the provision that the 5-membered heterocyclic ring contains at least one N atom.

In some embodiments,

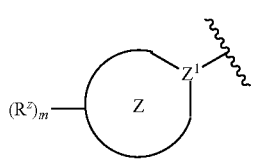

is substituted or unsubstituted pyrrolidinyl, substituted or unsubstituted imidazolidinyl, substituted or unsubstituted pyrazolidinyl, substituted or unsubstituted oxazolidinyl, substituted or unsubstituted isoxazolidinyl, substituted or unsubstituted thiazolidinyl, or substituted or unsubstituted isothiazolidinyl.

In some embodiments,

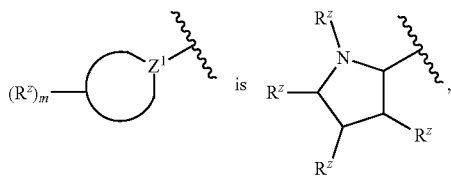

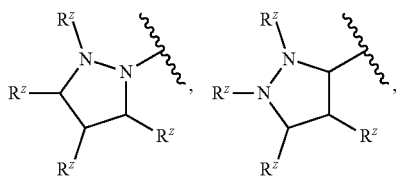

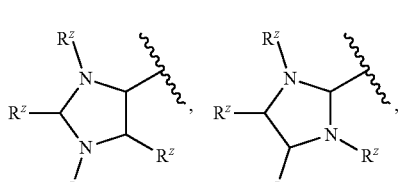

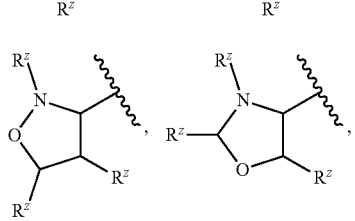

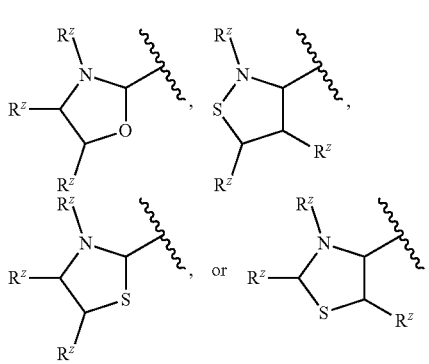

In some embodiments,

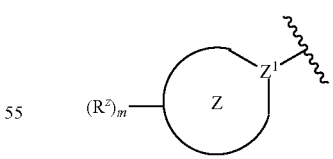

is substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazoyl, substituted or unsubstituted tetrazoyl, substituted or unsubstituted oxadiazolyl, substituted or unsubstituted thiadiazolyl, or substituted or unsubstituted dithiazolyl.

In some embodiments,
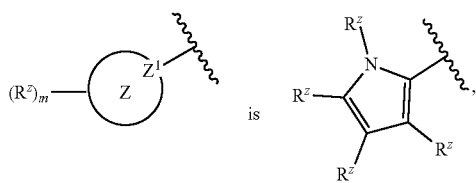 is 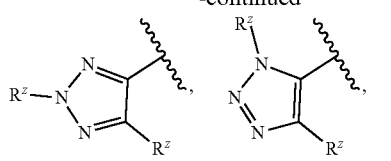
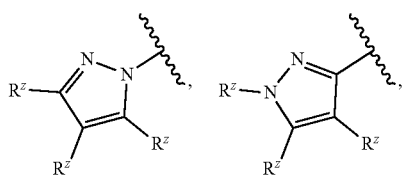
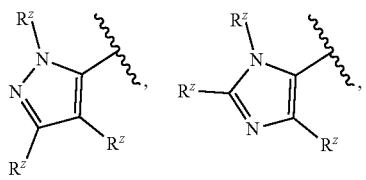
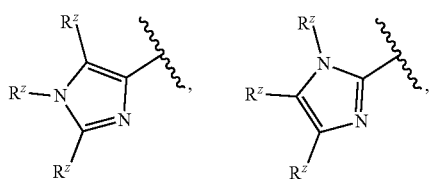
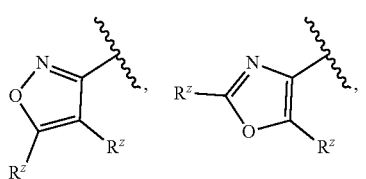
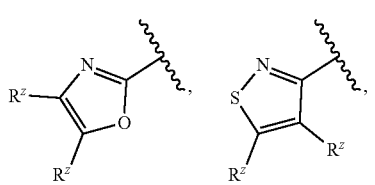
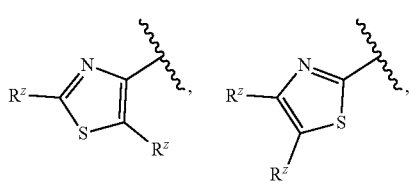
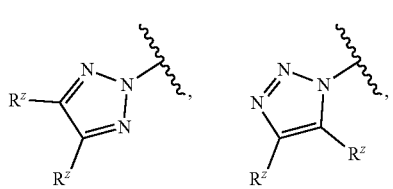
-continued
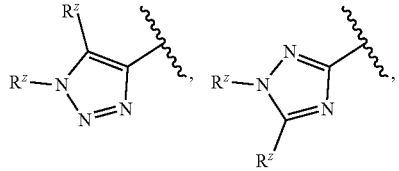
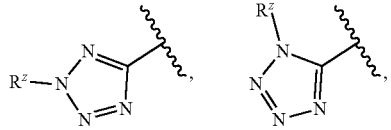
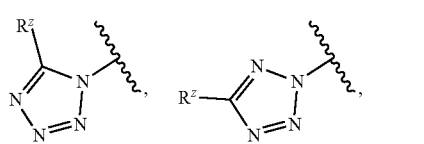
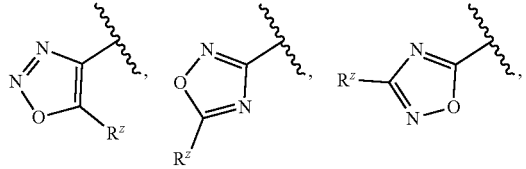
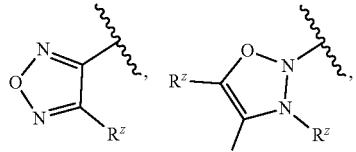
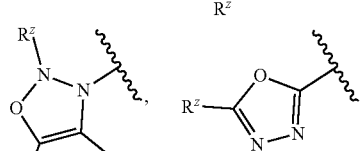
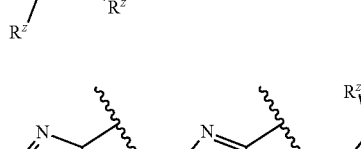
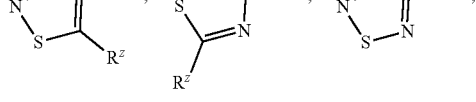
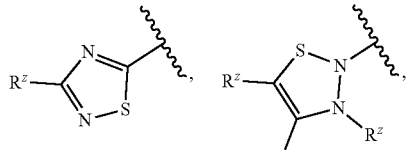
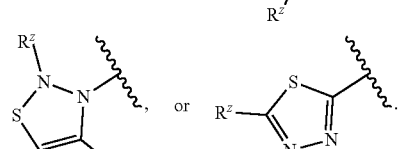 or 

In some embodiments,

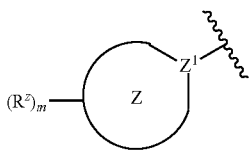

is a substituted or unsubstituted monocyclic 6-membered heteroaryl ring containing at least one N atom, and wherein the at least one N atom is adjacent to $Z^1$.

In some embodiments,

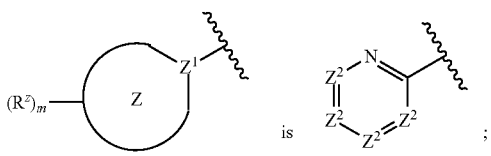

and
each $Z^2$ is independently $CR^z$ or N.

In some embodiments,

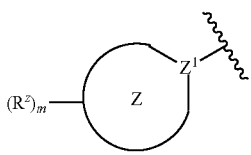

is substituted or unsubstituted pyridinyl, substituted or unsubstituted pyrazinyl, substituted or unsubstituted pyrimidinyl, or substituted or unsubstituted pyridazinyl.

In some embodiments,

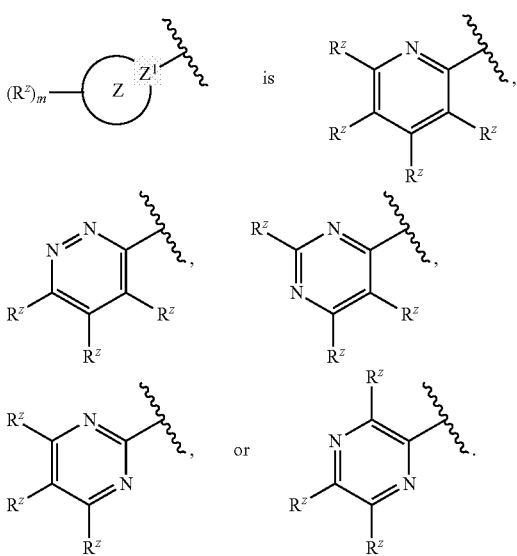

In some embodiments, each $R^z$ is independently H, halogen, —CN, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl. In some embodiments, each $R^z$ is independently H, halogen, substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl. In some embodiments, each $R^z$ is independently H, —F, —Cl, —Br, —I, methyl, ethyl, n-propyl, iso-propyl, n-butyl, iso-butyl, tert-butyl, cyclopropyl, cyclobutyl, cyclopentyl, cyclohexyl, or phenyl.

In some embodiments, each $R^z$ is -$L^1$-$Y^1$. In some embodiments, $L^1$ is substituted or unsubstituted $C_1$-$C_4$alkylene; and $Y^1$ is substituted or unsubstituted $C_3$-$C_{10}$cycloalkyl, substituted or unsubstituted $C_2$-$C_{10}$ heterocycloalkyl, substituted or unsubstituted aryl, or substituted or unsubstituted heteroaryl. In some embodiments, each R is -$L^2$-$L^3$-$Y^2$. In some embodiments, $L^2$ is substituted or unsubstituted $C_1$-$C_6$alkylene; $L^3$ is —O—, —S—, —(S=O)—, —(SO$_2$)—, —$NR^3$—, —(C=O)—, —(C=O)O—, —O(C=O)—, —(C=O)$NR^3$—, —(C=O)$NR^3$—O—, —$NR^3$(C=O)—, —$NR^3$(C=O)$NR^3$—, —O(C=O)$NR^3$—, —$NR^3$(C=O)O—, —$NR^3$(SO$_2$)$NR^3$—, —$NR^3$(SO$_2$)—, —(SO$_2$)$NR^3$—, —(SO$_2$)$NR^3$—(C=O)—, —(SO$_2$)$NR^3$—(C=O)O—, —$NR^3$(SO$_2$)$NR^3$—(C=O)—, or —$NR^3$(SO$_2$)$NR^3$—(C=O)O—; each $R^3$ is independently H or substituted or unsubstituted $C_1$-$C_6$alkyl; and $Y^2$ is H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl.

In some embodiments, $L^2$ is absent; $L^3$ is —O—, —S—, —(S=O)—, —(SO$_2$)—, —$NR^3$—, —(C=O)—, —(C=O)O—, —O(C=O)—, —(C=O)$NR^3$—, —(C=O)$NR^3$—O—, —$NR^3$(C=O)—, —$NR^3$(C=O)$NR^3$—, —O(C=O)$NR^3$—, —$NR^3$(C=O)O—, —$NR^3$(SO$_2$)$NR^3$—, —$NR^3$(SO$_2$)—, —(SO$_2$)$NR^3$—, —(SO$_2$)$NR^3$—(C=O)—, —(SO$_2$)$NR^3$—(C=O)O—, —$NR^3$(SO$_2$)$NR^3$—(C=O)—, or —$NR^3$(SO$_2$)$NR^3$—(C=O)O—; each $R^3$ is independently H or substituted or unsubstituted $C_1$-$C_6$alkyl; and $Y^2$ is H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl.

In some embodiments, is

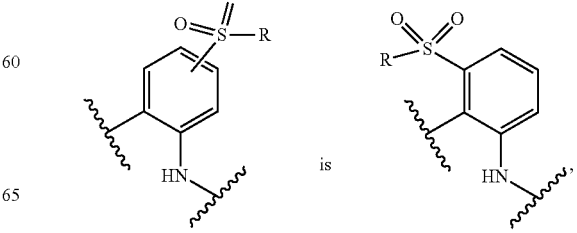

-continued

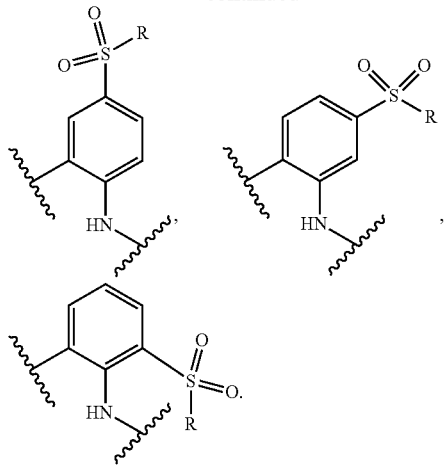

In some embodiments, is

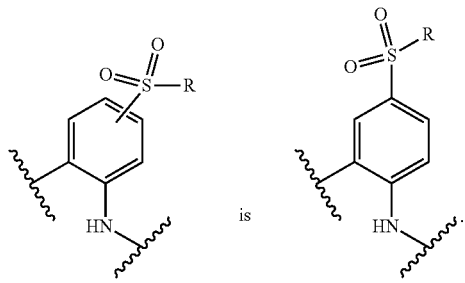

is

In some embodiments, R is NHR¹; and R is substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments, R¹ is methyl, ethyl, n-propyl, iso-propyl, n-butyl, iso-butyl, tert-butyl, cyclopropyl, cyclobutyl, cyclopentyl, cyclohexyl, or phenyl.

In some embodiments, R is R¹; and R is substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments, R is methyl, ethyl, n-propyl, iso-propyl, n-butyl, iso-butyl, tert-butyl, cyclopropyl, cyclobutyl, cyclopentyl, cyclohexyl, or phenyl.

In some embodiments,

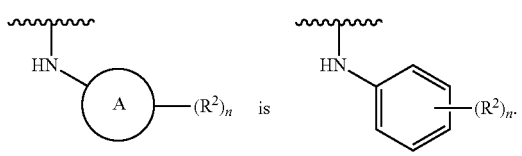

is

In some embodiments, the compound has the structure of Formula (Ib), or a pharmaceutically acceptable salt thereof:

Formula (Ib)

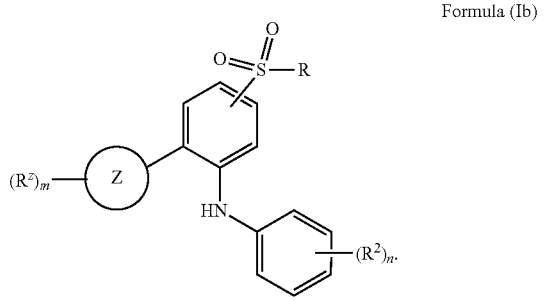

In some embodiments,

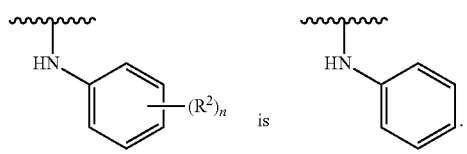

is

In some embodiments,

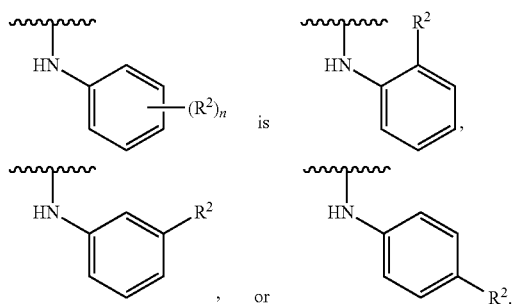

In some embodiments,

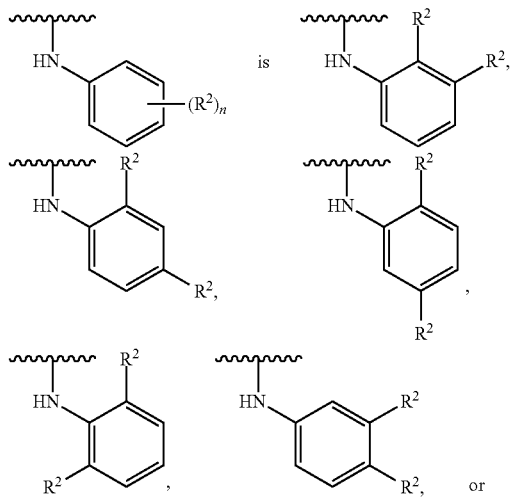

-continued

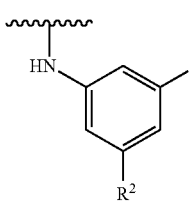

In some embodiments,

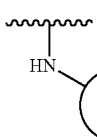 is 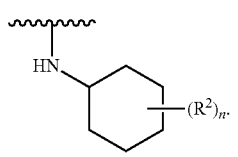.

In some embodiments, the compound has the structure of Formula (Ic), or a pharmaceutically acceptable salt thereof:

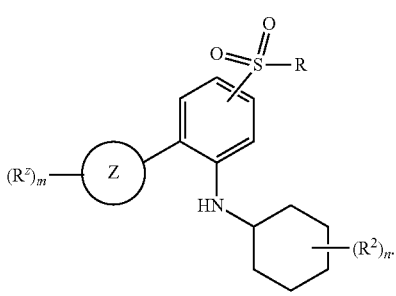

Formula (Ic)

In some embodiments,

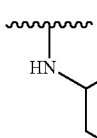 is 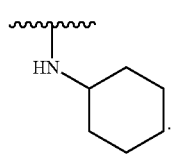.

In some embodiments,

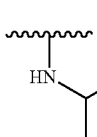 is 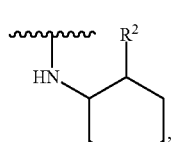,

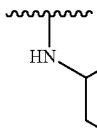 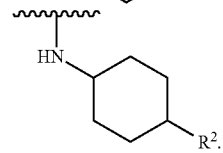, or

In some embodiments,

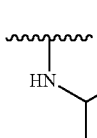 is 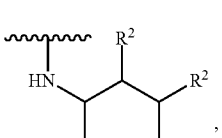,

-continued

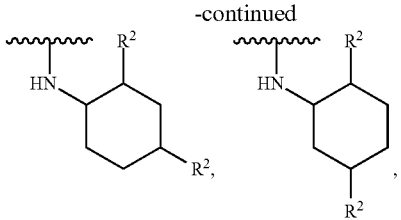

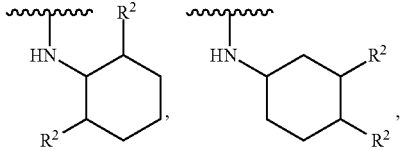

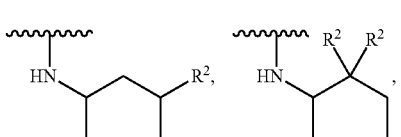

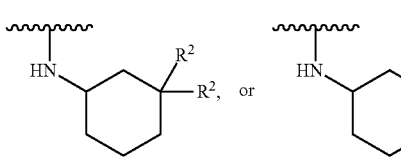

In some embodiments, each $R^2$ is independently H, halogen, —$N_3$, —CN, —$OR^4$, —$SR^4$, —$(SO_2)R^4$, —$N(R^4)_2$, —$CO_2R^4$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

In some embodiments, the compound has the structure of Formula (Id), or a pharmaceutically acceptable salt thereof:

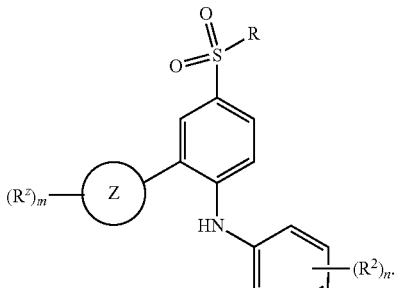

Formula (Id)

In some embodiments, the compound has the structure of Formula (Ie), or a pharmaceutically acceptable salt thereof:

Formula (Ie)

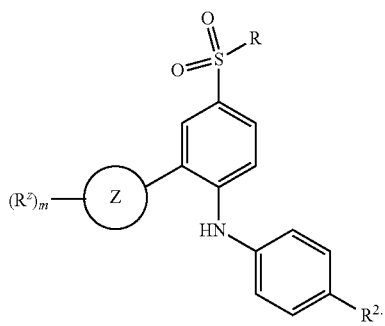

In some embodiments, the compound has the structure of Formula (If), or a pharmaceutically acceptable salt thereof:

Formula (If)

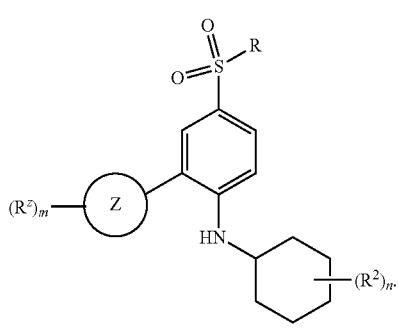

In some embodiments, the compound has the structure of Formula (Ig), or a pharmaceutically acceptable salt thereof:

Formula (Ig)

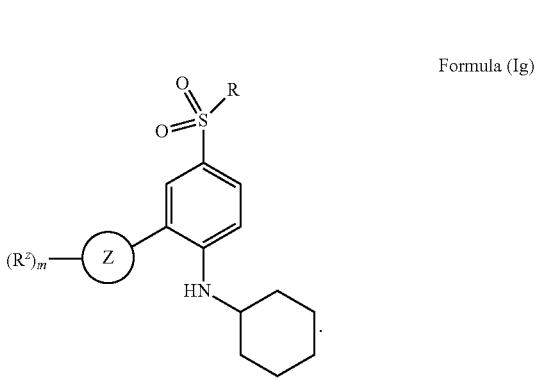

In some embodiments, the compound disclosed herein has the structure provided in Table 1.

TABLE 1

| Compound No. | Structure | Name |
|---|---|---|
| 1 | 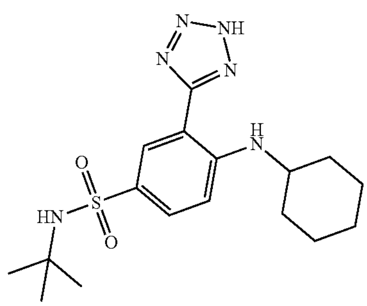 [SMILES: CC(C)(C)NS(=O)(=O)c1ccc(NC2CCCCC2)c(-c2nn[nH]n2)c1] | N-(tert-butyl)-4-(cyclohexylamino)-3-(2H-tetrazol-5-yl)benzenesulfonamide |
| 2 | 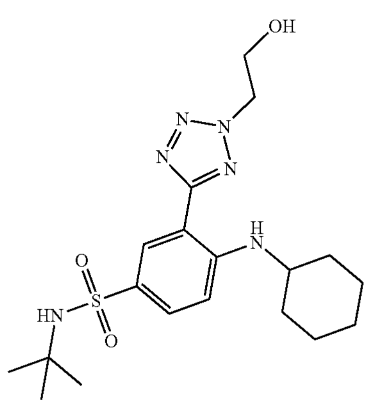 [SMILES: CC(C)(C)NS(=O)(=O)c1ccc(NC2CCCCC2)c(-c2nnn(CCO)n2)c1] | N-(tert-butyl)-4-(cyclohexylamino)-3-(2-(2-hydroxyethyl)-2H-tetrazol-5-yl)benzenesulfonamide |

TABLE 1-continued

| Compound No. | Structure | Name |
|---|---|---|
| 3 | 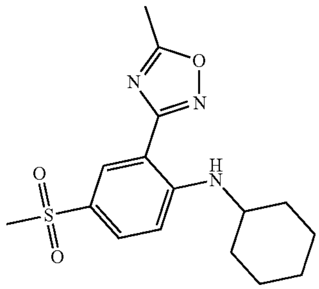 [SMILES: Cc1nc(-c2cc(S(C)(=O)=O)ccc2NC2CCCCC2)no1] | N-cyclohexyl-2-(5-methyl-1,2,4-oxadiazol-3-yl)-4-(methylsulfonyl)aniline |
| 4 | 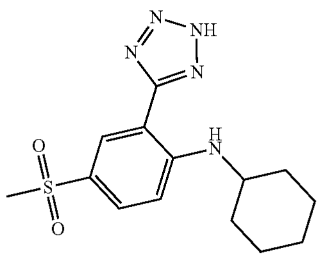 [SMILES: CS(=O)(=O)c1ccc(NC2CCCCC2)c(-c2nn[nH]n2)c1] | N-cyclohexyl-4-(methylsulfonyl)-2-(2H-tetrazol-5-yl)aniline |
| 5 | 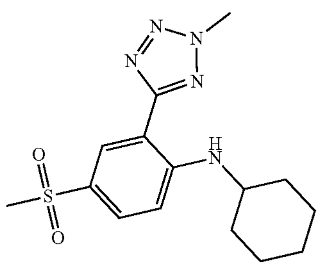 [SMILES: Cn1nnc(-c2cc(S(C)(=O)=O)ccc2NC2CCCCC2)n1] | N-cyclohexyl-2-(2-methyl-2H-tetrazol-5-yl)-4-(methylsulfonyl)aniline |
| 6 | 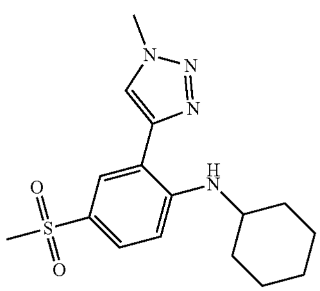 [SMILES: Cn1cc(-c2cc(S(C)(=O)=O)ccc2NC2CCCCC2)nn1] | N-cyclohexyl-2-(1-methyl-1H-1,2,3-triazol-4-yl)-4-(methylsulfonyl)aniline |
| 7 | 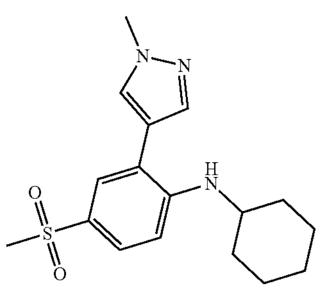 [SMILES: Cn1cc(-c2cc(S(C)(=O)=O)ccc2NC2CCCCC2)cn1] | N-cyclohexyl-2-(1-methyl-1H-pyrazol-4-yl)-4-(methylsulfonyl)aniline |

TABLE 1-continued

| Compound No. | Structure | Name |
|---|---|---|
| 8 | 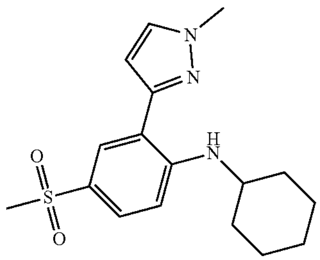 [SMILES: Cn1ccc(-c2cc(S(C)(=O)=O)ccc2NC2CCCCC2)n1] | N-cyclohexyl-2-(1-methyl-1H-pyrazol-3-yl)-4-(methylsulfonyl)aniline |
| 9 | 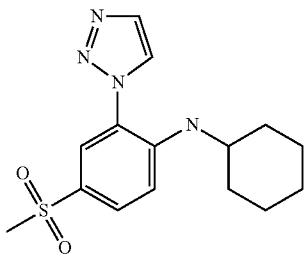 [SMILES: CS(=O)(=O)c1ccc(NC2CCCCC2)c(-n2ccnn2)c1] | N-cyclohexyl-4-(methylsulfonyl)-2-(1H-1,2,3-triazol-1-yl)aniline |
| 10 | 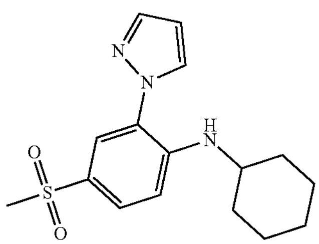 [SMILES: CS(=O)(=O)c1ccc(NC2CCCCC2)c(-n2cccn2)c1] | N-cyclohexyl-4-(methylsulfonyl)-2-(1H-pyrazol-1-yl)aniline |
| 11 | 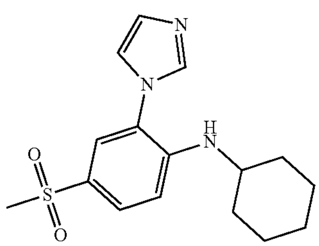 [SMILES: CS(=O)(=O)c1ccc(NC2CCCCC2)c(-n2ccnc2)c1] | N-cyclohexyl-2-(1H-imidazol-1-yl)-4-(methylsulfonyl)aniline |
| 12 | 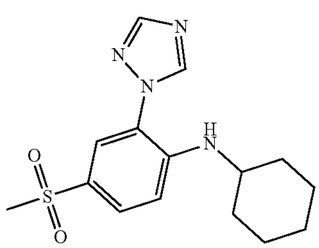 | N-cyclohexyl-4-(methylsulfonyl)-2-(1H-1,2,4-triazol-1-yl)aniline |
| 13 | 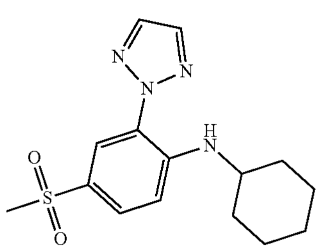 [SMILES: CS(=O)(=O)c1ccc(NC2CCCCC2)c(-n2nccn2)c1] | N-cyclohexyl-4-(methylsulfonyl)-2-(2H-1,2,3-triazol-2-yl)aniline |

TABLE 1-continued
| Compound No. | Structure | Name |
|---|---|---|
| 14 | 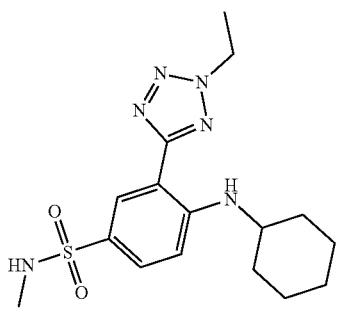 [SMILES: CCn1nnc(-c2cc(S(=O)(=O)NC)ccc2NC2CCCCC2)n1] | 4-(cyclohexylamino)-3-(2-ethyl-2H-tetrazol-5-yl)-N-methylbenzenesulfonamide |
| 15 | 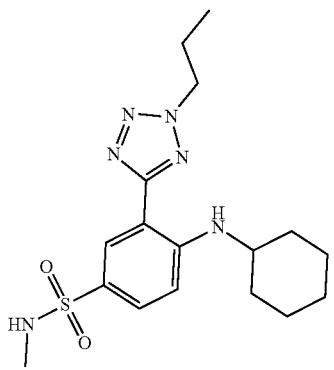 [SMILES: CCCn1nnc(-c2cc(S(=O)(=O)NC)ccc2NC2CCCCC2)n1] | 4-(cyclohexylamino)-N-methyl-3-(2-propyl-2H-tetrazol-5-yl)benzenesulfonamide |
| 16 | 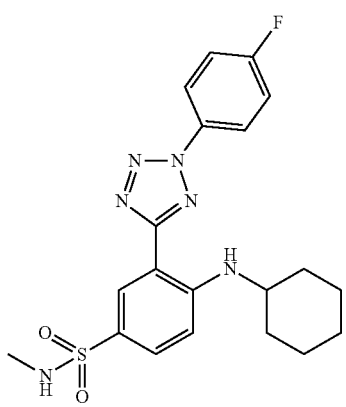 [SMILES: CNS(=O)(=O)c1ccc(NC2CCCCC2)c(-c2nnn(-c3ccc(F)cc3)n2)c1] | 4-(cyclohexylamino)-3-(2-(4-fluorophenyl)-2H-tetrazol-5-yl)-N-methylbenzenesulfonamide |
| 17 | 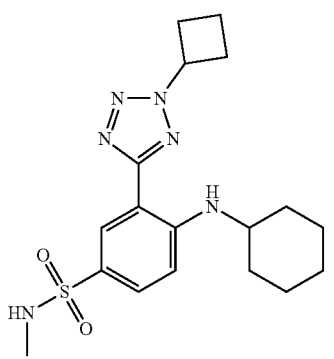 [SMILES: CNS(=O)(=O)c1ccc(NC2CCCCC2)c(-c2nnn(C3CCC3)n2)c1] | 3-(2-cyclobutyl-2H-tetrazol-5-yl)-4-(cyclohexylamino)-N-methylbenzenesulfonamide |

TABLE 1-continued

| Compound No. | Structure | Name |
|---|---|---|
| 18 | 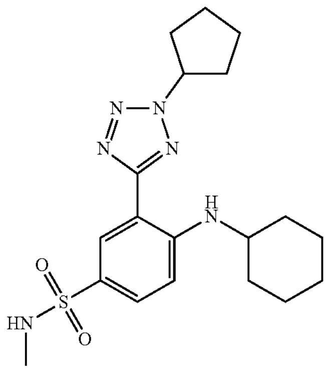 [SMILES: CNS(=O)(=O)c1ccc(NC2CCCCC2)c(-c2nnn(C3CCCC3)n2)c1] | 4-(cyclohexylamino)-3-(2-cyclopentyl-2H-tetrazol-5-yl)-N-methylbenzenesulfonamide |
| 19 | 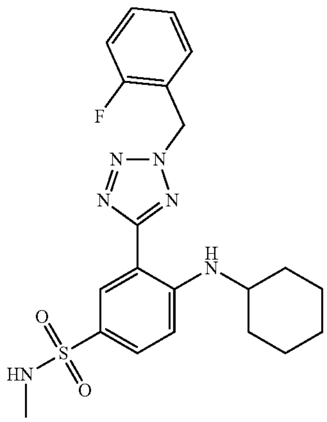 [SMILES: CNS(=O)(=O)c1ccc(NC2CCCCC2)c(-c2nnn(Cc3ccccc3F)n2)c1] | 4-(cyclohexylamino)-3-(2-(2-fluorobenzyl)-2H-tetrazol-5-yl)-N-methylbenzenesulfonamide |
| 20 | 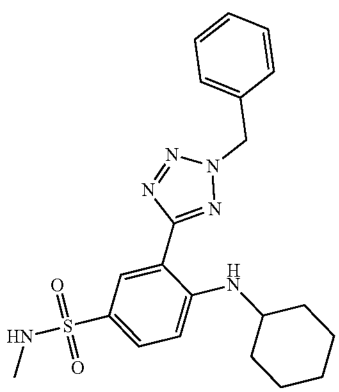 [SMILES: CNS(=O)(=O)c1ccc(NC2CCCCC2)c(-c2nnn(Cc3ccccc3)n2)c1] | 3-(2-benzyl-2H-tetrazol-5-yl)-4-(cyclohexylamino)-N-methylbenzenesulfonamide |
| 21 | 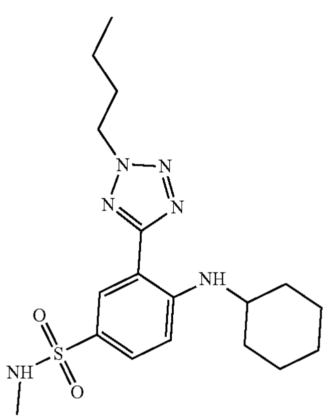 [SMILES: CCCCn1nnc(-c2cc(S(=O)(=O)NC)ccc2NC2CCCCC2)n1] | 3-(2-butyltetrazol-5-yl)-4-(cyclohexylamino)-N-methyl-benzenesulfonamide |

TABLE 1-continued

| Compound No. | Structure | Name |
|---|---|---|
| 22 | 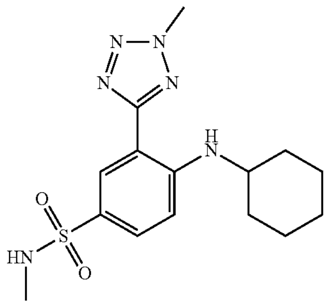 [SMILES: CNS(=O)(=O)c1ccc(NC2CCCCC2)c(-c2nnn(C)n2)c1] | 4-(cyclohexylamino)-N-methyl-3-(2-methyl-2H-tetrazol-5-yl)benzenesulfonamide |
| 23 | 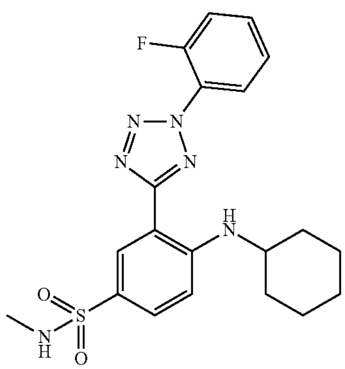 [SMILES: CNS(=O)(=O)c1ccc(NC2CCCCC2)c(-c2nnn(-c3ccccc3F)n2)c1] | 4-(cyclohexylamino)-3-(2-(2-fluorophenyl)-2H-tetrazol-5-yl)-N-methylbenzenesulfonamide |
| 24 | 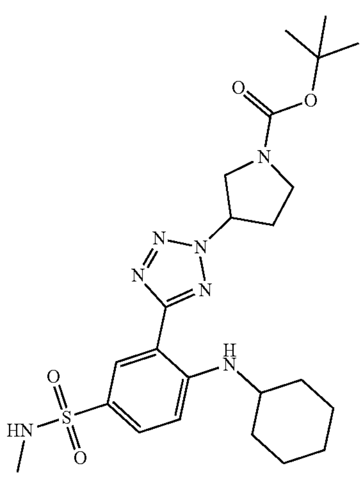 [SMILES: CNS(=O)(=O)c1ccc(NC2CCCCC2)c(-c2nnn(C3CCN(C(=O)OC(C)(C)C)C3)n2)c1] | tert-butyl 3-(5-(2-(cyclohexylamino)-5-(N-methylsulfamoyl)phenyl)-2H-tetrazol-2-yl)pyrrolidine-1-carboxylate |

TABLE 1-continued

| Compound No. | Structure | Name |
|---|---|---|
| 25 | 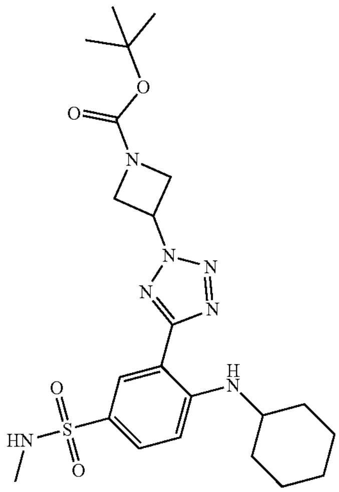 [SMILES: CNS(=O)(=O)c1ccc(NC2CCCCC2)c(-c2nnn(C3CN(C(=O)OC(C)(C)C)C3)n2)c1] | tert-butyl 3-(5-(2-(cyclohexylamino)-5-(N-methylsulfamoyl)phenyl)-2H-tetrazol-2-yl)azetidine-1-carboxylate |
| 26 | 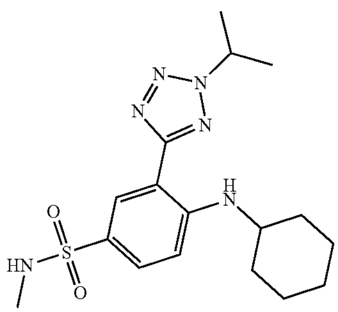 [SMILES: CNS(=O)(=O)c1ccc(NC2CCCCC2)c(-c2nnn(C(C)C)n2)c1] | 4-(cyclohexylamino)-3-(2-isopropyl-2H-tetrazol-5-yl)-N-methylbenzenesulfonamide |
| 27 | 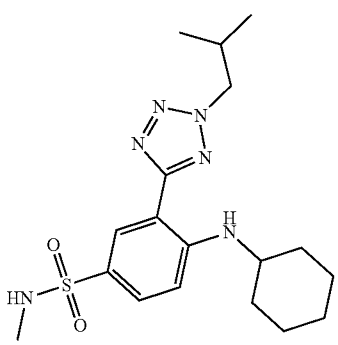 [SMILES: CNS(=O)(=O)c1ccc(NC2CCCCC2)c(-c2nnn(CC(C)C)n2)c1] | 4-(cyclohexylamino)-3-(2-isobutyl-2H-tetrazol-5-yl)-N-methylbenzenesulfonamide |
| 28 | 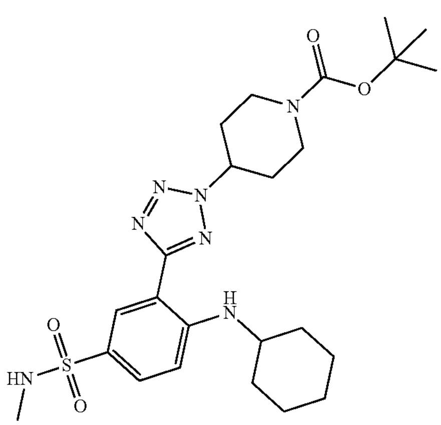 [SMILES: CNS(=O)(=O)c1ccc(NC2CCCCC2)c(-c2nnn(C3CCN(C(=O)OC(C)(C)C)CC3)n2)c1] | tert-butyl 4-(5-(2-(cyclohexylamino)-5-(N-methylsulfamoyl)phenyl)-2H-tetrazol-2-yl)piperidine-1-carboxylate |

TABLE 1-continued
| Compound No. | Structure | Name |
|---|---|---|
| 29 | 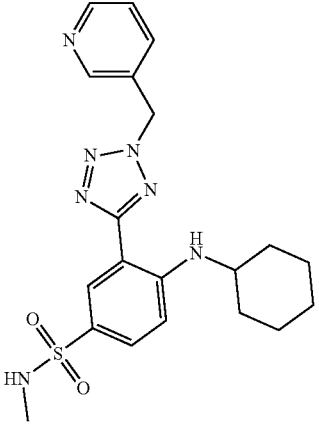 [SMILES: CNS(=O)(=O)c1ccc(NC2CCCCC2)c(-c2nnn(Cc3cccnc3)n2)c1] | 4-(cyclohexylamino)-N-methyl-3-(2-(pyridin-3-ylmethyl)-2H-tetrazol-5-yl)benzenesulfonamide |
| 30 | 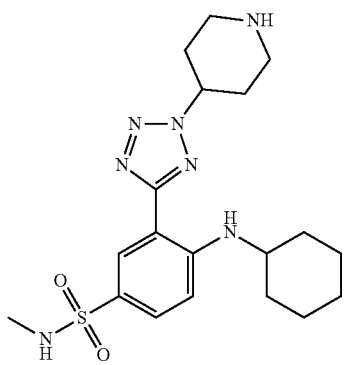 [SMILES: CNS(=O)(=O)c1ccc(NC2CCCCC2)c(-c2nnn(C3CCNCC3)n2)c1] | 4-(cyclohexylamino)-N-methyl-3-(2-(piperidin-4-yl)-2H-tetrazol-5-yl)benzenesulfonamide |
| 31 | 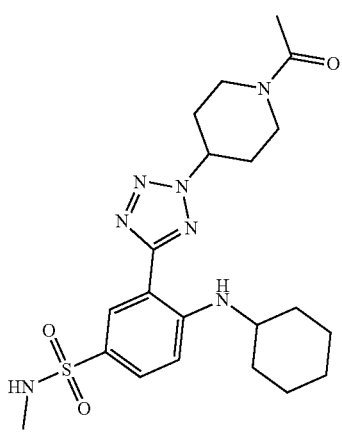 [SMILES: CNS(=O)(=O)c1ccc(NC2CCCCC2)c(-c2nnn(C3CCN(C(C)=O)CC3)n2)c1] | 3-(2-(1-acetylpiperidin-4-yl)-2H-tetrazol-5-yl)-4-(cyclohexylamino)-N-methylbenzenesulfonamide |

TABLE 1-continued

| Compound No. | Structure | Name |
|---|---|---|
| 32 | 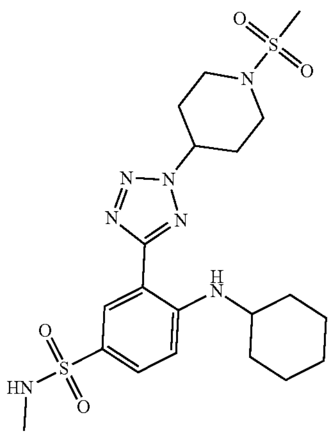 [SMILES: CNS(=O)(=O)c1ccc(NC2CCCCC2)c(-c2nnn(C3CCN(S(C)(=O)=O)CC3)n2)c1] | 4-(cyclohexylamino)-N-methyl-3-(2-(1-(methylsulfonyl)piperidin-4-yl)-2H-tetrazol-5-yl)benzenesulfonamide |
| 33 | 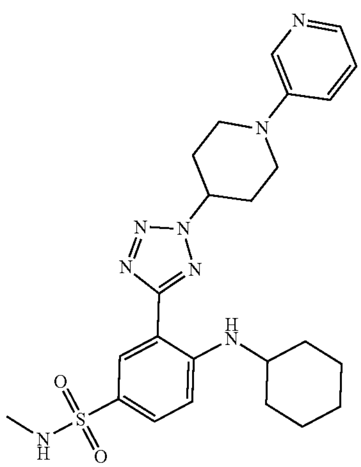 [SMILES: CNS(=O)(=O)c1ccc(NC2CCCCC2)c(-c2nnn(C3CCN(c4cccnc4)CC3)n2)c1] | 4-(cyclohexylamino)-N-methyl-3-(2-(1-(pyridin-3-yl)piperidin-4-yl)-2H-tetrazol-5-yl)benzenesulfonamide |
| 34 | 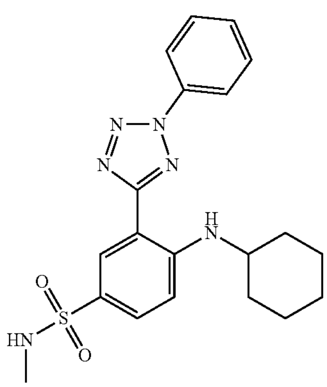 [SMILES: CNS(=O)(=O)c1ccc(NC2CCCCC2)c(-c2nnn(-c3ccccc3)n2)c1] | 4-(cyclohexylamino)-N-methyl-3-(2-phenyl-2H-tetrazol-5-yl)benzenesulfonamide |

TABLE 1-continued

| Compound No. | Structure | Name |
|---|---|---|
| 35 | 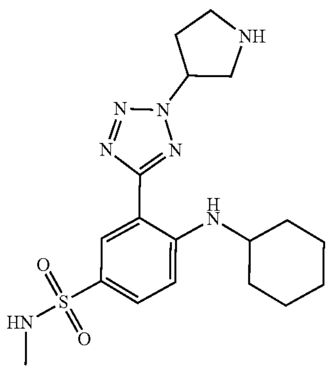 [SMILES: CNS(=O)(=O)c1ccc(NC2CCCCC2)c(-c2nnn(C3CCNC3)n2)c1] | 4-(cyclohexylamino)-N-methyl-3-(2-(pyrrolidin-3-yl)-2H-tetrazol-5-yl)benzenesulfonamide |
| 36 | 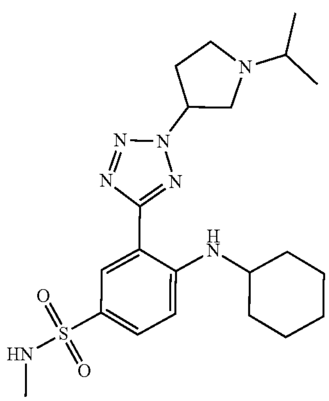 [SMILES: CNS(=O)(=O)c1ccc(NC2CCCCC2)c(-c2nnn(C3CCN(C(C)C)C3)n2)c1] | 4-(cyclohexylamino)-3-(2-(1-isopropylpyrrolidin-3-yl)-2H-tetrazol-5-yl)-N-methylbenzenesulfonamide |
| 37 | 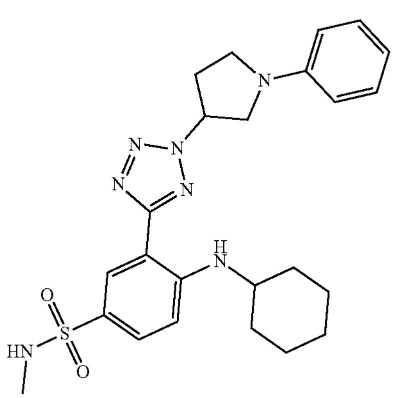 [SMILES: CNS(=O)(=O)c1ccc(NC2CCCCC2)c(-c2nnn(C3CCN(c4ccccc4)C3)n2)c1] | 4-(cyclohexylamino)-N-methyl-3-(2-(1-phenylpyrrolidin-3-yl)-2H-tetrazol-5-yl)benzenesulfonamide |

TABLE 1-continued

| Compound No. | Structure | Name |
|---|---|---|
| 38 | 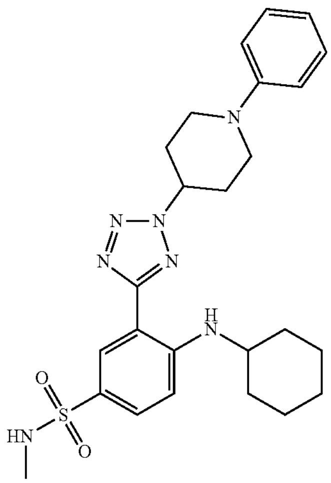 [SMILES: CNS(=O)(=O)c1ccc(NC2CCCCC2)c(-c2nnn(C3CCN(c4ccccc4)CC3)n2)c1] | 4-(cyclohexylamino)-N-methyl-3-(2-(1-phenylpiperidin-4-yl)-2H-tetrazol-5-yl)benzenesulfonamide |
| 39 | 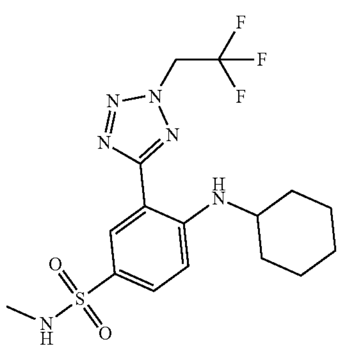 [SMILES: CNS(=O)(=O)c1ccc(NC2CCCCC2)c(-c2nnn(CC(F)(F)F)n2)c1] | 4-(cyclohexylamino)-N-methyl-3-(2-(2,2,2-trifluoroethyl)-2H-tetrazol-5-yl)benzenesulfonamide |
| 40 | 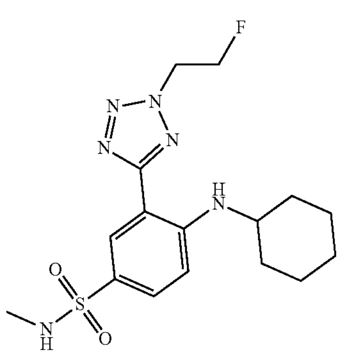 [SMILES: CNS(=O)(=O)c1ccc(NC2CCCCC2)c(-c2nnn(CCF)n2)c1] | 4-(cyclohexylamino)-3-(2-(2-fluoroethyl)-2H-tetrazol-5-yl)-N-methylbenzenesulfonamide |

TABLE 1-continued

| Compound No. | Structure | Name |
|---|---|---|
| 41 | 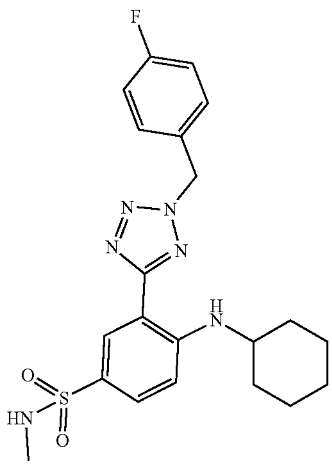 [SMILES: CNS(=O)(=O)c1ccc(NC2CCCCC2)c(-c2nnn(Cc3ccc(F)cc3)n2)c1] | 4-(cyclohexylamino)-3-(2-(4-fluorobenzyl)-2H-tetrazol-5-yl)-N-methylbenzenesulfonamide |
| 42 | 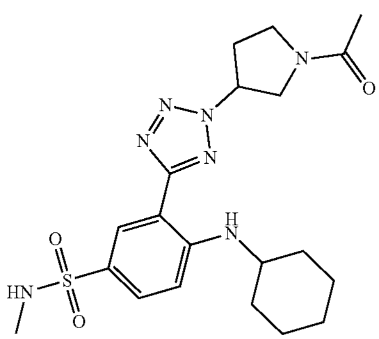 [SMILES: CNS(=O)(=O)c1ccc(NC2CCCCC2)c(-c2nnn(C3CCN(C(C)=O)C3)n2)c1] | 3-(2-(1-acetylpyrrolidin-3-yl)-2H-tetrazol-5-yl)-4-(cyclohexylamino)-N-methylbenzenesulfonamide |
| 43 | 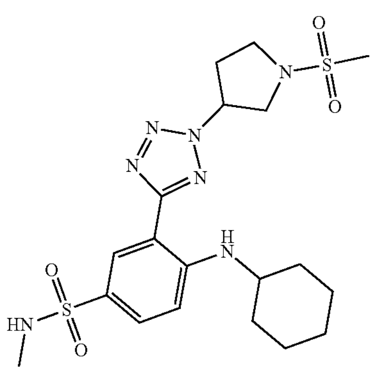 | 4-(cyclohexylamino)-N-methyl-3-(2-(1-(methylsulfonyl)pyrrolidin-3-yl)-2H-tetrazol-5-yl)benzenesulfonamide |
| 44 | 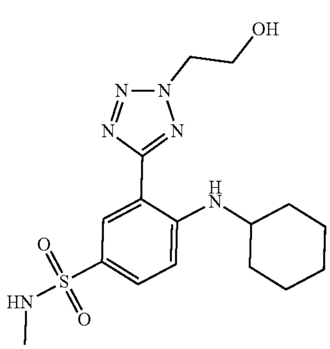 [SMILES: CNS(=O)(=O)c1ccc(NC2CCCCC2)c(-c2nnn(CCO)n2)c1] | 4-(cyclohexylamino)-3-(2-(2-hydroxyethyl)-2H-tetrazol-5-yl)-N-methylbenzenesulfonamide |

TABLE 1-continued

| Compound No. | Structure | Name |
|---|---|---|
| 45 | 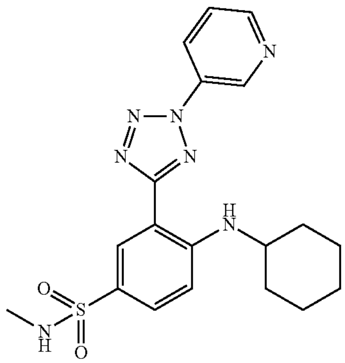 [SMILES: CNS(=O)(=O)c1ccc(NC2CCCCC2)c(-c2nnn(-c3cccnc3)n2)c1] | 4-(cyclohexylamino)-N-methyl-3-(2-(pyridin-3-yl)-2H-tetrazol-5-yl)benzenesulfonamide |
| 46 | 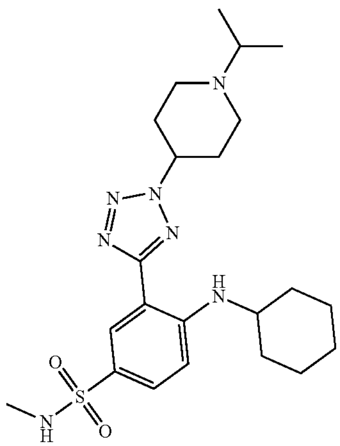 [SMILES: CNS(=O)(=O)c1ccc(NC2CCCCC2)c(-c2nnn(C3CCN(C(C)C)CC3)n2)c1] | 4-(cyclohexylamino)-3-(2-(1-isopropylpiperidin-4-yl)-2H-tetrazol-5-yl)-N-methylbenzenesulfonamide |
| 47 | 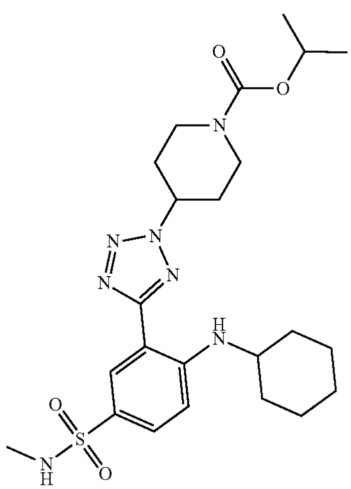 [SMILES: CNS(=O)(=O)c1ccc(NC2CCCCC2)c(-c2nnn(C3CCN(C(=O)OC(C)C)CC3)n2)c1] | isopropyl 4-(5-(2-(cyclohexylamino)-5-(N-methylsulfamoyl)phenyl)-2H-tetrazol-2-yl)piperidine-1-carboxylate |
| 48 | 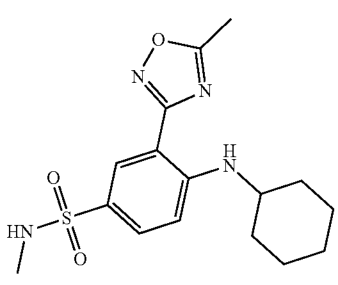 [SMILES: CNS(=O)(=O)c1ccc(NC2CCCCC2)c(-c2noc(C)n2)c1] | 4-(cyclohexylamino)-N-methyl-3-(5-methyl-1,2,4-oxadiazol-3-yl)benzenesulfonamide |

TABLE 1-continued

| Compound No. | Structure | Name |
|---|---|---|
| 49 | 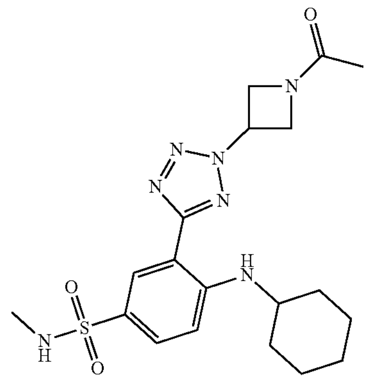 [SMILES: CNS(=O)(=O)c1ccc(NC2CCCCC2)c(-c2nnn(C3CN(C(C)=O)C3)n2)c1] | 3-(2-(1-acetylazetidin-3-yl)-2H-tetrazol-5-yl)-4-(cyclohexylamino)-N-methylbenzenesulfonamide |
| 50 | 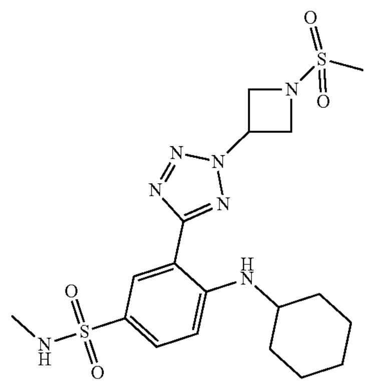 | 4-(cyclohexylamino)-N-methyl-3-(2-(1-(methylsulfonyl)azetidin-3-yl)-2H-tetrazol-5-yl)benzenesulfonamide |
| 51 | 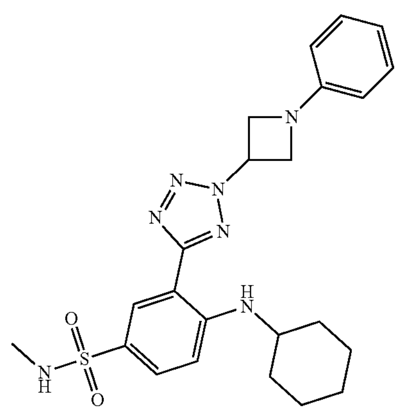 [SMILES: CNS(=O)(=O)c1ccc(NC2CCCCC2)c(-c2nnn(C3CN(c4ccccc4)C3)n2)c1] | 4-(cyclohexylamino)-N-methyl-3-(2-(1-phenylazetidin-3-yl)-2H-tetrazol-5-yl)benzenesulfonamide |
| 52 | 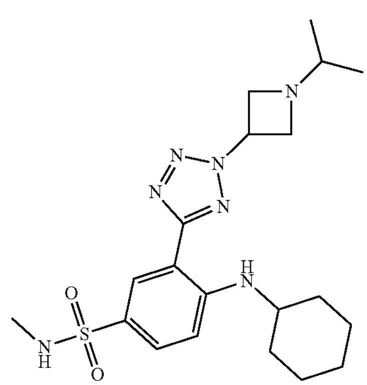 [SMILES: CNS(=O)(=O)c1ccc(NC2CCCCC2)c(-c2nnn(C3CN(C(C)C)C3)n2)c1] | 4-(cyclohexylamino)-3-(2-(1-isopropylazetidin-3-yl)-2H-tetrazol-5-yl)-N-methylbenzenesulfonamide |

TABLE 1-continued

| Compound No. | Structure | Name |
|---|---|---|
| 53 | 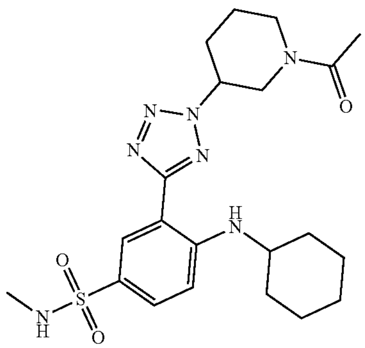 [SMILES: CNS(=O)(=O)c1ccc(NC2CCCCC2)c(-c2nnn(C3CCCN(C(C)=O)C3)n2)c1] | 3-(2-(1-acetylpiperidin-3-yl)-2H-tetrazol-5-yl)-4-(cyclohexylamino)-N-methylbenzenesulfonamide |
| 54 | 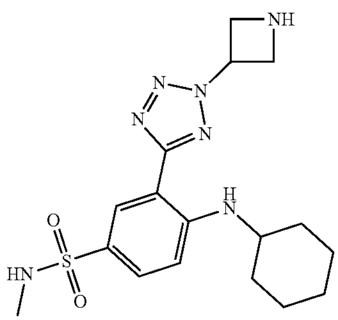 [SMILES: CNS(=O)(=O)c1ccc(NC2CCCCC2)c(-c2nnn(C3CNC3)n2)c1] | 3-(2-(azetidin-3-yl)-2H-tetrazol-5-yl)-4-(cyclohexylamino)-N-methylbenzenesulfonamide |
| 55 | 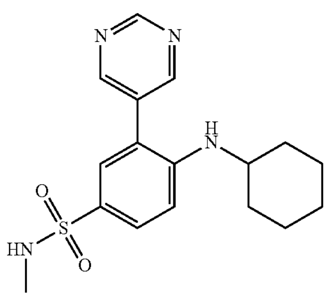 | 4-(cyclohexylamino)-N-methyl-3-(pyrimidin-5-yl)benzenesulfonamide |
| 56 | 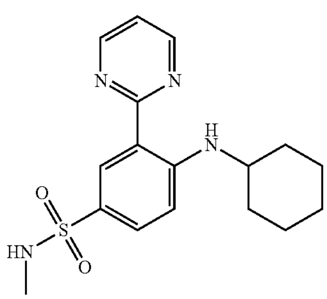 [SMILES: CNS(=O)(=O)c1ccc(NC2CCCCC2)c(-c2ncccn2)c1] | 4-(cyclohexylamino)-N-methyl-3-(pyrimidin-2-yl)benzenesulfonamide |
| 57 | 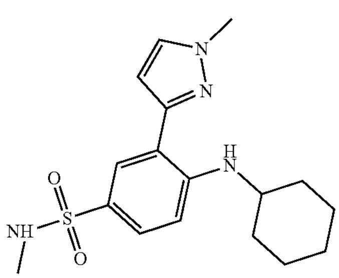 [SMILES: CNS(=O)(=O)c1ccc(NC2CCCCC2)c(-c2ccn(C)n2)c1] | 4-(cyclohexylamino)-N-methyl-3-(1-methyl-1H-pyrazol-3-yl)benzenesulfonamide |

TABLE 1-continued

| Compound No. | Structure | Name |
|---|---|---|
| 58 | 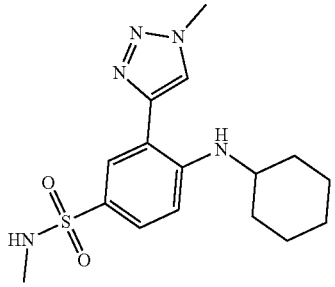 [SMILES: CNS(=O)(=O)c1ccc(NC2CCCCC2)c(-c2cn(C)nn2)c1] | 4-(cyclohexylamino)-N-methyl-3-(1-methyl-1H-1,2,3-triazol-4-yl)benzenesulfonamide |
| 59 | 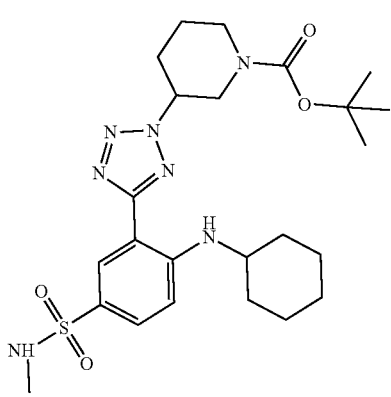 [SMILES: CNS(=O)(=O)c1ccc(NC2CCCCC2)c(-c2nnn(C3CCCN(C(=O)OC(C)(C)C)C3)n2)c1] | tert-butyl 3-(5-(2-(cyclohexylamino)-5-(N-methylsulfamoyl)phenyl)-2H-tetrazol-2-yl)piperidine-1-carboxylate |
| 60 | 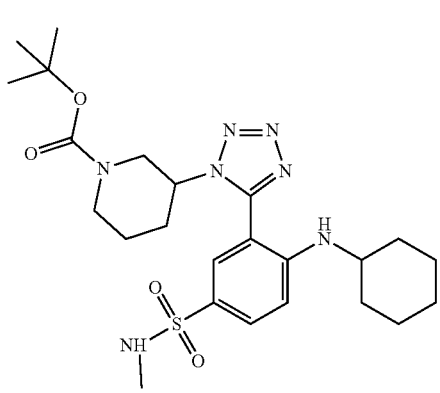 [SMILES: CNS(=O)(=O)c1ccc(NC2CCCCC2)c(-c2nnnn2C2CCCN(C(=O)OC(C)(C)C)C2)c1] | tert-butyl 3-(5-(2-(cyclohexylamino)-5-(N-methylsulfamoyl)phenyl)-1H-tetrazol-1-yl)piperidine-1-carboxylate |
| 61 | 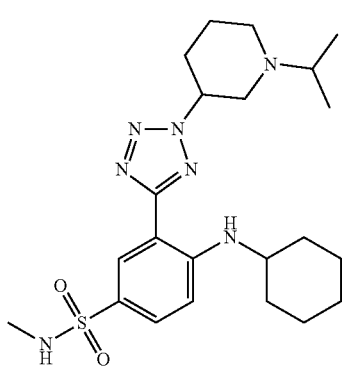 [SMILES: CNS(=O)(=O)c1ccc(NC2CCCCC2)c(-c2nnn(C3CCCN(C(C)C)C3)n2)c1] | 4-(cyclohexylamino)-3-(2-(1-isopropylpiperidin-3-yl)-2H-tetrazol-5-yl)-N-methylbenzenesulfonamide |

TABLE 1-continued

| Compound No. | Structure | Name |
|---|---|---|
| 62 | 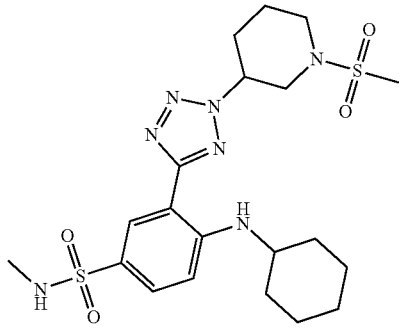 | 4-(cyclohexylamino)-N-methyl-3-(2-(1-(methylsulfonyl)piperidin-3-yl)-2H-tetrazol-5-yl)benzenesulfonamide |
| 63 | 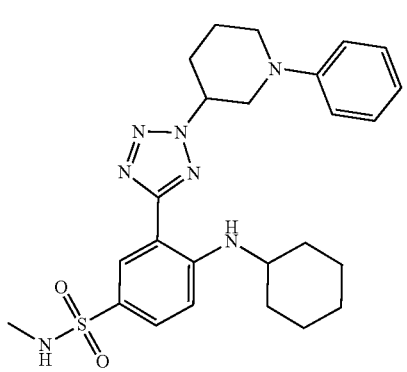 [SMILES: CNS(=O)(=O)c1ccc(NC2CCCCC2)c(-c2nnn(C3CCCN(c4ccccc4)C3)n2)c1] | 4-(cyclohexylamino)-N-methyl-3-(2-(1-phenylpiperidin-3-yl)-2H-tetrazol-5-yl)benzenesulfonamide |
| 64 | 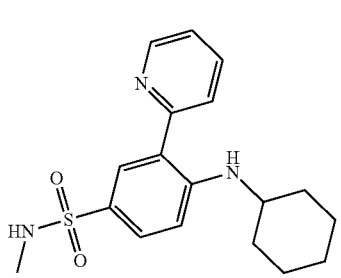 [SMILES: CNS(=O)(=O)c1ccc(NC2CCCCC2)c(-c2ccccn2)c1] | 4-(cyclohexylamino)-N-methyl-3-(pyridin-2-yl)benzenesulfonamide |
| 65 | 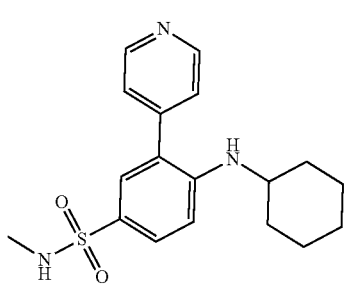 [SMILES: CNS(=O)(=O)c1ccc(NC2CCCCC2)c(-c2ccncc2)c1] | 4-(cyclohexylamino)-N-methyl-3-(pyridin-4-yl)benzenesulfonamide |
| 66 | 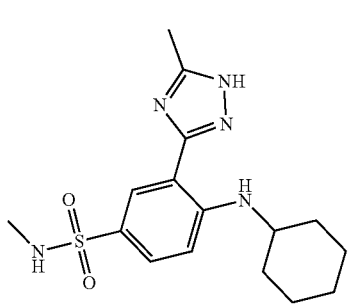 [SMILES: CNS(=O)(=O)c1ccc(NC2CCCCC2)c(-c2n[nH]c(C)n2)c1] | 4-(cyclohexylamino)-N-methyl-3-(5-methyl-1H-1,2,4-triazol-3-yl)benzenesulfonamide |

TABLE 1-continued

| Compound No. | Structure | Name |
|---|---|---|
| 67 | 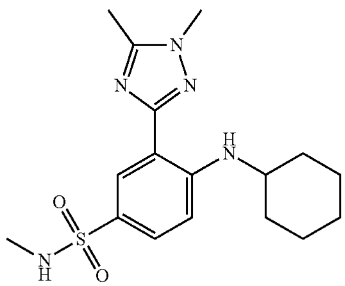 [SMILES: CNS(=O)(=O)c1ccc(NC2CCCCC2)c(-c2nc(C)n(C)n2)c1] | 4-(cyclohexylamino)-3-(1,5-dimethyl-1H-1,2,4-triazol-3-yl)-N-methylbenzenesulfonamide |
| 68 | 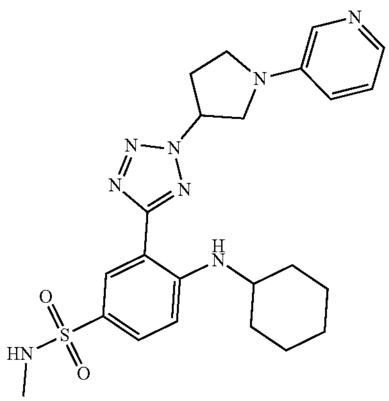 [SMILES: CNS(=O)(=O)c1ccc(NC2CCCCC2)c(-c2nnn(C3CCN(c4cccnc4)C3)n2)c1] | 4-(cyclohexylamino)-N-methyl-3-(2-(1-(pyridin-3-yl)pyrrolidin-3-yl)-2H-tetrazol-5-yl)benzenesulfonamide |
| 69 | 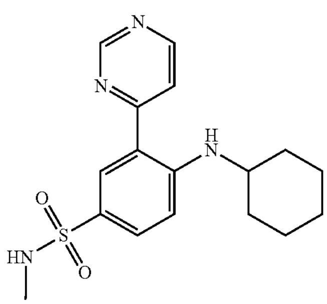 | 4-(cyclohexylamino)-N-methyl-3-(pyrimidin-4-yl)benzenesulfonamide |
| 70 | 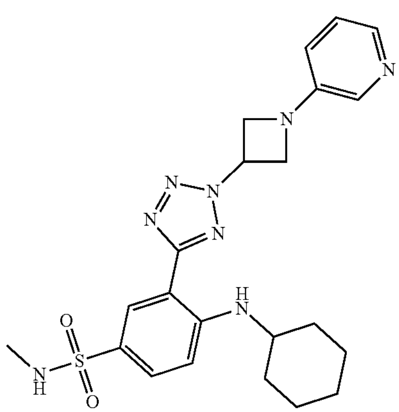 [SMILES: CNS(=O)(=O)c1ccc(NC2CCCCC2)c(-c2nnn(C3CN(c4cccnc4)C3)n2)c1] | 4-(cyclohexylamino)-N-methyl-3-(2-(1-(pyridin-3-yl)azetidin-3-yl)-2H-tetrazol-5-yl)benzenesulfonamide |

TABLE 1-continued

| Compound No. | Structure | Name |
|---|---|---|
| 71 | 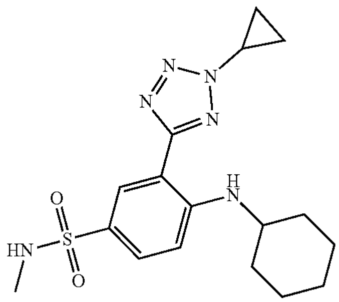 [SMILES: CNS(=O)(=O)c1ccc(NC2CCCCC2)c(-c2nnn(C3CC3)n2)c1] | 4-(cyclohexylamino)-3-(2-cyclopropyl-2H-tetrazol-5-yl)-N-methylbenzenesulfonamide |
| 72 | 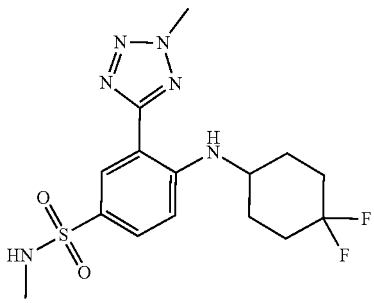 [SMILES: CNS(=O)(=O)c1ccc(NC2CCC(F)(F)CC2)c(-c2nnn(C)n2)c1] | 4-((4,4-difluorocyclohexyl)amino)-N-methyl-3-(2-methyl-2H-tetrazol-5-yl)benzenesulfonamide |
| 73 | 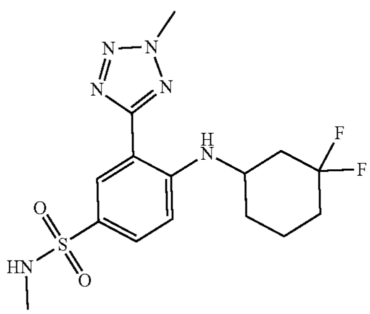 [SMILES: CNS(=O)(=O)c1ccc(NC2CCCC(F)(F)C2)c(-c2nnn(C)n2)c1] | 4-((3,3-difluorocyclohexyl)amino)-N-methyl-3-(2-methyl-2H-tetrazol-5-yl)benzenesulfonamide |
| 74 | 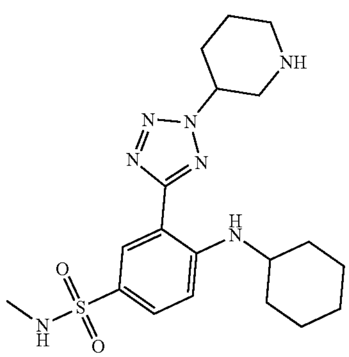 [SMILES: CNS(=O)(=O)c1ccc(NC2CCCCC2)c(-c2nnn(C3CCCNC3)n2)c1] | 4-(cyclohexylamino)-N-methyl-3-(2-(piperidin-3-yl)-2H-tetrazol-5-yl)benzenesulfonamide |
| 75 | 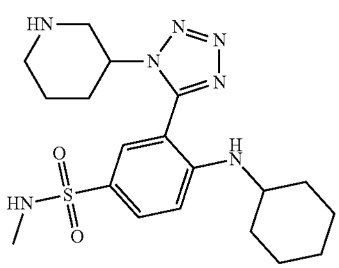 [SMILES: CNS(=O)(=O)c1ccc(NC2CCCCC2)c(-c2nnnn2C2CCCNC2)c1] | 4-(cyclohexylamino)-N-methyl-3-(1-(piperidin-3-yl)-1H-tetrazol-5-yl)benzenesulfonamide |

TABLE 1-continued

| Compound No. | Structure | Name |
|---|---|---|
| 76 | 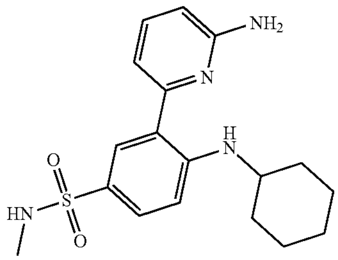 [SMILES: CNS(=O)(=O)c1ccc(NC2CCCCC2)c(-c2cccc(N)n2)c1] | 3-(6-aminopyridin-2-yl)-4-(cyclohexylamino)-N-methylbenzenesulfonamide |
| 77 | 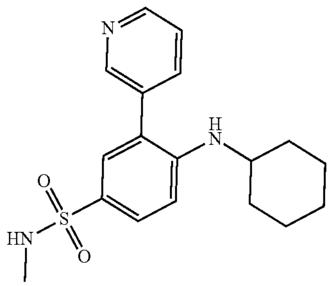 [SMILES: CNS(=O)(=O)c1ccc(NC2CCCCC2)c(-c2cccnc2)c1] | 4-(cyclohexylamino)-N-methyl-3-(pyridin-3-yl)benzenesulfonamide |
| 78 | 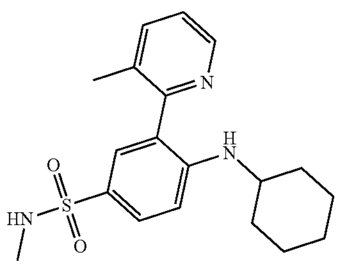 [SMILES: CNS(=O)(=O)c1ccc(NC2CCCCC2)c(-c2ncccc2C)c1] | 4-(cyclohexylamino)-N-methyl-3-(3-methylpyridin-2-yl)benzenesulfonamide |
| 79 | 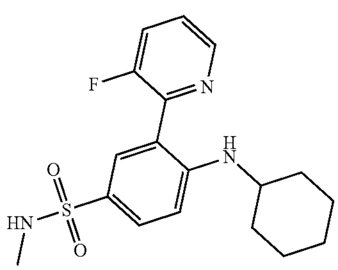 [SMILES: CNS(=O)(=O)c1ccc(NC2CCCCC2)c(-c2ncccc2F)c1] | 4-(cyclohexylamino)-3-(3-fluoropyridin-2-yl)-N-methylbenzenesulfonamide |
| 80 | 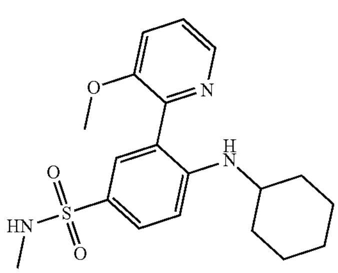 [SMILES: CNS(=O)(=O)c1ccc(NC2CCCCC2)c(-c2ncccc2OC)c1] | 4-(cyclohexylamino)-3-(3-methoxypyridin-2-yl)-N-methylbenzenesulfonamide |

TABLE 1-continued

| Compound No. | Structure | Name |
|---|---|---|
| 81 | 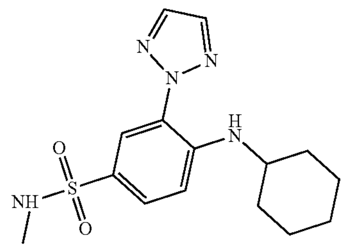 [SMILES: CNS(=O)(=O)c1ccc(NC2CCCCC2)c(-n2nccn2)c1] | 4-(cyclohexylamino)-N-methyl-3-(2H-1,2,3-triazol-2-yl)benzenesulfonamide |
| 82 | 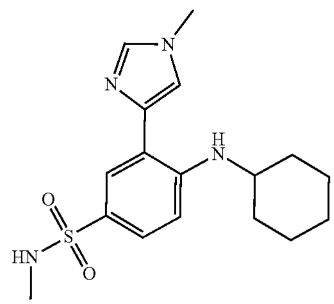 [SMILES: CNS(=O)(=O)c1ccc(NC2CCCCC2)c(-c2cn(C)cn2)c1] | 4-(cyclohexylamino)-N-methyl-3-(1-methyl-1H-imidazol-4-yl)benzenesulfonamide |
| 83 | 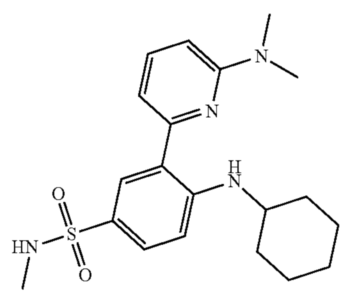 [SMILES: CNS(=O)(=O)c1ccc(NC2CCCCC2)c(-c2cccc(N(C)C)n2)c1] | 4-(cyclohexylamino)-3-(6-(dimethylamino)pyridin-2-yl)-N-methylbenzenesulfonamide |
| 84 | 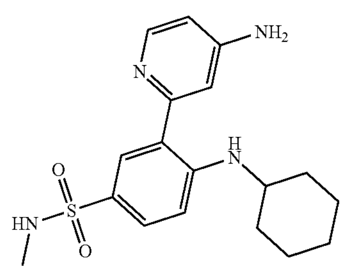 [SMILES: CNS(=O)(=O)c1ccc(NC2CCCCC2)c(-c2cc(N)ccn2)c1] | 3-(4-aminopyridin-2-yl)-4-(cyclohexylamino)-N-methylbenzenesulfonamide |
| 85 | 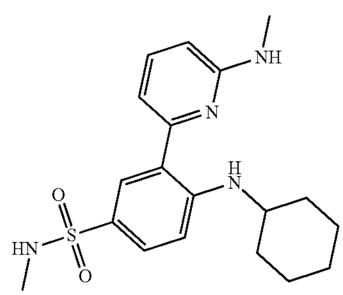 [SMILES: CNc1cccc(-c2cc(S(=O)(=O)NC)ccc2NC2CCCCC2)n1] | 4-(cyclohexylamino)-N-methyl-3-(6-(methylamino)pyridin-2-yl)benzenesulfonamide |

TABLE 1-continued

| Compound No. | Structure | Name |
|---|---|---|
| 86 | 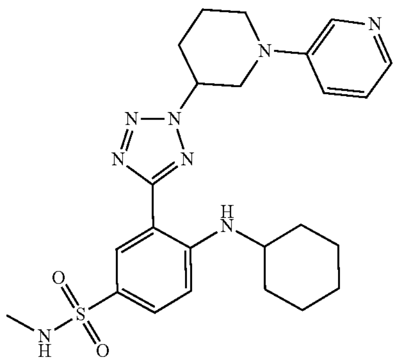 [SMILES: CNS(=O)(=O)c1ccc(NC2CCCCC2)c(-c2nnn(C3CCCN(c4cccnc4)C3)n2)c1] | 4-(cyclohexylamino)-N-methyl-3-(2-(1-(pyridin-3-yl)piperidin-3-yl)-2H-tetrazol-5-yl)benzenesulfonamide |
| 87 | 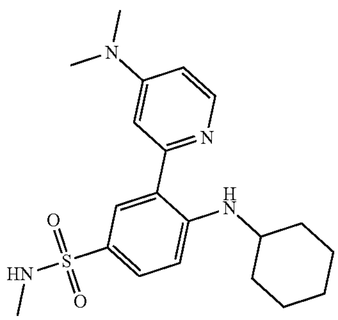 [SMILES: CNS(=O)(=O)c1ccc(NC2CCCCC2)c(-c2cc(N(C)C)ccn2)c1] | 4-(cyclohexylamino)-3-(4-(dimethylamino)pyridin-2-yl)-N-methylbenzenesulfonamide |
| 88 | 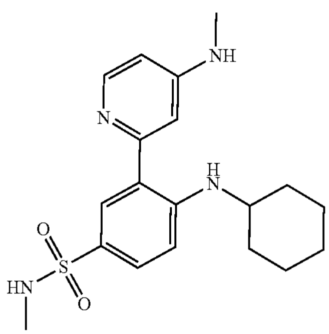 [SMILES: CNc1ccnc(-c2cc(S(=O)(=O)NC)ccc2NC2CCCCC2)c1] | 4-(cyclohexylamino)-N-methyl-3-(4-(methylamino)pyridin-2-yl)benzenesulfonamide |
| 89 | 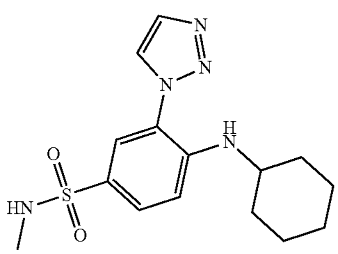 [SMILES: CNS(=O)(=O)c1ccc(NC2CCCCC2)c(-n2ccnn2)c1] | 4-(cyclohexylamino)-N-methyl-3-(1H-1,2,3-triazol-1-yl)benzenesulfonamide |
| 90 | 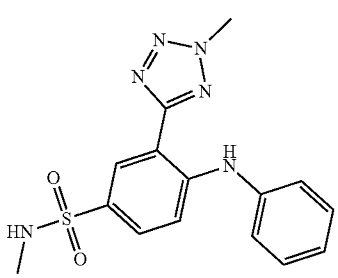 [SMILES: CNS(=O)(=O)c1ccc(Nc2ccccc2)c(-c2nnn(C)n2)c1] | N-methyl-3-(2-methyl-2H-tetrazol-5-yl)-4-(phenylamino)benzenesulfonamide |

TABLE 1-continued

| Compound No. | Structure | Name |
|---|---|---|
| 91 | 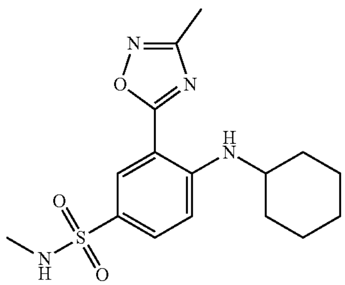 [SMILES: CNS(=O)(=O)c1ccc(NC2CCCCC2)c(-c2nc(C)no2)c1] | 4-(cyclohexylamino)-N-methyl-3-(3-methyl-1,2,4-oxadiazol-5-yl)benzenesulfonamide |
| 92 | 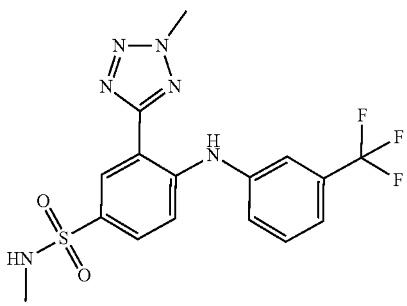 [SMILES: CNS(=O)(=O)c1ccc(Nc2cccc(C(F)(F)F)c2)c(-c2nnn(C)n2)c1] | N-methyl-3-(2-methyl-2H-tetrazol-5-yl)-4-((3-(trifluoromethyl)phenyl)amino)benzenesulfonamide |
| 93 | 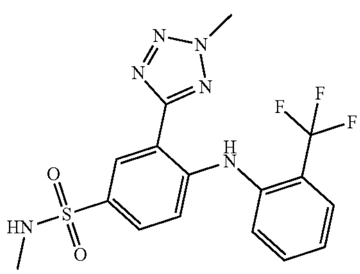 [SMILES: CNS(=O)(=O)c1ccc(Nc2ccccc2C(F)(F)F)c(-c2nnn(C)n2)c1] | N-methyl-3-(2-methyl-2H-tetrazol-5-yl)-4-((2-(trifluoromethyl)phenyl)amino)benzenesulfonamide |
| 94 | 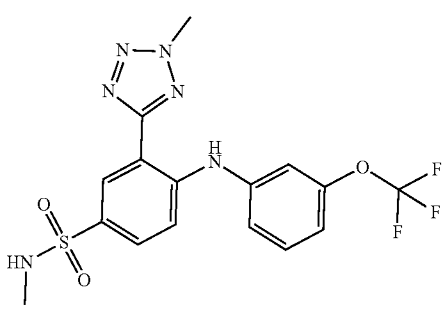 [SMILES: CNS(=O)(=O)c1ccc(Nc2cccc(OC(F)(F)F)c2)c(-c2nnn(C)n2)c1] | N-methyl-3-(2-methyl-2H-tetrazol-5-yl)-4-((3-(trifluoromethoxy)phenyl)amino)benzenesulfonamide |
| 95 | 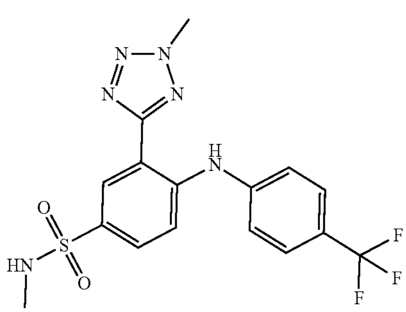 [SMILES: CNS(=O)(=O)c1ccc(Nc2ccc(C(F)(F)F)cc2)c(-c2nnn(C)n2)c1] | N-methyl-3-(2-methyl-2H-tetrazol-5-yl)-4-((4-(trifluoromethyl)phenyl)amino)benzenesulfonamide |

TABLE 1-continued

| Compound No. | Structure | Name |
|---|---|---|
| 96 | 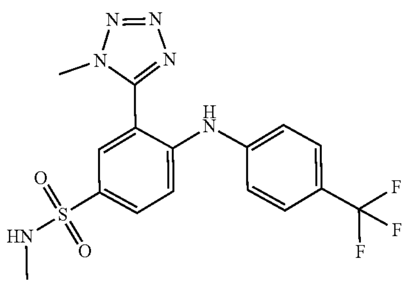 [SMILES: CNS(=O)(=O)c1ccc(Nc2ccc(C(F)(F)F)cc2)c(-c2nnnn2C)c1] | N-methyl-3-(1-methyl-1H-tetrazol-5-yl)-4-((4-(trifluoromethyl)phenyl)amino)benzenesulfonamide |
| 97 | 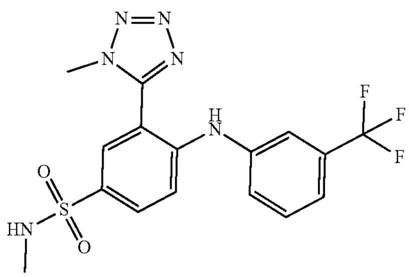 [SMILES: CNS(=O)(=O)c1ccc(Nc2cccc(C(F)(F)F)c2)c(-c2nnnn2C)c1] | N-methyl-3-(1-methyl-1H-tetrazol-5-yl)-4-((3-(trifluoromethyl)phenyl)amino)benzenesulfonamide |
| 98 | 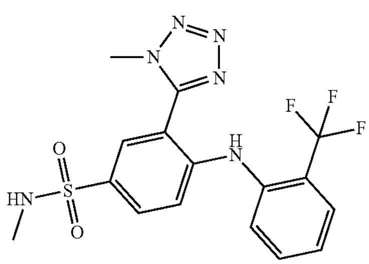 [SMILES: CNS(=O)(=O)c1ccc(Nc2ccccc2C(F)(F)F)c(-c2nnnn2C)c1] | N-methyl-3-(1-methyl-1H-tetrazol-5-yl)-4-((2-(trifluoromethyl)phenyl)amino)benzenesulfonamide |
| 99 | 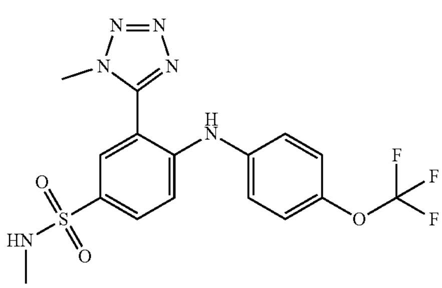 [SMILES: CNS(=O)(=O)c1ccc(Nc2ccc(OC(F)(F)F)cc2)c(-c2nnnn2C)c1] | N-methyl-3-(1-methyl-1H-tetrazol-5-yl)-4-((4-(trifluoromethoxy)phenyl)amino)benzenesulfonamide |
| 100 | 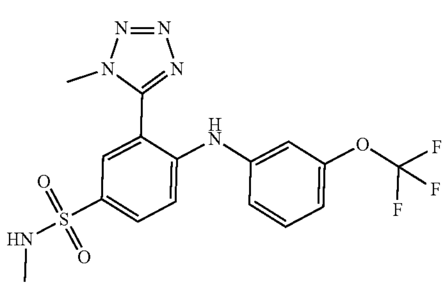 [SMILES: CNS(=O)(=O)c1ccc(Nc2cccc(OC(F)(F)F)c2)c(-c2nnnn2C)c1] | N-methyl-3-(1-methyl-1H-tetrazol-5-yl)-4-((3-(trifluoromethoxy)phenyl)amino)benzenesulfonamide |

TABLE 1-continued

| Compound No. | Structure | Name |
|---|---|---|
| 101 | 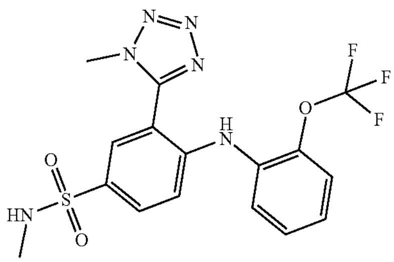 [SMILES: CNS(=O)(=O)c1ccc(Nc2ccccc2OC(F)(F)F)c(-c2nnnn2C)c1] | N-methyl-3-(1-methyl-1H-tetrazol-5-yl)-4-((2-(trifluoromethoxy)phenyl)amino)benzenesulfonamide |
| 102 | 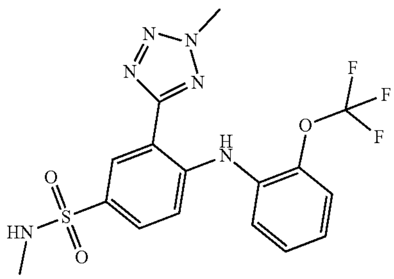 [SMILES: CNS(=O)(=O)c1ccc(Nc2ccccc2OC(F)(F)F)c(-c2nnn(C)n2)c1] | N-methyl-3-(2-methyl-2H-tetrazol-5-yl)-4-((2-(trifluoromethoxy)phenyl)amino)benzenesulfonamide |
| 103 | 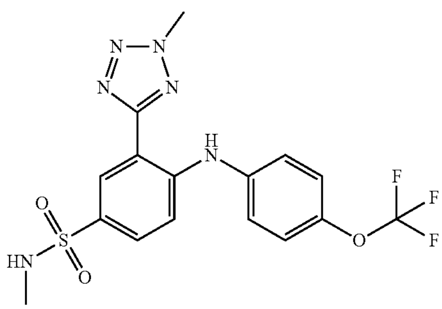 [SMILES: CNS(=O)(=O)c1ccc(Nc2ccc(OC(F)(F)F)cc2)c(-c2nnn(C)n2)c1] | N-methyl-3-(2-methyl-2H-tetrazol-5-yl)-4-((4-(trifluoromethoxy)phenyl)amino)benzenesulfonamide |
| 104 | 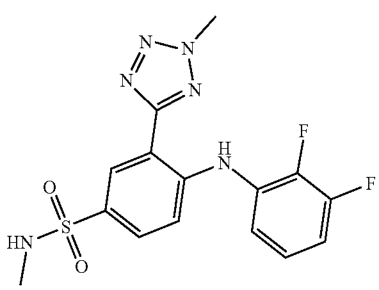 [SMILES: CNS(=O)(=O)c1ccc(Nc2cccc(F)c2F)c(-c2nnn(C)n2)c1] | 4-((2,3-difluorophenyl)amino)-N-methyl-3-(2-methyl-2H-tetrazol-5-yl)benzenesulfonamide |
| 105 | 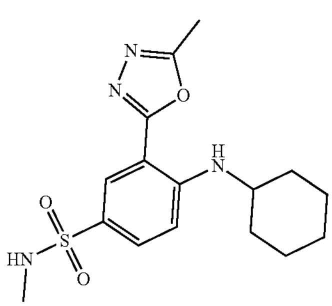 [SMILES: CNS(=O)(=O)c1ccc(NC2CCCCC2)c(-c2nnc(C)o2)c1] | 4-(cyclohexylamino)-N-methyl-3-(5-methyl-1,3,4-oxadiazol-2-yl)benzenesulfonamide |

TABLE 1-continued

| Compound No. | Structure | Name |
|---|---|---|
| 106 | 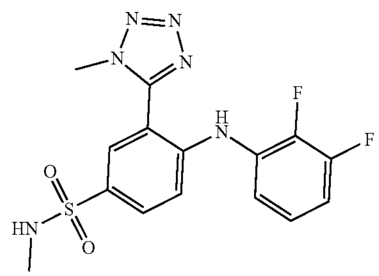 [SMILES: CNS(=O)(=O)c1ccc(Nc2cccc(F)c2F)c(-c2nnnn2C)c1] | 4-((2,3-difluorophenyl)amino)-N-methyl-3-(1-methyl-1H-tetrazol-5-yl)benzenesulfonamide |
| 107 | 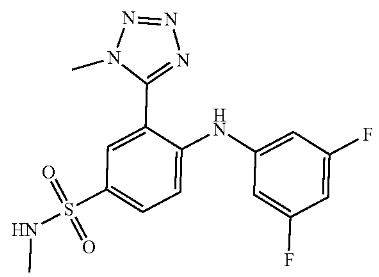 [SMILES: CNS(=O)(=O)c1ccc(Nc2cc(F)cc(F)c2)c(-c2nnnn2C)c1] | 4-((3,5-difluorophenyl)amino)-N-methyl-3-(1-methyl-1H-tetrazol-5-yl)benzenesulfonamide |
| 108 | 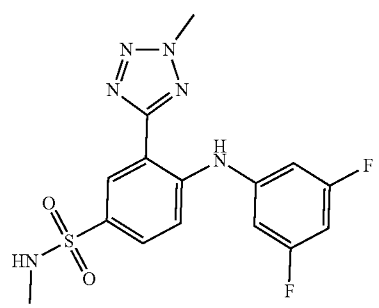 [SMILES: CNS(=O)(=O)c1ccc(Nc2cc(F)cc(F)c2)c(-c2nnn(C)n2)c1] | 4-((3,5-difluorophenyl)amino)-N-methyl-3-(2-methyl-2H-tetrazol-5-yl)benzenesulfonamide |
| 109 | 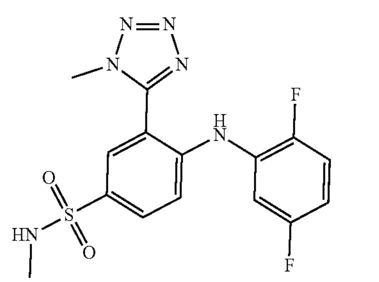 [SMILES: CNS(=O)(=O)c1ccc(Nc2cc(F)ccc2F)c(-c2nnnn2C)c1] | 4-((2,5-difluorophenyl)amino)-N-methyl-3-(1-methyl-1H-tetrazol-5-yl)benzenesulfonamide |
| 110 | 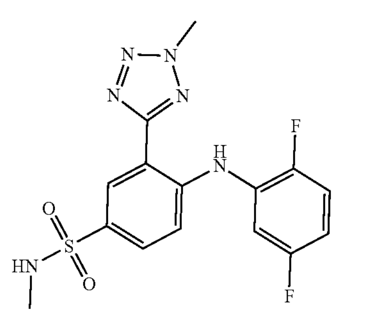 [SMILES: CNS(=O)(=O)c1ccc(Nc2cc(F)ccc2F)c(-c2nnn(C)n2)c1] | 4-((2,5-difluorophenyl)amino)-N-methyl-3-(2-methyl-2H-tetrazol-5-yl)benzenesulfonamide |

TABLE 1-continued

| Compound No. | Structure | Name |
|---|---|---|
| 111 | 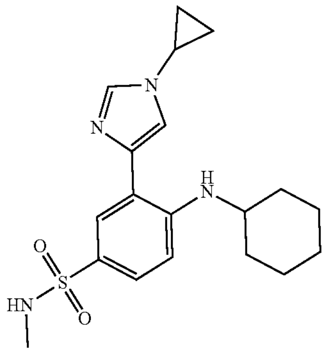 [SMILES: CNS(=O)(=O)c1ccc(NC2CCCCC2)c(-c2cn(C3CC3)cn2)c1] | 4-(cyclohexylamino)-3-(1-cyclopropyl-1H-imidazol-4-yl)-N-methylbenzenesulfonamide |
| 112 | 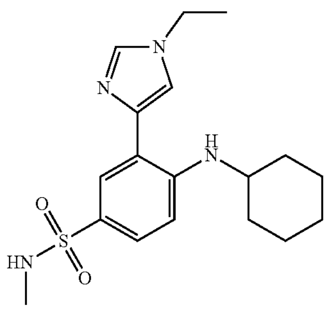 [SMILES: CCn1cnc(-c2cc(S(=O)(=O)NC)ccc2NC2CCCCC2)c1] | 4-(cyclohexylamino)-3-(1-ethyl-1H-imidazol-4-yl)-N-methylbenzenesulfonamide |
| 113 | 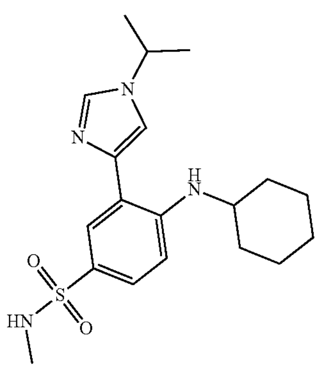 [SMILES: CNS(=O)(=O)c1ccc(NC2CCCCC2)c(-c2cn(C(C)C)cn2)c1] | 4-(cyclohexylamino)-3-(1-isopropyl-1H-imidazol-4-yl)-N-methylbenzenesulfonamide |
| 114 | 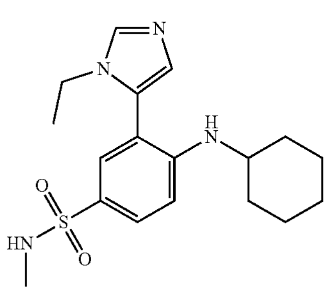 [SMILES: CCn1cncc1-c1cc(S(=O)(=O)NC)ccc1NC1CCCCC1] | 4-(cyclohexylamino)-3-(1-ethyl-1H-imidazol-5-yl)-N-methylbenzenesulfonamide |

TABLE 1-continued

| Compound No. | Structure | Name |
|---|---|---|
| 115 | 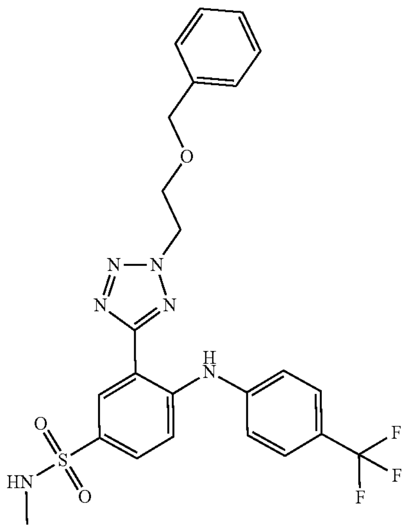 [SMILES: CNS(=O)(=O)c1ccc(Nc2ccc(C(F)(F)F)cc2)c(-c2nnn(CCOCc3ccccc3)n2)c1] | 3-(2-(2-(benzyloxy)ethyl)-2H-tetrazol-5-yl)-N-methyl-4-((4-(trifluoromethyl)phenyl)amino)benzenesulfonamide |
| 116 | 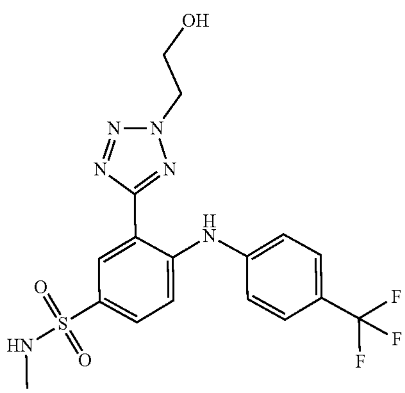 [SMILES: CNS(=O)(=O)c1ccc(Nc2ccc(C(F)(F)F)cc2)c(-c2nnn(CCO)n2)c1] | 3-(2-(2-hydroxyethyl)-2H-tetrazol-5-yl)-N-methyl-4-((4-(trifluoromethyl)phenyl)amino)benzenesulfonamide |
| 117 | 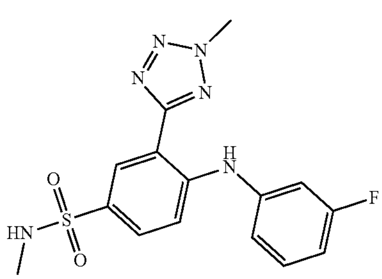 [SMILES: CNS(=O)(=O)c1ccc(Nc2cccc(F)c2)c(-c2nnn(C)n2)c1] | 4-((3-fluorophenyl)amino)-N-methyl-3-(2-methyl-2H-tetrazol-5-yl)benzenesulfonamide |
| 118 | 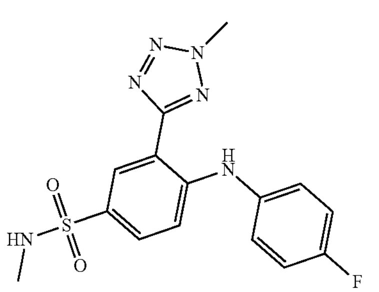 [SMILES: CNS(=O)(=O)c1ccc(Nc2ccc(F)cc2)c(-c2nnn(C)n2)c1] | 4-((4-fluorophenyl)amino)-N-methyl-3-(2-methyl-2H-tetrazol-5-yl)benzenesulfonamide |

TABLE 1-continued

| Compound No. | Structure | Name |
|---|---|---|
| 119 | 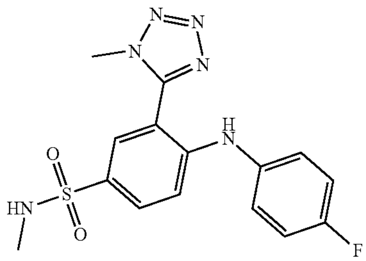 [SMILES: CNS(=O)(=O)c1ccc(Nc2ccc(F)cc2)c(-c2nnnn2C)c1] | 4-((4-fluorophenyl)amino)-N-methyl-3-(1-methyl-1H-tetrazol-5-yl)benzenesulfonamide |
| 120 | 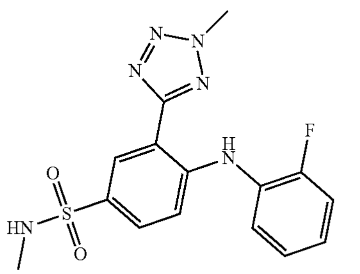 [SMILES: CNS(=O)(=O)c1ccc(Nc2ccccc2F)c(-c2nnn(C)n2)c1] | 4-((2-fluorophenyl)amino)-N-methyl-3-(2-methyl-2H-tetrazol-5-yl)benzenesulfonamide |
| 121 | 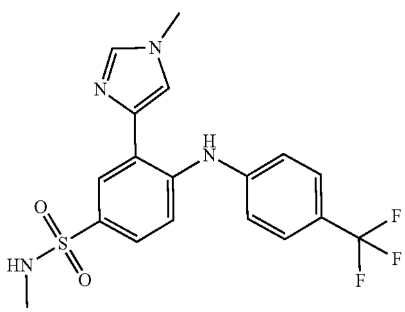 [SMILES: CNS(=O)(=O)c1ccc(Nc2ccc(C(F)(F)F)cc2)c(-c2cn(C)cn2)c1] | N-methyl-3-(1-methyl-1H-imidazol-4-yl)-4-((4-(trifluoromethyl)phenyl)amino)benzenesulfonamide |
| 122 | 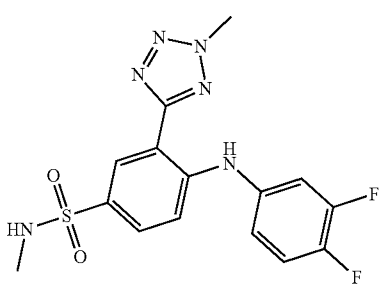 [SMILES: CNS(=O)(=O)c1ccc(Nc2ccc(F)c(F)c2)c(-c2nnn(C)n2)c1] | 4-((3,4-difluorophenyl)amino)-N-methyl-3-(2-methyl-2H-tetrazol-5-yl)benzenesulfonamide |
| 123 | 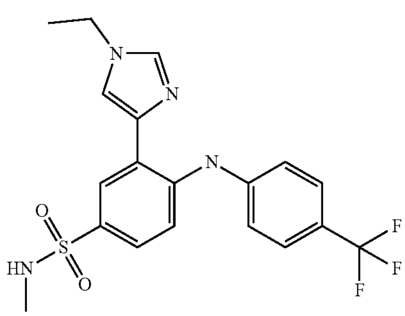 | 3-(1-ethyl-1H-imidazol-4-yl)-N-methyl-4-((4-(trifluoromethyl)phenyl)amino)benzenesulfonamide |

TABLE 1-continued

| Compound No. | Structure | Name |
|---|---|---|
| 124 | 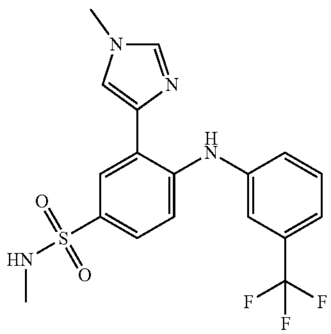 [SMILES: CNS(=O)(=O)c1ccc(Nc2cccc(C(F)(F)F)c2)c(-c2cn(C)cn2)c1] | N-methyl-3-(1-methyl-1H-imidazol-4-yl)-4-((3-(trifluoromethyl)phenyl)amino)benzenesulfonamide |
| 125 | 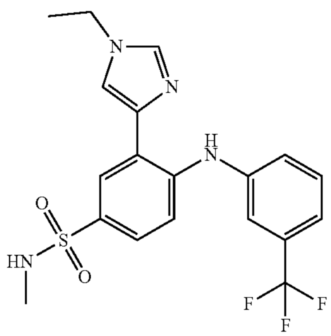 [SMILES: CCn1cnc(-c2cc(S(=O)(=O)NC)ccc2Nc2cccc(C(F)(F)F)c2)c1] | 3-(1-ethyl-1H-imidazol-4-yl)-N-methyl-4-((3-(trifluoromethyl)phenyl)amino)benzenesulfonamide |
| 126 | 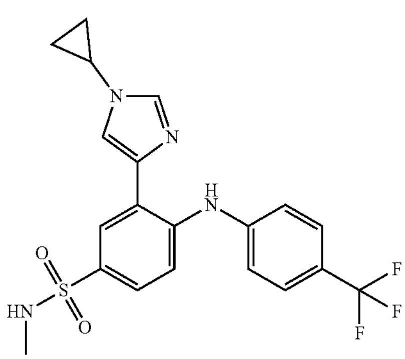 [SMILES: CNS(=O)(=O)c1ccc(Nc2ccc(C(F)(F)F)cc2)c(-c2cn(C3CC3)cn2)c1] | 3-(1-cyclopropyl-1H-imidazol-4-yl)-N-methyl-4-((4-(trifluoromethyl)phenyl)amino)benzenesulfonamide |
| 127 | 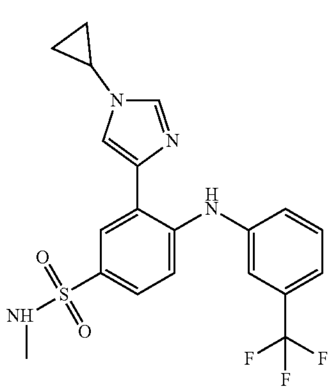 [SMILES: CNS(=O)(=O)c1ccc(Nc2cccc(C(F)(F)F)c2)c(-c2cn(C3CC3)cn2)c1] | 3-(1-cyclopropyl-1H-imidazol-4-yl)-N-methyl-4-((3-(trifluoromethyl)phenyl)amino)benzenesulfonamide |

TABLE 1-continued
| Compound No. | Structure | Name |
|---|---|---|
| 128 | 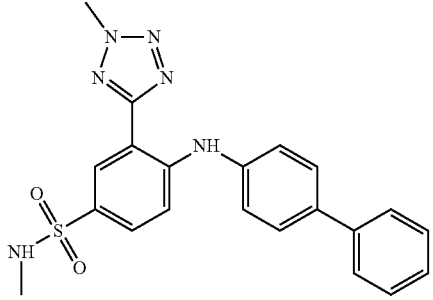 [SMILES: CNS(=O)(=O)c1ccc(Nc2ccc(-c3ccccc3)cc2)c(-c2nnn(C)n2)c1] | N-methyl-3-(2-methyltetrazol-5-yl)-4-(4-phenylanilino)benzenesulfonamide |
| 129 | 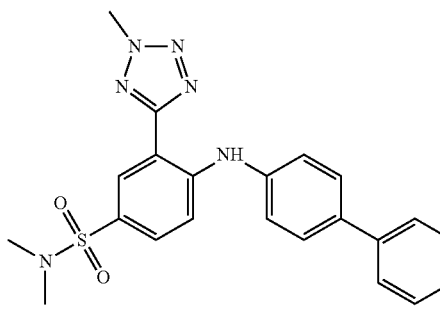 | N,N-dimethyl-3-(2-methyltetrazol-5-yl)-4-(4-phenylanilino)benzenesulfonamide |
| 130 | 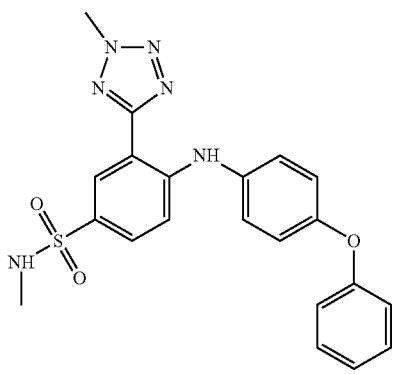 [SMILES: CNS(=O)(=O)c1ccc(Nc2ccc(Oc3ccccc3)cc2)c(-c2nnn(C)n2)c1] | N-methyl-3-(2-methyltetrazol-5-yl)-4-(4-phenoxyanilino)benzenesulfonamide |
| 131 | 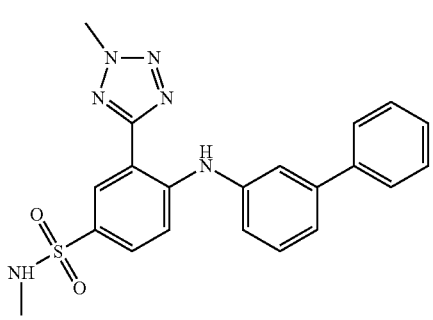 [SMILES: CNS(=O)(=O)c1ccc(Nc2cccc(-c3ccccc3)c2)c(-c2nnn(C)n2)c1] | N-methyl-3-(2-methyltetrazol-5-yl)-4-(3-phenylanilino)benzenesulfonamide |

TABLE 1-continued

| Compound No. | Structure | Name |
|---|---|---|
| 132 | 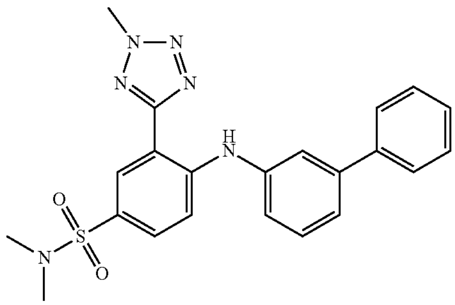 [SMILES: CN(C)S(=O)(=O)c1ccc(Nc2cccc(-c3ccccc3)c2)c(-c2nnn(C)n2)c1] | N,N-dimethyl-3-(2-methyltetrazol-5-yl)-4-(3-phenylanilino)benzenesulfonamide |
| 133 | 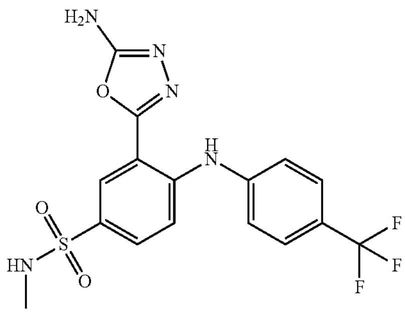 [SMILES: CNS(=O)(=O)c1ccc(Nc2ccc(C(F)(F)F)cc2)c(-c2nnc(N)o2)c1] | 3-(5-amino-1,3,4-oxadiazol-2-yl)-N-methyl-4-[4-(trifluoromethyl)anilino]benzenesulfonamide |
| 134 | 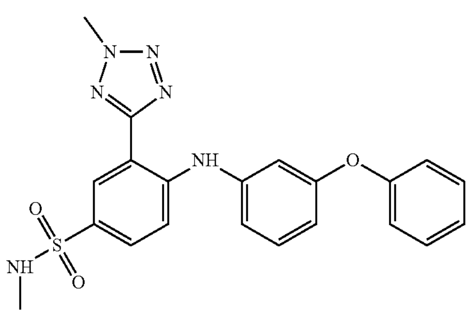 [SMILES: CNS(=O)(=O)c1ccc(Nc2cccc(Oc3ccccc3)c2)c(-c2nnn(C)n2)c1] | N-methyl-3-(2-methyltetrazol-5-yl)-4-(3-phenoxyanilino)benzenesulfonamide |
| 135 | 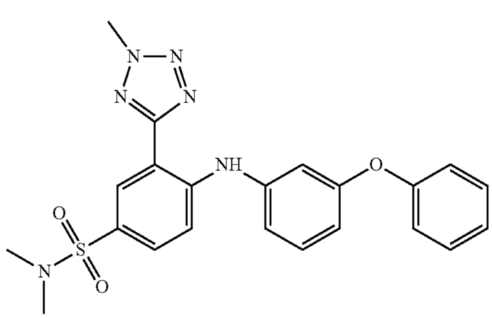 [SMILES: CN(C)S(=O)(=O)c1ccc(Nc2cccc(Oc3ccccc3)c2)c(-c2nnn(C)n2)c1] | N,N-dimethyl-3-(2-methyltetrazol-5-yl)-4-(3-phenoxyanilino)benzenesulfonamide |

TABLE 1-continued

| Compound No. | Structure | Name |
|---|---|---|
| 136 | 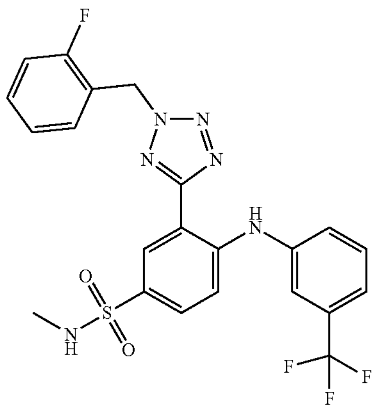 [SMILES: CNS(=O)(=O)c1ccc(Nc2cccc(C(F)(F)F)c2)c(-c2nnn(Cc3ccccc3F)n2)c1] | 3-[2-[(2-Fluorophenyl)methyl]tetrazol-5-yl]-N-methyl-4-[3-(trifluoromethyl)anilino]benzenesulfonamide |
| 137 | 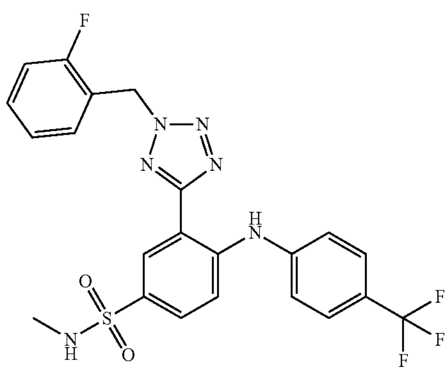 [SMILES: CNS(=O)(=O)c1ccc(Nc2ccc(C(F)(F)F)cc2)c(-c2nnn(Cc3ccccc3F)n2)c1] | 3-[2-[(2-Fluorophenyl)methyl]tetrazol-5-yl]-N-methyl-4-[4-(trifluoromethyl)anilino]benzenesulfonamide |
| 138 | 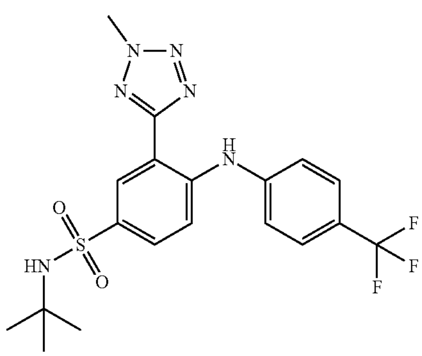 [SMILES: Cn1nnc(-c2cc(S(=O)(=O)NC(C)(C)C)ccc2Nc2ccc(C(F)(F)F)cc2)n1] | N-(tert-butyl)-3-(2-methyl-2H-tetrazol-5-yl)-4-((4-(trifluoromethyl)phenyl)amino)benzenesulfonamide |
| 139 | 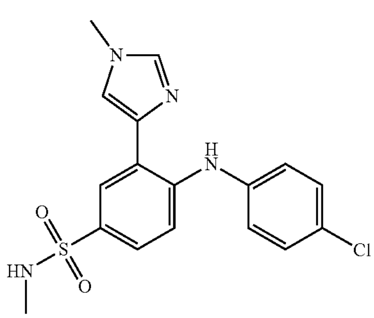 [SMILES: CNS(=O)(=O)c1ccc(Nc2ccc(Cl)cc2)c(-c2cn(C)cn2)c1] | 4-(4-chloroanilino)-N-methyl-3-(1-methylimidazol-4-yl)benzenesulfonamide |

TABLE 1-continued

| Compound No. | Structure | Name |
|---|---|---|
| 140 | 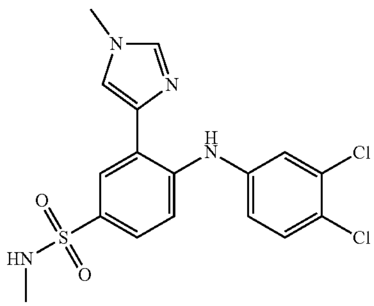 [SMILES: CNS(=O)(=O)c1ccc(Nc2ccc(Cl)c(Cl)c2)c(-c2cn(C)cn2)c1] | 4-(3,4-dichloroanilino)-N-methyl-3-(1-methylimidazol-4-yl)benzenesulfonamide |
| 141 | 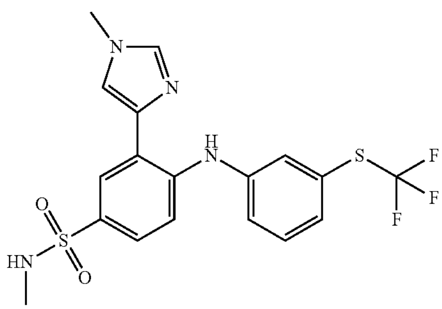 [SMILES: CNS(=O)(=O)c1ccc(Nc2cccc(SC(F)(F)F)c2)c(-c2cn(C)cn2)c1] | N-methyl-3-(1-methylimidazol-4-yl)-4-[3-(trifluoromethylsulfanyl)anilino]benzenesulfonamide |
| 142 | 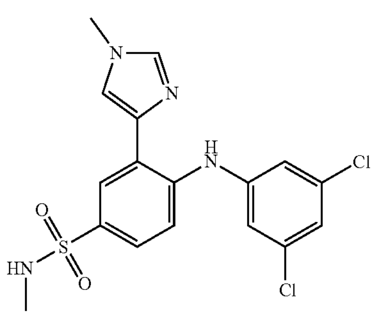 [SMILES: CNS(=O)(=O)c1ccc(Nc2cc(Cl)cc(Cl)c2)c(-c2cn(C)cn2)c1] | 4-(3,5-dichloroanilino)-N-methyl-3-(1-methylimidazol-4-yl)benzenesulfonamide |
| 143 | 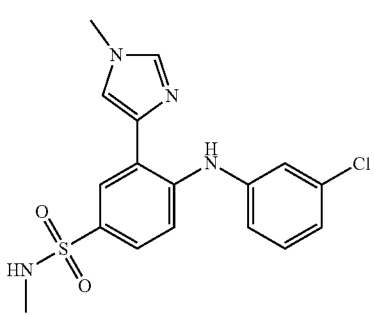 [SMILES: CNS(=O)(=O)c1ccc(Nc2cccc(Cl)c2)c(-c2cn(C)cn2)c1] | 4-(3-Chloroanilino)-N-methyl-3-(1-methylimidazol-4-yl)benzenesulfonamide |
| 144 | 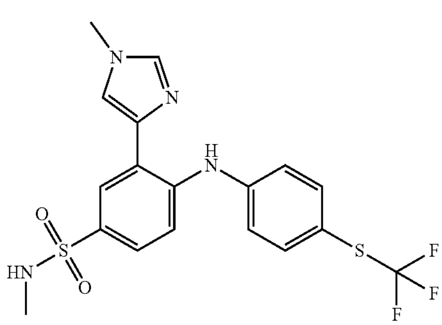 [SMILES: CNS(=O)(=O)c1ccc(Nc2ccc(SC(F)(F)F)cc2)c(-c2cn(C)cn2)c1] | N-methyl-3-(1-methylimidazol-4-yl)-4-[4-(trifluoromethylsulfanyl)anilino]benzenesulfonamide |

TABLE 1-continued
| Compound No. | Structure | Name |
|---|---|---|
| 145 | 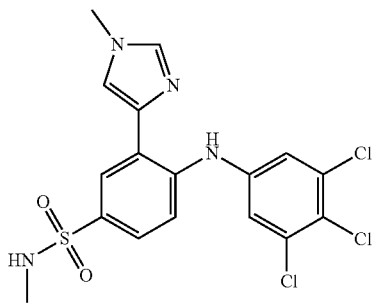 [SMILES: CNS(=O)(=O)c1ccc(Nc2cc(Cl)c(Cl)c(Cl)c2)c(-c2cn(C)cn2)c1] | N-methyl-3-(1-methylimidazol-4-yl)-4-(3,4,5-trichloroanilino)benzenesulfonamide |
| 146 | 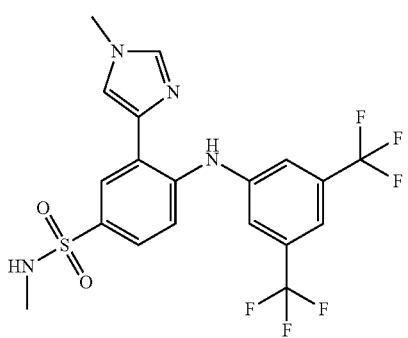 [SMILES: CNS(=O)(=O)c1ccc(Nc2cc(C(F)(F)F)cc(C(F)(F)F)c2)c(-c2cn(C)cn2)c1] | 4-[3,5-Bis(trifluoromethyl)anilino]-N-methyl-3-(1-methylimidazol-4-yl)benzenesulfonamide |
| 147 | 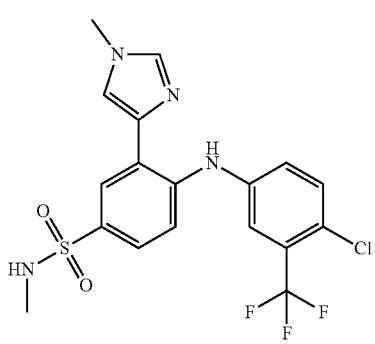 [SMILES: CNS(=O)(=O)c1ccc(Nc2ccc(Cl)c(C(F)(F)F)c2)c(-c2cn(C)cn2)c1] | 4-[4-Chloro-3-(trifluoromethyl)anilino]-N-methyl-3-(1-methylimidazol-4-yl)benzenesulfonamide |
| 148 | 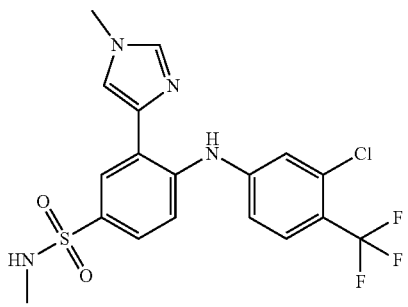 [SMILES: CNS(=O)(=O)c1ccc(Nc2ccc(C(F)(F)F)c(Cl)c2)c(-c2cn(C)cn2)c1] | 4-[3-Chloro-4-(trifluoromethyl)anilino]-N-methyl-3-(1-methylimidazol-4-yl)benzenesulfonamide |

TABLE 1-continued

| Compound No. | Structure | Name |
|---|---|---|
| 149 | 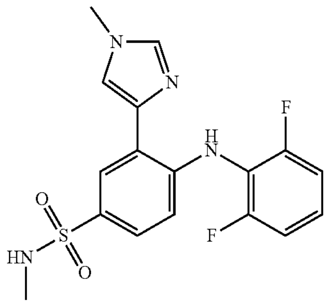 [SMILES: CNS(=O)(=O)c1ccc(Nc2c(F)cccc2F)c(-c2cn(C)cn2)c1] | 4-((2,6-Difluorophenyl)amino)-N-methyl-3-(1-methyl-1H-imidazol-4-yl)benzenesulfonamide |
| 150 | 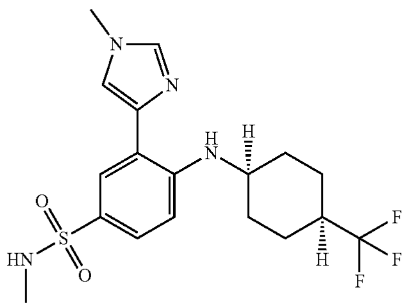 [SMILES: CNS(=O)(=O)c1ccc(N[C@H]2CC[C@@H](C(F)(F)F)CC2)c(-c2cn(C)cn2)c1] | N-methyl-3-(1-methyl-1H-imidazol-4-yl)-4-(((1s,4s)-4-(trifluoromethyl)cyclohexyl)amino)benzenesulfonamide |
| 151 | 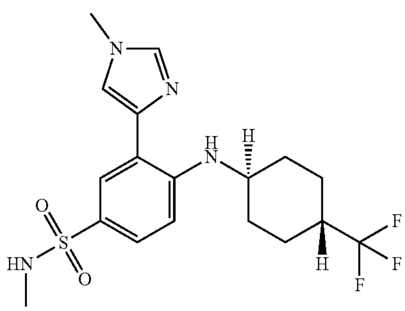 [SMILES: CNS(=O)(=O)c1ccc(N[C@H]2CC[C@H](C(F)(F)F)CC2)c(-c2cn(C)cn2)c1] | N-methyl-3-(1-methyl-1H-imidazol-4-yl)-4-(((1r,4r)-4-(trifluoromethyl)cyclohexyl)amino)benzenesulfonamide |
| 152 | 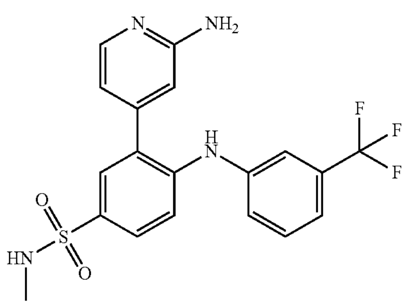 [SMILES: CNS(=O)(=O)c1ccc(Nc2cccc(C(F)(F)F)c2)c(-c2ccnc(N)c2)c1] | 3-(2-Aminopyridin-4-yl)-N-methyl-4-((3-(trifluoromethyl)phenyl)amino)benzenesulfonamide |
| 153 | 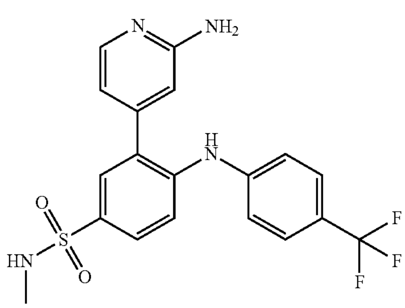 [SMILES: CNS(=O)(=O)c1ccc(Nc2ccc(C(F)(F)F)cc2)c(-c2ccnc(N)c2)c1] | 3-(2-Aminopyridin-4-yl)-N-methyl-4-((4-(trifluoromethyl)phenyl)amino)benzenesulfonamide |

Preparation of the Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

In some instances, specific and analogous reactants are identified through the indices of known chemicals prepared by the Chemical Abstract Service of the American Chemical Society, which are available in most public and university libraries, as well as through on-line databases (the American Chemical Society, Washington, D.C., is contacted for more details). Chemicals that are known but not commercially available in catalogs are prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

In some embodiments, the compounds disclosed herein are prepared as described in the Examples section.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, disclosed herein are dissociable complexes (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. In some embodiments, examples of isotopes that are incorporated into compounds of the disclosure include isotopes of hydrogen, carbon, nitrogen, oxygen, phosphorous, sulfur, fluorine, and chlorine, such as $^2$H, $^3$H, $^{13}$C, $^{14}$C, $^5$N, $^{18}$O, $^{17}$O, $^{31}$P, $^{32}$P, $^{35}$S, $^{18}$F, and $^{36}$C, respectively. Compounds described herein, and the metabolites, pharmaceutically acceptable salts, esters, prodrugs, solvates, hydrates, or derivatives thereof which contain the aforementioned isotopes and/or other isotopes of other atoms are within the scope of this disclosure. Certain isotopically-labeled compounds, for example those into which radioactive isotopes such as $^3$H and $^{14}$C are incorporated, are useful in drug and/or substrate tissue distribution assays. Tritiated, i. e., $^3$H and carbon-14, i. e., $^1$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the disclosure, or by separately reacting a purified compound in its free form with a suitable acid or base, and isolating the salt thus formed.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. In some embodiments, solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or methanol. In some embodiments, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The disclosure provides for methods of treating diseases by administering such prodrugs. The disclosure further provides for methods of treating diseases by administering such prodrugs as pharmaceutical compositions.

In some embodiments, prodrugs include compounds wherein an amino acid residue, or a polypeptide chain of two or more (e. g., two, three, or four) amino acid residues is covalently joined through an amide or ester bond to a free amino, hydroxy, or carboxylic acid group of compounds of the present disclosure. The amino acid residues include, but are not limited to, the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine, and methionine sulfone. In other embodiments, prodrugs include compounds wherein a nucleic acid residue, or an oligonucleotide of two or more (e. g., two, three or four) nucleic acid residues is covalently joined to a compound of the present disclosure.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, metal salts, and sulfonate esters. In some embodiments, compounds having free amino, amido, hydroxy, or carboxylic groups are converted into prodrugs. For instance, free carboxyl groups are derivatized as amides or alkyl esters. In certain instances, all of these prodrug moieties incorporate groups including, but not limited to, ether, amine, and carboxylic acid functionalities.

Hydroxy prodrugs include esters such as, though not limited to, acyloxyalkyl (e.g. acyloxymethyl, acyloxyethyl) esters, alkoxycarbonyloxyalkyl esters, alkyl esters, aryl esters, sulfonate esters, sulfate esters and disulfide containing esters, ethers, amides, carbamates, hemisuccinates, dimethylaminoacetates, and phosphoryloxymethyloxycarbonyls, as outlined in *Advanced Drug Delivery Reviews* 1996, 19, 115.

Amine derived prodrugs include, but are not limited to, the following groups and combinations of groups:

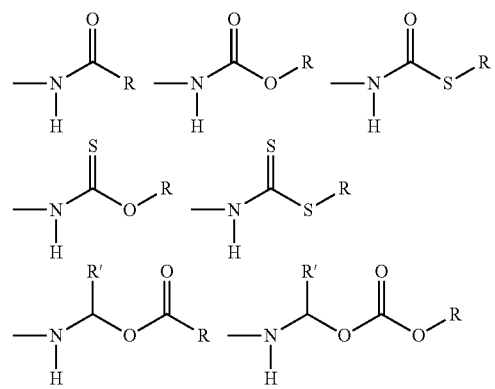

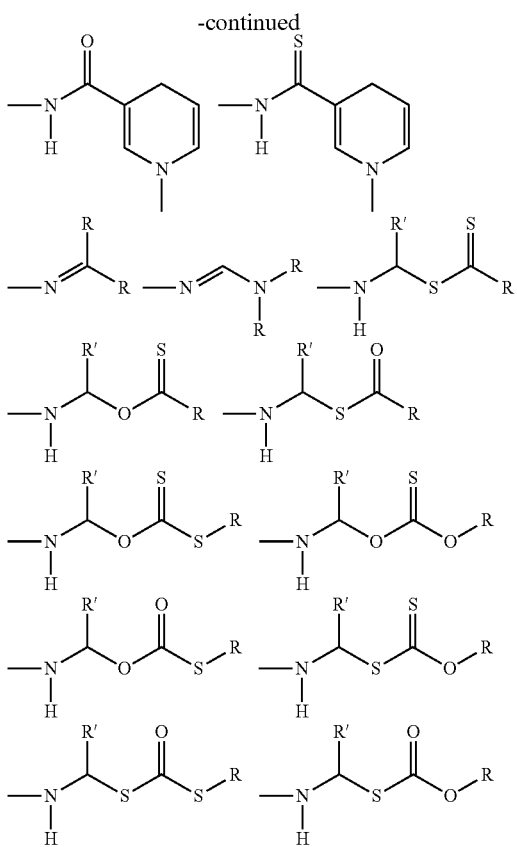

as well as sulfonamides and phosphonamides.

In certain instances, sites on any aromatic ring portions are susceptible to various metabolic reactions, therefore incorporation of appropriate substituents on the aromatic ring structures reduce, minimize, or eliminate this metabolic pathway.

Metabolites

In some embodiments, compounds described herein are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen or an alkyl group.

In additional or further embodiments, the compounds described herein are metabolized upon administration to an organism in need to produce a metabolite that is then used to produce a desired effect, including a desired therapeutic effect.

Pharmaceutical Compositions

In certain embodiments, the compound as described herein is administered as a pure chemical. In other embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)), the disclosure of which is hereby incorporated herein by reference in its entirety.

Accordingly, provided herein is a pharmaceutical composition comprising at least one compound described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), or a pharmaceutically acceptable salt thereof.

Another embodiment provides a pharmaceutical composition consisting essentially of a pharmaceutically acceptable carrier and a compound of Formula (I), or a pharmaceutically acceptable salt thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous), rectal, vaginal, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

In some instances, exemplary pharmaceutical compositions are used in the form of a pharmaceutical preparation, for example, in solid, semisolid, or liquid form, which includes one or more of a disclosed compound, as an active ingredient, in admixture with an organic or inorganic carrier or excipient suitable for external, enteral, or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets in some instances, the principal active ingredient is mixed with a pharmaceutical carrier, e.g., conventional tableting ingredients such as corn starch, lactose, sucrose, sorbitol, talc, stearic acid, magnesium stearate, dicalcium phosphate, or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills, and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions also comprise buffering agents in some embodiments. Solid compositions of a similar type are also employed as fillers in soft and hard-filled gelatin capsules using such excipients as lactose or milk sugars, as well as high molecular weight polyethylene glycols and the like.

In some instances, a tablet is made by compression or molding, optionally with one or more accessory ingredients. Compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets are made by molding in a suitable machine a mixture of the subject composition moistened with an inert liquid diluent. Tablets, and other solid dosage forms, such as dragees, capsules, pills and granules, are optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms contain optionally inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, optionally contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component is optionally mixed under sterile conditions with a pharmaceutically acceptable carrier, and with any preservatives, buffers, or propellants which are required in some embodiments.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. Sprays additionally contain customary propellants, such as chlorofluorohydrocarbons and volatile unsubstituted hydrocarbons, such as butane and propane.

Compositions and compounds disclosed herein are alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are used because they minimize exposing the agent to shear, which result in degradation of the compounds contained in the subject compositions in some embodiments. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which optionally contain antioxidants, buffers, bacteriostats, solutes which render the formulation isotonic with the blood of the intended recipient or suspending or thickening agents.

Examples of suitable aqueous and non-aqueous carriers employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. In some embodiments, proper fluidity is maintained, for example, by the use of coating materials, such as lecithin, by the maintenance of the required particle size in the case of dispersions, and by the use of surfactants Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure will recognize that it is not comprehensive and that there are other enteric materials that meet the objectives of the present disclosure.

In some embodiments, the dose of the composition comprising at least one compound as described herein differ, depending upon the patient's (e.g., human) condition, that is, stage of the disease, general health status, age, and other factors that a person skilled in the medical art will use to determine dose.

In some instances, pharmaceutical compositions are administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

In some embodiments, oral doses typically range from about 1.0 mg to about 1000 mg, one to four times, or more, per day.

The Hippo Signaling Network

The Hippo signaling network (also known as the Salvador/Warts/Hippo (SWH) pathway) is a master regulator of cell proliferation, death, and differentiation. In some embodiments, the main function of the Hippo signaling pathway is to regulate negatively the transcriptional co-activators Yes-associated protein (YAP) and its paralogue, the transcriptional co-activator with PDZ-binding motif (TAZ; also known as WWTR1) (FIG. 1). The Hippo kinase cascade phosphorylates and inhibits YAP/TAZ by promoting its cytoplasmic retention and degradation, thereby inhibiting the growth promoting function regulated under the YAP/TAZ control. In an un-phosphorylated/de-phosphorylated state, YAP, also known as YAP1 or YAP65, together with TAZ, are transported into the nucleus where they interact with TEAD family of transcription factors to upregulate genes that promote proliferation and migration, and inhibit apoptosis. In some instances, unregulated upregulation of these genes involved in proliferation, migration, and anti-apoptosis leads to development of cancer. In some instances, overexpression of YAP/TAZ is associated with cancer.

Additional core members of the Hippo signaling pathway comprise the serine/threonine kinases MST/2 (homologues of Hippo/Hpo in Drosophila), Lats1/2 (homologues of Warts/Wts), and their adaptor proteins Sav (homologue of Salvador/Sav) and Mob (MOBKL1A and MOBKL1B; homologues of Mats), respectively (FIG. 1). In general, MST1/2 kinase complexes with the scaffold protein Sav1, which in turn phosphorylates and activates Lats1/2 kinase. Lats1/2 is also activated by the scaffold protein Mob. The activated Lats1/2 then phosphorylates and inactivates YAP or its paralog TAZ. The phosphorylation of YAP/TAZ leads to their nuclear export, retention within the cytoplasm, and degradation by the ubiquitin proteasome system.

In some instances, Lats1/2 phosphorylates YAP at the [HXRXXS] consensus motifs. YAP comprises five [HXRXXS] consensus motifs, wherein X denotes any amino acid residue. In some instances, Lats1/2 phosphorylates YAP at one or more of the consensus motifs. In some instances, Lats1/2 phosphorylates YAP at all five of the consensus motifs. In some instances, Lats1/2 phosphorylate at the S127 amino acid position. The phosphorylation of YAP S127 promotes 14-3-3 protein binding and results in cytoplasmic sequestration of YAP. Mutation of YAP at the S127 position thereby disrupts its interaction with 14-3-3 and subsequently promotes nuclear translocation.

Additional phosphorylation occurs at the S381 amino acid position in YAP. Phosphorylation of YAP at the S381 position and on the corresponding site in TAZ primes both proteins for further phosphorylation events by CK1δ/ε in the degradation motif, which then signals for interaction with the β-TRCP E3 ubiquitin ligase, leading to polyubiquitination and degradation of YAP.

In some instances, Lats1/2 phosphorylates TAZ at the [HXRXXS] consensus motifs. TAZ comprises four [HXRXXS] consensus motifs, wherein X denotes any amino acid residues. In some instances, Lats1/2 phosphorylates TAZ at one or more of the consensus motifs. In some instances, Lats1/2 phosphorylates TAZ at all four of the consensus motifs. In some instances, Lats1/2 phosphorylate at the S89 amino acid position. The phosphorylation of TAZ S89 promotes 14-3-3 protein binding and results in cytoplasmic sequestration of TAZ. Mutation of TAZ at the S89 position thereby disrupts its interaction with 14-3-3 and subsequently promotes nuclear translocation.

In some embodiments, phosphorylated YAP/TAZ accumulates in the cytoplasm, and undergoes $SCF^{\beta-TRCP}$-mediated ubiquitination and subsequent proteasomal degradation. In some instances, the Skp, Cullin, F-box containing complex (SCF complex) is a multi-protein E3 ubiquitin ligase complex that comprises a F-box family member protein (e.g. Cdc4), Skp1, a bridging protein, and RBX1, which contains a small RING Finger domain which interacts with E2-ubiquitin conjugating enzyme. In some cases, the F-box family comprises more than 40 members, in which exemplary members include F-box/WD repeat-containing protein 1A (FBXW1A, OTrCP1, Fbxw1, hsSlimb, plkappaBalpha-E3 receptor subunit) and S-phase kinase-associated proteins 2 (SKP2). In some embodiments, the SCF complex (e.g. SCF$^{BTrCP1}$) interacts with an E1 ubiquitin-activating enzyme and an E2 ubiquitin-conjugating enzyme to catalyze the transfer of ubiquitin to the YAP/TAZ substrate. Exemplary E1 ubiquitin-activating enzymes include those encoded by the following genes: UBA1, UBA2, UBA3, UBA5, UBA5, UBA7, ATG7, NAE1, and SAE1. Exemplary E2 ubiquitin-conjugating enzymes include those encoded by the following genes: UBE2A, UBE2B, UBE2C, UBE2D1, UBE2D2, UBE2D3, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2M, UBE2N, UBE2O, UBE2Q1, UBE2Q2, UBE2R1, UBE2R2, UBE2S, UBE2T, UBE2U, UBE2V1, UBE2V2, UBE2Z, ATG2, BIRC5, and UFC. In some embodiments, the ubiquitinated YAP/TAZ further undergoes the degradation process through the 26S proteasome.

In some embodiments, the Hippo pathway is regulated upstream by several different families of regulators (FIG. 1). In some instances, the Hippo pathway is regulated by the G-protein and its coupled receptors, the Crumbs complex, regulators upstream of the MST kinases, and the adherens junction.

YAP/TAZ Interaction with TEAD

In some embodiments, un-phosphorylated and/or dephosphorylated YAP/TAZ accumulates in the nucleus. Within the nucleus, YAP/TAZ interacts with the TEAD family of transcription factors (e.g. TEAD1, TEAD2, TEAD3, or TEAD4) to activate genes involved in anti-apoptosis and proliferation, such as for example CTFG, Cyr61, and FGF1.

In some embodiments, the compounds disclosed herein modulate the interaction between YAP/TAZ and TEAD. In some embodiments, the compounds disclosed herein bind to TEAD, YAP, or TAZ and prevent the interaction between YAP/TAZ and TEAD.

YAP/TAZ Regulation Mediated by G-Proteins/GPCRs

Figure 2:
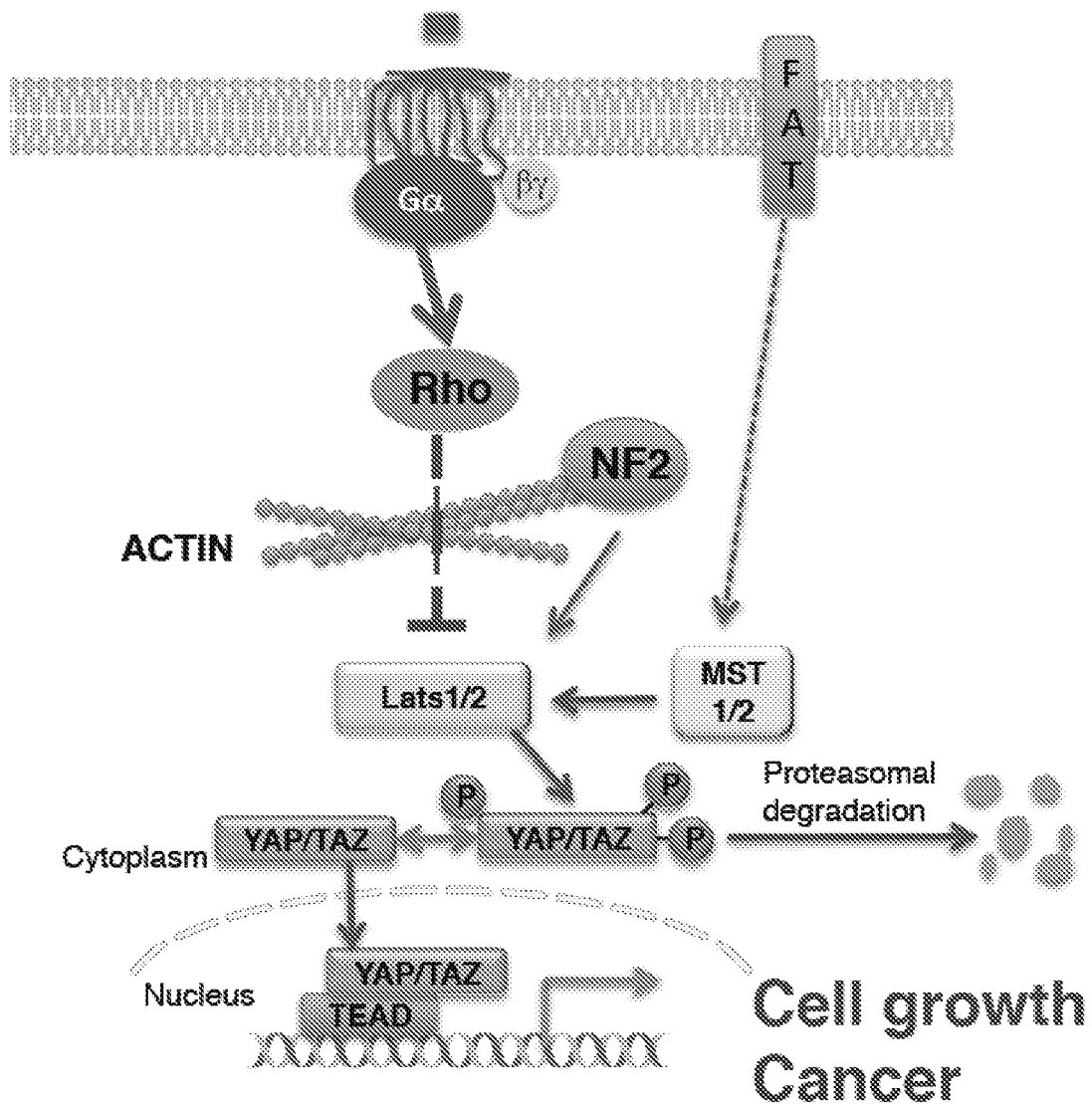
FIG. 2 illustrates a schematic representation of the Hippo signaling pathway regulated by G alpha proteins.

In some embodiments, the Hippo pathway is regulated by the G protein-coupled receptor (GPCR) and G protein (also known as guanine nucleotide-binding proteins) family of proteins (FIG. 2). G proteins are molecular switches that transmit extracellular stimuli into the cell through GPCRs. In some instances, there are two classes of G proteins: monomeric small GTPases and heterotrimeric G protein complexes. In some instances, the latter class of complexes comprise of alpha ($G_\alpha$), beta ($G_\beta$), and gamma ($G_\gamma$) subunits. In some cases, there are several classes of $G_\alpha$ subunits: $G_{q/11}\alpha$, $G_{12/13}\alpha$, $G_{i/o}\alpha$ (G inhibitory, G other), and $G_s\alpha$ (G stimulatory).

In some instances, $G_i\alpha$ (G inhibitory), $G_o\alpha$ (G other), $G_{q/11}\alpha$, and $G_{11/13}\alpha$ coupled GPCRs activate YAP/TAZ and promote nuclear translocation. In other instances, $G_s\alpha$ (G stimulatory) coupled GPCRs suppress YAP/TAZ activity, leading to YAP/TAZ degradation.

In some cases, $G_i\alpha$ (G inhibitory), $G_o\alpha$ (G other), $G_{q/11}\alpha$, and $G_{12/13}\alpha$ coupled GPCRs activate YAP/TAZ through repression of Lats1/2 activities. In contrast, $G_s\alpha$, in some embodiments, induces Lats1/2 activity, thereby promoting YAP/TAZ degradation.

$G_q$ Family $G_q\alpha$ (also known as $G_{q/11}$ protein), participates in the inositol trisphosphate (IP$_3$) signal transduction pathway and calcium (Ca$^{2+}$) release from intracellular storage through the activation of phospholipase C (PLC). The activated PLC hydrolyzes phosphatidylinositol 4,5-bisphosphate (PIP$_2$) to diacyl glycerol (DAG) and IP$_3$. In some instances, IP$_3$ then diffuses through the cytoplasm into the ER or the sarcoplasmic reticulum (SR) in the case of muscle cells, and then binds to inositol trisphosphate receptor (InsP3R), which is a Ca$^{2+}$ channel. In some cases, the binding triggers the opening of the Ca$^{2+}$ channel, and thereby increases the release of Ca$^{2+}$ into the cytoplasm.

In some embodiments, the GPCRs that interact with $G_q\alpha$ include, but are not limited to, 5-hydroxytryptamine receptor (5-HT receptor) types 5-HT$_2$ and 5-HT$_3$; alpha-1 adrenergic receptor; vasopressin type 1 receptors 1A and 1B; angiotensin II receptor type 1; calcitonin receptor; histamine H1 receptor; metabotropic glutamate receptor, group I; muscarinic receptors M$_1$, M$_3$, and M$_5$; and trace amine-associated receptor 1.

In some instances, there are several types of $G_q\alpha$: $G_q$, $G_{q/11}$, $G_{q/14}$, and $G_{q/15}$. The $G_q$ protein is encoded by GNAQ. $G_{q/11}$ is encoded by GNA11. $G_{q/14}$ is encoded by GNA14. $G_{q/15}$ is encoded by GNA15.

In some instances, mutations or modifications of the $G_q\alpha$ genes have been associated with cancer. Indeed, studies have shown that mutations in $G_q\alpha$ promote uveal melanoma (UM) tumorigenesis. In some instances, about 80% of UM cases have been detected to contain a mutation in GNAQ and/or GNA11.

In some instances, mutations or modifications of the $G_q\alpha$ genes have been associated with congenital diseases. In some instances, mutations of $G_q\alpha$ have been observed in congenital diseases such as Port-Wine Stain and/or Sturge-Weber Syndrome. In some instances, about 92% of Port-Wine stain cases harbors a mutation in GNAQ. In some instances, about 88% of Sturge-Weber Syndrome harbors a mutation in GNAQ.

$G_{12/13}$ Family $G_{12/13}\alpha$ modulates actin cytoskeletal remodeling in cells and regulates cell processes through guanine nucleotide exchange factors (GEFs). GEFs participate in the activation of small GTPases which acts as molecular switches in a variety of intracellular signaling pathways. Examples of small GTPases include the Ras-related GTPase superfamily (e.g. Rho family such as Cdc42), which is involved in cell differentiation, proliferation, cytoskeletal organization, vesicle trafficking, and nuclear transport.

In some embodiments, the GPCRs that interact with $G_{12}$/13a include, but are not limited to, purinergic receptors (e.g. P2Y$_1$, P2Y$_2$, P2Y$_4$, P2Y$_6$); muscarinic acetylcholine receptors M1 and M3; receptors for thrombin [protease-activated receptor (PAR)-1, PAR-2]; thromboxane (TXA2); sphingosine 1-phosphate (e.g. S1P$_2$, S1P$_3$, S1P$_4$ and SIP); lysophosphatidic acid (e.g. LPA$_1$, LPA$_2$, LPA$_3$); angiotensin II (AT1); serotonin (5-HT$_{2c}$ and 5-HT$_4$); somatostatin (sst$_5$); endothelin (ET$_A$ and ET$_B$); cholecystokinin (CCK$_1$); V$_{1a}$ vasopressin receptors; D$_5$ dopamine receptors; fMLP formyl peptide receptors; GAL$_2$ galanin receptors; EP$_3$ prostanoid receptors; A$_1$ adenosine receptors; u$_1$ adrenergic receptors; BB$_2$ bombesin receptors; B$_2$ bradykinin receptors; calcium-sensing receptors; KSHV-ORF74 chemokine receptors; NK$_1$ tachykinin receptors; and thyroid-stimulating hormone (TSH) receptors.

In some instances, $G_{12/13}\alpha$ is further subdivided into $G_{12}$ and $G_{13}$ types which are encoded by GNA12 and GNA13, respectively.

$G_{i/o}$ Family $G_{i/o}\alpha$ (G inhibitory, G other) (also known as $G_i/G_0$ or $G_i$ protein) suppresses the production of 3',5'-cyclic AMP (cAMP) from adenosine triphosphate (ATP) through an inhibition of adenylate cyclase activity, which converts ATP to cAMP.

In some embodiments, the GPCRs that interact with $G_i\alpha$ include, but are not limited to, 5-hydroxytryptamine receptor (5-HT receptor) types 5-HT$_1$ and 5-HT$_5$; muscarinic acetylcholine receptors such as $M_2$ and $M_4$; adenosine receptors such as $A_1$ and $A_3$; adrenergic receptors such as $\alpha_{2A}$, $\alpha_{2B}$, and $\alpha_{2C}$; apelin receptors; calcium-sensing receptor; cannabinoid receptors CB1 and CB2; chemokine CXCR4 receptor; dopamines $D_2$, $D_3$, and $D_4$; $GABA_B$ receptor; glutamate receptors such as metabotropic glutamate receptor 2 (mGluR2), metabotropic glutamate receptor 3 (mGluR3), metabotropic glutamate receptor 4 (mGluR4), metabotropic glutamate receptor 6 (mGluR6), metabotropic glutamate receptor 7 (mGluR7), and metabotropic glutamate receptor 8 (mGluR8); histamine receptors such as $H_3$ and $H_4$ receptors; melatonin receptors such as melatonin receptor type 1 (MT1), melatonin receptor type 2 (MT2), and melatonin receptor type 3 (MT3); niacin receptors such as NIACR1 and NIACR2; opioid receptors such as δ, κ, μ, and nociceptin receptors; prostaglandin receptors such as prostaglandin E receptor 1 ($EP_1$), prostaglandin E receptor 3 ($EP_3$), prostaglandin F receptor (FP), and thromboxane receptor (TP); somatostatin receptors sst1, sst2, sst3, sst4, and sst5; and trace amine-associated receptor 8.

In some instances, there are several types of $G_i\alpha$: $G_i\alpha1$, $G_i\alpha2$, $G_i\alpha3$, $G_i\alpha4$, $G_o\alpha$, $G_t$, $G_{gust}$, and $G_z$. $G_i\alpha1$ is encoded by GNAI1. $G_i\alpha2$ is encoded by GNAI2. $G_i\alpha3$ is encoded by GNAI3. $G_o\alpha$, the $a_o$ subunit, is encoded by GNAO1. $G_t$ is encoded by GNAT1 and GNAT2. $G_{gust}$ is encoded by GNAT3. $G_z$ is encoded by GNAZ.

$G_s$ Family $G_s\alpha$ (also known as G stimulatory, $G_s$ alpha subunit, or $G_s$ protein) activates the cAMP-dependent pathway through the activation of adenylate cyclase, which convers adenosine triphosphate (ATP) to 3',5'-cyclic AMP (cAMP) and pyrophosphate. In some embodiments, the GPCRs that interact with $G_s\alpha$ include, but are not limited to, 5-hydroxytryptamine receptor (5-HT receptor) types $5-HT_4$, $5-HT_6$, and $5-HT_7$; adrenocorticotropic hormone receptor (ACTH receptor) (also known as melanocortin receptor 2 or MC2R); adenosine receptor types $A_{2a}$ and $A_{2b}$; arginine vasopressin receptor 2 (AVPR2); β-adrenergic receptors $β_1$, $β_2$, and $β_3$; calcitonin receptor; calcitonin gene-related peptide receptor; corticotropin-releasing hormone receptor; dopamine receptor $D_1$-like family receptors such as D and $D_5$; follicle-stimulating hormone receptor (FSH-receptor); gastric inhibitory polypeptide receptor; glucagon receptor; histamine $H_2$ receptor; luteinizing hormone/choriogonadotropin receptor; melanocortin receptors such as MC1R, MC2R, MC3R, MC4R, and MC5R; parathyroid hormone receptor 1; prostaglandin receptor types $D_2$ and $I_2$; secretin receptor; thyrotropin receptor; trace amine-associated receptor 1; and box jellyfish opsin.

In some instances, there are two types of $G_s\alpha$: $G_s$ and $G_{olf}$. $G_s$ is encoded by GNAS. $G_{olf}$ is encoded by GNAL.

Additional Regulators of the Hippo Signaling Network

In some embodiments, the additional regulator of the Hippo signaling pathway is the Crumbs (Crb) complex. The Crumbs complex is a key regulator of cell polarity and cell shape. In some instances, the Crumbs complex comprises transmembrane CRB proteins which assemble multi-protein complexes that function in cell polarity. In some instances, CRB complexes recruit members of the Angiomotin (AMOT) family of adaptor proteins that interact with the Hippo pathway components. In some instances, studies have shown that AMOT directly binds to YAP, promotes YAP phosphorylation, and inhibits its nuclear localization.

In some instances, the additional regulator of the Hippo signaling pathway comprises regulators of the MST kinase family. MST kinases monitor actin cytoskeletal integrity. In some instances, the regulators include TAO kinases and cell polarity kinase PAR-1.

In some instances, the additional regulator of the Hippo signaling pathway comprises molecules of the adherens junction. In some instances, E-Cadherin (E-cad) suppresses YAP nuclear localization and activity through regulating MST activity. In some embodiments, E-cad-associated protein α-catenin regulates YAP through sequestering YAP/14-3-3 complexes in the cytoplasm. In other instances, Ajuba protein family members interact with Lats1/2 kinase activity, thereby preventing inactivation of YAP/TAZ.

In some embodiments, additional proteins that interact with YAP/TAZ either directly or indirectly include, but are not limited to, Merlin, protocadherin Fat 1, MASK/2, HIPK2, PTPN14, RASSF, PP2A, Salt-inducible kinases (SIKs), Scribble (SCRIB), the Scribble associated proteins Discs large (Dlg), KIBRA, PTPN14, NPHP3, LKB1, Ajuba, and ZO1/2.

In some embodiments, the compounds described herein are inhibitors of transcriptional coactivator with PDZ binding motif/Yes-associated protein transcriptional coactivator (TAZ/YAP). In some embodiments, the compounds described herein increase the phosphorylation of transcriptional coactivator with PDZ binding motif/Yes-associated protein transcriptional coactivator (TAZ/YAP) or decrease the dephosphorylation of transcriptional coactivator with PDZ binding motif/Yes-associated protein transcriptional coactivator (TAZ/YAP). In some embodiments, the compounds increase the ubiquitination of transcriptional coactivator with PDZ binding motif/Yes-associated protein transcriptional coactivator (TAZ/YAP) or decrease the deubiquitination of transcriptional coactivator with PDZ binding motif/Yes-associated protein transcriptional coactivator (TAZ/YAP).

In some embodiments, the compounds disclosed herein are inhibitors of one or more of the proteins encompassed by, or related to, the Hippo pathway. In some instances, the one or more proteins comprise a protein shown in FIGS. 1 and/or 2. In some embodiments, an inhibitor of the Hippo pathway is an inhibitor of a G-protein and/or its coupled GPCR. In some embodiments, an inhibitor of the Hippo pathway is an inhibitor of a G-protein. In some embodiments, an inhibitor of the Hippo pathway is an inhibitor of the $G_q\alpha$ family proteins such as $G_q$, $G_{q/11}$, $G_{q/14}$, and $G_{q/15}$; the $G_{12/13}\alpha$ family of proteins such as $G_{12}$ and $G_{13}$; or the $G_i\alpha$ family of proteins such as $G_i\alpha1$, $G_i\alpha2$, $G_i\alpha3$, $G_i\alpha4$, $G_o\alpha$, $G_t$, $G_{gust}$, and $G_z$. In some embodiments, an inhibitor of the Hippo pathway is an inhibitor of $G_q$. In some embodiments, an inhibitor of the Hippo pathway is an inhibitor of $G_{q/11}$. In some embodiments, an inhibitor of the Hippo pathway is an inhibitor of $G_{q/14}$. In some embodiments, an inhibitor of the Hippo pathway is an inhibitor of $G_{q/15}$. In some embodiments, an inhibitor of the Hippo pathway is an inhibitor of $G_{12}$. In some embodiments, an inhibitor of the Hippo pathway is an inhibitor of $G_{13}$. In some embodiments, an inhibitor of the Hippo pathway is an inhibitor of $G_i\alpha1$. In some embodiments, an inhibitor of the Hippo pathway is an inhibitor of $G_i\alpha2$. In some embodiments, an inhibitor of the Hippo pathway is an inhibitor of $G_i\alpha3$. In some embodiments, an inhibitor of the Hippo pathway is an inhibitor of $G_i\alpha4$. In some embodiments, an inhibitor of the Hippo pathway is an inhibitor of $G_o\alpha$. In some embodiments, an inhibitor of the Hippo pathway is an inhibitor of $G_t$. In some embodiments, an inhibitor of the Hippo pathway is an inhibitor of $G_{gust}$. In some embodiments, an inhibitor of the Hippo pathway is an inhibitor of $G_z$.

In some embodiments, an inhibitor of the Hippo pathway is an inhibitor of a core protein of the Hippo pathway. In some embodiments, an inhibitor of the Hippo pathway is an inhibitor of Sav1. In some embodiments, an inhibitor of the Hippo pathway is an inhibitor of Mob. In some embodiments, an inhibitor of the Hippo pathway is an inhibitor of YAP. In some embodiments, an inhibitor of the Hippo pathway is an inhibitor of TAZ. In some embodiments, an inhibitor of the Hippo pathway is an inhibitor of TEAD.

In some embodiments, an inhibitor of the Hippo pathway is an inhibitor of a protein associated with the ubiquitination and proteasomal degradation pathway. In some embodiments, an inhibitor of the Hippo pathway is an inhibitor of a proteasomal degradation pathway protein (e.g. 26S proteasome).

In some embodiments, an inhibitor of the Hippo pathway is an inhibitor of a protein of the Ras superfamily of proteins. In some embodiments, an inhibitor of the Hippo pathway is an inhibitor of a protein of the Rho family of proteins. In some embodiments, an inhibitor of the Hippo pathway is an inhibitor of Cdc42.

Cdc42 is a member of the Ras superfamily of small GTPases. Specifically, Cdc42 belongs to the Rho family of GTPases, in which the family members participate in diverse and critical cellular processes such as gene transcription, cell-cell adhesion, and cell cycle progression. Cdc42 is involved in cell growth and polarity, and in some instances, Cdc42 is activated by guanine nucleotide exchange factors (GEFs). In some cases, an inhibitor of Cdc42 is a compound disclosed herein.

In some embodiments, an inhibitor of the Hippo pathway is an inhibitor of a deubiquitinating enzyme. In some embodiments, an inhibitor of the Hippo pathway is an inhibitor of a cysteine protease or a metalloprotease. In some embodiments, an inhibitor of the Hippo pathway is an inhibitor of an ubiquitin-specific protease. USP47 is a member of the ubiquitin-specific protease (USP/UBP) superfamily of cysteine proteases. In some embodiments, the compounds disclosed herein are inhibitors of USP47.

Further embodiments provided herein include combinations of one or more of the particular embodiments set forth above.

Diseases

Cancer

In some embodiments, the compounds disclosed herein are useful for treating cancer. In some embodiments, the cancer is mediated by activation of transcriptional coactivator with PDZ binding motif/Yes-associated protein transcription coactivator (TAZ/YAP). In some embodiments, the cancer is mediated by modulation of the interaction of YAP/TAZ with TEAD. In some embodiments, the cancer is characterized by a mutant Gα-protein. In some embodiments, the mutant Gα-protein is selected from G12, G13, Gq, G11, Gi, Go, and Gs. In some embodiments, the mutant Gα-protein is G12. In some embodiments, the mutant Gα-protein is G13. In some embodiments, the mutant Gα-protein is Gq. In some embodiments, the mutant Gα-protein is G11. In some embodiments, the mutant Gα-protein is Gi. In some embodiments, the mutant Gα-protein is Go. In some embodiments, the mutant Gα-protein is Gs.

In some embodiments, the cancer is a solid tumor. In some instances, the cancer is a hematologic malignancy. In some instances, the solid tumor is a sarcoma or carcinoma. In some instances, the solid tumor is a sarcoma. In some instances, the solid tumor is a carcinoma.

Exemplary sarcoma includes, but is not limited to, alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epithelioid cell differentiation, osteosarcoma, parosteal osteosarcoma, neoplasm with perivascular epithelioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, and telangiectatic osteosarcoma.

Exemplary carcinoma includes, but is not limited to, adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer. In some instances, the liver cancer is primary liver cancer.

In some instances, the cancer is selected from uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the cancer is uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the cancer is uveal melanoma, mesothelioma, esophageal cancer, or liver cancer. In some cases, the cancer is uveal melanoma. In some cases, the cancer is mesothelioma. In some cases, the cancer is esophageal cancer. In some cases, the cancer is liver cancer. In some cases, the cancer is primary liver cancer.

In some instances, the cancer is a hematologic malignancy. In some embodiments, a hematologic malignancy is a leukemia, a lymphoma, a myeloma, a non-Hodgkin's lymphoma, a Hodgkin's lymphoma, a T-cell malignancy, or a B-cell malignancy. In some instances, a hematologic malignancy is a T-cell malignancy. Exemplary T-cell malignancy includes, but is not limited to, peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, and treatment-related T-cell lymphomas.

In some instances, a hematologic malignancy is a B-cell malignancy. Exemplary B-cell malignancy includes, but is not limited to, chronic lymphocytic leukemia (CLL), small lymphocytic lymphoma (SLL), high risk CLL, and a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, the cancer is a relapsed or refractory cancer. In some embodiments, the relapsed or refractory cancer is a relapsed or refractory solid tumor. In some embodiments, the relapsed or refractory solid tumor is a relapsed or refractory sarcoma or a relapsed or refractory carcinoma. In some embodiments, the relapsed or refractory carcinoma includes adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer.

In some instances, the relapsed or refractory cancer is selected from relapsed or refractory uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the relapsed or refractory cancer is relapsed or refractory uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the relapsed or refractory cancer is relapsed or refractory uveal melanoma, mesothelioma, esophageal cancer, or liver cancer. In some cases, the relapsed or refractory cancer is relapsed or refractory uveal melanoma. In some cases, the relapsed or refractory cancer is relapsed or refractory mesothelioma. In some cases, the relapsed or refractory cancer is relapsed or refractory esophageal cancer. In some cases, the relapsed or refractory cancer is relapsed or refractory liver cancer. In some cases, the relapsed or refractory cancer is relapsed or refractory primary liver cancer.

In some instances, the relapsed or refractory cancer is a relapsed or refractory hematologic malignancy. In some embodiments, a relapsed or refractory hematologic malignancy is a relapsed or refractory leukemia, a relapsed or refractory lymphoma, a relapsed or refractory myeloma, a relapsed or refractory non-Hodgkin's lymphoma, a relapsed or refractory Hodgkin's lymphoma, a relapsed or refractory T-cell malignancy, or a relapsed or refractory B-cell malignancy. In some instances, a relapsed or refractory hematologic malignancy is a relapsed or refractory T-cell malignancy. In some instances, a relapsed or refractory hematologic malignancy is a relapsed or refractory B-cell malignancy, such as for example, chronic lymphocytic leukemia (CLL), small lymphocytic lymphoma (SLL), high risk CLL, or a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, the cancer is a metastasized cancer. In some instances, the metastasized cancer is a metastasized solid tumor. In some instances, the metastasized solid tumor is a metastasized sarcoma or a metastasized carcinoma. In some embodiments, the metastasized carcinoma includes adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer.

In some instances, the metastasized cancer is selected from metastasized uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the metastasized cancer is metastasized uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the metastasized cancer is metastasized uveal melanoma, mesothelioma, esophageal cancer, or liver cancer. In some cases, the metastasized cancer is metastasized uveal melanoma. In some cases, the metastasized cancer is metastasized mesothelioma. In some cases, the metastasized cancer is metastasized esophageal cancer. In some cases, the metastasized cancer is metastasized liver cancer. In some cases, the metastasized cancer is metastasized primary liver cancer.

In some instances, the metastasized cancer is a metastasized hematologic malignancy. In some embodiments, the metastasized hematologic malignancy is a metastasized leukemia, a metastasized lymphoma, a metastasized myeloma, a metastasized non-Hodgkin's lymphoma, a metastasized Hodgkin's lymphoma, a metastasized T-cell malignancy, or a metastasized B-cell malignancy. In some instances, a metastasized hematologic malignancy is a metastasized T-cell malignancy. In some instances, a metastasized hematologic malignancy is a metastasized B-cell malignancy, such as for example, chronic lymphocytic leukemia (CLL), small lymphocytic lymphoma (SLL), high risk CLL, or a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

Congenital Diseases

In some embodiments, the compounds disclosed herein are useful for treating a congenital disease. In some embodiments, the congenital disease is mediated by activation of transcriptional coactivator with PDZ binding motif/Yes-associated protein transcription coactivator (TAZ/YAP). In some embodiments, the congenital disease is characterized by a mutant Gα-protein. In some embodiments, the mutant Gα-protein is selected from G12, G13, Gq, G11, Gi, Go, and Gs. In some embodiments, the mutant Gα-protein is G12. In some embodiments, the mutant Gα-protein is G13. In some embodiments, the mutant Gα-protein is Gq. In some embodiments, the mutant Gα-protein is G11. In some embodiments, the mutant Gα-protein is Gi. In some embodiments, the mutant Gα-protein is Go. In some embodiments, the mutant Gα-protein is Gs.

In some embodiments, the congenital disease is the result of a genetic abnormality, an intrauterine environment, errors related to morphogenesis, infection, epigenetic modifications on a parental germline, or a chromosomal abnormality. Exemplary congenital diseases include, but are not limited to, Sturge-Weber Syndrome, Port-Wine stain, Holt-Oram syndrome, abdominal wall defects, Becker muscular dystrophy (BMD), biotinidase deficiency, Charcot-Marie-Tooth (CMT), cleft lip, cleft palate, congenital adrenal hyperplasia, congenital heart defects, congenital hypothyroidism, congenital muscular dystrophy, cystic fibrosis, Down syndrome, Duchenne muscular dystrophy, Fragile X syndrome, Friedreich's ataxia, galactosemia, hemoglobinopathies, Krabbe disease, limb-girdle muscular dystrophy, medium chain acyl-CoA dehydrogenase deficiency, myasthenia gravis, neural tube defects, phenylketonuria, Pompe disease, severe combined immunodeficiency (SCID), Stickler syndrome (or hereditary progressive arthro-ophthalmopathy), spinal muscular atrophy, and trisomy 18. In some embodiments, the congenital disease is Sturge-Weber Syndrome or Port-Wine stain. In some embodiments, the congenital disease is Sturge-Weber Syndrome. In some embodiments, the congenital disease is Port-Wine stain.

EXAMPLES

These examples are provided for illustrative purposes only and not to limit the scope of the claims provided herein.

List of Abbreviations

As used above, and throughout the disclosure, the following abbreviations, unless otherwise indicated, shall be understood to have the following meanings:
ACN or MeCN acetonitrile
Ac acetyl
Bn benzyl
BOC or Boc tert-butyl carbamate
t-Bu tert-butyl
Cy cyclohexyl
° C. degrees Celsius
DBA or dba dibenzylideneacetone
DCE dichloroethane ($CCH_2CH_2Cl$)
DCM dichloromethane ($CH_2Cl_2$)
DIAD diisopropyl azodicarboxylate
DIPEA or DIEA diisopropylethylamine
DMAP 4-(N,N-dimethylamino)pyridine
DMF dimethylformamide
DMA N,N-dimethylacetamide
DMSO dimethylsulfoxide
Dppf or dppf 1,1'-bis(diphenylphosphino)ferrocene
EA or EtOAc ethyl acetate
eq equivalent(s)
Et ethyl
$Et_2O$ diethyl ether
EtOH ethanol
g gram(s)
h hour(s)
HPLC high performance liquid chromatography
Hz hertz
LAH lithium aluminum anhydride
LCMS liquid chromatography mass spectrometry
m/z mass-to-charge ratio
M molar
Me methyl
MeI methyl iodide
MeOH methanol
mg milligram(s)
MHz megahertz
umol micromole(s)
uL microliter(s)
mL milliliter(s)
mmol millimole(s)
MS mass spectroscopy
MsCl methanesulfonyl chloride
MW microwave radiation
NCS N-chlorosuccinimide
NMM N-methyl-morpholine
NMP N-methyl-pyrrolidin-2-one
NMR nuclear magnetic resonance
PE petroleum ether
Ph phenyl
prep-HPLC preparative high pressure liquid chromatography
prep-TLC preparative thin layer chromatography
Py pyridine RP-HPLC reverse phase-high pressure liquid chromatography
RT retention time
TEA triethylamine
TFA trifluoroacetic acid
THF tetrahydrofuran
TLC thin layer chromatography
TMSCl trimethylsilyl chloride
Xantphos 4,5-bis(diphenylphosphino)-9,9-dimethylxanthene
XPhos 2-dicyclohexylphosphino-2',4',6'-triisopropylbiphenyl
XPhos Pd G II chloro(2-dicyclohexylphosphino-2',4',6'-triisopropyl-1,1'-biphenyl)[2-(2'-amino-1,1'-biphenyl)]palladium(II)

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times were approximate and were not optimized. Column chromatography and thin layer chromatography (TLC) were performed on silica gel unless otherwise noted.

Example 1: N-(tert-butyl)-4-(cyclohexylamino)-3-(2H-tetrazol-5-yl)benzenesulfonamide (Compound 1)

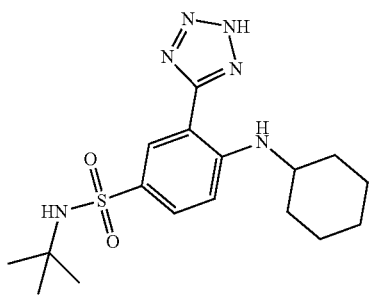 [SMILES: CC(C)(C)NS(=O)(=O)c1ccc(NC2CCCCC2)c(-c2nn[nH]n2)c1]

Preparation of Compound 1:

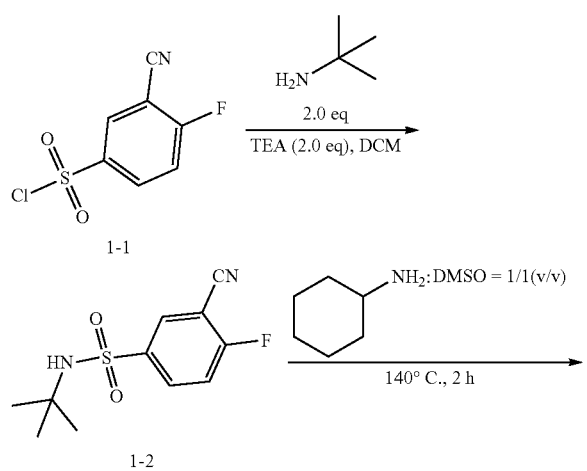

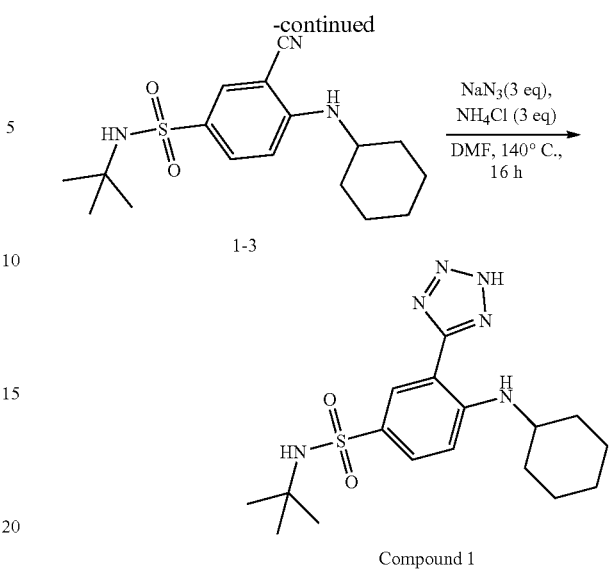

Compound 1

Step 1:
N-tert-butyl-3-cyano-4-fluoro-benzenesulfonamide

To a solution of compound 1-1 (500 mg, 2.28 mmol, 1.0 eq) and 2-methylpropan-2-amine (334 mg, 4.56 mmol, 2.0 eq) in DCM (10 mL) was added TEA (461 mg, 4.56 mmol, 2.0 eq). The resulted mixture was stirred at 30° C. for 16 hr. LCMS and TLC (Petroleum ether: Ethyl acetate=3/1) showed desired compound was found and all the starting material was consumed completely. The reaction mixture was poured into cold water (10 mL), extracted by DCM (3×10 mL). The combined organic layers were washed with brine (10 mL*2) dried over $Na_2SO_4$, concentrated under reduced pressure to give compound 1-2 (550 mg, 2.15 mmol, 94% yield), which was directly used without further purification. $^1$HNMR (400 MHz, $CDCl_3$) δ 8.20 (dd, J=2.3, 5.8 Hz, 1H), 8.15 (ddd, J=2.4, 4.8, 8.8 Hz, 1H), 7.38 (t, J=8.5 Hz, 1H), 1.29 (s, 9H).

Step 2: 5-[2-[3-(trifluoromethyl)phenoxy]phenyl]-2H-tetrazole

A solution of compound 1-2 (450 mg, 1.76 mmol, 1.0 eq) and cyclohexylamine (870 mg, 8.76 mmol, 1 mL, 5.0 eq) in DMSO (1 mL) was heated to 140° C. for 2 hr. LCMS showed 85% desired compound was found and the starting material was consumed completely. The reaction mixture was combined and poured into cold water (10 mL), and then extracted by ethyl acetate (3×10 mL). The combined organic layers were washed with brine (10 mL*2) dried over $Na_2SO_4$, filtered, concentrated under reduced pressure to give the crude product. The crude product was purified by column chromatography (silica) to give compound 1-3 (580 mg, 1.69 mmol, 96% yield). LCMS (ESI): RT=0.861 min, mass calc. for $C_{17}H_{25}N_3O_2S$ 335.17, m/z found 335.7 $[M+H]^+$.

Step 3: N-tert-butyl-4-(cyclohexylamino)-3-(2H-tetrazol-5-yl)benzenesulfonamide

To a solution of compound 1-3 (300 mg, 0.89 mmol, 1.0 eq) and $NH_4Cl$ (144 mg, 2.7 mmol, 3.0 eq) in DMF (2 mL) was added $NaN_3$ (174 mg, 2.7 mmol, 3.0 eq). The resulted mixture was stirred at 140° C. for 16 hr. LCMS showed 93% desired compound was found and the starting material was consumed completely. The reaction mixture was poured into cold water (10 mL), HCl (1N, 1 mL) and then extracted by ethyl acetate (3×10 mL). The combined organic layers were washed with brine (10 mL*2) dried over Na$_2$SO$_4$, concentrated under reduced pressure to give the crude product (350 mg, 0.83 mmol, 93% yield). The crude product (230 mg) was directly used without further purification. 120 mg of crude product was purified by HPLC to give Compound 1 (90.52 mg). LCMS (ESI): RT=2.200 min, mass calc. for C$_{17}$H$_{26}$N$_6$O$_2$S 378.18, m/z found 379.1 [M+H]$^+$; $^1$H NMR (400 MHz, DMSO-d$_6$) δ 8.52 (br s, 1H), 8.41 (d, J=2.3 Hz, 1H), 7.63 (dd, J=2.3, 8.8 Hz, 1H), 7.26-7.05 (m, 2H), 6.94 (d, J=9.0 Hz, 1H), 3.59 (s, 1H), 2.04-1.94 (m, 2H), 1.79-1.68 (m, 2H), 1.64-1.54 (m, 1H), 1.50-1.28 (m, 5H), 1.10 (s, 9H).

Example 2: N-(tert-butyl)-4-(cyclohexylamino)-3-(2-(2-hydroxyethyl)-2H-tetrazol-5-yl)benzenesulfonamide (Compound 2)

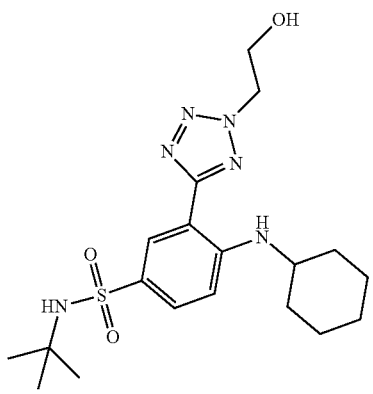 [SMILES: CC(C)(C)NS(=O)(=O)c1ccc(NC2CCCCC2)c(-c2nnn(CCO)n2)c1]

Preparation of Compound 2:

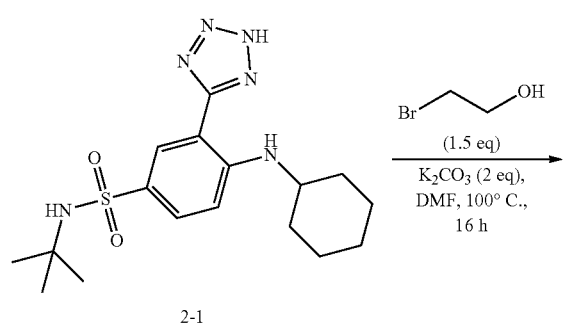

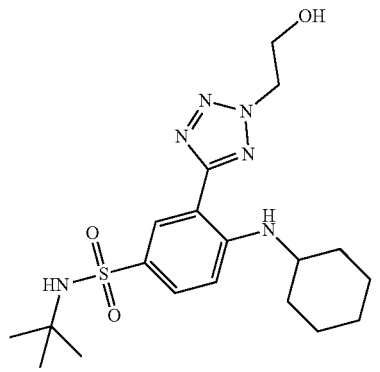

Compound 2

To a solution of 2-1 (80 mg, 0.21 mmol, 1.0 eq) and 2-bromoethanol (40 mg, 0.32 mmol, 1.5 eq) in DMF (2 mL) was added K$_2$CO$_3$ (58 mg, 0.42 mmol, 2.0 eq). The resulted mixture was stirred at 100° C. for 16 hr. LCMS showed 75% desired compound was found and the starting material was consumed completely. The reaction mixture was poured into cold water (10 mL) and then extracted by ethyl acetate (3×10 mL). The combined organic layers were washed with brine (10 mL*2) dried over Na$_2$SO$_4$, concentrated under reduced pressure to give a brown solid. The crude product was purified by HPLC to give Compound 2 (23 mg, 54 umol, 26% yield). LCMS (ESI): RT=2.160 min, mass calc. for C$_{19}$H$_{30}$N$_6$O$_3$S 422.21, m/z found 423.2 [M+H]$^+$; $^1$H NMR (400 MHz, DMSO-d$_6$) δ 8.47 (d, J=2.0 Hz, 1H), 7.69 (dd, J=1.8, 8.8 Hz, 1H), 7.60 (d, J=7.3 Hz, 1H), 7.30 (s, 1H), 7.01 (d, J=9.0 Hz, 1H), 5.12 (t, J=5.6 Hz, 1H), 4.81 (t, J=4.9 Hz, 2H), 3.98 (q, J=5.1 Hz, 2H), 3.69-3.59 (m, 1H), 2.04-1.94 (m, 2H), 1.70 (s, 2H), 1.59 (d, J=12.0 Hz, 1H), 1.50-1.28 (m, 5H), 1.09 (s, 9H).

Example 3: N-cyclohexyl-2-(5-methyl-1,2,4-oxadiazol-3-yl)-4-(methylsulfonyl)aniline (Compound 3)

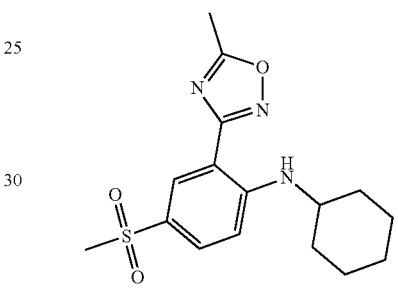

Preparation of Compound 3:

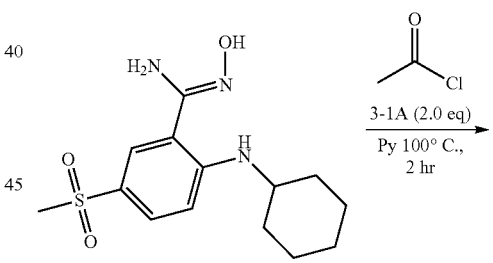

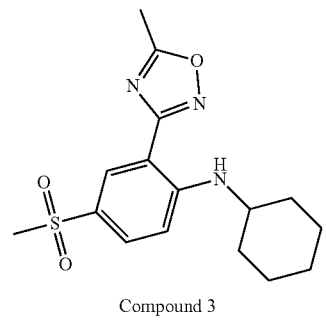

Compound 3

Compound 3-1A (10 mg, 0.13 mmol, 2.0 eq) was added to a solution of compound 3-1 (20 mg, 64 umol, 1.0 eq) in pyridine (1 mL). The reaction mixture was stirred at 100° C. for 2 hours. The reaction mixture was concentrated under reduced pressure. The residue was purified by preparative high performance liquid chromatography. The fractions were collected and the volatiles were removed under vacuum. The residue was re-suspended in water (10 mL) and the resulting mixture was lyophilized to dryness to remove the solvent residue completely and to obtain the title compound (2.16 mg, 9.4% yield). LCMS (ESI): RT=2.356 min, mass calcd. for $C_{16}H_{21}N_3O_3S$ 335.13, m/z found 358.0 [M+Na]$^+$, $^1$H NMR (400 MHz, CDCl$_3$) δ 8.64 (d, J=2.2 Hz, 1H), 7.78 (dd, J=2.2, 8.8 Hz, 1H), 7.35 (d, J=7.3 Hz, 1H), 6.81 (d, J=9.0 Hz, 1H), 3.60-3.48 (m, 1H), 3.03 (s, 3H), 2.65 (s, 3H), 2.08-2.00 (m, 2H), 1.84-1.73 (m, 2H), 1.69-1.59 (m, 1H), 1.47-1.31 (m, 5H).

Example 4: N-cyclohexyl-4-(methylsulfonyl)-2-(2H-tetrazol-5-yl)aniline (Compound 4)

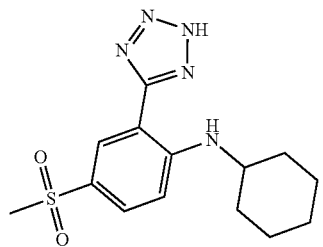 [SMILES: CS(=O)(=O)c1ccc(NC2CCCCC2)c(-c2nn[nH]n2)c1]

Preparation of Compound 4:

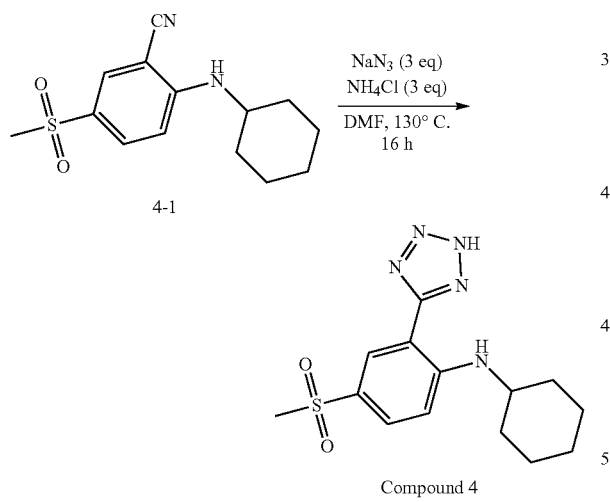

Compound 4

To a mixture of 4-1 (145 mg, 0.52 mmol, 1.0 eq) and NaN$_3$ (102 mg, 1.56 mmol, 3.0 eq) in DMF (3 mL) was added NH$_4$Cl (84 mg, 1.56 mmol, 3.00 eq) in one portion at 25° C. under N$_2$. The mixture was heated to 130° C. for 16 h. LCMS showed the compound 4-1 was consumed completely and one main peak with desired MS was detected. The reaction mixture was added EA (35 mL) and washed with water (30 mL) and then washed with brine (25 mL*2). The organic layer was dried with anhydrous Na$_2$SO$_4$, filtered and concentrated in vacuum. The residue was purified by prep-HPLC to obtain Compound 4 (80 mg, 0.25 mmol, 47.3% yield). LCMS (ESI): RT=1.197 min, mass calcd. For $C_{14}H_{19}N_5O_2S$, 321.15 m/z found 321.9[M+H]$^+$. H NMR (400 MHz, CDCl$_3$) δ 8.45-8.20 (m, 2H), 7.55 (br d, J=9.20 Hz, 1H), 6.65 (br d, J=9.20 Hz, 1H), 3.35 (br s, 1H), 2.92 (s, 3H), 2.00-1.85 (m, 2H), 1.80-1.65 (m, 2H), 1.65-1.50 (m, 1H), 1.36-1.19 (m, 5H).

Example 5: N-cyclohexyl-2-(2-methyl-2H-tetrazol-5-yl)-4-(methylsulfonyl)aniline (Compound 5)

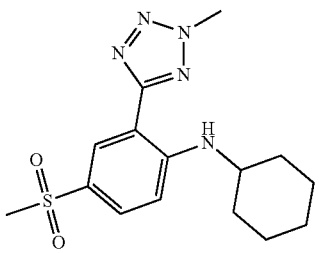 [SMILES: Cn1nnc(-c2cc(S(C)(=O)=O)ccc2NC2CCCCC2)n1]

Preparation of Compound 5:

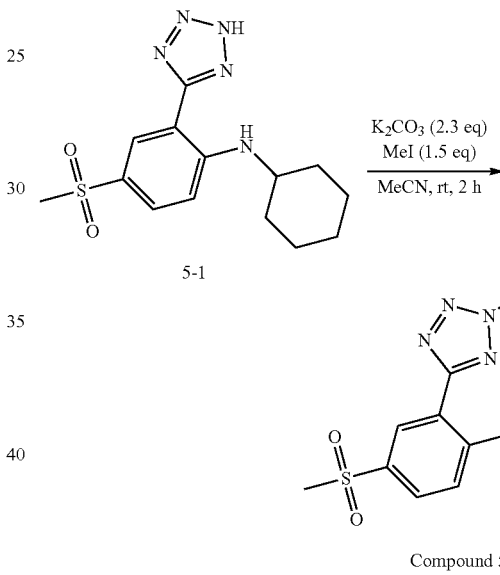

Compound 5

To a mixture of 5-1 (30 mg, 93 umol, 1.00 eq) in CH$_3$CN (5 mL) was added K$_2$CO$_3$ (26 mg, 0.19 mmol, 2.0 eq) and CH$_3$I (20 mg, 0.14 mmol, 8.7 uL, 1.50 eq) in one portion at 20° C. under N$_2$. The mixture was stirred at 20° C. for 2 h. LCMS showed the starting material was consumed completely and one small peak with desired MS was detected. TCL indicated one new spot was formed. The reaction mixture was concentrated under reduced pressure to remove solvent. The residue was diluted with water (10 mL) and extracted with EA (20 mL*3). The combined organic layers were washed with brine (40 mL), dried with anhydrous Na$_2$SO$_4$, filtered and concentrated in vacuum. LCMS showed 88% of desired product was found. The residue was purified by prep-HPLC to provide Compound 5 (8.84 mg, 26.4 umol, 28.2% yield). LCMS (ESI): RT=0.810 min, mass calcd. For $C_{15}H_{21}N_5O_2S$, 335.14 m/z found 335.9[M+H]$^+$. $^1$H NMR (400 MHz, CDCl$_3$) δ 8.68 (d, J=2.00 Hz, 1H), 7.86 (br d, J=7.20 Hz, 1H), 7.78 (dd, J=9.20, 2.40 Hz, 1H), 6.84 (d, J=9.20 Hz, 1H), 4.44 (s, 3H), 3.55 (br s, 1H), 3.06 (s, 3H), 2.14-2.04 (m, 2H), 1.88-1.77 (m, 2H), 1.72-1.64 (m, 1H), 1.50-1.27 (m, 5H).

Example 6: N-cyclohexyl-2-(1-methyl-1H-1,2,3-triazol-4-yl)-4-(methylsulfonyl)aniline (Compound 6)

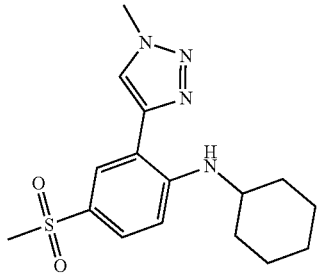 [SMILES: Cn1cc(-c2cc(S(C)(=O)=O)ccc2NC2CCCCC2)nn1]

Preparation of Compound 6:

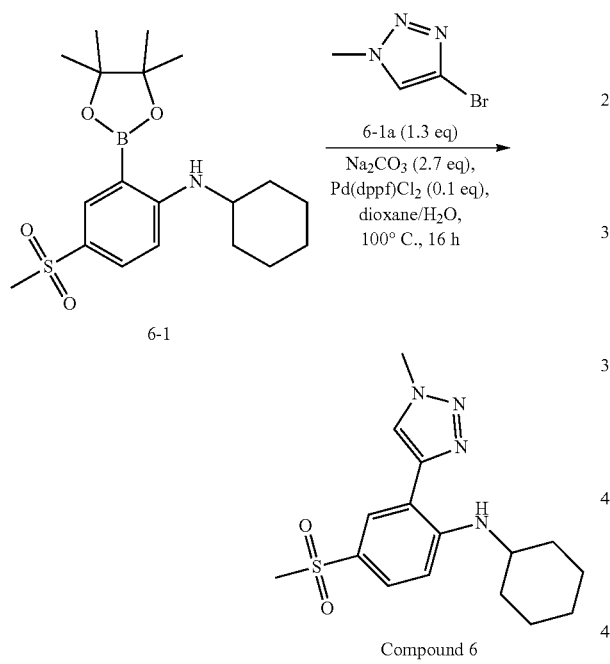

To a mixture of 6-1 (50 mg, 0.13 mmol, 1.0 eq) and 6-1a (28 mg, 0.17 mmol, 1.30 eq) in dioxane (2 mL) and H$_2$O (0.5 mL) was added Na$_2$CO$_3$ (38 mg, 0.36 mmol, 2.7 eq) and Pd(dppf)Cl$_2$ (10 mg, 13 umol, 0.1 eq) in one portion under N$_2$. The mixture was stirred at 100° C. for 16 h. LCMS showed the starting material was consumed completely and one peak with desired MS was detected. The reaction mixture was concentrated under reduced pressure to remove solvent, and then added CH$_3$CN (5 mL), filtered to give a black-brown liquid. The residue was purified by prep-HPLC. LCMS and $^1$H NMR confirmed Compound 6 was obtained (2.06 mg, 5.5 umol, 4.2% yield, HCl). LCMS (ESI): RT=0.752 min, mass calcd. For C$_{16}$H$_{22}$N$_4$O$_2$S, 334.15 m/z found 334.9[M+H]$^+$. $^1$H NMR (400 MHz, DMSO-d$_6$) δ8.76 (s, 1H), 8.34 (br s, 1H), 7.95 (d, J=2.00 Hz, 1H), 7.60 (dd, J=8.80, 2.00 Hz, 1H), 6.91 (d, J=8.80 Hz, 1H), 4.13 (s, 3H), 3.11 (s, 3H), 2.60-2.53 (m, 1H), 2.02-1.89 (m, 2H), 1.74-1.63 (m, 2H), 1.62-1.51 (m, 1H), 1.49-1.26 (m, 5H).

Example 7: N-cyclohexyl-2-(1-methyl-1H-pyrazol-4-yl)-4-(methylsulfonyl)aniline (Compound 7)

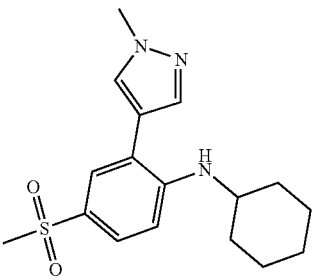 [SMILES: Cn1cc(-c2cc(S(C)(=O)=O)ccc2NC2CCCCC2)cn1]

Preparation of Compound 7:

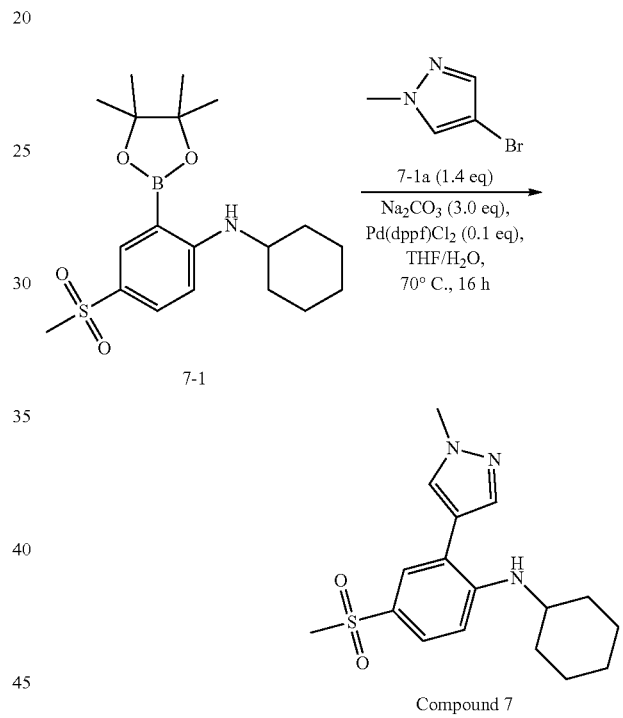

To a mixture of 7-1 (50 mg, 0.13 mmol, 1.0 eq) and 7-1a (30 mg, 0.18 mmol, 1.40 eq) in H$_2$O (0.4 mL) and dioxane (2 mL) was added Pd(dppf)Cl$_2$ (10 mg, 13.2 umol, 0.1 eq) and Na$_2$CO$_3$ (42 mg, 0.40 mmol, 3.0 eq) in one portion under N$_2$. The mixture was stirred at 70° C. for 16 h. LCMS showed the compound 7-1 was consumed completely and one peak with desired MS was detected. The reaction mixture was concentrated under reduced pressure to remove solvent, and then added CH$_3$CN (5 mL), filtered to give a black-brown liquid. The residue was purified by prep-HPLC to obtain Compound 7 (4.70 mg, 12.7 umol, 9.6% yield, HCl). LCMS (ESI): RT=0.737 min, mass calcd. For C$_{17}$H$_{23}$N$_3$O$_2$S, 333.15 m/z found 333.9[M+H]$^+$. $^1$H NMR (400 MHz, DMSO-d$_6$) δ8.01 (s, 1H), 7.68 (s, 1H), 7.56 (dd, J=8.40, 2.00 Hz, 1H), 7.49 (d, J=2.00 Hz, 1H), 6.82 (d, J=9.20 Hz, 1H), 3.90 (s, 3H), 3.45-3.35 (m, 1H), 3.08 (s, 3H), 1.97-1.86 (m, 2H), 1.72-1.53 (m, 3H), 1.43-1.15 (m, 5H).

Example 8: N-cyclohexyl-2-(1-methyl-1H-pyrazol-3-yl)-4-(methylsulfonyl)aniline (Compound 8)

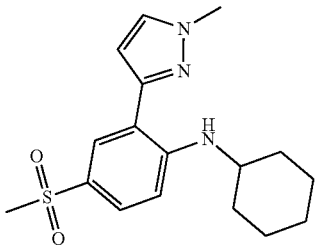 [SMILES: Cn1ccc(-c2cc(S(C)(=O)=O)ccc2NC2CCCCC2)n1]

Preparation of Compound 8:

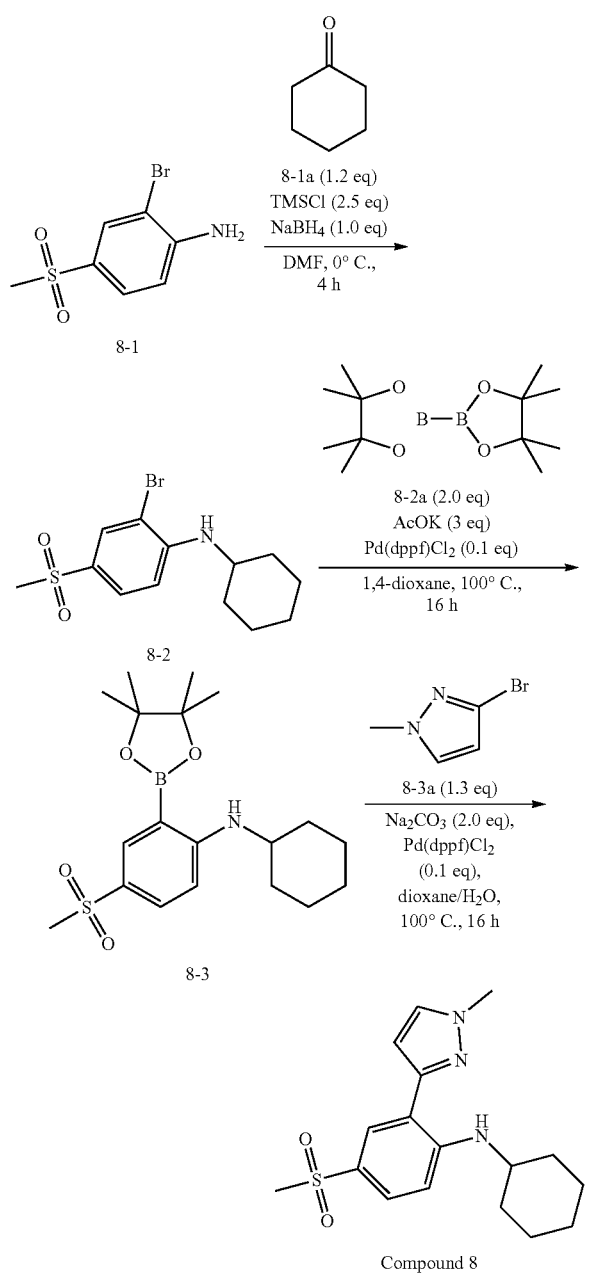

Step 1: 2-bromo-N-cyclohexyl-4-methylsulfonyl-aniline

To a mixture of 8-1 (500 mg, 2.0 mmol, 1.0 eq) and TMSCl (543 mg, 5.0 mmol, 0.63 mL, 2.5 eq) and 8-1a (235 mg, 2.4 mmol, 0.25 mL, 1.2 eq) in DMF (10 mL) was stirred at 0° C. for 5 min under $N_2$. The mixture was added $NaBH_4$ (76 mg, 2.0 mmol, 1.0 eq) and stirred at 0° C. for 3 h. LCMS showed no MS of the reactant 8-1, but one main peak with desired MS was detected. The reaction mixture was quenched by addition sat.$NaHCO_3$ (30 mL), and extracted with EA (30 mL*3). The combined organic layers were washed with brine (30 mL*2), dried with anhydrous $Na_2SO_4$, filtered and concentrated in vacuum. The residue was purified by flash silica gel chromatography to provide 8-2 (750 mg, 2.3 mmol, 113% yield). LCMS (ESI): RT=0.829 min, mass calcd. For $C_{13}H_{18}BrNO_2S$, 331.02 m/z found 331.9[M+H]$^+$ and 333.9 [M+H+2]$^+$.

Step 2: N-cyclohexyl-4-methylsulfonyl-2-(4,4,5,5-tetramethyl-1,3,2-dioxaborolan-2-yl)aniline To a mixture of 8-2 (390 mg, 1.2 mmol, 1.0 eq) and 8-2a (594 mg, 2.3 mmol, 2.00 eq) in dioxane (7 mL) was added AcOK (344 mg, 3.5 mmol, 3.00 eq) in one portion at 14° C. under $N_2$. The mixture was degassed under vacuum and purged with $N_2$ for 3 times. The resulted mixture was stirred at 100° C. under $N_2$ for 16 hour. LCMS showed the starting material was consumed completely and one main peak with desired MS was detected. TLC showed many new spots were formed. The reaction mixture was filtered and concentrated under reduced pressure to give a residue. The residue was purified by flash silica gel chromatography to provide 8-3 (400 mg, 0.74 mmol, 63.1% yield) which was used next step without further purification. LCMS (ESI): RT=0.931 min, mass calcd. For $C_{19}H_{30}BNO_4S$, 379.20 m/z found 380.1 [M+H]$^+$.

Step 3: N-cyclohexyl-2-(1-methylpyrazol-3-yl)-4-methylsulfonyl-aniline

To a mixture of 8-3 (80 mg, 0.21 mmol, 1.0 eq) and 8-3a (44 mg, 0.27 mmol, 1.3 eq) in dioxane (3 mL) and $H_2O$ (0.15 mL) was added $Na_2CO_3$ (44 mg, 0.42 mmol, 2.0 eq) and Pd(dppf)$Cl_2$ (16 mg, 21 umol, 0.1 eq) in one portion under $N_2$. The mixture was stirred at 100° C. for 16 h. LCMS showed the starting material was consumed completely and one peak with desired MS was detected. The reaction mixture was concentrated under reduced pressure to remove solvent, and then added $CH_3CN$ (5 mL), filtered to give a black-brown liquid. The residue was purified by prep-HPLC. LCMS and $^1$H NMR confirmed that Compound 8 was obtained (2.20 mg, 6.4 umol, 3.0% yield). LCMS (ESI): RT=0.835 min, mass calcd. For $C_{17}H_{23}N_3O_2S$, 333.15 m/z found 333.9[M+H]$^+$. $^1$H NMR (400 MHz, CDCl$_3$) δ 8.44 (br d, J=7.20 Hz, 1H), 8.04 (s, 1H), 7.64 (br d, J=8.00 Hz, 1H), 7.41 (br s, 1H), 6.76 (br d, J=8.80 Hz, 1H), 6.68 (s, 1H), 3.96 (s, 3H), 3.54 (br s, 1H), 3.04 (s, 3H), 2.10-2.00 (m, 2H), 1.87-1.75 (m, 2H), 1.68-1.55 (m, 2H), 1.50-1.42 (m, 3H).

Example 9: N-cyclohexyl-4-(methylsulfonyl)-2-(1H-1,2,3-triazol-1-yl)aniline (Compound 9) and N-cyclohexyl-4-(methylsulfonyl)-2-(2H-1,2,3-triazol-2-yl)aniline (Compound 13)

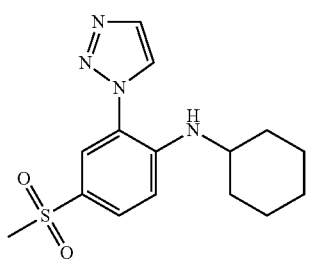

Compound 9

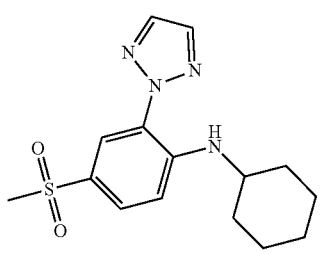 [SMILES: CS(=O)(=O)c1ccc(NC2CCCCC2)c(-n2cccn2)c1]

Compound 13

Preparation of Compound 9 and Compound 13:

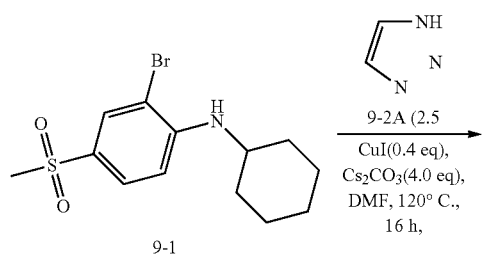

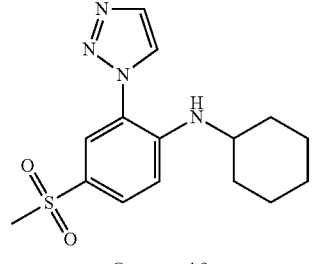

To a mixture of compound 9-1 (50 mg, 0.15 mmol, 1.0 eq), $Cs_2CO_3$ (196 mg, 0.60 mmol, 4.0 eq) and compound 9-2A (26 mg, 0.38 mmol, 22 uL, 2.5 eq) in DMF (2 mL) was added CuI (11 mg, 60 umol, 0.4 eq). The reaction mixture was heated at 120° C. for 16 hour under $N_2$. LCMS and HPLC showed 18%+14% desired compound was found (m/z=320.9; RT: 0.743 and 0.834 min) and the starting material was consumed completely. The reaction mixture was poured into water (5 mL) and stirred for 5 min. The aqueous phase was extracted with ethyl acetate (5 mL*3). The combined organics phase were washed with brine (5 mL*2), dried with anhydrous $Na_2SO_4$, filtered and concentrated in vacuum to give a residue. The residue was purified by prep-HPLC to give Compound 9 (7 mg, 22 umol, 15% yield) and Compound 13 (6 mg, 19 umol, 12% yield).

Compound 9: LCMS (ESI): RT=0.754 min, mass calc. for $C_{15}H_{20}N_4O_2S$ 320.13, m/z found 320.9 [M+H]$^+$; $^1$HNMR (400 MHz, CDCl$_3$) δ 7.93 (d, J=6.3 Hz, 2H), 7.80 (dd, J=1.9, 8.9 Hz, 1H), 7.75 (d, J=2.0 Hz, 1H), 6.92 (d, J=9.0 Hz, 1H), 6.27 (d, J=7.3 Hz, 1H), 3.50-3.39 (m, 1H), 3.05 (s, 3H), 2.01 (d, J=11.5 Hz, 2H), 1.82-1.71 (m, 2H), 1.69-1.61 (m, 1H), 1.46-1.35 (m, 2H), 1.34-1.23 (m, 3H).

Compound 13: LCMS (ESI): RT=0.830 min, mass calc. for $C_{15}H_2N_4O_2S$ 320.13, m/z found 320.9 [M+H]$^+$; HNMR (400 MHz, CDCl$_3$) δ 8.51 (d, J=2.0 Hz, 1H), 7.86 (s, 2H), 7.73 (dd, J=1.9, 8.7 Hz, 2H), 6.89 (d, J=9.0 Hz, 1H), 3.56-3.45 (m, 1H), 3.07 (s, 3H), 2.06 (d, J=11.5 Hz, 2H), 1.79 (dd, J=3.9, 9.2 Hz, 2H), 1.71-1.62 (m, 1H), 1.48-1.30 (m, 5H).

Example 10: N-cyclohexyl-4-(methylsulfonyl)-2-(1H-pyrazol-1-yl)aniline (Compound 10)

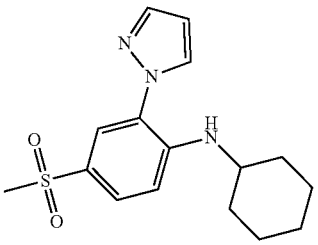

Preparation of Compound 10:

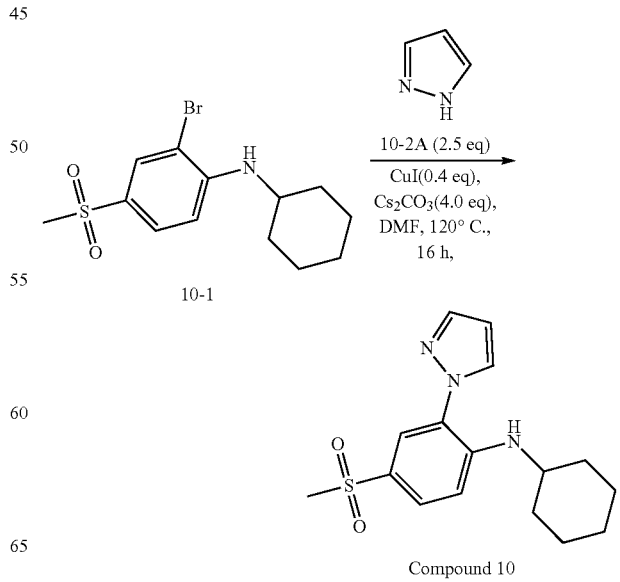

To a mixture of compound 10-1 (100 mg, 0.3 mmol, 1.0 eq), Cs$_2$CO$_3$ (392 mg, 1.2 mmol, 4.0 eq) and compound 10-2a (51 mg, 0.75 mmol, 2.5 eq) in DMF (2 mL) was added CuI (23 mg, 0.12 mmol, 0.4 eq). The reaction mixture was heated at 120° C. for 16 hour under N$_2$. LCMS showed 88% desired compound was found (m/z=320.0; RT: 0.803 min) and the starting material was consumed completely. The reaction mixture was poured into water (5 mL) and stirred for 5 min. The aqueous phase was extracted with ethyl acetate (5 mL*3). The combined organics phase were washed with brine (5 mL*2), dried with anhydrous Na$_2$SO$_4$, filtered and concentrated in vacuum to give a residue. The residue was purified by prep-HPLC to give Compound 10 (50 mg, 0.16 mmol, 52% yield). LCMS (ESI): RT=0.820 min, mass calc. for C$_{16}$H$_{21}$N$_3$O$_2$S 319.14, m/z found 319.9 [M+H]$^+$; $^1$H NMR (400 MHz, CDCl$_3$) δ 7.78 (s, 2H), 7.74-7.68 (m, 2H), 6.82 (d, J=8.5 Hz, 1H), 6.72 (d, J=7.3 Hz, 1H), 6.50 (t, J=2.0 Hz, 1H), 3.47-3.37 (m, 1H), 3.03 (s, 3H), 2.05-1.96 (m, 2H), 1.79-1.70 (m, 2H), 1.68-1.60 (m, 1H), 1.46-1.25 (m, 5H).

Example 11: N-cyclohexyl-2-(1H-imidazol-1-yl)-4-(methylsulfonyl)aniline (Compound 11)

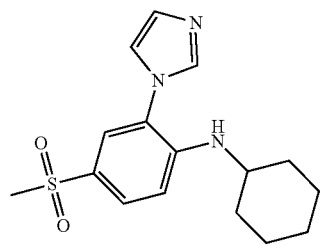 [SMILES: CS(=O)(=O)c1ccc(NC2CCCCC2)c(-n2ccnc2)c1]

Preparation of Compound 11:

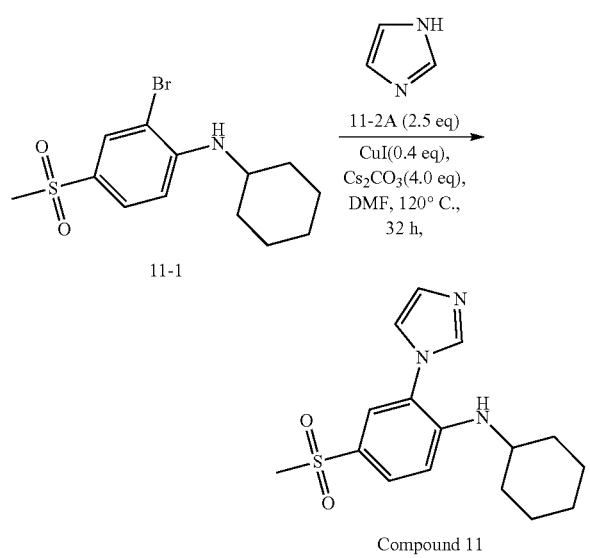

Compound 11

To a mixture of compound 11-1 (50 mg, 0.15 mmol, 1.0 eq), compound 11-2A (26 mg, 0.38 mmol, 2.5 eq), and Cs$_2$CO$_3$ (196 mg, 0.60 mmol, 4.0 eq) in DMF (2 mL) was added CuI (15 mg, 60 umol, 0.4 eq). The reaction mixture was heated at 120° C. for 32 hour under N$_2$. LCMS showed 50% of desired compound was found (m/z=319.9; RT: 0.642 min) and 39% of the starting material was remained. The reaction mixture was poured into water (5 mL) and stirred for 5 min. The aqueous phase was extracted with ethyl acetate (5 mL*3). The combined organics phase were washed with brine (5 mL*2), dried with anhydrous Na$_2$SO$_4$, filtered and concentrated in vacuum to give a residue. The residue was purified by HPLC to give Compound 11 (20 mg, 61 umol, 40% yield). LCMS (ESI): RT=0.649 min, mass calc. for C$_{16}$H$_{21}$N$_3$O$_2$S 319.14, m/z found 319.9 [M+H]$^+$; $^1$HNMR (400 MHz, CDCl$_3$) δ 7.82 (dd, J=2.0, 8.8 Hz, 1H), 7.65 (d, J=2.0 Hz, 1H), 7.62 (s, 1H), 7.31 (s, 1H), 7.08 (s, 1H), 6.82 (d, J=8.8 Hz, 1H), 4.03 (d, J=7.5 Hz, 1H), 3.42-3.31 (m, 1H), 3.05 (s, 3H), 1.95 (d, J=12.3 Hz, 2H), 1.71 (d, J=13.6 Hz, 2H), 1.64 (d, J=13.3 Hz, 1H), 1.44-1.32 (m, 2H), 1.27-1.08 (m, 3H).

Example 12: N-cyclohexyl-4-(methylsulfonyl)-2-(1H-1,2,4-triazol-1-yl)aniline (Compound 12)

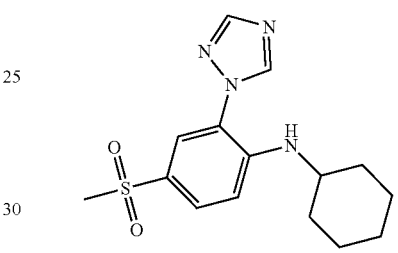

Preparation of Compound 12:

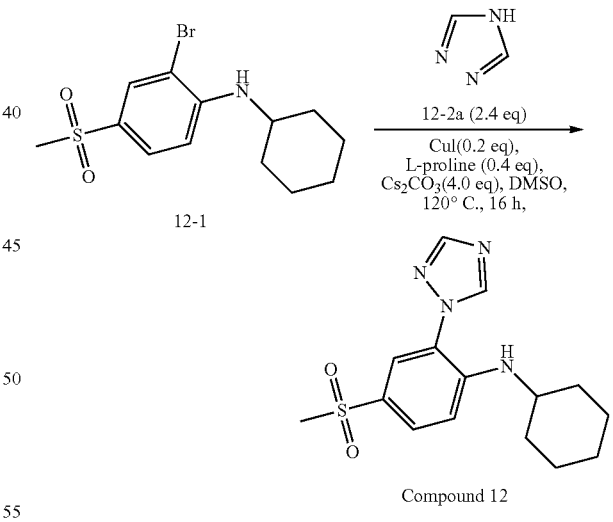

Compound 12

To a mixture of compound 12-1 (50 mg, 0.15 mmol, 1.0 eq), Cs$_2$CO$_3$ (196 mg, 0.60 mmol, 4.0 eq) and compound 12-2a (25 mg, 0.36 mmol, 2.4 eq) in DMSO (2 mL) was added CuI (6 mg, 30 umol, 0.2 eq) and L-PROLINE (7 mg, 60 umol, 0.4 eq). The reaction mixture was heated at 120° C. for 16 hour under N$_2$. LCMS showed desired compound was found and the starting material was remained. The reaction mixture was poured into water (5 mL) and stirred for 5 min. The aqueous phase was extracted with ethyl acetate (5 mL*3). The combined organics phase were washed with brine (8 mL), dried with anhydrous Na$_2$SO$_4$, filtered and concentrated in vacuum to give a crude product. The crude product was combined and purified by prep-TLC to give Compound 12 (35 mg, 0.1 mmol, 34% yield). LCMS (ESI): RT=0.732 min, mass calc. for $C_{15}H_{20}N_4O_2S$ 320.13, m/z found 320.9 [M+H]$^+$; $^1$HNMR (400 MHz, CDCl$_3$) δ 8.43 (s, 1H), 8.21 (s, 1H), 7.80 (dd, J=2.0, 8.8 Hz, 1H), 7.73 (d, J=2.0 Hz, 1H), 6.87 (d, J=9.0 Hz, 1H), 6.08 (d, J=7.5 Hz, 1H), 3.48-3.37 (m, 1H), 3.05 (s, 3H), 2.00 (d, J=11.0 Hz, 2H), 1.80-1.70 (m, 2H), 1.65 (d, J=12.5 Hz, 1H), 1.47-1.36 (m, 2H), 1.28 (d, J=11.0 Hz, 3H).

Example 13: 4-(cyclohexylamino)-3-(2-ethyl-2H-tetrazol-5-yl)-N-methylbenzenesulfonamide (Compound 14)

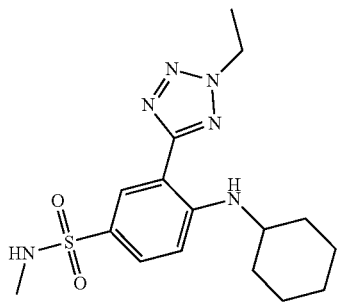 [SMILES: CCn1nnc(-c2cc(S(=O)(=O)NC)ccc2NC2CCCCC2)n1]

Preparation of Compound 14:

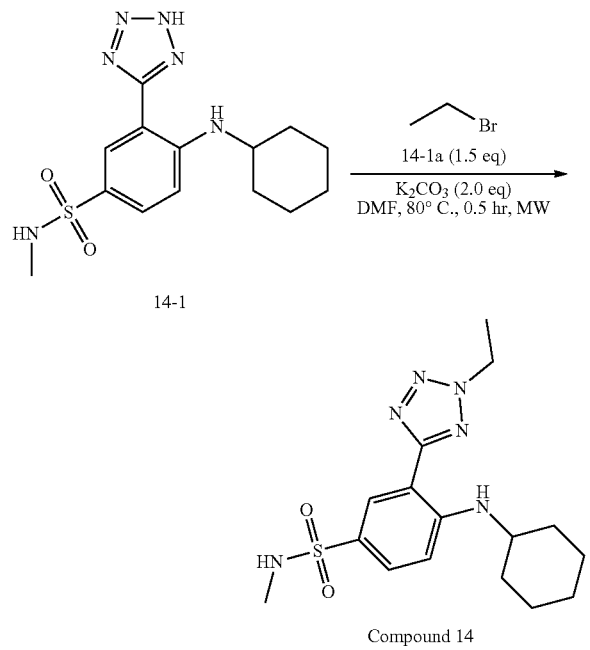

Compound 14

To the solution of compound 14-1 (30 mg, 89 umol, 1.0 eq) in DMF (4 mL) was added compound 14-1a (15 mg, 0.1 mmol, 10 uL, 1.5 eq) and K$_2$CO$_3$ (24.65 mg, 0.18 mmol, 2.0 eq). The mixture was stirred at 80° C. for 0.5 hr under microwave. The reaction was monitored by LCMS. The reaction was concentrated under reduced pressure. The residue was purified by prep-HPLC to give Compound 14 (6.13 mg, 16.8 umol, 18.9% yield). LCMS (ESI): RT=0.850 min, mass calcd. for $C_{16}H_{24}N_6O_2S$ 364.17, m/z found 365.0 [M+H]$^+$, $^1$H NMR (400 MHz, DMSO-d$_6$) δ 8.41 (d, J=2.3 Hz, 1H), 7.66-7.63 (m, 2H), 7.25 (br, 1H), 7.04 (d, J=9.0 Hz, 1H), 4.82 (q, J=7.4 Hz, 2H), 3.64-3.63 (m, 1H), 2.38 (s, 3H), 2.04-1.94 (m, 2H), 1.77-1.67 (m, 2H), 1.60 (t, J=7.3 Hz, 3H), 1.51-1.23 (m, 6H).

Example 14: 4-(cyclohexylamino)-N-methyl-3-(2-propyl-2H-tetrazol-5-yl)benzenesulfonamide (Compound 15)

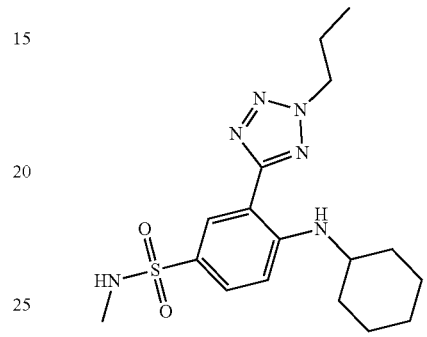

Preparation of Compound 15:

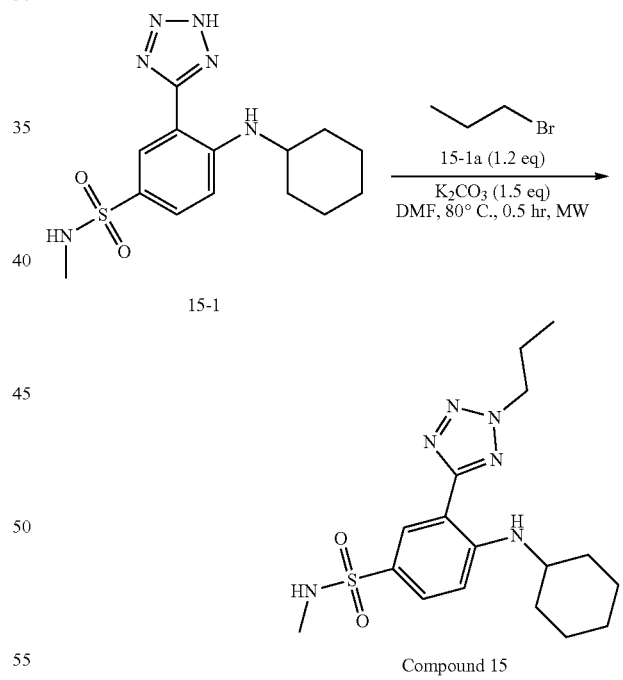

Compound 15

To the solution of 15-1 (30 mg, 89 umol, 1.0 eq) in DMF (4 mL) was added compound 15-1a (12 mg, 98 umol, 9 uL, 1.1 eq) and K$_2$CO$_3$ (18 mg, 0.1 mmol, 1.5 eq). The mixture was stirred at 80° C. for 0.5 hr under microwave. The reaction was monitored by LCMS. The reaction was concentrated under reduced pressure. The residue was purified by prep-HPLC to give Compound 15 (3.06 mg, 8.1 umol, 9.1% yield). LCMS (ESI): RT=0.885 min, mass calcd. for $C_{17}H_{26}N_6O_2S$ 378.18, m/z found 379.1 [M+H]$^+$, $^1$HNMR (400 MHz, DMSO-d$_6$) δ 8.42 (s, 1H), 7.69-7.60 (m, 2H), 7.28-7.19 (m, 1H), 7.05 (d, J=8.8 Hz, 1H), 4.76 (t, J=6.8 Hz, 2H), 3.69-3.58 (m, 1H), 2.38 (d, J=5.0 Hz, 3H), 2.08-1.95 (m, 4H), 1.77-1.68 (m, 2H), 1.64-1.54 (m, 1H), 1.46-1.23 (m, 5H), 0.91 (t, J=7.3 Hz, 3H).

Example 15: 4-(cyclohexylamino)-3-(2-(4-fluorophenyl)-2H-tetrazol-5-yl)-N-methylbenzenesulfonamide (Compound 16)

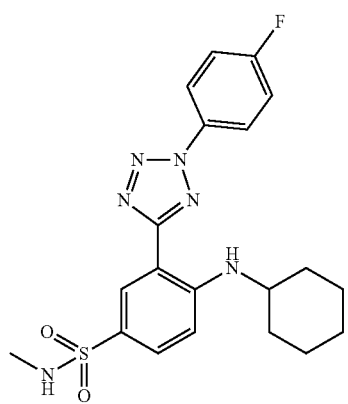 [SMILES: CNS(=O)(=O)c1ccc(NC2CCCCC2)c(-c2nnn(-c3ccc(F)cc3)n2)c1]

Preparation of Compound 16:

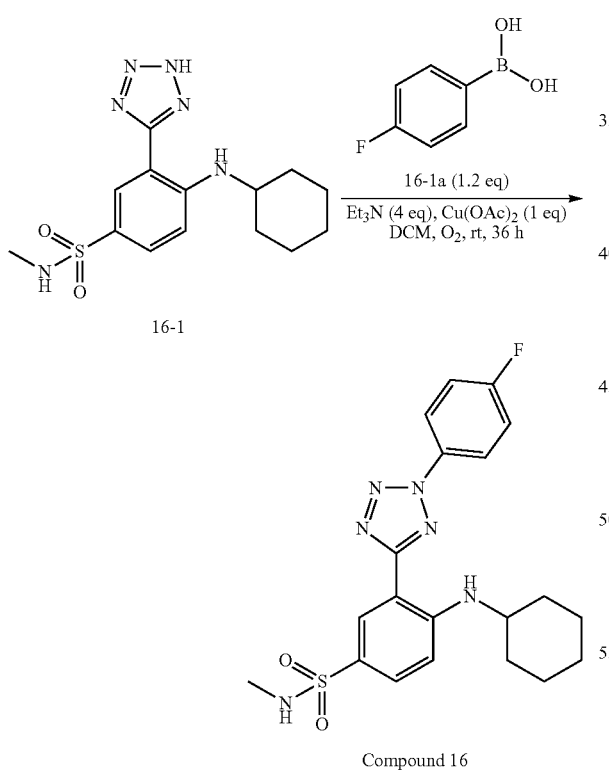

Compound 16

A mixture of compound 16-1 (50 mg, 0.13 mmol, 1.00 eq, HCl), (4-fluorophenyl)boronic acid (24.4 mg, 0.17 mmol, 1.30 eq), DIEA (69.3 mg, 0.54 mmol, 93.7 uL, 4.0 eq) and Cu(OAc)$_2$ (24.4 mg, 0.13 mmol, 1.0 eq) was degassed under vacuum and purged with O2 several times. The mixture was stirred at 20° C. for 20 hr. LCMS showed that starting material was remained and no desired MS signal was detected. Additional of (4-fluorophenyl)boronic acid (24.4 mg, 0.17 mmol, 1.30 eq) was added. The reaction was stirred at 20° C. for 16 hr. LCMS showed that desired MS signal was detected. The reaction was filtered and concentrated. The residue was purified by Prep HPLC to give Compound 16 (3.10 mg, 7.1 umol, 5.3% yield). $^1$HNMR and LCMS confirmed that desired product was obtained. LCMS (ESI): RT=0.890 min, mass calcd. for $C_{20}H_{23}N_6SO_2F$ 430.16, m/z found 431.1 [M+H]$^+$. $^1$H NMR (400 MHz, CDCl$_3$) δ 8.73 (d, J=2.4 Hz, 1H), 8.25-8.10 (m, 2H), 7.90-7.80 (m, 1H), 7.76 (dd, J=8.8 Hz, 2.4 Hz, 1H), 7.40-7.25 (m, 2H), 6.86 (d, J=9.2 Hz, 1H), 4.40-4.25 (m, 1H), 3.65-3.50 (m, 1H), 2.69 (d, J=5.6 Hz, 3H), 2.10-2.00 (m, 2H), 1.90-1.75 (m, 2H), 1.75-1.65 (m, 2H), 1.50-1.40 (m, 4H).

Example 16: 3-(2-cyclobutyl-2H-tetrazol-5-yl)-4-(cyclohexylamino)-N-methylbenzene sulfonamide (Compound 17)

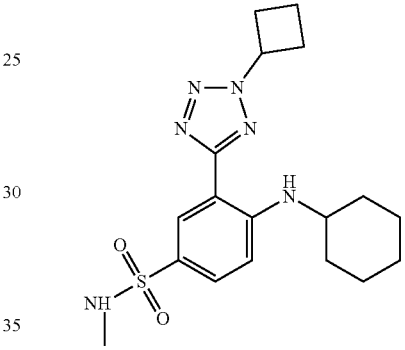

Preparation of Compound 17:

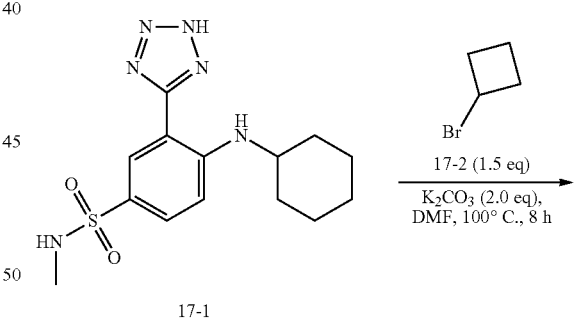

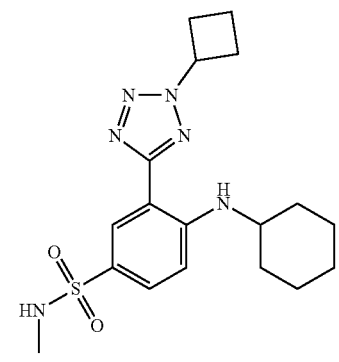 [SMILES: CNS(=O)(=O)c1ccc(NC2CCCCC2)c(-c2nnn(C3CCC3)n2)c1]

Compound 17

To a solution of compound 17-1 (30.0 mg, 89.2 umol, 1.0 eq) in DMF (2.0 mL) was added K$_2$CO$_3$ (24.7 mg, 0.18 mmol, 2.0 eq) and compound 17-2 (18.1 mg, 0.13 mmol, 12.6 uL, 1.5 eq). The mixture was stirred at 100° C. for 16 hour at N$_2$ atmosphere. LCMS showed desired compound was found. The reaction was filtered to give a crude product. The crude product was purified by prep-HPLC to give Compound 17 (2.01 mg, 5.2 umol, 5.8% yield). LCMS (ESI): RT=0.900 min, mass calc. for C$_{18}$H$_{26}$N$_6$O$_2$S 390.18, m/z found 391.1 [M+H]$^+$; $^1$HNMR (400 MHz, CDCl$_3$) δ 8.64 (d, J=2.3 Hz, 1H), 7.89 (d, J=7.0 Hz, 1H), 7.73 (dd, J=2.1, 8.9 Hz, 1H), 6.82 (d, J=9.0 Hz, 1H), 5.42 (q, J=8.3 Hz, 1H), 4.26 (q, J=5.3 Hz, 1H), 3.55 (s, 1H), 2.90-2.79 (m, 2H), 2.67 (d, J=5.3 Hz, 5H), 2.16-1.99 (m, 4H), 1.87-1.77 (m, 2H), 1.66 (d, J=11.5 Hz, 1H), 1.51-1.35 (m, 5H).

Example 17: 4-(cyclohexylamino)-3-(2-cyclopentyl-2H-tetrazol-5-yl)-N-methylbenzenesulfonamide (Compound 18)

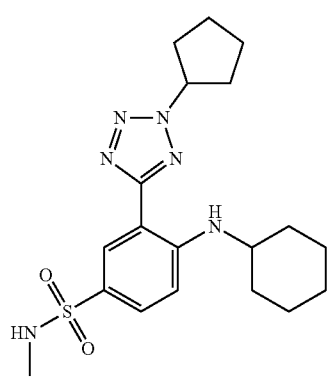 [SMILES: CNS(=O)(=O)c1ccc(NC2CCCCC2)c(-c2nnn(C3CCCC3)n2)c1]

Preparation of Compound 18:

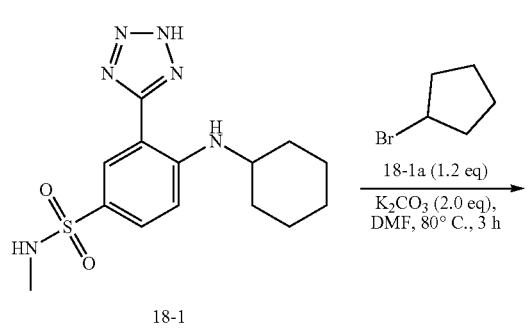

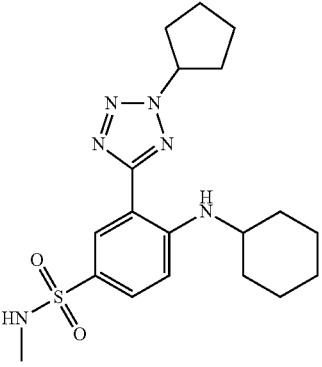

Compound 18

To a stirred solution of compound 18-1 (50 mg, 0.15 mmol, 1.0 eq) and K$_2$CO$_3$ (41 mg, 0.30 mmol, 2.0 eq) in DMF (1 mL) was compound 18-1a (27 mg, 0.18 mmol, 19 uL, 1.2 eq). The resulted mixture was heated to 80° C. for 3 hours. LCMS showed 80% desired compound was found and the starting material was consumed completely. The mixture was cooled. The reaction was diluted with DMF (2 mL), filtered to give a mixture. The mixture was purified by prep-HPLC to give Compound 18 (30 mg, 74 umol, 50% yield). LCMS (ESI): RT=0.879 min, mass calc. for C$_{19}$H$_{28}$N$_6$O$_2$S 404.20, m/z found 405.1 [M+H]$^+$; $^1$H NMR (400 MHz, DMSO-d$_6$) δ 8.41 (d, J=2.0 Hz, 1H), 7.70-7.56 (m, 2H), 7.24 (d, J=5.0 Hz, 1H), 7.04 (d, J=9.0 Hz, 1H), 5.50-5.39 (m, 1H), 3.64 (d, J=4.3 Hz, 1H), 2.38 (d, J=5.0 Hz, 3H), 2.29 (td, J=6.8, 13.4 Hz, 2H), 2.23-2.10 (m, 2H), 1.99 (d, J=9.5 Hz, 2H), 1.90-1.67 (m, 6H), 1.58 (s, 1H), 1.51-1.30 (m, 5H).

Example 18: 4-(cyclohexylamino)-3-(2-(2-fluorobenzyl)-2H-tetrazol-5-yl)-N-methylbenzenesulfonamide (Compound 19)

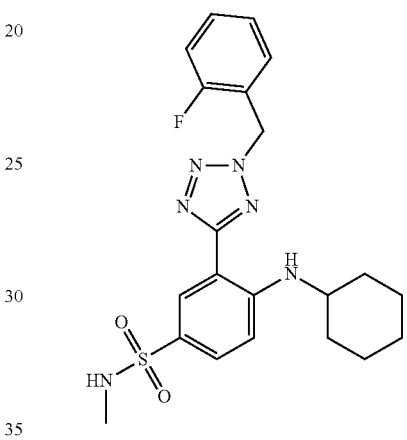

Preparation of Compound 19:

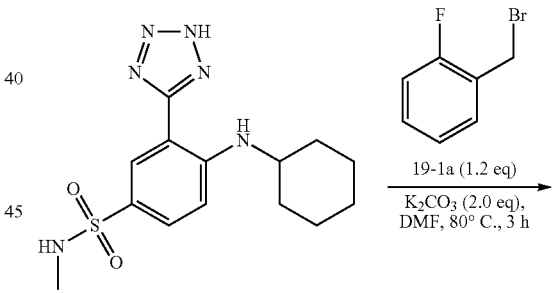

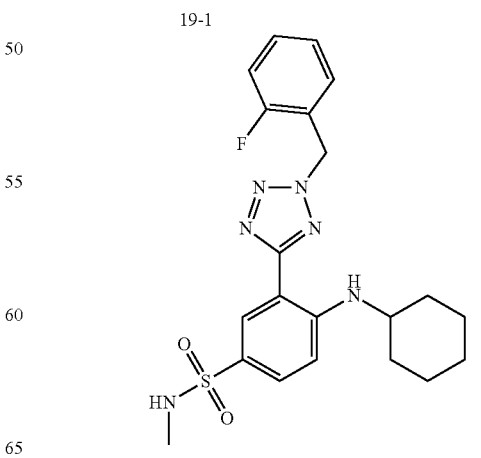

Compound 19

-continued

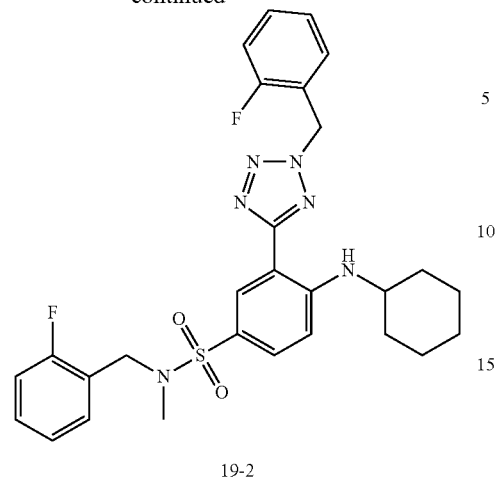

19-2

To a stirred solution of compound 19-1 (50 mg, 0.15 mmol, 1.0 eq) and K₂CO₃ (41 mg, 0.30 mmol, 2.0 eq) in DMF (1 mL) was added compound 19-1a (34 mg, 0.18 mmol, 21 uL, 1.2 eq). The resulted mixture was heated at 80° C. for 3 hour. Reaction was monitored by LCMS and the starting material was consumed completely. The mixture was cooled and diluted with DMF (2 mL), filtered to give a mixture. The mixture was purified by prep-HPLC to give the Compound 19 (20 mg, 42.7 umol, 29% yield) and 19-2 crude (12 mg). The crude 19-2 was re-purified by prep-HPLC (7 mg, 11.9 umol, 7.99% yield, HCl salt).

Compound 19: LCMS (ESI): RT=0.879 min, mass calc. for $C_{21}H_{25}FN_6O_2S$ 444.17, m/z found 405.1 [M+H]⁺; ¹H NMR (400 MHz, DMSO-d₆) δ 8.40 (d, J=2.3 Hz, 1H), 7.64 (dd, J=2.0, 8.8 Hz, 1H), 7.59 (t, J=7.7 Hz, 1H), 7.54-7.45 (m, 2H), 7.34-7.21 (m, 3H), 7.02 (d, J=9.0 Hz, 1H), 6.11 (s, 2H), 3.68-3.55 (m, 1H), 2.36 (d, J=5.0 Hz, 3H), 1.92 (d, J=9.5 Hz, 2H), 1.62 (s, 2H), 1.56 (d, J=11.5 Hz, 1H), 1.47-1.35 (m, 2H), 1.34-1.20 (m, 3H).

Example 19: 3-(2-benzyl-2H-tetrazol-5-yl)-4-(cyclohexylamino)-N-methylbenzenesulfonamide (Compound 20)

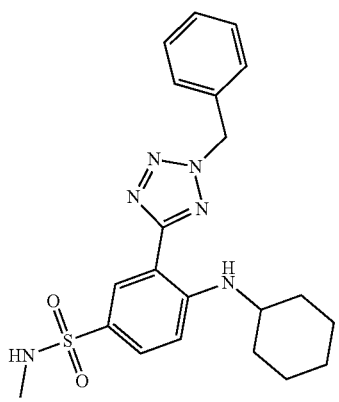 [SMILES: CNS(=O)(=O)c1ccc(NC2CCCCC2)c(-c2nnn(Cc3ccccc3)n2)c1]

Preparation of Compound 20:

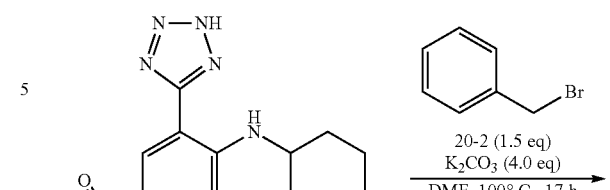

20-1

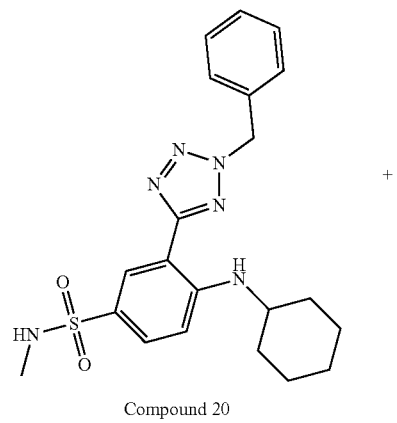

Compound 20

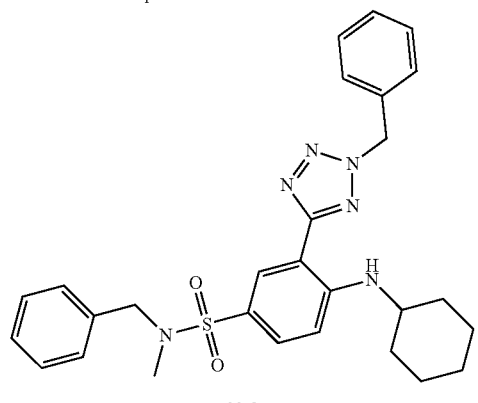

20-3

To a mixture of 20-1 (30.0 mg, 80.5 umol, 1.0 eq, HCl) and K₂CO₃ (44.5 mg, 0.3 mmol, 4.0 eq) in DMF (3.0 mL), was added 20-2 (20.6 mg, 0.1 mmol, 14 uL, 1.5 eq). The resulted mixture was stirred at 100° C. under N₂ for 17 h. LCMS showed the reaction was completed. The mixture was filtered, and the solid was washed with DMF (1 mL). The filtrate was purified by prep-HPLC. Compound 20 (2.07 mg, 4.8 umol, 6.0% yield) was obtained, which was confirmed by LCMS, ¹H NMR and NOE. LCMS (ESI): RT=0.906 min, mass calcd. for $C_{21}H_{26}N_6O_2S$ 426.18, m/z found 427.1 [M+H]⁺. ¹H NMR (400 MHz, DMSO-d₆) δ 8.39 (d, J=2.3 Hz, 1H), 7.63 (dd, J=2.0, 9.0 Hz, 1H), 7.54 (d, J=7.3 Hz, 1H), 7.47-7.37 (m, 5H), 7.20 (s, 1H), 7.02 (d, J=9.0 Hz, 1H), 6.05 (s, 2H), 3.66-3.58 (m, 1H), 2.36 (s, 3H), 1.98-1.89 (m, 2H), 1.70-1.61 (m, 2H), 1.61-1.51 (m, 1H), 1.48-1.37 (m, 2H), 1.35-1.25 (m, 3H).

Compound 20-3 (7.54 mg, 14.6 umol, 18.1% yield) was obtained, which was confirmed by LCMS and ¹H NMR. LCMS (ESI): RT=1.029 min, mass calcd. for $C_2H_{32}N_6O_2S$ 516.23, m/z found 517.2 [M+H]⁺. ¹H NMR (400 MHz, CDCl₃) δ 8.61 (d, J=2.3 Hz, 1H), 7.79 (d, J=7.0 Hz, 1H), 7.70 (dd, J=2.1, 8.9 Hz, 1H), 7.48-7.37 (m, 5H), 7.35-7.28 (m, 5H), 6.83 (d, J=9.3 Hz, 1H), 5.83 (s, 2H), 4.14 (s, 2H), 3.58-3.50 (m, 1H), 2.59 (s, 3H), 2.09-2.01 (m, 2H), 1.84-1.75 (m, 2H), 1.70-1.62 (m, 1H), 1.47-1.41 (m, 3H).

Example 20: 3-(2-butyltetrazol-5-yl)-4-(cyclohexylamino)-N-methyl-benzenesulfonamide (Compound 21)

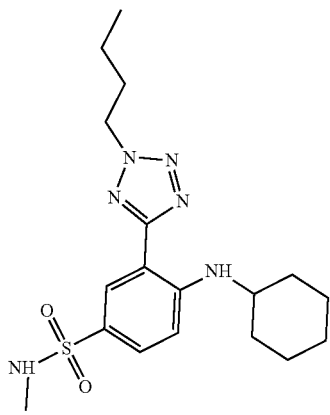 [SMILES: CCCCn1nnc(-c2cc(S(=O)(=O)NC)ccc2NC2CCCCC2)n1]

Preparation of Compound 21:

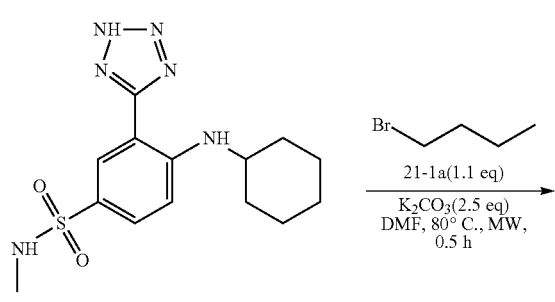

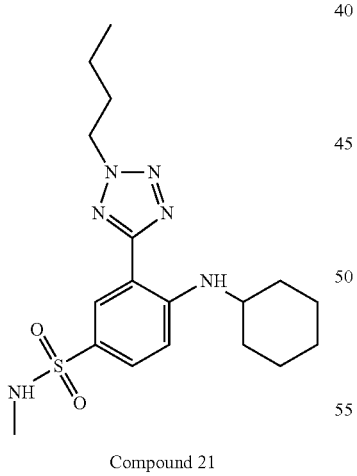

Compound 21

To a solution of 21-1 (50.0 mg, 0.1 mmol, 1.0 eq) in DMF (3.0 mL) was added K₂CO₃ (41.0 mg, 0.3 mmol, 2.0 eq) and 1-bromobutane (20.3 mg, 0.1 mmol, 16.0 uL, 1.0 eq). The mixture was stirred at 80° C. under microwave condition for 0.5 hour. LCMS showed 23% of 21-1 was remained. Several new peaks were shown on LCMS and 68% of desired compound was detected. The residue was purified by prep-HPLC to give Compound 21 (12.91 mg, 32.9 umol, 22% yield). LCMS (ESI): RT=0.872 min, mass calc. for $C_{18}H_{28}N_6O_2S$ 392.20, m/z found 393.1 [M+Na]⁺; ¹HNMR (400 MHz, CDCl₃) δ 8.62 (d, J=2.3 Hz, 1H), 7.84 (d, J=7.0 Hz, 1H), 7.74-7.71 (m, 1H), 6.82 (d, J=9.0 Hz, 1H), 4.69 (t, J=7.0 Hz, 2H), 4.23 (q, J=5.4 Hz, 1H), 3.55 (s, 1H), 2.67 (d, J=5.5 Hz, 3H), 2.13-2.01 (m, 4H), 1.88-1.78 (m, 2H), 1.67 (d, J=11.8 Hz, 1H), 1.49-1.36 (m, 7H), 1.00 (t, J=7.4 Hz, 3H).

Example 21: 4-(cyclohexylamino)-N-methyl-3-(2-methyl-2H-tetrazol-5-yl)benzenesulfonamide (Compound 22)

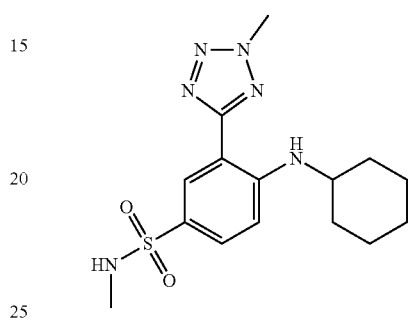

Preparation of Compound 22:

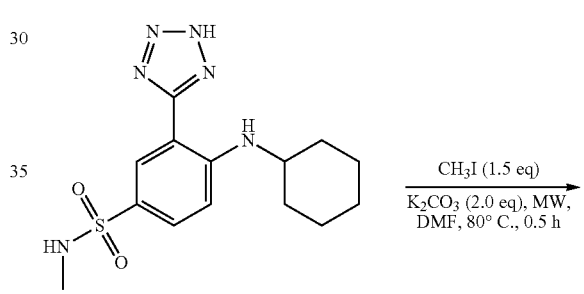

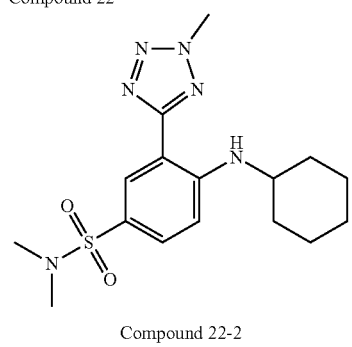

Compound 22

Compound 22-2

Compound 22-1 (50.0 mg, 0.15 mmol, 1.0 eq), CH₃I (31.6 mg, 0.22 mmol, 13.9 uL, 1.5 eq) and K₂CO₃ (41.1 mg, 0.30 mmol, 2.0 eq) were taken up into a microwave tube in DMF (2.0 mL). The sealed tube was heated at 100° C. for 0.5 hour under microwave. LCMS showed desired compound was found. The reaction was filtered to give a crude product. The crude product was purified by prep-HPLC to give two products. Compound 22 (14.5 mg, 41.3 umol, 27.8% yield) was obtained. LCMS (ESI): RT=0.773 min, mass calc. for $C_{15}H_{22}N_6O_2S$ 350.15, m/z found 351.1 [M+H]⁺; ¹HNMR (400 MHz, CDCl₃) δ 8.61 (d, J=2.3 Hz, 1H), 7.79-7.70 (m, 2H), 6.82 (d, J=9.0 Hz, 1H), 4.43 (s, 3H), 4.27 (q, J=5.5 Hz, 1H), 3.59-3.49 (m, 1H), 2.67 (d, J=5.5 Hz, 3H), 2.13-2.04 (m, 2H), 1.86-1.78 (m, 2H), 1.67 (d, J=11.8 Hz, 1H), 1.51-1.36 (m, 5H).

Compound 22-2 (2.3 mg, 6.4 umol, 4.3% yield) was obtained. LCMS (ESI): RT=0.828 min, mass calc. for $C_{16}H_{24}N_6O_2S$ 364.17, m/z found 365.1 [M+H]⁺; ¹HNMR (400 MHz, CDCl₃) δ 8.53 (d, J=2.3 Hz, 1H), 7.77 (d, J=7.3 Hz, 1H), 7.66 (dd, J=2.1, 8.9 Hz, 1H), 6.83 (d, J=9.0 Hz, 1H), 4.44 (s, 3H), 3.54 (s, 1H), 2.72 (s, 6H), 2.09 (s, 2H), 1.82 (s, 2H), 1.66 (s, 1H), 1.52-1.40 (m, 5H).

Example 22: 4-(cyclohexylamino)-3-(2-(2-fluorophenyl)-2H-tetrazol-5-yl)-N-methylbenzenesulfonamide (Compound 23)

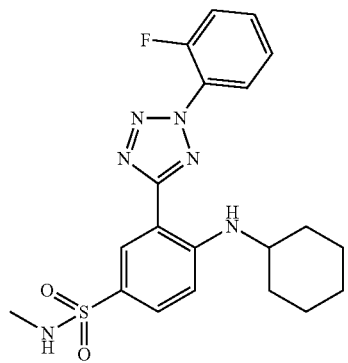 [SMILES: CNS(=O)(=O)c1ccc(NC2CCCCC2)c(-c2nnn(-c3ccccc3F)n2)c1]

Preparation of Compound 23:

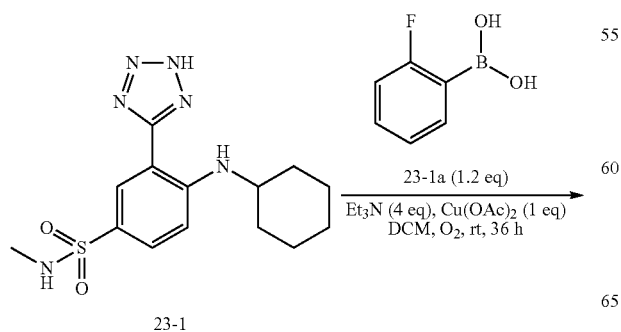

23-1

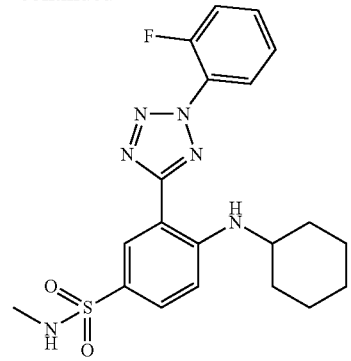

Compound 23

A mixture of compound 23-1 (50 mg, 0.13 mmol, 1.00 eq, HCl), 23-1a (28.1 mg, 0.2 mmol, 1.5 eq) DIEA (69.3 mg, 0.54 mmol, 93.7 uL, 4.0 eq) and Cu(OAc)₂ (36.5 mg, 0.2 mmol, 1.5 eq) was degassed under vacuum and purged with O₂ several times. The mixture was stirred at 20° C. for 20 hr. LCMS showed that starting material was remained and no desired MS signal was detected. Additional of 23-1a (28.1 mg, 0.2 mmol, 1.5 eq) was added. The reaction was stirred at 20° C. for another 16 hr. LCMS showed that 10% of desired MS signal was detected. The reaction was filtered and concentrated. The residue was purified by prep-HPLC to give Compound 23 (1.90 mg, 4.4 umol, 3.3% yield). LCMS (ESI): RT=0.884 min, mass calcd. for $C_{20}H_{23}N_6SO_2F$ 430.16, m/z found 431.1 [M+H]⁺. ¹H NMR (400 MHz, CDCl₃) δ 8.49 (d, J=2.4 Hz, 1H), 8.07 (d, J=7.6 Hz, 1H), 7.75-7.55 (m, 3H), 7.55-7.45 (m, 2H), 7.30-7.20 (m, 1H), 7.07 (d, J=9.2 Hz, 1H), 3.60-3.50 (m, 1H), 2.36 (d, J=5.2 Hz, 3H), 2.10-2.00 (m, 2H), 1.90-1.75 (m, 2H), 1.75-1.65 (m, 1H), 1.50-1.40 (m, 5H).

Example 23: tert-butyl 3-(5-(2-(cyclohexylamino)-5-(N-methylsulfamoyl)phenyl)-2H-tetrazol-2-yl) pyrrolidine-1-carboxylate (Compound 24)

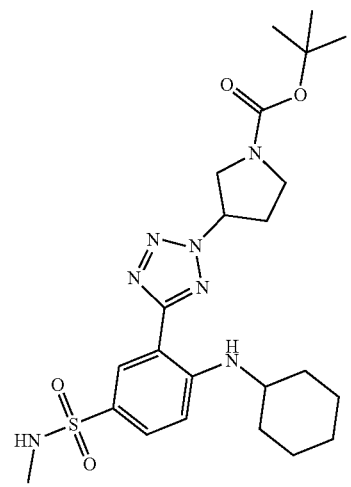 [SMILES: CNS(=O)(=O)c1ccc(NC2CCCCC2)c(-c2nnn(C3CCN(C(=O)OC(C)(C)C)C3)n2)c1]

Preparation of Compound 24:

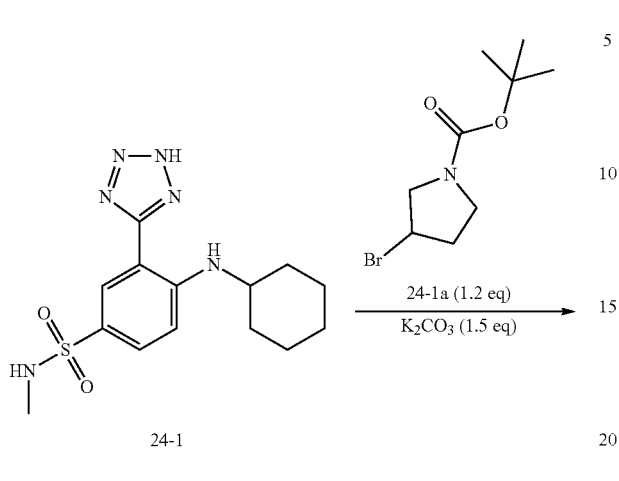

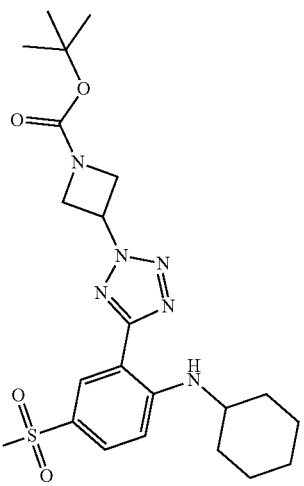

To a solution of compound 24-1 (10 mg, 30 umol, 1.0 eq) in DMF (2 mL) was added 24-1a (9 mg, 36 umol, 1.2 eq) and K$_2$CO$_3$ (6 mg, 45 umol, 1.5 eq). The mixture was stirred at 100° C. for 16 hr. The reaction was monitored by LCMS. The reaction was concentrated under reduced pressure. The residue was purified by prep-HPLC to give Compound 24 (2.09 mg, 4.1 umol, 7.0% yield). LCMS (ESI): RT=0.850 min, mass calcd. for C$_{23}$H$_{35}$N$_7$O$_4$S 505.25, m/z found 528.1 [M+Na]$^+$, $^1$HNMR (400 MHz, CDCl$_3$) δ 8.61 (s, 1H), 7.74 (d, J=7.8 Hz, 2H), 6.83 (d, J=8.8 Hz, 1H), 5.51-5.44 (m, 1H), 4.27 (s, 1H), 4.00 (s, 2H), 3.79-3.63 (m, 2H), 3.54 (s, 1H), 2.77-2.69 (m, 1H), 2.67 (s, 3H), 2.60-2.52 (m, 1H), 2.08 (d, J=7.5 Hz, 2H), 1.87-1.79 (m, 2H), 1.71-1.63 (m, 3H), 1.49 (s, 9H), 1.44 (d, J=8.8 Hz, 3H).

Example 24: tert-butyl 3-(5-(2-(cyclohexylamino)-5-(N-methylsulfamoyl)phenyl)-2H-tetrazol-2-yl)azetidine-1-carboxylate (Compound 25)

Preparation of Compound 25:

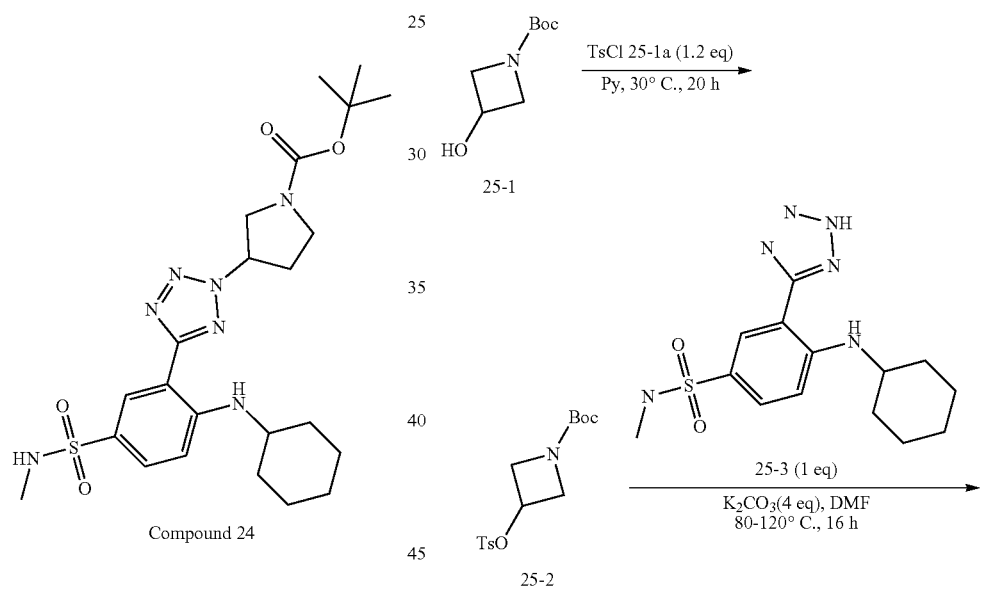

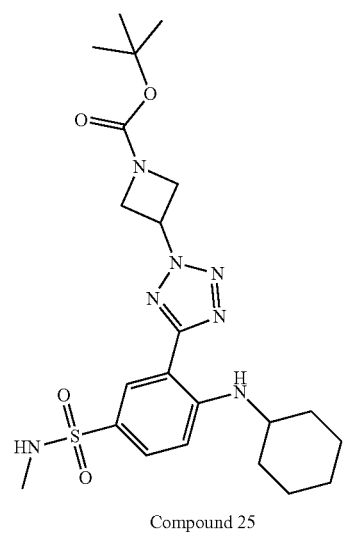

Compound 25

Step 1: tert-butyl 3-(p-tolylsulfonyloxy)azetidine-1-carboxylate

To a mixture of 25-1 (3.0 g, 17.3 mmol, 1.0 eq) in pyridine (16 mL) was added 25-1a (3.96 g, 20.8 mmol, 1.2 eq) in one portion under N₂. The mixture was stirred at 30° C. and stirred for 20 h. LCMS showed compound 25-1 was consumed completely and one main peak with desired MS was detected. The reaction mixture was diluted with water (40 mL) and extracted with EA (30 mL*3). The combined organic layers were washed with brine (30 mL*3), dried with anhydrous Na₂SO₄, filtered and concentrated in vacuum. 25-2 (5.50 g, crude) was obtained as a red oil, which was used in the next step without further purification.

Step 2: 3-[5-[2-(cyclohexylamino)-5-(methylsulfamoyl)phenyl]tetrazol-2-yl]azetidine-1-carboxylate To a mixture of 25-2 (70 mg, 0.15 mmol, 1.2 eq) and 25-3 (50 mg, 0.13 mmol, 1.0 eq) in DMF (1 mL) was added K₂CO₃ (70 mg, 0.51 mmol, 4.0 eq) in one portion under N₂. The mixture was stirred at 80° C. for 2.5 hr. LCMS showed only starting material was remained. The reaction mixture was continued stirred at 120° C. for 16 hr. LCMS showed one main peak with desired MS was detected. The reaction mixture was diluted with water (5 mL) and extracted with EA (5 mL*4). The combined organic layers were dried with anhydrous Na₂SO₄, filtered and concentrated in vacuum. HPLC indicated 52% of desired product was found. The residue was purified by prep-HPLC. LCMS and ¹H NMR confirmed Compound 25 (14.2 mg, 28.8 umol, 22.6% yield). LCMS (ESI): RT=0.842 min, mass calcd. For C₂₂H₃₃N₇O₄S, 491.23 m/z found 514.1 [M+23]⁺. ¹H NMR (400 MHz, CDCl₃) δ 8.64 (d, J=2.0 Hz, 1H), 7.82-7.72 (m, 2H), 6.84 (d, J=9.2 Hz, 1H), 5.75-5.66 (m, 1H), 4.60-4.51 (m, 4H), 4.27-4.21 (m, 1H), 3.61-3.52 (m, 1H), 2.68 (d, J=5.6 Hz, 3H), 2.11-2.03 (m, 2H), 1.88-1.77 (m, 2H), 1.69-1.63 (m, 1H), 1.51 (s, 9H), 1.48-1.36 (m, 5H).

Example 25: 4-(cyclohexylamino)-3-(2-isopropyl-2H-tetrazol-5-yl)-N-methylbenzenesulfonamide (Compound 26)

Preparation of Compound 26:

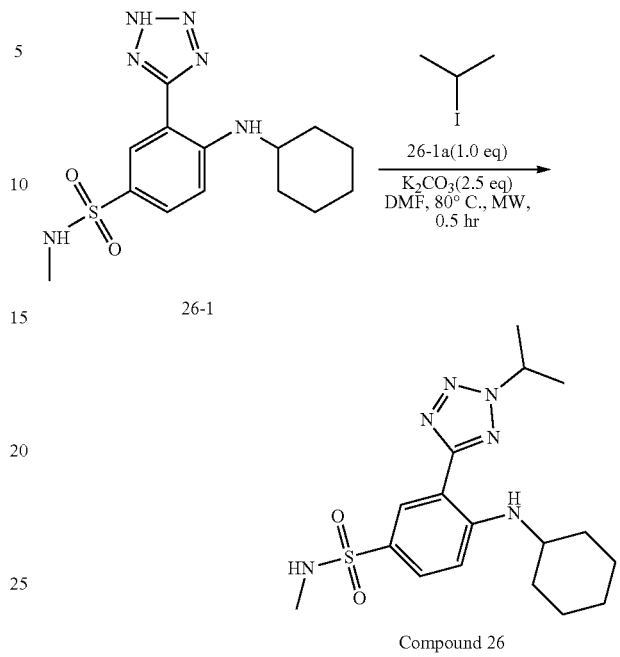

To a solution of 26-1 (60.0 mg, 0.2 mmol, 1.0 eq) in DMF (3.0 mL) was added K₂CO₃ (49.3 mg, 0.4 mmol, 2.0 eq) and 2-iodopropane 26-1a (30.3 mg, 0.2 mmol, 17.8 uL, 1.0 eq). The mixture was stirred at 80° C. under microwave condition for 0.5 hr. LCMS showed 39% of 1 was remained. Several new peaks were shown on LCMS and 55% of desired compound was detected. The reaction mixture was purified by prep-HPLC to give Compound 26 (18.86 mg, 49.8 umol, 28% yield). LCMS (ESI): RT=0.835 min, mass calc. for C₁₇H₂₆N₆O₂S 378.18, m/z found 379.0 [M+H]⁺; ¹HNMR (400 MHz, CDCl₃) δ (ppm) 8.63 (d, J=2.2 Hz, 1H), 7.90 (d, J=7.1 Hz, 1H), 7.73-7.70 (m, 1H), 6.82 (d, J=9.0 Hz, 1H), 5.19-5.09 (m, 1H), 4.28 (q, J=5.3 Hz, 1H), 3.55 (s, 1H), 2.67 (d, J=5.5 Hz, 3H), 2.15-2.02 (m, 2H), 1.86-1.78 (m, 2H), 1.73 (d, J=6.6 Hz, 6H), 1.66 (d, J=11.9 Hz, 1H), 1.52-1.36 (m, 5H).

Example 26: 4-(cyclohexylamino)-3-(2-isobutyl-2H-tetrazol-5-yl)-N-methylbenzenesulfonamide (Compound 27)

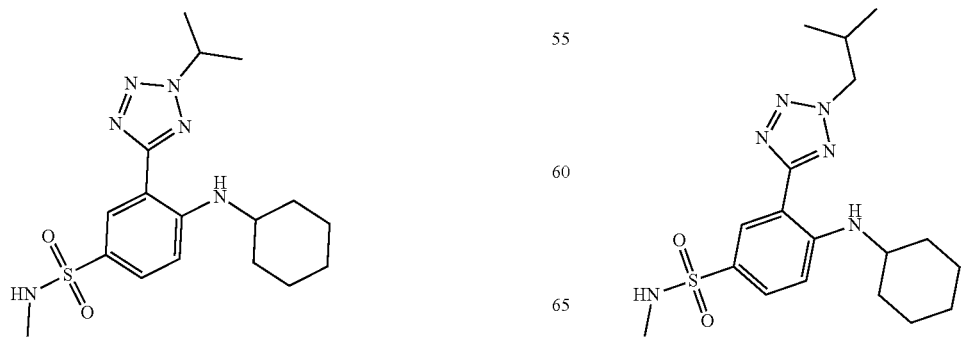

Preparation of Compound 27:

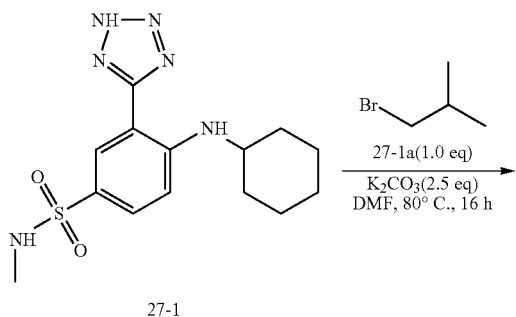

To a solution of 27-1 (60.0 mg, 0.2 mmol, 1.0 eq) in DMF (2.0 mL) was added K$_2$CO$_3$ (49.3 mg, 0.4 mmol, 2.0 eq) and 27-1a (24.4 mg, 0.2 mmol, 19.4 uL, 1.0 eq). The mixture was stirred at 80° C. for 16 h. LCMS showed 35% of 27-1 was remained. Several new peaks were shown on LCMS and 40% of desired compound was detected. The mixture was purified by prep-HPLC to give Compound 27 (6.53 mg, 16.6 umol, 9% yield). LCMS (ESI): RT=0.863 min, mass calc. for C$_{18}$H$_{28}$N$_6$O$_2$S 392.20, m/z found 393.1 [M+H]$^+$; $^1$H NMR (400 MHz, CDCl$_3$) δ 8.63 (d, J=2.3 Hz, 1H), 7.84 (d, J=7.0 Hz, 1H), 7.74-7.71 (m, 1H), 7.27 (s, 1H), 6.82 (d, J=9.0 Hz, 1H), 4.50 (d, J=7.0 Hz, 2H), 4.28 (q, J=5.4 Hz, 1H), 3.54 (s, 1H), 2.67 (d, J=5.5 Hz, 3H), 2.50-2.40 (m, 1H), 2.12-2.03 (m, 2H), 1.87-1.78 (m, 2H), 1.67 (d, J=12.0 Hz, 1H), 1.53-1.35 (m, 5H), 1.02 (d, J=6.8 Hz, 6H).

Example 27: tert-butyl 4-(5-(2-(cyclohexylamino)-5-(N-methylsulfamoyl)phenyl)-2H-tetrazol-2-yl)piperidine-1-carboxylate (Compound 28)

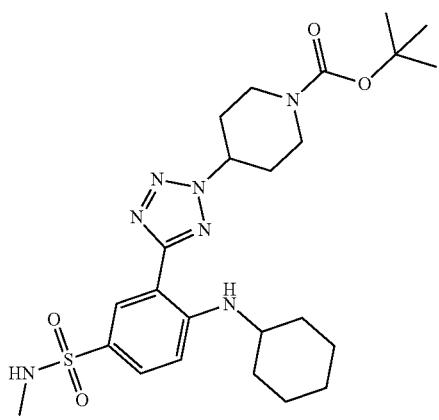 [SMILES: CNS(=O)(=O)c1ccc(NC2CCCCC2)c(-c2nnn(C3CCN(C(=O)OC(C)(C)C)CC3)n2)c1]

Preparation of Compound 28:

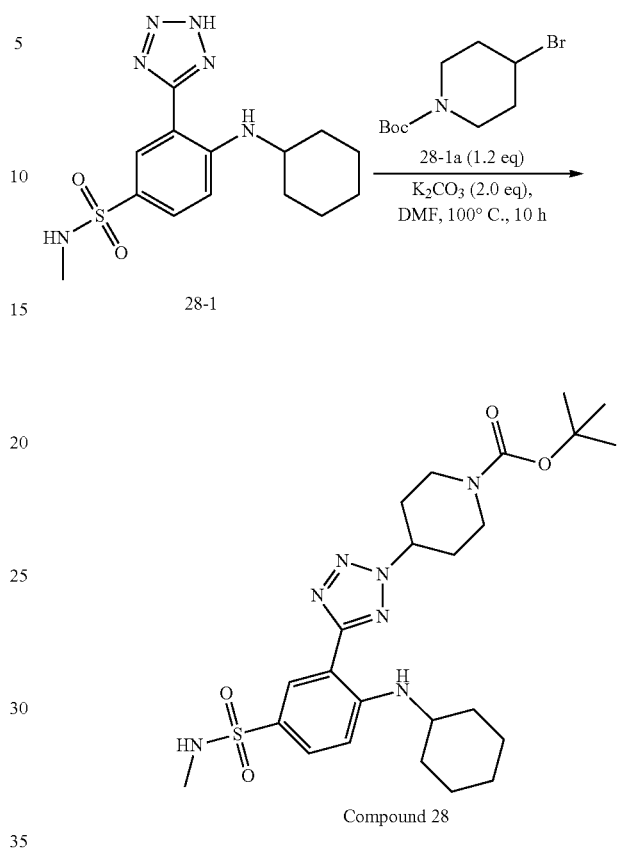

To a stirring solution of compound 28-1 (200 mg, 0.60 mmol, 1.0 eq) and K$_2$CO$_3$ (247 mg, 1.78 mmol, 3.0 eq) in DMF (4 mL) was added compound 28-1a (251 mg, 0.95 mmol, 1.6 eq). The resulting mixture was heated to 80° C. for 16 h. LCMS showed 58% of desired compound was found and 35% of the starting material was remained. The resulted mixture was heated at 100° C. for 16 hr. LCMS showed 58% of desired compound was found and 35% of the starting material was remained. The mixture was cooled and poured into water (8 mL) and stirred for 5 min. The aqueous phase was extracted with ethyl acetate (8 mL*3). The combined organic phases were washed with brine (8 mL*2), dried with anhydrous Na$_2$SO$_4$, filtered and concentrated in vacuum to give a residue which was purified by flash column chromatography to give the product (160 mg, 0.28 mmol, 47% yield). The product (30 mg) was re-purified by prep-HPLC to give Compound 28 (9.64 mg). LCMS (ESI): RT=0.880 min, mass calc. for C$_{24}$H$_{37}$N$_7$O$_4$S 519.26, m/z found 542.1 [M+23]$^+$; $^1$H NMR (400 MHz, CDCl$_3$) δ 8.61 (d, J=2.3 Hz, 1H), 7.82 (d, J=7.0 Hz, 1H), 7.72 (dd, J=2.3, 9.0 Hz, 1H), 6.82 (d, J=9.0 Hz, 1H), 4.99-4.87 (m, 1H), 4.26-4.20 (m, 2H), 3.54 (s, 1H), 3.08 (s, 2H), 2.66 (d, J=5.5 Hz, 3H), 2.35-2.16 (m, 4H), 2.08 (d, J=8.8 Hz, 2H), 1.81 (d, J=5.0 Hz, 2H), 1.67 (d, J=10.5 Hz, 1H), 1.50 (s, 9H), 1.48-1.34 (m, 5H).

Example 28: 4-(cyclohexylamino)-N-methyl-3-(2-(pyridin-3-ylmethyl)-2H-tetrazol-5-yl)benzenesulfonamide (Compound 29)

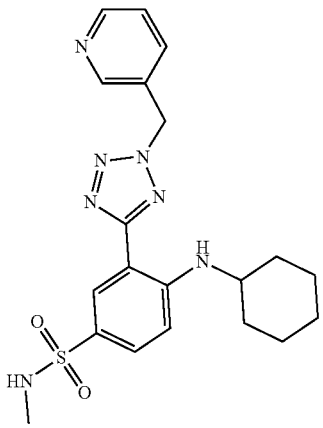 [SMILES: CNS(=O)(=O)c1ccc(NC2CCCCC2)c(-c2nnn(Cc3cccnc3)n2)c1]

Preparation of Compound 29:

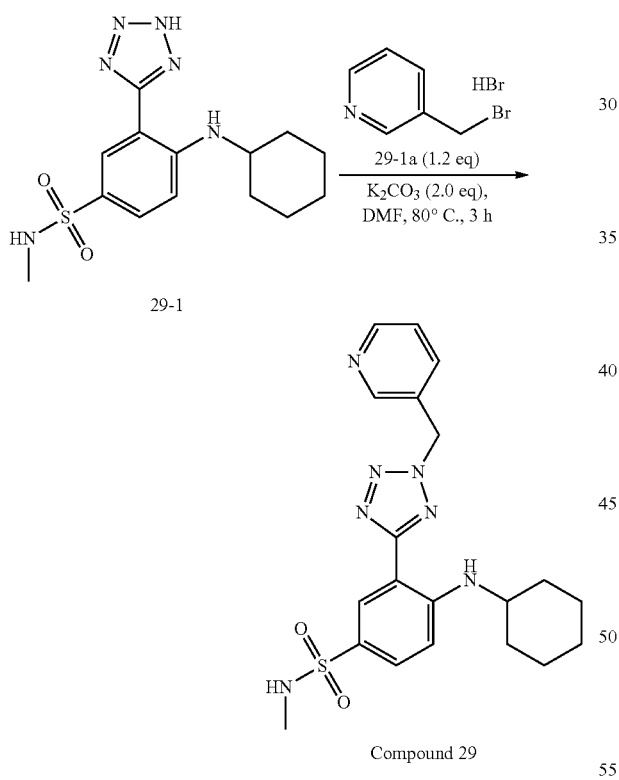

To a stirring solution of compound 29-1 (50 mg, 0.15 mmol, 1.0 eq) and K$_2$CO$_3$ (62 mg, 0.45 mmol, 3.0 eq) in DMF (1 mL) was added compound 29-1a (45 mg, 0.18 mmol, 1.2 eq). The resulting mixture was heated at 100° C. for 16 hr. LCMS showed 66% of desired compound was found and the starting material was consumed completely. The mixture was cooled and diluted with DMF (2 mL) and filtered. The filtrate was purified by prep-HPLC to give Compound 29 (20 mg, 46 umol, 31% yield). LCMS (ESI): RT=0.687 min, mass calc. for C$_{20}$H$_{25}$N$_7$O$_2$S 427.18, m/z found 428.1 [M+H]$^+$; $^1$H NMR (400 MHz, CHLORO-FORM-d) δ 8.88-8.53 (m, 3H), 7.86-7.66 (m, 3H), 7.36 (s, 1H), 6.80 (d, J=8.5 Hz, 1H), 5.86 (s, 2H), 4.22 (s, 1H), 3.52 (s, 1H), 2.65 (d, J=4.5 Hz, 3H), 2.05 (s, 2H), 1.77 (s, 2H), 1.59 (s, 3H), 1.42 (d, J=9.3 Hz, 5H).

Example 29: 4-(cyclohexylamino)-N-methyl-3-(2-(piperidin-4-yl)-2H-tetrazol-5-yl)benzenesulfonamide (Compound 30)

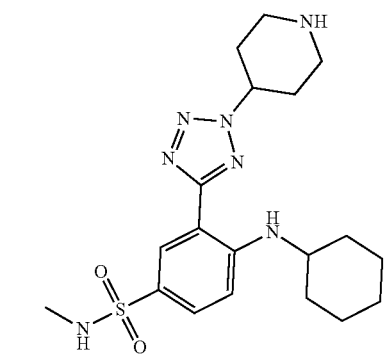 [SMILES: CNS(=O)(=O)c1ccc(NC2CCCCC2)c(-c2nnn(C3CCNCC3)n2)c1]

Preparation of Compound 30:

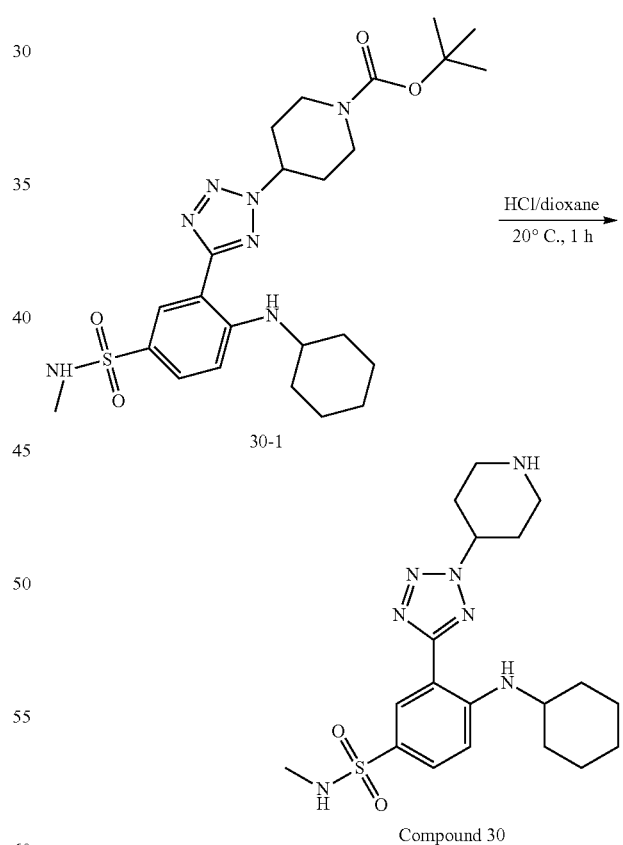

A solution of 30-1 (130 mg, 0.25 mmol, 1.0 eq) in HCl/dioxane (3 mL) was stirred at 20° C. for 1 h. LCMS showed desired compound was found and the starting material was consumed completely. The mixture was concentrated to give the product (130 mg crude). The product (100 mg) was directly used without further purification. The product (30 mg) was purified by prep-HPLC to give Compound 30 (11.26 mg). LCMS (ESI): RT=0.655 min, mass calc. for $C_{19}H_{29}N_7O_2S$ 419.21, m/z found 420.1 [M+H]$^+$; $^1$H NMR (400 MHz, DMSO-d$_6$) δ 9.51-9.06 (m, 2H), 8.41 (d, J=1.8 Hz, 1H), 7.66 (d, J=8.5 Hz, 1H), 7.58 (d, J=7.3 Hz, 1H), 7.27 (d, J=5.0 Hz, 1H), 7.06 (d, J=9.0 Hz, 1H), 5.39-5.28 (m, 1H), 3.62 (s, 1H), 3.48-3.44 (m, 2H), 3.19 (s, 2H), 2.47-2.31 (m, 7H), 2.00 (d, J=9.3 Hz, 2H), 1.71 (s, 2H), 1.59 (s, 1H), 1.52-1.26 (m, 5H).

Example 30: 3-(2-(1-acetylpiperidin-4-yl)-2H-tetrazol-5-yl)-4-(cyclohexylamino)-N-methylbenzenesulfonamide (Compound 31)

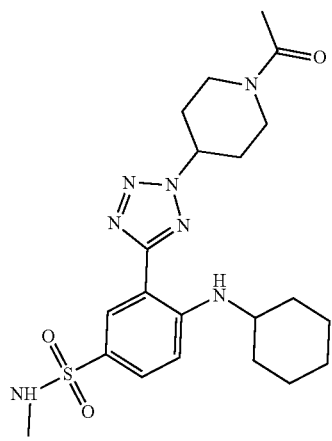 [SMILES: CNS(=O)(=O)c1ccc(NC2CCCCC2)c(-c2nnn(C3CCN(C(C)=O)CC3)n2)c1]

Preparation of Compound 31:

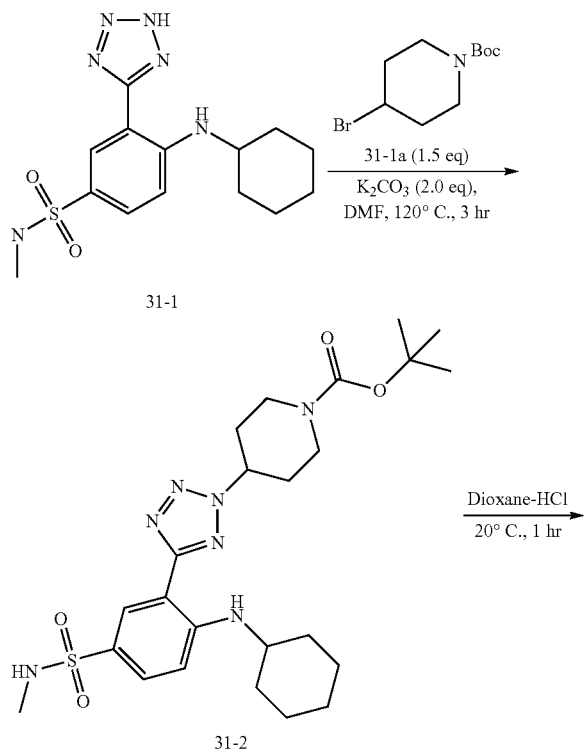

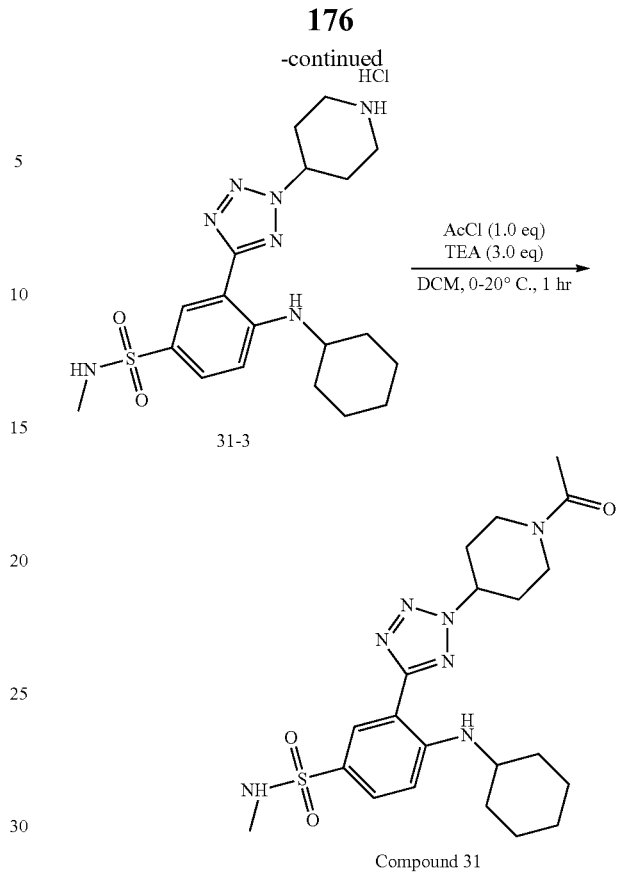

Step 1: tert-Butyl 4-(5-(2-(cyclohexylamino)-5-(N-methylsulfamoyl)phenyl)-2H-tetrazol-2-yl) piperidine-1-carboxylate To a solution of compound 31-1 (300 mg, 0.89 mmol, 1.0 eq) and compound 31-1a (353 mg, 1.34 mmol, 1.5 eq) in DMF (4 mL) was added K$_2$CO$_3$ (247 mg, 1.78 mmol, 2.0 eq). The reaction mixture was stirred at 120° C. for 3 hours. The reaction mixture was concentrated under reduced pressure. The mixture was diluted with water (30 mL) and the resultant mixture was extracted with DCM (50 mL*3). The combined organic layers were dried over Na$_2$SO$_4$, filtered and concentrated to dryness under reduced pressure. The residue was purified by column chromatography over silica gel to afford 31-2 (410 mg, 78% yield). LCMS (ESI): RT=0.892 min, mass calcd. for $C_{24}H_{37}N_7O_4S$ 519.26, m/z found 542.3 [M+Na]$^+$.

Step 2: 4-(Cyclohexylamino)-N-methyl-3-(2-(piperidin-4-yl)-2H-tetrazol-5-yl)benzene sulfonamide hydrochloride A solution of compound 31-2 (410 mg, 0.79 mmol, 1.0 eq) in Dioxane/HCl (8 mL) was stirred at 20° C. for 1 hour. The reaction mixture was concentrated under reduced pressure to obtain 31-3 (350 mg, 97% yield). LCMS (ESI): RT=0.646 min, mass calcd. for $C_{19}H_{29}N_7O_2S$ 419.21, m/z found 420.2 [M+H]$^+$.

Step 3: 3-(2-(1-Acetylpiperidin-4-yl)-2H-tetrazol-5-yl)-4-(cyclohexylamino)-N-methyl benzenesulfonamide To a solution of compound 31-3 (40 mg, 88 umol, 1.0 eq, HCl) and TEA (27 mg, 0.26 mmol, 3.0 eq) in DCM (1.5 mL)

was added dropwise a solution of acetyl chloride (6.9 mg, 88 umol, 1.0 eq) in DCM (0.5 mL) at 0° C. The reaction mixture was allowed to warm up to 20° C. and stirred at 20° C. for 1 hour. The mixture was diluted with water (10 mL) and the resultant mixture was extracted with DCM (30 mL*3). The combined organic layers were dried over $Na_2SO_4$, filtered and concentrated to dryness under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. Compound 31 (14.47 mg, 36% yield) was obtained. LCMS (ESI): RT=0.747 min, mass calcd. for $C_{21}H_{31}N_7O_3S$ 461.22, m/z found 462.1 [M+H]$^+$, $^1$HNMR (400 MHz, DMSO-$d_6$) δ 8.41 (d, J=1.8 Hz, 1H), 7.74-7.55 (m, 2H), 7.24 (d, J=4.0 Hz, 1H), 7.05 (d, J=9.0 Hz, 1H), 5.30-5.15 (m, 1H), 4.39 (d, J=12.3 Hz, 1H), 3.94 (d, J=13.6 Hz, 1H), 3.76-3.57 (m, 1H), 3.02-2.88 (m, 1H), 2.42-2.24 (m, 4H), 2.17-1.85 (m, 8H), 1.80-1.65 (m, 2H), 1.58 (br s, 1H), 1.53-1.20 (m, 6H).

Example 31: 4-(cyclohexylamino)-N-methyl-3-(2-(1-(methylsulfonyl)piperidin-4-yl)-2H-tetrazol-5-yl)benzenesulfonamide (Compound 32)

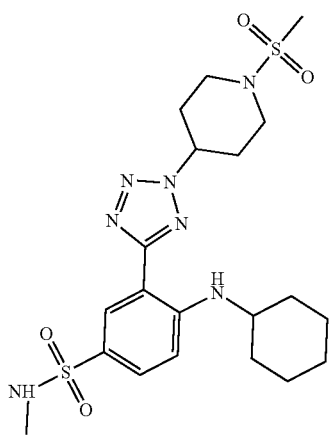 [SMILES: CNS(=O)(=O)c1ccc(NC2CCCCC2)c(-c2nnn(C3CCN(S(C)(=O)=O)CC3)n2)c1]

Compound 32

Preparation of Compound 32:

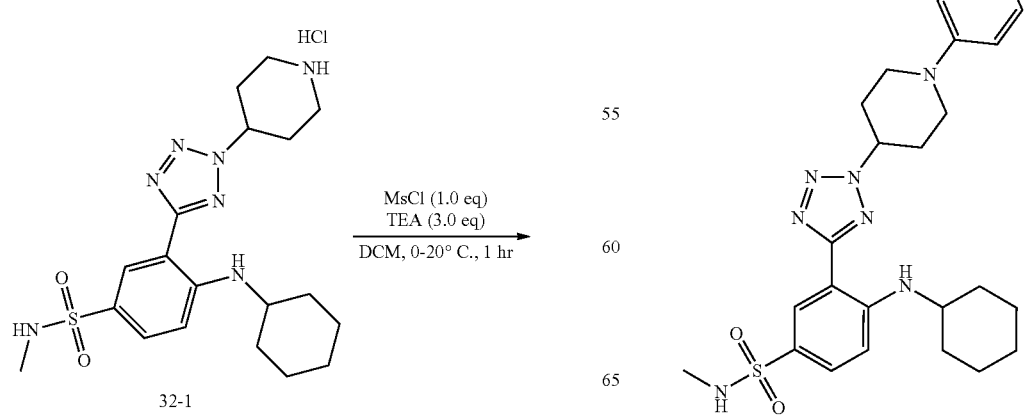

To a solution of compound 32-1 (40 mg, 88 umol, 1.0 eq, HCl) and TEA (27 mg, 0.26 mmol, 3.0 eq) in DCM (1.5 mL) was added dropwise a solution of MsCl (10 mg, 88 umol, 1.0 eq) in DCM (0.5 mL) at 0° C. The reaction mixture was allowed to warm up to 20° C. and stirred at 20° C. for 1 hour. The mixture was diluted with water (10 mL) and the resultant mixture was extracted with DCM (30 mL*3). The combined organic layers were dried over $Na_2SO_4$, filtered and concentrated to dryness under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. Compound 32 (19.06 mg, 44% yield) was obtained. LCMS (ESI): RT=0.774 min, mass calcd. for $C_{20}H_{31}N_7O_4S_2$ 497.19, m/z found 498.1 [M+H]$^+$, $^1$HNMR (400 MHz, DMSO-$d_6$) δ 8.42 (s, 1H), 7.75-7.51 (m, 2H), 7.35-7.15 (m, 1H), 7.13-6.95 (m, 1H), 5.25-5.05 (m, 1H), 3.74-3.54 (m, 3H), 3.15-3.05 (m, 2H), 2.95 (s, 3H), 2.38 (s, 3H), 2.28-2.10 (m, 3H), 2.10-1.90 (m, 2H), 1.83-1.56 (m, 3H), 1.55-1.17 (m, 6H).

Example 32: 4-(cyclohexylamino)-N-methyl-3-(2-(1-(pyridin-3-yl)piperidin-4-yl)-2H-tetrazol-5-yl)benzenesulfonamide (Compound 33)

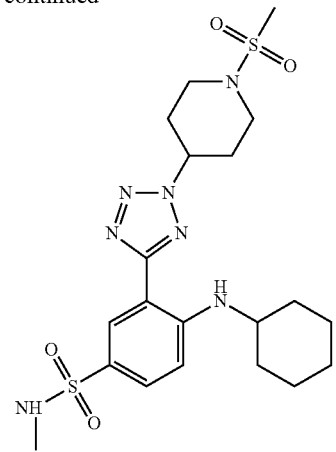

Preparation of Compound 33:

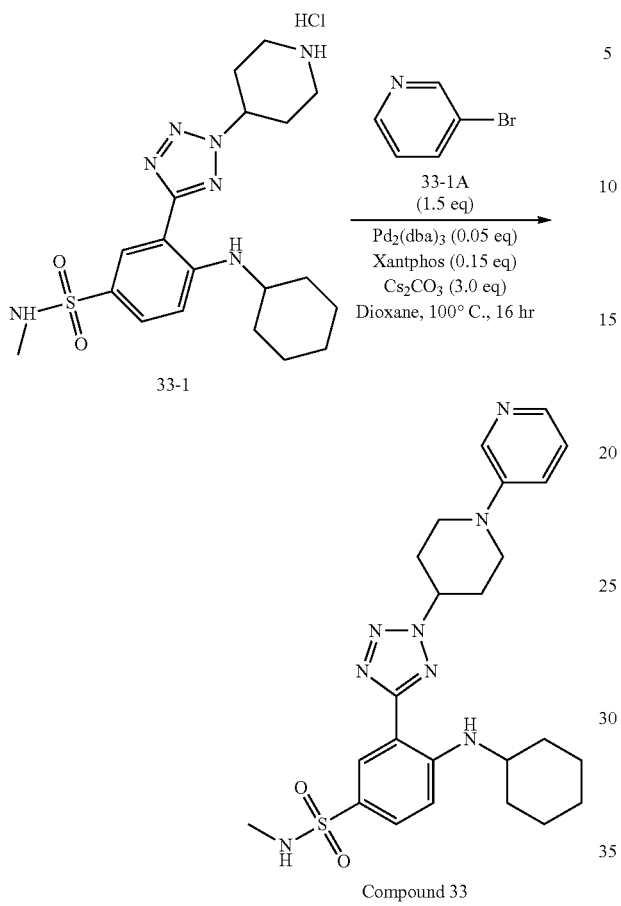

Example 33: 4-(cyclohexylamino)-N-methyl-3-(2-phenyl-2H-tetrazol-5-yl)benzenesulfonamide (Compound 34)

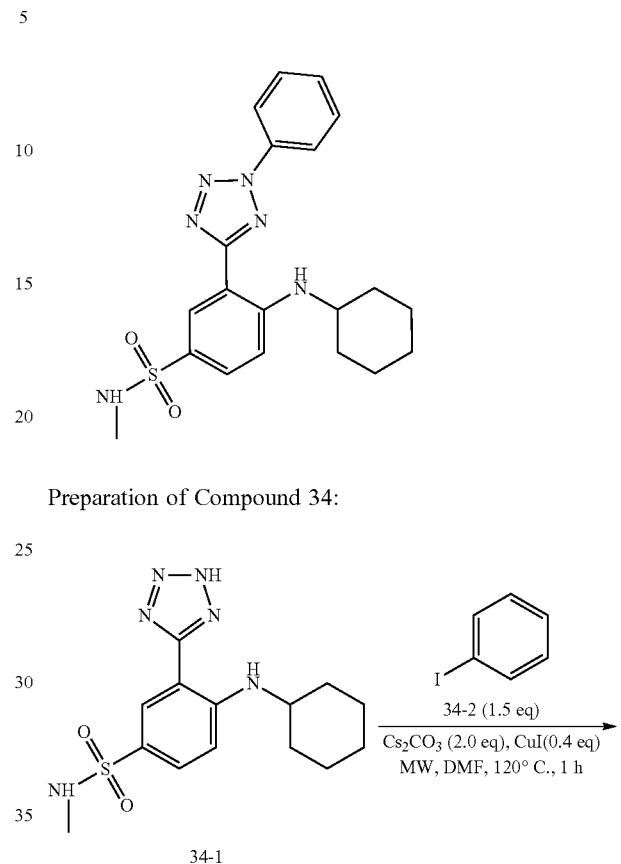

Preparation of Compound 34:

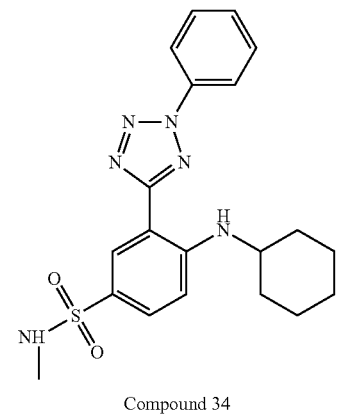

A solution of compound 33-1 (40 mg, 88 umol, 1.0 eq, HCl), compound 33-1A (21 mg, 0.13 mmol, 1.5 eq) and Pd$_2$(dba)$_3$ (4.0 mg, 4.4 umol, 0.05 eq), Xantphos (7.6 mg, 13 umol, 0.15 eq), Cs$_2$CO$_3$ (86 mg, 0.26 mmol, 3.0 eq) in Dioxane (2 mL) under N$_2$. The suspension was degassed under vacuum and purged with N$_2$ several times. The reaction mixture was stirred at 100° C. for 16 hours. The reaction mixture was concentrated under reduced pressure. The mixture was diluted with water (10 mL) and the resultant mixture was extracted with DCM (30 mL*3). The combined organic layers were dried over Na$_2$SO$_4$, filtered and concentrated to dryness under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. Compound 33 (5.12 mg, 11% yield) was obtained. LCMS (ESI): RT=0.685 min, mass calcd. for C$_{24}$H$_{32}$N$_8$O$_2$S 496.24, m/z found 497.2 [M+H]$^+$, $^1$HNMR (400 MHz, CDCl$_3$) δ 8.62 (d, J=2.0 Hz, 1H), 8.56-8.30 (m, 1H), 8.28-8.00 (m, 1H), 7.83 (d, J=7.0 Hz, 1H), 7.72 (dd, J=2.3, 9.0 Hz, 1H), 7.31-7.27 (m, 1H), 7.25-7.17 (m, 1H), 6.82 (d, J=9.0 Hz, 1H), 5.01-4.91 (m, 1H), 4.26 (q, J=5.4 Hz, 1H), 3.83 (d, J=12.8 Hz, 2H), 3.60-3.48 (m, 1H), 3.19-3.06 (m, 2H), 2.66 (d, J=5.5 Hz, 3H), 2.56-2.42 (m, 4H), 2.13-2.02 (m, 2H), 1.86-1.76 (m, 2H), 1.71-1.66 (m, 1H), 1.52-1.24 (m, 5H).

To a solution of compound 34-1 (50.0 mg, 0.15 mmol, 1.0 eq) and compound 34-2 (45.5 mg, 0.22 mmol, 24.9 uL, 1.5 eq) in DMF (2.0 mL) was added Cs$_2$CO$_3$ (193.7 mg, 0.59 mmol, 4.0 eq) and CuI (11.3 mg, 59.4 umol, 0.4 eq). The mixture was stirred at 100° C. for 3 hour at N$_2$ atmosphere. LCMS showed desired compound was found. The reaction was filtered to give a crude product which was purified by prep-HPLC to give Compound 34 (6.48 mg, 15.1 umol, 10.2% yield) was obtained. LCMS (ESI): RT=0.839 min, mass calc. for C$_{20}$H$_{24}$N$_6$O$_2$S 412.17, m/z found 413.1 [M+H]$^+$; $^1$HNMR (400 MHz, CDCl$_3$) δ 8.11 (s, 1H), 7.48 (dd, J=1.8, 9.0 Hz, 1H), 7.34-7.24 (m, 4H), 7.22-7.15 (m, 2H), 6.88 (d, J=9.0 Hz, 1H), 3.57 (s, 1H), 3.20 (s, 3H), 2.11 (d, J=10.8 Hz, 2H), 1.88 (d, J=8.5 Hz, 2H), 1.71 (d, J=10.5 Hz, 1H), 1.58-1.52 (m, 1H), 1.49-1.28 (m, 4H).

Example 34: 4-(cyclohexylamino)-N-methyl-3-(2-(pyrrolidin-3-yl)-2H-tetrazol-5-yl)benzenesulfonamide (Compound 35)

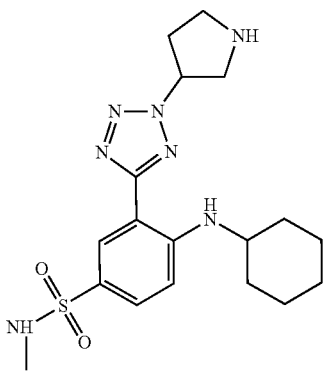 [SMILES: CNS(=O)(=O)c1ccc(NC2CCCCC2)c(-c2nnn(C3CCNC3)n2)c1]

Preparation of Compound 35:

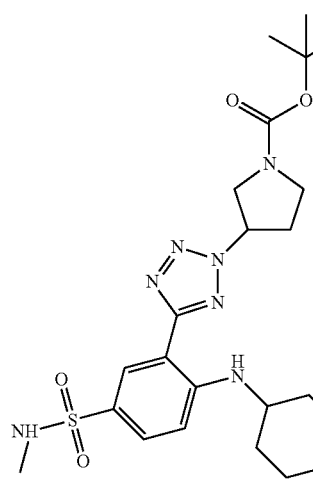

35-1

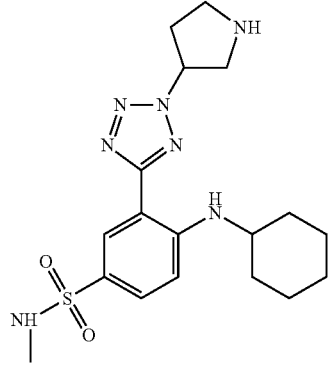

Compound 35

A mixture of compound 35-1 (0.31 g, 0.61 mmol, 1.0 eq) in HCl/dioxane (4 M, 4 mL, 26.1 eq) stirred at 20° C. for 1 hour. LCMS showed the desired compound was found. TLC showed desired compound was found and the starting material was consumed completely. The reaction mixture was concentrated to give the crude Compound 35 (0.23 g, 0.52 mmol, 84.9% yield, HCl). The residue was directly used without further purification. The crude product (15.0 mg) was purified by prep-HPLC to give the title compound (2.60 mg). LCMS (ESI): RT=0.643 min, mass calc. for $C_{18}H_{27}N_7O_2S$ 405.19, m/z found 406.1 [M+H]$^+$; $^1$HNMR (400 MHz, DMSO-d$_6$) δ 9.92 (s, 1H), 9.68 (s, 1H), 8.42 (s, 1H), 7.71-7.45 (m, 2H), 7.30 (s, 1H), 7.05 (d, J=8.8 Hz, 1H), 5.86 (s, 1H), 3.85 (s, 2H), 3.46 (d, J=15.6 Hz, 2H), 2.72-2.57 (m, 2H), 2.36 (s, 3H), 1.99 (s, 2H), 1.70 (s, 2H), 1.58 (s, 1H), 1.49-1.27 (m, 5H). $^1$HNMR (400 MHz, MeOD-d$_4$) δ8.56 (d, J=2.3 Hz, 1H), 7.72 (dd, J=2.3, 9.0 Hz, 1H), 7.01 (d, J=9.0 Hz, 1H), 5.96-5.89 (m, 1H), 4.11-4.05 (m, 1H), 4.01-3.93 (m, 1H), 3.70-3.61 (m, 3H), 2.81-2.74 (m, 2H), 2.51 (s, 3H), 2.14-2.04 (m, 2H), 1.82 (dd, J=4.5, 8.8 Hz, 2H), 1.67 (s, 1H), 1.57-1.37 (m, 5H).

Example 35: 4-(cyclohexylamino)-3-(2-(1-isopropylpyrrolidin-3-yl)-2H-tetrazol-5-yl)-N-methylbenzenesulfonamide (Compound 36)

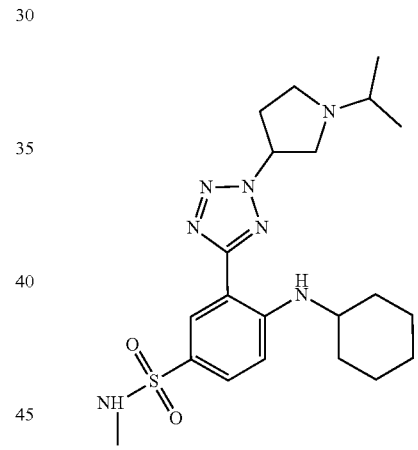

Preparation of Compound 36:

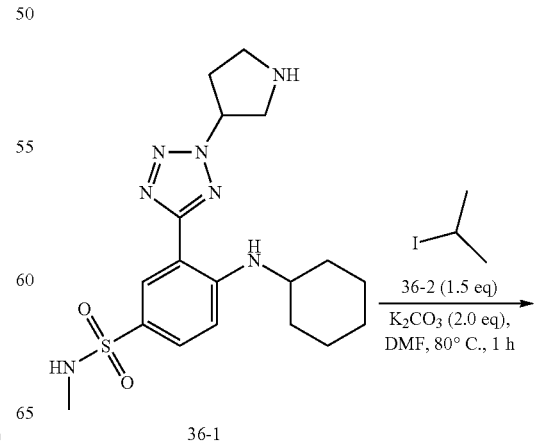

36-1

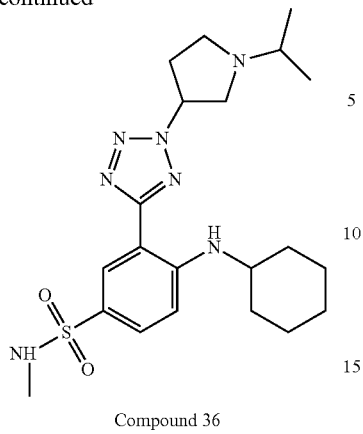

Compound 36

To a solution of compound 36-1 (30 mg, 73.9 umol, 1.0 eq) in DMF (2.0 mL) was added K$_2$CO$_3$ (20.5 mg, 0.15 mmol, 2.0 eq) and compound 36-2 (18.9 mg, 0.11 mmol, 11.1 uL, 1.5 eq). The mixture was stirred at 80° C. for 2 hr at N$_2$ atmosphere. LCMS showed desired compound was found. The reaction was filtered to give a crude product which was purified by prep-HPLC to give Compound 36 (2.48 mg, 5.3 umol, 7.2% yield) was obtained. LCMS (ESI): RT=0.659 min, mass calc. for C$_{21}$H$_{33}$N$_7$O$_2$S 447.60, m/z found 448.1 [M+H]$^+$; $^1$HNMR (400 MHz, CDCl$_3$) δ 8.62 (d, J=2.3 Hz, 1H), 7.86 (d, J=7.5 Hz, 1H), 7.73 (dd, J=2.3, 9.0 Hz, 1H), 6.82 (d, J=9.0 Hz, 1H), 5.46 (s, 1H), 4.24 (q, J=5.4 Hz, 1H), 3.59-3.41 (m, 2H), 3.14-3.05 (m, 1H), 3.01-2.87 (m, 2H), 2.67 (d, J=5.5 Hz, 3H), 2.63-2.52 (m, 3H), 2.07 (d, J=5.3 Hz, 2H), 1.81 (s, 2H), 1.64 (s, 1H), 1.51-1.29 (m, 5H), 1.17 (d, J=6.3 Hz, 6H).

Example 36: 4-(cyclohexylamino)-N-methyl-3-(2-(1-phenylpyrrolidin-3-yl)-2H-tetrazol-5-yl)benzenesulfonamide (Compound 37)

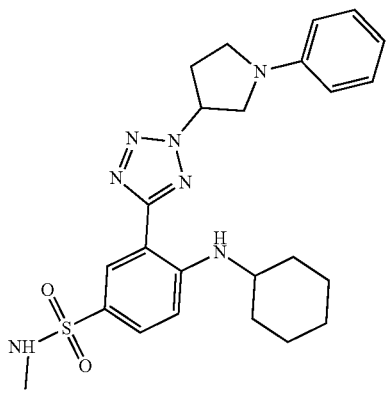 [SMILES: CNS(=O)(=O)c1ccc(NC2CCCCC2)c(-c2nnn(C3CCN(c4ccccc4)C3)n2)c1]

Preparation of Compound 37:

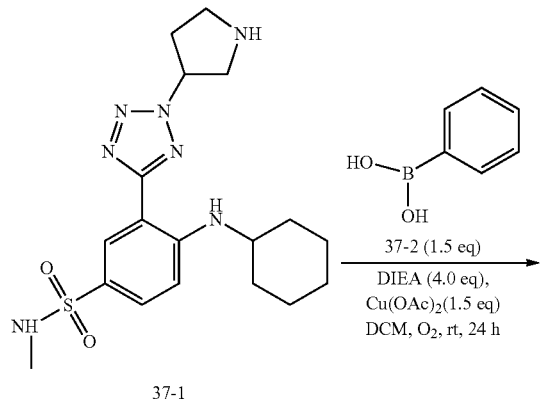

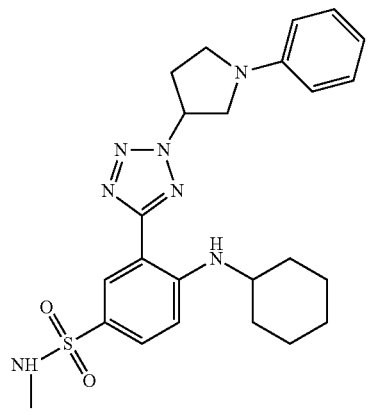

Compound 37

To a solution of compound 37-1 (30 mg, 73.9 umol, 1.0 eq) and compound 37-2 (18.0 mg, 0.15 mmol, 2.0 eq) in DCM (5.0 mL) was added DIEA (38.2 mg, 0.30 mmol, 51.5 uL, 4.0 eq) and Cu(OAc)$_2$ (20.1 mg, 0.11 mmol, 1.5 eq). The mixture was stirred at 20° C. for 16 hr at O2 atmosphere. LCMS showed desired compound was found. The reaction was filtered to give a crude product. The crude product was purified by prep-HPLC to give Compound 37 (4.9 mg, 10.2 umol, 13.8% yield) was obtained. LCMS (ESI): RT=0.912 min, mass calc. for C$_{24}$H$_{31}$N$_7$O$_2$S 481.23, m/z found 482.1 [M+H]$^+$; $^1$HNMR (400 MHz, CDC$_3$-d) δ 8.61 (d, J=2.0 Hz, 1H), 7.75-7.65 (m, 2H), 7.30 (s, 2H), 6.82-6.74 (m, 2H), 6.63 (d, J=8.3 Hz, 2H), 5.65 (d, J=3.3 Hz, 1H), 4.20 (d, J=5.5 Hz, 1H), 4.06-3.93 (m, 2H), 3.74 (q, J=7.9 Hz, 1H), 3.62 (dt, J=4.1, 8.7 Hz, 1H), 3.48 (s, 1H), 2.94-2.85 (m, 1H), 2.78-2.69 (m, 1H), 2.65 (d, J=5.5 Hz, 3H), 2.02 (s, 2H), 1.77 (s, 2H), 1.63 (s, 1H), 1.45-1.27 (m, 5H).

Example 37: 4-(cyclohexylamino)-N-methyl-3-(2-(1-phenylpiperidin-4-yl)-2H-tetrazol-5-yl)benzenesulfonamide (Compound 38)

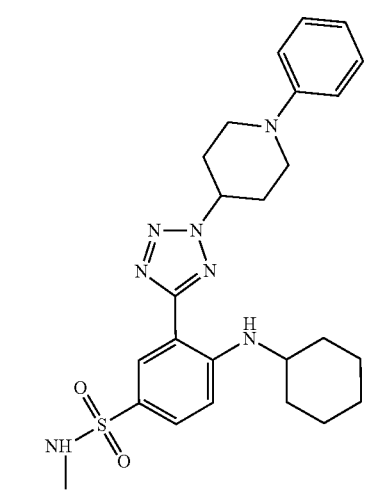 [SMILES: CNS(=O)(=O)c1ccc(NC2CCCCC2)c(-c2nnn(C3CCN(c4ccccc4)CC3)n2)c1]

Preparation of Compound 38:

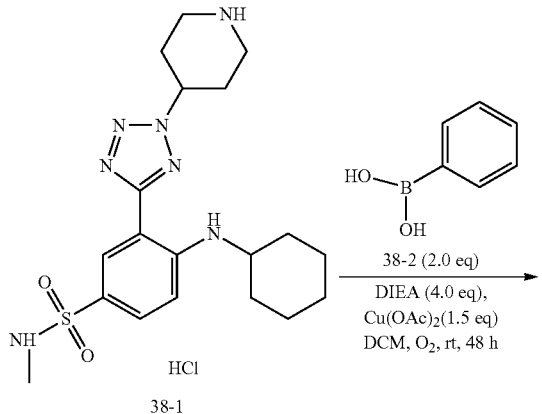

Compound 38

Example 38: 4-(cyclohexylamino)-N-methyl-3-(2-(2,2,2-trifluoroethyl)-2H-tetrazol-5-yl)benzenesulfonamide (Compound 39)

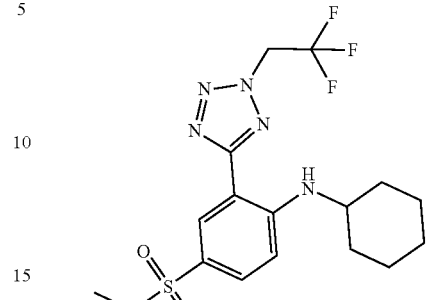

Preparation of Compound 39:

Compound 39

Compound 39-3

To a solution of compound 38-1 (50.0 mg, 0.12 mmol, 1.0 eq) and compound 38-2 (43.6 mg, 0.36 mmol, 3.0 eq) in DCM (5.0 mL) was added DIEA (61.6 mg, 0.47 mmol, 83.3 uL, 4.0 eq) and Cu(OAc)$_2$ (32.5 mg, 0.18 mmol, 1.5 eq). The mixture was stirred at 25° C. for 16 hr at O2 atmosphere. LCMS showed desired compound was found. The reaction was filtered to give a crude product which was purified by prep-HPLC to give Compound 38 (9.24 mg, 18.6 umol, 15.6% yield) was obtained. LCMS (ESI): RT=0.845 min, mass calc. for $C_{25}H_{33}N_7O_2S$ 495.24, m/z found 496.2 [M+H]$^+$; $^1$HNMR (400 MHz, CDC$_3$-d) δ 8.63 (d, J=2.3 Hz, 1H), 7.83 (d, J=7.0 Hz, 1H), 7.73 (dd, J=2.1, 8.9 Hz, 1H), 7.31 (t, J=7.9 Hz, 2H), 7.01 (d, J=8.0 Hz, 2H), 6.92 (t, J=7.3 Hz, 1H), 6.82 (d, J=9.0 Hz, 1H), 4.93 (tt, J=5.0, 10.0 Hz, 1H), 4.28 (q, J=5.5 Hz, 1H), 3.83 (d, J=12.8 Hz, 2H), 3.54 (s, 1H), 3.12-3.01 (m, 2H), 2.67 (d, J=5.5 Hz, 3H), 2.54-2.42 (m, 4H), 2.08 (d, J=9.3 Hz, 2H), 1.87-1.78 (m, 2H), 1.67 (d, J=12.8 Hz, 1H), 1.50-1.34 (m, 5H).

To a mixture of 39-1 (40.0 mg, 0.1 mmol, 1.0 eq, HCl) and Cs$_2$CO$_3$ (104.9 mg, 0.3 mmol, 3.0 eq) in CH$_3$CN (3.0 mL) was added 39-2 (29.9 mg, 0.1 mmol, 1.2 eq) at 0° C. The resulted mixture was stirred at 15° C. for 20 h. LCMS showed there's 16% desired compound, and 66% starting material remained. Another 39-2 (60 mg) was added. The mixture was stirred at 15° C. for 20 h. LCMS and HPLC showed the reaction was completed. The mixture was filtered, and the solid was washed with DMF (1 mL). The filtrate was purified by prep-HPLC. Compound 39 (2.20 mg, 5.3 umol, 4.9% yield) was obtained. LCMS (ESI): RT=0.828 min, mass calcd. for $C_{16}H_{21}F_3N_6O_2S$ 418.14, m/z found 419.1 [M+H]$^+$. $^1$H NMR (400 MHz, CDCl$_3$) δ 8.67 (d, J=2.5 Hz, 1H), 7.76 (dd, J=2.3, 8.8 Hz, 1H), 7.60 (d, J=7.0 Hz, 1H), 6.85 (d, J=9.0 Hz, 1H), 5.34-5.28 (m, 2H), 4.25 (q, J=5.3 Hz, 1H), 3.58-3.55 (m, 1H), 2.68 (d, J=5.5 Hz, 3H), 2.08 (d, J=10.3 Hz, 2H), 1.86-1.78 (m, 2H), 1.71-1.63 (m, 1H), 1.53-1.36 (m, 5H).

Compound 39-3 (6.43 mg, 12.8 umol, 12.0% yield) was obtained. LCMS (ESI): RT=0.910 min, mass calcd. for $C_{18}H_{22}F_6N_6O_2S$ 500.14, m/z found 501.1 [M+H]$^+$. $^1$H NMR (400 MHz, CDCl$_3$) δ 8.63 (d, J=2.3 Hz, 1H), 7.73-7.63 (m, 2H), 6.85 (d, J=9.0 Hz, 1H), 5.32 (q, J=7.6 Hz, 2H), 3.76 (q, J=8.7 Hz, 2H), 3.61-3.51 (m, 1H), 2.92 (s, 3H), 2.09-2.07 (m, 2H), 1.87-1.76 (m, 2H), 1.69-1.67 (m, 1H), 1.53-1.35 (m, 5H).

Example 39: 4-(cyclohexylamino)-3-(2-(2-fluoroethyl)-2H-tetrazol-5-yl)-N-methylbenzenesulfonamide (Compound 40)

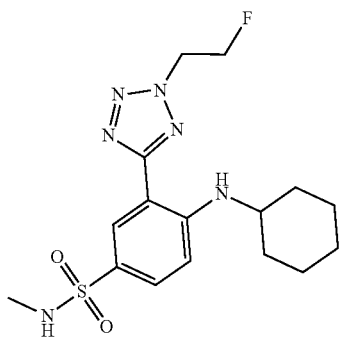 [SMILES: CNS(=O)(=O)c1ccc(NC2CCCCC2)c(-c2nnn(CCF)n2)c1]

Preparation of Compound 40:

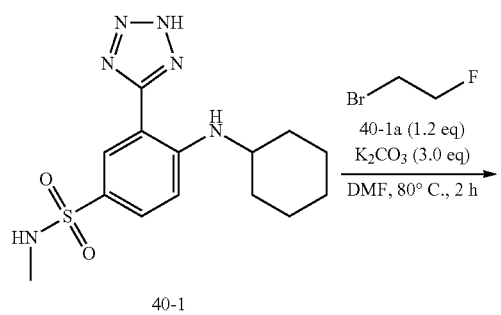

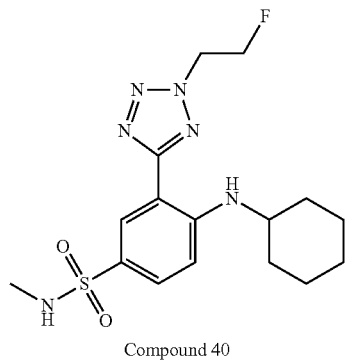

Compound 40

To a mixture of 40-1 (40.0 mg, 0.1 mmol, 1.0 eq, HCl) and K$_2$CO$_3$ (44.5 mg, 0.3 mmol, 3.0 eq) in DMF (2.0 mL) was added 40-1a (16.3 mg, 0.1 mmol, 1.2 eq). The resulted mixture was stirred at 80° C. for 2 h. The reaction was monitored by LCMS. The mixture was filtered, and the solid was washed with DMF (1 mL). The filtrate was checked by HPLC. The filtrate was purified by prep-HPLC. Compound 40 (4.48 mg, 11.7 umol, 10.9% yield) was obtained. LCMS (ESI): RT=0.779 min, mass calcd. for $C_{16}H_{23}FN_6O_2S$ 382.16, m/z found 383.1 [M+H]$^+$. $^1$H NMR (400 MHz, DMSO-d$_6$) δ 8.41 (d, J=2.0 Hz, 1H), 7.66 (dd, J=2.0, 8.8 Hz, 1H), 7.60 (d, J=7.5 Hz, 1H), 7.26 (q, J=5.0 Hz, 1H), 7.05 (d, J=9.0 Hz, 1H), 5.21 (t, J=4.5 Hz, 1H), 5.14 (t, J=4.5 Hz, 1H), 5.09-5.04 (m, 1H), 4.95 (t, J=4.5 Hz, 1H), 3.69-3.60 (m, 1H), 2.37 (d, J=4.8 Hz, 3H), 2.03-1.95 (m, 2H), 1.76-1.67 (m, 2H), 1.63-1.55 (m, 1H), 1.51-1.32 (m, 5H).

Example 40: 4-(cyclohexylamino)-3-(2-(4-fluorobenzyl)-2H-tetrazol-5-yl)-N-methylbenzenesulfonamide (Compound 41)

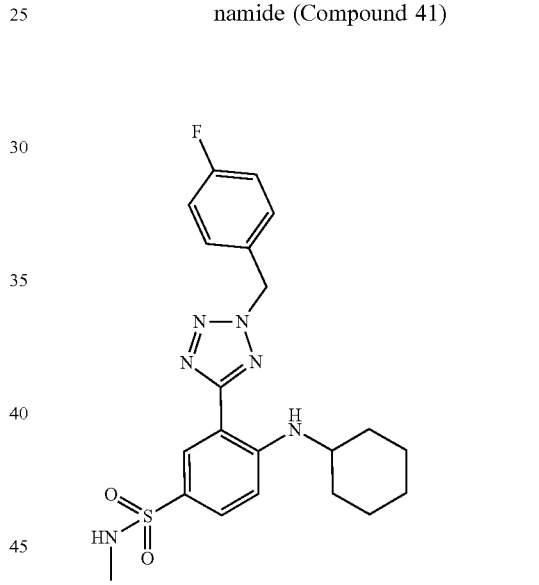

Preparation of Compound 41:

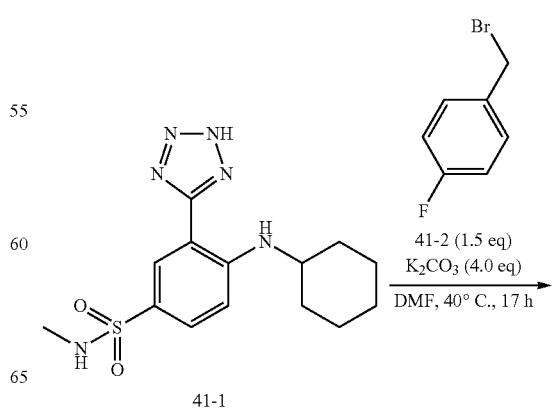

41-1

189

-continued

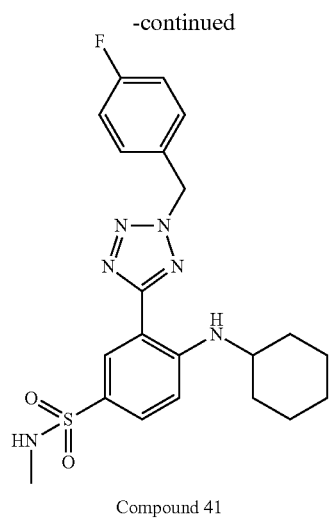

Compound 41

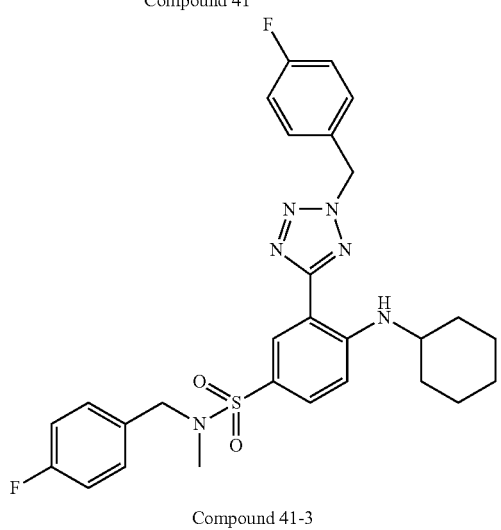

Compound 41-3

To a mixture of 41-1 (40.0 mg, 0.1 mmol, 1.0 eq, HCl) and K₂CO₃ (59.3 mg, 0.4 mmol, 4.0 eq) in DMF (3.0 mL), was added 41-2 (30.4 mg, 0.2 mmol, 20 uL, 1.5 eq). The resultant mixture was stirred at 40° C. under N₂ for 17 h. The reaction was monitored by LCMS. The mixture was filtered, and the solid was washed with DMF (1 mL) and checked by HPLC. The filtrate was purified by prep-HPLC. Compound 41 (6.61 mg, 14.9 umol, 13.9% yield) was obtained. LCMS (ESI): RT=0.868 min, mass calcd. for $C_{21}H_{25}FN_6O_2S$ 444.17, m/z found 445.0 [M+H]⁺. ¹H NMR (400 MHz, DMSO-d₆) δ 8.38 (d, J=2.3 Hz, 1H), 7.63 (dd, J=2.0, 8.8 Hz, 1H), 7.56-7.50 (m, 3H), 7.30-7.20 (m, 3H), 7.02 (d, J=9.3 Hz, 1H), 6.05 (s, 2H), 3.66-3.57 (m, 1H), 2.35 (d, J=5.0 Hz, 3H), 1.97-1.89 (m, 2H), 1.65 (td, J=3.2, 6.1 Hz, 2H), 1.60-1.52 (m, 1H), 1.47-1.36 (m, 2H), 1.35-1.22 (m, 3H).

Compound 41-3 (6.72 mg, 12.2 umol, 11.3% yield) was obtained, which was confirmed by LCMS and ¹H NMR. LCMS (ESI): RT=0.988 min, mass calcd. for $C_{28}H_{30}F_2N_6O_2S$ 552.21, m/z found 553.1 [M+H]⁺. ¹H NMR (400 MHz, DMSO-d₆) δ 8.38 (d, J=2.3 Hz, 1H), 7.70 (dd, J=1.9, 8.9 Hz, 1H), 7.59 (d, J=7.5 Hz, 1H), 7.54 (dd, J=5.6, 8.4 Hz, 2H), 7.34 (dd, J=5.6, 8.2 Hz, 2H), 7.26 (t, J=8.8 Hz, 2H), 7.16 (t, J=8.8 Hz, 2H), 7.05 (d, J=9.0 Hz, 1H), 6.06 (s, 2H), 4.06 (s, 2H), 3.69-3.59 (m, 1H), 1.98-1.89 (m, 2H), 1.65 (dd, J=3.5, 8.8 Hz, 2H), 1.60-1.52 (m, 1H), 1.47-1.37 (m, 2H), 1.36-1.25 (m, 3H).

190

Example 41: 3-(2-(1-acetylpyrrolidin-3-yl)-2H-tetra-zol-5-yl)-4-(cyclohexylamino)-N-methylbenzene-sulfonamide (Compound 42)

Preparation of Compound 42:

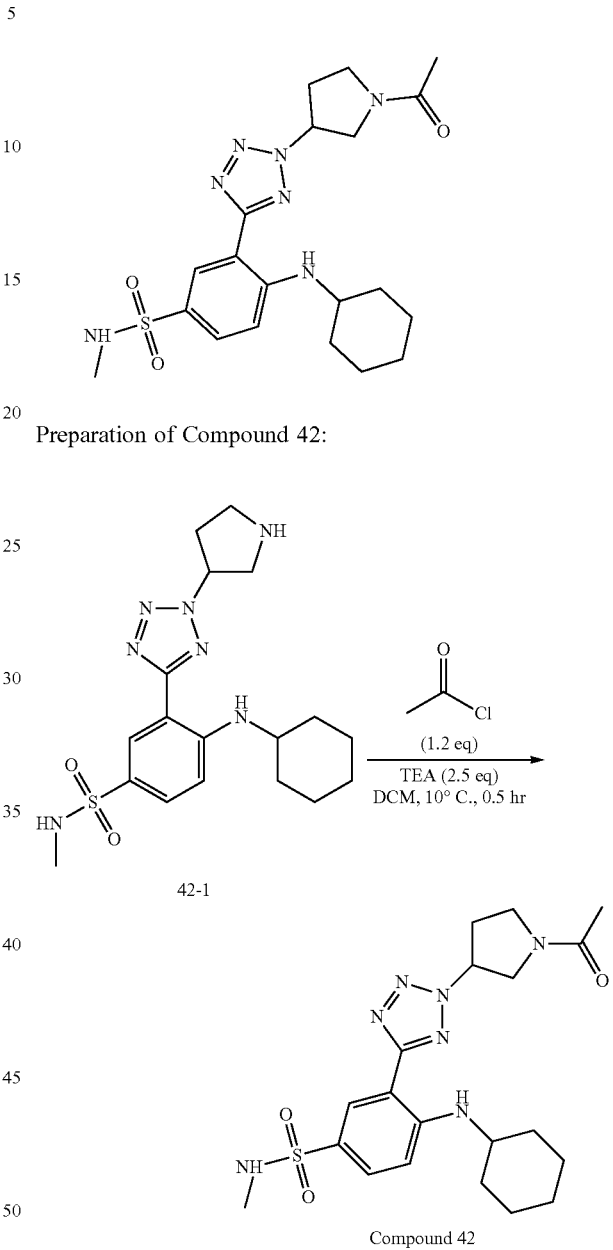

Compound 42

To the solution of compound 42-1 (30 mg, 68 umol, 1 eq, HCl) in DCM (3 mL) was added TEA (17 mg, 0.17 mmol, 24 uL, 2.5 eq). Then acetyl chloride (6 mg, 81 umol, 6 uL, 1.2 eq) was added to the mixture. The solution was stirred at 10° C. for 0.5 hr. The reaction was monitored by LCMS. The reaction was concentrated under reduced pressure. The residue was purified by prep-HPLC to give Compound 42 (9.21 mg, 20.6 umol, 30.3% yield). LCMS (ESI): RT=0.722 min, mass calcd. for $C_{20}H_{29}N_7O_3S$ 447.21, m/z found 448.1 [M+H]⁺, ¹HNMR (400 MHz, CHLOROFORM-d) δ 8.59 (br, 1H), 7.73 (d, J=7.8 Hz, 2H), 6.83 (d, J=8.3 Hz, 1H), 5.65-5.44 (m, 1H), 4.39-3.71 (m, 5H), 3.58-3.44 (m, 1H), 2.91-2.59 (m, 5H), 2.23-2.03 (m, 5H), 1.89-1.76 (m, 2H), 1.71-1.67 (m, 1H), 1.48-1.35 (m, 5H).

Example 42: 4-(cyclohexylamino)-N-methyl-3-(2-(1-(methylsulfonyl)pyrrolidin-3-yl)-2H-tetrazol-5-yl)benzenesulfonamide (Compound 43)

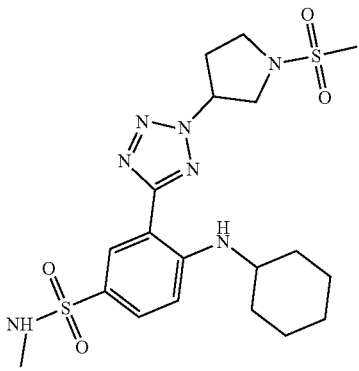

Preparation of Compound 43:

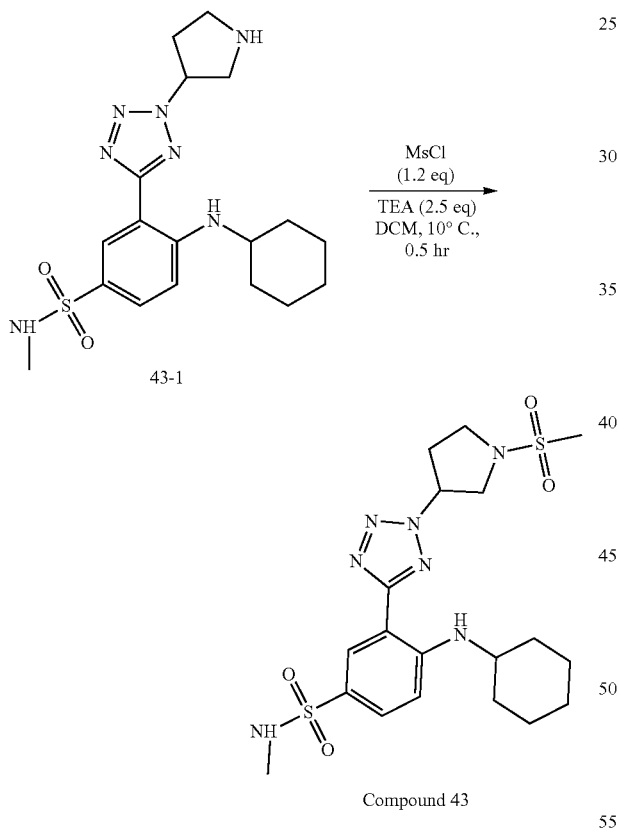

To the solution of compound 43-1 (30 mg, 68 umol, 1 eq, HCl) in DCM (3 mL) was added TEA (17 mg, 0.17 mmol, 24 uL, 2.5 eq). Then methanesulfonyl chloride (9 mg, 81 umol, 6 uL, 1.2 eq) was added to the mixture. The solution was stirred at 10° C. for 0.5 hr. The reaction was monitored by LCMS. The reaction was concentrated under reduced pressure. The residue was purified by prep-HPLC to give Compound 43 (3.71 mg, 7.7 umol, 11.3% yield). LCMS (ESI): RT=0.754 min, mass calcd. for $C_{19}H_{29}N_7O_4S_2$ 483.17, m/z found 484.1 [M+H]$^+$, HNMR (400 MHz, CHLOROFORM-d) δ 8.57 (d, J=2.3 Hz, 1H), 7.78-7.71 (m, 2H), 6.84 (d, J=9.0 Hz, 1H), 5.61-5.54 (m, 1H), 4.30-4.22 (m, 1H), 4.10-4.02 (m, 2H), 3.81-3.73 (m, 1H), 3.70-3.62 (m, 1H), 3.59-3.50 (m, 1H), 2.95 (s, 3H), 2.79-2.69 (m, 2H), 2.68-2.66 (m, 3H), 2.13-2.03 (m, 2H), 1.87-1.78 (m, 2H), 1.72-1.64 (m, 1H), 1.51-1.41 (m, 5H).

Example 43: 4-(cyclohexylamino)-3-(2-(2-hydroxyethyl)-2H-tetrazol-5-yl)-N-methylbenzenesulfonamide (Compound 44)

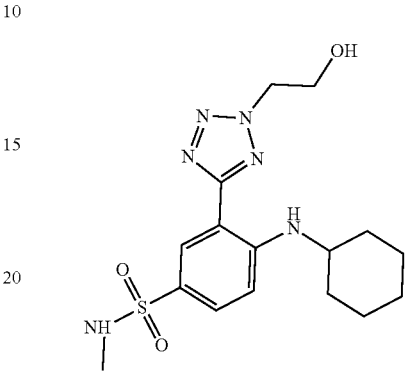

Preparation of Compound 44:

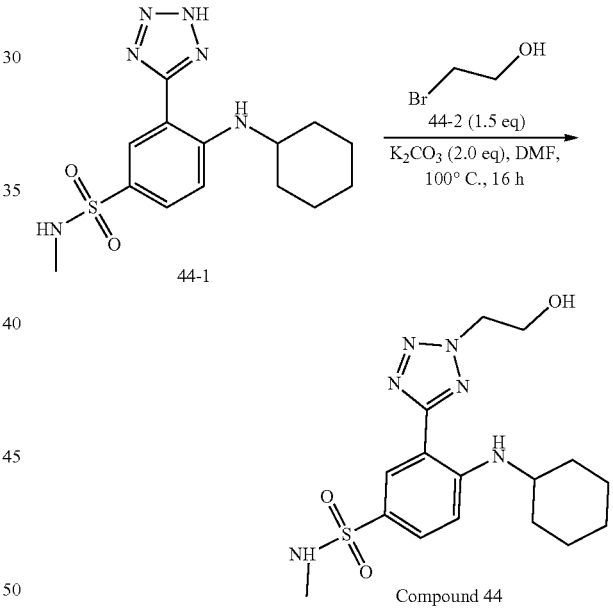

To a solution of compound 44-1 (30.0 mg, 89.2 umol, 1.0 eq) in DMF (2.0 mL) was added K$_2$CO$_3$ (24.7 mg, 0.18 mmol, 2.0 eq) and compound 44-2 (16.7 mg, 0.13 mmol, 9.5 uL, 1.5 eq). The mixture was stirred at 100° C. for 16 hour at N$_2$ atmosphere. LCMS showed desired compound was found. The reaction was filtered to give a crude product. The crude product was purified by prep-HPLC to give Compound 44 (6.16 mg, 16.2 umol, 18.2% yield) was obtained. LCMS (ESI): RT=0.725 min, mass calc. for $C_{16}H_{24}N_6O_3S$ 380.16, m/z found 381.0 [M+H]$^+$; $^1$HNMR (400 MHz, CDCl$_3$) δ 8.60 (d, J=2.3 Hz, 1H), 7.82 (d, J=7.0 Hz, 1H), 7.73 (dd, J=2.3, 9.0 Hz, 1H), 6.82 (d, J=9.0 Hz, 1H), 4.88-4.80 (m, 2H), 4.33-4.24 (m, 3H), 3.54 (s, 1H), 2.66 (d, J=5.5 Hz, 3H), 2.30 (t, J=6.3 Hz, 1H), 2.08 (d, J=8.0 Hz, 2H), 1.86-1.77 (m, 2H), 1.67 (d, J=12.3 Hz, 1H), 1.52-1.35 (m, 5H).

Example 44: 4-(cyclohexylamino)-N-methyl-3-(2-(pyridin-3-yl)-2H-tetrazol-5-yl)benzenesulfonamide (Compound 45)

Preparation of Compound 45:

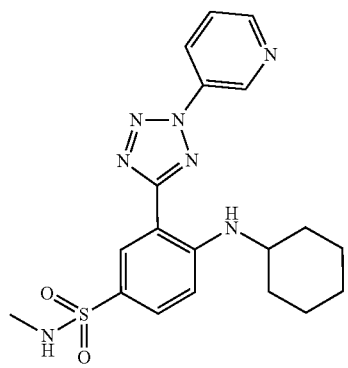 [SMILES: CNS(=O)(=O)c1ccc(NC2CCCCC2)c(-c2nnn(-c3cccnc3)n2)c1]

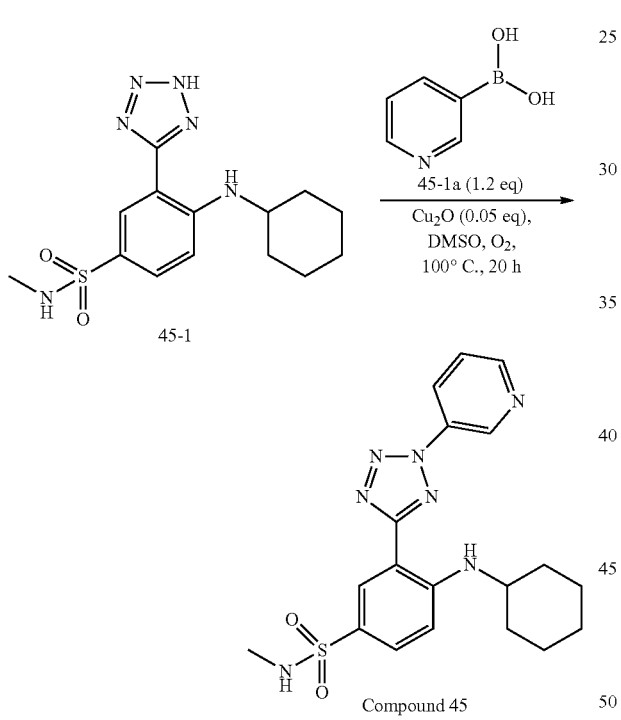

A solution of compound 45-1 (50 mg, 0.13 mmol, 1.0 eq, HCl), 45-1a (33 mg, 0.27 mmol, 2.0 eq) and Cu₂O (1 mg, 6.70 umol, 0.05 eq) in DMSO (3 mL) was degassed under vacuum and purged with O2 several times. The mixture was stirred at 100° C. for 20 hr. LCMS showed that ~60% of desired MS signal was detected. The reaction was filtered and concentrated. The residue was purified by prep-HPLC to give Compound 45 (2.30 mg, 5.6 umol, 4.2% yield). The HNMR and LCMS confirmed that desired product was obtained. LCMS (ESI): RT=2.779 min, mass calcd. for $C_{19}H_{23}N_7SO_2$ 413.16, m/z found 414.0 [M+H]⁺. ¹H NMR (400 MHz, CDCl₃) δ 9.39 (s, 1H), 8.85 (s, 1H), 8.75-8.50 (m, 2H), 7.80 (dd, J=8.0 Hz, 4.8 Hz, 1H), 7.71 (dd, J=9.2 Hz, 2.0 Hz, 1H), 7.40-7.25 (m, 2H), 6.86 (d, J=9.2 Hz, 1H), 7.40-7.25 (m, 1H), 7.11 (d, J=9.2 Hz, 1H), 3.65-3.50 (m, 1H), 2.41 (d, J=4.8 Hz, 3H), 2.10-2.00 (m, 2H), 1.90-1.75 (m, 2H), 1.75-1.65 (m, 2H), 1.50-1.40 (m, 4H).

Example 45: 4-(cyclohexylamino)-3-(2-(1-isopropylpiperidin-4-yl)-2H-tetrazol-5-yl)-N-methylbenzenesulfonamide (Compound 46) and isopropyl 4-(5-(2-(cyclohexylamino)-5-(N-methylsulfamoyl)phenyl)-2H-tetrazol-2-yl)piperidine-1-carboxylate (Compound 47)

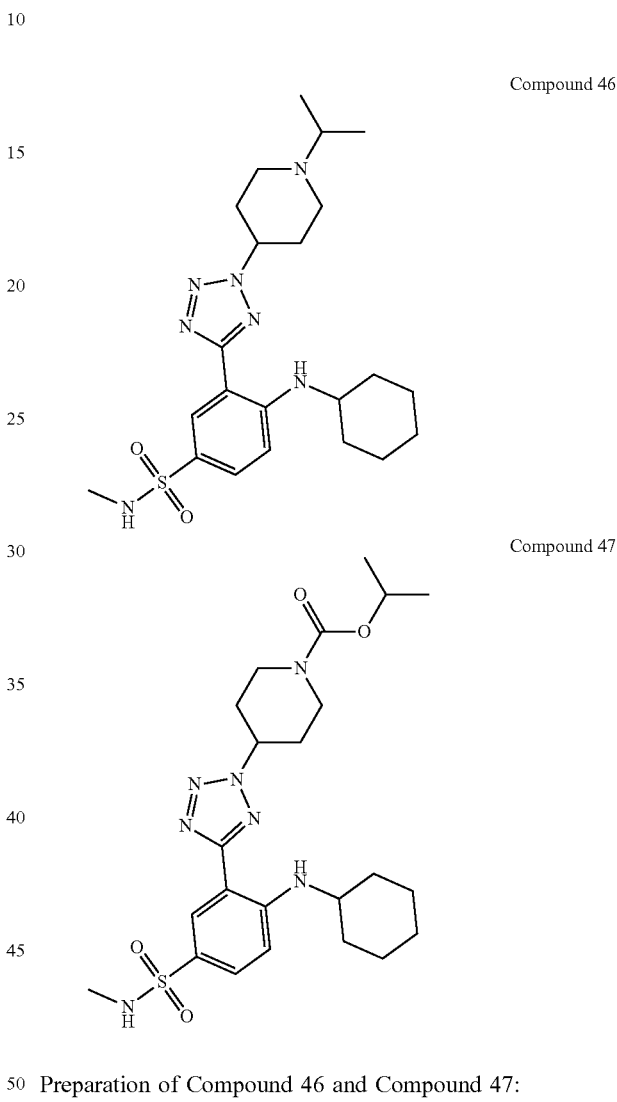

Preparation of Compound 46 and Compound 47:

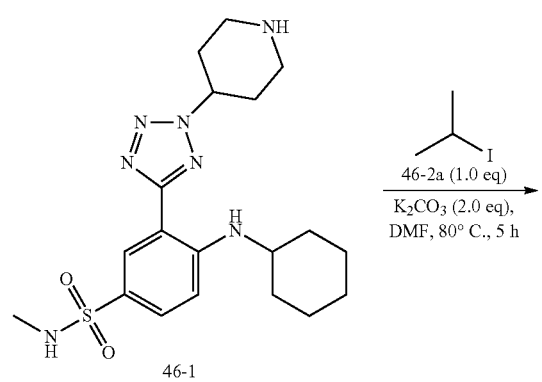

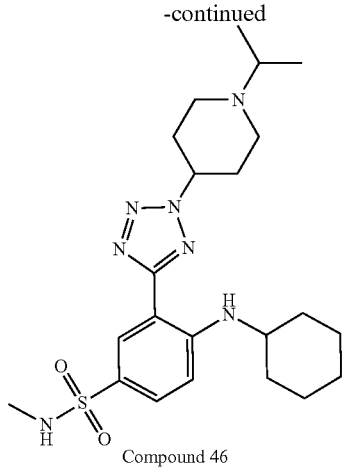

Compound 46

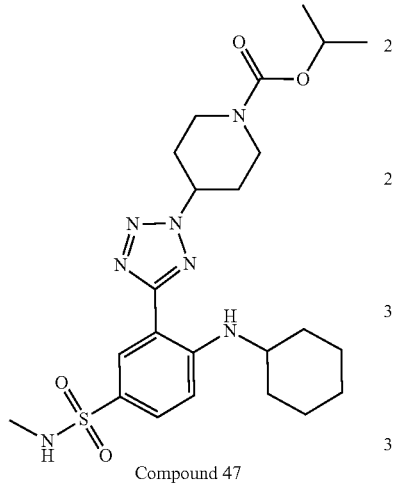

Compound 47

To a stirred solution of 46-1 (30 mg, 66 umol, 1.0 eq, HCl) and K₂CO₃ (18.2 mg, 0.13 mmol, 2.0 eq) in DMF (1 mL) was added compound 46-2a (11 mg, 66 umol, 7 uL, 1.0 eq). The resulting mixture was heated at 80° C. for 5 hr. The reaction was monitored by LCMS. The reaction mixture was poured into water (3 mL) and the resulting mixture was stirred for 5 min. The aqueous phase was extracted with ethyl acetate (3 mL*3). The combined organic phase were washed with brine (3 mL*2), dried with anhydrous Na₂SO₄, filtered and concentrated in vacuum to give a residue. The residue was purified by prep-HPLC to give Compound 46 (6 mg, 13 umol, 20% yield) and Compound 47 (1.49 mg, 3 umol, 5% yield).

Compound 46: LCMS (ESI): RT=0.647 min, mass calc. for C₂₂H₃₅N₇O₂S 461.26, m/z found 462.2 [M+H]⁺; ¹H NMR (400 MHz, CDCl₃) δ 8.61 (d, J=2.0 Hz, 1H), 7.82 (d, J=7.3 Hz, 1H), 7.71 (dd, J=2.1, 8.9 Hz, 1H), 6.81 (d, J=9.0 Hz, 1H), 4.72 (quin, J=7.5 Hz, 1H), 4.24 (q, J=5.3 Hz, 1H), 3.52 (s, 1H), 3.03 (d, J=11.5 Hz, 2H), 2.84 (td, J=6.5, 13.1 Hz, 1H), 2.66 (d, J=5.5 Hz, 3H), 2.48-2.37 (m, 2H), 2.33 (d, J=3.3 Hz, 4H), 2.08 (d, J=8.5 Hz, 2H), 1.87-1.75 (m, 2H), 1.66 (s, 1H), 1.51-1.33 (m, 5H), 1.09 (d, J=6.5 Hz, 6H).

Compound 47: LCMS (ESI): RT=0.8648 min, mass calc. for C23H35N7O4S 505.25, m/z found 528.1 [M+23]+; 1H NMR (400 MHz, CDCl₃) δ 8.60 (d, J=2.3 Hz, 1H), 7.82 (d, J=7.3 Hz, 1H), 7.72 (dd, J=2.3, 8.8 Hz, 1H), 6.82 (d, J=9.0 Hz, 1H), 5.01-4.89 (m, 2H), 4.34-4.16 (m, 3H), 3.53 (s, 1H), 3.13 (t, J=11.2 Hz, 2H), 2.66 (d, J=5.5 Hz, 3H), 2.35-2.20 (m, 4H), 2.07 (d, J=9.3 Hz, 2H), 1.81 (s, 2H), 1.65 (s, 1H), 1.50-1.39 (m, 5H), 1.29 (d, J=6.3 Hz, 6H).

Example 46: 4-(cyclohexylamino)-N-methyl-3-(5-methyl-1,2,4-oxadiazol-3-yl)benzene sulfonamide (Compound 48)

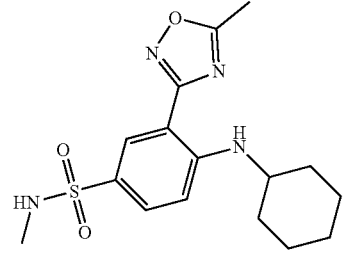 [SMILES: CNS(=O)(=O)c1ccc(NC2CCCCC2)c(-c2noc(C)n2)c1]

Preparation of Compound 48:

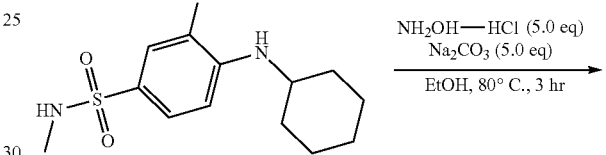

48-1

48-2

Compound 48

Step 1: 2-(Cyclohexylamino)-N'-hydroxy-5-(N-methylsulfamoyl)benzimidamide

To a solution of compound 48-1 (100 mg, 0.34 mmol, 1.0 eq) and hydroxylamine (118 mg, 1.7 mmol, 5.0 eq, HCl) in EtOH (4 mL) was added Na₂CO₃ (181 mg, 1.7 mmol, 5.0 eq) and then stirred at 80° C. for 3 hours. The reaction mixture was concentrated under reduced pressure. The mixture was diluted with water (10 mL) and the resultant mixture was extracted with EA (30 mL*3). The combined organic layers were dried over Na₂SO₄, filtered and concentrated to dryness under reduced pressure to obtain 48-2 (90 mg, 81% yield). LCMS (ESI): RT=0.604 min, mass calcd. for $C_{14}H_{22}N_4O_3S$ 326.14, m/z found 326.9 [M+H]+.

Step 2: 4-(Cyclohexylamino)-N-methyl-3-(5-methyl-1,2,4-oxadiazol-3-yl)benzenesulfonamide Acetyl chloride (11 mg, 0.13 mmol, 1.1 eq) was added to a solution of compound 48-2 (40 mg, 0.12 mmol, 1.0 eq) in Pyridine (1 mL). The reaction mixture was stirred at 100° C. for 16 hours. The reaction mixture was concentrated under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. Compound 48 (12.18 mg, 28% yield) was obtained. LCMS (ESI): RT=1.242 min, mass calcd. for $C_{16}H_{22}N_4O_3S$ 350.14, m/z found 351.0 [M+H]+, 1HNMR (400 MHz, CDCl3) δ 8.59 (d, J=2.3 Hz, 1H), 7.75 (dd, J=2.3, 9.0 Hz, 1H), 7.29 (d, J=7.3 Hz, 1H), 6.81 (d, J=9.0 Hz, 1H), 4.23 (q, J=5.2 Hz, 1H), 3.62-3.48 (m, 1H), 2.68-2.63 (m, 6H), 2.12-2.02 (m, 2H), 1.86-1.76 (m, 2H), 1.70-1.62 (m, 1H), 1.51-1.34 (m, 5H).

Example 47: 3-(2-(1-acetylazetidin-3-yl)-2H-tetrazol-5-yl)-4-(cyclohexylamino)-N-methylbenzenesulfonamide (Compound 49)

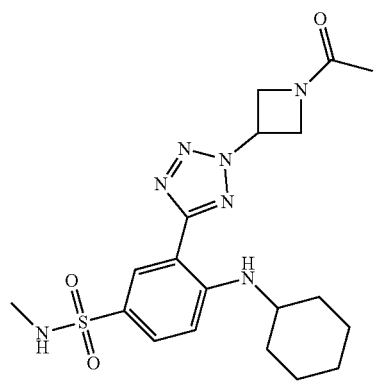 [SMILES: CNS(=O)(=O)c1ccc(NC2CCCCC2)c(-c2nnn(C3CN(C(C)=O)C3)n2)c1]

Preparation of Compound 49:

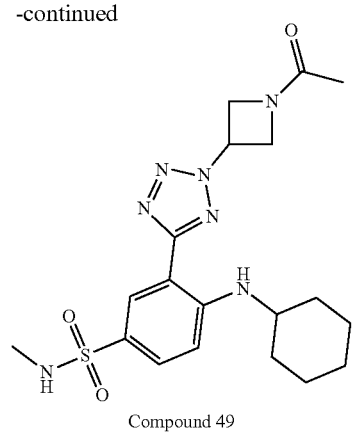

Compound 49

To a mixture of 49-1 (25 mg, 58 umol, 1 eq, HCl) and Et3N (24 mg, 0.23 mmol, 33 uL, 4 eq) in DCM (1 mL) was added 49-1a (9 mg, 0.12 mmol, 9 uL, 2 eq) in one portion at 15° C. under N2. The mixture was stirred at 15° C. for 2 h. LCMS showed the compound 1 was consumed completely and one main peak with desired MS was detected. The reaction mixture was concentrated under reduced pressure to remove solvent. HPLC showed 64% of desired product was formed. The residue was purified by prep-HPLC. LCMS and 1H NMR confirmed the product was Compound 49 (2.13 mg, 4.7 umol, 8.0% yield). LCMS (ESI): RT=0.709 min, mass calcd. For $C_{19}H_{27}N_7O_3S$, 433.19 m/z found 434.1 [M+H]+ and 456.1 [M+23]+. 1H NMR (400 MHz, DMSO-d6) δ 8.43 (d, J=2.00 Hz, 1H), 7.66 (dd, J=8.80, 2.00 Hz, 1H), 7.60 (br s, 1H), 7.27 (br s, 1H), 7.05 (d, J=9.20 Hz, 1H), 6.02-5.87 (m, 1H), 4.78 (t, J=8.80 Hz, 1H), 4.66-4.56 (m, 1H), 4.53-4.43 (m, 1H), 4.37-4.27 (m, 1H), 2.37 (s, 3H), 2.36-2.28 (m, 1H), 2.01-1.91 (m, 2H), 1.85 (s, 3H), 1.74-1.64 (m, 2H), 1.61-1.51 (m, 1H), 1.50-1.31 (m, 5H).

Example 48: 4-(cyclohexylamino)-N-methyl-3-(2-(1-(methylsulfonyl)azetidin-3-yl)-2H-tetrazol-5-yl)benzenesulfonamide (Compound 50)

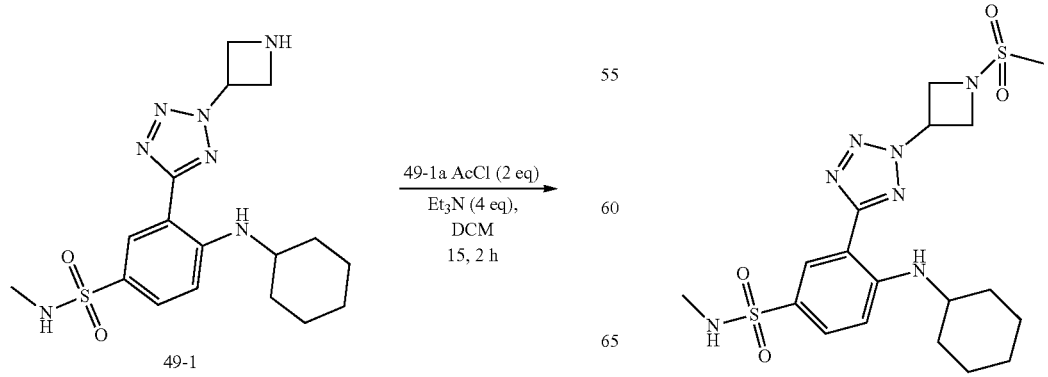

Preparation of Compound 50:

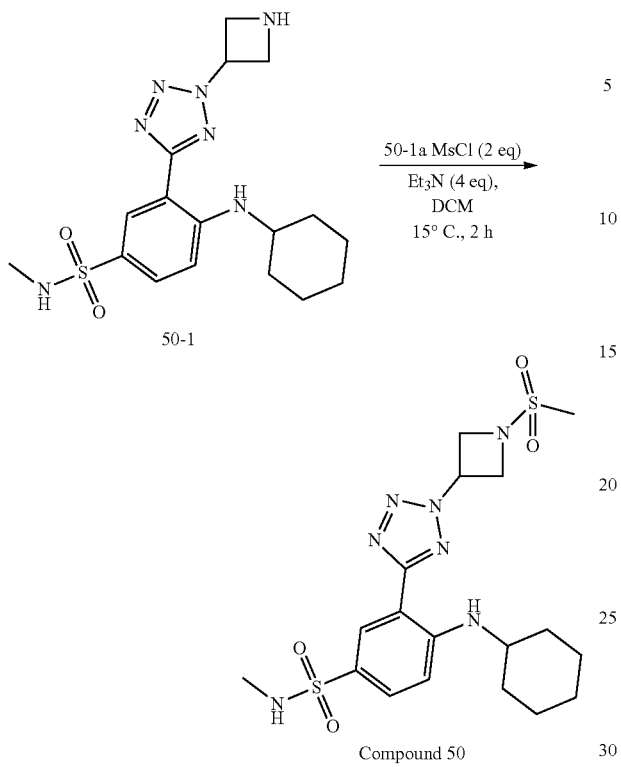

To a mixture of 50-1 (25 mg, 58 umol, 1 eq, HCl) and Et₃N (24 mg, 0.23 mmol, 33 uL, 4 eq) in DCM (1 mL) was added 50-1a (70 mg, 0.61 mmol, 47 uL, 10.5 eq) in one portion at 15° C. under $N_2$. The mixture was stirred at 15° C. for 2 h. LCMS showed compound 50-1 was consumed completely and one main peak with desired MS was detected. The reaction mixture was concentrated under reduced pressure to remove solvent. HPLC showed 54% of desired product was formed. The residue was purified by prep-HPLC. LCMS and $^1$H NMR confirmed that the product was Compound 50 (4.39 mg, 9.4 umol, 16.0% yield). LCMS (ESI): RT=0.749 min, mass calcd. For $C_{18}H_{27}N_7O_4S_2$, 469.16 m/z found 470.0[M+H]⁺. $^1$H NMR (400 MHz, DMSO-$d_6$) δ 8.43 (d, J=2.00 Hz, 1H), 7.66 (dd, J=8.80, 2.00 Hz, 1H), 7.59-7.46 (m, 1H), 7.30-7.22 (m, 1H), 7.06 (d, J=8.80 Hz, 1H), 6.04-5.95 (m, 1H), 4.59-4.41 (m, 4H), 3.70-3.60 (m, 1H), 3.17 (s, 3H), 2.38 (d, J=4.40 Hz, 3H), 2.02-1.94 (m, 2H), 1.76-1.67 (m, 2H), 1.64-1.54 (m, 1H), 1.51-1.30 (m, 5H)

Example 49: 4-(cyclohexylamino)-N-methyl-3-(2-(1-phenylazetidin-3-yl)-2H-tetrazol-5-yl)benzene-sulfonamide (Compound 51)

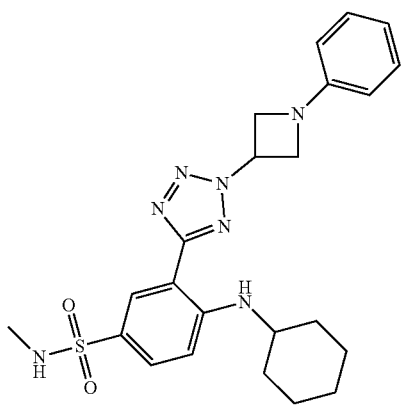 [SMILES: CNS(=O)(=O)c1ccc(NC2CCCCC2)c(-c2nnn(C3CN(c4ccccc4)C3)n2)c1]

Preparation of Compound 49:

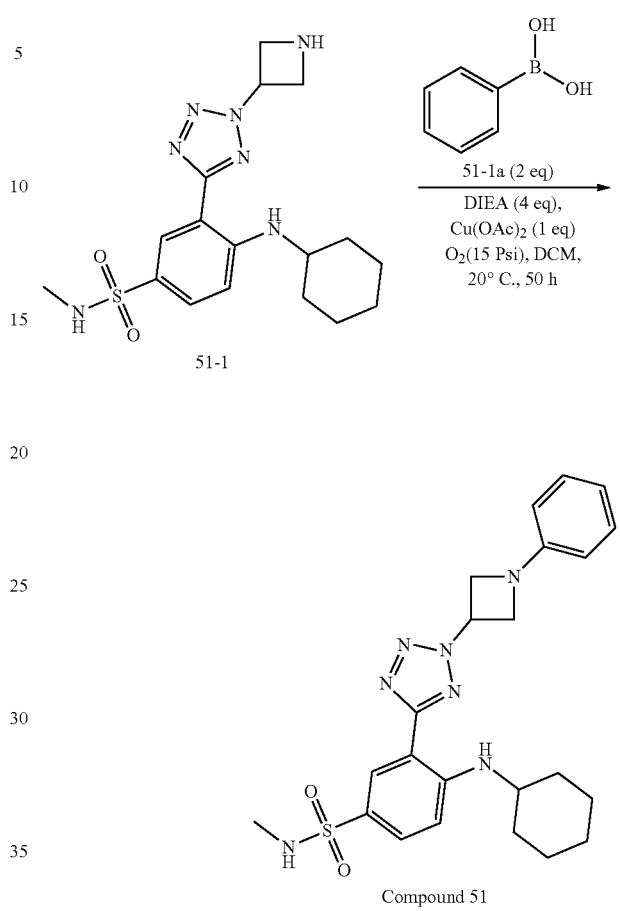

To a mixture of 51-1 (50 mg, 0.12 mmol, 1 eq, HCl) and DIPEA (60 mg, 0.47 mmol, 4 eq) in DCM (1.5 mL) was added Cu(OAc)₂ (21 mg, 0.12 mmol, 1 eq) and 51-1a (29 mg, 0.23 mmol, 2 eq) in one portion under $N_2$. The mixture was stirred at 20° C. for 50 h. LCMS showed 24% of compound 51-1 was remained. Several new peaks were shown on LCMS and 40% of desired compound was detected. The reaction mixture was concentrated under reduced pressure to remove solvent. The residue was diluted with water (5 mL) and extracted with EA (5 mL*3), the combined organic phase was dried with anhydrous Na₂SO₄, filtered and concentrated in vacuum. HPLC indicated 35% of desired product was formed. The residue was purified by prep-HPLC. LCMS and $^1$HNMR confirmed the product was Compound 51 (2.04 mg, 4.3 umol, 3.7% yield). LCMS (ESI): RT=0.885 min, mass calcd. For $C_{23}H_{29}N_7O_2S$, 467.21 m/z found 468.1 [M+H]⁺. $^1$H NMR (400 MHz, CDCl₃) δ 8.63 (d, J=2.00 Hz, 1H), 7.81-7.70 (m, 2H), 7.34-7.27 (m, 2H), 6.91-6.78 (m, 2H), 6.59 (d, J=8.00 Hz, 2H), 5.93-5.83 (m, 1H), 4.56 (t, J=8.00 Hz, 2H), 4.50-4.43 (m, 2H), 4.35-4.28 (m, 1H), 3.53 (br s, 1H), 2.66 (d, J=5.20 Hz, 3H), 2.05-1.96 (m, 2H), 1.82-1.72 (m, 2H), 1.62-1.56 (m, 1H), 1.45-1.28 (m, 5H).

Example 50: 4-(cyclohexylamino)-3-(2-(1-isopropylazetidin-3-yl)-2H-tetrazol-5-yl)-N-methylbenzenesulfonamide (Compound 52)

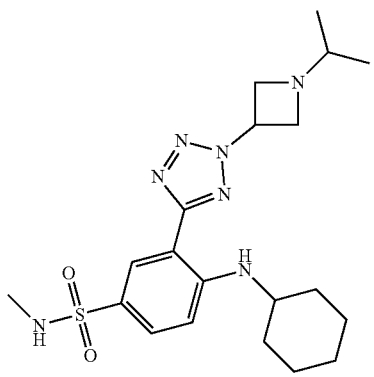 [SMILES: CNS(=O)(=O)c1ccc(NC2CCCCC2)c(-c2nnn(C3CN(C(C)C)C3)n2)c1]

Preparation of Compound 52:

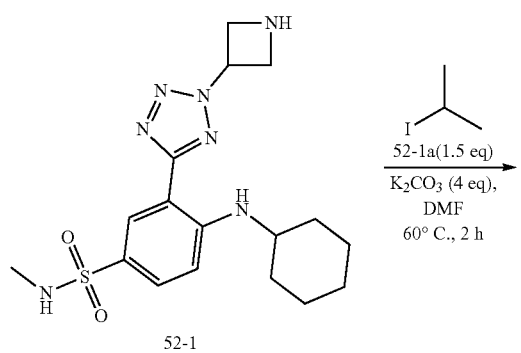

To a mixture of 52-1 (30 mg, 70 umol, 1 eq, HCl) and K₂CO₃ (39 mg, 0.28 mmol, 4 eq) in CH₃CN (2 mL) was added 52-1a (18 mg, 0.10 mmol, 1.5 eq) in one portion under N₂. The mixture was stirred at 40° C. for 2 h. LCMS showed the starting material was remained and no desired MS was detected. The reaction mixture was added DMF (1 mL) and heated to 60° C. for 2 h. LCMS showed 30% of compound 52-1 was remained. Several new peaks were shown on LCMS and 25% of desired compound was detected. The reaction mixture was concentrated under reduced pressure to remove CH₃CN. The residue was diluted with water (3 mL) and extracted with EA (5 mL*3). The combined organic layers were dried with anhydrous Na₂SO₄, filtered and concentrated in vacuum. The residue was purified by prep-HPLC. LCMS and ¹HNMR confirmed the product was Compound 52 (3.55 mg, 8.2 umol, 11.7% yield). LCMS (ESI): RT=0.663 min, mass calcd. For $C_{20}H_{31}N_7O_2S$, 433.23 m/z found 434.1 [M+H]⁺. H NMR (400 MHz, CDCl₃) δ 13.39 (br s, 1H), 8.60 (br s, 1H), 7.75 (br d, J=8.40 Hz, 2H), 6.84 (br d, J=8.40 Hz, 1H), 6.17 (br s, 1H), 4.96 (br s, 2H), 4.48 (br s, 2H), 3.67 (br s, 1H), 3.54 (br s, 1H), 2.65 (br s, 3H), 2.10-2.04 (m, 2H), 1.87-1.78 (m, 2H), 1.69-1.66 (m, 1H), 1.51-1.40 (m, 11H).

Example 51: 3-(2-(1-acetylpiperidin-3-yl)-2H-tetrazol-5-yl)-4-(cyclohexylamino)-N-methylbenzenesulfonamide (Compound 53)

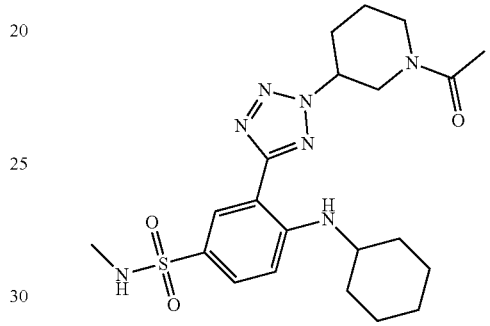

Preparation of Compound 53:

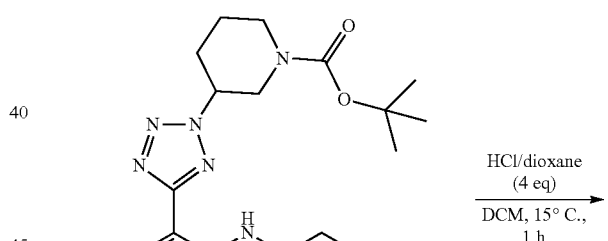

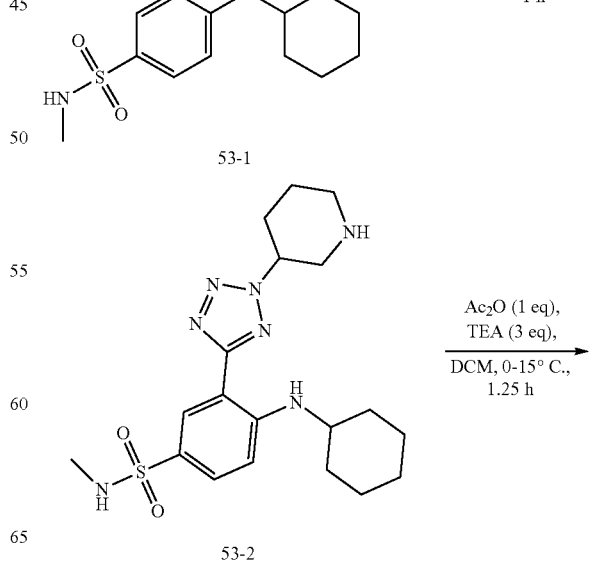

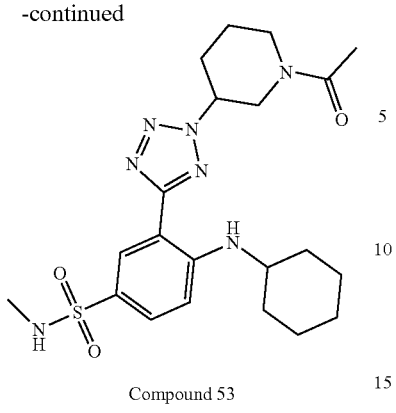

Compound 53

Step 1: 4-(cyclohexylamino)-N-methyl-3-(2-(piperidin-3-yl)-2H-tetrazol-5-yl)benzenesulfonamide To a mixture of compound 53-1 (0.26 g, 500 umol, 1 eq) in DCM (2 mL) was added HCl/dioxane (1 M, 2 mL, 4.0 eq). The mixture was stirred at 15° C. for 1 h. The crude LCMS showed 95% of desired product was detected. The reaction mixture was concentrated under reduced pressure to give a residue as a light yellow solid. The residue was diluted with MeOH (5 mL) and water (5 mL), and the most of MeOH was removed under reduced pressure, the remaining aqueous was lyophilized to give compound 53-2 (210 mg, 460 umol, 92% yield, HCl). 20 mg of the solid was purified by prep-HPLC to give 53-2 (2.19 mg). LCMS (ESI): RT=2.089 min, mass calc. for $C_{19}H_{29}N_7O_2S$ 419.54, m/z found 420.0 [M+1]$^+$. $^1$HNMR (400 MHz, METHANOL-$d_4$) δ 1.23-2.27 (m, 16H), 2.33-2.58 (m, 4H), 2.90 (s, 1H), 3.36-3.52 (m, 3H), 3.65 (br s, 1H), 4.29 (br s, 1H), 5.04-5.46 (m, 2H), 7.01 (br d, J=9.29 Hz, 1H), 7.72 (br d, J=7.03 Hz, 1H), 8.58 (s, 1H).

Step 2: 3-(2-(1-acetylpiperidin-3-yl)-2H-tetrazol-5-yl)-4-(cyclohexylamino)-N-methylbenzenesulfonamide To a mixture of compound 53-2 (30 mg, 65.8 umol, 1 eq, HCl) and TEA (20.0 mg, 197 umol, 27.5 uL, 3 eq) in DCM (1 mL) was added Ac$_2$O (6.7 mg, 65.8 umol, 6.2 uL, 1 eq) in one portion at 0° C. and stirred for 15 min. The mixture was stirred at 15° C. for 1 h. The crude LCMS showed 85% of desired product was detected. The reaction mixture was quenched by water (10 mL) and extracted with DCM (10 mL*4). The combined organic layers were dried over anhydrous Na$_2$SO$_4$, filtered and concentrated under reduced pressure to give a residue (25 mg) as colorless oil. The residue was purified by prep-HPLC to give Compound 53 (2.41 mg, 5.1 umol, 7.8% yield). LCMS (ESI): RT=2.047 min, mass calc. for $C_{21}H_{31}N_7O_3S$ 461.58, m/z found 462.1 [M+1]$^+$. $^1$HNMR (400 MHz, DMSO-$d_6$, t=80° C.) δ 1.29-1.54 (m, 6H), 1.57-1.76 (m, 4H), 1.79-1.93 (m, 1H), 1.95-2.07 (m, 5H), 2.23-2.36 (m, 1H), 2.44 (s, 4H), 3.27-3.51 (m, 1H), 3.59-3.80 (m, 2H), 4.88-5.17 (m, 1H), 6.89-7.05 (m, 2H), 7.48 (br d, J=7.53 Hz, 1H), 7.67 (dd, J=8.78, 2.26 Hz, 1H), 8.44 (d, J=2.26 Hz, 1H).

Example 52: 3-(2-(azetidin-3-yl)-2H-tetrazol-5-yl)-4-(cyclohexylamino)-N-methylbenzenesulfonamide (Compound 54)

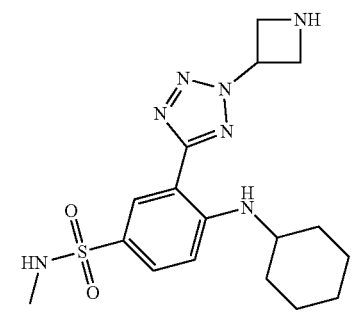 [SMILES: CNS(=O)(=O)c1ccc(NC2CCCCC2)c(-c2nnn(C3CNC3)n2)c1]

Preparation of Compound 54:

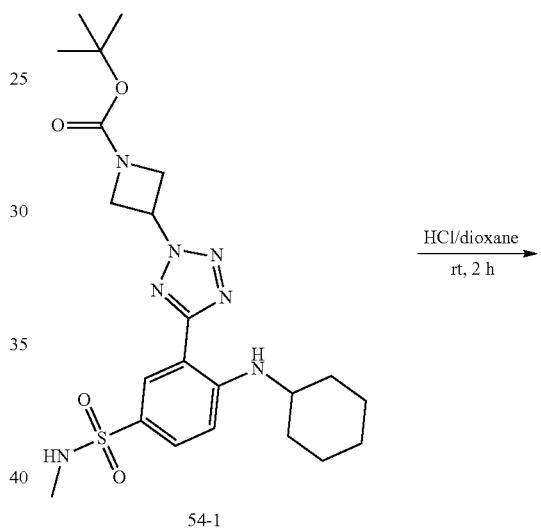

54-1

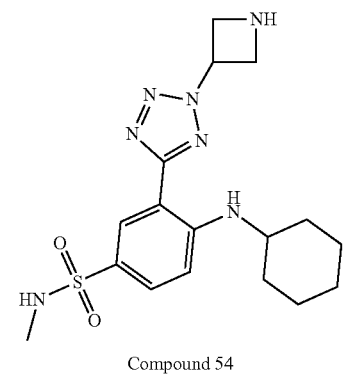

Compound 54

To a mixture of 54-1 (12 mg, 24.4 umol, 1.0 eq) in MeOH (1 mL) was added HCl/dioxane (4 M, 3 mL, 492 eq). The reaction mixture was stirred at 15° C. for 2 h. LCMS showed the starting material was consumed completely and one main peak with desired MS was detected. The reaction mixture was concentrated under reduced pressure to remove solvent. HPLC showed 92% of desired product was formed. The residue was purified by prep-HPLC. LCMS and $^1$H NMR confirmed the product was Compound 54 (4.30 mg, 10.1 umol, 41.2% yield, HCl). LCMS (ESI): RT=0.646 min, mass calcd. For $C_{17}H_{25}N_7O_2S$, 391.18 m/z found 392.1 [M+H]$^+$. $^1$H NMR (400 MHz, DMSO-d$_6$) δ 9.96-9.57 (m, 2H), 8.43 (d, J=2.40 Hz, 1H), 7.73-7.63 (m, 1H), 7.60-7.42 (m, 1H), 7.36-7.22 (m, 1H), 7.07 (d, J=9.20 Hz, 1H), 6.15-6.02 (m, 1H), 4.61-4.51 (m, 4H), 3.67-3.63 (m, 1H), 2.37 (s, 3H), 2.04-1.94 (m, 2H), 1.79-1.67 (m, 2H), 1.64-1.53 (m, 1H), 1.50-1.29 (m, 5H).

Example 53: 4-(cyclohexylamino)-N-methyl-3-(pyrimidin-5-yl)benzenesulfonamide (Compound 55)

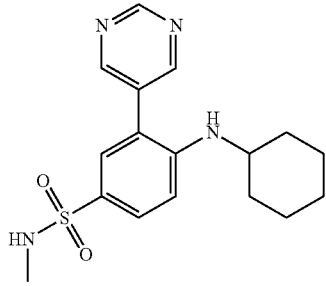

Preparation of Compound 55:

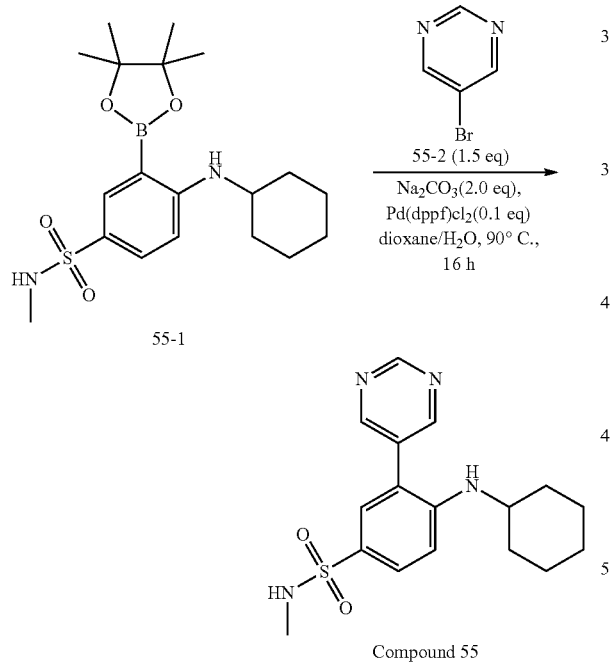

Compound 55

To a solution of compound 55-1 (50.0 mg, 0.13 mmol, 1.0 eq) and compound 2 (30.2 mg, 0.19 mmol, 1.5 eq) in dioxane (5.0 mL) was added H$_2$O (0.5 mL), Pd(dppf)Cl$_2$ (9.3 mg, 12.7 umol, 0.1 eq) and Na$_2$CO$_3$ (26.9 mg, 0.25 mmol, 2.0 eq). The mixture was stirred at 90° C. for 16 hours under N$_2$ atmosphere. LCMS showed desired compound was found. The reaction was filtered through Celite and concentrated under reduced pressure to give a residue. The crude product was purified by prep-HPLC to give Compound 55 (5.25 mg, 14.7 umol, 11.6% yield). LCMS (ESI): RT=0.695 min, mass calc. for $C_{17}H_{22}N_4O_2S$ 346.15, m/z found 347.0 [M+H]$^+$; $^1$HNMR (400 MHz, CDC$_3$-d) δ 9.28 (s, 1H), 8.82 (s, 2H), 7.76 (dd, J=2.3, 8.8 Hz, 1H), 7.51 (d, J=2.3 Hz, 1H), 6.78 (d, J=8.8 Hz, 1H), 4.34 (q, J=5.3 Hz, 1H), 3.99 (d, J=7.5 Hz, 1H), 3.43-3.32 (m, 1H), 2.68 (d, J=5.5 Hz, 3H), 2.04-1.97 (m, 2H), 1.78-1.70 (m, 2H), 1.45-1.32 (m, 2H), 1.29-1.06 (m, 4H).

Example 54: 4-(cyclohexylamino)-N-methyl-3-(pyrimidin-2-yl)benzenesulfonamide (Compound 56)

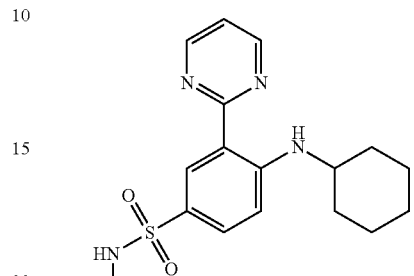

Preparation of Compound 56:

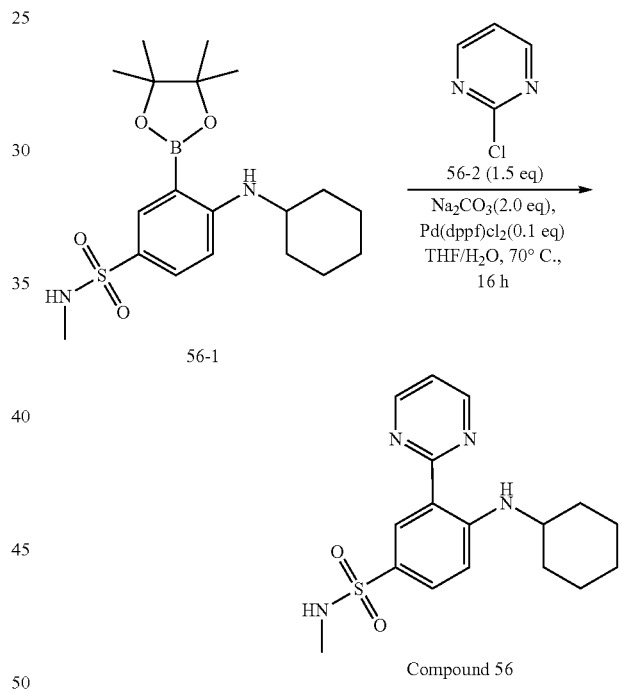

Compound 56

To a solution of compound 56-1 (50.0 mg, 0.13 mmol, 1.0 eq) and compound 56-2 (21.8 mg, 0.19 mmol, 1.5 eq) in H$_2$O (0.5 mL) was added THF (3.0 mL), Pd(dppf)Cl$_2$ (9.3 mg, 12.7 umol, 0.1 eq) and Na$_2$CO$_3$ (26.9 mg, 0.25 mmol, 2.0 eq). The mixture was stirred at 70° C. for 16 hours under N$_2$ atmosphere. LCMS showed desired compound was found. The reaction was filtered through Celite and concentrated under reduced pressure to give a residue. The crude product was purified by prep-HPLC to give Compound 56 (2.51 mg, 7.2 umol, 5.7% yield). LCMS (ESI): RT=0.793 min, mass calc. for $C_{17}H_{22}N_4O_2S$ 346.15, m/z found 347.0 [M+H]$^+$; $^1$HNMR (400 MHz, CDC$_3$-d) δ 9.76 (d, J=6.8 Hz, 1H), 9.11 (d, J=2.3 Hz, 1H), 8.78 (d, J=5.0 Hz, 2H), 7.72 (dd, J=2.4, 8.9 Hz, 1H), 7.16 (t, J=4.9 Hz, 1H), 6.81 (d, J=9.0 Hz, 1H), 4.20 (q, J=5.4 Hz, 1H), 3.56 (s, 1H), 2.67 (d, J=5.5 Hz, 3H), 2.07 (d, J=5.5 Hz, 2H), 1.85-1.76 (m, 2H), 1.67 (d, J=11.5 Hz, 1H), 1.53-1.36 (m, 5H).

Example 55: 4-(cyclohexylamino)-N-methyl-3-(1-methyl-1H-pyrazol-3-yl)benzenesulfonamide (Compound 57)

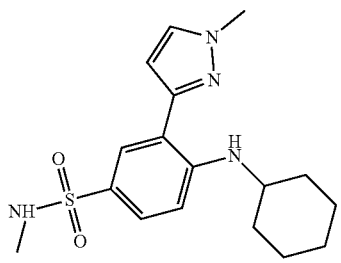 [SMILES: CNS(=O)(=O)c1ccc(NC2CCCCC2)c(-c2ccn(C)n2)c1]

Preparation of Compound 57:

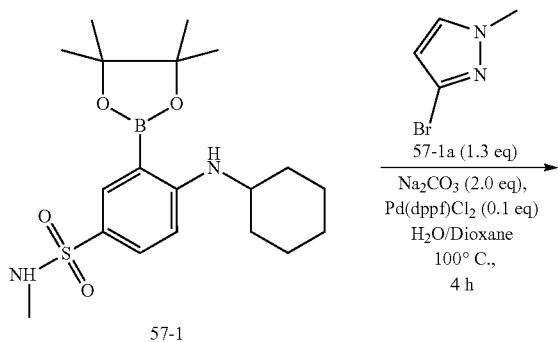

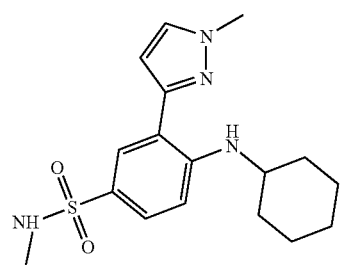

Compound 57

To the solution of compound 57-1 (50 mg, 0.13 mmol, 1 eq) in dioxane (3 mL) and H₂O (0.15 mL) was added compound 57-1a (27 mg, 0.16 mmol, 1.3 eq), Na₂CO₃ (27 mg, 0.25 mmol, 2 eq) and Pd(dppf)Cl₂ (9 mg, 12.7 umol, 0.1 eq). The mixture was stirred at 100° C. for 4 hr under N₂ atmosphere. The reaction was monitored by LCMS. The reaction was concentrated under reduced pressure. The reaction solution was concentrated under reduced pressure. The residue was purified by prep-HPLC to give Compound 57 (2.06 mg, 5.9 umol, 4.7% yield). LCMS (ESI): RT=0.784 min, mass calcd. for $C_{17}H_{24}N_4O_2S$ 348.16, m/z found 349.1 [M+H]⁺, ¹HNMR (400 MHz, CDCl₃) δ 8.33 (d, J=7.5 Hz, 1H), 7.99 (d, J=2.3 Hz, 1H), 7.63-7.56 (m, 1H), 7.41 (d, J=2.5 Hz, 1H), 6.74 (d, J=9.0 Hz, 1H), 6.66 (d, J=2.5 Hz, 1H), 4.15 (q, J=5.4 Hz, 1H), 3.96 (s, 3H), 3.58-3.46 (m, 1H), 2.64 (d, J=5.5 Hz, 3H), 2.08-2.01 (m, 2H), 1.84-1.74 (m, 2H), 1.68-1.61 (m, 1H), 1.51-1.36 (m, 5H).

Example 56: 4-(cyclohexylamino)-N-methyl-3-(1-methyl-1H-1,2,3-triazol-4-yl)benzenesulfonamide (Compound 58)

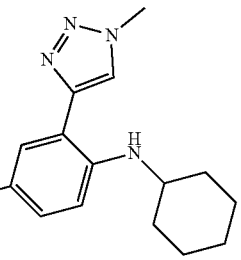

Preparation of Compound 58:

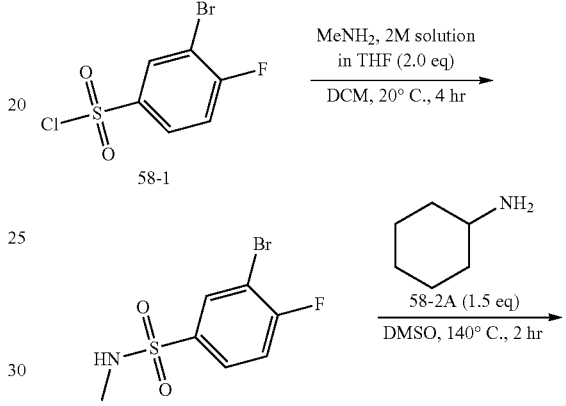

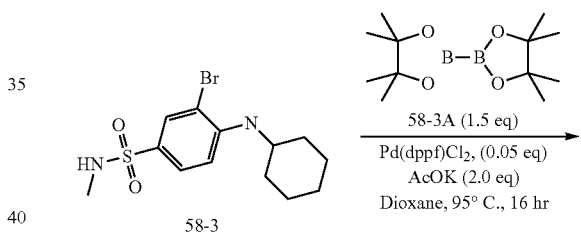

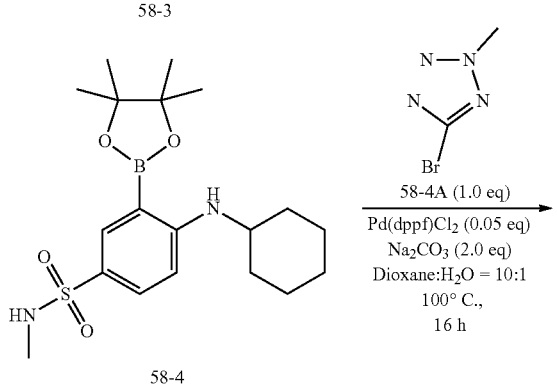

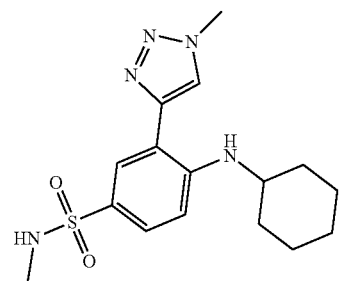

Compound 58

Step 1: 3-Bromo-4-fluoro-N-methylbenzenesulfonamide

To a solution of compound 58-1 (1.0 g, 3.7 mmol, 1.0 eq) in DCM (8 mL) was added $MeNH_2$ (2 M, 3.7 mL, 2.0 eq). The reaction mixture was stirred at 20° C. for 4 hours. The reaction mixture was concentrated under reduced pressure. The mixture was diluted with water (15 mL) and the resultant mixture was extracted with DCM (30 mL*2). The combined organic layers were dried over $Na_2SO_4$, filtered and concentrated to dryness under reduced pressure to obtain the title compound (950 mg, 97% yield).

Step 2: 3-Bromo-4-(cyclohexylamino)-N-methyl-benzenesulfonamide

A solution of compound 58-2 (950 mg, 3.54 mmol, 1.0 eq) and compound 58-2A (879 mg, 8.86 mmol, 1.0 mL, 2.5 eq) in DMSO (6 mL) was stirred at 140° C. for 2 hours. The reaction mixture was concentrated under reduced pressure. The mixture was diluted with water (20 mL) and the resultant mixture was extracted with EA (40 mL*2). The combined organic layers were dried over $Na_2SO_4$, filtered and concentrated to dryness under reduced pressure. The residue was purified by column chromatography over silica gel to afford the title compound (1.2 g, 98% yield). LCMS (ESI): RT=0.801 min, mass calcd. for $C_{13}H_{19}BrN_2O_2S$ 347.27, m/z found 348.9 $[M+H]^+$.

Step 3: 4-(Cyclohexylamino)-N-methyl-3-(4,4,5,5-tetramethyl-1,3,2-dioxaborolan-2-yl)benzenesulfona-mide A solution of compound 58-3 (230 mg, 0.662 mmol, 1.0 eq), compound 58-3A (252 mg, 0.993 mmol, 1.5 eq), $Pd(dppf)Cl_2$ (24 mg, 33 umol, 0.05 eq) and AcOK (130 mg, 1.32 mmol, 2.0 eq) in dioxane (4 mL) was heated to 95° C. and stirred at 95° C. for 16 hours under $N_2$. The reaction mixture was concentrated under reduced pressure. The mixture was diluted with water (20 mL) and the resultant mixture was extracted with EA (50 mL*3). The combined organic layers were dried over $Na_2SO_4$, filtered and concentrated to dryness under reduced pressure. The residue was purified by column chromatography over silica gel (to afford the title compound (240 mg, 92% yield). LCMS (ESI): RT=0.886 min, mass calcd. for $C_{19}H_{31}BN_2O_4S$ 394.34, m/z found 395.1 $[M+H]^+$.

Step 4: 4-(Cyclohexylamino)-N-methyl-3-(5-methyl-1,2,4-oxadiazol-3-yl)benzenesulfonamide Compound 58-4 (50 mg, 0.13 mmol, 1.0 eq), compound 58-4A (21 mg, 0.13 mmol, 1.0 eq), $Pd(dppf)Cl_2$ (4.6 mg, 6.3 umol, 0.05 eq) and $Na_2CO_3$ (27 mg, 0.26 mmol, 2.0 eq) in Dioxane (2 mL) and $H_2O$ (0.2 mL) was de-gassed and then stirred at 100° C. for 16 hours under $N_2$. The mixture was diluted with water (10 mL) and the resultant mixture was extracted with EA (25 mL*3). The combined organic layers were dried over $Na_2SO_4$, filtered and concentrated to dryness under reduced pressure. The residue was purified by preparative high performance liquid chromatography. The pure fractions were collected and the volatiles were removed under vacuum. The residue was re-suspended in water (5 mL) and the resulting mixture was lyophilized to dryness to remove the solvent residue completely. Compound 58 (2.13 mg, 4.8% yield) was obtained. LCMS (ESI): RT=0.740 min, mass calcd. for $C_{16}H_{23}N_5O_2S$ 349.45, m/z found 350.0 $[M+H]^+$, $^1$HNMR (400 MHz, $CDC_3$-d) δ 8.29 (d, J=7.3 Hz, 1H), 7.89 (s, 1H), 7.83 (d, J=2.3 Hz, 1H), 7.60 (dd, J=2.1, 8.9 Hz, 1H), 6.77 (d, J=8.8 Hz, 1H), 4.25-4.20 (m, 1H), 4.18 (s, 3H), 3.56-3.44 (m, 1H), 2.63 (d, J=5.5 Hz, 3H), 2.11-2.00 (m, 2H), 1.86-1.77 (m, 2H), 1.69-1.61 (m, 1H), 1.50-1.28 (m, 5H).

Example 57: tert-butyl 3-(5-(2-(cyclohexylamino)-5-(N-methylsulfamoyl)phenyl)-2H-tetrazol-2-yl)piperidine-1-carboxylate (Compound 59) and tert-butyl 3-(5-(2-(cyclohexylamino)-5-(N-methylsulfamoyl)phenyl)-1H-tetrazol-1-yl)piperidine-1-carboxylate (Compound 60)

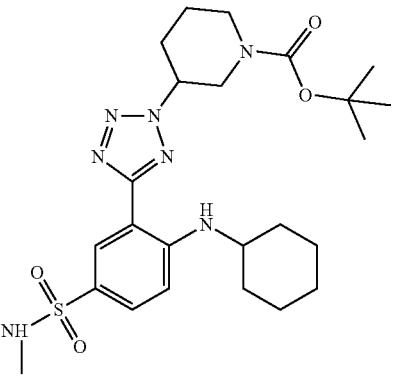

Compound 59

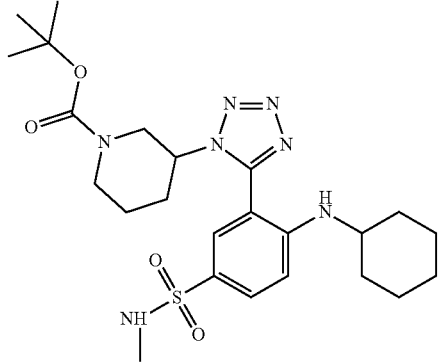

Compound 60

Preparation of Compound 59 and Compound 60:

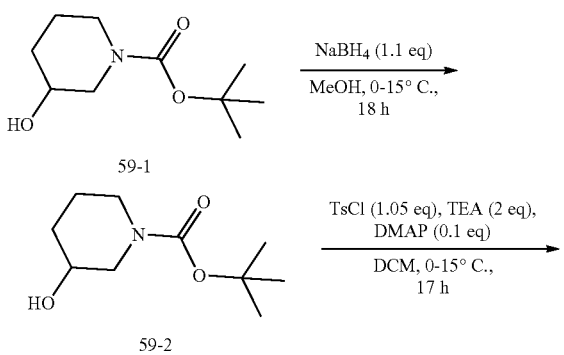

-continued

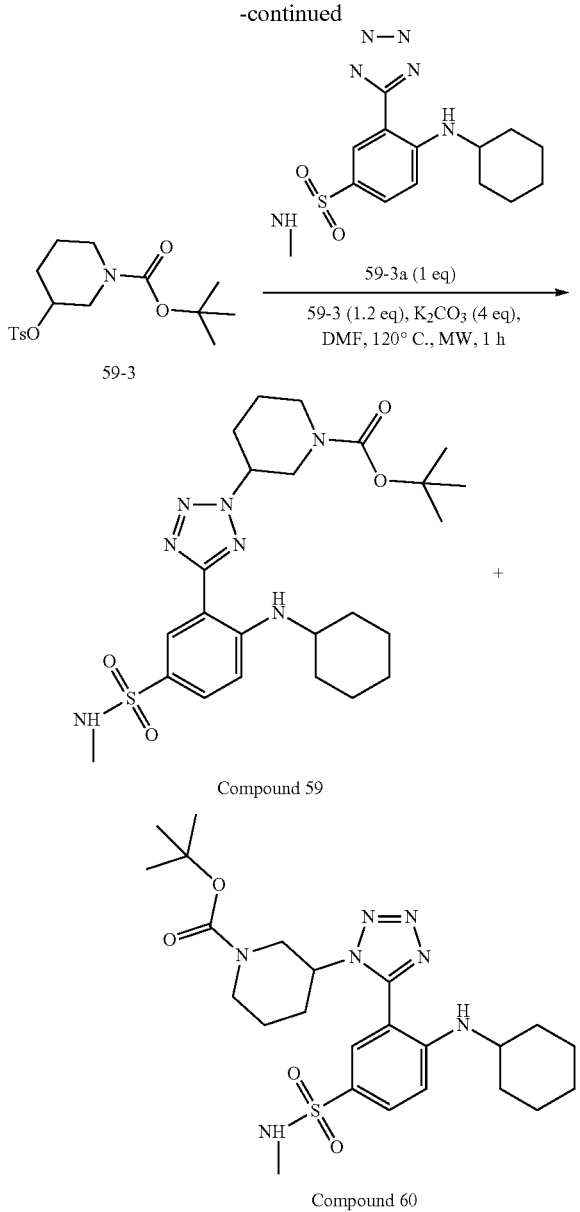

Step 1: tert-butyl 3-hydroxypiperidine-1-carboxylate

Compound 59-1 (3.50 g, 17.57 mmol, 1.0 eq) was dissolved in MeOH (150 mL) and cooled to 0° C., NaBH$_4$ (731.1 mg, 19.3 mmol, 1.1 eq) was added. The mixture was stirred at 0° C. for 2 hours and then at 15° C. for 16 h. The crude LCMS showed the desired product MS value was detected. The reaction mixture was quenched by saturated aq. NH$_4$Cl (20 mL) and water (30 mL) and then extracted with DCM (50 mL*4). The combined organic layers were dried over Na$_2$SO$_4$, filtered and concentrated under pressure to give a residue. The residue was purified by flash silica gel chromatography to give compound 59-2 (1.80 g, 8.94 mmol, 50.9% yield) as a colorless oil, which solidified upon standing. $^1$H NMR (400 MHz, CDCl$_3$) δ 1.17-1.58 (m, 12H), 1.74 (m, 1H), 1.88 (s, 1H), 2.94-3.16 (m, 2H), 3.55 (br s, 1H), 3.64-3.82 (m, 2H).

Step 2: tert-butyl 3-(tosyloxy)piperidine-1-carboxylate

A mixture of compound 59-2 (1.0 g, 4.97 mmol, 1.0 eq), 4-methylbenzenesulfonyl chloride (995 mg, 5.22 mmol, 1.05 eq) and TEA (1.01 g, 9.94 mmol, 1.38 mL, 2.00 eq) in DCM (50.00 mL) was stirred at 0° C. for 5 min under N$_2$. Then DMAP (60.7 mg, 0.50 mmol, 0.10 eq) was added, and the mixture was stirred at 0° C. for 1 h. Then the mixture was stirred at 15° C. for 16 h. The crude LCMS showed the desired product MS value was detected. The reaction mixture was quenched by water (35 mL) and extracted with DCM (10 mL*3). The combined organic layer was washed with brine (20 mL), dried over Na$_2$SO$_4$, filtered and concentrated under reduced pressure to give a residue. The residue was purified by flash silica gel chromatography to give compound 59-3 (0.5 g, 1.41 mmol, 28.3% yield) as colorless oil. $^1$HNMR (400 MHz, CDCl$_3$) δ 1.38-1.47 (m, 11H) 1.67-1.86 (m, 3H) 2.43 (s, 3H) 3.14-3.45 (m, 3H) 3.54 (d, J=13.01 Hz, 1H) 4.44 (s, 1H) 7.33 (d, J=7.94 Hz, 2H) 7.79 (d, J=8.16 Hz, 2H).

Step 3: tert-butyl 3-(5-(2-(cyclohexylamino)-5-(N-methylsulfamoyl)phenyl)-2H-tetrazol-2-yl)piperidine-1-carboxylate (Compound 59) and tert-butyl 3-(5-(2-(cyclohexylamino)-5-(N-methylsulfamoyl)phenyl)-1H-tetrazol-1-yl)piperidine-1-carboxylate (Compound 60)

Compound 59-3a (0.05 g, 0.15 mmol, 1.0 eq), compound 59-3 (63.4 mg, 0.18 mmol, 1.2 eq) and K$_2$CO$_3$ (82.2 mg, 0.59 mmol, 4.0 eq) were taken up into a microwave tube in DMF (2 mL). The sealed tube was heated at 80° C. for 1 h under microwave. Then the sealed tube was heated at 120° C. for 1 h under microwave. TLC indicated compound 3 was consumed completely and one new spot formed. The reaction mixture was filtered. The filtrate was quenched by water (15 ml) and extracted with EtOAc (15 mL*3). The combined organic layers were washed with brine (10 mL*2), dried over with anhydrous Na$_2$SO$_4$, filtered and concentrated under reduced pressure to give a residue. The residue was purified by prep-HPLC to give Compound 59 (4.33 mg, 8.0 umol, 5.4% yield) and Compound 60 (5.47 mg, 10.5 umol, 7.1% yield).

Compound 59: LCMS (ESI): RT=2.405 min, mass calc. for C$_{24}$H$_{37}$N$_7$O$_4$S 519.66, m/z found 464.0 [M-55]$^+$; $^1$H NMR (400 MHz, CDCl$_3$) δ 1.27-1.57 (m, 17H), 1.66 (s, 1H), 1.83-1.93 (m, 2H), 1.94-2.03 (m, 1H), 2.09 (s, 2H), 2.67 (d, J=5.52 Hz, 3H), 3.22-3.48 (m, 2H), 3.53 (br s, 1H), 4.23 (s, 1H), 4.29-4.51 (m, 1H), 4.66 (d, J=12.55 Hz, 1H), 4.77-4.99 (m, 2H), 6.82 (d, J=9.03 Hz, 1H), 7.70-7.75 (m, 1H), 7.80 (s, 1H) 8.62 (br s, 1H).

Compound 60: LCMS (ESI): RT=2.485 min, mass calc. for C$_{24}$H$_{37}$N$_7$O$_4$S 519.66, m/z found 464.0 [M-55]$^+$; $^1$H NMR (400 MHz, CDCl$_3$) δ 1.45 (s, 14H), 1.69 (s, 2H), 1.81 (s, 2H), 1.91-2.16 (m, 3H), 2.27 (s, 1H), 2.40 (s, 1H), 2.66 (d, J=5.27 Hz, 3H), 3.05 (s, 1H), 3.53 (br s, 2H), 4.00 (d, J=13.05 Hz, 1H), 4.15-4.55 (m, 2H), 4.85 (s, 1H), 6.81 (d, J=9.03 Hz, 1H), 7.72 (d, J=7.78 Hz, 1H), 7.83 (d, J=6.27 Hz, 1H), 8.61 (br s, 1H).

213

Example 58: 4-(cyclohexylamino)-3-(2-(1-isopropylpiperidin-3-yl)-2H-tetrazol-5-yl)-N-methylbenzenesulfonamide (Compound 61)

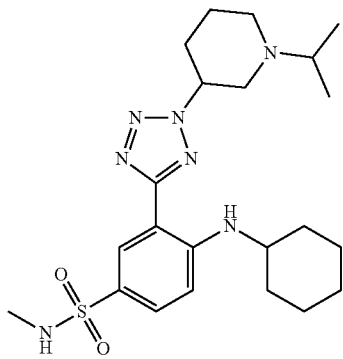 [SMILES: CNS(=O)(=O)c1ccc(NC2CCCCC2)c(-c2nnn(C3CCCN(C(C)C)C3)n2)c1]

Preparation of Compound 61:

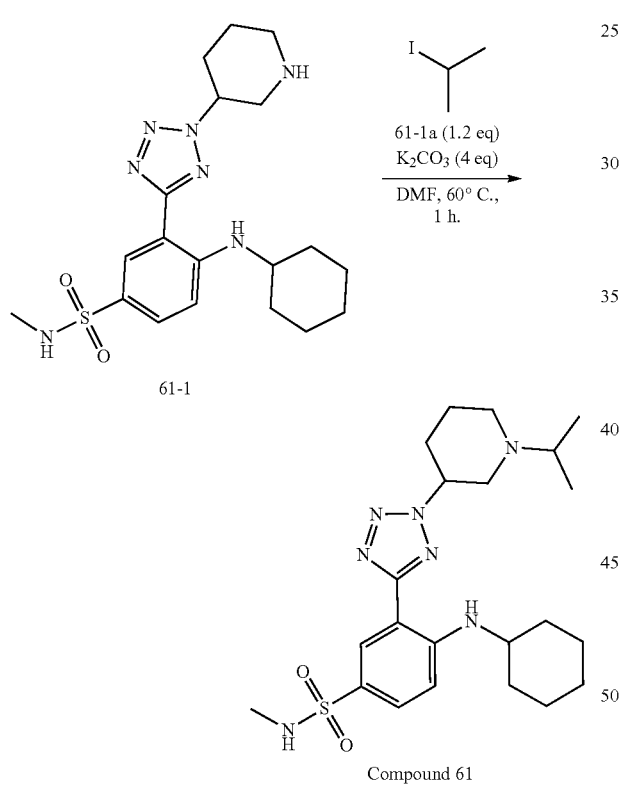

Compound 61

To a mixture of compound 61-1 (30 mg, 65.8 umol, 1.0 eq, HCl) and K$_2$CO$_3$ (36.4 mg, 0.26 mmol, 4.0 eq) in DMF (1 mL) was added compound 61-1a (16.8 mg, 98.7 umol, 9.9 uL, 1.5 eq) in one portion at 15° C. under N$_2$. The mixture was stirred at 60° C. for 2 h. The crude LCMS showed 84% of the desired product was detected. The reaction mixture was filtered. The filtrate was quenched by water (10 mL) and extracted with EtOAc (15 mL*3). The combined organic layer was washed with brine (10 mL*2), dried over anhydrous Na$_2$SO$_4$, filtered and concentrated under reduced pressure to give a residue (18 mg) as colorless oil. The residue was purified by prep-HPLC to give Compound 61

214

(2.10 mg, 4.4 umol, 6.7% yield). LCMS (ESI): RT=2.457 min, mass calc. for C$_{22}$H$_{35}$N$_7$O$_2$S 461.62, m/z found 462.1 [M+1]$^+$.

Example 59: 4-(cyclohexylamino)-N-methyl-3-(2-(1-(methylsulfonyl)piperidin-3-yl)-2H-tetrazol-5-yl)benzenesulfonamide (Compound 62)

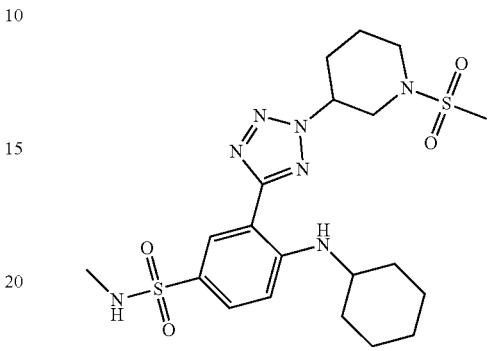

Preparation of Compound 62:

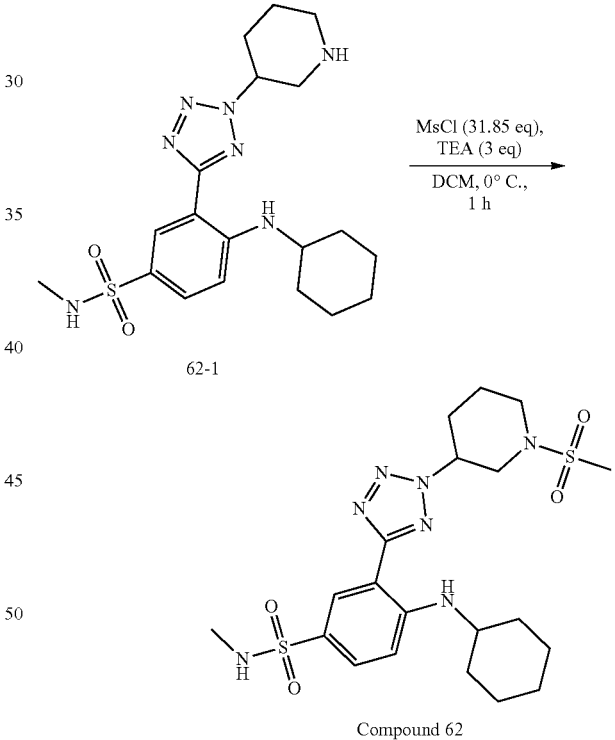

Compound 62

To a mixture of compound 62-1 (20 mg, 43.9 umol, 1.0 eq, HCl) and TEA (13.3 mg, 0.13 mmol, 18.3 uL, 3.0 eq) in DCM (1 mL) was added MsCl (0.16 g, 1.40 mmol, 0.11 mL, 31.8 eq) in one portion at 0° C. The mixture was stirred at 0° C. for 1 h. The crude LCMS showed 62% of the desired product was detected. The reaction mixture was diluted with DCM (20 mL), washed with brine (15 mL) and concentrated under reduced pressure to give a residue (21 mg). The residue was purified by prep-HPLC to give Compound 62 (2.49 mg, 5.0 umol, 11.4% yield). LCMS (ESI): RT=2.171 min, mass calc. for C$_{20}$H$_{31}$N$_7$O$_4$S$_2$ 497.63, m/z found 498.0

[M+1]+; 1H NMR (400 MHz, DMSO-d6) δ 1.24-1.51 (m, 5H), 1.58 (s, 1H), 1.67-1.85 (m, 3H), 1.98 (s, 3H), 2.24-2.33 (m, 1H), 2.37 (d, J=5.02 Hz, 4H), 2.94 (s, 3H), 3.09 (t, J=9.03 Hz, 1H), 3.36-3.46 (m, 2H), 3.53-3.72 (m, 2H), 3.92 (dd, J=11.80, 3.26 Hz, 1H), 5.17 (dt, J=7.97, 4.17 Hz, 1H), 7.05 (d, J=9.29 Hz, 1H), 7.25 (q, J=5.02 Hz, 1H), 7.59 (d, J=7.53 Hz, 1H), 7.65 (dd, J=8.91, 2.13 Hz, 1H), 8.42 (d, J=2.26 Hz, 1H).

Example 60: 4-(cyclohexylamino)-N-methyl-3-(2-(1-phenylpiperidin-3-yl)-2H-tetrazol-5-yl)benzenesulfonamide (Compound 63)

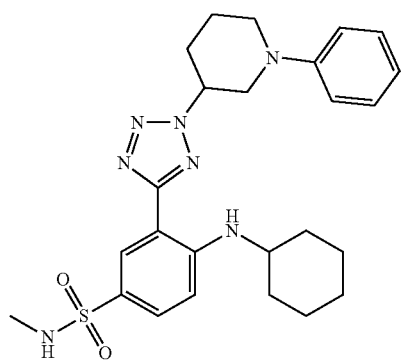 [SMILES: CNS(=O)(=O)c1ccc(NC2CCCCC2)c(-c2nnn(C3CCCN(c4ccccc4)C3)n2)c1]

Preparation of Compound 63:

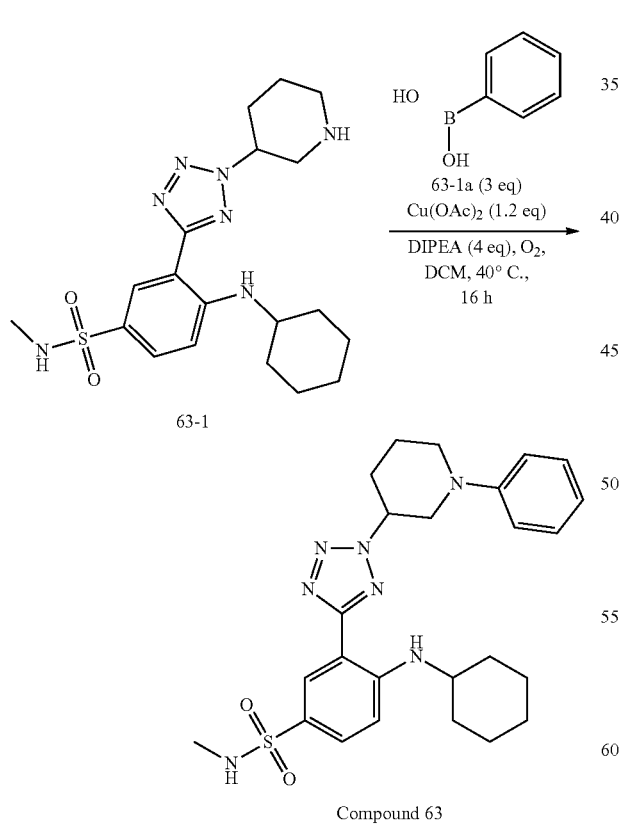

To a mixture of compound 63-1 (40 mg, 87.7 umol, 1.0 eq, HCl) and compound 63-1a (32.1 mg, 0.26 mmol, 3 eq) in DCM (1 mL) were added Cu(OAc)2 (19.1 mg, 0.11 mmol, 1.2 eq) and DIPEA (45.4 mg, 0.35 mol, 61.1 uL, 4 eq) in one portion at 15° C. under O2. The mixture was stirred at 40° C. for 16 h. The crude LCMS showed 40% of the desired product was detected. The reaction mixture was purified by flash silica gel chromatography to give a product (34 mg), which was further purified by prep-HPLC to still give an impure product (9 mg). The impure product was further purified by prep-HPLC to give Compound 63 (2.23 mg, 4.5 umol, 5.1% yield). LCMS (ESI): RT=2.070 min, mass calc. for C25H33N7O2S 495.64, m/z found 496.1 [M+1]+. 1HNMR (400 MHz, CDCl3) δ 1.33-1.44 (m, 3H), 1.48-1.72 (m, 4H), 1.81 (br s, 2H), 1.88-2.01 (m, 1H), 2.02-2.14 (m, 3H), 2.29-2.41 (m, 1H), 2.42-2.53 (m, 1H), 2.67 (d, J=5.27 Hz, 3H), 2.94-3.06 (m, 1H), 3.41-3.60 (m, 2H), 3.65 (br d, J=12.30 Hz, 1H), 4.05 (br d, J=12.05 Hz, 1H), 4.23 (q, J=5.44 Hz, 1H), 4.98-5.12 (m, 1H), 6.83 (d, J=9.03 Hz, 1H), 6.91 (t, J=7.28 Hz, 1H), 7.00 (d, J=8.28 Hz, 2H), 7.27-7.34 (m, 2H), 7.73 (dd, J=8.78, 2.01 Hz, 1H), 7.87 (br d, J=7.03 Hz, 1H), 8.64 (d, J=2.01 Hz, 1H).

Example 61: 4-(cyclohexylamino)-N-methyl-3-(pyridin-2-yl)benzenesulfonamide (Compound 64)

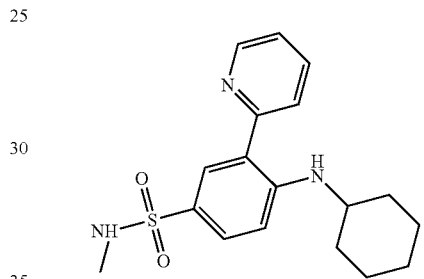

Preparation of Compound 64:

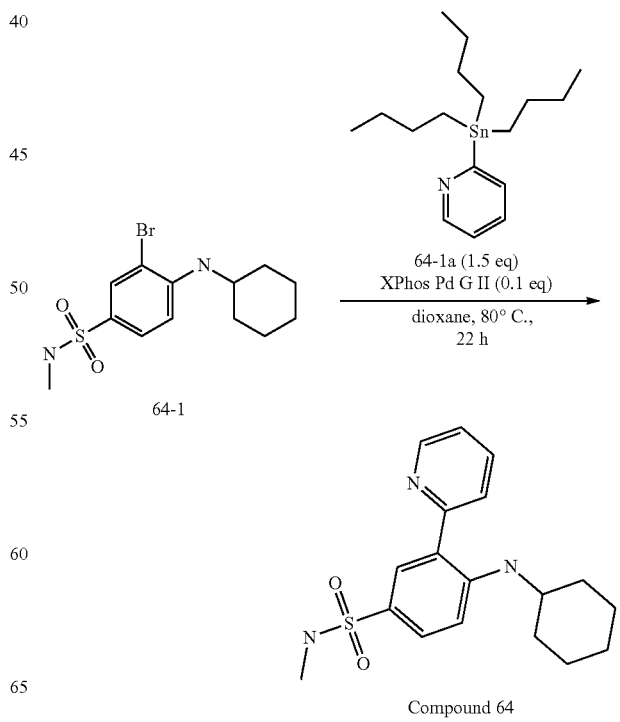

To a mixture of compound 64-1 (40 mg, 0.12 mmol, 1.0 eq) and compound 64-1a (63.6 mg, 0.17 mmol, 1.5 eq) in dioxane (1 mL) was added XPhos Pd G II (9.1 mg, 11.5 umol, 0.1 eq) in one portion at 15° C. under N₂. The mixture was stirred at 80° C. for 22 hours. The crude LCMS showed 43% of the desired product was detected. The reaction mixture was quenched by water (10 mL) and extracted with EtOAc (15 mL*3). The combined organic layer was washed with brine (15 mL), dried over anhydrous Na₂SO₄, filtered and concentrated under reduced pressure to give a residue. The residue was purified by prep-HPLC to give Compound 64 (2.34 mg, 6.8 umol, 4.7% yield). LCMS (ESI): RT=2.280 min, mass calc. for $C_{18}H_{23}N_3O_2S$ 345.46, m/z found 346.0 [M+1]⁺. ¹HNMR (400 MHz, CDCl₃) δ 1.24-1.50 (m, 5H), 1.64 (br d, J=12.55 Hz, 1H), 1.71-1.84 (m, 2H), 2.04 (br d, J=8.78 Hz, 2H), 2.64 (d, J=5.52 Hz, 3H), 3.43-3.55 (m, 1H), 4.28 (q, J=5.44 Hz, 1H), 6.78 (d, J=9.03 Hz, 1H), 7.24 (ddd, J=6.59, 4.83, 1.88 Hz, 1H), 7.66 (dd, J=8.91, 2.13 Hz, 1H), 7.74-7.84 (m, 2H), 8.07 (d, J=2.26 Hz, 1H), 8.53-8.69 (m, 1H), 9.25 (br d, J=6.78 Hz, 1H).

Example 62: 4-(cyclohexylamino)-N-methyl-3-(pyridin-4-yl)benzenesulfonamide (Compound 65)

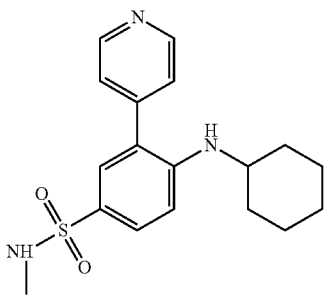 [SMILES: CNS(=O)(=O)c1ccc(NC2CCCCC2)c(-c2ccncc2)c1]

Preparation of Compound 65:

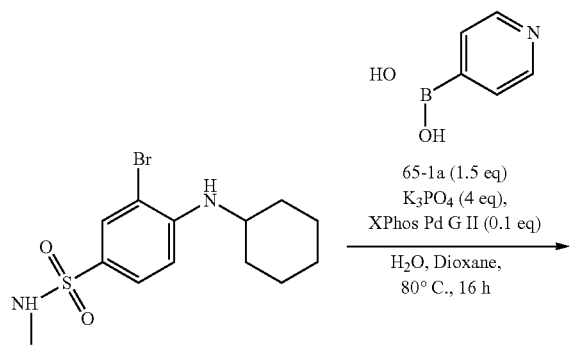

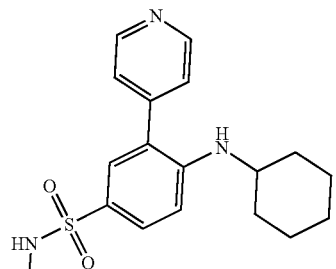

Compound 65

To a mixture of compound 65-1 (40 mg, 0.12 mmol, 1.0 eq) and compound 65-1a (21.2 mg, 0.18 mmol, 1.5 eq) in dioxane (1 mL) was added K₃PO₄ (3 M, 0.15 mL, 4.0 eq) in one portion at 15° C. under N₂. The mixture was stirred at 15° C. for 5 min, then XPhos Pd G II (9.1 mg, 11.5 umol, 0.1 eq) was added, and the mixture was heated to 80° C. and stirred for 16 hours. The crude LCMS showed 31% of the compound 1 was remained and 22% of the desired product was detected. The resulting reaction mixture was quenched by water (15 mL), and then extracted with EtOAc (20 mL*3). The combined organic layer was washed with brine (15 mL), dried over anhydrous Na₂SO₄, filtered and concentrated under reduced pressure to give a residue. The residue was purified by prep-HPLC to give Compound 65 (3.34 mg, 9.8 umol, 4.2% yield). LCMS (ESI): RT=1.933 min, mass calc. for $C_{18}H_{23}N_3O_2S$ 345.46, m/z found 346.0 [M+1]⁺; ¹HNMR (400 MHz, CDCl₃) δ 1.09-1.28 (m, 3H), 1.33-1.46 (m, 2H), 1.63 (br d, J=4.02 Hz, 1H), 1.69-1.78 (m, 2H), 2.00 (br dd, J=12.55, 3.01 Hz, 2H), 2.67 (d, J=5.52 Hz, 3H), 3.30-3.43 (m, 1H), 4.27 (br d, J=7.53 Hz, 1H), 4.37 (q, J=5.27 Hz, 1H), 6.74 (d, J=9.03 Hz, 1H), 7.32-7.40 (m, 2H), 7.52 (d, J=2.26 Hz, 1H), 7.72 (dd, J=8.78, 2.26 Hz, 1H), 8.72 (d, J=5.77 Hz, 2H).

Example 63: 4-(cyclohexylamino)-N-methyl-3-(5-methyl-1H-1,2,4-triazol-3-yl)benzenesulfonamide (Compound 66)

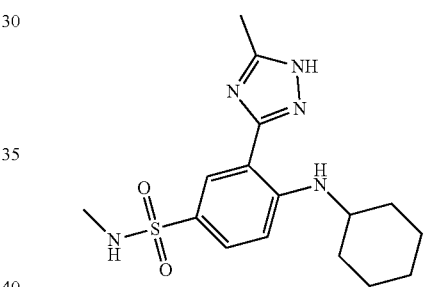

Preparation of Compound 66:

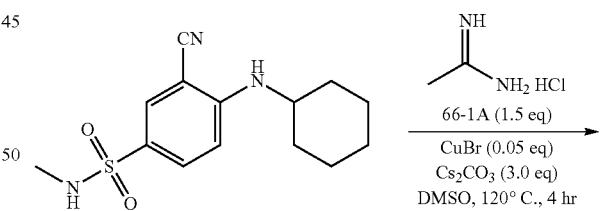

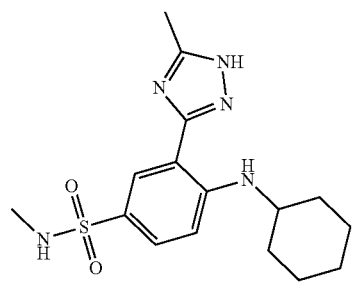

Compound 66

To a solution of compound 66-1 (100 mg, 0.34 mmol, 1.0 eq), compound 66-1A (48 mg, 0.51 mmol, 1.5 eq, HCl) and Cs$_2$CO$_3$ (333 mg, 1.02 mmol, 3.0 eq) in DMSO (2 mL) was added CuBr (2.4 mg, 17 umol, 0.05 eq). The reaction mixture was stirred at 120° C. for 4 hours under air. The mixture was diluted with water (10 mL) and the resultant mixture was extracted with EA (30 mL*2). The combined organic layers were dried over Na$_2$SO$_4$, filtered and concentrated to dryness under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. Compound 66 (28.07 mg, 24% yield) was obtained. LCMS (ESI): RT=0.705 min, mass calcd. for C$_{16}$H$_{23}$N$_5$O$_2$S 349.45, m/z found 349.9 [M+H]$^+$, $^1$HNMR (400 MHz, DMSO-d$_6$) δ 13.92 (s, 1H), 8.42 (s, 1H), 8.35-8.16 (m, 1H), 7.53 (dd, J=2.1, 8.9 Hz, 1H), 7.13-7.05 (m, 1H), 6.89 (d, J=9.0 Hz, 1H), 3.64-3.53 (m, 1H), 2.44 (s, 3H), 2.36 (d, J=5.0 Hz, 3H), 2.02-1.92 (m, 2H), 1.76-1.66 (m, 2H), 1.63-1.52 (m, 1H), 1.49-1.39 (m, 2H), 1.38-1.28 (m, 3H).

Example 64: 4-(cyclohexylamino)-3-(1,5-dimethyl-1H-1,2,4-triazol-3-yl)-N-methylbenzenesulfonamide (Compound 67)

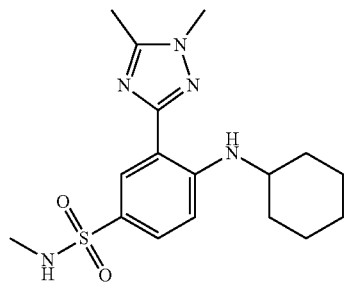 [SMILES: CNS(=O)(=O)c1ccc(NC2CCCCC2)c(-c2nc(C)n(C)n2)c1]

Preparation of Compound 67:

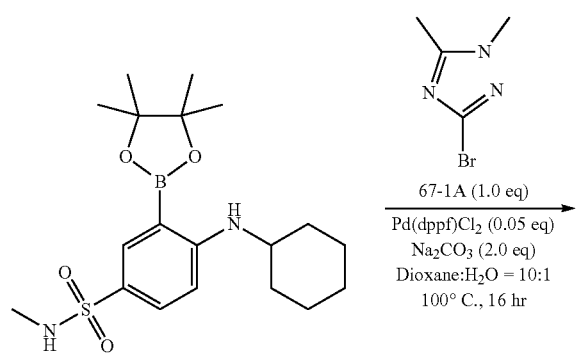

67-1

Compound 67-1 (50 mg, 0.13 mmol, 1.0 eq), compound 67-1A (22 mg, 0.13 mmol, 1.0 eq), Pd(dppf)Cl$_2$ (4.6 mg, 6.3 umol, 0.05 eq) and Na$_2$CO$_3$ (27 mg, 0.25 mmol, 2.0 eq) in Dioxane (2 mL) and H$_2$O (0.2 mL) was degassed and then stirred at 100° C. for 16 hours under N$_2$. The mixture was diluted with water (10 mL) and the resultant mixture was extracted with EA (25 mL*3). The combined organic layers were dried over Na$_2$SO$_4$, filtered and concentrated to dryness under reduced pressure. The residue was purified by preparative high performance liquid chromatography. The pure fractions were collected and the volatiles were removed under vacuum. The residue was re-suspended in water (5 mL) and the resulting mixture was lyophilized to dryness to remove the solvent residue completely. Compound 67 (6.75 mg, 15% yield) was obtained. LCMS (ESI): RT=0.742 min, mass calcd. for C$_{17}$H$_{25}$N$_5$O$_2$S 363.48, m/z found 364.0 [M+H]$^+$, $^1$HNMR (400 MHz, DMSO-d$_6$) δ 8.38 (d, J=2.3 Hz, 1H), 8.22 (d, J=7.5 Hz, 1H), 7.52 (dd, J=2.3, 8.8 Hz, 1H), 7.14-7.07 (m, 1H), 6.89 (d, J=8.8 Hz, 1H), 3.86 (s, 3H), 3.64-3.53 (m, 1H), 2.48 (s, 3H), 2.36 (d, J=5.0 Hz, 3H), 2.02-1.92 (m, 2H), 1.76-1.66 (m, 2H), 1.63-1.53 (m, 1H), 1.50-1.29 (m, 5H).

Example 65: 4-(cyclohexylamino)-N-methyl-3-(2-(1-(pyridin-3-yl)pyrrolidin-3-yl)-2H-tetrazol-5-yl)benzenesulfonamide (Compound 68)

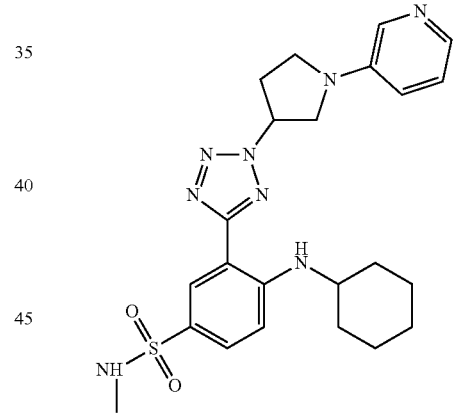

Preparation of Compound 68:

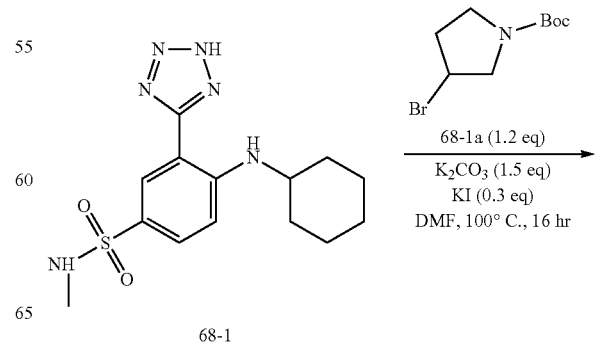

68-1

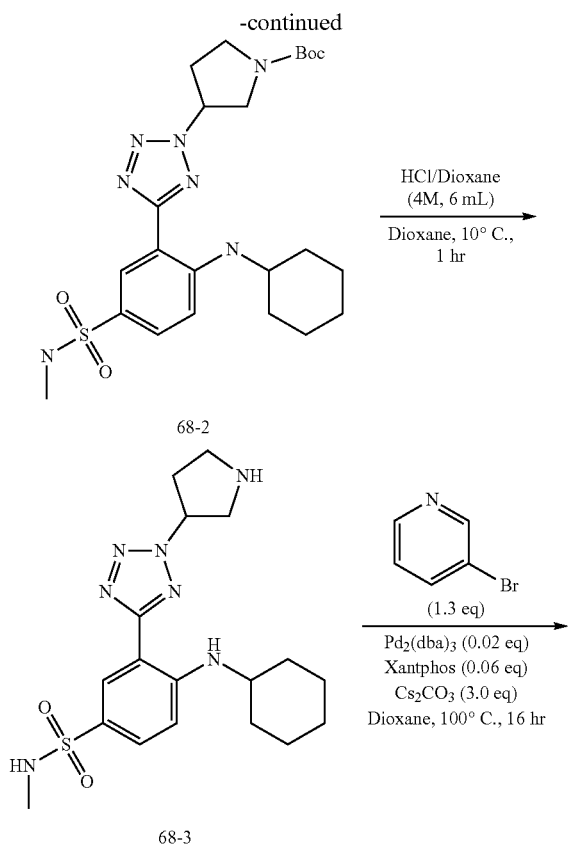

Step 2: 4-(cyclohexylamino)-N-methyl-3-(2-(pyrrolidin-3-yl)-2H-tetrazol-5-yl)benzene sulfonamide To the solution of compound 68-2 (180 mg, 0.36 mmol, 1 eq) in dioxane (6 mL) was added HCl/dioxane (4 M, 6 mL, 67 eq). The mixture was stirred at 10° C. for 1 hr. The reaction was monitored by TLC. TLC showed that the starting material was consumed and a new spot with larger polarity was observed. The reaction solution was concentrated under reduced pressure to give compound 68-3 (170 mg, crude, HCl).

Step 3: 4-(cyclohexylamino)-N-methyl-3-(2-(1-(pyridin-3-yl)pyrrolidin-3-yl)-2H-tetrazol-5-yl)benzenesulfonamide To the solution of compound 68-3 (170 mg, 0.38 mmol, 1 eq, HCl) in dioxane (5 mL) was added 3-bromopyridine (79 mg, 0.5 mmol, 48 uL, 1.3 eq), $Pd_2(dba)_3$ (7 mg, 7.7 umol, 0.02 eq), $Cs_2CO_3$ (376 mg, 1.2 mmol, 3 eq), Xantphos (13 mg, 23 umol, 0.06 eq). The mixture was stirred at 100° C. for 16 hr. The reaction was monitored by LCMS. The reaction was concentrated under reduced pressure. The reaction solution was concentrated under reduced pressure. The residue was purified by prep-HPLC to give Compound 68 (8.66 mg, 17.9 umol, 4.7% yield). LCMS (ESI): RT=0.670 min, mass calcd. for $C_{23}H_{30}N_8O_2S$ 482.22, m/z found 483.1 $[M+H]^+$, $^1$HNMR (400 MHz, $CDCl_3$) δ 8.60 (d, J=2.3 Hz, 1H), 8.10-8.02 (m, 2H), 7.75-7.65 (m, 2H), 7.18 (dd, J=4.5, 8.3 Hz, 1H), 6.93-6.89 (m, 1H), 6.81 (d, J=9.0 Hz, 1H), 5.72-5.63 (m, 1H), 4.27 (q, J=5.5 Hz, 1H), 4.05-3.95 (m, 2H), 3.80-3.72 (m, 1H), 3.68-3.61 (m, 1H), 3.56-3.45 (m, 1H), 2.96-2.87 (m, 1H), 2.82-2.70 (m, 1H), 2.65 (d, J=5.5 Hz, 3H), 2.09-1.97 (m, 2H), 1.83-1.72 (m, 2H), 1.49-1.23 (m, 6H).

Example 66: 4-(cyclohexylamino)-N-methyl-3-(pyrimidin-4-yl)benzenesulfonamide (Compound 69)

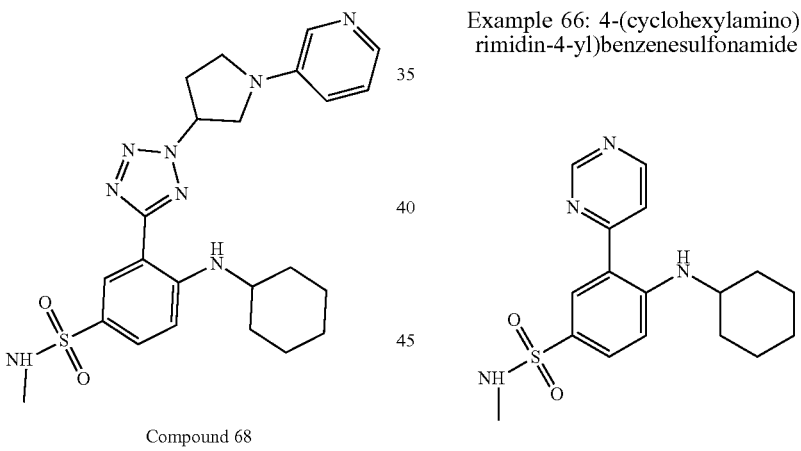

Compound 68

Preparation of Compound 69:

Step 1: tert-butyl 3-(5-(2-(cyclohexylamino)-5-(N-methylsulfamoyl)phenyl)-2H-tetrazol-2-yl)pyrrolidine-1-carboxylate To the solution of compound 68-1 (200 mg, 0.59 mmol, 1.0 eq) in DMF (2 mL) was added compound 68-1a (178 mg, 0.71 mmol, 1.2 eq), KI (30 mg, 0.18 mmol, 0.3 eq) and $K_2CO_3$ (123 mg, 0.89 mmol, 1.5 eq). The mixture was stirred at 100° C. for 16 hr. The reaction was monitored by TLC. The reaction solution was washed with $H_2O$ (10 mL). The mixture was extracted with EtOAc (10 mL). The organic layer was washed with $H_2O$ (10 mL). The organic layer was dried with $Na_2SO_4$ and concentrated under reduced pressure. The residue was purified by column chromatography) to give compound 68-2 (180 mg, 0.35 mmol, 58% yield).

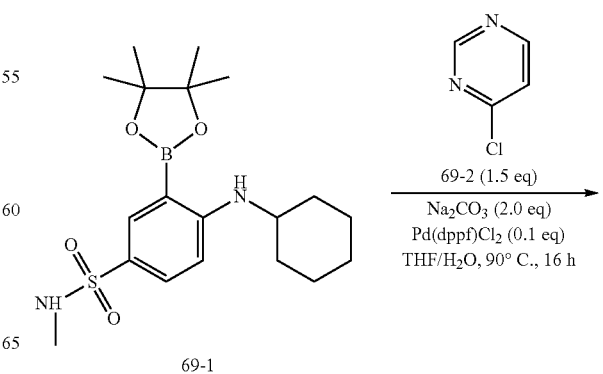

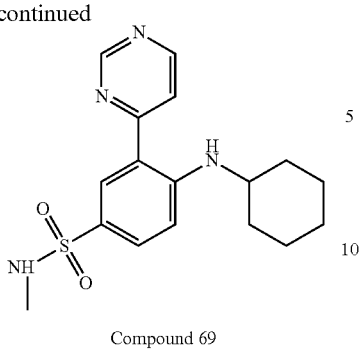

Compound 69

To a solution of compound 69-1 (50.0 mg, 0.13 mmol, 1.0 eq) and compound 69-2 (21.8 mg, 0.19 mmol, 1.5 eq) in H₂O (0.5 mL) was added dioxane (5 mL), Pd(dppf)Cl₂ (9.3 mg, 12.7 umol, 0.1 eq) and Na₂CO₃ (26.9 mg, 0.25 mmol, 2.0 eq). The mixture was stirred at 90° C. for 16 hour under N₂ atmosphere. LCMS showed desired compound was found. The reaction was filtered through Celite and concentrated under reduced pressure to give a residue. The crude product was purified by prep-HPLC to give Compound 69 (4.99 mg, 14.4 umol, 11.4% yield). LCMS (ESI): RT=0.748 min, mass calc. for C₁₇H₂₂N₄O₂S 346.15, m/z found 346.9 [M+H]⁺; ¹HNMR (400 MHz, CDC₃-d) δ 9.71 (d, J=7.0 Hz, 1H), 9.18 (d, J=1.0 Hz, 1H), 8.76 (d, J=5.8 Hz, 1H), 8.21 (d, J=2.0 Hz, 1H), 7.79 (dd, J=1.0, 5.8 Hz, 1H), 7.70 (dd, J=2.0, 9.0 Hz, 1H), 6.83 (d, J=9.3 Hz, 1H), 4.29 (q, J=5.5 Hz, 1H), 3.54 (s, 1H), 2.66 (d, J=5.5 Hz, 3H), 2.09-2.02 (m, 2H), 1.80 (d, J=4.8 Hz, 2H), 1.66 (d, J=11.0 Hz, 1H), 1.52-1.35 (m, 5H).

Example 67: 4-(cyclohexylamino)-N-methyl-3-(2-(1-(pyridin-3-yl)azetidin-3-yl)-2H-tetrazol-5-yl)benzenesulfonamide (Compound 70)

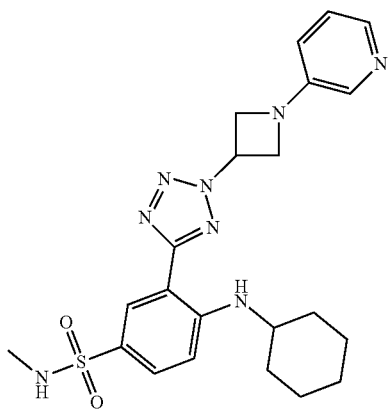 [SMILES: CNS(=O)(=O)c1ccc(NC2CCCCC2)c(-c2nnn(C3CN(c4cccnc4)C3)n2)c1]

Compound 70

Preparation of Compound 70:

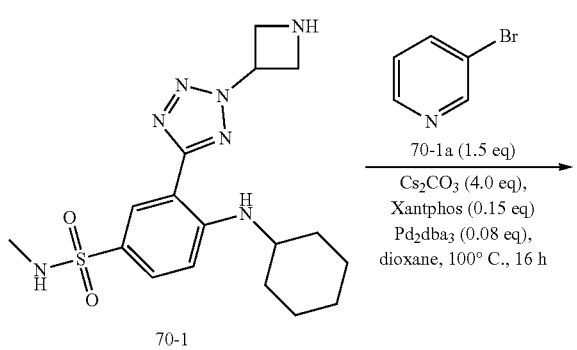

70-1

-continued

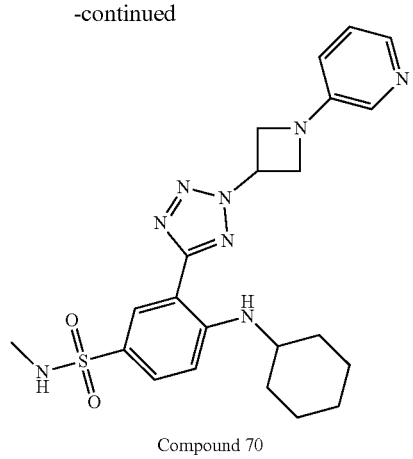

Compound 70

To a mixture of 70-1 (80 mg, 0.19 mmol, 1 eq, HCl) and Cs₂CO₃ (244 mg, 0.748 mmol, 4 eq) in dioxane (4 mL) was added Pd₂(dba)₃ (14 mg, 15 umol, 0.08 eq) and Xantphos (16 mg, 28 umol, 0.15 eq) and 3-bromopyridine (70-1a) (44 mg, 0.28 mmol, 1.5 eq) in one portion under N₂. The mixture was stirred at 100° C. for 16 h. The reaction was monitored by LCMS. The reaction mixture was diluted with water (10 mL) and extracted with EA (15 mL*3). The combined organic layers were dried with anhydrous Na₂SO₄, filtered and concentrated in vacuum. The reaction was monitored by LCMS. The residue was purified by prep-HPLC. LCMS and ¹H NMR confirmed the product was Compound 70 (2.73 mg, 5.8 umol, 3.1% yield). LCMS (ESI): RT=2.083 min, mass calcd. For C₂₂H₂₈N₈O₂S, 468.21 m/z found 469.0[M+H]⁺. ¹H NMR (400 MHz, CDCl₃) δ 8.64 (d, J=2.40 Hz, 1H), 8.19-8.12 (m, 1H), 8.01 (d, J=2.40 Hz, 1H), 7.80-7.70 (m, 2H), 7.24-7.17 (m, 1H), 6.92-6.85 (m, 1H), 6.82 (d, J=9.20 Hz, 1H), 6.00-5.86 (m, 1H), 4.63 (t, J=8.00 Hz, 2H), 4.58-4.50 (m, 2H), 4.32-4.24 (m, 1H), 3.60-3.49 (m, 1H), 2.66 (d, J=5.60 Hz, 3H), 2.05-1.98 (m, 2H), 1.82-1.71 (m, 2H), 1.66-1.62 (m, 1H), 1.46-1.27 (m, 5H).

Example 68: 4-(cyclohexylamino)-3-(2-cyclopropyl-2H-tetrazol-5-yl)-N-methylbenzene sulfonamide (Compound 71)

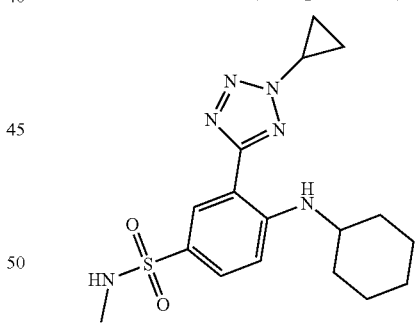

Preparation of Compound 71:

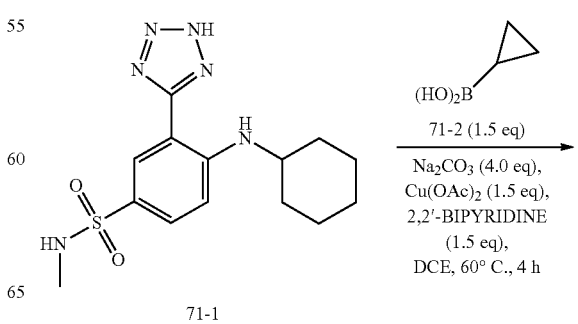

71-1

225

-continued

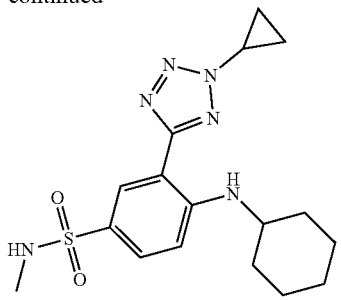

Compound 71

To a solution of compound 71-1 (0.1 g, 0.30 mmol, 1.0 eq) and compound 71-2 (30.6 mg, 0.36 mmol, 1.2 eq) in DCE (5.0 mL) was added Cu(OAc)$_2$ (81.0 mg, 0.45 mmol, 1.5 eq) Na$_2$CO$_3$ (74.0 mg, 0.89 mmol, 3.0 eq) and 2,2'-BIPYRIDINE (69.6 mg, 0.45 mmol, 1.5 eq). The mixture was stirred at 60° C. for 4 hr at N$_2$ atmosphere. LCMS showed the desired compound. The reaction was filtered through Celite and concentrated under reduced pressure to give a residue. The crude product was purified by prep-HPLC to give Compound 71 (2.33 mg, 6.2 umol, 2.1% yield). LCMS (ESI): RT=0.813 min, mass calc. for C$_{17}$H$_{24}$N$_6$O$_2$S 376.17, m/z found 377.2 [M+H]$^+$; $^1$HNMR (400 MHz, CDCl$_3$) δ 8.41 (s, 2H), 7.69 (d, J=8.0 Hz, 1H), 6.87 (d, J=7.0 Hz, 1H), 4.60 (s, 1H), 3.53 (s, 1H), 2.70 (s, 3H), 2.13-1.97 (m, 2H), 1.84 (s, 3H), 1.65 (s, 1H), 1.44 (s, 5H), 0.85-0.57 (m, 4H). $^1$HNMR (400 MHz, DMSO-d$_6$) δ 8.47 (s, 2H), 7.71-7.61 (m, 1H), 7.11-7.02 (m, 1H), 3.64 (s, 1H), 2.65 (s, 3H), 2.00 (s, 2H), 1.82 (s, 1H), 1.74 (d, J=15.6 Hz, 2H), 1.58 (s, 1H), 1.50-1.29 (m, 5H), 0.75-0.63 (m, 4H).

Example 69: 4-((4,4-difluorocyclohexyl)amino)-N-methyl-3-(2-methyl-2H-tetrazol-5-yl)benzenesulfonamide (Compound 72)

Preparation of Compound 72:

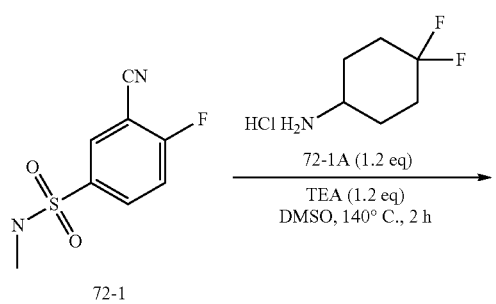

226

-continued

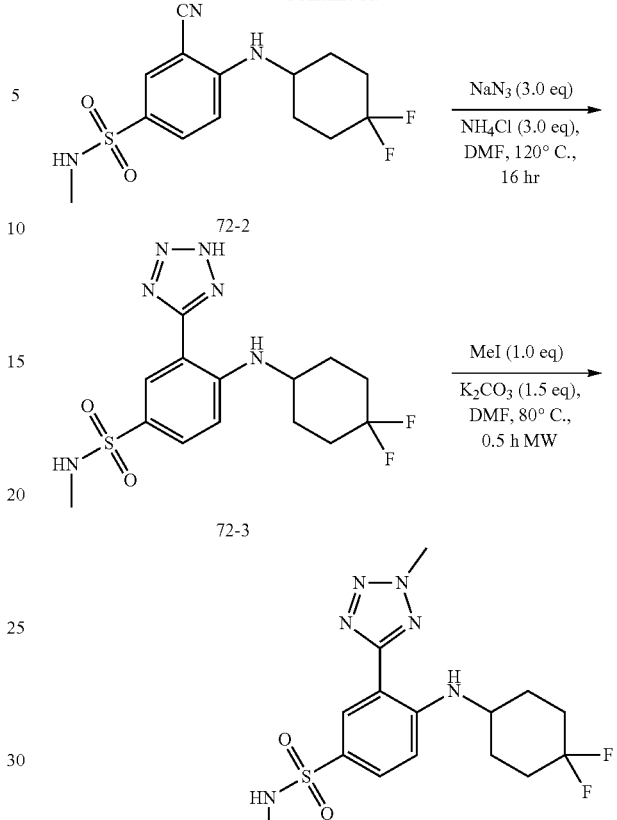

Compound 72

Step 1: 3-Cyano-4-((4,4-difluorocyclohexyl)amino)-N-methylbenzenesulfonamide

To a stirring solution of compound 72-1A (96 mg, 0.56 mmol, 1.2 eq, HCl) and TEA (57 mg, 0.56 mmol, 1.2 eq) in DMSO (1.5 mL) was added compound 72-1 (100 mg, 0.47 mmol, 1.0 eq). The reaction mixture was stirred at 140° C. for 16 hours. The mixture was diluted with water (10 mL) and the resultant mixture was extracted with EA (50 mL*3). The combined organic layers were dried over Na$_2$SO$_4$, filtered and concentrated to dryness under reduced pressure. The residue was purified by column chromatography over silica gel to afford the title compound (100 mg, 65% yield).

Step 2: 4-((4,4-Difluorocyclohexyl)amino)-N-methyl-3-(2H-tetrazol-5-yl)benzenesulfonamide A solution of compound 72-2 (100 mg, 0.30 mmol, 1.0 eq), NaN$_3$ (59 mg, 0.91 mmol, 3.0 eq) and NH$_4$Cl (49 mg, 0.91 mmol, 3.0 eq) in DMF (4 mL) was stirred at 120° C. for 16 hours. The mixture was diluted with water (10 mL) and the resultant mixture was extracted with EA (30 mL*3). The combined organic layers were dried over Na$_2$SO$_4$, filtered and concentrated to dryness under reduced pressure. LCMS (ESI): RT=0.697 min, mass calcd. for C$_{14}$H$_{18}$F$_2$N$_6$O$_2$S 372.12, m/z found 373.0 [M+H]$^+$.

Step 3: 4-((4,4-Difluorocyclohexyl)amino)-N-methyl-3-(2-methyl-2H-tetrazol-5-yl)benzenesulfonamide Compound 72-3 (90 mg, 0.24 mmol, 1.0 eq), CH$_3$I (34 mg, 0.24 mmol, 1.0 eq) and K$_2$CO$_3$ (50 mg, 0.36 mmol, 1.5 eq) were taken up into a microwave tube in DMF (3 mL). The sealed tube was heated at 80° C. for 30 min under microwave. The reaction mixture was concentrated under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. Compound 72 (15.34 mg, 16% yield) was obtained. LCMS (ESI): RT=0.735 min, mass calcd. for $C_{15}H_{20}F_2N_6O_2S$ 386.13, m/z found 387.0 $[M+H]^+$, $^1$HNMR (400 MHz, DMSO-$d_6$) δ 8.40 (d, J=2.3 Hz, 1H), 7.68 (dd, J=2.3, 8.8 Hz, 1H), 7.56 (d, J=7.5 Hz, 1H), 7.32-7.22 (m, 1H), 7.16-7.09 (m, 1H), 4.48 (s, 3H), 3.92-3.80 (m, 1H), 2.38 (d, J=3.3 Hz, 3H), 2.15-2.01 (m, 6H), 1.68-1.54 (m, 2H).

Example 70: 4-((3,3-difluorocyclohexyl)amino)-N-methyl-3-(2-methyl-2H-tetrazol-5-yl)benzenesulfonamide (Compound 73)

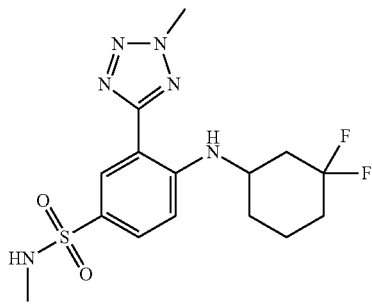 [SMILES: CNS(=O)(=O)c1ccc(NC2CCCC(F)(F)C2)c(-c2nnn(C)n2)c1]

Preparation of Compound 73:

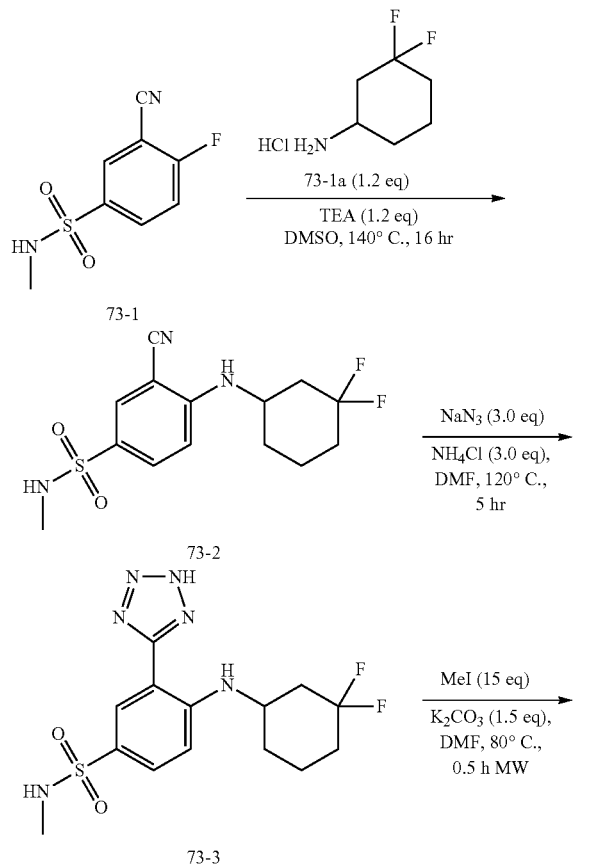

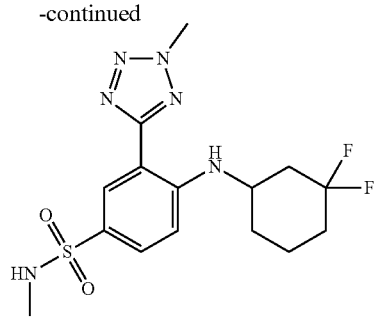

Compound 73

Step 1: 3-Cyano-4-((3,3-difluorocyclohexyl)amino)-N-methylbenzenesulfonamide

To a stirring solution of compound 73-1a (53 mg, 0.39 mmol, 1.2 eq, HCl) and TEA (40 mg, 0.39 mmol, 1.2 eq) in DMSO (1.5 mL) was added compound 73-1 (70 mg, 0.32 mmol, 1.0 eq). The reaction mixture was stirred at 140° C. for 16 hours. The mixture was diluted with water (10 mL) and the resultant mixture was extracted with EA (50 mL*3). The combined organic layers were dried over $Na_2SO_4$, filtered and concentrated to dryness under reduced pressure. The residue was purified by column chromatography over silica gel to afford the title compound (70 mg, 65% yield) as a light yellow solid. LCMS (ESI): RT=0.700 min, mass calcd. for $C_{14}H_{17}F_2N_3O_2S$ 329.10, m/z found 329.9 $[M+H]^+$.

Step 2: 4-((3,3-Difluorocyclohexyl)amino)-N-methyl-3-(2H-tetrazol-5-yl)benzenesulfonamide A solution of compound 73-2 (70 mg, 0.21 mmol, 1.0 eq), $NaN_3$ (41 mg, 0.64 mmol, 3.0 eq) and $NH_4Cl$ (34 mg, 0.64 mmol, 3.0 eq) in DMF (4 mL) was stirred at 120° C. for 5 hours. The mixture was diluted with water (10 mL) and the resultant mixture was extracted with EA (30 mL*3). The combined organic layers were dried over $Na_2SO_4$, filtered and concentrated to dryness under reduced pressure. LCMS (ESI): RT=0.701 min, mass calcd. for $C_{14}H_{18}F_2N_6O_2S$ 372.12, m/z found 373.0 $[M+H]^+$.

Step 3: 4-((3,3-Difluorocyclohexyl)amino)-N-methyl-3-(2-methyl-2H-tetrazol-5-yl)benzenesulfonamide Compound 73-3 (70 mg, 0.24 mmol, 1.0 eq), $CH_3I$ (400 mg, 2.82 mmol, 15 eq) and $K_2CO_3$ (39 mg, 0.28 mmol, 1.5 eq) were taken up into a microwave tube in DMF (3 mL). The sealed tube was heated at 80° C. for 30 min under microwave. The reaction mixture was concentrated under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. Compound 73 (9.83 mg, 14% yield) was obtained. LCMS (ESI): RT=0.733 min, mass calcd. for $C_{15}H_{20}F_2N_6O_2S$ 386.13, m/z found 387.0 [M+H]+, 1HNMR (400 MHz, DMSO-$d_6$) δ 8.40 (d, J=2.3 Hz, 1H), 7.72-7.61 (m, 2H), 7.32-7.22 (m, 1H), 7.07 (d, J=9.0 Hz, 1H), 4.48 (s, 3H), 3.98-3.85 (m, 1H), 2.46-2.36 (m, 4H), 2.11-1.74 (m, 5H), 1.70-1.56 (m, 1H), 1.56-1.44 (m, 1H).

Example 71:4-(cyclohexylamino)-N-methyl-3-(2-(piperidin-3-yl)-2H-tetrazol-5-yl)benzenesulfonamide (Compound 74) and 4-(cyclohexylamino)-N-methyl-3-(1-(piperidin-3-yl)-1H-tetrazol-5-yl)benzenesulfonamide (Compound 75)

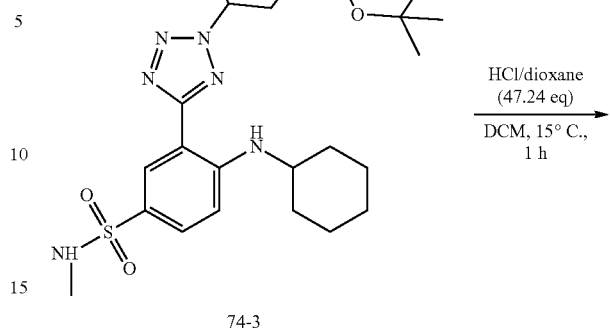

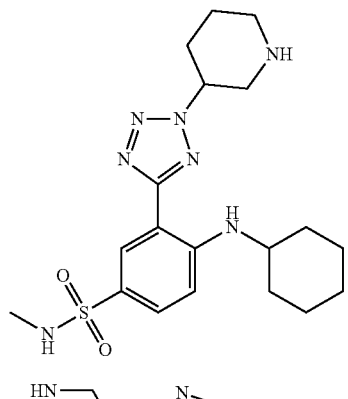

Compound 74

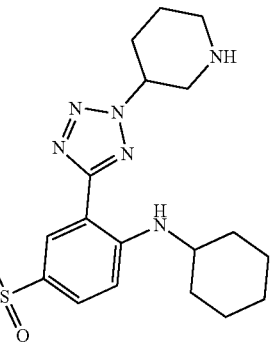

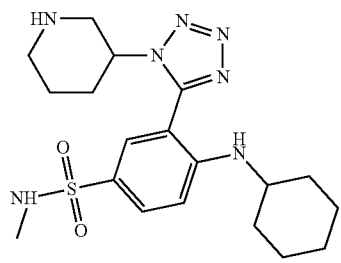

Compound 75

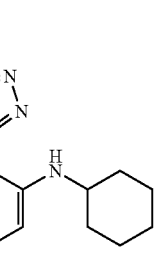

Preparation of Compound 74 and Compound 75:

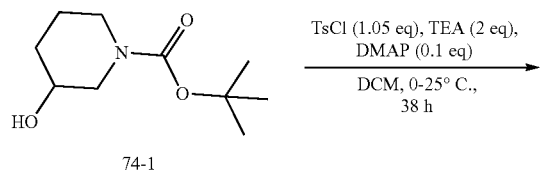

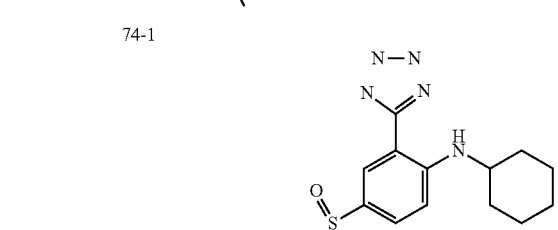

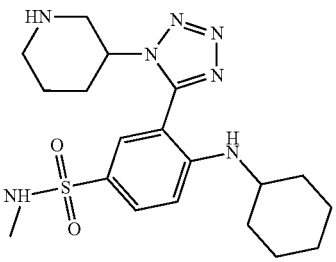

Compound 75

Step 1: tert-butyl 3-(tosyloxy)piperidine-1-carboxylate

A mixture of compound 74-1 (0.75 g, 3.73 mmol, 1.00 eq), 4-methylbenzenesulfonyl chloride (0.74 g, 3.91 mmol, 1.05 eq) and TEA (0.75 g, 7.45 mmol, 1.03 mL, 2.0 eq) in DCM (20 mL) was stirred at 0° C. for 5 min under $N_2$. Then DMAP (45.5 mg, 0.37 mmol, 0.1 eq) was added, and the mixture was stirred at 0° C. The mixture was stirred at 15° C. for 16 h. Reaction was monitored by LCMS and TLC.

373 mg of 4-methylbenzenesulfonyl chloride and TEA (0.5 mL) were added, and then the mixture was stirred at 15° C. for 2 h. The mixture was stirred at 25° C. for 20 h. The reaction mixture was quenched by water (10 mL) and brine (20 mL), and then extracted with DCM (10 mL*3). The combined organic layer was dried over anhydrous $Na_2SO_4$, filtered and concentrated under reduced pressure to give a residue. The residue was purified by flash silica gel chromatography to give the compound 74-2 (841 mg, 2.37 mmol, 63.5% yield) as a colorless oil, which solidified upon standing. $^1$HNMR (400 MHz, $CDCl_3$) δ 1.39-1.51 (m, 10H), 1.65-1.99 (m, 3H), 2.45 (s, 3H), 3.28 (s, 1H), 3.33-3.48 (m, 2H), 3.56 (d, J=12.05 Hz, 1H), 4.46 (s, 1H), 7.35 (d, J=8.28 Hz, 2H), 7.81 (d, J=8.28 Hz, 2H).

Step 2: tert-butyl 3-(5-(2-(cyclohexylamino)-5-(N-methylsulfamoyl)phenyl)-2H-tetrazol-2-yl)piperidine-1-carboxylate and tert-butyl 3-(5-(2-(cyclohexylamino)-5-(N-methylsulfamoyl)phenyl)-1H-tetrazol-1-yl)piperidine-1-carboxylate To a mixture of compound 74-2a (0.2 g, 0.59 mmol, 1 eq) and compound 74-2 (295.8 mg, 0.83 mmol, 1.4 eq) in DMF (5 mL) was added $K_2CO_3$ (328.7 mg, 2.38 mmol, 4 eq) in one portion. The mixture was stirred at 120° C. for 17 hours. The reaction mixture was filtered off, and then quenched by water (20 mL), extracted with EtOAc (20 mL*3). The combined organic layer was washed with brine (20 mL*2), dried over $Na_2SO_4$, filtered and concentrated under reduced pressure to give a residue. The residue was purified by flash silica gel chromatography to give the product as light yellow oil (175 mg), which was further purified by prep-HPLC to give compound 74-3 (11 mg, 20.1 umol, 3.4% yield) and compound 74-4 (65 mg, 121.3 umol, 20.4% yield).

Compound 74-3: LCMS (ESI): RT=2.405 min, mass calc. for $C_{24}H_{37}N_7O_4S$ 519.66, m/z found 464.0 [M-55]$^+$; $^1$HNMR (400 MHz, $CDCl_3$) δ 1.28-1.53 (m, 14H), 1.67 (d, J=11.80 Hz, 2H), 1.82 (s, 3H), 1.88 (s, 1H), 1.97 (d, J=7.03 Hz, 1H), 2.08 (d, J=4.52 Hz, 2H), 2.67 (d, J=5.52 Hz, 3H), 3.24-3.48 (m, 2H), 3.53 (br s, 1H), 4.19-4.45 (m, 2H), 4.61-4.73 (m, 1H), 4.79-5.01 (m, 2H), 6.82 (d, J=9.03 Hz, 1H), 7.73 (dd, J=9.03, 2.26 Hz, 1H), 7.79 (d, J=5.77 Hz, 1H), 8.62 (br s, 1H).

Compound 74-4: LCMS (ESI): RT=2.461 min, mass calc. for $C_{24}H_{37}N_7O_4S$ 519.66, m/z found 464.0 [M-55]$^+$; $^1$HNMR (400 MHz, $CDCl_3$) δ 1.35-1.53 (m, 15H), 1.63-1.75 (m, 2H), 1.78-1.88 (m, 2H), 1.98 (s, 1H), 2.08 (d, J=5.52 Hz, 2H), 2.27 (d, J=11.04 Hz, 1H), 2.36-2.50 (m, 1H), 2.67 (d, J=5.52 Hz, 3H), 3.06 (t, J=11.04 Hz, 1H), 3.54 (br s, 2H), 3.91-4.07 (m, 1H), 4.24 (q, J=5.52 Hz, 1H), 4.33 (s, 1H), 4.80-4.95 (m, 1H), 6.82 (d, J=9.03 Hz, 1H), 7.73 (dd, J=9.03, 2.26 Hz, 1H), 7.83 (br d, J=7.03 Hz, 1H), 8.62 (d, J=2.51 Hz, 1H).

Step 3: 4-(cyclohexylamino)-N-methyl-3-(2-(piperidin-3-yl)-2H-tetrazol-5-yl)benzenesulfonamide (Compound 74)

To a mixture of compound 74-3 (11 mg, 21.2 umol, 1 eq) in DCM (1 mL) was added HCl/MeOH (1 M, 1 mL, 47.2 eq). The mixture was stirred at 15° C. for 1 h. The crude LCMS showed 98% of the desired product was detected. The reaction mixture was concentrated under reduced pressure to give a residue. The residue was purified by prep-HPLC to give Compound 74 (2.47 mg, 5.2 umol, 24.6% yield, HCl). LCMS (ESI): RT=2.083 min, mass calc. for $C_{19}H_{29}N_7O_2S$ 419.54, m/z found 420.0 [M+H]$^+$; $^1$HNMR (400 MHz, METHANOL-$d_4$) δ 1.28-1.59 (m, 5H), 1.62-1.73 (m, 1H), 1.82 (dd, J=9.03, 3.76 Hz, 2H), 1.90-2.03 (m, 1H), 2.03-2.26 (m, 4H), 2.37-2.49 (m, 1H), 2.51 (s, 3H), 3.35-3.51 (m, 2H), 3.60-3.71 (m, 1H), 4.29 (br d, J=9.03 Hz, 1H), 5.11 (dd, J=14.93, 9.41 Hz, 1H), 5.30 (dd, J=15.06, 3.26 Hz, 1H), 7.00 (d, J=9.03 Hz, 1H), 7.71 (dd, J=9.03, 2.26 Hz, 1H), 8.57 (d, J=2.26 Hz, 1H).

Step 4: 4-(cyclohexylamino)-N-methyl-3-(1-(piperidin-3-yl)-1H-tetrazol-5-yl)benzenesulfonamide (Compound 75)

To a mixture of compound 74-4 (65 mg, 0.12 mmol, 1 eq) in DCM (2 mL) was added HCl/MeOH (1 M, 2 mL, 16.0 eq) in one portion. The mixture was stirred at 15° C. for 1 hour. The crude LCMS showed 99% of the desired product was detected and HPLC showed the reaction was completed. The reaction mixture was concentrated under reduced pressure to give Compound 75 (62 mg, crude, HCl). 12 mg of the product was diluted with MeOH (0.2 mL) and water (2 mL), then the most of the solvent was removed under reduced pressure, the remaining aqueous layer was lyophilized to give Compound 75 (2.32 mg, HCl). The remaining product (50 mg) was used in the next step without further purification.

Compound 75: LCMS (ESI): RT=2.053 min, mass calc. for $C_{19}H_{29}N_7O_2S$ 419.54, m/z found 420.0 [M+H]$^+$; $^1$H NMR (400 MHz, METHANOL-$d_4$) δ 1.60-1.39 (m, 5H), 1.70 (d, J=12.5 Hz, 1H), 1.84 (dd, J=4.0, 9.5 Hz, 2H), 1.96 (td, J=4.7, 9.2 Hz, 1H), 2.15-2.03 (m, 3H), 2.53 (s, 3H), 2.52-2.40 (m, 2H), 3.18-3.08 (m, 1H), 3.30 (br s, 1H), 3.75-3.63 (m, 2H), 3.86-3.77 (m, 1H), 5.23 (dd, J=3.8, 7.8 Hz, 1H), 7.02 (d, J=9.0 Hz, 1H), 7.73 (dd, J=2.5, 9.0 Hz, 1H), 8.58 (d, J=2.5 Hz, 1H).

Example 72: 3-(6-aminopyridin-2-yl)-4-(cyclohexylamino)-N-methylbenzenesulfonamide (Compound 76)

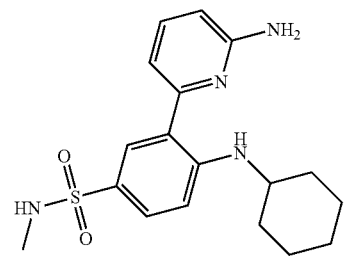 [SMILES: CNS(=O)(=O)c1ccc(NC2CCCCC2)c(-c2cccc(N)n2)c1]

Preparation of Compound 76:

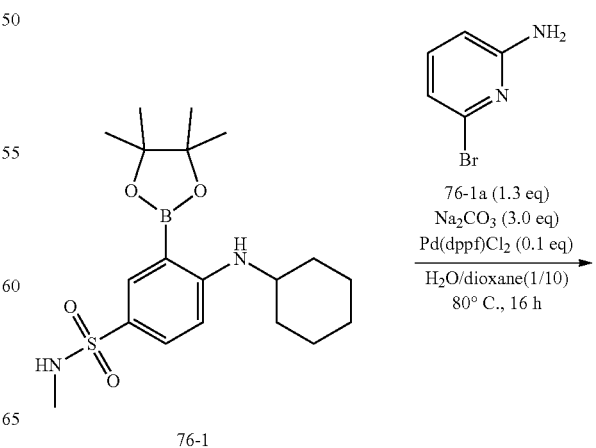

76-1

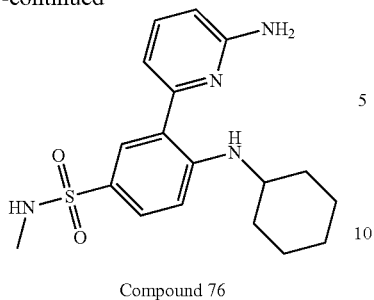

Compound 76

To a suspension of compound 76-1 (50 mg, 0.13 mmol, 1 eq) and 76-1a (29 mg, 0.16 mmol, 1.3 eq) in mix solution of dioxane (1.5 mL) and H$_2$O (0.15 mL) were added Pd(dppf)Cl$_2$ (9 mg, 13 umol, 0.1 eq) and Na$_2$CO$_3$ (40 mg, 0.38 mmol, 3 eq) in one portion under N$_2$. The resulting mixture was stirred at 80° C. for 16 h. LCMS showed the starting material was consumed completely and 44% of desired product was formed. The reaction mixture was diluted with water (10 mL) and extracted with EA (10 mL*4). The combined organic layers were concentrated under reduced pressure to give a residue. HPLC indicated 61% of desired product was detected. The residue was purified by prep-HPLC. LCMS and $^1$H NMR confirmed Compound 76 (6.76 mg, 18.6 umol, 14.6% yield). LCMS (ESI): RT=0.632 min, mass calcd. For CH$_{24}$N$_4$O$_2$S, 360.16 m/z found 361.0[M+23]$^+$. $^1$H NMR (400 MHz, CDCl$_3$) δ 8.53 (br d, J=6.00 Hz, 1H), 7.94 (d, J=2.00 Hz, 1H), 7.63 (dd, J=2.00, 8.40 Hz, 1H), 7.56 (t, J=7.60 Hz, 1H), 7.04 (d, J=7.60 Hz, 1H), 6.72 (d, J=9.20 Hz, 1H), 6.47 (d, J=8.40 Hz, 1H), 4.44 (br s, 2H), 4.23-4.14 (m, 1H), 3.53-3.40 (m, 1H), 2.61 (d, J=5.60 Hz, 3H), 2.08-2.01 (m, 2H), 1.82-1.72 (m, 2H), 1.67-1.61 (m, 1H), 1.48-1.27 (m, 5H).

Example 73: 4-(cyclohexylamino)-N-methyl-3-(pyridin-3-yl)benzenesulfonamide (Compound 77)

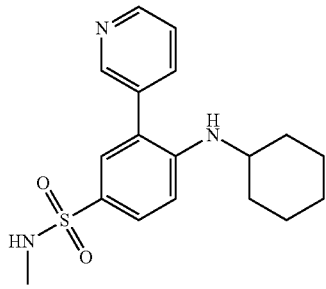

Preparation of Compound 77:

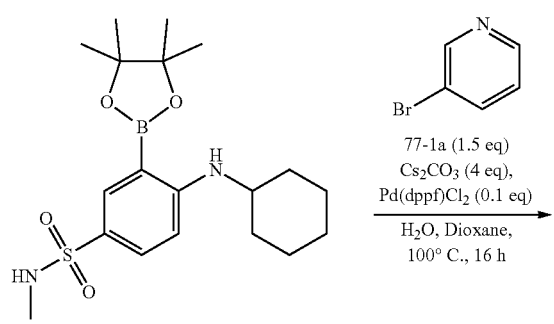

77-1

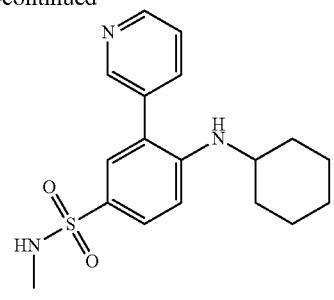

Compound 77

To a mixture of compound 77-1 (50 mg, 0.13 mmol, 1 eq) and compound 77-1a (30.1 mg, 0.19 mmol, 18.3 uL, 1.5 eq) in a solution of dioxane (2 mL) and H$_2$O (0.3 mL) was added Pd(dppf)Cl$_2$ (9.3 mg, 12.7 umol, 0.1 eq) and Cs$_2$CO$_3$ (165.3 mg, 0.51 mmol, 4 eq) in one portion under N$_2$. The mixture was stirred at 100° C. for 16 hours. The crude LCMS showed 49% of the desired product was detected. The reaction mixture was quenched by water (15 mL), and then extracted with EtOAc (20 mL*3). The combined organic layer was washed with brine (15 mL), dried over anhydrous Na$_2$SO$_4$, filtered and concentrated under reduced pressure to give a residue. The residue was purified by flash silica gel chromatography to give the product (92 mg), which was further purified by prep-HPLC to provide the product (15.54 mg), which was further purified by prep-HPLC to give the Compound 77 (6.9 mg, 18.1 umol, 7.1% yield, HCl salt). LCMS (ESI): RT=1.941 min, mass calc. for C$_{18}$H$_{23}$N$_3$O$_2$S 345.46, m/z found 346.0 [M+H]$^+$. HNMR (400 MHz, DMSO-d$_6$) δ 8.60 (td, J=5.02, 1.51 Hz, 2H), 7.84 (dt, J=7.78, 1.88 Hz, 1H), 7.56 (dd, J=8.78, 2.26 Hz, 1H), 7.51 (dd, J=7.65, 4.89 Hz, 1H), 7.32 (d, J=2.26 Hz, 1H), 7.11 (q, J=5.02 Hz, 1H), 6.86 (d, J=8.78 Hz, 1H), 4.99 (d, J=8.03 Hz, 1H), 2.52 (d, J=1.76 Hz, 1H), 2.37 (d, J=5.02 Hz, 3H), 1.85 (d, J=10.29 Hz, 2H), 1.51-1.70 (m, 3H), 1.32 (q, J=12.21 Hz, 2H), 1.04-1.24 (m, 3H).

Example 74: 4-(cyclohexylamino)-N-methyl-3-(3-methylpyridin-2-yl)benzenesulfonamide (Compound 78)

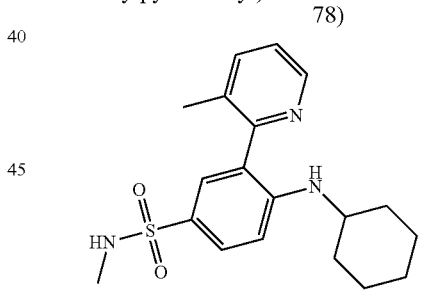

Preparation of Compound 78:

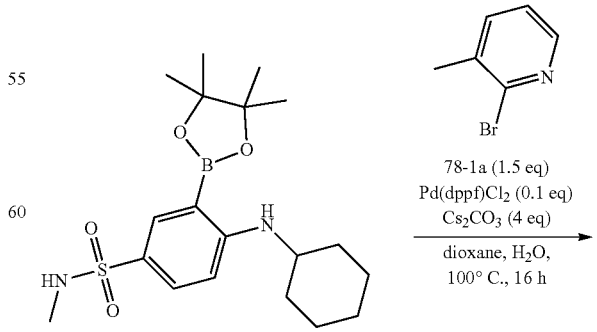

78-1

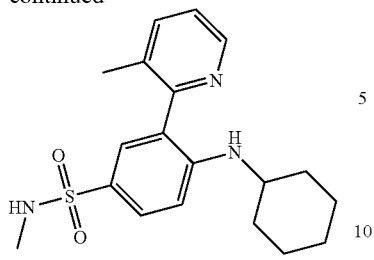

Compound 78

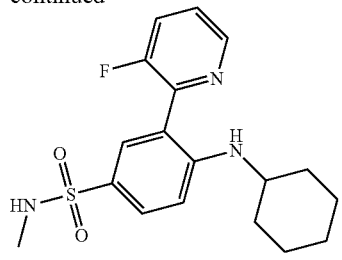

Compound 79

To a mixture of compound 78-1 (25 mg, 63.4 umol, 1 eq) and compound 78-1a (16.4 mg, 95.1 umol, 10.6 uL, 1.5 eq) in a solution of dioxane (0.7 mL) and H₂O (0.3 mL) were added Pd(dppf)Cl₂ (4.6 mg, 6.3 umol, 0.1 eq) and Cs₂CO₃ (82.6 mg, 0.25 mmol, 4 eq) in one portion at room temperature (15° C.) under N₂. The mixture was stirred at 100° C. for 16 h. The crude LCMS showed 33% of the desired product was detected and the compound 78-1 was consumed completely. The mixture was quenched by water (15 mL), extracted with EtOAc (10 mL*3). The combined organic layer was dried over anhydrous Na₂SO₄, filtered and concentrated under reduced pressure to give a residue (46 mg). The residue was purified by prep-HPLC to give Compound 78 (10.5 mg, 29.3 umol, 33.0% yield). LCMS (ESI): RT=2.055 min, mass calc. for C₁₉H₂₅N₃O₂S 359.17, m/z found 360.0 [M+H]⁺; ¹H NMR (400 MHz, CDCl₃) δ 8.54 (br d, J=4.02 Hz, 1H), 7.64-7.73 (m, 2H), 7.54 (d, J=2.26 Hz, 1H), 7.21-7.27 (m, 1H), 6.76 (d, J=8.78 Hz, 1H), 4.91 (br d, J=7.28 Hz, 1H), 4.30 (q, J=5.52 Hz, 1H), 3.28-3.44 (m, 1H), 2.60 (d, J=5.52 Hz, 3H), 2.25 (s, 3H), 1.93-2.06 (m, 2H), 1.62-1.76 (m, 3H), 1.28-1.43 (m, 2H), 1.07-1.27 (m, 3H).

Example 75: 4-(cyclohexylamino)-3-(3-fluoropyridin-2-yl)-N-methylbenzenesulfonamide (Compound 79)

To a mixture of compound 79-1 (25 mg, 63.4 umol, 1 eq) and compound 79-1a (16.7 mg, 95.1 umol, 1.5 eq) in a solution of dioxane (0.7 mL) and H₂O (0.3 mL) were added Pd(dppf)Cl₂ (4.6 mg, 6.3 umol, 0.1 eq) and Cs₂CO₃ (82.6 mg, 0.25 mmol, 4 eq) in one portion at room temperature (15° C.) under N₂. The mixture was stirred at 100° C. for 16 h. The crude LCMS showed 33% of the desired product was detected and the compound 79-1 was consumed completely. The reaction mixture was combined with another batch, the mixture was quenched by water (15 mL), extracted with EtOAc (10 mL*4). The combined organic layer was dried over anhydrous Na₂SO₄, filtered and concentrated under reduced pressure to give a residue (51 mg). The residue was purified by prep-HPLC to give the Compound 79 (15.2 mg, 41.7 umol, 47.0% yield). LCMS (ESI): RT=2.172 min, mass calc. for C₁₈H₂₂FN₃O₂S 363.14, m/z found 364.0 [M+H]⁺; H NMR (400 MHz, CDCl₃) δ 8.46 (d, J=4.77 Hz, 1H), 8.02 (t, J=2.64 Hz, 1H), 7.70 (dd, J=8.91, 2.13 Hz, 1H), 7.49-7.61 (m, 2H), 7.32 (dt, J=8.34, 4.24 Hz, 1H), 6.80 (d, J=9.03 Hz, 1H), 4.21 (q, J=5.35 Hz, 1H), 3.38-3.50 (m, 1H), 2.66 (d, J=5.52 Hz, 3H), 1.97-2.08 (m, 2H), 1.70-1.80 (m, 2H), 1.64 (br dd, J=8.28, 4.27 Hz, 1H), 1.36-1.49 (m, 2H), 1.23-1.35 (m, 3H).

Example 76: 4-(cyclohexylamino)-3-(3-methoxypyridin-2-yl)-N-methylbenzenesulfonamide (Compound 80)

Preparation of Compound 79:

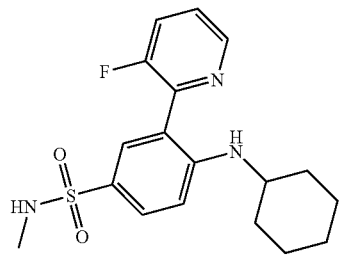 [SMILES: CNS(=O)(=O)c1ccc(NC2CCCCC2)c(-c2ncccc2C)c1]

Preparation of Compound 80:

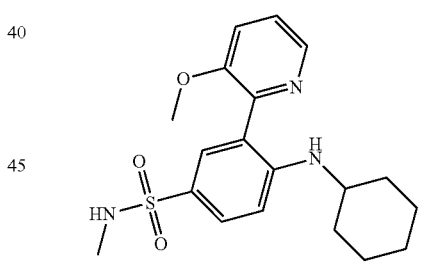

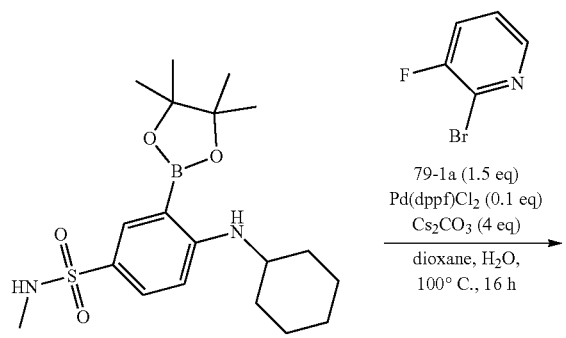

79-1

79-1a (1.5 eq)
Pd(dppf)Cl₂ (0.1 eq)
Cs₂CO₃ (4 eq)
─────────────→
dioxane, H₂O,
100° C., 16 h

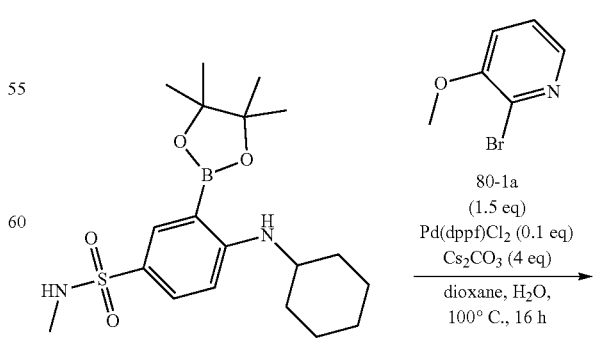

80-1

80-1a
(1.5 eq)
Pd(dppf)Cl₂ (0.1 eq)
Cs₂CO₃ (4 eq)
─────────────→
dioxane, H₂O,
100° C., 16 h

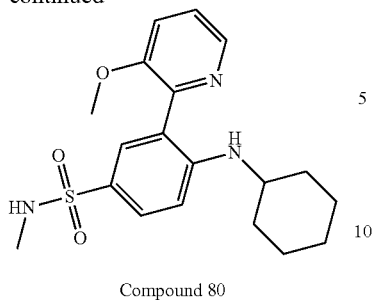

Compound 80

To a mixture of compound 80-1 (25 mg, 63.4 umol, 1 eq) and compound 80-1a (17.9 mg, 95.1 umol, 1.5 eq) in a solution of dioxane (0.7 mL) and H$_2$O (0.3 mL) were added Pd(dppf)Cl$_2$ (4.6 mg, 6.3 umol, 0.1 eq) and Cs$_2$CO$_3$ (82.6 mg, 0.25 mmol, 4 eq) in one portion at room temperature (15° C.) under N$_2$. The mixture was stirred at 100° C. for 16 h. The crude LCMS showed 39% of the desired product was detected and the compound 80-1 was consumed completely. The mixture was quenched by water (15 mL), extracted with EtOAc (10 mL*3). The combined organic layer was dried over anhydrous Na$_2$SO$_4$, filtered and concentrated under reduced pressure to give a residue (42 mg). The residue was purified by prep-HPLC to give the Compound 80 (8.2 mg, 21.7 umol, 24.5% yield). LCMS (ESI): RT=2.049 min, mass calc. for C$_{19}$H$_{25}$N$_3$O$_3$S 375.16, m/z found 376.0 [M+H]$^+$; $^1$H NMR (400 MHz, CDCl$_3$) δ 8.26 (dd, J=4.64, 1.13 Hz, 1H), 7.98 (d, J=2.26 Hz, 1H), 7.65 (dd, J=8.91, 2.13 Hz, 1H), 7.32-7.38 (m, 1H), 7.25-7.31 (m, 1H), 6.76 (d, J=9.03 Hz, 1H), 6.59 (br d, J=7.03 Hz, 1H), 4.27 (q, J=5.35 Hz, 1H), 3.83 (s, 3H), 3.29-3.50 (m, 1H), 2.64 (d, J=5.52 Hz, 3H), 1.93-2.10 (m, 3H), 1.72 (br dd, J=9.16, 4.14 Hz, 2H), 1.61 (d, J=4.52 Hz, 1H), 1.33-1.46 (m, 2H), 1.17-1.31 (m, 3H).

Example 77: 4-(cyclohexylamino)-N-methyl-3-(2H-1,2,3-triazol-2-yl)benzenesulfonamide (Compound 81)

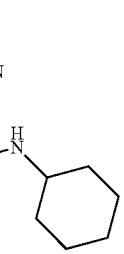

Preparation of Compound 81:

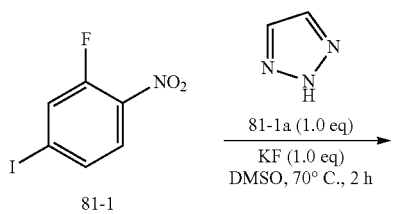

Step 1: 2-(5-Iodo-2-nitrophenyl)-2H-1,2,3-triazole

To a solution of compound 81-1 (450 mg, 1.69 mmol, 1.0 eq) in DMSO (5 mL) were added compound 81-1a (116 mg, 1.69 mmol, 1.0 eq) and KF (98 mg, 1.7 mmol, 1.0 eq). The reaction mixture was stirred at 70° C. for 2 hours. The mixture was diluted with water (30 mL) and the resultant mixture was extracted with EA (50 mL*3). The combined organic layers were dried over Na$_2$SO$_4$, filtered and con-

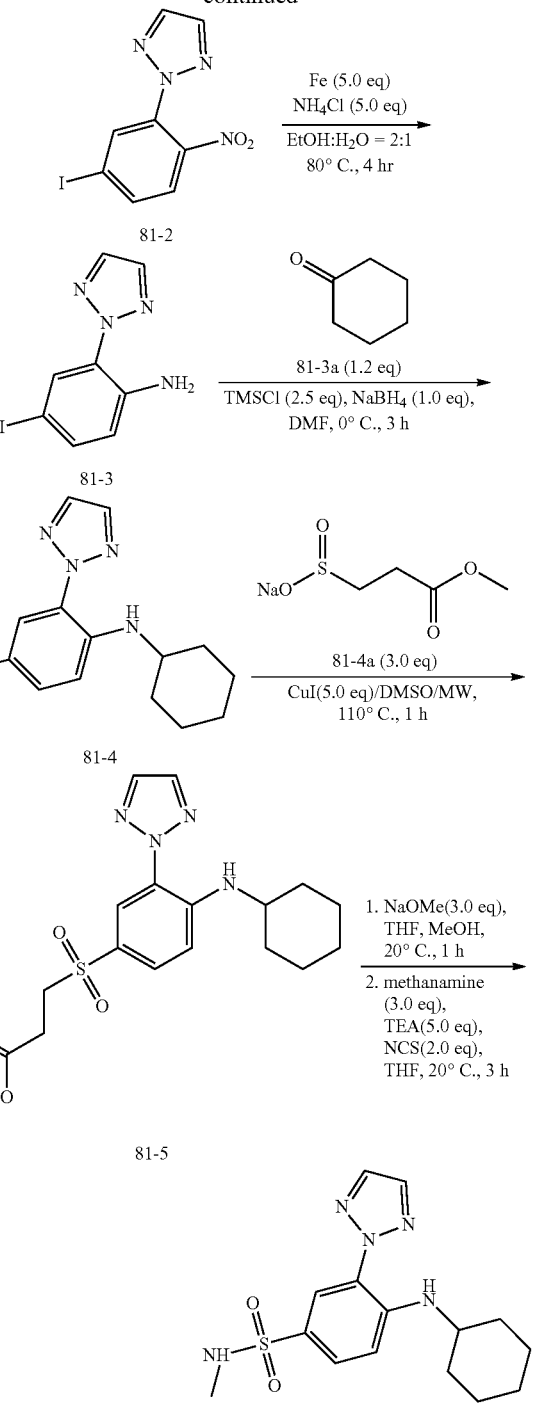

Compound 81 centrated to dryness under reduced pressure. The residue was purified by column chromatography over silica gel to afford the title compound 81-2 (150 mg, 28% yield). $^1$HNMR (400 MHz, DMSO-$d_6$) δ 8.35 (s, 1H), 8.23 (s, 2H), 8.13 (d, J=8.3 Hz, 1H), 7.86 (d, J=8.3 Hz, 1H).

Step 2: 4-Iodo-2-(2H-1,2,3-triazol-2-yl)aniline

A solution of compound 81-2 (100 mg, 0.316 mmol, 1.0 eq), Fe (88 mg, 1.6 mmol, 5.0 eq) and NH$_4$Cl (85 mg, 1.6 mmol, 5.0 eq) in EtOH (4 mL) and H$_2$O (2 mL) was stirred at 80° C. for 4 hours. The mixture was diluted with water (30 mL) and the resultant mixture was extracted with EA (50 mL*3). The combined organic layers were dried over Na$_2$SO$_4$, filtered and concentrated to dryness under reduced pressure to obtain compound 81-3 (85 mg, 94% yield). LCMS (ESI): RT=0.735 min, mass calcd. for $C_8H_7IN_4$ 285.97, m/z found 286.7 [M+H]$^+$.

Step 3: N-Cyclohexyl-4-iodo-2-(2H-1,2,3-triazol-2-yl)aniline

A mixture of compound 81-3 (60 mg, 0.21 mmol, 1.0 eq), compound 81-3a (25 mg, 0.25 mmol, 1.2 eq) and TMSCl (57 mg, 0.52 mmol, 2.5 eq) in DMF (2 mL) was stirred at 0° C. for 10 min under N$_2$. NaBH$_4$ (8.0 mg, 0.21 mmol, 1.0 eq) was added, the reaction mixture was stirred at 0° C. for 2 hours. The mixture was diluted with water (10 mL) and the resultant mixture was extracted with EA (30 mL*3). The combined organic layers were dried over Na$_2$SO$_4$, filtered and concentrated to dryness under reduced pressure. The residue was purified by column chromatography over silica gel to afford the title compound 81-4 (50 mg, crude) as a white solid.

Step 4: Methyl 3-((4-(cyclohexylamino)-3-(2H-1,2,3-triazol-2-yl)phenyl)sulfonyl)propanoate Compound 81-4 (50 mg, 0.14 mmol, 1.0 eq), compound 81-4a (71 mg, 0.41 mmol, 3.0 eq) and CuI (129 mg, 0.679 mmol, 5.0 eq) were taken up into a microwave tube in DMSO (1.5 mL). The sealed tube was heated at 110° C. for 1 hour under microwave. The mixture was diluted with water (10 mL) and EA (30 mL). The suspension was filtered and the filtrate was separation, the water layer was extracted with EA (20 mL*2). The combined organic layers were dried over Na$_2$SO$_4$, filtered and concentrated to dryness under reduced pressure. The residue was purified by column chromatography over silica gel to afford the title compound 81-5 (40 mg, 75% yield). LCMS (ESI): RT=0.813 min, mass calcd. for $C_{18}H_{24}N_4O_4S$ 392.15, m/z found 393.0 [M+H]$^+$.

Step 5: 4-(Cyclohexylamino)-N-methyl-3-(2H-1,2,3-triazol-2-yl)benzenesulfonamide To a solution of compound 81-5 (40 mg, 0.10 mmol, 1.0 eq) in MeOH (1 mL) and THF (2 mL) was added NaOMe (17 mg, 0.31 mmol, 3.0 eq). The reaction mixture was stirred at 20° C. for 1 hour, and then removed solvent to give a residue. The residue was dissolved with THF (2 mL). After MeNH$_2$ (2 M, 0.15 mL, 3.0 eq), TEA (52 mg, 0.51 mmol, 5.0 eq) and NCS (27 mg, 0.20 mmol, 2.0 eq) were added, the reaction mixture was stirred at 20° C. for 3 hours. The mixture was diluted with water (30 mL) and the resultant mixture was extracted with EA (50 mL*3). The combined organic layers were dried over Na$_2$SO$_4$, filtered and concentrated to dryness under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. Compound 81 (26.59 mg, 77% yield) was obtained. LCMS (ESI): RT=0.792 min, mass calcd. for $C_{15}H_{21}N_5O_2S$ 335.14, m/z found 335.9 [M+H]$^+$, $^1$HNMR (400 MHz, CDCl$_3$) δ=8.43 (d, J=2.0 Hz, 1H), 7.85 (s, 2H), 7.67 (dd, J=2.3, 8.8 Hz, 1H), 7.64-7.57 (m, 1H), 6.86 (d, J=9.0 Hz, 1H), 4.26 (q, J=5.4 Hz, 1H), 3.54-3.43 (m, 1H), 2.67 (d, J=5.3 Hz, 3H), 2.10-2.02 (m, 2H), 1.83-1.74 (m, 2H), 1.70-1.62 (m, 1H), 1.49-1.28 (m, 5H).

Example 78: 4-(cyclohexylamino)-N-methyl-3-(1-methyl-1H-imidazol-4-yl)benzenesulfonamide (Compound 82)

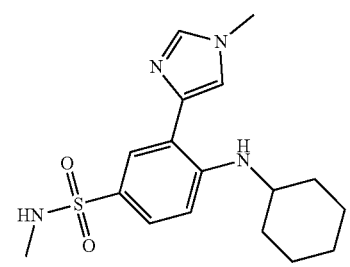 [SMILES: CNS(=O)(=O)c1ccc(NC2CCCCC2)c(-c2cn(C)cn2)c1]

Preparation of Compound 82:

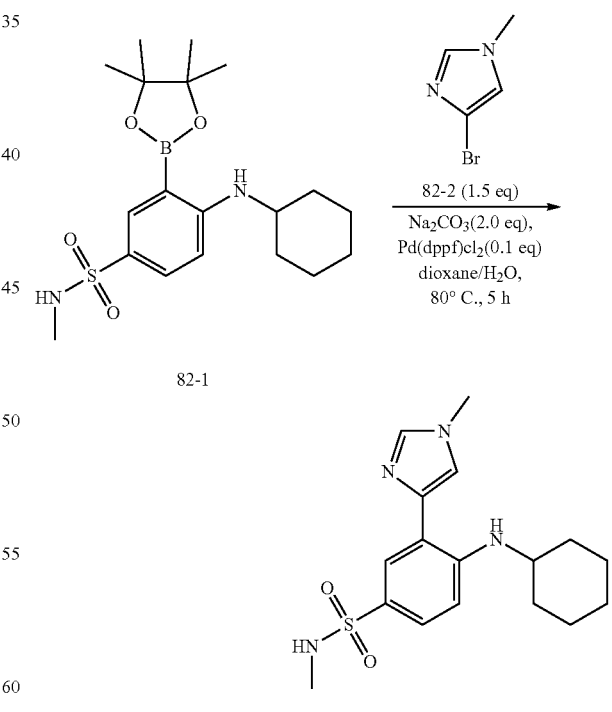

Compound 82

To a solution of compound 82-1 (0.04 g, 0.10 mmol, 1.0 eq) and compound 82-2 (16.3 mg, 0.10 mmol, 1.0 eq) in dioxane (5.0 mL) was added H$_2$O (0.5 mL) Pd(dppf)Cl$_2$ (7.4 mg, 10.14 umol, 0.1 eq) and Na$_2$CO$_3$ (21.5 mg, 0.20 mmol, 2.0 eq). The mixture was stirred at 80° C. for 16 hour under N₂ atmosphere. LCMS showed desired compound was found. The reaction was filtered through Celite and concentrated under reduced pressure to give a residue. The crude product was purified by prep-HPLC to give Compound 82 (6.64 mg, 18.86 umol, 18.60% yield). LCMS (ESI): RT=0.634 min, mass calc. for $C_{17}H_{24}N_4O_2S$ 348.16, m/z found 348.9 [M+H]⁺; ¹HNMR (400 MHz, CDCl₃) δ 8.55 (s, 1H), 7.81 (d, J=2.0 Hz, 1H), 7.54 (dd, J=2.3, 8.8 Hz, 1H), 7.47 (s, 1H), 7.24 (s, 1H), 6.69 (d, J=9.0 Hz, 1H), 4.24 (q, J=5.4 Hz, 1H), 3.75 (s, 3H), 3.44 (s, 1H), 2.62 (d, J=5.5 Hz, 3H), 2.12-2.00 (m, 2H), 1.86-1.75 (m, 2H), 1.69-1.64 (m, 1H), 1.48-1.25 (m, 5H).

Example 79: 4-(cyclohexylamino)-3-(6-(dimethylamino)pyridin-2-yl)-N-methylbenzenesulfonamide (Compound 83)

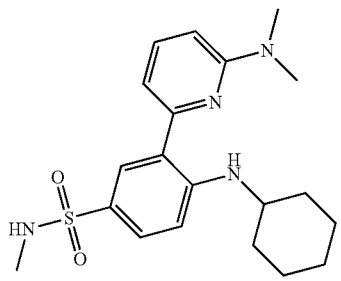 [SMILES: CNS(=O)(=O)c1ccc(NC2CCCCC2)c(-c2cccc(N(C)C)n2)c1]

Preparation of Compound 83:

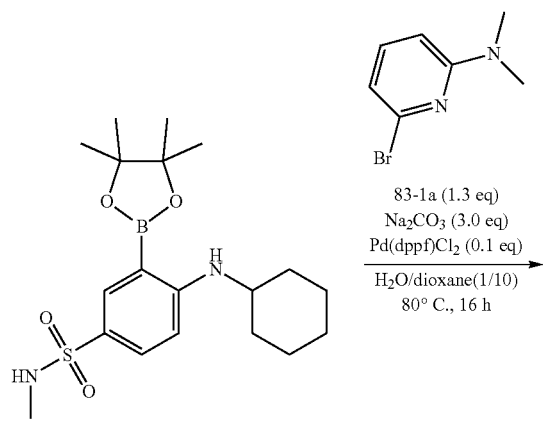

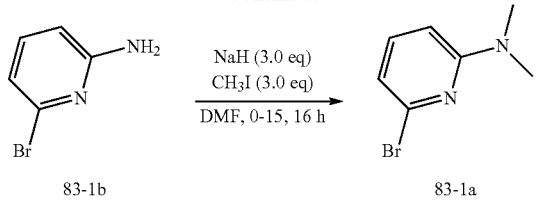

Step 1: 6-bromo-N,N-dimethyl-pyridin-2-amine

To a mixture of the compound 83-1b (100 mg, 0.578 mmol, 1 eq) in DMF (2 mL) was added NaH (69 mg, 1.73 mmol, 60% purity, 3 eq) in one portion at 0° C. under N₂. The reaction mixture was stirred at 0° C. for 15 min, then CH₃I (246 mg, 1.73 mmol, 3 eq) was added at 0° C. and the mixture was warmed to 15° C. and stirred for 16 h. LCMS showed one main peak with desired MS was detected. TLC indicated the starting material was consumed completely. The reaction mixture was diluted with water (15 mL) and extracted with EA (15 mL*4). The combined organic layers were dried with anhydrous Na₂SO₄, filtered and concentrated in vacuum to provide compound 83-1a (130 mg, crude), which was used next step without further purification Step 2: 4-(cyclohexylamino)-3-[6-(dimethylamino)-2-pyridyl]-N-methyl-benzenesulfonamide To a suspension of the compound 83-1a (33 mg, 0.132 mmol, 1.3 eq) and the compound 83-1 (40 mg, 0.101 mmol, 1 eq) in mix solution of H₂O (0.1 mL) and dioxane (1 mL) were added Pd(dppf)Cl₂ (7.5 mg, 10 umol, 0.1 eq) and Na₂CO₃ (32 mg, 0.304 mmol, 3 eq) in one portion under N₂. The mixture was stirred at 80° C. for 16 h. LCMS showed the starting material was consumed completely and one main peak with desired MS was detected. The reaction mixture was diluted with water (10 mL) and extracted with EA (10 mL*3). The combined organic layers were concentrated under reduced pressure to give a residue. HPLC showed 68% of desired product was detected. The residue was purified by prep-HPLC. LCMS and ¹H NMR that the Compound 83 (4.81 mg, 12 umol, 11.8% yield). LCMS (ESI): RT=0.755 min, mass calcd. For $C_{20}H_{28}N_4O_2S$, 388.19 m/z found 389.1 [M+H]⁺. ¹H NMR (400 MHz, CDCl₃) δ 8.62 (br d, J=6.80 Hz, 1H), 7.96 (d, J=2.40 Hz, 1H), 7.68-7.52 (m, 2H), 6.94 (d, J=7.60 Hz, 1H), 6.74 (d, J=9.20 Hz, 1H), 6.48 (d, J=8.40 Hz, 1H), 4.18-4.09 (m, 1H), 3.47-3.35 (m, 1H), 3.14 (s, 6H), 2.64 (d, J=5.60 Hz, 3H), 2.17-2.06 (m, 2H), 1.84-1.75 (m, 2H), 1.73-1.66 (m, 1H), 1.45-1.35 (m, 2H), 1.29-1.20 (m, 3H).

Example 80: 3-(4-aminopyridin-2-yl)-4-(cyclohexylamino)-N-methylbenzenesulfonamide (Compound 84)

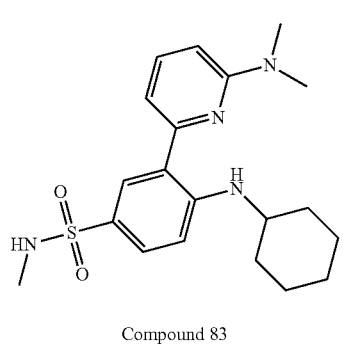

Compound 83

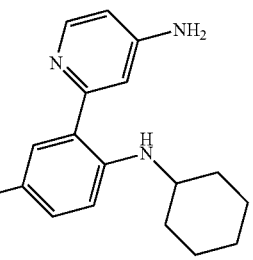

Preparation of Compound 84:

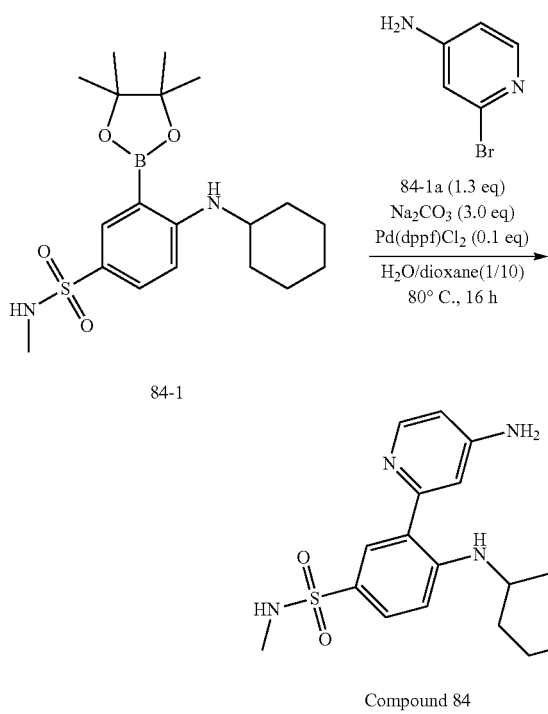

84-1

Compound 84

To a suspension of the compound 84-1 (40 mg, 0.101 mmol, 1 eq) and the compound 84-1a (22 mg, 0.131 mmol, 1.3 eq) in mix solvent of dioxane (1 mL) and H$_2$O (0.15) were added Pd(dppf)Cl$_2$ (7 mg, 10 umol, 0.1 eq) and Na$_2$CO$_3$ (32 mg, 0.304 mmol, 3 eq) in one portion under N$_2$. The mixture was stirred at 80° C. for 16 h. LCMS showed the starting material was consumed completely and 40% of desired product was formed. The reaction mixture was diluted with water (10 mL) and extracted with EA (10 mL*4). The combined organic layers were concentrated under reduced pressure to give a residue. HPLC indicated 60% of desired product was detected. The residue was purified by prep-HPLC. LCMS and $^1$H NMR confirmed the white solid was the Compound 84 (14.25 mg, 39 umol, 39% yield). LCMS (ESI): RT=0.618 min, mass calcd. For C$_{18}$H$_{24}$N$_4$O$_2$S, 360.16 m/z found 361.0[M+H]$^+$. $^1$H NMR (400 MHz, CDCl$_3$) δ 9.19 (br s, 1H), 8.19 (d, J=5.60 Hz, 1H), 8.02 (d, J=2.40 Hz, 1H), 7.63 (dd, J=2.00, 8.80 Hz, 1H), 7.03 (d, J=2.00 Hz, 1H), 6.72 (d, J=8.80 Hz, 1H), 6.47 (dd, J=2.00, 5.60 Hz, 1H), 4.69 (q, J=5.30 Hz, 1H), 4.36 (s, 2H), 3.45 (br s, 1H), 2.60 (d, J=5.20 Hz, 3H), 2.05-1.98 (m, 2H), 1.80-1.71 (m, 2H), 1.64-1.58 (m, 1H), 1.44-1.25 (m, 4H).

Example 81: 4-(cyclohexylamino)-N-methyl-3-(6-(methylamino)pyridin-2-yl)benzenesulfonamide (Compound 85)

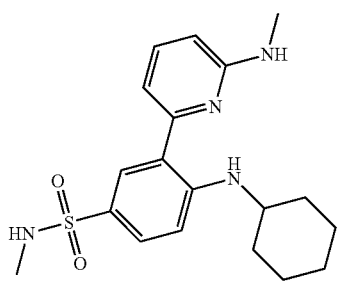 [SMILES: CNc1cccc(-c2cc(S(=O)(=O)NC)ccc2NC2CCCCC2)n1]

Preparation of Compound 85:

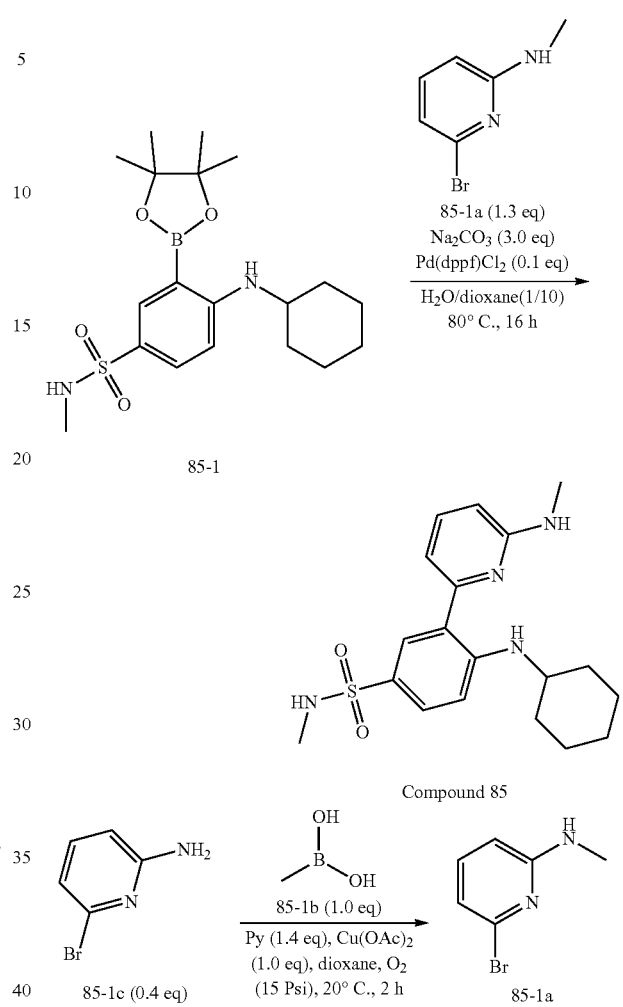

85-1

Compound 85

Step 1: 6-bromo-N-methyl-pyridin-2-amine

Cu(OAc)$_2$ (303 mg, 1.67 mmol, 1 eq) was added to a solution of the compound 85-1c (116 mg, 0.67 mmol, 0.4 eq) and pyridine (185 mg, 2.34 mmol, 1.40 eq) in dioxane (6 mL). The reaction mixture was stirred at 15° C. for 15 min. The compound 85-1b (100 mg, 1.67 mmol, 1 eq) was added and the reaction was heated to 100° C., and stirred at 100° C. under O$_2$ (15 Psi) for 16 h. LCMS showed no desired MS was detected. TLC indicated the compound 85-1c was remained and two new spots were formed. The reaction mixture was filtered and concentrated under reduced pressure to give a residue. The residue was purified by flash silica gel chromatography. $^1$H NMR confirmed that the product was compound 85-1a (37 mg, 0.20 mmol, 11.9% yield). $^1$H NMR (400 MHz, CDCl$_3$) δ 7.31-7.27 (m, 1H), 6.74 (d, J=7.60 Hz, 1H), 6.29 (d, J=8.00 Hz, 1H), 4.69 (br s, 1H), 2.91 (d, J=5.20 Hz, 3H).

Step 2: 4-(cyclohexylamino)-N-methyl-3-[6-(methylamino)-2-pyridyl]benzenesulfonamide To a suspension of the compound 85-1a (31 mg, 0.131 mmol, 1.3 eq) and the compound 85-1 (40 mg, 0.10 mmol, 1 eq) in mix solvent of H₂O (0.1 mL) and dioxane (1 mL) were added Na₂CO₃ (32 mg, 0.304 mmol, 3 eq) and Pd(dppf)Cl₂ (7 mg, 10 umol, 0.1 eq) in one portion under N₂. The mixture was stirred at 80° C. for 16 h. LCMS showed the starting material was consumed completely and one main peak with desired MS was detected. The reaction mixture was diluted with water (10 mL) and extracted with EA (10 mL*3). The combined organic layers were concentrated under reduced pressure to give a residue. HPLC showed 66% of desired product was detected. The residue was purified by prep-HPLC. LCMS and ¹H NMR confirmed that the product was the Compound 85 (9.94 mg, 26 umol, 26.2% yield). LCMS (ESI): RT=0.664 min, mass calcd. For $C_{19}H_{26}N_4O_2S$ 374.18 m/z found 375.0 [M+H]⁺. ¹H NMR (400 MHz, CDCl₃) δ 8.70 (d, J=6.5 Hz, 1H), 7.97 (d, J=2.3 Hz, 1H), 7.63 (dd, J=2.3, 8.8 Hz, 1H), 7.54 (t, J=7.9 Hz, 1H), 6.98 (d, J=7.5 Hz, 1H), 6.73 (d, J=9.0 Hz, 1H), 6.36 (d, J=8.3 Hz, 1H), 4.53-4.45 (m, 1H), 4.13 (q, J=5.7 Hz, 1H), 3.48-3.37 (m, 1H), 3.00 (d, J=5.0 Hz, 3H), 2.63 (d, J=5.5 Hz, 3H), 2.17-2.05 (m, 2H), 1.85-1.74 (m, 2H), 1.73-1.62 (m, 1H), 1.47-1.38 (m, 2H), 1.33-1.24 (m, 3H).

Example 82: 4-(cyclohexylamino)-N-methyl-3-(2-(1-(pyridin-3-yl)piperidin-3-yl)-2H-tetrazol-5-yl)benzenesulfonamide (Compound 86)

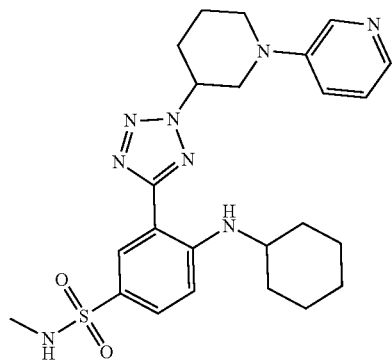 [SMILES: CNS(=O)(=O)c1ccc(NC2CCCCC2)c(-c2nnn(C3CCCN(c4cccnc4)C3)n2)c1]

Preparation of Compound 86:

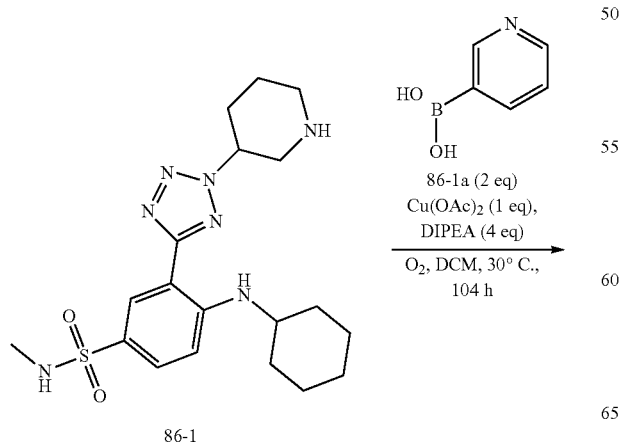

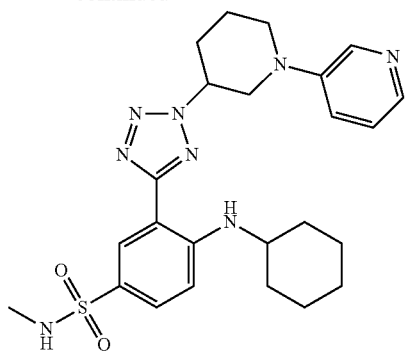

Compound 86

To a mixture of 86-1 (50 mg, 0.110 mmol, 1 eq, HCl salt) and compound 86-1a (27.0 mg, 0.219 mmol, 2 eq) in DCM (1 mL) were added Cu(OAc)₂ (19.9 mg, 0.110 umol, 1 eq) and DIPEA (56.7 mg, 0.439 mmol, 76.4 uL, 4 eq) in one portion at 15° C. under O₂. The mixture was stirred at 30° C. for 88 h. The mixture was stirred at 30° C. for 16 h. The reaction mixture was diluted with DCM (15 mL), and then concentrated under reduced pressure to give a residue. The residue was purified by flash silica gel chromatography to give the product as yellow oil (37 mg), which was further purified by prep-HPLC to give the impure product (6.53 mg), which was further purified by prep-HPLC to give the Compound 86 (2.91 mg, 5.9 umol, 5.3% yield). LCMS (ESI): RT=2.247 min, mass calc. for $C_{24}H_{32}N_8O_2S$ 496.24, m/z found 497.1 [M+H]⁺; ¹H NMR (400 MHz, CDCl₃) δ 8.61 (br s, 1H), 8.41 (s, 1H), 8.05 (s, 1H), 7.59-7.92 (m, 3H), 6.80 (d, J=8.53 Hz, 1H), 5.07 (s, 1H), 4.51 (s, 1H), 3.88-4.24 (m, 1H), 3.53 (br s, 3H), 2.78 (s, 1H), 2.63 (s, 3H), 2.46 (s, 1H), 2.07 (s, 2H), 1.60-1.99 (m, 7H), 1.22-1.44 (m, 4H).

Example 83: 4-(cyclohexylamino)-3-(4-(dimethylamino)pyridin-2-yl)-N-methylbenzenesulfonamide (Compound 87)

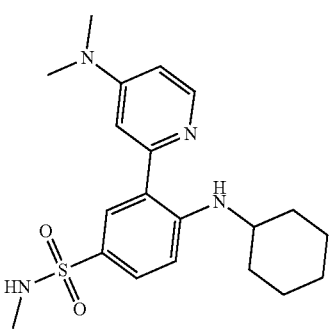 [SMILES: CNS(=O)(=O)c1ccc(NC2CCCCC2)c(-c2cc(N(C)C)ccn2)c1]

Preparation of Compound 87:

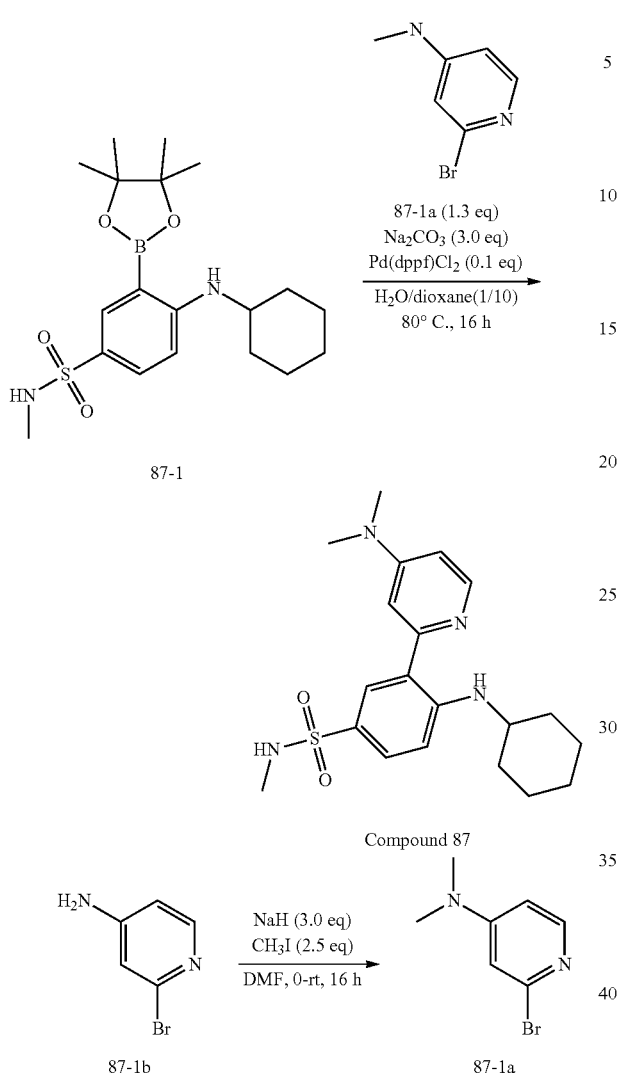

Step 1: 2-bromo-N,N-dimethyl-pyridin-4-amine

To a mixture of the compound 87-1b (100 mg, 0.578 mmol, 1 eq) in DMF (2 mL) was added NaH (92 mg, 2.31 mmol, 4 eq) in one portion at 0° C. under $N_2$. The mixture was stirred at 0° C. for 15 min, then $CH_3I$ (0.63 g, 4.44 mmol, 0.27 mL, 7.68 eq) was added at 0° C. and then the mixture was warmed to 15° C. and stirred for 16 h. The reaction was monitored by LCMS. The reaction mixture was diluted with water (15 mL) and extracted with EA (15 mL*4). The combined organic layers were dried with anhydrous $Na_2SO_4$, filtered and concentrated in vacuum to give the compound 87-1a (130 mg, crude), which was used next step without further purification. $^1H$ NMR (400 MHz, $CDCl_3$) δ 7.95 (d, J=6.00 Hz, 1H), 6.65 (d, J=2.40 Hz, 1H), 6.44 (dd, J=2.50, 6.10 Hz, 1H), 3.00 (s, 6H).

Step 2: 4-(cyclohexylamino)-3-[4-(dimethylamino)-2-pyridyl]-N-methyl-benzenesulfonamide To a suspension of the compound 87-1a (38 mg, 0.132 mmol, 1.3 eq) and the compound 1 (40 mg, 0.101 mmol, 1 eq) in mix solvent of $H_2O$ (0.1 mL) and dioxane (1 mL) were added $Pd(dppf)Cl_2$ (7 mg, 10 umol, 0.1 eq) and $Na_2CO_3$ (38 mg, 0.355 mmol, 3.5 eq) in one portion under $N_2$. The mixture was stirred at 80° C. for 16 h. LCMS showed the starting material was consumed completely and one main peak with desired MS was detected. The reaction mixture was diluted with water (10 mL) and extracted with EA (10 mL*3). The combined organic layers were concentrated under reduced pressure to give a residue. The residue was purified by prep-HPLC. LCMS and $^1H$ NMR confirmed the Compound 87 (5.88 mg, 15 umol, 14.9% yield). LCMS (ESI): RT=0.642 min, mass calcd. For $C_{20}H_{28}N_4O_2S$, 388.19 m/z found 389.1[M+H]$^+$. $^1H$ NMR (400 MHz, $CDCl_3$) δ 8.60 (br d, J=6.00 Hz, 1H), 8.22 (d, J=6.00 Hz, 1H), 7.90 (d, J=2.00 Hz, 1H), 7.63 (dd, J=2.40, 8.80 Hz, 1H), 6.77 (d, J=2.40 Hz, 1H), 6.71 (d, J=8.80 Hz, 1H), 6.48 (dd, J=2.40, 6.00 Hz, 1H), 4.40-4.27 (m, 1H), 3.49-3.35 (m, 1H), 3.07 (s, 6H), 2.60 (d, J=5.60 Hz, 3H), 2.06-1.99 (m, 2H), 1.81-1.71 (m, 2H), 1.62-1.57 (m, 1H), 1.49-1.31 (m, 5H).

Example 84: 4-(cyclohexylamino)-N-methyl-3-(4-(methylamino)pyridin-2-yl)benzenesulfonamide (Compound 88)

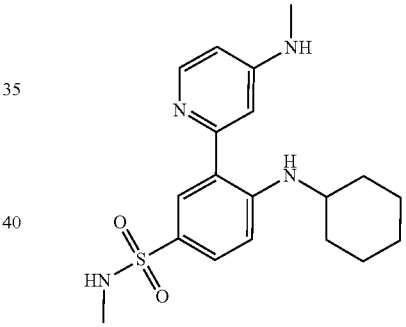

Preparation of Compound 88:

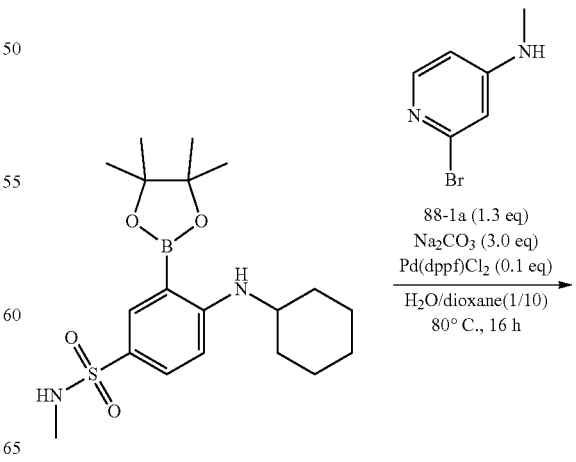

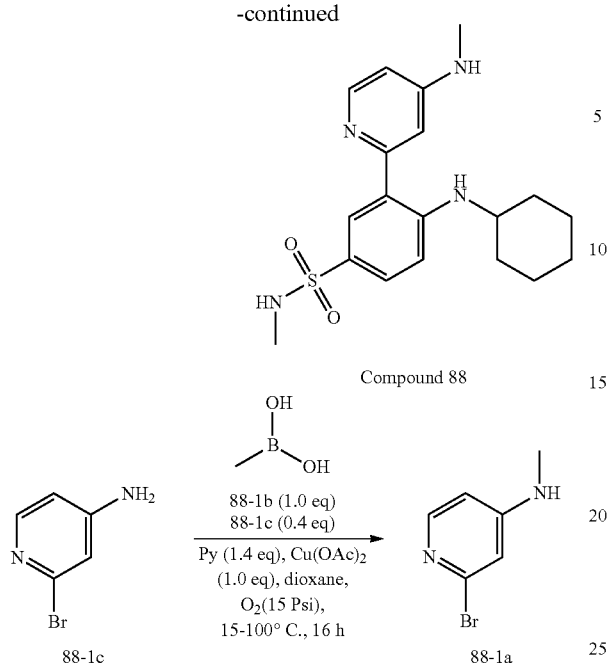

Compound 88

Step 1: 2-bromo-N-methyl-pyridin-4-amine

Cu(OAc)₂ (303 mg, 1.67 mmol, 1 eq) was added to a solution of the compound 88-1c (116 mg, 0.668 mmol, 0.4 eq) and pyridine (185 mg, 2.34 mmol, 0.19 mL, 1.40 eq) in dioxane (6 mL). The reaction mixture was stirred at 15° C. for 15 min. The compound 88-1b (100 mg, 1.67 mmol, 1 eq) was added and the reaction was heated to 100° C. and stirred at 100° C. under O₂ (15 Psi) for 16 h. LCMS showed no desired MS was detected. TLC indicated the compound 88-1c was remained and one new spot was formed. The reaction mixture was filtered and concentrated under reduced pressure to give a residue. The residue was purified by flash silica gel chromatography. ¹H NMR confirmed that the product was 88-1a (35 mg, 0.187 mmol, 11.2% yield). ¹H NMR (400 MHz, CDCl₃) δ 7.93 (d, J=5.60 Hz, 1H), 6.62 (d, J=2.00 Hz, 1H), 6.39 (dd, J=2.20, 5.60 Hz, 1H), 4.32 (br s, 1H), 2.87 (d, J=5.20 Hz, 3H).

Step 2: 4-(cyclohexylamino)-N-methyl-3-[4-(methylamino)-2-pyridyl]benzenesulfonamide To a suspension of the compound 88-1a (29 mg, 0.132 mmol, 1.3 eq) and the compound 88-1 (40 mg, 101.44 umol, 1 eq) in a mix solvent of H₂O (0.1 mL) and dioxane (1 mL) were added Na₂CO₃ (32 mg, 0.304 mmol, 3 eq) and Pd(dppf)Cl₂ (7.4 mg, 10 umol, 0.1 eq) in one portion under N₂. The mixture was stirred at 80° C. for 16 h. LCMS showed the starting material was consumed completely and one main peak with desired MS was detected. The reaction mixture was diluted with water (5 mL) and extracted with EA (7 mL*3). The combined organic layers were concentrated under reduced pressure to give a residue. The residue was purified by prep-HPLC. LCMS and ¹H NMR confirmed that the product was Compound 88 (8.07 mg, 20.9 umol, 20.6% yield). LCMS (ESI): RT=0.630 min, mass calcd. For C₁₉H₂₆N₄O₂S, 374.18 m/z found 375.0[M+H]⁺. ¹H NMR (400 MHz, CDCl₃) δ 8.97 (br d, J=7.60 Hz, 1H), 8.20 (d, J=6.00 Hz, 1H), 7.96 (d, J=2.00 Hz, 1H), 7.63 (dd, J=2.10, 8.90 Hz, 1H), 6.82 (d, J=2.00 Hz, 1H), 6.72 (d, J=8.80 Hz, 1H), 6.41 (dd, J=2.00, 5.80 Hz, 1H), 4.47-4.35 (m, 2H), 3.50-3.37 (m, 1H), 2.92 (d, J=5.20 Hz, 3H), 2.61 (d, J=5.60 Hz, 3H), 2.06-2.00 (m, 2H), 1.81-1.73 (m, 2H), 1.68-1.61 (m, 1H), 1.45-1.30 (m, 5H).

Example 85: 4-(cyclohexylamino)-N-methyl-3-(1H-1,2,3-triazol-1-yl)benzenesulfonamide (Compound 89)

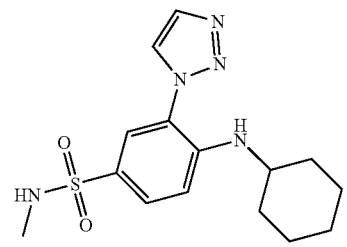 [SMILES: CNS(=O)(=O)c1ccc(NC2CCCCC2)c(-n2ccnn2)c1]

Preparation of Compound 89:

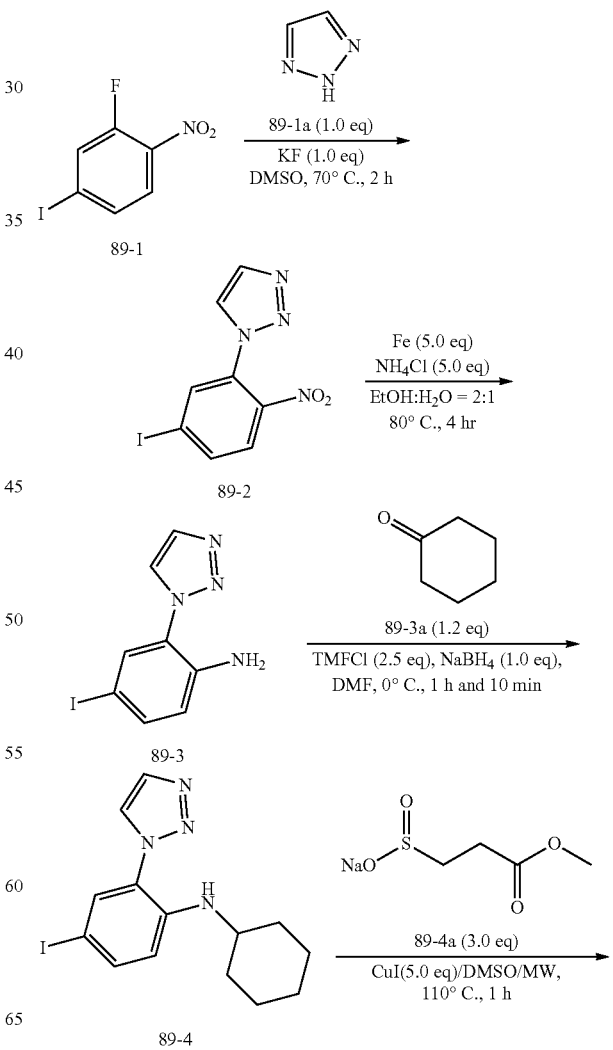

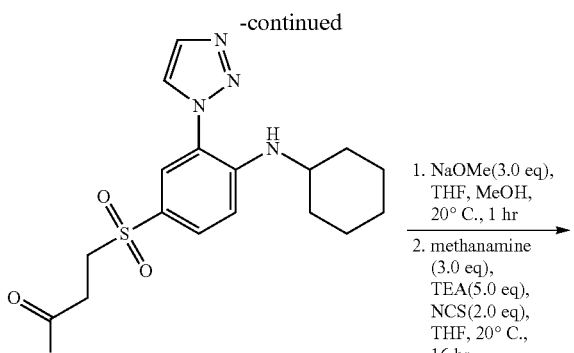

89-5

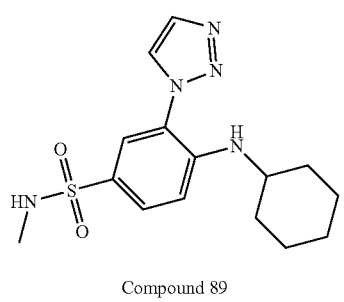

Compound 89

Step 1: 1-(5-Iodo-2-nitrophenyl)-1H-1,2,3-triazole

To a solution of compound 89-1 (450 mg, 1.69 mmol, 1.0 eq) in DMSO (5 mL) were added compound 89-1a (116 mg, 1.69 mmol, 1.0 eq) and KF (98 mg, 1.7 mmol, 1.0 eq). The reaction mixture was stirred at 70° C. for 2 hours. The mixture was diluted with water (30 mL) and the resultant mixture was extracted with EA (50 mL*3). The combined organic layers were dried over $Na_2SO_4$, filtered and concentrated to dryness under reduced pressure. The residue was purified by column chromatography over silica gel to afford the title compound 89-2 (200 mg, 37% yield). $^1$HNMR (400 MHz, DMSO-$d_6$) δ 8.75 (s, 1H), 8.33 (s, 1H), 8.23 (d, J=8.3 Hz, 1H), 8.01 (s, 1H), 7.97 (d, J=8.3 Hz, 1H).

Step 2: 4-Iodo-2-(1H-1,2,3-triazol-2-yl)aniline

A solution of compound 89-2 (200 mg, 0.633 mmol, 1.0 eq), Fe (177 mg, 3.16 mmol, 5.0 eq) and $NH_4Cl$ (169 mg, 3.16 mmol, 5.0 eq) in EtOH (5 mL) and $H_2O$ (2.5 mL) was stirred at 80° C. for 4 hours. The mixture was diluted with water (30 mL) and the resultant mixture was extracted with EA (50 mL*3). The combined organic layers were dried over $Na_2SO_4$, filtered and concentrated to dryness under reduced pressure to obtain the title compound 89-3 (180 mg, 99% yield). LCMS (ESI): RT=0.654 min, mass calcd. for $C_8H_7IN_4$ 285.97, m/z found 286.8 [M+H]$^+$.

Step 3: N-Cyclohexyl-4-iodo-2-(1H-1,2,3-triazol-2-yl)aniline

A mixture of compound 89-3 (100 mg, 0.350 mmol, 1.0 eq), compound 89-3a (41 mg, 0.42 mmol, 1.2 eq) and TMSCl (95 mg, 0.87 mmol, 2.5 eq) in DMF (2 mL) was stirred at 0° C. for 10 min under $N_2$. $NaBH_4$ (13 mg, 0.35 mmol, 1.0 eq) was added, the reaction mixture was stirred at 0° C. for 1 hour. The mixture was diluted with water (10 mL) and the resultant mixture was extracted with EA (30 mL*3). The combined organic layers were dried over $Na_2SO_4$, filtered and concentrated to dryness under reduced pressure. The residue was purified by column chromatography over silica gel to afford the title compound 89-4 (120 mg, crude). LCMS (ESI): RT=0.868 min, mass calcd. for $C_{14}H_{17}IN_4$ 368.05, m/z found 368.9 [M+H]$^+$.

Step 4: Methyl 3-((4-(cyclohexylamino)-3-(1H-1,2,3-triazol-2-yl)phenyl)sulfonyl)propanoate Compound 89-4 (60 mg, 0.16 mmol, 1.0 eq), compound 89-4a (85 mg, 0.49 mmol, 3.0 eq) and CuI (155 mg, 0.815 mmol, 5.0 eq) were taken up into a microwave tube in DMSO (1.5 mL). The sealed tube was heated at 110° C. for 1 hour under microwave. The mixture was diluted with water (10 mL) and EA (30 mL). The suspension was filtered and the filtrate was separation, the water layer was extracted with EA (20 mL*2). The combined organic layers were dried over $Na_2SO_4$, filtered and concentrated to dryness under reduced pressure. The residue was purified by column chromatography over silica gel to afford compound 89-5 (60 mg, 94% yield). LCMS (ESI): RT=0.748 min, mass calcd. for $C_{18}H_{24}N_4O_4S$ 392.15, m/z found 393.0 [M+H]$^+$.

Step 5: 4-(Cyclohexylamino)-N-methyl-3-(1H-1,2,3-triazol-2-yl)benzenesulfonamide To a solution of compound 89-5 (60 mg, 0.15 mmol, 1.0 eq) in MeOH (1 mL) and THF (2 mL) was added NaOMe (25 mg, 0.46 mmol, 3.0 eq). The reaction mixture was stirred at 20° C. for 1 hour, and then removed solvent to give a residue. The residue was dissolved with THF (2 mL). After $MeNH_2$ (2 M, 0.23 mL, 3.0 eq), TEA (77 mg, 0.76 mmol, 5.0 eq) and NCS (41 mg, 0.31 mmol, 2.0 eq) were added, the reaction mixture was stirred at 20° C. for 3 hours. The mixture was diluted with water (30 mL) and the resultant mixture was extracted with EA (50 mL*3). The combined organic layers were dried over $Na_2SO_4$, filtered and concentrated to dryness under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. Compound 89 (16.13 mg, 31% yield) was obtained. LCMS (ESI): RT=0.739 min, mass calcd. for $C_{15}H_{21}N_5O_2S$ 335.14, m/z found 335.9 [M+H]$^+$, $^1$HNMR (400 MHz, DMSO-$d_6$) δ 8.59 (d, J=1.0 Hz, 1H), 8.03 (d, J=1.0 Hz, 1H), 7.67 (dd, J=2.3, 8.8 Hz, 1H), 7.58 (d, J=2.3 Hz, 1H), 7.09 (d, J=8.8 Hz, 1H), 5.91 (d, J=8.0 Hz, 1H), 3.51-3.41 (m, 1H), 2.53-2.51 (m, 1H), 2.40 (s, 3H), 1.93-1.83 (m, 2H), 1.71-1.61 (m, 2H), 1.61-1.52 (m, 1H), 1.43-1.28 (m, 2H), 1.28-1.11 (m, 3H).

Example 86: N-methyl-3-(2-methyl-2H-tetrazol-5-yl)-4-(phenylamino)benzenesulfonamide (Compound 90)

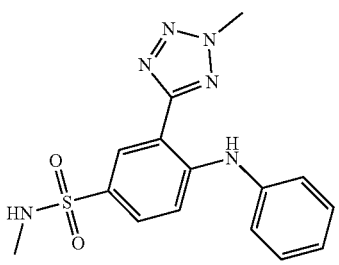 [SMILES: CNS(=O)(=O)c1ccc(Nc2ccccc2)c(-c2nnn(C)n2)c1]

Preparation of Compound 90:

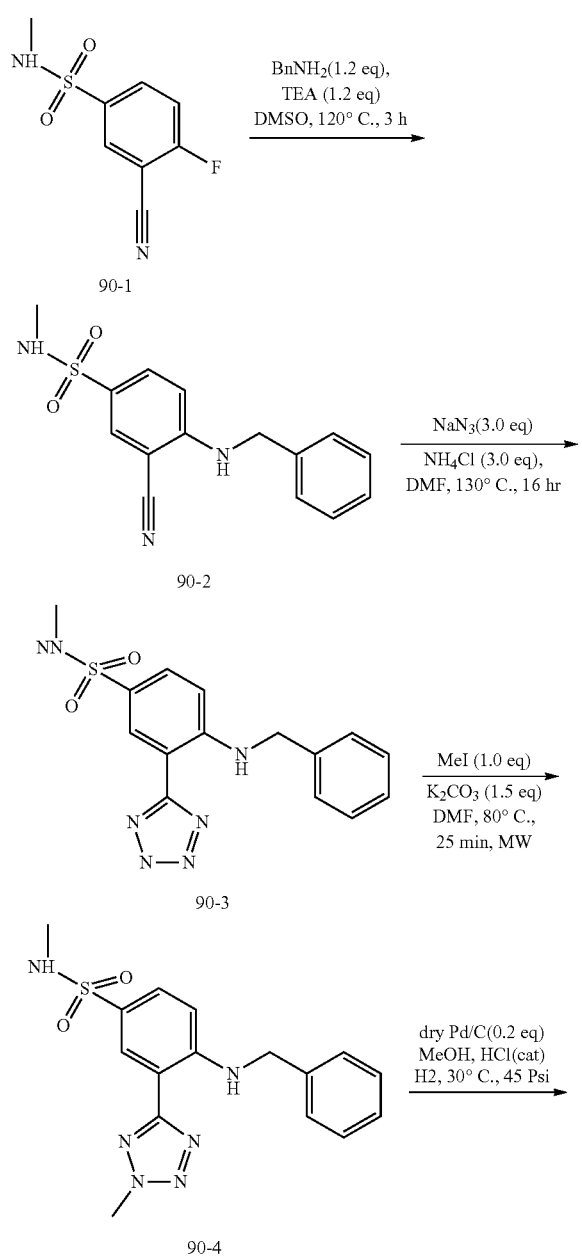

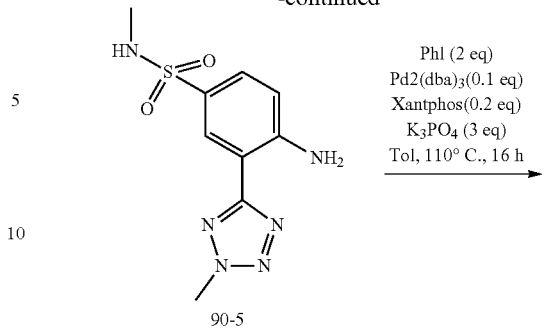

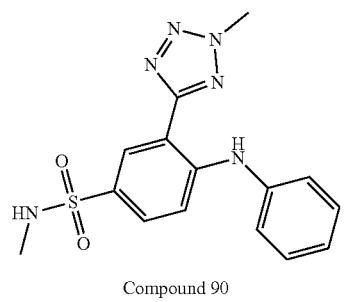

Compound 90

Step 1: 4-(benzylamino)-3-cyano-N-methylbenzenesulfonamide

To a solution of 3-cyano-4-fluoro-N-methyl-benzenesulfonamide 90-1 (1 g, 4.67 mmol, 1 eq) and BnNH$_2$ (600.2 mg, 5.6 mmol, 610.63 uL, 1.2 eq) in DMSO (5 mL) was added TEA (566.8 mg, 5.6 mmol, 779.71 uL, 1.2 eq) in one portion at 15° C. The mixture was stirred at 120° C. for 3 h. LCMS showed the reaction was complete and 93% of desired product was formed. The resulting yellow mixture was combined with other batches and diluted with water (15 mL) and EA (80 mL) and separated. The separated organic layer was washed with brine (10 mL*6), dried over anhydrous Na$_2$SO$_4$, filtered and concentrated under vacuum to give a white residue A. The residue A was triturated with a mixture solution of EA:PE=1:2 solvent (15 mL) and then filtered. The filter cake was washed with a mixture solution of EA:PE=1:2 solvent (25 mL) and dried to give compound 90-2 (1 g, 3.32 mmol, 71.12% yield). The filtrate was concentrated to give a residue B. The residue B was purified by flash silica gel chromatography to give compound 90-2 (0.3 g, 0.99 mmol, 21.32% yield). $^1$H NMR (400 MHz, DMSO-d$_6$) δ 7.81 (d, J=2.5 Hz, 1H), 7.71 (t, J=6.0 Hz, 1H), 7.62 (dd, J=2.0, 9.0 Hz, 1H), 7.39-7.31 (m, 4H), 7.29-7.18 (m, 2H), 6.78 (d, J=9.0 Hz, 1H), 4.51 (d, J=6.0 Hz, 2H), 2.37-2.33 (m, 3H).

Step 2: 4-(benzylamino)-N-methyl-3-(2H-tetrazol-5-yl)benzenesulfonamide

To a mixture of compound 90-2 (1 g, 3.32 mmol, 1 eq) and NaN3 (647.2 mg, 9.95 mmol, 3 eq) in DMF (15 mL) was added NH$_4$Cl (532.5 mg, 9.95 mmol, 0.35 mL, 3 eq) in one portion at 15° C. under N$_2$. The mixture was heated to 130° C. for 16 h. LCMS showed the reaction was complete and 90% of desired product was formed. The mixture was diluted with water (20 mL). The resulting solution was added into a 0.5 M HCl solution (50 mL), along with lots of solid formed. Then the mixture was filtered. The filter cake was washed with water (25 mL) and dried to give compound 90-3 (1.2 g, crude).

Step 3: 4-(benzylamino)-N-methyl-3-(2-methyl-2H-tetrazol-5-yl)benzenesulfonamide To a mixture of compound 90-3 (0.66 g, 1.92 mmol, 1 eq) and K2CO3 (397.3 mg, 2.87 mmol, 1.5 eq) in DMF (12 mL) was added MeI (272 mg, 1.92 mmol, 0.12 mL, 1 eq) in one portion at 15° C. under $N_2$. The mixture was heated at 80° C. under microwave for 25 min. LCMS showed the reaction was complete and 71% of desired product was formed. The mixture was combined with another batch and diluted with water (15 mL) and EA (100 mL) and separated, along with some solid formed. Then the mixture was filtered. The filter cake was washed with water (15 mL) and dried under vacuum to give compound 90-4 (0.29 g, 0.81 mmol, 42.22% yield). The filtrate was washed with brine (15 mL*3), dried over anhydrous $Na_2SO_4$, filtered and concentrated under vacuum to give compound 90-4 (0.9 g, crude), which was used for next step without further purification. $^1$H NMR (400 MHz, DMSO-$d_6$) δ 8.40 (d, J=2.5 Hz, 1H), 8.08 (t, J=5.8 Hz, 1H), 7.64-7.58 (m, 1H), 7.42-7.33 (m, 4H), 7.31-7.20 (m, 2H), 6.93 (d, J=9.0 Hz, 1H), 4.66 (d, J=6.0 Hz, 2H), 4.49 (s, 3H), 2.37 (d, J=5.0 Hz, 3H).

Step 4: 4-amino-N-methyl-3-(2-methyl-2H-tetrazol-5-yl)benzenesulfonamide

To a solution of compound 90-4 (0.9 g, 2.51 mmol, 1 eq) in MeOH (20 mL) were added dry Pd/C (0.45 g, 0.42 mmol, 10% purity, 0.5 eq) and HCl (12 M, 0.21 mL, 1 eq) at 15° C. The resulting dark mixture was degassed and refilled with $H_2$ for three times and then stirred at 30° C. for 16 h under 45 Psi $H_2$. TLC showed the mixture was complete and new spots were formed. The dark mixture was filtered via a pad of Celite. The filter cake was washed with methanol (10 mL). The filtrate was concentrated to give compound 90-5 (0.55 g, 1.80 mmol, 71.87% yield, HCl), which was used for next step without further purification. H NMR (400 MHz, DMSO-$d_6$) δ 8.34 (d, J=2.0 Hz, 1H), 7.58-7.53 (m, 1H), 7.24-7.17 (m, 1H), 7.00 (d, J=9.0 Hz, 1H), 4.47 (s, 3H), 2.38 (d, J=4.0 Hz, 3H).

Step 5: N-methyl-3-(2-methyl-2H-tetrazol-5-yl)-4-(phenylamino)benzenesulfonamide To a solution of compound 90-5 (20 mg, 74.5 umol, 1 eq), iodobenzene (30.4 mg, 0.15 mmol, 16 uL, 2 eq) and $K_3PO_4$ (47.5 mg, 0.22 mmol, 3 eq) in toluene (1 mL) were added $Pd_2(dba)_3$ (6.8 mg, 7.4 umol, 0.1 eq) and Xantphos (8.6 mg, 14.9 umol, 0.2 eq) at 15° C. under nitrogen. The resulting mixture was degassed and refilled with nitrogen for three times and then stirred at 110° C. for 16 h under $N_2$. LCMS showed the reaction was complete and 38% of desired product was formed. TLC showed the reaction was complete and new spots were formed. The mixture was combined with another batch and filtered via a pad of Celite. The filter cake was washed with EA (30 mL). The filtrate was concentrated to give a residue. The residue was purified by prep-TLC and then purified by prep-HPLC to give Compound 90 (5.46 mg, 15.9 umol, 21.27% yield). LCMS (ESI): RT=1.465 min, mass calc. for $C_{15}H_{16}N_6O_2S$ 344.11, m/z found 345.0 [M+1]$^+$. $^1$H NMR (400 MHz, DMSO-$d_6$) δ 9.14 (s, 1H), 8.45 (d, J=2.5 Hz, 1H), 7.69 (dd, J=2.0, 9.0 Hz, 1H), 7.50-7.40 (m, 2H), 7.40-7.31 (m, 4H), 7.23-7.13 (m, 1H), 4.51 (s, 3H), 2.42 (d, J=4.5 Hz, 3H).

Example 87: 4-(cyclohexylamino)-N-methyl-3-(3-methyl-1,2,4-oxadiazol-5-yl)benzenesulfonamide (Compound 91)

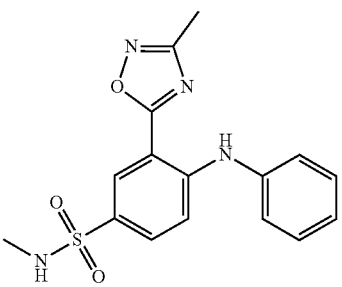 [SMILES: CNS(=O)(=O)c1ccc(Nc2ccccc2)c(-c2nc(C)no2)c1]

Preparation of Compound 91:

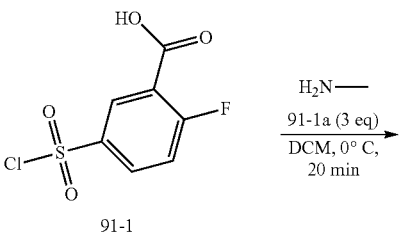

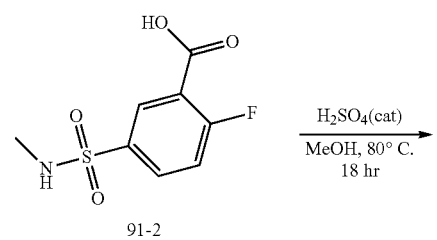

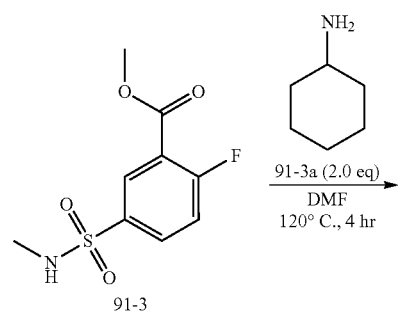

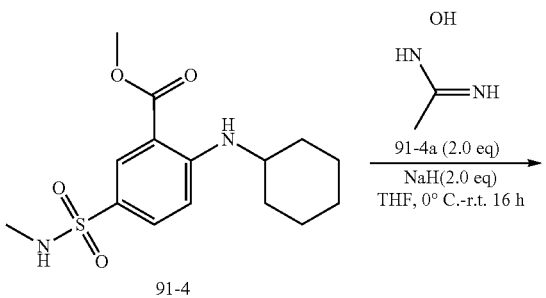

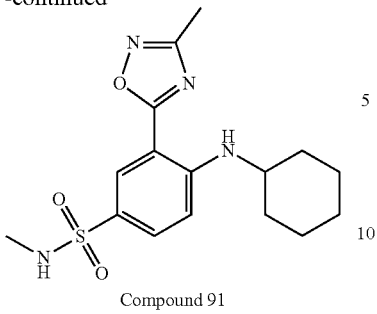

Compound 91

Step 1: 2-fluoro-5-(methylsulfamoyl)benzoic acid

To a solution of 91-1 (1 g, 4.2 mmol, 1 eq) in DCM (10 mL) was added 91-1a (2 M, 6.3 mL, 3 eq) at 0° C. under $N_2$ atmosphere. The mixture was stirred at this temperature for 20 min. LCMS showed reactant 1 was consumed completely and one main peak with MS of 247 was detected (the sample was dissolved in MeOH). The reaction was quenched by adding HCl (5 mL, 2M) and separated. The organic layer was washed with brine (10 mL), dried over $Na_2SO_4$ and filtered. The filtrate was concentrated to give a residue 91-2 (910 mg, crude). The crude product was used in next step directly without further purification. $^1$H NMR (400 MHz, DMSO-$d_6$) δ 8.26 (dd, J=2.3, 6.8 Hz, 1H), 8.02 (ddd, J=2.5, 4.4, 8.7 Hz, 1H), 7.66 (q, J=4.8 Hz, 1H), 7.58 (dd, J=8.8, 10.5 Hz, 1H), 2.43 (d, J=4.8 Hz, 3H).

Step 2: methyl 2-fluoro-5-(methylsulfamoyl)benzoate

To a solution of 91-2 (910 mg, 3.90 mmol, 1 eq) in MeOH (10 mL) was added $H_2SO_4$ (38.27 mg, 0.39 mmol, 20.8 uL, 0.1 eq). The mixture was stirred at 80° C. for 4 hr. TLC showed reactant was consumed completely and one new spot was formed. The reaction mixture was concentrated and the residue was poured into water (20 mL). The aqueous layer was extracted with EtOAc (5 mL*3), the combined organic layer was washed with brine (10 mL), dried over $Na_2SO_4$ and filtered. The filtrate was concentrated to give crude product 91-3 (900 mg, 3.64 mmol, 93.3% yield). The crude product was used in next step directly without further purification. $^1$H NMR (400 MHz, DMSO-$d_6$) δ 8.27 (dd, J=2.4, 6.7 Hz, 1H), 8.05 (ddd, J=2.5, 4.3, 8.8 Hz, 1H), 7.70 (br d, J=4.8 Hz, 1H), 7.63 (dd, J=8.8, 10.5 Hz, 1H), 3.91 (s, 3H), 2.43 (d, J=5.0 Hz, 3H).

Step 3: methyl 2-(cyclohexylamino)-5-(methylsulfamoyl)benzoate

To a solution of methyl 91-3 (900 mg, 3.64 mmol, 1 eq) in DMSO (4 mL) was added 91-3a (722.0 mg, 7.3 mmol, 833.3 uL, 2.0 eq). The mixture was stirred at 130° C. for 4 h. TLC showed reactant was consumed completely and one new spot was formed. LCMS showed 50% desired MS. The reaction mixture was poured into water (20 mL) and extracted with EtOAc (10 mL*3). The combined organic layer was washed with brine (10 mL), dried over $Na_2SO_4$ and filtered. The filtrate was concentrated to give a residue. The residue was purified by flash silica gel chromatography to give compound 91-4 (750 mg, 2.16 mmol, 59.3% yield). LCMS (ESI): RT=0.824 min, mass calc. for $C_{15}H_{22}N_2O_4S$ 326.13, m/z found 326.9[M+H]$^+$; $^1$H NMR (400 MHz, DMSO-$d_6$) δ 8.23-8.18 (m, 2H), 7.67 (dd, J=2.3, 9.0 Hz, 1H), 7.21 (q, J=5.2 Hz, 1H), 7.00 (d, J=9.3 Hz, 1H), 3.84 (s, 3H), 3.64-3.52 (m, 1H), 2.35 (d, J=5.3 Hz, 3H), 1.94 (br dd, J=3.5, 8.8 Hz, 2H), 1.68 (br dd, J=4.3, 9.0 Hz, 2H), 1.58 (br dd, J=4.0, 8.5 Hz, 1H), 1.49-1.36 (m, 2H), 1.36-1.21 (m, 3H).

Step 4: 4-(cyclohexylamino)-N-methyl-3-(3-methyl-1,2,4-oxadiazol-5-yl)benzenesulfonamide To a solution of 91-4 (100 mg, 0.31 mmol, 1 eq) in THF (5 mL) was added NaH (24.5 mg, 0.61 mmol, 60% purity, 2.0 eq) at 0° C., the mixture was stirred for 30 min at this temperature. Then, 91-4a (45.4 mg, 0.61 mmol, 2.0 eq) was added and the mixture was allowed warmed to 10-15° C. and stirred for 16 hr. LCMS showed 39% of Reactant 91-4 was remained. Several new peaks were shown on LCMS and 37% of desired compound was detected. The reaction was poured into sat. aq. $NH_4Cl$ (10 mL) and extracted with EtOAc (5 mL*3). The combined organic layer was washed with brine (10 mL), dried over $Na_2SO_4$ and filtered to give a residue. The residue was purified by prep-HPLC to give Compound 91 (19.10 mg, 45.91 umol, 15% yield, HCl). LCMS (ESI): RT=1.234 min, mass calc. for $C_{16}H_{22}N_4O_3S$ 350.14, m/z found 351.0 [M+H]$^+$; $^1$H NMR (400 MHz, DMSO-$d_6$) δ 8.23 (d, J=2.3 Hz, 1H), 8.19 (d, J=7.5 Hz, 1H), 7.73 (dd, J=2.3, 9.0 Hz, 1H), 7.30 (d, J=5.3 Hz, 1H), 7.12 (d, J=9.3 Hz, 1H), 3.85 (s, 1H), 3.73-3.62 (m, 1H), 2.46 (s, 3H), 2.39 (d, J=5.3 Hz, 3H), 1.99 (d, J=9.5 Hz, 2H), 1.70 (s, 2H), 1.61-1.58 (m, 1H), 1.49-1.30 (m, 5H).

Example 88: N-methyl-3-(2-methyl-2H-tetrazol-5-yl)-4-((3-(trifluoromethyl)phenyl)amino)benzenesulfonamide (Compound 92)

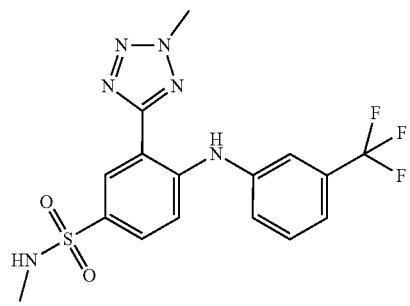 [SMILES: CNS(=O)(=O)c1ccc(Nc2cccc(C(F)(F)F)c2)c(-c2nnn(C)n2)c1]

Preparation of Compound 92:

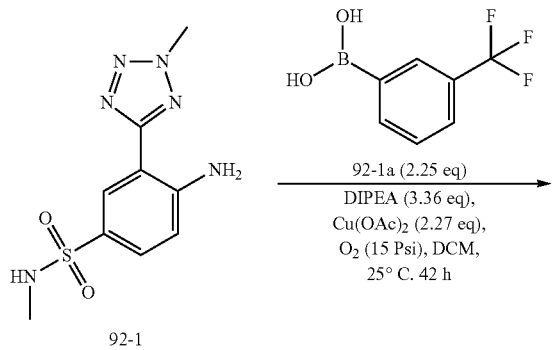

92-1a (2.25 eq)
DIPEA (3.36 eq),
Cu(OAc)$_2$ (2.27 eq),
$O_2$ (15 Psi), DCM,
25° C. 42 h 92-1

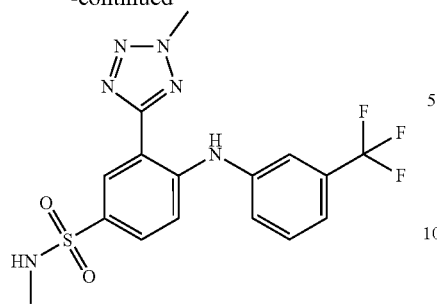

Compound 92

To a suspension of the compound 92-1 (40 mg, 0.131 mmol, 1 eq, HCl), DIPEA (57 mg, 0.441 mmol, 3.36 eq) and the compound 92-1a (56 mg, 0.295 mmol, 2.25 eq) in DCM (1 mL) was added Cu(OAc)$_2$ (54 mg, 0.297 mmol, 2.27 eq) in one portion under O$_2$ (15 Psi). The reaction mixture was stirred at 25° C. for 42 h. LCMS showed 26% of the starting material was remained and 32% of desired product was formed. The reaction mixture was filtered and concentrated in vacuum. LCMS showed 30% of desired product was detected. HPLC indicated 39% of desired product was formed. The residue was purified by prep-HPLC. LCMS and $^1$H NMR and HMBC confirmed that the product was Compound 92 (9.64 mg, 22.9 umol, 17.5% yield). LCMS (ESI): RT=0.808 min, mass calcd. For C$_{16}$H$_{15}$F$_3$N$_6$O$_2$S, 412.09 m/z found 413.0[M+H]$^+$. $^1$H NMR (400 MHz, CDCl$_3$) δ 9.55 (s, 1H), 8.71 (d, J=2.40 Hz, 1H), 7.76 (dd, J=2.40, 9.20 Hz, 1H), 7.58-7.49 (m, 3H), 7.46-7.41 (m, 1H), 7.35 (d, J=8.40 Hz, 1H), 4.48 (s, 3H), 4.43-4.35 (m, 1H), 2.72 (d, J=5.60 Hz, 3H).

Example 89: N-methyl-3-(2-methyl-2H-tetrazol-5-yl)-4-((2-(trifluoromethyl)phenyl)amino)benzenesulfonamide (Compound 93)

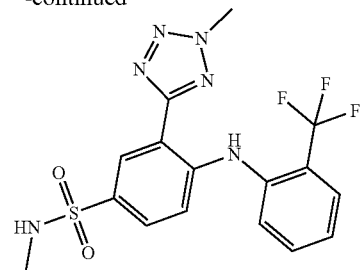

Compound 93

To a suspension of the compound 93-1 (40 mg, 0.13 mmol, 1 eq, HCl), DIPEA (57 mg, 0.441 mmol, 3.36 eq) and the compound 93-1a (56 mg, 0.295 mmol, 2.25 eq) in DCM (1 mL) was added Cu(OAc)$_2$ (54 mg, 0.297 mmol, 2.27 eq) in one portion under O$_2$ (15 Psi). The reaction mixture was stirred at 25° C. for 42 h. LCMS showed 47% of the starting material was remained and 23% of desired product was formed. The reaction mixture was filtered and concentrated in vacuum. LCMS showed 18% of desired product was detected. HPLC indicated 26% of desired product was formed. The residue was purified by prep-HPLC. LCMS and $^1$H NMR confirmed the product was Compound 93 (6.06 mg, 14.7 umol, 11.2% yield). LCMS (ESI): RT=0.789 min, mass calcd. For C$_{16}$H$_{15}$F$_3$N$_6$O$_2$S, 412.09 m/z found 413.0 [M+H]$^+$. $^1$H NMR (400 MHz, CDCl$_3$) δ 9.54 (s, 1H), 8.76 (d, J=2.00 Hz, 1H), 7.76 (d, J=8.00 Hz, 1H), 7.72 (dd, J=2.30, 8.80 Hz, 1H), 7.62-7.54 (m, 2H), 7.35-7.28 (m, 1H), 7.21 (d, J=8.80 Hz, 1H), 4.46 (s, 3H), 4.39 (br d, J=5.50 Hz, 1H), 2.71 (d, J=5.50 Hz, 3H).

Example 90: N-methyl-3-(2-methyl-2H-tetrazol-5-yl)-4-((3-(trifluoromethoxy)phenyl)amino)benzenesulfonamide (Compound 94)

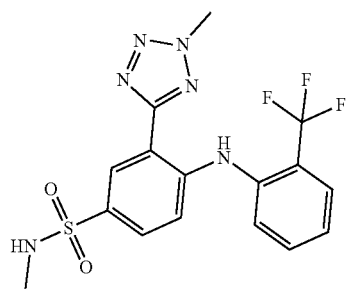 [SMILES: CNS(=O)(=O)c1ccc(Nc2ccccc2C(F)(F)F)c(-c2nnn(C)n2)c1]

Preparation of Compound 93:

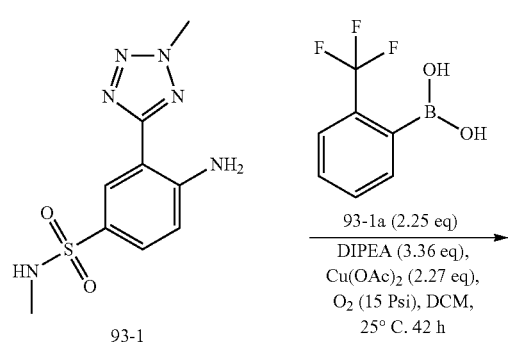

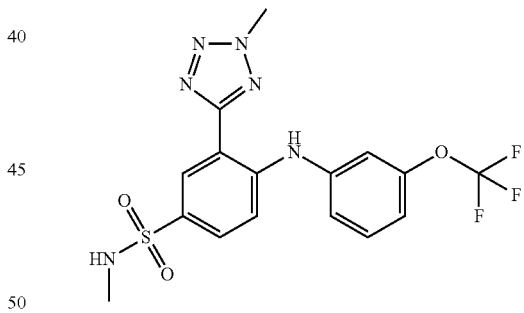

Preparation of Compound 94:

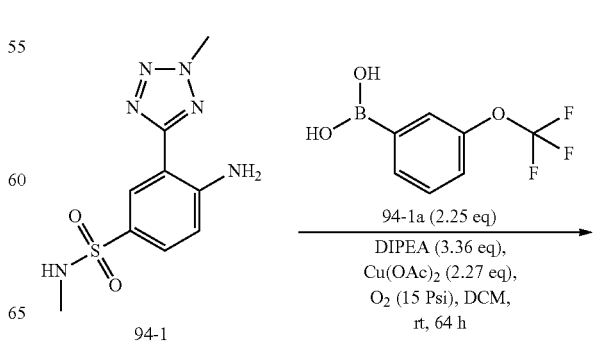

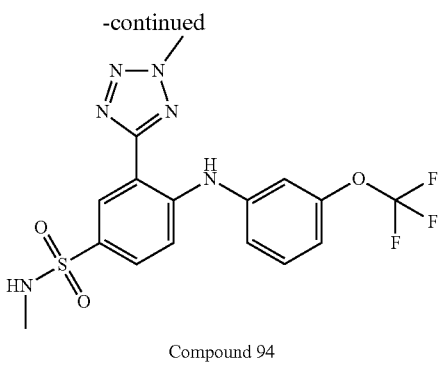

Compound 94

To a suspension of the compound 94-1 (40 mg, 0.131 mmol, 1 eq, HCl), DIPEA (57 mg, 0.441 mmol, 3.36 eq) and the compound 94-1a (61 mg, 0.296 mmol, 2.26 eq) in DCM (1.5 mL) was added Cu(OAc)$_2$ (54 mg, 0.297 mmol, 2.27 eq) in one portion under O2 (15 Psi). The mixture was stirred at 12° C. for 64 h. LCMS showed 36% of the starting material was remained and 23% of desired product was formed. The reaction mixture was filtered and concentrated in vacuum. LCMS showed 17% of desired product was detected. HPLC indicated 18% of desired product was formed. The residue was purified by prep-HPLC. LCMS and $^1$H NMR confirmed that the product was Compound 94 (5.35 mg, 12.5 umol, 9.5% yield). LCMS (ESI): RT=0.815 min, mass calcd. For C$_{16}$H$_{15}$F$_3$N$_6$O$_3$S, 428.09 m/z found 429.0[M+H]$^+$. H NMR (400 MHz, CDCl$_3$) δ 9.52 (s, 1H), 8.71 (d, J=2.2 Hz, 1H), 7.75 (dd, J=2.20, 9.00 Hz, 1H), 7.47-7.35 (m, 2H), 7.24 (s, 1H), 7.19 (s, 1H), 7.07-7.00 (m, 1H), 4.48 (s, 3H), 4.31 (br d, J=5.30 Hz, 1H), 2.72 (d, J=5.50 Hz, 3H).

Example 91: N-methyl-3-(2-methyl-2H-tetrazol-5-yl)-4-((4-(trifluoromethyl)phenyl)amino)benzenesulfonamide (Compound 95)

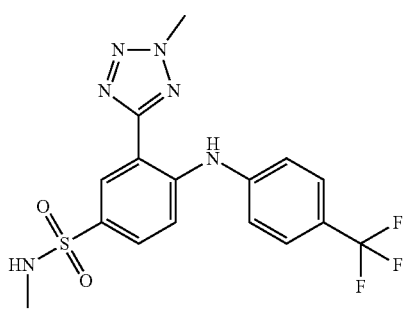 [SMILES: CNS(=O)(=O)c1ccc(Nc2ccc(C(F)(F)F)cc2)c(-c2nnn(C)n2)c1]

Preparation of Compound 95:

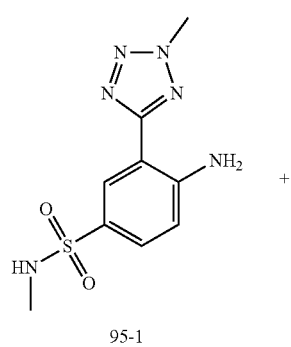

95-1

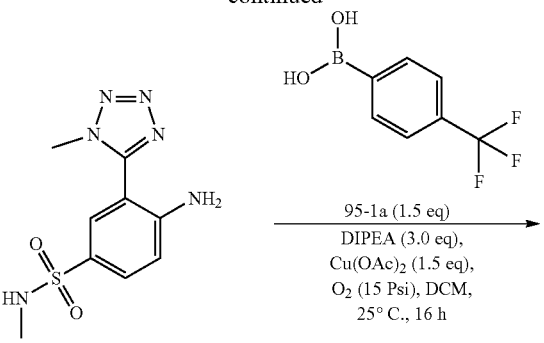

95-2

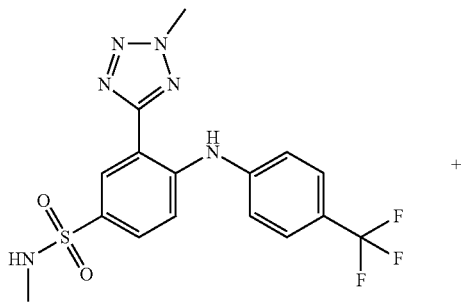

Compound 95

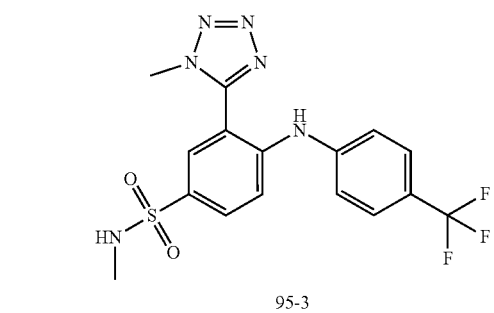

95-3

To a mixture of compound 95-1 and compound 95-2 (350 mg, 1.30 mmol, 1 eq), compound 95-1a (370.4 mg, 1.95 mmol, 1.5 eq) in DCM (10 mL) was added Cu(OAc)$_2$ (354.2 mg, 1.95 mmol, 1.5 eq) followed by DIEA (504 mg, 3.90 mmol, 0.68 mL, 3 eq) under N$_2$. The suspension was degassed under vacuum and purged with O2 several times. The mixture was stirred under O$_2$ (15 psi) at 25° C. for 16 hours. LCMS showed that desired product was detected. The reaction was filtered and concentrated. The crude product was purified by prep-HPLC to give Compound 95 (38.35 mg, 92.99 umol, 7.15% yield). $^1$HNMR and LCMS confirmed that desired product was obtained. LCMS (ESI): RT=0.784 min, mass calcd. For C$_{16}$H$_{15}$F$_3$N$_6$O$_2$S, 412.09 m/z found 412.9[M+H]$^+$. $^1$H NMR (400 MHz, CDCl$_3$) δ 9.62 (s, 1H), 8.71 (d, J=2.0 Hz, 1H), 7.77 (dd, J=8.80, 2.40 Hz, 1H), 7.65 (d, J=8.80 Hz, 2H), 7.48 (d, J=8.40 Hz, 1H), 7.40 (d, J=8.40 Hz, 2H), 4.48 (s, 3H), 4.33 (q, J=5.60 Hz, 1H), 2.71 (d, J=5.60 Hz, 3H).

Example 92: N-methyl-3-(1-methyl-1H-tetrazol-5-yl)-4-((4-(trifluoromethyl)phenyl)amino)benzenesulfonamide (Compound 96)

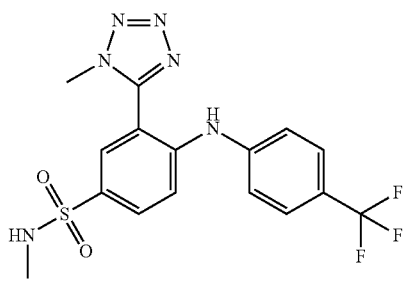 [SMILES: CNS(=O)(=O)c1ccc(Nc2ccc(C(F)(F)F)cc2)c(-c2nnnn2C)c1]

Preparation of Compound 96:

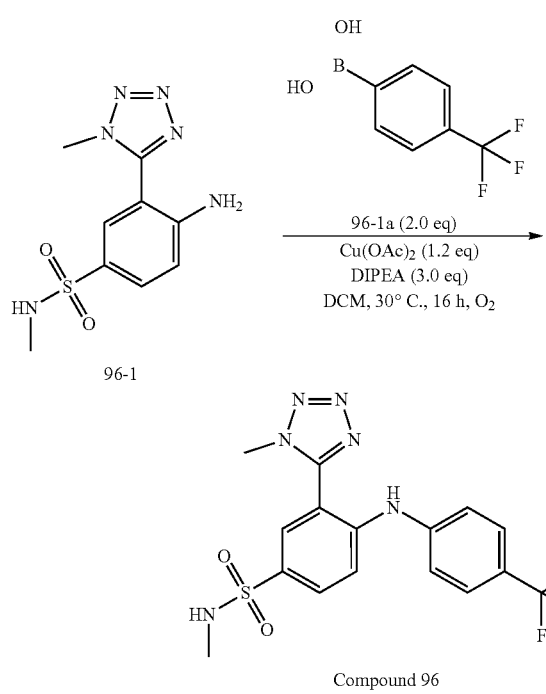

Compound 96

A solution of compound 96-1 (100 mg, 0.328 mmol, 1.0 eq, HCl), compound 96-1a (125 mg, 0.656 mmol, 2.0 eq), Cu(OAc)$_2$ (72 mg, 0.39 mmol, 1.2 eq) and DIPEA (127 mg, 0.984 mmol, 3.0 eq) in DCM (4 mL) was stirred at 30° C. for 16 hours under O$_2$. The mixture was diluted with water (20 mL) and the resultant mixture was extracted with DCM (50 mL*3). The combined organic layers were dried over Na$_2$SO$_4$, filtered and concentrated to dryness under reduced pressure. The residue was purified by column chromatography over silica gel to afford the residue. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. Compound 96 (14.04 mg, 10% yield) was obtained. LCMS (ESI): RT=0.784 min, mass calcd. for C$_{16}$H$_{15}$F$_3$N$_6$O$_2$S 412.09, m/z found 413.0 [M+H]$^+$, $^1$HNMR (400 MHz, CDCl$_3$) δ 9.24 (s, 1H), 8.02 (d, J=2.3 Hz, 1H), 7.82 (dd, J=2.0, 8.8 Hz, 1H), 7.64 (d, J=8.5 Hz, 2H), 7.55 (d, J=9.0 Hz, 1H), 7.34 (d, J=8.3 Hz, 2H), 4.41-4.34 (m, 1H), 4.32 (s, 3H), 2.70 (d, J=5.3 Hz, 3H).

Example 93: N-methyl-3-(1-methyl-1H-tetrazol-5-yl)-4-((3-(trifluoromethyl)phenyl)amino)benzenesulfonamide (Compound 97)

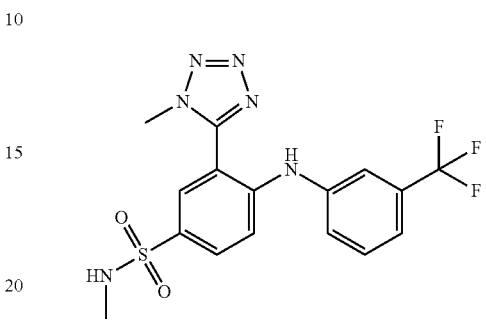

Preparation of Compound 97:

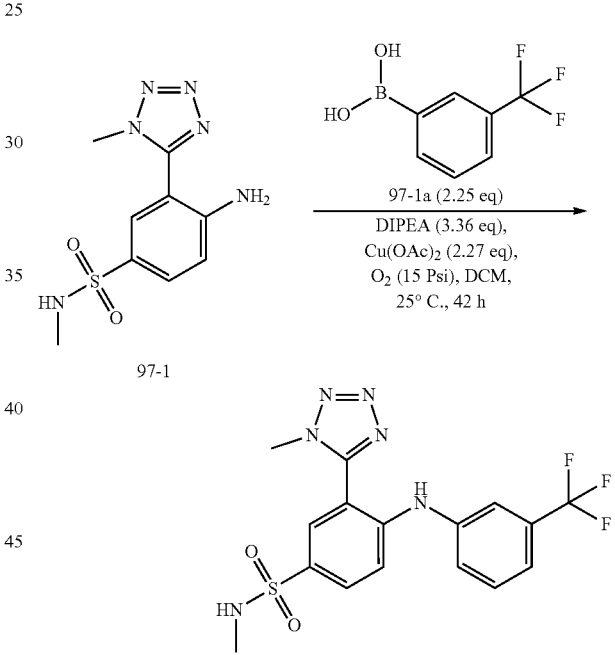

Compound 97

To a suspension of compound 97-1 (40 mg, 0.131 mmol, 1 eq, HCl), DIPEA (57 mg, 0.441 mmol, 3.36 eq) and compound 97-1a (56 mg, 0.295 mmol, 2.25 eq) in DCM (1 mL) was added Cu(OAc)$_2$ (54 mg, 0.297 mmol, 2.27 eq) in one portion under O$_2$ (15 Psi). The reaction mixture was stirred at 25° C. for 42 h. LCMS showed 26% of the starting material was remained and 32% of desired product was formed. The reaction mixture was filtered and concentrated in vacuum. LCMS showed 30% of desired product was detected. HPLC indicated 39% of desired product was formed. The residue was purified by prep-HPLC to give Compound 97 (2.80 mg, 6.7 umol, 5.1% yield). LCMS (ESI): RT=0.748 min, mass calcd. For C$_{16}$H$_{15}$F$_3$N$_6$O$_2$S, 412.09 m/z found 412.9[M+H]$^+$. $^1$H NMR (400 MHz, CDCl$_3$) δ 9.21 (s, 1H), 8.03 (d, J=2.00 Hz, 1H), 7.82 (dd, J=2.00, 8.80 Hz, 1H), 7.57-7.50 (m, 2H), 7.47-7.40 (m, 3H), 4.43-4.35 (br d, J=5.3 Hz, 1H), 4.33 (s, 3H), 2.70 (d, J=5.60 Hz, 3H).

Example 94: N-methyl-3-(1-methyl-1H-tetrazol-5-yl)-4-((2-(trifluoromethyl)phenyl)amino)benzene-sulfonamide (Compound 98)

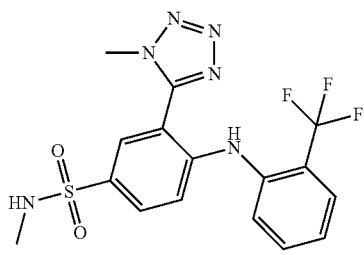 [SMILES: CNS(=O)(=O)c1ccc(Nc2ccccc2C(F)(F)F)c(-c2nnnn2C)c1]

Preparation of Compound 98:

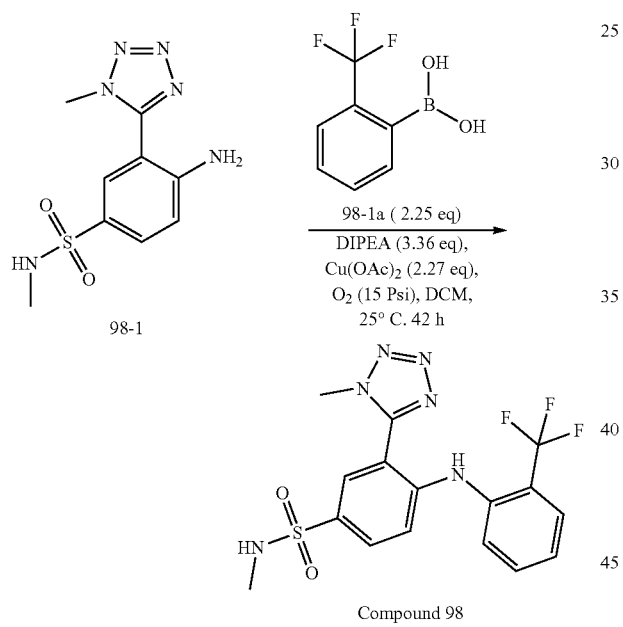

Compound 98

To a suspension of compound 98-1 (40 mg, 0.131 mmol, 1 eq, HCl), DIPEA (57 mg, 0.441 mmol, 3.36 eq) and compound 98-1a (56 mg, 0.295 mmol, 2.25 eq) in DCM (1 mL) was added Cu(OAc)$_2$ (54 mg, 0.297 mmol, 2.27 eq) in one portion under O$_2$ (15 Psi). The reaction mixture was stirred at 25° C. for 42 h. LCMS showed 47% of the starting material was remained and 23% of desired product was formed. The reaction mixture was filtered and concentrated in vacuum. LCMS showed 18% of desired product was detected. HPLC indicated 26% of desired product was formed. The residue was purified by prep-HPLC to give Compound 98 (2.22 mg, 5.4 umol, 4.1% yield). LCMS (ESI): RT=0.749 min, mass calcd. For C$_{16}$H$_{15}$F$_3$N$_6$O$_2$S, 412.09 m/z found 413.1 [M+H]$^+$. $^1$H NMR (400 MHz, CDCl$_3$) δ 9.22 (s, 1H), 8.04 (d, J=2.00 Hz, 1H), 7.79-7.73 (m, 2H), 7.63-7.56 (m, 1H), 7.45 (d, J=8.00 Hz, 1H), 7.35 (t, J=7.50 Hz, 1H), 7.17 (d, J=9.00 Hz, 1H), 4.38-4.32 (m, 4H), 2.70 (d, J=5.50 Hz, 3H).

Example 95: N-methyl-3-(1-methyl-1H-tetrazol-5-yl)-4-((4-(trifluoromethoxy)phenyl)amino)benzene-sulfonamide (Compound 99)

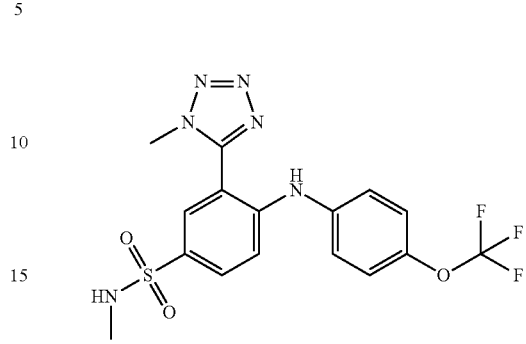

Preparation of Compound 99:

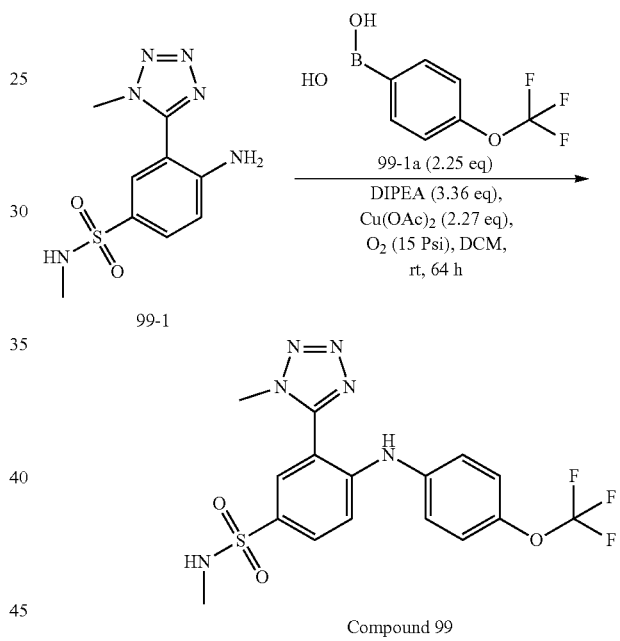

Compound 99

To a suspension of compound 99-1 (40 mg, 0.131 mmol, 1 eq, HCl), DIPEA (57 mg, 0.441 mmol, 3.36 eq) and compound 99-1a (61 mg, 0.296 mmol, 2.26 eq) in DCM (1.5 mL) was added Cu(OAc)$_2$ (54 mg, 0.297 mmol, 2.27 eq) in one portion under O$_2$ (15 Psi). The mixture was stirred at 12° C. for 64 h. LCMS showed 46% of the starting material was remained and 15% of desired product was formed. The reaction mixture was filtered and concentrated in vacuum. LCMS showed 11% of desired product was detected. HPLC indicated 9% of desired product was formed. The residue was purified by prep-HPLC to give Compound 99 (2.89 mg, 6.3 umol, 4.8% yield). LCMS (ESI): RT=0.769 min, mass calcd. For C$_{16}$H$_{15}$F$_3$N$_6$O$_3$S, 428.09 m/z found 429.0[M+H]$^+$. H NMR (400 MHz, CDCl$_3$) δ 9.08 (s, 1H), 8.01 (d, J=2.00 Hz, 1H), 7.78 (dd, J=2.30, 9.00 Hz, 1H), 7.36 (d, J=9.00 Hz, 1H), 7.28 (s, 2H), 4.43 (d, J=5.00 Hz, 1H), 4.33 (s, 3H), 2.69 (d, J=5.30 Hz, 3H).

Example 96: N-methyl-3-(1-methyl-1H-tetrazol-5-yl)-4-((3-(trifluoromethoxy)phenyl)amino)benzenesulfonamide_(Compound 100)

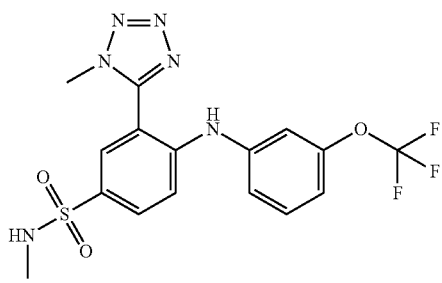 [SMILES: CNS(=O)(=O)c1ccc(Nc2cccc(OC(F)(F)F)c2)c(-c2nnnn2C)c1]

Preparation of Compound 100:

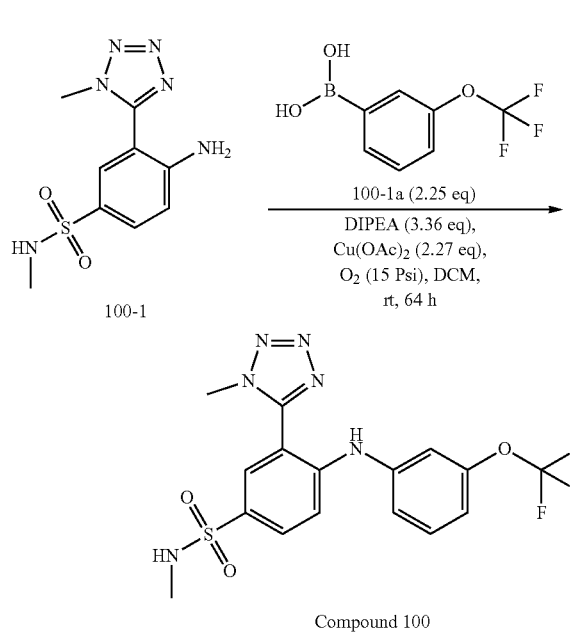

To a suspension of compound 100-1 (40 mg, 0.131 mmol, 1 eq, HCl), DIPEA (57 mg, 0.441 mmol, 3.36 eq) and compound 100-1a (61 mg, 0.296 mmol, 2.26 eq) in DCM (1.5 mL) was added Cu(OAc)$_2$ (54 mg, 0.297 mmol, 2.27 eq) in one portion under O2 (15 Psi). The mixture was stirred at 12° C. for 64 h. LCMS showed 36% of the starting material was remained and 23% of desired product was formed. The reaction mixture was filtered and concentrated in vacuum. LCMS showed 17% of desired product was detected. HPLC indicated 18% of desired product was formed. The residue was purified by prep-HPLC to provide Compound 100 (2.61 mg, 5.73 umol, 4.4% yield). LCMS (ESI): RT=0.764 min, mass calcd. For $C_{16}H_{15}F_3N_6O_3S$, 428.09 m/z found 429.0[M+H]$^+$. $^1$H NMR (400 MHz, CDCl$_3$) δ 9.15 (s, 1H), 8.02 (d, J=2.3 Hz, 1H), 7.81 (dd, J=2.10, 8.90 Hz, 1H), 7.49-7.39 (m, 2H), 7.22-7.16 (m, 1H), 7.13 (s, 1H), 7.05 (br d, J=8.30 Hz, 1H), 4.44-4.36 (m, 1H), 4.33 (s, 3H), 2.70 (d, J=5.30 Hz, 3H).

Example 97: N-methyl-3-(1-methyl-1H-tetrazol-5-yl)-4-((2-(trifluoromethoxy)phenyl)amino)benzenesulfonamide (Compound 101)

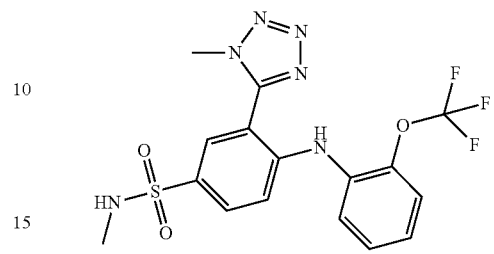

Preparation of Compound 101:

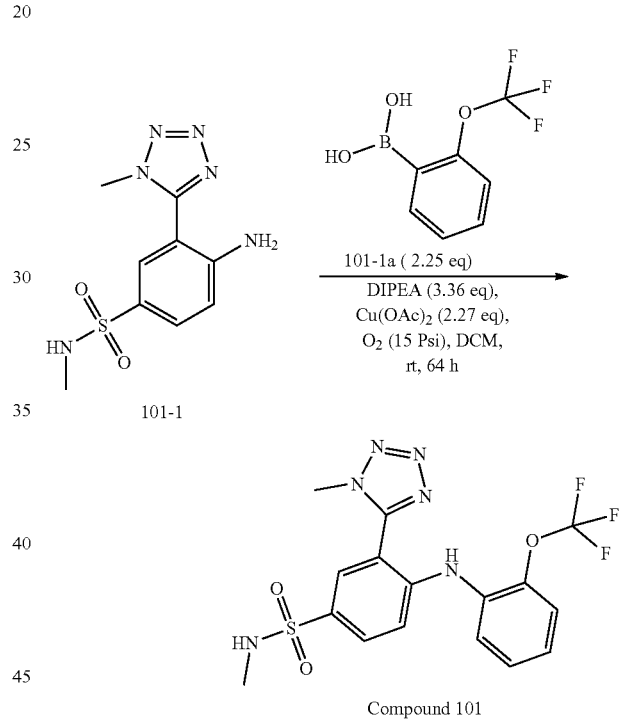

To a suspension of compound 101-1 (40 mg, 0.131 mmol, 1 eq, HCl), DIPEA (57 mg, 0.441 mmol, 3.36 eq) and compound 101-1a (61 mg, 0.296 mmol, 2.26 eq) in DCM (1.5 mL) was added Cu(OAc)$_2$ (54 mg, 0297 mmol, 2.27 eq) in one portion under O$_2$ (15 Psi). The reaction mixture was stirred at 12° C. for 64 h. LCMS showed 45% of the starting material was remained and 16% of desired product was formed. The reaction mixture was filtered and concentrated in vacuum. LCMS showed 12% of desired product was detected. HPLC indicated 14% of desired product was formed. The residue was purified by prep-HPLC to provide Compound 101 (2.86 mg, 6.3 umol, 4.8% yield). LCMS (ESI): RT=0.754 min, mass calcd. For $C_{16}H_{15}F_3N_6O_3S$, 428.09 m/z found 429.0[M+H]$^+$. $^1$H NMR (400 MHz, CDCl$_3$) δ 9.06 (s, 1H), 8.01 (d, J=2.30 Hz, 1H), 7.80 (dd, J=2.10, 8.90 Hz, 1H), 7.44 (dd, J=1.50, 8.00 Hz, 1H), 7.38 (br d, J=8.00 Hz, 1H), 7.36-7.28 (m, 2H), 7.26-7.21 (m, 1H), 4.46-4.39 (m, 1H), 4.31 (s, 3H), 2.69 (d, J=5.30 Hz, 3H).

Example 98: N-methyl-3-(2-methyl-2H-tetrazol-5-yl)-4-((2-(trifluoromethoxy)phenyl)amino)benzenesulfonamide (Compound 102)

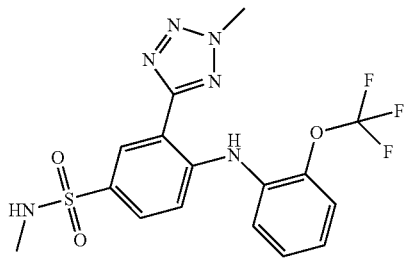 [SMILES: CNS(=O)(=O)c1ccc(Nc2ccccc2OC(F)(F)F)c(-c2nnn(C)n2)c1]

Preparation of Compound 102:

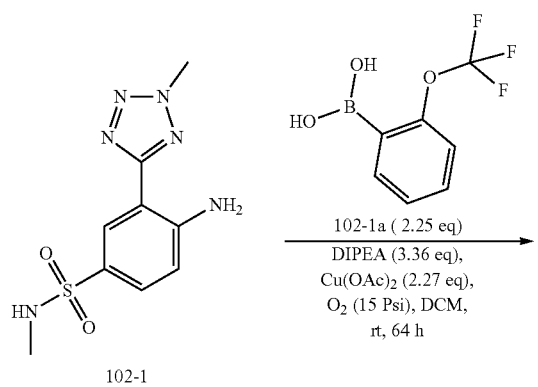

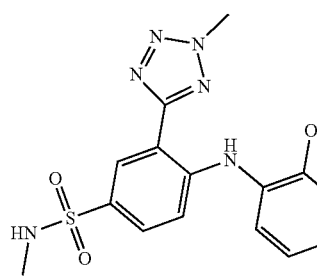

Compound 102

To a suspension of compound 102-1 (40 mg, 0.131 mmol, 1 eq, HCl), DIPEA (57 mg, 0.441 mmol, 3.36 eq) and compound 102-1a (61 mg, 0.296 mmol, 2.26 eq) in DCM (1.5 mL) was added Cu(OAc)$_2$ (54 mg, 0297 mmol, 2.27 eq) in one portion under O$_2$ (15 Psi). The reaction mixture was stirred at 12° C. for 64 h. LCMS showed 45% of the starting material was remained and 16% of desired product was formed. The reaction mixture was filtered and concentrated in vacuum. LCMS showed 12% of desired product was detected. HPLC indicated 14% of desired product was formed. The residue was purified by prep-HPLC to provide Compound 102 (4.84 mg, 11.3 umol, 8.6% yield). LCMS (ESI): RT=0.808 min, mass calcd. For C$_{16}$H$_{15}$F$_3$N$_6$O$_3$S, 428.09 m/z found 429.0[M+H]$^+$. $^1$H NMR (400 MHz, CDCl$_3$) δ 9.52 (s, 1H), 8.71 (d, J=2.30 Hz, 1H), 7.75 (dd, J=2.10, 8.90 Hz, 1H), 7.46-7.37 (m, 2H), 7.25 (br d, J=1.30 Hz, 1H), 7.19 (s, 1H), 7.04 (br d, J=8.30 Hz, 1H), 4.48 (s, 3H), 4.31 (br d, J=5.50 Hz, 1H), 2.72 (d, J=5.50 Hz, 3H).

Example 99: N-methyl-3-(2-methyl-2H-tetrazol-5-yl)-4-((4-(trifluoromethoxy)phenyl)amino)benzenesulfonamide (Compound 103)

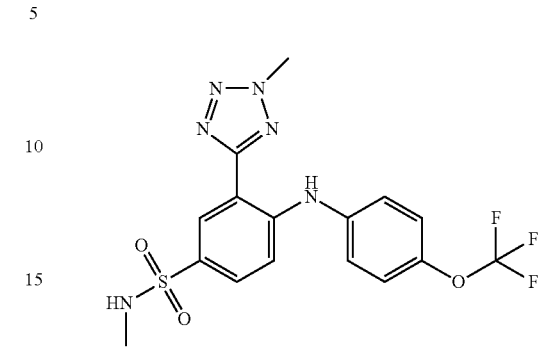

Preparation of Compound 103:

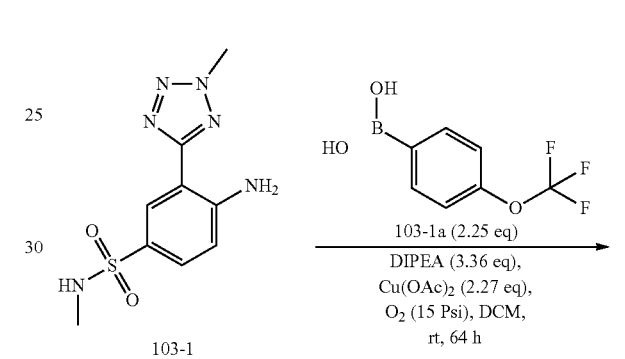

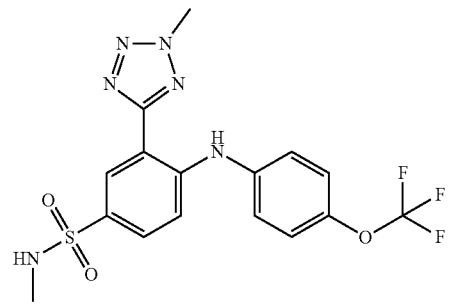

Compound 103

To a suspension of the compound 103-1 (40 mg, 0.131 mmol, 1 eq, HCl), DIPEA (57 mg, 0.441 mmol, 3.36 eq) and the compound 103-1a (61 mg, 0.296 mmol, 2.26 eq) in DCM (1.5 mL) was added Cu(OAc)$_2$ (54 mg, 0.297 mmol, 2.27 eq) in one portion under O$_2$ (15 Psi). The mixture was stirred at 12° C. for 64 h. LCMS showed 46% of the starting material was remained and 15% of desired product was formed. The reaction mixture was filtered and concentrated in vacuum. LCMS showed 11% of desired product was detected. HPLC indicated 9% of desired product was formed. The residue was purified by prep-HPLC to provide Compound 103 (3.65 mg, 8.5 umol, 6.5% yield). LCMS (ESI): RT=0.824 min, mass calcd. For C$_{16}$H$_{15}$F$_3$N$_6$O$_3$S, 428.09 m/z found 429.0[M+H]$^+$. $^1$H NMR (400 MHz, CDCl$_3$) δ 9.45 (s, 1H), 8.70 (d, J=2.30 Hz, 1H), 7.73 (dd, J=2.30, 8.80 Hz, 1H), 7.37-7.33 (m, 2H), 7.29 (d, J=3.80 Hz, 3H), 4.48 (s, 3H), 4.29 (br d, J=5.50 Hz, 1H), 2.71 (d, J=5.50 Hz, 3H).

Example 100: 4-((2,3-difluorophenyl)amino)-N-methyl-3-(2-methyl-2H-tetrazol-5-yl)benzenesulfonamide (Compound 104) and 4-((2,3-difluorophenyl)amino)-N-methyl-3-(1-methyl-1H-tetrazol-5-yl)benzenesulfonamide (Compound 106)

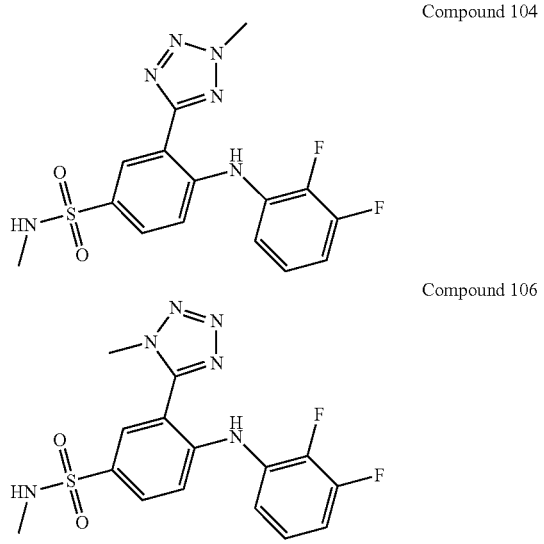

Compound 104

Compound 106

Preparation of Compound 104 and Compound 106:

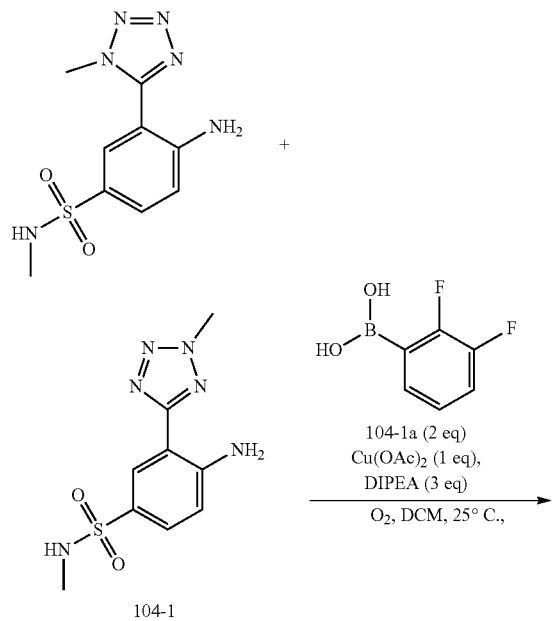

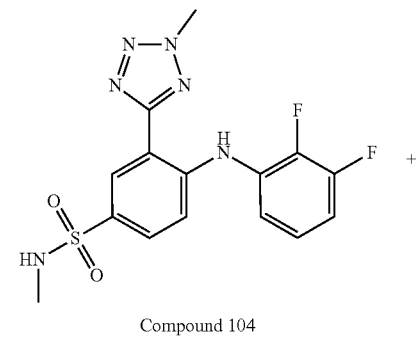

Compound 104

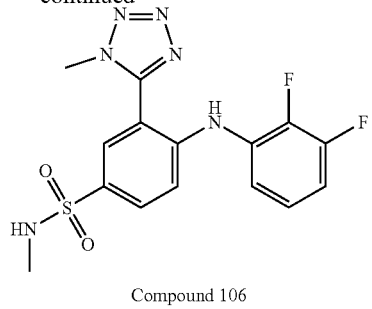

Compound 106

To a mixture of compound 104-1 (0.1 g, 0.22 mmol, 1.0 eq, HCl) and compound 104-1a (70 mg, 0.45 mmol, 2.0 eq) in DCM (4 mL) were added Cu(OAc)$_2$ (41 mg, 0.22 mmol, 1.0 eq) and DIPEA (87 mg, 0.67 mmol, 117 uL, 3.0 eq) under O$_2$ (15 psi). The mixture was stirred at 25° C. for 16 h. LCMS showed 6% of the desired product was detected and 30% of the starting material was remained. Compound 104-1a (70 mg, 0.45 mmol, 2.0 eq), Cu(OAc)$_2$ (41 mg, 0.22 mmol, 1.0 eq) and DIPEA (87 mg, 0.67 mmol, 116 uL, 3.0 eq) were added. The mixture was stirred at 35° C. for 36 h under O$_2$ (15 psi). The reaction was monitored by LCMS. The product was isolated and the filtrate was concentrated. The residue was purified by prep-HPLC to give Compound 104 (4 mg, 11 umol, 5% yield) and Compound 106 (10 mg). Compound 106 was re-purified by prep-TLC to give Compound 106 (6.0 mg, 16 umol, 7% yield).

Compound 104: LCMS (ESI): RT=0.749 min, mass calc. for C$_{15}$H$_{14}$F$_2$N$_6$O$_2$S 380.09, m/z found 380.9 [M+H]$^+$; $^1$H NMR (400 MHz, CDCl$_3$) δ 9.39 (s, 1H), 8.73 (d, J=2.3 Hz, 1H), 7.76 (dd, J=2.3, 8.8 Hz, 1H), 7.22 (d, J=8.8 Hz, 2H), 7.16-7.07 (m, 1H), 7.06-6.96 (m, 1H), 4.48 (s, 3H), 4.27 (d, J=5.5 Hz, 1H), 2.71 (d, J=5.5 Hz, 3H).

Compound 106: LCMS (ESI): RT=0.677 min, mass calc. for C$_{15}$H$_{14}$F$_2$N$_6$O$_2$S 380.09, m/z found 380.9 [M+H]$^+$; $^1$H NMR (400 MHz, CDCl$_3$) δ 9.03 (s, 1H), 8.02 (d, J=2.0 Hz, 1H), 7.81 (d, J=8.8 Hz, 1H), 7.20 (d, J=8.8 Hz, 1H), 7.15-7.10 (m, 2H), 7.09-7.00 (m, 1H), 4.33 (s, 4H), 2.69 (d, J=5.5 Hz, 3H).

Example 101: 4-(cyclohexylamino)-N-methyl-3-(5-methyl-1,3,4-oxadiazol-2-yl)benzenesulfonamide (Compound 105)

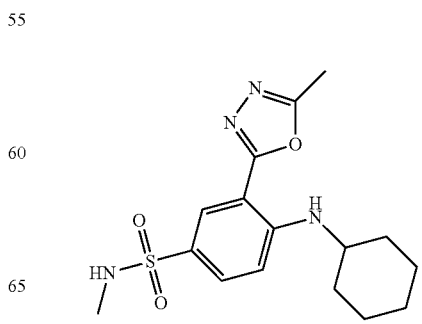

Preparation of Compound 105:

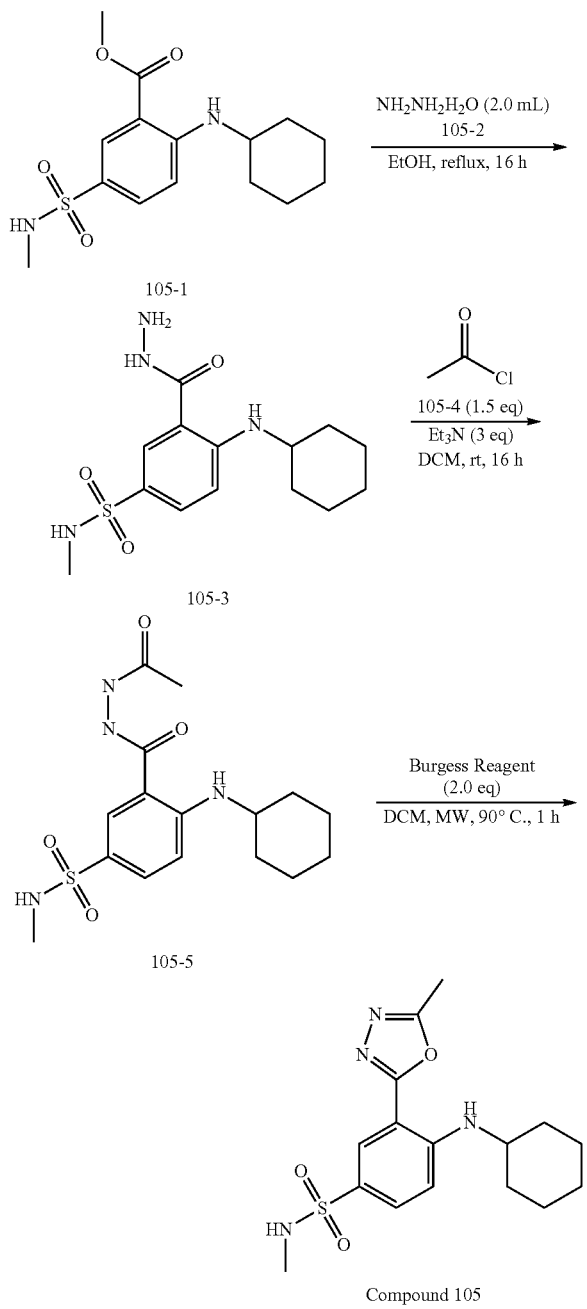

Step 1: 4-(cyclohexylamino)-3-(hydrazinecarbonyl)-N-methyl-benzenesulfonamide

To a solution of compound 105-1 (0.2 g, 0.61 mmol, 1.0 eq) in EtOH (5.0 mL) was added compound 105-2 (36.8 mg, 0.74 mmol, 35.7 uL, 1.2 eq). The resulted mixture was stirred at 80° C. for 16 hr. LCMS showed desired compound was found. TLC showed new spots appeared and the starting material was consumed completely. The reaction mixture was concentrated under reduced pressure to give a crude product. The crude product was purified by column chromatography over silica gel to give compound 105-3 (0.1 g, 0.306 mmol, 50.0% yield). LCMS (ESI): RT=0.665 min, mass calc. for $C_{14}H_{22}N_4O_3S$ 326.14 m/z found 326.9 [M+H]$^+$.

Step 2: 3-(acetamidocarbamoyl)-4-(cyclohexylamino)-N-methyl-benzenesulfonamide

To a solution of compound 105-4 (36.1 mg, 0.46 mmol, 32.8 uL, 1.5 eq) and TEA (62.0 mg, 0.61 mmol, 85.3 uL, 2.0 eq) in DCM (3.0 mL) was added compound 105-3 (0.1 g, 0.31 mmol, 1.0 eq). The resulting mixture was stirred at 20° C. for 16 hr. LCMS showed desired compound was found. TLC showed a new spot appeared. The reaction mixture was concentrated under reduced pressure to give a crude product. The crude product was purified by column chromatography over silica gel to give compound 105-5 (70.0 mg, 0.19 mmol, 62.0% yield). The residue was directly used without further purification. LCMS (ESI): RT=0.723 min, mass calc. for $C_{16}H_{24}N_4O_4S$ 368.15 m/z found 369.0 [M+H]$^+$.

Step 3: 4-(cyclohexylamino)-N-methyl-3-(5-methyl-1,3,4-oxadiazol-2-yl)benzenesulfonamide Compound 105-5 (20.0 mg, 54.2 umol, 1.0 eq), and Burgess Reagent (51.7 mg, 0.22 mmol, 4.0 eq) were taken up into a microwave tube in DCM (2.0 mL). The sealed tube was heated at 90° C. for 1 hr under microwave. LCMS showed desired compound was found. The reaction was filtered to give a crude product. The crude product was purified by prep-HPLC to give Compound 105 (1.70 mg, 4.85 umol, 8.94% yield) was obtained. LCMS (ESI): RT=0.479 min, mass calc. for $C_{16}H_{22}N_4O_3S$ 350.14, m/z found 350.9 [M+H]$^+$; $^1$HNMR (400 MHz, CDCl$_3$) δ 8.27 (d, J=2.3 Hz, 1H), 8.19 (d, J=6.5 Hz, 1H), 7.73 (dd, J=2.1, 8.9 Hz, 1H), 6.84 (d, J=9.3 Hz, 1H), 4.23 (d, J=5.5 Hz, 1H), 3.55 (s, 1H), 2.67 (d, J=5.5 Hz, 3H), 2.63 (s, 3H), 2.06 (d, J=8.5 Hz, 2H), 1.83 (s, 2H), 1.65 (s, 1H), 1.51-1.34 (m, 5H).

Example 102: 4-((3,5-difluorophenyl)amino)-N-methyl-3-(1-methyl-1H-tetrazol-5-yl)benzenesulfonamide (Compound 107) and 4-((3,5-difluorophenyl)amino)-N-methyl-3-(2-methyl-2H-tetrazol-5-yl)benzenesulfonamide (Compound 108)

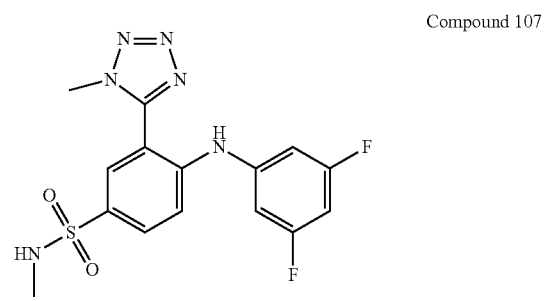

Compound 107

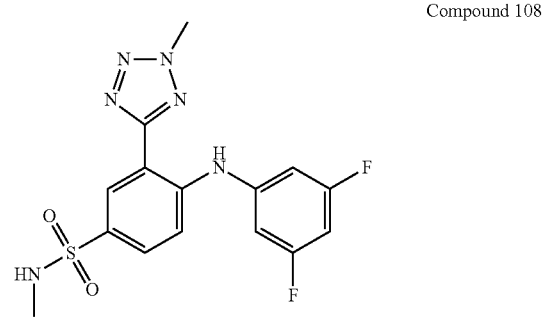

Compound 108

Preparation of Compound 107 and Compound 108:

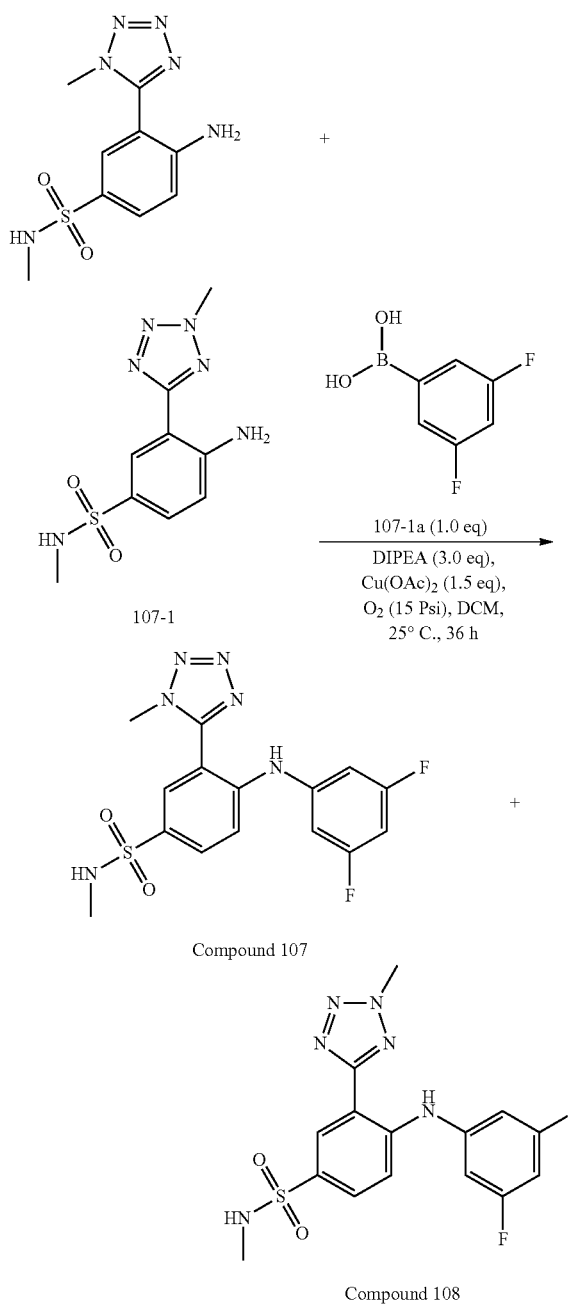

Compound 107

Compound 108

To a solution of a mixture of compounds 107-1 (80 mg, 0.20 mmol, 1 eq), compound 107-1a (32.0 mg, 0.20 mmol, 1 eq) and DIEA (78.6 mg, 0.6 mmol, 0.11 mL, 3 eq) in DCM (2 mL) was added Cu(OAc)$_2$ (55.2 mg, 0.3 mmol, 1.5 eq). The reaction was degassed with O$_2$ for three times and stirred at 25° C. for 36 hr. LCMS showed that 9% and 20% of desired MS signal was detected. The reaction was filtered and concentrated. The crude product was purified by prep HPLC to give Compound 108 (12.37 mg, 32.52 umol, 16.04% yield) and Compound 107 (6.57 mg, 17.27 umol, 8.52% yield). HNMR and LCMS confirmed that desired products were obtained.

Compound 107: LCMS (ESI): RT=0.684 min, mass calcd. For C$_{15}$H$_{14}$F$_2$N$_6$O$_2$S, 380.09 m/z found 380.90[M+H]$^+$. $^1$H NMR (400 MHz, CDCl$_3$) δ 9.17 (s, 1H), 8.02 (d, J=1.60 Hz, 1H), 7.85 (d, J=8.80 Hz, 1H), 7.56 (d, J=9.20 Hz, 1H), 6.85-6.70 (m, 2H), 6.68-6.55 (m, 1H), 4.45-4.35 (m, 1H), 4.31 (s, 3H), 2.70 (d, J=5.60 Hz, 3H).

Compound 108: LCMS (ESI): RT=0.745 min, mass calcd. For C$_{15}$H$_{14}$F$_2$N$_6$O$_2$S, 380.09 m/z found 380.80[M+H]$^+$. $^1$H NMR (400 MHz, CDCl$_3$) δ 9.54 (s, 1H), 8.70 (d, J=2.00 Hz, 1H), 7.79 (dd, J=8.80, 2.40 Hz, 1H), 7.49 (d, J=8.80 Hz, 1H), 6.84 (dd, J=8.00, 2.00 Hz, 2H), 6.61-6.50 (m, 1H), 4.48 (s, 3H), 4.49-4.38 (m, 1H), 2.72 (d, J=5.60 Hz, 3H).

Example 103: 4-((2,5-difluorophenyl)amino)-N-methyl-3-(1-methyl-1H-tetrazol-5-yl)benzenesulfonamide (Compound 109) and 4-((2,5-difluorophenyl)amino)-N-methyl-3-(2-methyl-2H-tetrazol-5-yl)benzenesulfonamide (Compound 110)

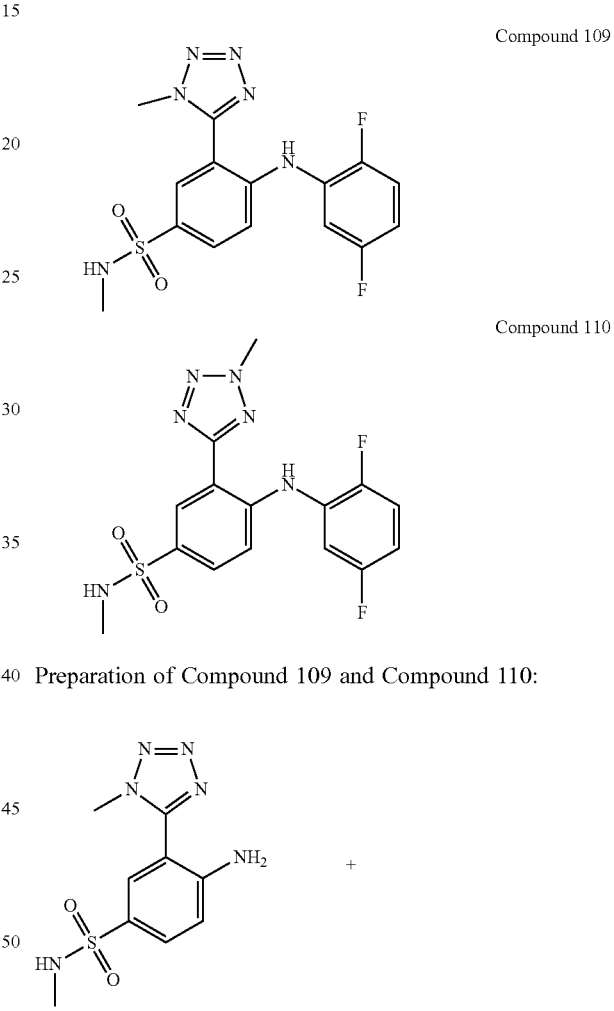

Compound 109

Compound 110

Preparation of Compound 109 and Compound 110:

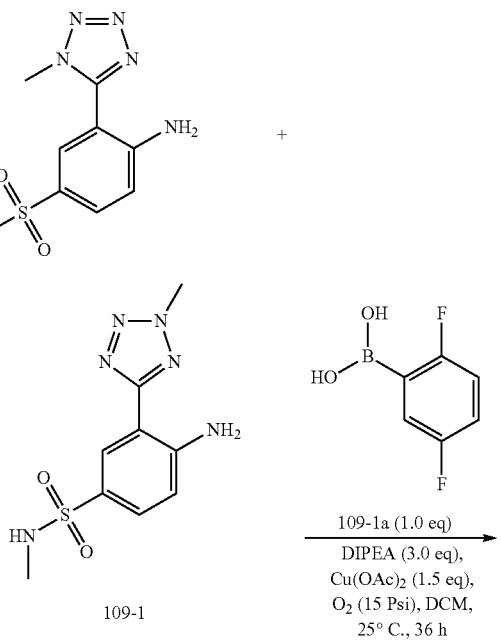

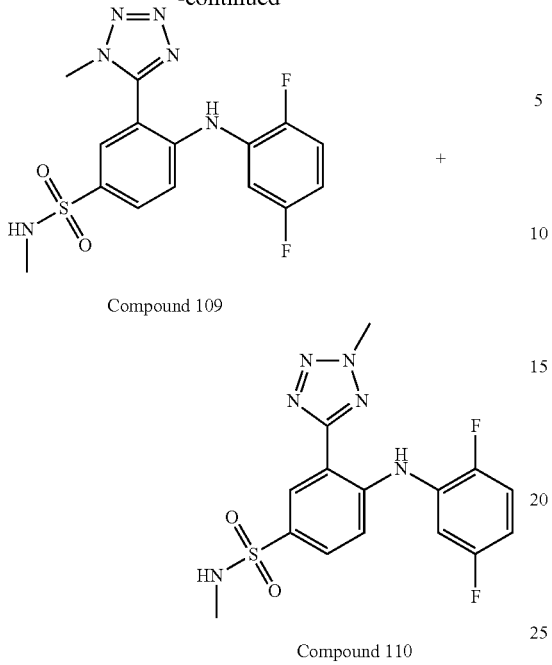

Compound 109

Compound 110

To a solution of a mixture of compounds 109-1 (80 mg, 0.20 mmol, 1 eq), compound 109-1a (32.0 mg, 0.20 mmol, 1 eq) and DIEA (78.6 mg, 0.6 mmol, 0.11 mL, 3 eq) in DCM (2 mL) was added Cu(OAc)$_2$ (55.2 mg, 0.30 mmol, 1.5 eq). The reaction was degassed with O2 for three times and stirred at 25° C. for 36 hr. LCMS showed that 7% and 4% of desired MS signal was detected. The reaction was filtered and concentrated. The crude product was purified by prep-HPLC to give Compound 110 (2.22 mg, 5.84 umol, 2.9% yield) and Compound 109 (4.31 mg, 11.33 umol, 5.6% yield). HNMR and LCMS confirmed that desired product was obtained.

Compound 109: LCMS (ESI): RT=0.671 min, mass calcd. For C$_{15}$H$_{14}$F$_2$N$_6$O$_2$S, 380.09 m/z found 380.80[M+H]$^+$. $^1$H NMR (400 MHz, CDCl$_3$) δ 9.01 (s, 1H), 8.02 (d, J=2.00 Hz, 1H), 7.83 (dd, J=8.80, 2.00 Hz, 1H), 7.30 (d, J=8.80 Hz, 1H), 7.20-7.05 (m, 2H), 6.90-6.75 (m, 1H), 4.41-4.33 (m, 1H), 4.31 (s, 3H), 2.70 (d, J=5.60 Hz, 3H).

Compound 110: LCMS (ESI): RT=0.733 min, mass calcd. For C$_{15}$H$_{14}$F$_2$N$_6$O$_2$S, 380.09 m/z found 443.90 [M+Na+MeCN]$^+$. $^1$H NMR (400 MHz, CDCl$_3$) δ 9.42 (s, 1H), 8.73 (d, J=2.00 Hz, 1H), 7.79 (dd, J=9.20, 2.40 Hz, 1H), 7.31 (d, J=9.20 Hz, 1H), 7.25-7.15 (m, 2H), 6.90-6.75 (m, 1H), 4.48 (s, 3H), 4.41-4.25 (m, 1H), 2.72 (d, J=5.60 Hz, 3H).

Example 104: 4-(cyclohexylamino)-3-(1-cyclopropyl-1H-imidazol-4-yl)-N-methylbenzenesulfonamide (Compound 111)

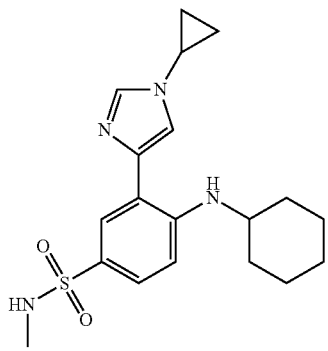 [SMILES: CNS(=O)(=O)c1ccc(NC2CCCCC2)c(-c2cn(C3CC3)cn2)c1]

Preparation of Compound 111:

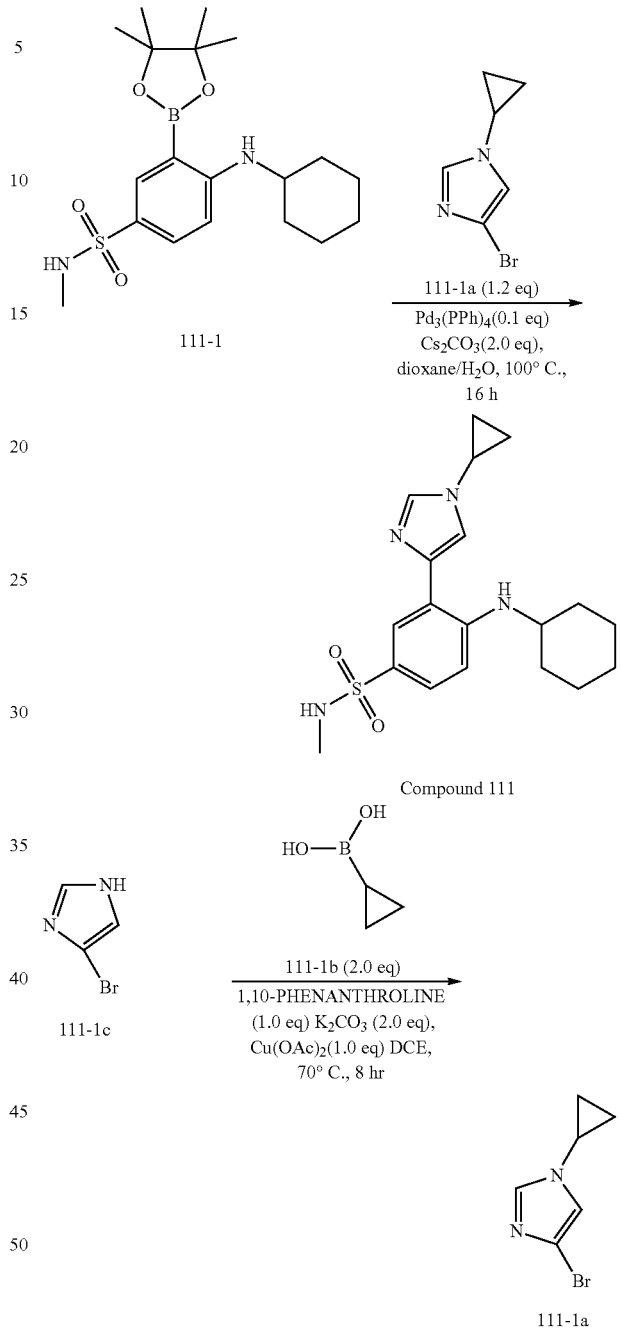

Step 1: 4-bromo-1-cyclopropyl-imidazole

A mixture of 111-1c (500.0 mg, 3.4 mmol, 1.0 eq), 111-1b (584.4 mg, 6.8 mmol, 2.0 eq), 1,10-PHENANTHROLINE (613.0 mg, 3.4 mmol, 1.0 eq), K$_2$CO$_3$ (940.3 mg, 6.8 mmol, 2.0 eq) and Cu(OAc)$_2$ (617.9 mg, 3.4 mmol, 1.0 eq) in DCE (25.0 mL) was degassed and purged with N$_2$ for 3 times, and then the mixture was stirred at 70° C. for 8 h under N$_2$ atmosphere. TLC indicated 50% of 111-1c was remained, and one major new spot with lower polarity was detected. The reaction mixture was concentrated under reduced pressure to remove DCE. The residue was diluted with EtOAc (50.0 mL) and extracted with EtOAc (20 mL*3). The combined organic layers were washed with brine (20 mL*3), dried over Na$_2$SO$_4$, filtered and concentrated under reduced pressure to give a residue. The residue was purified by column chromatography to give 111-1a (70.0 mg, 0.374 mmol, 11% yield). H NMR (400 MHz, CDCl$_3$) δ 7.42 (d, J=1.0 Hz, 1H), 6.95 (d, J=1.3 Hz, 1H), 3.37-3.27 (m, 1H), 1.03-0.94 (m, 4H).

Step 2: 4-(cyclohexylamino)-3-(1-cyclopropyl-1H-imidazol-4-yl)-N-methylbenzenesulfonamide A mixture of 111-1 (139.1 mg, 0.4 mmol, 1.1 eq), 111-1a (60 mg, 0.3 mmol, 1 eq), Pd(PPh$_3$)$_4$ (37.0 mg, 32.0 umol, 0.1 eq) and Cs$_2$CO$_3$ (209.0 mg, 0.6 mmol, 2.0 eq) in dioxane (2.0 mL) and H$_2$O (0.3 mL) was degassed and purged with N$_2$ for 3 times, and then the mixture was stirred at 100° C. for 16 h under N$_2$ atmosphere. LCMS showed 111-1 was consumed completely. Several new peaks were shown on LCMS and 27% of desired compound was detected. The residue was purified by prep-HPLC to give Compound 111 (7.82 mg, 20.46 umol, 6% yield). LCMS (ESI): RT=0.716 min, mass calc. for C$_{19}$H$_{26}$N$_4$O$_2$S 374.18, m/z found 375.0 [M+H]$^+$; $^1$H NMR (400 MHz, CDCl$_3$) δ 8.55 (d, J=5.5 Hz, 1H), 7.85 (s, 1H), 7.55 (s, 2H), 7.32 (s, 1H), 6.66 (d, J=8.5 Hz, 1H), 4.78 (d, J=3.0 Hz, 1H), 3.58-3.25 (m, 2H), 2.58 (d, J=3.0 Hz, 3H), 2.03 (s, 2H), 1.76 (s, 2H), 1.62 (s, 1H), 1.39 (d, J=7.5 Hz, 5H), 0.98 (s, 4H).

Example 105: 4-(cyclohexylamino)-3-(1-ethyl-1H-imidazol-4-yl)-N-methylbenzenesulfonamide (Compound 112)

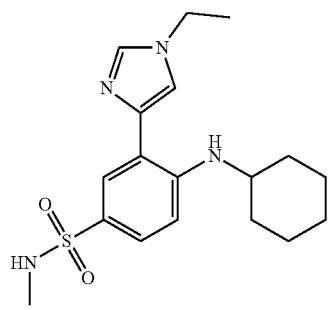

Preparation of Compound 112:

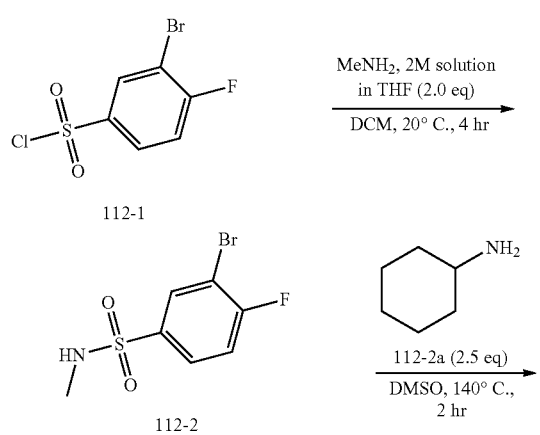

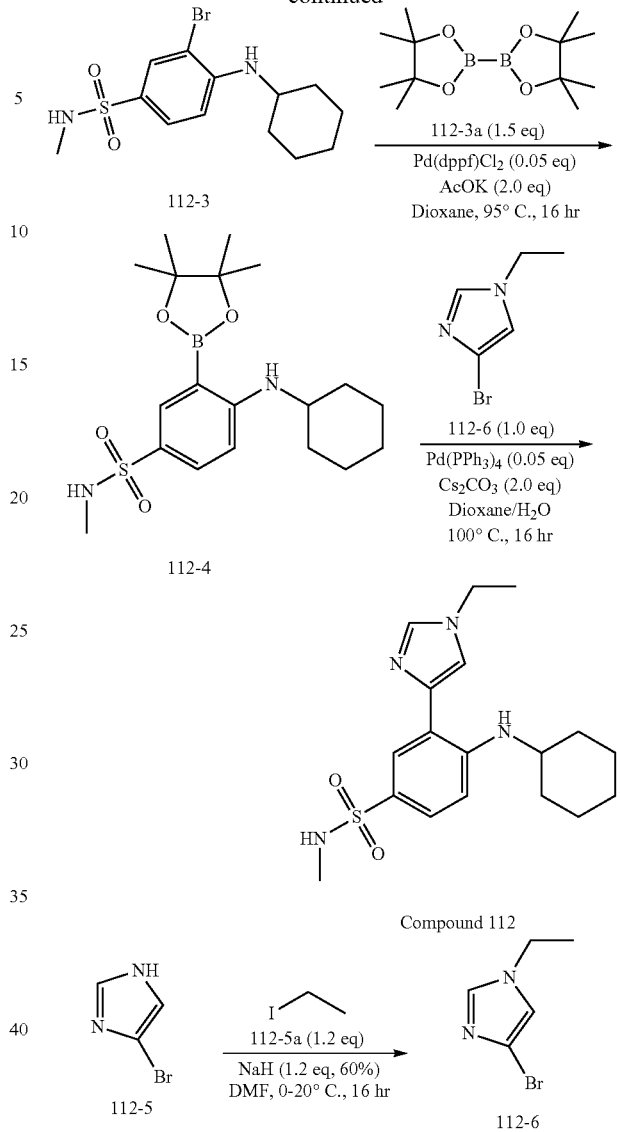

Step 1: 3-Bromo-4-fluoro-N-methylbenzenesulfonamide

To a solution of compound 112-1 (1.6 g, 5.9 mmol, 1.0 eq) in DCM (16 mL) was added MeNH$_2$ (2 M, 5.9 mL, 2.0 eq). The reaction mixture was stirred at 20° C. for 4 hours. The mixture was diluted with water (15 mL) and the resultant mixture was extracted with DCM (30 mL*2). The combined organic layers were dried over Na$_2$SO$_4$, filtered and concentrated to dryness under reduced pressure to obtain compound 112-2 (1.5 g, 96% yield).

Step 2: 3-Bromo-4-(cyclohexylamino)-N-methyl-benzenesulfonamide

A solution of compound 112-2 (1.5 g, 5.6 mmol, 1.0 eq) and compound 112-2a (1.4 g, 14 mmol, 2.5 eq) in DMSO (8 mL) was stirred at 140° C. for 2 hours. The mixture was diluted with water (30 mL) and the resultant mixture was extracted with EA (50 mL*3). The combined organic layers were dried over Na$_2$SO$_4$, filtered and concentrated to dryness under reduced pressure. The residue was purified by column chromatography over silica gel to afford the title compound 112-3 (1.8 g, 93% yield). LCMS (ESI): RT=0.794 min, mass calcd. for $C_{13}H_{19}BrN_2O_2S$ 346.04, m/z found 348.9 $[M+H]^+$.

Step 3: 4-(Cyclohexylamino)-N-methyl-3-(4,4,5,5-tetramethyl-1,3,2-dioxaborolan-2-yl)benzenesulfonamide A solution of compound 112-3 (2.0 g, 5.8 mmol, 1.0 eq), compound 112-3a (2.2 g, 8.6 mmol, 1.5 eq), Pd(dppf)Cl$_2$ (211 mg, 0.288 mmol, 0.05 eq) and AcOK (1.1 g, 12 mmol, 2.0 eq) in Dioxane (25 mL) was heated to 95° C. and stirred at 95° C. for 16 hours under N$_2$. The reaction mixture was concentrated under reduced pressure. The mixture was diluted with water (20 mL) and extracted with EA (50 mL*3). The combined organic layers were dried over Na$_2$SO$_4$, filtered and concentrated to dryness under reduced pressure. The residue was purified by column chromatography over silica gel to afford the title compound 112-4 (1.6 g, 70% yield). LCMS (ESI): RT=0.876 min, mass calcd. for $C_{19}H_{31}BN_2O_4S$ 394.21, m/z found 395.1 $[M+H]^+$.

Step 4: 4-Bromo-1-ethyl-1H-imidazole

To a solution of compound 112-5 (500 mg, 3.40 mmol, 1.0 eq) in DMF (6 mL) was added NaH (163 mg, 4.08 mmol, 60% purity, 1.2 eq) at 0° C. The reaction mixture was allowed to warm up to 20° C. and then stirred at 20° C. for 0.5 hour. The mixture was cooling to 0° C. and followed by compound 112-5a (637 mg, 4.08 mmol, 1.2 eq). The reaction mixture was stirred at 20° C. for 2.5 hours. The reaction mixture was concentrated under reduced pressure. The mixture was diluted with water (30 mL) and the resultant mixture was extracted with DCM (50 mL*3). The combined organic layers were dried over Na$_2$SO$_4$, filtered and concentrated to dryness under reduced pressure. The residue was purified by column chromatography over silica gel to afford a residue. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. The title compound 112-6 (150 mg, 25% yield) was obtained. $^1$H NMR (400 MHz, CDCl$_3$) δ 7.36 (d, J=1.0 Hz, 1H), 6.90 (d, J=1.5 Hz, 1H), 3.96 (q, J=7.3 Hz, 2H), 1.45 (t, J=7.4 Hz, 3H).

Step 5: 4-(Cyclohexylamino)-3-(1-ethyl-1H-imidazol-4-yl)-N-methylbenzenesulfonamide To a solution of compound 112-4 (100 mg, 0.254 mmol, 1.0 eq), compound 112-6 (44 mg, 0.25 mmol, 1.0 eq), Cs$_2$CO$_3$ (165 mg, 0.507 mmol, 2.0 eq) in Dioxane (2 mL) and H$_2$O (0.2 mL) was added Pd(PPh$_3$)$_4$ (15 mg, 13 umol, 0.05 eq) under N$_2$. The reaction mixture was stirred at 100° C. for 16 hours. The mixture was diluted with water (10 mL) and the resultant mixture was extracted with EA (30 mL*3). The combined organic layers were dried over Na$_2$SO$_4$, filtered and concentrated to dryness under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. Compound 112 (33.80 mg, 36% yield) was obtained. LCMS (ESI): RT=0.641 min, mass calcd. for $C_{18}H_{26}N_4O_2S$ 362.18, m/z found 363.0 $[M+H]^+$, $^1$H NMR (400 MHz, CDCl$_3$) δ 7.83 (d, J=2.3 Hz, 1H), 7.57-7.49 (m, 2H), 7.30 (d, J=1.3 Hz, 1H), 6.69 (d, J=9.0 Hz, 1H), 4.26 (q, J=5.3 Hz, 1H), 4.04 (q, J=7.4 Hz, 2H), 3.50-3.38 (m, 1H), 2.62 (d, J=5.5 Hz, 3H), 2.13-1.99 (m, 2H), 1.85-1.73 (m, 2H), 1.69-1.58 (m, 2H), 1.51 (t, J=7.4 Hz, 3H), 1.45-1.34 (m, 4H).

Example 106: 4-(cyclohexylamino)-3-(1-isopropyl-1H-imidazol-4-yl)-N-methylbenzenesulfonamide (Compound 113)

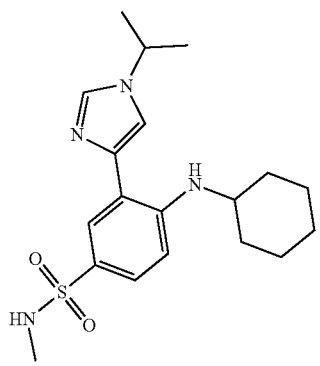 [SMILES: CNS(=O)(=O)c1ccc(NC2CCCCC2)c(-c2cn(C(C)C)cn2)c1]

Preparation of Compound 113:

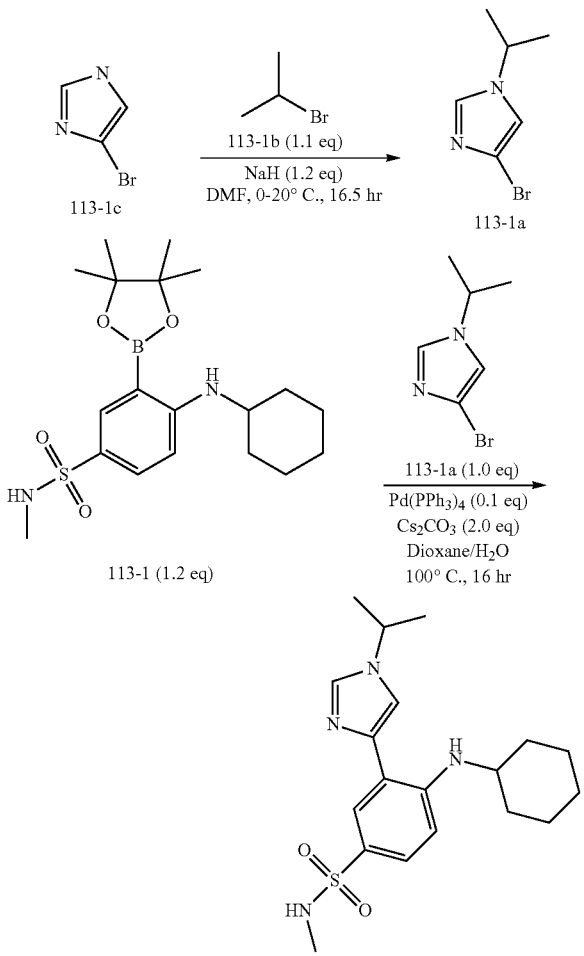

Compound 113

Step 1: 4-bromo-1-isopropyl-1H-imidazole

To the solution of compound 113-1c (500 mg, 3.4 mmol, 1 eq) in DMF (2.5 mL) was added NaH (163 mg, 4.1 mmol, 60% purity, 1.2 eq) at 0° C. The mixture was stirred at 0° C. for 30 min. Then compound 113-1b (460 mg, 3.7 mmol, 351 uL, 1.1 eq) was added to the mixture. The solution was warmed up to 20° C. and stirred for 16 hr. The reaction was monitored by LCMS. LCMS showed that the starting material remained and the desired MS was observed. H$_2$O (20 mL) was added to the solution. The mixture was extracted with EtOAc (20 mL*3). The combined organic layer was dried with Na$_2$SO$_4$ and concentrated under reduced pressure. The residue was purified by to give compound 113-1a (100 mg, 528.95 umol, 15.55% yield). It was confirmed by HNMR and HMBC. $^1$H NMR (400 MHz, CDCl$_3$) δ 7.41 (d, J=1.3 Hz, 1H), 6.93 (d, J=1.5 Hz, 1H), 4.37-4.27 (m, 1H), 1.48 (d, J=6.8 Hz, 6H).

Step 2: 4-(cyclohexylamino)-3-(1-isopropyl-1H-imidazol-4-yl)-N-methylbenzenesulfonamide To the solution of compound 113-1a (50 mg, 0.26 mmol, 1 eq) in dioxane (2 mL) was added compound 113-1 (125 mg, 0.32 mmol, 1.2 eq), Pd(PPh$_3$)$_4$ (31 mg, 26.5 umol, 0.1 eq), Cs$_2$CO$_3$ (172 mg, 0.53 mol, 2 eq) and H$_2$O (0.4 mL). The mixture was stirred at 100° C. for 16 hr. The reaction was monitored by LCMS. LCMS showed that the starting material was consumed and the desired MS was observed. The reaction solution was filtered. The residue was purified by HPLC to give Compound 113 (9.07 mg, 23.61 umol, 8.9% yield). LCMS (ESI): RT=0.649 min, mass calcd. for C$_{19}$H$_{23}$N$_9$O 376.19, m/z found 377.0 [M+H]$^+$, $^1$H NMR (400 MHz, CDCl$_3$) δ 8.71 (br, 1H), 7.89 (d, J=2.5 Hz, 1H), 7.57-7.51 (m, 2H), 7.36 (d, J=1.0 Hz, 1H), 6.68 (d, J=8.8 Hz, 1H), 4.52 (q, J=5.4 Hz, 1H), 4.41-4.30 (m, 1H), 3.44 (br, 1H), 2.61 (d, J=5.5 Hz, 3H), 2.10-2.02 (m, 2H), 1.84-1.75 (m, 2H), 1.69-1.60 (m, 1H), 1.51 (d, J=6.8 Hz, 6H), 1.46-1.27 (m, 5H).

Example 107: 4-(cyclohexylamino)-3-(1-ethyl-1H-imidazol-5-yl)-N-methylbenzenesulfonamide (Compound 114)

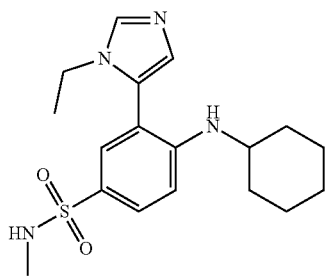

Preparation of Compound 114:

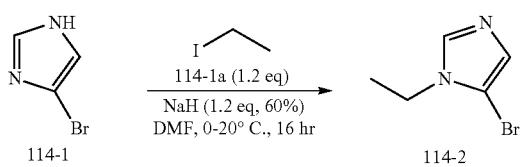

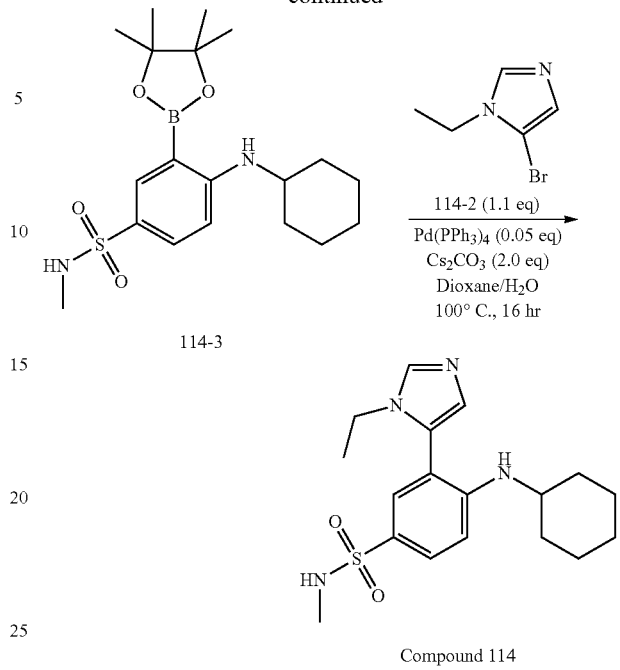

Compound 114

Step 1: 5-Bromo-1-ethyl-1H-imidazole

To a solution of compound 114-1 (500 mg, 3.40 mmol, 1.0 eq) in DMF (6 mL) was added NaH (163 mg, 4.08 mmol, 60% purity, 1.2 eq) at 0° C. The reaction mixture was allowed to warm up to 20° C. and then stirred at 20° C. for 0.5 hour. The mixture was cooling to 0° C. and followed by compound 114-1a (637 mg, 4.08 mmol, 1.2 eq). The reaction mixture was stirred at 20° C. for 2.5 hours. The reaction mixture was concentrated under reduced pressure. The mixture was diluted with water (30 mL) and the resultant mixture was extracted with DCM (50 mL*3). The combined organic layers were dried over Na$_2$SO$_4$, filtered and concentrated to dryness under reduced pressure. The residue was purified by column chromatography over silica gel to afford the title compound. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. The title compound (60 mg, 25% yield) was obtained. $^1$H NMR (400 MHz, CDCl$_3$) δ 7.58 (s, 1H), 7.02 (s, 1H), 3.99 (q, J=7.3 Hz, 2H), 1.43 (t, J=7.3 Hz, 3H).

Step 2: 4-(Cyclohexylamino)-3-(1-ethyl-1H-imidazol-5-yl)-N-methylbenzenesulfonamide To a solution of compound 114-3 (120 mg, 0.304 mmol, 1.0 eq), compound 114-2 (60 mg, 0.33 mmol, 1.1 eq), Cs$_2$CO$_3$ (198 mg, 0.609 mmol, 2.0 eq) in Dioxane (2 mL) and H$_2$O (0.2 mL) was added Pd(PPh$_3$)$_4$ (18 mg, 15 umol, 0.05 eq) under N$_2$. The reaction mixture was stirred at 100° C. for 16 hours. The mixture was diluted with water (10 mL) and the resultant mixture was extracted with EA (30 mL*3). The combined organic layers were dried over Na$_2$SO$_4$, filtered and concentrated to dryness under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. Compound 114 (37.86 mg, 34% yield) was obtained. LCMS (ESI): RT=0.630 min, mass calcd. for $C_{18}H_{26}N_4O_2S$ 362.18, m/z found 362.9 [M+H]$^+$, $^1$H NMR (400 MHz, CDCl$_3$) δ 7.79-7.68 (m, 2H), 7.53 (d, J=2.3 Hz, 1H), 7.18-7.05 (m, 1H), 6.73 (d, J=9.0 Hz, 1H), 4.48-4.38 (m, 1H), 4.26 (d, J=7.8 Hz, 1H), 3.82 (q, J=7.3 Hz, 2H), 3.41-3.29 (m, 1H), 2.68 (d, J=5.3 Hz, 3H), 2.02-1.92 (m, 2H), 1.76-1.61 (m, 3H), 1.45-1.32 (m, 2H), 1.28 (t, J=7.3 Hz, 3H), 1.26-1.58 (m, 1H), 1.17-1.06 (m, 2H).

Example 108: 3-(2-(2-(benzyloxy)ethyl)-2H-tetrazol-5-yl)-N-methyl-4-((4-(trifluoromethyl)phenyl)amino)benzenesulfonamide (Compound 115)

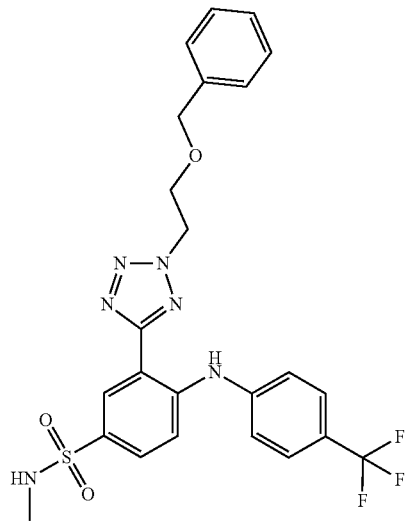 [SMILES: CNS(=O)(=O)c1ccc(Nc2ccc(C(F)(F)F)cc2)c(-c2nnn(CCOCc3ccccc3)n2)c1]

Preparation of Compound 115:

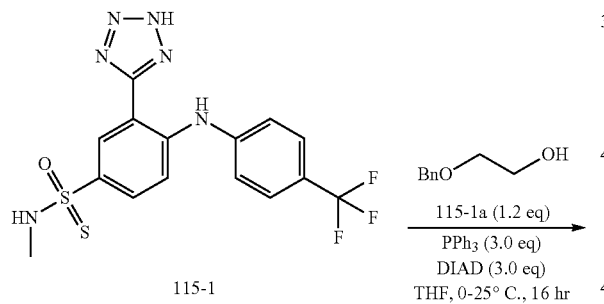

To a stirring solution of compound 115-1 (20 mg, 50 umol, 1.0 eq), compound 115-1a (9.1 mg, 60 umol, 1.2 eq) and PPh$_3$ (40 mg, 0.15 mmol, 3.0 eq) in THF (1 mL) was added DIAD (30 mg, 0.15 mmol, 3.0 eq) slowly at 0° C. under N$_2$. The reaction mixture was stirred at 25° C. for 16 hours. The reaction mixture was concentrated under reduced pressure. The mixture was diluted with water (5 mL) and the resultant mixture was extracted with EA (20 mL*3). The combined organic layers were dried over Na$_2$SO$_4$, filtered and concentrated to dryness under reduced pressure. The residue was purified by column chromatography over silica gel to afford Compound 115 (6.76 mg, 25% yield). LCMS (ESI): RT=0.857 min, mass calcd. for $C_{24}H_{23}F_3N_6O_3S$ 532.15, m/z found 533.0 [M+H]$^+$, $^1$H NMR (400 MHz, CDCl$_3$) δ 9.70 (s, 1H), 8.73 (d, J=2.3 Hz, 1H), 7.79 (dd, J=2.1, 8.9 Hz, 1H), 7.66 (d, J=8.5 Hz, 2H), 7.51 (d, J=8.8 Hz, 1H), 7.41 (d, J=8.3 Hz, 2H), 7.34-7.29 (m, 3H), 7.27-7.23 (m, 2H), 4.93 (t, J=5.4 Hz, 2H), 4.57 (s, 2H), 4.32 (q, J=5.5 Hz, 1H), 4.11 (t, J=5.4 Hz, 2H), 2.74 (d, J=5.3 Hz, 3H).

Example 109: 3-(2-(2-hydroxyethyl)-2H-tetrazol-5-yl)-N-methyl-4-((4-(trifluoromethyl)phenyl) amino)benzenesulfonamide (Compound 116)

Preparation of Compound 116:

287

-continued

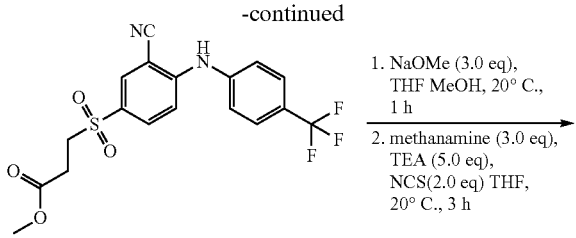
116-3

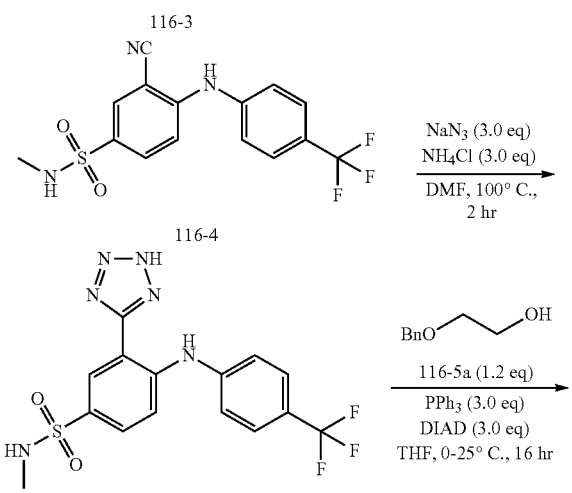
116-4

1. NaOMe (3.0 eq), THF MeOH, 20° C., 1 h
2. methanamine (3.0 eq), TEA (5.0 eq), NCS(2.0 eq) THF, 20° C., 3 h NaN₃ (3.0 eq)
NH₄Cl (3.0 eq)
DMF, 100° C., 2 hr BnO⌒OH
116-5a (1.2 eq)
PPh₃ (3.0 eq)
DIAD (3.0 eq)
THF, 0-25° C., 16 hr

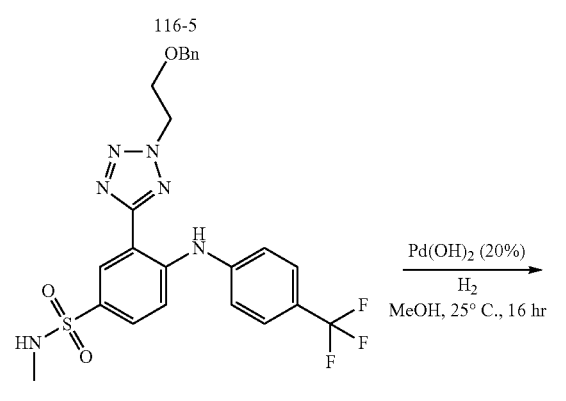
116-5

Pd(OH)₂ (20%)
H₂
MeOH, 25° C., 16 hr 116-6

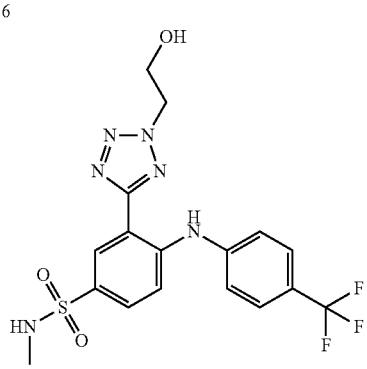
Compound 116

Step 1: 5-Iodo-2-((4-(trifluoromethyl)phenyl)amino)benzonitrile

To a solution of compound 116-1 (450 mg, 1.84 mmol, 1.0 eq), compound 116-1a (420 mg, 2.21 mmol, 1.2 eq) and Cu(OAc)₂ (402 mg, 2.21 mmol, 1.2 eq) in DCM (5 mL) was added DIPEA (477 mg, 3.69 mmol, 2.0 eq) under O₂. The reaction mixture was stirred at 25° C. for 72 hours. The reaction mixture was concentrated under reduced pressure. The residue was purified by column chromatography over silica gel to afford the title compound 116-2 (180 mg, 25% yield). ¹H NMR (400 MHz, CDCl₃) δ 7.84 (d, J=2.0 Hz, 1H), 7.70 (dd, J=2.0, 8.8 Hz, 1H), 7.61 (d, J=8.5 Hz, 2H), 7.23 (d, J=8.5 Hz, 2H), 7.11 (d, J=9.0 Hz, 1H), 6.46 (s, 1H).

Step 2: Methyl 3-((3-cyano-4-((4-(trifluoromethyl)phenyl)amino)phenyl)sulfonyl)propanoate Compound 116-2 (130 mg, 0.335 mmol, 1.0 eq), compound 116-2a (175 mg, 1.00 mmol, 3.0 eq) and CuI (319 mg, 1.67 mmol, 5.0 eq) were taken up into a microwave tube in DMSO (3 mL). The sealed tube was heated at 110° C. for 1 hour under microwave. The mixture was diluted with water (10 mL) and EA (30 mL). The suspension was filtered and the filtrate was separation, the water layer was extracted with EA (20 mL*2). The combined organic layers were dried over Na₂SO₄, filtered and concentrated to dryness under reduced pressure. The residue was purified by column chromatography over silica gel to afford the title compound 116-3 (110 mg, 80% yield).

Step 3: 3-Cyano-N-methyl-4-((4-(trifluoromethyl)phenyl)amino)benzenesulfonamide To a solution of compound 116-3 (110 mg, 0.267 mmol, 1.0 eq) in MeOH (1.5 mL) and THF (3 mL) was added NaOMe (43 mg, 0.80 mmol, 3.0 eq). The reaction mixture was stirred at 20° C. for 1 hour, and then removed solvent to give a residue. The residue was dissolved with THF (2 mL). After MeNH₂ (2 M, 0.40 mL, 3.0 eq), TEA (135 mg, 1.33 mmol, 5.0 eq) and NCS (71 mg, 0.53 mmol, 2.0 eq) were added, the reaction mixture was stirred at 20° C. for 3 hours. The mixture was diluted with water (10 mL) and the resultant mixture was extracted with EA (30 mL*3). The combined organic layers were dried over Na₂SO₄, filtered and concentrated to dryness under reduced pressure. The residue was purified by column chromatography over silica gel to afford the title compound 116-4 (80 mg, 84% yield). ¹H NMR (400 MHz, CDCl₃) δ 8.06 (d, J=2.3 Hz, 1H), 7.85 (dd, J=2.1, 8.9 Hz, 1H), 7.69 (d, J=8.5 Hz, 2H), 7.35 (d, J=8.5 Hz, 2H), 7.31 (d, J=9.0 Hz, 1H), 6.84 (s, 1H), 4.37 (q, J=5.3 Hz, 1H), 2.71 (d, J=5.5 Hz, 3H).

Step 4: N-methyl-3-(2H-tetrazol-5-yl)-4-((4-(trifluoromethyl)phenyl)amino)benzenesulfonamide To a solution of compound 116-4 (80 mg, 0.23 mmol, 1.0 eq) in DMF (2 mL) were added NaN₃ (60 mg, 0.92 mmol, 4.1 eq) and NH₄Cl (36 mg, 0.68 mmol, 3.0 eq). The reaction mixture was stirred at 100° C. for 2 hours. The mixture was diluted with water (30 mL) and the resultant mixture was extracted with EA (50 mL*3). The combined organic layers were dried over Na₂SO₄, filtered and concentrated to dryness under reduced pressure to obtain the title compound 116-5 (85 mg, 95% yield). LCMS (ESI): RT=0.746 min, mass calcd. for C₁₅H₁₃F₃N₆O₂S 398.08, m/z found 399.1 [M+H]⁺.

Step 5: 3-(2-(2-(Benzyloxy)ethyl)-2H-tetrazol-5-yl)-N-methyl-4-((4-(trifluoromethyl)phenyl) amino) benzenesulfonamide To a stirring solution of compound 116-5 (65 mg, 0.16 mmol, 1.0 eq), compound 116-5a (30 mg, 0.20 mmol, 1.2 eq) and PPh$_3$ (128 mg, 0.490 mmol, 3.0 eq) in THF (2 mL) was added DIAD (99 mg, 0.49 mmol, 3.0 eq) slowly at 0° C. under N$_2$. The reaction mixture was stirred at 25° C. for 16 hours. The reaction mixture was concentrated under reduced pressure. The mixture was diluted with water (10 mL) and the resultant mixture was extracted with EA (30 mL*3). The combined organic layers were dried over Na$_2$SO$_4$, filtered and concentrated to dryness under reduced pressure. The residue was purified by column chromatography over silica gel to afford compound 116-6 (70 mg, 78% yield). LCMS (ESI): RT=0.865 min, mass calcd. for C$_{24}$H$_{23}$F$_3$N$_6$O$_3$S 532.15, m/z found 533.1 [M+H]$^+$, $^1$H NMR (400 MHz, CDCl$_3$) δ 9.67 (s, 1H), 8.70 (d, J=2.3 Hz, 1H), 7.77 (dd, J=2.4, 8.9 Hz, 1H), 7.64 (d, J=8.5 Hz, 2H), 7.49 (d, J=9.0 Hz, 1H), 7.39 (d, J=8.5 Hz, 2H), 7.32-7.26 (m, 3H), 7.25-7.21 (m, 2H), 4.91 (t, J=5.4 Hz, 2H), 4.55 (s, 2H), 4.30 (q, J=5.4 Hz, 1H), 4.09 (t, J=5.3 Hz, 2H), 2.71 (d, J=5.5 Hz, 3H).

Step 6: 3-(2-(2-Hydroxyethyl)-2H-tetrazol-5-yl)-N-methyl-4-((4-(trifluoromethyl)phenyl) amino)benzenesulfonamide To a solution of compound 116-6 (40 mg, 75 umol, 1 eq) in MeOH (3 mL) was added Pd(OH)$_2$ (10 mg, 20% purity) under N$_2$. The suspension was degassed under vacuum and purged with H$_2$ several times. The mixture was stirred under H$_2$ (15 psi) at 25° C. for 16 hours. The reaction mixture was filtered and the filtrate was concentrated. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. Compound 116 (6.67 mg, 20% yield) was obtained. LCMS (ESI): RT=0.748 min, mass calcd. for C$_{17}$H$_7$F$_3$N$_6$O$_3$S 442.10, m/z found 442.9 [M+H]$^+$, $^1$H NMR (400 MHz, CDCl$_3$) δ 9.67 (s, 1H), 8.69 (d, J=2.3 Hz, 1H), 7.77 (dd, J=2.1, 8.9 Hz, 1H), 7.65 (d, J=8.5 Hz, 2H), 7.49 (d, J=9.0 Hz, 1H), 7.40 (d, J=8.5 Hz, 2H), 4.92-4.86 (m, 2H), 4.37 (q, J=5.5 Hz, 1H), 4.33-4.27 (m, 2H), 2.71 (d, J=5.5 Hz, 3H), 2.22 (t, J=6.0 Hz, 1H).

Example 110: 4-((3-fluorophenyl)amino)-N-methyl-3-(2-methyl-2H-tetrazol-5-yl)benzenesulfonamide (Compound 117)

Preparation of Compound 117:

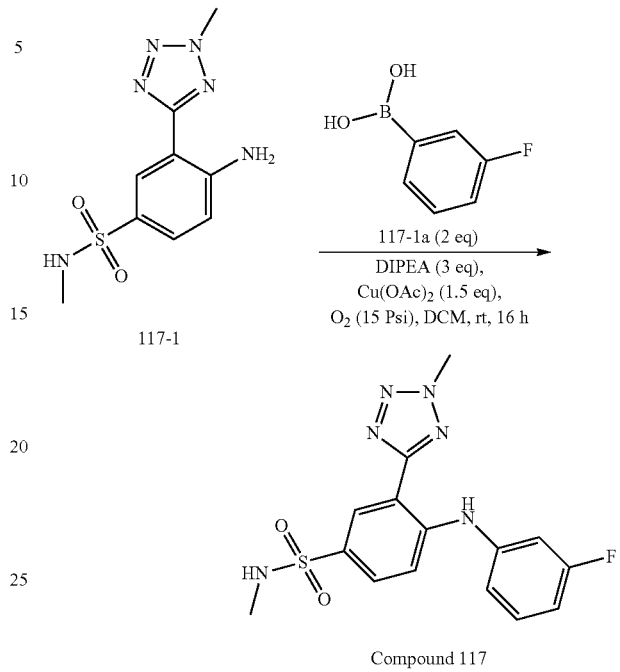

To a solution of compound 117-1 (40 mg, 0.15 mmol, 1 eq), (3-fluorophenyl)boronic acid (117-1a) (41.7 mg, 0.30 mmol, 2 eq) and DIEA (57.8 mg, 0.45 mmol, 77.90 uL, 3 eq) in DCM (2 mL) was added Cu(OAc)$_2$ (40.6 mg, 0.22 mmol, 1.5 eq). The reaction was stirred at 25° C. under O$_2$ (15 Psi) for 16 hr. LCMS showed that 50% of desired MS signal was detected. The reaction was filtered and concentrated. The crude product was purified by prep HPLC to give Compound 117 (8.74 mg, 24.12 umol, 16.18% yield). HNMR and LCMS confirmed that desired product was obtained. LCMS (ESI): RT=0.746 min, mass calcd. For C$_{15}$H$_{15}$FN$_6$O$_2$S, 362.10 m/z found 362.9[M+H]$^+$. $^1$H NMR (400 MHz, CDCl$_3$) δ 9.47 (s, 1H), 8.69 (d, J=2.4 Hz, 1H), 7.74 (d, J=9.2 Hz, 1H), 7.45-7.30 (m, 2H), 7.15-7.00 (m, 2H), 7.00-6.95 (m, 1H), 4.47 (s, 3H), 4.28 (d, J=5.6 Hz, 1H), 2.70 (d, J=5.6 Hz, 3H).

Example 111: 4-((4-fluorophenyl)amino)-N-methyl-3-(2-methyl-2H-tetrazol-5-yl)benzenesulfonamide (Compound 118) and 4-((4-fluorophenyl)amino)-N-methyl-3-(1-methyl-1H-tetrazol-5-yl)benzenesulfonamide (Compound 119)

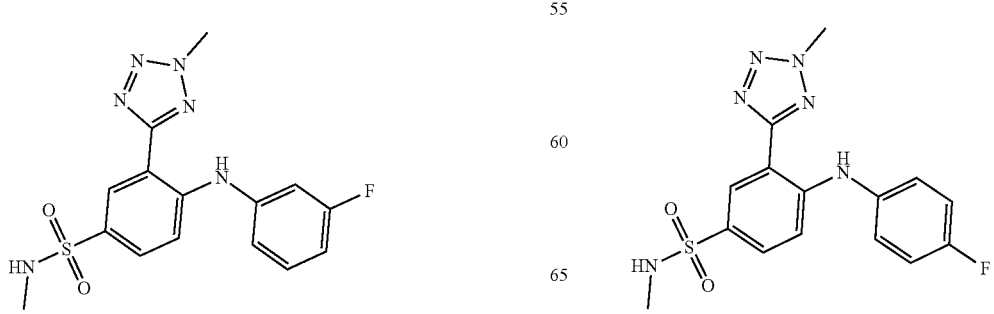

-continued

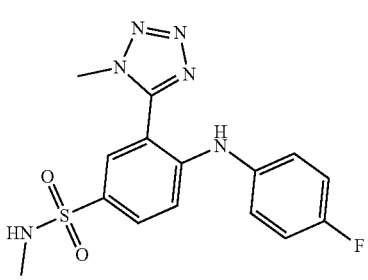

Compound 119

Preparation of Compound 118:

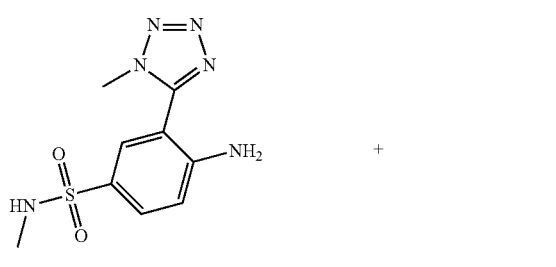

118-1

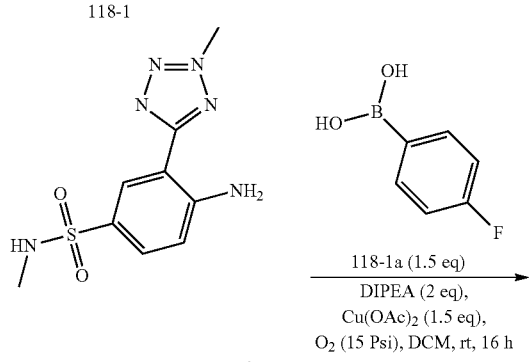

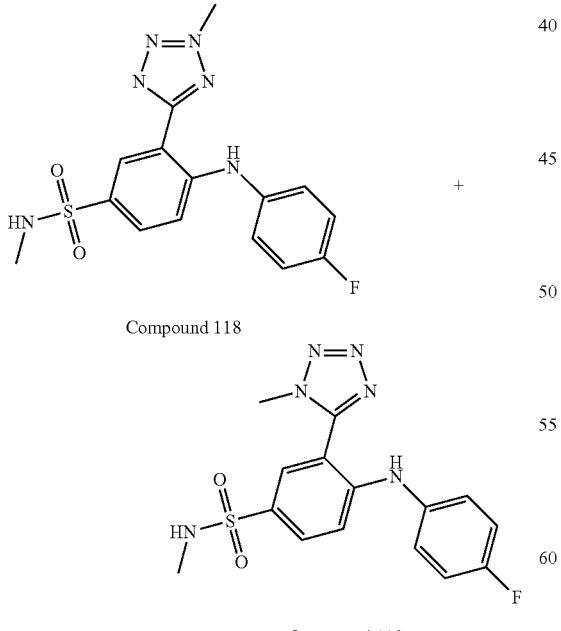

Compound 118

Compound 119

To a solution of a mixture of compounds 118-1 (50 mg, 0.18 mmol, 1 eq) in DCM (3 mL) was added compound 118-1a (39.1 mg, 0.28 mmol, 1.5 eq), Cu(OAc)₂ (50.8 mg, 0.28 mmol, 1.5 eq) followed by DIEA (48.2 mg, 0.37 mmol, 64.92 uL, 2 eq) under N₂. The suspension was degassed under vacuum and purged with O2 several times. The mixture was stirred under O₂ (15 psi) at 25° C. for 16 hours. LCMS showed that 5.6% and 50% of desired product were detected. The reaction was filtered and concentrated. The residue was added MeOH (4 mL) and filtered to give Compound 118 (18.83 mg, 50.30 umol, 27% yield). The filtrate was concentrated. The crude product was purified by Prep HPLC to give Compound 119 (2.85 mg, 7.86 umol, 4.2% yield).

Compound 118: LCMS (ESI): RT=0.733 min, mass calcd. For C₁₅H₁₅FN₆O₂S, 362.10 m/z found 362.9[M+H]⁺. ¹H NMR (400 MHz, CDCl₃) δ 9.32 (s, 1H), 8.68 (d, J=2.4 Hz, 1H), 7.68 (dd, J=8.8, 2.4 Hz, 1H), 7.46-7.37 (m, 3H), 7.25-7.15 (m, 3H), 4.47 (s, 3H), 4.24 (d, J=5.6 Hz, 1H), 2.69 (d, J=5.6 Hz, 3H).

Compound 119: LCMS (ESI): RT=0.679 min, mass calcd. For C₁₅H₁₅FN₆O₂S, 362.10 m/z found 362.9[M+H]⁺. ¹H NMR (400 MHz, CHLOROFORM-d) δ 8.97 (s, 1H), 7.99 (d, J=2.0 Hz, 1H), 7.80-7.60 (m, 1H), 7.25-7.15 (m, 3H), 7.15-7.05 (m, 3H), 4.40-4.25 (m, 4H), 2.67 (d, J=4.4 Hz, 3H).

Example 112: 4-((2-fluorophenyl)amino)-N-methyl-3-(2-methyl-2H-tetrazol-5-yl)benzenesulfonamide (Compound 120)

Preparation of Compound 120:

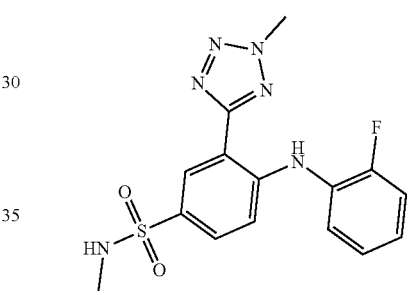

120-1

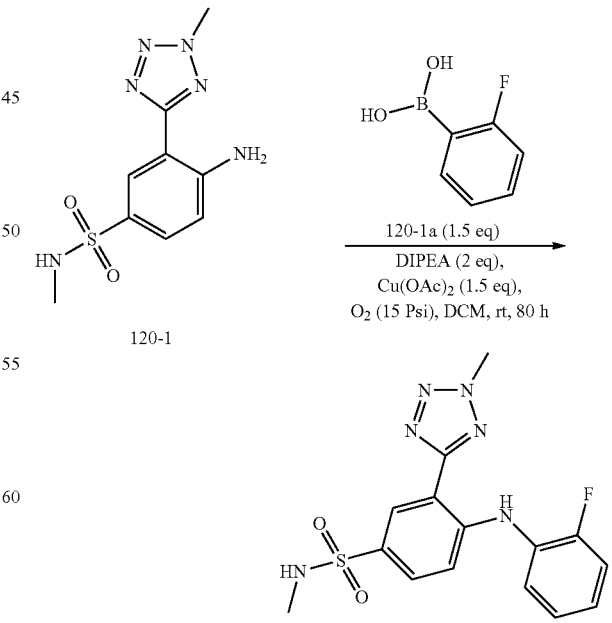

Compound 120

To a solution of compound 120-1 (50 mg, 0.19 mmol, 1 eq) in DCM (3 mL) was added (2-fluorophenyl)boronic acid 120-1a (39.1 mg, 0.28 mmol, 1.50 eq), Cu(OAc)$_2$ (50.8 mg, 0.28 mmol, 1.5 eq) followed by DIEA (48.2 mg, 0.37 mmol, 64.92 uL, 2 eq) under N$_2$. The suspension was degassed under vacuum and purged with 02 several times. The mixture was stirred under O$_2$ (15 psi) at 25° C. for 16 hours. LCMS showed that starting material was remained and 2% of desired product was detected. The reaction was continued to stir at 25° C. for 16 hr. LCMS showed that 5% of desired MS signal was detected. The reaction was continued to stir at 25° C. for 48 hr. LCMS showed that 3% and 8% desired product was detected. The reaction was filtered and concentrated. The crude product was purified by Prep HPLC to give Compound 120 (2.04 mg, 5.63 umol, 3.0% yield). HNMR and LCMS confirmed that desired product was detected. LCMS (ESI): RT=0.735 min, mass calcd. For C$_{15}$H$_{15}$FN$_6$O$_2$S, 362.10 m/z found 362.9[M+H]$^+$. $^1$H NMR (400 MHz, CDCl$_3$) δ 9.30 (s, 1H), 8.71 (d, J=2.0 Hz, 1H), 7.72 (dd, J=9.2, 2.4 Hz, 1H), 7.50-7.40 (m, 1H), 7.25-7.00 (m, 4H), 4.47 (s, 3H), 4.28 (d, J=5.6 Hz, 1H), 2.70 (d, J=5.2 Hz, 3H).

Example 113: N-methyl-3-(1-methyl-1H-imidazol-4-yl)-4-((4-(trifluoromethyl)phenyl)amino)benzenesulfonamide (Compound 121)

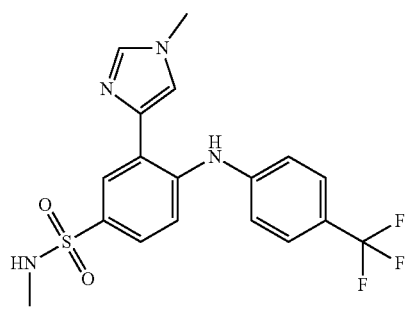 [SMILES: CNS(=O)(=O)c1ccc(Nc2ccc(C(F)(F)F)cc2)c(-c2cn(C)cn2)c1]

Preparation of Compound 121:

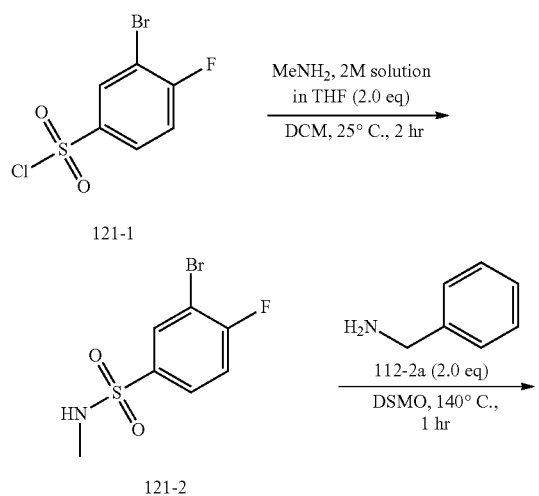

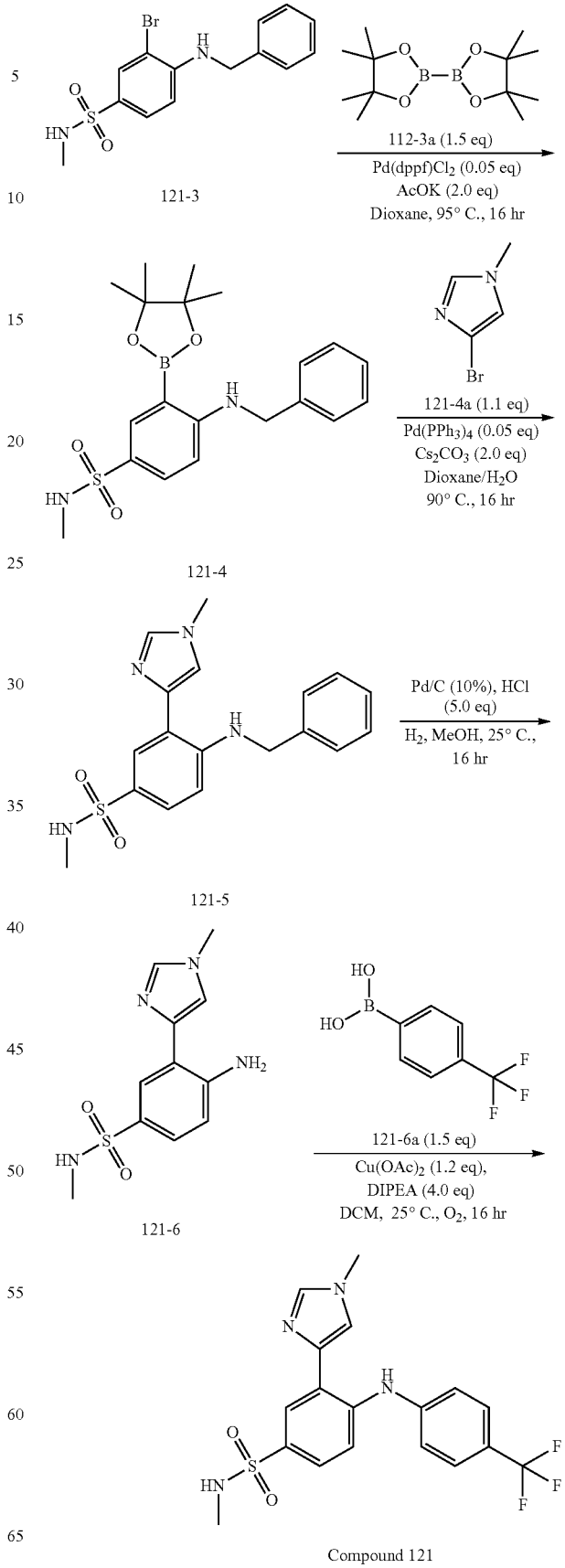

Step 1: 3-Bromo-4-fluoro-N-methylbenzenesulfonamide

To a solution of compound 121-1 (1.0 g, 3.7 mmol, 1.0 eq) in DCM (10 mL) was added MeNH$_2$ (2 M, 3.7 mL, 2.0 eq). The reaction mixture was stirred at 25° C. for 2 hours. The mixture was diluted with water (15 mL) and the resultant mixture was extracted with DCM (30 mL*2). The combined organic layers were dried over Na$_2$SO$_4$, filtered and concentrated to dryness under reduced pressure to obtain the title compound 121-2 (950 mg, 97% yield).

Step 2: 4-(Benzylamino)-3-bromo-N-methylbenzenesulfonamide

A solution of compound 121-2 (850 mg, 3.17 mmol, 1.0 eq) and compound 121-2a (679 mg, 6.34 mmol, 2.0 eq) in DMSO (4 mL) was stirred at 140° C. for 1 hour. The mixture was diluted with water (30 mL) and the resultant mixture was extracted with EA (50 mL*3). The combined organic layers were dried over Na$_2$SO$_4$, filtered and concentrated to dryness under reduced pressure. The residue was purified by column chromatography over silica gel to afford the title compound 121-3 (1.0 g, 89% yield). LCMS (ESI): RT=0.798 min, mass calcd. for C$_{14}$H$_{15}$BrN$_{22}$S 354.00, m/z found 356.7 [M+H]$^+$.

Step 3: 4-(Benzylamino)-N-methyl-3-(4,4,5,5-tetramethyl-1,3,2-dioxaborolan-2-yl)benzenesulfonamide A solution of compound 121-3 (850 mg, 2.39 mmol, 1.0 eq), compound 121-3a (911 mg, 3.59 mmol, 1.5 eq), Pd(dppf)Cl$_2$ (88 mg, 0.12 mmol, 0.05 eq) and AcOK (470 mg, 4.79 mmol, 2.0 eq) in Dioxane (10 mL) was heated to 90° C. and stirred at 90° C. for 16 hours under N$_2$. The reaction mixture was concentrated under reduced pressure. The mixture was diluted with water (30 mL) and the resultant mixture was extracted with EA (50 mL*3). The combined organic layers were dried over Na$_2$SO$_4$, filtered and concentrated under reduced pressure. The residue was purified by column chromatography over silica gel to afford the title compound 121-4 (800 mg, 68% yield). LCMS (ESI): RT=0.827 min, mass calcd. for C$_2$H$_{27}$BN$_2$O$_4$S 402.18, m/z found 402.9 [M+H]$^+$.

Step 4: 4-(Benzylamino)-N-methyl-3-(1-methyl-1H-imidazol-4-yl)benzenesulfonamide To a solution of compound 121-4 (700 mg, 1.74 mmol, 1.0 eq), compound 121-4a (308 mg, 1.91 mmol, 1.1 eq), Cs$_2$CO$_3$ (1.13 g, 3.48 mmol, 2.0 eq) in Dioxane (8 mL) and H$_2$O (2 mL) was added Pd(PPh$_3$)$_4$ (101 mg, 87.0 umol, 0.05 eq) under N$_2$. The reaction mixture was stirred at 90° C. for 16 hours. The reaction mixture was concentrated under reduced pressure. The mixture was diluted with water (20 mL) and the resultant mixture was extracted with EA (50 mL*3). The combined organic layers were dried over Na$_2$SO$_4$, filtered and concentrated to dryness under reduced pressure. The residue was purified by preparative high performance liquid chromatography. The pure fractions were collected and the volatiles were removed under vacuum. The resulting mixture was lyophilized to dryness to remove the solvent residue completely. The title compound 121-5 (180 mg, 28% yield) was obtained. LCMS (ESI): RT=0.592 min, mass calcd. for C$_{18}$H$_{20}$N$_4$O$_2$S 356.13, m/z found 356.9 [M+H]$^+$, $^1$H NMR (400 MHz, CDCl$_3$) δ 9.09 (s, 1H), 7.86 (d, J=2.3 Hz, 1H), 7.49 (dd, J=2.3, 8.8 Hz, 1H), 7.46 (s, 1H), 7.41-7.30 (m, 4H), 7.29-7.26 (m, 2H), 6.62 (d, J=8.8 Hz, 1H), 4.53 (s, 2H), 4.21 (q, J=5.4 Hz, 1H), 3.75 (s, 3H), 2.61 (d, J=5.5 Hz, 3H).

Step 5: 4-Amino-N-methyl-3-(1-methyl-1H-imidazol-4-yl)benzenesulfonamide

To a solution of compound 121-5 (170 mg, 0.477 mmol, 1.0 eq) in MeOH (5 mL) were added Pd/C (50 mg, 10% purity) and HCl (242 mg, 2.38 mmol, 236.79 uL, 36% purity, 5.0 eq) under N$_2$. The suspension was degassed under vacuum and purged with H$_2$ several times. The mixture was stirred under H$_2$ (45 psi) at 25° C. for 16 hours. The reaction mixture was filtered and the filtration was concentrated to obtain the title compound 121-6 (140 mg, crude).

Step 6: N-Methyl-3-(1-methyl-1H-imidazol-4-yl)-4-((4-(trifluoromethyl)phenyl)amino) benzenesulfonamide To a solution of compound 121-6 (140 mg, 0.526 mmol, 1.0 eq), compound 121-6a (150 mg, 0.789 mmol, 1.5 eq) and Cu(OAc)$_2$ (115 mg, 0.631 mmol, 1.2 eq) in DCM (5 mL) was added DIPEA (272 mg, 2.10 mmol, 4.0 eq). The reaction mixture was stirred at 25° C. for 16 hours. The reaction mixture was concentrated under reduced pressure. The mixture was diluted with water (30 mL) and the resultant mixture was extracted with EA (50 mL*3). The combined organic layers were dried over Na$_2$SO$_4$, filtered and concentrated to dryness under reduced pressure. The residue was purified by preparative high performance liquid chromatography. The pure fractions were collected and the volatiles were removed under vacuum. The residue was re-suspended in water (10 mL) and the resulting mixture was lyophilized to dryness to remove the solvent residue completely. Compound 121 (16.20 mg, 39.47 umol, 7.5% yield) was obtained. LCMS (ESI): RT=0.653 min, mass calcd. for C$_{18}$H$_{17}$F$_3$N$_4$O$_2$S 410.10, m/z found 410.9 [M+H]$^+$, H NMR (400 MHz, CDCl$_3$) δ 10.88 (s, 1H), 7.97 (s, 1H), 7.61-7.51 (m, 4H), 7.48 (d, J=8.8 Hz, 1H), 7.33 (d, J=8.3 Hz, 3H), 4.38-4.30 (m, 1H), 3.79 (s, 3H), 2.67 (d, J=5.5 Hz, 3H).

Example 114: 4-((3,4-difluorophenyl)amino)-N-methyl-3-(2-methyl-2H-tetrazol-5-yl)benzenesulfonamide (Compound 122)

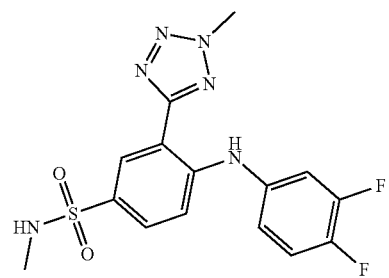 [SMILES: CNS(=O)(=O)c1ccc(Nc2ccc(F)c(F)c2)c(-c2nnn(C)n2)c1]

Preparation of Compound 122:

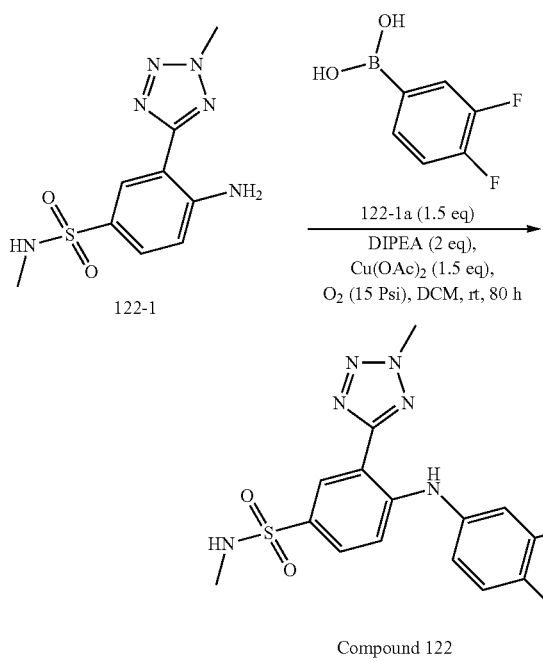

Compound 122

To a solution of compound 122-1 (50 mg, 0.19 mmol, 1 eq) in DCM (3 mL) was added 3,4-difluorophenyl)boronic acid (122-1a, 44.1 mg, 0.28 mmol, 1.5 eq), Cu(OAc)$_2$ (50.8 mg, 0.28 mmol, 1.5 eq) followed by DIEA (72.3 mg, 0.56 mmol, 97.38 uL, 3 eq) under N$_2$. The suspension was degassed under vacuum and purged with 02 several times. The mixture was stirred under O$_2$ (15 psi) at 25° C. for 16 hours. LCMS showed that 7.6% and 55% of desired product were detected. The reaction was filtered and concentrated. The crude product was purified by Prep HPLC to give Compound 122 (21.1 mg, 54.92 umol, 29.47% yield). $^1$HNMR and LCMS confirmed that desired product was obtained. LCMS (ESI): RT=0.748 min, mass calcd. For C$_{15}$H$_{14}$F$_2$N$_6$O$_2$S, 380.10 m/z found 380.9[M+H]$^+$. $^1$H NMR (400 MHz, CDCl$_3$) δ 9.38 (s, 1H), 8.69 (d, J=2.0 Hz, 1H), 7.72 (dd, J=9.2, 2.0 Hz, 1H), 7.25-7.10 (m, 3H), 7.10-7.00 (m, 1H), 4.47 (s, 3H), 4.38 (d, J=5.6 Hz, 1H), 2.69 (d, J=5.2 Hz, 3H).

Example 115: 3-(1-ethyl-1H-imidazol-4-yl)-N-methyl-4-((4-(trifluoromethyl)phenyl)amino) benzenesulfonamide (Compound 123)

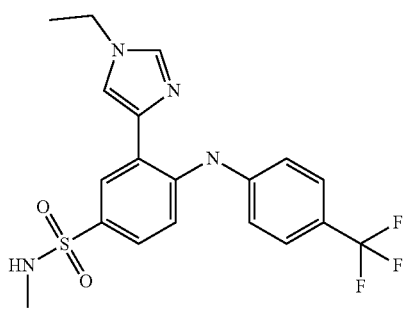

Preparation of Compound 123:

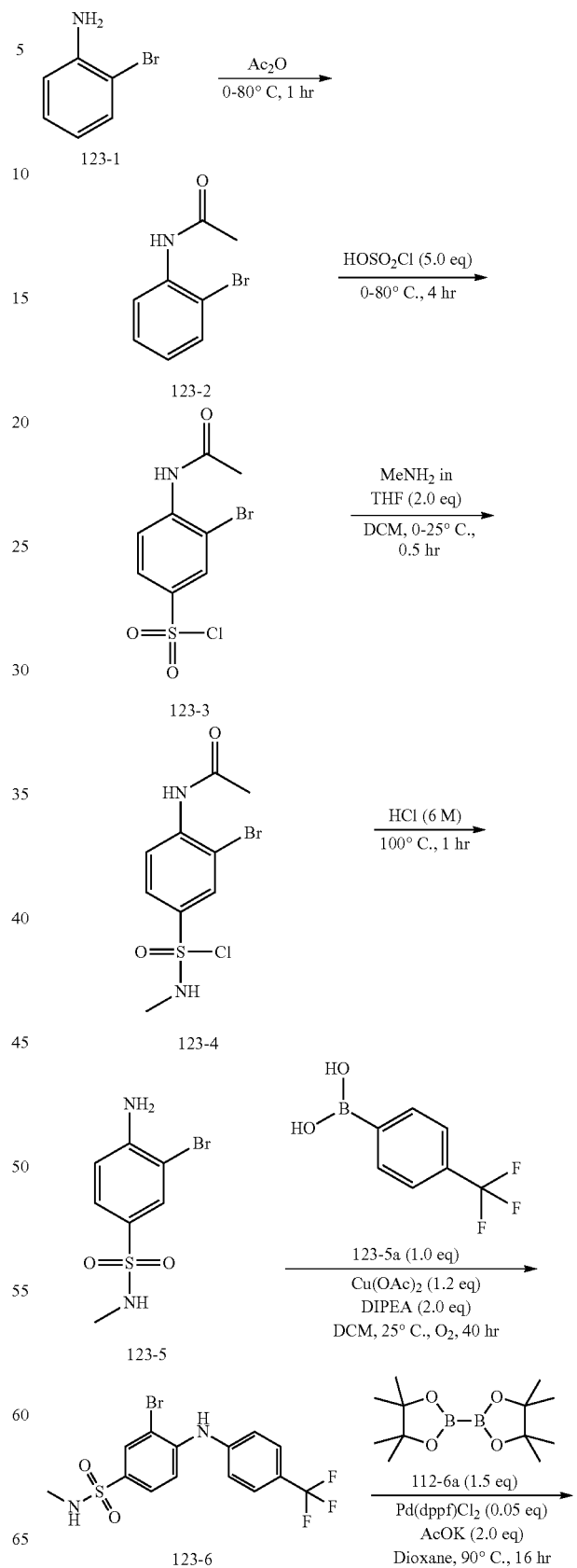

-continued

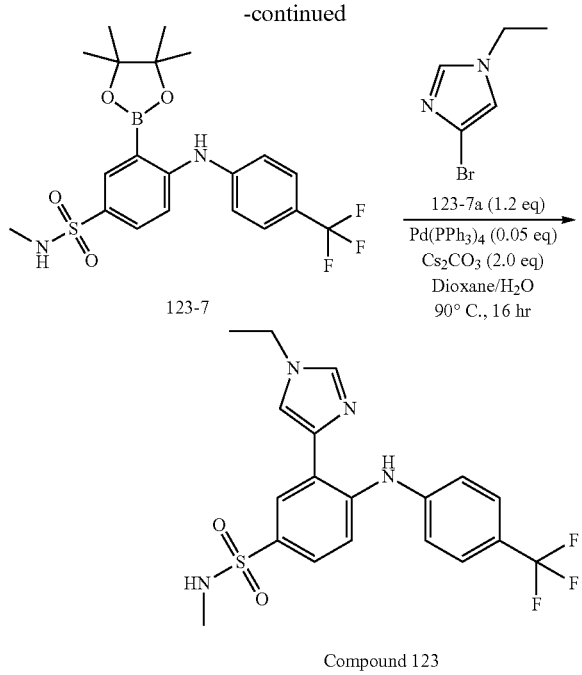

Compound 123

Step 1: N-(2-Bromophenyl)acetamide

To a stirring solution of $Ac_2O$ (54.5 g, 534 mmol, 2.3 eq) was added 2-bromoaniline (40.0 g, 233 mmol, 1.0 eq) at 0° C., and then the reaction mixture was stirred at 80° C. for 1 hour. TLC showed the starting material was consumed. The reaction mixture was concentrated under reduced pressure. Petroleum ether (80 mL) was added the residue, and then the suspension was stirred for 0.5 hour at 25° C. The suspension was filtered to obtain the title compound 123-2 (48 g, 96% yield). $^1$H NMR (400 MHz, $CDCl_3$) δ 8.34 (d, J=8.0 Hz, 1H), 7.61 (brs, 1H), 7.53 (dd, J=1.0, 8.0 Hz, 1H), 7.36-7.28 (m, 1H), 6.98 (t, J=7.4 Hz, 1H), 2.24 (s, 3H)

Step 2: 4-Acetamido-3-bromobenzene-1-sulfonyl chloride

To a stirring of $HSO_3Cl$ (24.1 g, 207 mmol, 4.4 eq) was added compound 123-2 (10.0 g, 46.7 mmol, 1.0 eq) at 0° C. After addition complete, the reaction mixture was stirred at 80° C. for 4 hours. TLC showed the starting material was consumed. The reaction mixture was added to ice (300 g) and then warm up to 25° C. The suspension was extracted with EA (3*80 mL) to obtain the title compound 123-3 (12 g, crude).

Step 3: N-(2-Bromo-4-(N-methylsulfamoyl)phenyl)acetamide

To a solution of compound 123-3 (12.0 g, 38.4 mmol, 1.0 eq) in DCM (120 mL) was added $MeNH_2$ (2 M, 38.4 mL, 2.0 eq) at 0° C. The reaction mixture was stirred at 25° C. for 0.5 hour. TLC showed the starting material was consumed. The reaction mixture was concentrated under reduced pressure. The mixture was diluted with water (50 ml) and the resultant mixture was extracted with EA (100 mL*3). The combined organic layers were dried over $Na_2SO_4$, filtered and concentrated to dryness under reduced pressure. EA (25 mL) was added to the crude product, and then the suspension was filtered to obtain the title compound 123-4 (4.7 g, 40% yield). $^1$H NMR (400 MHz, DMSO-$d_6$) δ 9.66 (s, 1H), 7.99-7.93 (m, 2H), 7.75 (dd, J=2.0, 8.5 Hz, 1H), 7.55 (q, J=4.9 Hz, 1H), 2.44 (d, J=5.0 Hz, 3H), 2.15 (s, 3H).

Step 4: 4-Amino-3-bromo-N-methylbenzenesulfonamide

A solution of compound 123-4 (4.7 g, 15 mmol, 1.0 eq) in HCl (50 mL) was stirred at 100° C. for 1 hour. TLC (Petroleum ether: Ethyl acetate=2:1) showed the starting material was consumed. The reaction mixture was basified with aq. NaOH (6M) until pH=9 and the resulting suspension was extracted with EA (150 mL*3). The combined organic layers were dried over $Na_2SO_4$, filtered and concentrated to dryness under reduced pressure to obtain the title compound 123-5 (3.9 g, 95% yield). $^1$H NMR (400 MHz, DMSO-$d_6$) δ 7.68 (d, J=1.8 Hz, 1H), 7.43 (dd, J=1.8, 8.5 Hz, 1H), 7.12 (q, J=4.9 Hz, 1H), 6.86 (d, J=8.5 Hz, 1H), 6.15 (s, 2H), 2.36 (d, J=5.0 Hz, 3H).

Step 5: 3-Bromo-N-methyl-4-((4-(trifluoromethyl) phenyl)amino)benzenesulfonamide To a solution of compound 123-5 (3.9 g, 15 mmol, 1.0 eq), compound 123-5a (4.2 g, 22 mmol, 1.5 eq) and $Cu(OAc)_2$ (3.2 g, 18 mmol, 1.2 eq) in DCM (40 mL) was added DIPEA (5.7 g, 44 mmol, 3.0 eq). The reaction mixture was stirred at 25° C. for 40 hours under $O_2$. LCMS showed ~50% of Reactant 123-5 was remained and one peak with desired MS was detected. The reaction mixture was concentrated under reduced pressure. EA (120 mL) was added, and then the suspension was filtered. The organic layer was washed with water (30 mL*2), dried over $Na_2SO_4$, filtered and concentrated to dryness under reduced pressure. The residue was purified by column chromatography over silica gel to afford the title compound as a mixture. The residue was purified by column chromatography over silica gel to afford the title compound 123-6 (620 mg, 10% yield). $^1$H NMR (400 MHz, DMSO-$d_6$) δ 8.51 (s, 1H), 7.96 (d, J=2.0 Hz, 1H), 7.68-7.61 (m, 3H), 7.49 (d, J=8.5 Hz, 1H), 7.45 (q, J=5.1 Hz, 1H), 7.31 (d, J=8.5 Hz, 2H), 2.43 (d, J=5.0 Hz, 3H).

Step 6: N-methyl-3-(4,4,5,5-tetramethyl-1,3,2-dioxaborolan-2-yl)-4-((4-(trifluoromethyl) phenyl) amino)benzenesulfonamide A solution of compound 123-6 (150 mg, 0.37 mmol, 1.0 eq), compound 123-6a (140 mg, 0.55 mmol, 1.5 eq), Pd(dppf)$Cl_2$ (13 mg, 18 umol, 0.05 eq) and AcOK (72 mg, 0.73 mmol, 2.0 eq) in Dioxane (3 mL) was heated to 90° C. and stirred at 90° C. for 16 hours under $N_2$. LCMS showed Reactant 123-6 was consumed completely and one main peak with desired MS was detected. TLC showed the starting material was consumed. The reaction mixture was concentrated under reduced pressure. The mixture was diluted with water (10 mL) and the resultant mixture was extracted with EA (30 mL*3). The combined organic layers were dried over $Na_2SO_4$, filtered and concentrated to dryness under reduced pressure. The residue was purified by Prep-TLC to obtain the title compound 123-7 (80 mg, 48% yield). $^1$H NMR (400 MHz, $CDCl_3$) δ 8.29 (s, 1H), 8.23 (d, J=2.3 Hz, 1H), 7.76 (dd, J=2.4, 8.9 Hz, 1H), 7.60 (d, J=8.5 Hz, 2H), 7.30 (t, J=8.9 Hz, 3H), 4.24 (q, J=5.4 Hz, 1H), 2.67 (d, J=5.3 Hz, 3H), 1.38 (s, 12H).

Step 7: 3-(1-Ethyl-H-imidazol-4-yl)-N-methyl-4-((4-(trifluoromethyl)phenyl)amino)benzenesulfonamide To a solution of compound 123-7 (80 mg, 0.18 mmol, 1.0 eq), compound 123-7a (37 mg, 0.21 mmol, 1.2 eq) and Cs$_2$CO$_3$ (114 mg, 0.35 mmol, 2.0 eq) in Dioxane (3 mL) and H$_2$O (0.6 mL) was added Pd(PPh$_3$)$_4$ (10 mg, 8.8 umol, 0.05 eq). The suspension was degassed under vacuum and purged with N$_2$ several times. The reaction mixture was stirred at 90° C. for 16 hours. LCMS showed Reactant 7 was consumed completely and one main peak with desired MS was detected. The reaction mixture was concentrated under reduced pressure. The mixture was diluted with water (10 mL) and the resultant mixture was extracted with EA (30 mL*3). The combined organic layers were dried over Na$_2$SO$_4$, filtered and concentrated to dryness under reduced pressure. The residue was purified by Prep-TLC to obtain the Compound 123 as a crude product. The residue was purified by prep-HPLC to obtain Compound 123 (4.68 mg, 6.2% yield). LCMS (ESI): RT=0.668 min, mass calcd. for C$_{19}$H$_{19}$F$_3$N$_4$O$_2$S 424.12, m/z found 425.0 [M+H]$^+$, $^1$H NMR (400 MHz, CDCl$_3$) δ 10.94 (s, 1H), 7.98 (d, J=2.3 Hz, 1H), 7.60-7.54 (m, 4H), 7.51-7.46 (m, 1H), 7.38 (s, 1H), 7.33 (d, J=8.3 Hz, 2H), 4.27 (q, J=5.2 Hz, 1H), 4.08 (q, J=7.4 Hz, 2H), 2.68 (d, J=5.5 Hz, 3H), 1.56-1.52 (m, 3H).

Example 116: N-methyl-3-(1-methyl-1H-imidazol-4-yl)-4-((3-(trifluoromethyl)phenyl) amino)benzenesulfonamide (Compound 124)

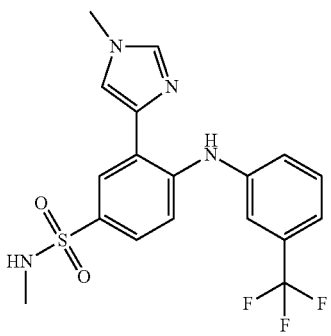

Preparation of Compound 124:

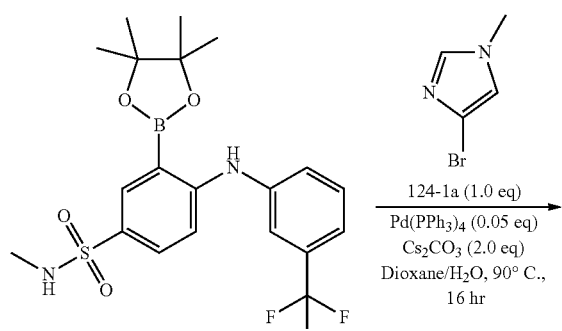

124-1

-continued

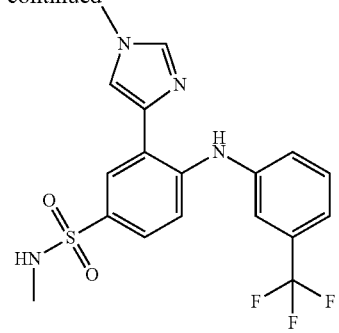

Compound 124

To a solution of compound 124-1 (120 mg, 0.26 mmol, 1.0 eq), compound 124-1a (42 mg, 0.26 mmol, 1.0 eq) and Cs$_2$CO$_3$ (325 mg, 0.17 mmol, 2.0 eq) in Dioxane (3 mL) and H$_2$O (0.6 mL) was added Pd(PPh$_3$)$_4$ (15 mg, 13 umol, 0.05 eq). The suspension was degassed under vacuum and purged with N$_2$ several times. The reaction mixture was stirred at 90° C. for 16 hours. LCMS showed Reactant 124-1 was consumed completely and one main peak with desired MS was detected. The reaction mixture was concentrated under reduced pressure. The mixture was diluted with water (10 mL) and the resultant mixture was extracted with EA (30 mL*3). The combined organic layers were dried over Na$_2$SO$_4$, filtered and concentrated to dryness under reduced pressure. The residue was purified by prep-HPLC to obtain Compound 124 (12.40 mg, 11% yield). LCMS (ESI): RT=0.650 min, mass calcd. for C$_{18}$H$_{17}$F$_3$N$_4$O$_2$S 410.10, m/z found 410.9 [M+H]$^+$, $^1$H NMR (400 MHz, CDCl$_3$) δ 10.83 (s, 1H), 7.97 (d, J=2.0 Hz, 1H), 7.56 (dd, J=2.3, 8.8 Hz, 1H), 7.51 (d, J=5.8 Hz, 2H), 7.48-7.41 (m, 2H), 7.38-7.33 (m, 2H), 7.29 (d, J=6.3 Hz, 1H), 4.33 (q, J=5.3 Hz, 1H), 3.78 (s, 3H), 2.67 (d, J=5.5 Hz, 3H).

Example 117: 3-(1-ethyl-1H-imidazol-4-yl)-N-methyl-4-((3-(trifluoromethyl)phenyl)amino) benzenesulfonamide (Compound 125)

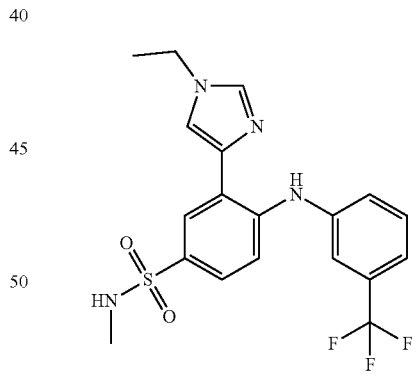

Preparation of Compound 125:

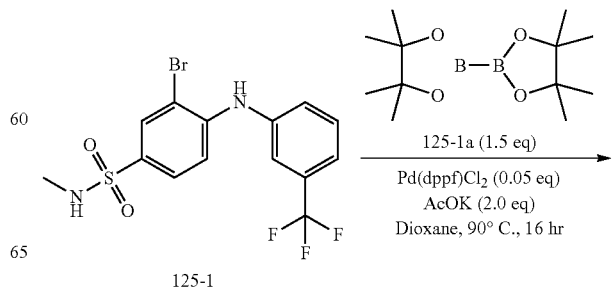

125-1

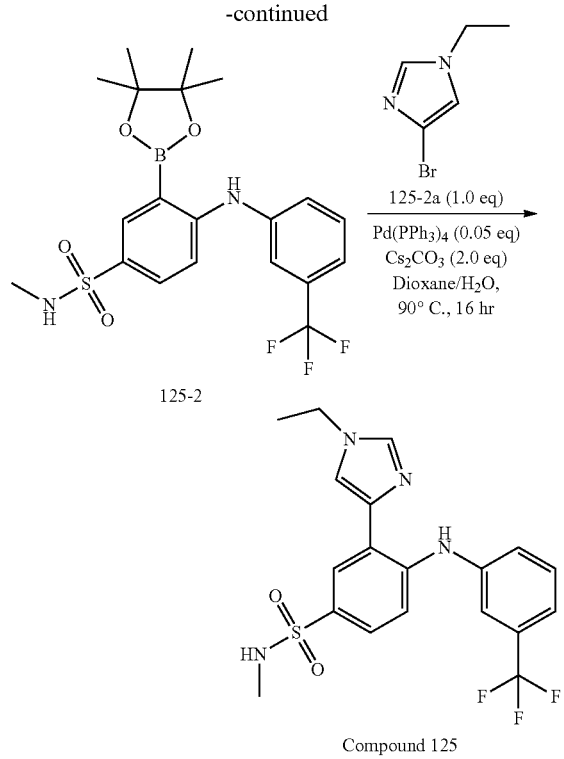

Compound 125

Step 1: N-Methyl-3-(4,4,5,5-tetramethyl-1,3,2-dioxaborolan-2-yl)-4-((3-(trifluoromethyl) phenyl) amino)benzenesulfonamide A solution of compound 125-1 (380 mg, 0.93 mmol, 1.0 eq), compound 125-1a (354 mg, 1.39 mmol, 1.5 eq), Pd(dppf)Cl$_2$ (34 mg, 46 umol, 0.05 eq) and AcOK (182 mg, 1.86 mmol, 2.0 eq) in Dioxane (5 mL) was heated to 90° C. and stirred at 90° C. for 16 hours under N$_2$. TLC showed the starting material was consumed. The reaction mixture was concentrated under reduced pressure. The mixture was diluted with water (30 mL) and the resultant mixture was extracted with EA (50 mL*3). The combined organic layers were dried over Na$_2$SO$_4$, filtered and concentrated to dryness under reduced pressure. The residue was purified by Prep-TLC to obtain the title compound 125-2 (310 mg, 73% yield).

Step 2: 3-(1-Ethyl-H-imidazol-4-yl)-N-methyl-4-((3-(trifluoromethyl)phenyl)amino) benzenesulfonamide To a solution of compound 125-2 (100 mg, 0.22 mmol, 1.0 eq), compound 125-2a (38 mg, 0.22 mmol, 1.0 eq) and Cs$_2$CO$_3$ (143 mg, 0.44 mmol, 2 eq) in Dioxane (3 mL) and H$_2$O (0.6 mL) was added Pd(PPh$_3$)$_4$ (13 mg, 11 umol, 0.05 eq). The suspension was degassed under vacuum and purged with N$_2$ several times. The reaction mixture was stirred at 90° C. for 16 hours. LCMS showed Reactant 125-2 was consumed completely and one main peak with desired MS was detected. The reaction mixture was concentrated under reduced pressure. The mixture was diluted with water (10 mL) and the resultant mixture was extracted with EA (30 mL*3). The combined organic layers were dried over Na$_2$SO$_4$, filtered and concentrated to dryness under reduced pressure. The residue was purified by prep-HPLC to obtain Compound 125 (15.56 mg, 16.7% yield). LCMS (ESI): RT=0.664 min, mass calcd. for C$_{19}$H$_{19}$F$_3$N$_4$O$_2$S 424.12, m/z found 424.9 [M+H]$^+$, $^1$H NMR (400 MHz, CDCl$_3$) δ 10.87 (s, 1H), 7.98 (d, J=2.3 Hz, 1H), 7.58-7.54 (m, 2H), 7.51 (s, 1H), 7.48-7.41 (m, 2H), 7.40-7.35 (m, 2H), 7.29 (d, J=6.8 Hz, 1H), 4.30 (d, J=5.0 Hz, 1H), 4.08 (q, J=7.4 Hz, 2H), 2.67 (d, J=5.5 Hz, 3H), 1.54 (t, J=7.4 Hz, 3H).

Example 118: 3-(1-cyclopropyl-1H-imidazol-4-yl)-N-methyl-4-((4-(trifluoromethyl)phenyl) amino) benzenesulfonamide (Compound 126)

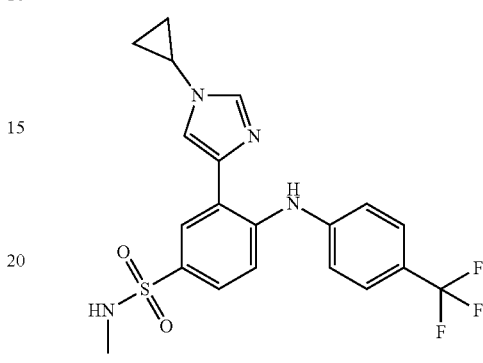

Preparation of Compound 126:

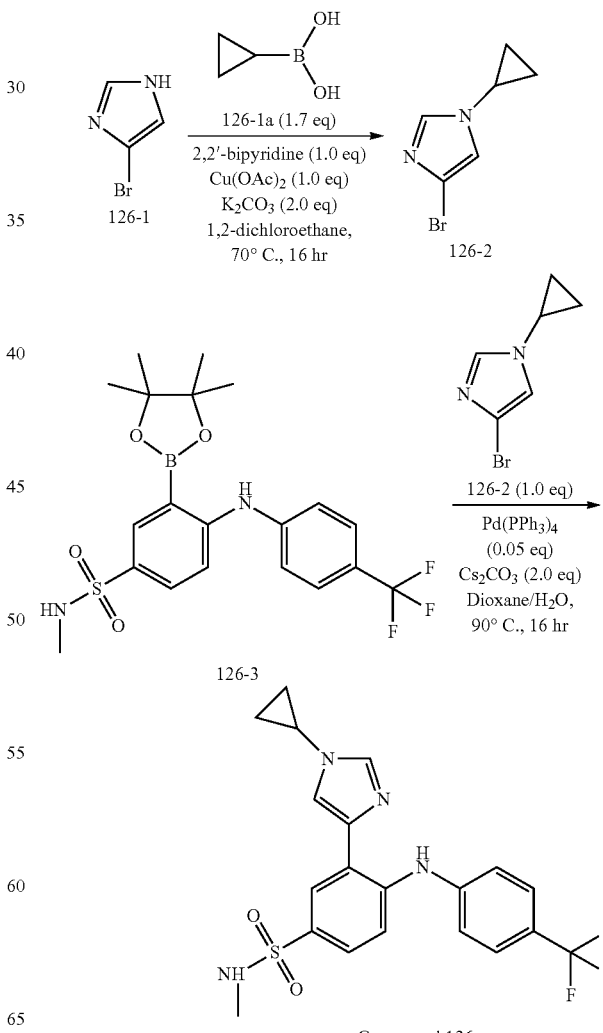

Compound 126

Step 1: 4-Bromo-1-cyclopropyl-1H-imidazole

A solution of compound 126-1 (5.0 g, 34 mmol, 1.0 eq), compound 126-1a (5.0 g, 58 mmol, 1.7 eq), Cu(OAc)$_2$ (6.2 g, 34 mmol, 1.0 eq), 2,2'-bipyridine (5.3 g, 34 mmol, 1.0 eq) and potassium carbonate (9.4 g, 68 mmol, 2.0 eq) in 1,2-dichloroethane (150 mL) was stirred at 70° C. for 16 hrs. TLC showed one new spot was formed. EA (220 mL) was added, and then the suspension was filtered. The organic layer was concentrated under reduced pressure. The mixture was diluted with water (80 mL) and the resultant mixture was extracted with EA (150 mL*3). The combined organic layers were dried over Na$_2$SO$_4$, filtered and concentrated to dryness under reduced pressure. The residue was purified by column chromatography over silica gel to afford the title compound 126-2 as a crude product. The residue was purified by Prep-TLC to obtain the title compound 126-2 (1.2 g, 18% yield). $^1$H NMR (400 MHz, CDCl$_3$) δ 7.42 (s, 1H), 6.95 (d, J=1.3 Hz, 1H), 3.36-3.28 (m, 1H), 1.06-0.90 (m, 4H).

Step 2: 3-(1-Cyclopropyl-1H-imidazol-4-yl)-N-methyl-4-((4-(trifluoromethyl)phenyl) amino)benzenesulfonamide To a solution of compound 126-3 (70 mg, 0.15 mmol, 1.0 eq), compound 126-3a (34 mg, 0.18 mmol, 1.2 eq) and Cs$_2$CO$_3$ (100 mg, 0.31 mmol, 2.0 eq) in Dioxane (3 mL) and H$_2$O (0.6 mL) was added Pd(PPh$_3$)$_4$ (8.9 mg, 7.7 umol, 0.05 eq). The suspension was degassed under vacuum and purged with N$_2$ several times. The reaction mixture was stirred at 90° C. for 16 hours. LCMS showed Reactant 126-3 was consumed completely and one main peak with desired MS was detected. The reaction mixture was concentrated under reduced pressure. The mixture was diluted with water (20 mL) and the resultant mixture was extracted with EA (50 mL*3). The combined organic layers were dried over Na$_2$SO$_4$, filtered and concentrated to dryness under reduced pressure. The residue was purified by Prep-TLC (to obtain Compound 126 as a crude product. The crude product was purified by prep-HPLC to obtain the title Compound 126 (5.39 mg, 7.4% yield, HCl). LCMS (ESI): RT=0.677 min, mass calcd. for C$_{20}$H$_{19}$F$_3$N$_4$O$_2$S 436.12, m/z found 436.9 [M+H]$^+$, H NMR (400 MHz, DMSO-d$_6$) δ 9.58-9.10 (m, 1H), 8.95 (s, 1H), 8.00 (s, 1H), 7.91 (s, 1H), 7.72-7.67 (m, 1H), 7.59 (dd, J=8.7, 15.7 Hz, 3H), 7.40 (d, J=4.5 Hz, 1H), 7.24 (d, J=8.5 Hz, 2H), 3.79-3.71 (m, 1H), 2.45 (d, J=4.5 Hz, 3H), 1.15-1.05 (m, 4H).

Example 119: 3-(1-cyclopropyl-1H-imidazol-4-yl)-N-methyl-4-((3-(trifluoromethyl)phenyl) amino) benzenesulfonamide (Compound 127)

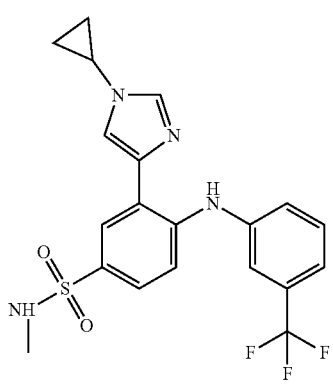 [SMILES: CNS(=O)(=O)c1ccc(Nc2cccc(C(F)(F)F)c2)c(-c2cn(C3CC3)cn2)c1]

Preparation of Compound 127:

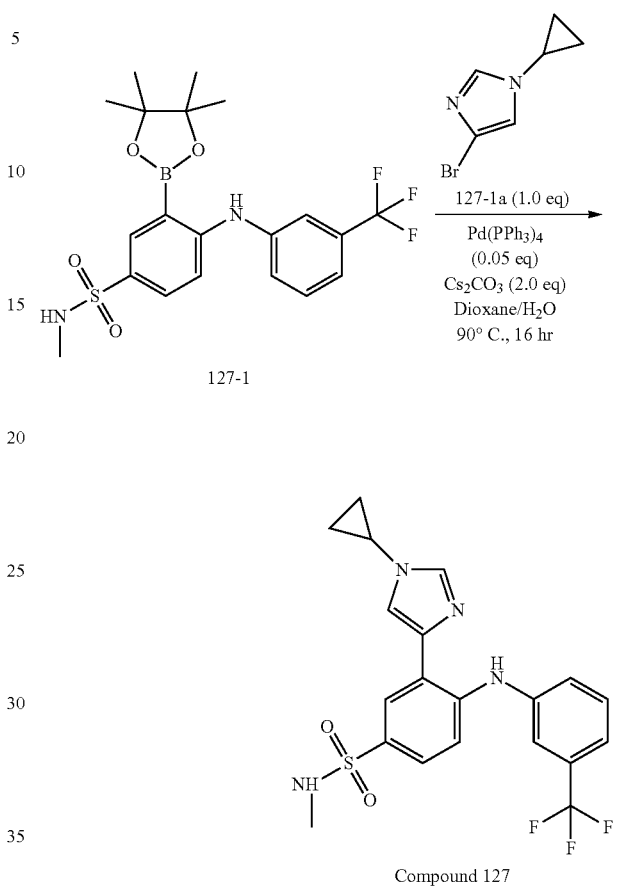

Compound 127

To a solution of compound 127-1 (100 mg, 0.22 mmol, 1.0 eq), compound 127-1a (41 mg, 0.22 mmol, 1.2 eq) and Cs$_2$CO$_3$ (143 mg, 0.438 mmol, 2.0 eq) in Dioxane (3 mL) and H$_2$O (0.6 mL) was added Pd(PPh$_3$)$_4$ (13 mg, 11 umol, 0.05 eq). The suspension was degassed under vacuum and purged with N$_2$ several times. The reaction mixture was stirred at 90° C. for 16 hours. LCMS showed Reactant 127-1 was consumed completely and one main peak with desired MS was detected. The reaction mixture was concentrated under reduced pressure. The mixture was diluted with water (10 mL) and the resultant mixture was extracted with EA (30 mL*3). The combined organic layers were dried over Na$_2$SO$_4$, filtered and concentrated to dryness under reduced pressure. The residue was purified by Prep-TLC to obtain Compound 127 as a crude product. The crude product was purified by prep-HPLC to obtain the title Compound 127 (19.18 mg, 18% yield, HCl). LCMS (ESI): RT=0.675 min, mass calcd. for C$_{20}$H$_{19}$F$_3$N$_4$O$_2$S 436.12, m/z found 436.9 [M+H]$^+$, $^1$H NMR (400 MHz, DMSO-d$_6$) δ 9.19-8.85 (m, 2H), 8.04 (s, 1H), 7.85 (d, J=2.0 Hz, 1H), 7.70 (dd, J=2.0, 8.5 Hz, 1H), 7.56-7.50 (m, 1H), 7.48-7.35 (m, 4H), 7.31 (d, J=7.8 Hz, 1H), 3.81-3.75 (m, 1H), 2.44 (d, J=4.3 Hz, 3H), 1.17-1.06 (m, 4H).

Example 120: N-methyl-3-(2-methyltetrazol-5-yl)-4-(4-phenylanilino) benzenesulfonamide (Compound 128) and N,N-dimethyl-3-(2-methyltetrazol-5-yl)-4-(4-phenylanilino)benzenesulfonamide (Compound 129)

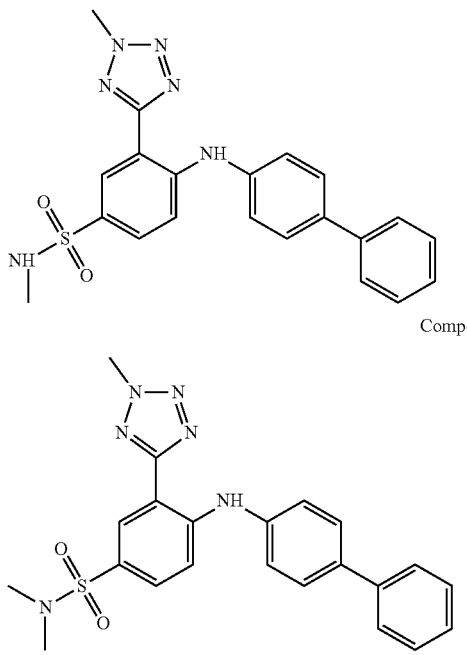

Preparation of Compound 128 and Compound 129:

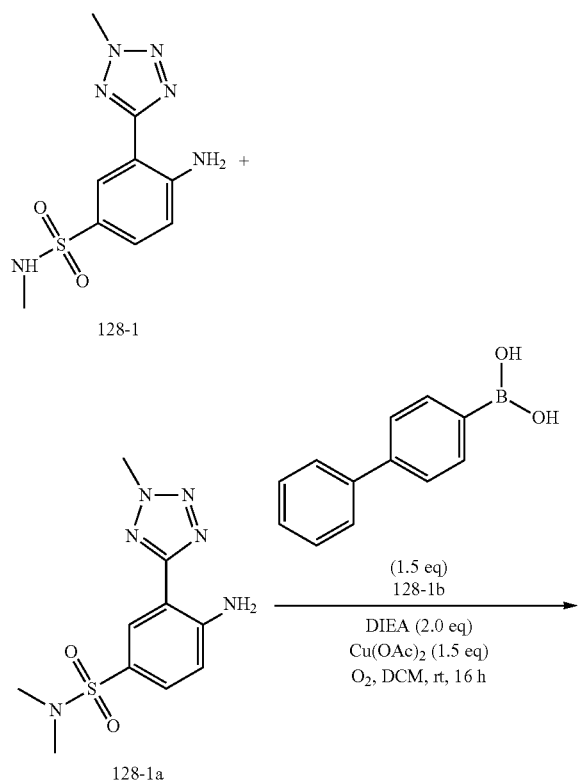

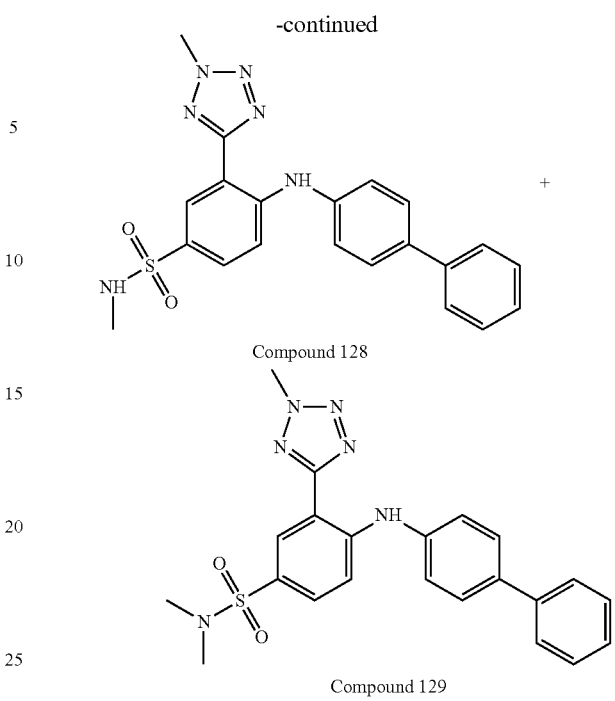

To a mixture of compound 128-1 and compound 128-1a (70 mg, 0.26 mol, 1 eq), compound 128-1b and Cu(OAc)$_2$ (71.1 mg, 0.39 mol, 1.5 eq) in DCM (30 mL) was added DIEA (67.4 mg, 0.52 mol, 91 uL, 2 eq). Then the suspension was degassed under vacuum and purged with O$_2$ several times. The mixture was stirred under O$_2$ (15 psi) at 25° C. for 16 hours. LCMS showed 41% of desired compound was detected. The reaction mixture was filtered and concentrated in vacuum to give the residue. The crude product was purified by prep-HPLC. LCMS and $^1$H NMR confirmed that Compound 128 (23.07 mg, 21.0% yield) was obtained. LCMS and $^1$H NMR confirmed that Compound 129 (2.02 mg, 1.8% yield) was obtained. Compound 128: LCMS (ESI): RT=0.809 min, mass calcd. for C$_{21}$H$_{20}$N$_6$O$_2$S, 420.14 m/z found 420.9[M+H]$^+$. $^1$H NMR (400 MHz, CDCl$_3$) δ 9.48 (s, 1H), 8.70 (d, J=2.0 Hz, 1H), 7.72 (dd, J=2.4, 8.9 Hz, 1H), 7.63 (dd, J=8.2, 13.2 Hz, 4H), 7.47 (t, J=7.7 Hz, 2H), 7.42-7.34 (m, 4H), 4.48 (s, 3H), 4.25 (d, J=5.0 Hz, 1H), 2.71 (d, J=5.5 Hz, 3H). Compound 129: LCMS (ESI): RT=0.856 min, mass calcd. for C$_{22}$H$_{22}$N$_6$O$_2$S, 434.15 m/z found 435.0[M+H]$^+$. $^1$H NMR (400 MHz, CDCl$_3$) δ 9.50 (s, 1H), 8.63 (d, J=2.3 Hz, 1H), 7.68-7.61 (m, 5H), 7.47 (t, J=7.7 Hz, 2H), 7.44-7.37 (m, 4H), 4.49 (s, 3H), 2.76 (s, 6H).

Example 121: N-methyl-3-(2-methyltetrazol-5-yl)-4-(4-phenoxyanilino) benzenesulfonamide (Compound 130)

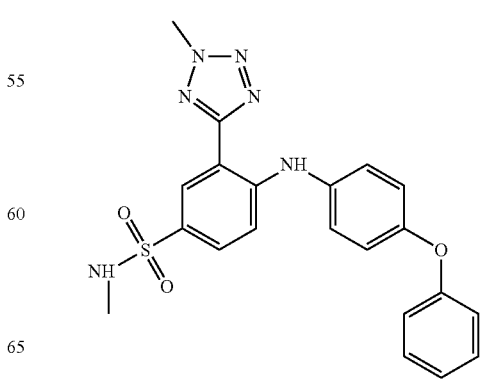

Preparation of Compound 130:

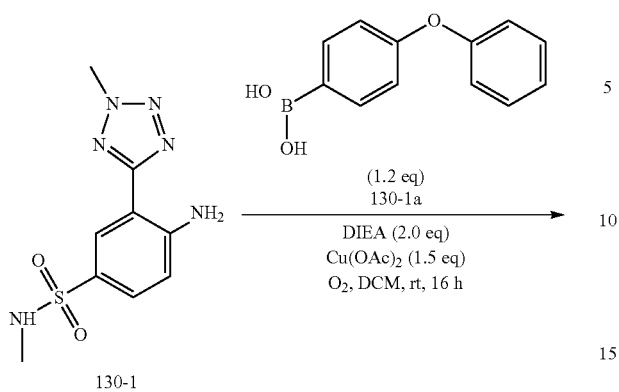

130-1

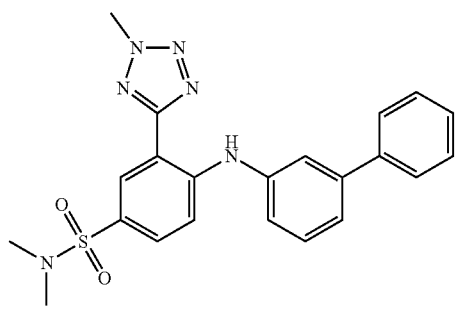

(1.2 eq)
130-1a

DIEA (2.0 eq)
Cu(OAc)₂ (1.5 eq)
O₂, DCM, rt, 16 h

Compound 130

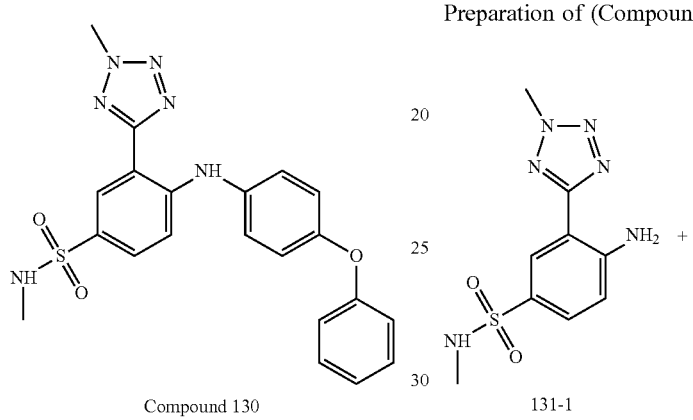

A mixture of compound 130-1 (70 mg, 0.26 mol, 1 eq), compound 130-1a (55.8 mg, 0.26 mol, 1 eq) and Cu(OAc)₂ (71.1 mg, 0.39 mol, 1.5 eq) in DCM (30 mL) was added DIEA (67.4 mg, 0.52 mol, 91 uL, 2 eq). The suspension was degassed under vacuum and purged with O₂ several times. The mixture was stirred under O₂ (15 psi) at 25° C. for 16 hours. LCMS showed 37% of desired product was detected. The reaction mixture was filtered and concentrated in vacuum to give the residue. The residue was purified by prep-HPLC. LCMS and H NMR confirmed that Compound 130 (22.02 mg, 19.3% yield) was obtained. LCMS (ESI): RT=0.804 min, mass calcd. for $C_{21}H_{20}N_6O_3S$, 436.49 m/z found 459.0[M+Na]⁺. ¹H NMR (400 MHz, CDCl₃) δ 9.34 (s, 1H), 8.71 (d, J=2.0 Hz, 1H), 7.74-7.68 (m, 1H), 7.39 (t, J=7.9 Hz, 2H), 7.31 (s, 2H), 7.24-7.13 (m, 2H), 7.09 (dd, J=6.0, 8.0 Hz, 4H), 4.49 (s, 3H), 4.27 (br d, J=5.5 Hz, 1H), 2.71 (d, J=5.5 Hz, 3H).

Example 122: N-methyl-3-(2-methyltetrazol-5-yl)-4-(3-phenylanilino) benzenesulfonamide (Compound 131) and N, N-dimethyl-3-(2-methyltetrazol-5-yl)-4-(3-phenylanilino) benzenesulfonamide (Compound 132)

Compound 131

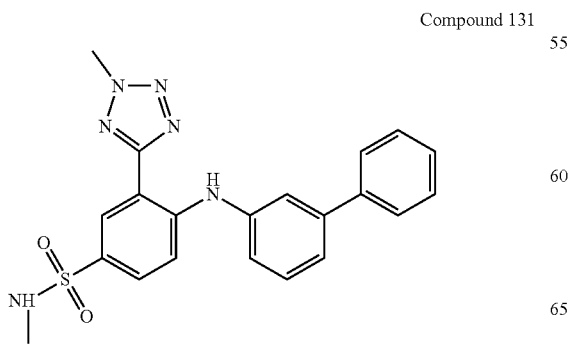

Compound 132

Preparation of (Compound 131) and (Compound 132):

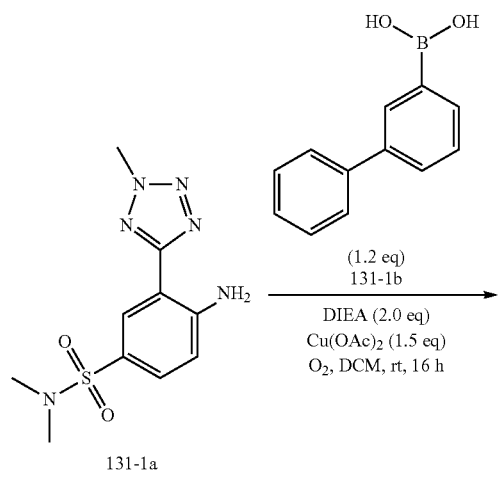

(1.2 eq)
131-1b

DIEA (2.0 eq)
Cu(OAc)₂ (1.5 eq)
O₂, DCM, rt, 16 h 131-1a

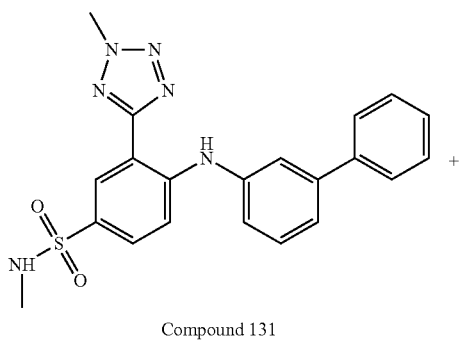

Compound 131

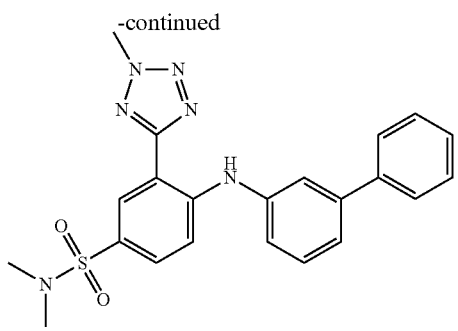

Compound 132

To a mixture of compound 131-1 (70 mg, 0.26 mol, 1 eq), compound 131-1a (1.00 eq), compound 131-1b (51.7 mg, 0.26 mol, 1 eq) and Cu(OAc)$_2$ (71.1 mg, 0.39 mol, 1.5 eq) in DCM (25 mL) was added DIEA (67.4 mg, 0.52 mol, 91 uL, 2 eq). The suspension was degassed under vacuum and purged with O2 several times. The mixture was stirred under O2 (15 psi) at 25° C. for 16 hours. LCMS showed 22% of desired compound was detected. The reaction mixture was filtered and concentrated in vacuum to give the residue. The crude product was purified by prep-HPLC. LCMS and H NMR confirmed that Compound 131 (9.86 mg, 8.9% yield) was obtained. LCMS (ESI): RT=0.807 min, mass calcd. for $C_{21}H_{20}N_6O_2S$, 420.49 m/z found 421.1[M+H]$^+$. $^1$H NMR (400 MHz, CDCl$_3$) δ 9.48 (s, 1H), 8.71 (d, J=2.3 Hz, 1H), 7.71 (dd, J=1.9, 9.2 Hz, 1H), 7.61 (d, J=7.3 Hz, 2H), 7.54 (s, 1H), 7.52-7.42 (m, 4H), 7.41-7.35 (m, 2H), 7.31 (br d, J=7.3 Hz, 1H), 4.47 (s, 3H), 4.25 (br d, J=5.5 Hz, 1H), 2.70 (d, J=5.3 Hz, 2H), 2.72-2.68 (m, 1H). LCMS and H NMR confirmed that Compound 132 (4.18 mg, 3.7% yield) was obtained. LCMS (ESI): RT=0.853 min, mass calcd. for $C_{22}H_{22}N_6O_2S$, 434.51 m/z found 435[M+H]$^+$. $^1$H NMR (400 MHz, CDCl$_3$) δ 8.62 (d, J=2.0 Hz, 1H), 7.66-7.59 (m, 3H), 7.54 (s, 1H), 7.50-7.42 (m, 5H), 7.39 (d, J=8.8 Hz, 2H), 7.31 (br d, J=6.8 Hz, 1H), 4.48 (s, 3H), 2.75 (s, 6H).

Example 123:3-(5-amino-1,3,4-oxadiazol-2-yl)-N-methyl-4-[4-(trifluoromethyl)anilino]benzenesulfonamide (Compound 133)

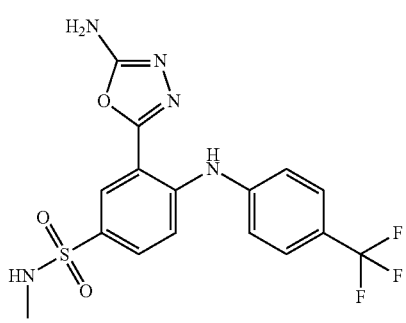

Preparation of Compound 133

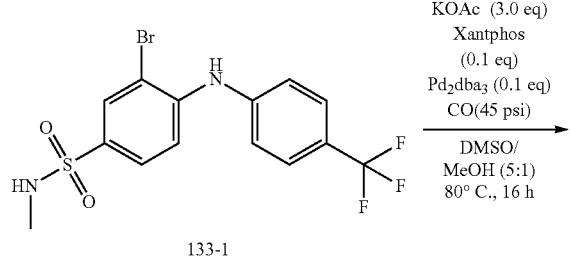

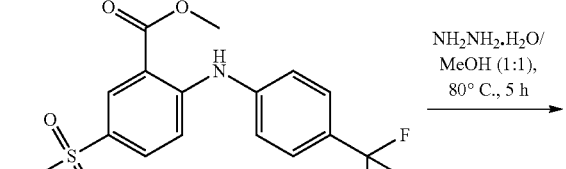

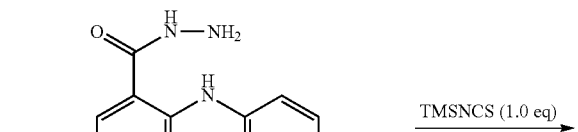

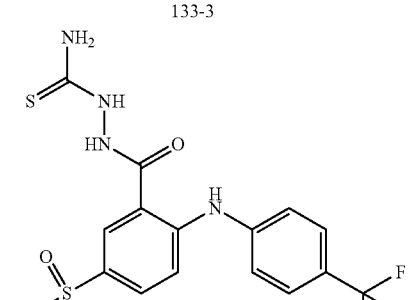

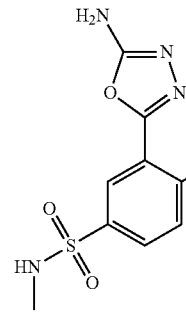

Compound 133

Step 1: methyl 5-(methylsulfamoyl)-2-[4-(trifluoromethyl)anilino]benzoate

To a solution of compound 133-1 (100 mg, 0.24 mmol, 1 eq), KOAc (71.9 mg, 0.73 mmol, 3 eq) and Xantphos (14.1 mg, 24.4 umol, 0.1 eq) in DMSO (10 mL) and MeOH (2 mL) was added Pd$_2$(dba)$_3$ (22.4 mg, 24.4 umol, 0.1 eq). The suspension was degassed under vacuum and purged with CO several times. The mixture was stirred under CO (45 psi) at 80° C. for 16 hours. LCMS showed that desired product was detected. The MeOH was removed. The residue was diluted with EA (40 mL) and washed with brine (2*20 mL). The organic layer was dried over Na$_2$SO$_4$ and concentrated. The residue was purified by flash silica gel chromatography to give compound 133-2 (80 mg, crude).

Step 2: 3-(hydrazinecarbonyl)-N-methyl-4-[4-(trifluoromethyl)anilino]benzenesulfonamide To a solution of compound 133-2 (80 mg, 0.2 mmol, 1 eq) in MeOH (1 mL) was added hydrazine hydrate (1.03 g, 17.5 mmol, 1.00 mL, 85% solution, 84.90 eq). The reaction was heated at 80° C. for 5 hr. LCMS showed that 40% of desired product was detected. The reaction was concentrated. The residue was diluted with EA (30 mL) and washed with water (2*10 mL). The organic layer was dried over Na$_2$SO$_4$ and concentrated. The crude product was purified by column chromatography on silica gel (EA:PE=1:10-1:1) to give compound 133-3 (15 mg, 18.0% yield).

Step 3: [[5-(methylsulfamoyl)-2-[4-(trifluoromethyl)anilino]benzoyl]amino]thiourea To a solution of compound 133-3 (15 mg, 38.6 umol, 1 eq) in THF (3 mL) was added isothiocyanatotrimethylsilane (5.07 mg, 38.6 umol, 1 eq). The reaction was stirred at 50° C. for 16 hr. LCMS showed that starting material was remained and desired product was detected. Additional of isothiocyanatotrimethylsilane (10 mg) was added. The reaction was stirred at 50° C. for 1 hr. LCMS showed that 95% of desired product was detected. The reaction was concentrated. The compound 133-4 (15 mg, 82.4% yield) was used for next step directly.

Step 4: 3-(5-amino-1,3,4-oxadiazol-2-yl)-N-methyl-4-[4-(trifluoromethyl)anilino]benzenesulfonamide To a solution of compound 133-4 (15 mg, 33.5 umol, 1 eq) in DMSO (1 mL) was added EDCI (9.6 mg, 50.3 umol, 1.5 eq). The reaction was heated at 100° C. for 2 hr. LCMS showed that 74% of desired product was detected. The reaction was diluted with EA (20 mL) and washed with brine (3*5 mL). The organic layer was dried over Na$_2$SO$_4$ and concentrated. The residue was purified by prep-HPLC to give Compound 133 (2.38 mg, 17.2% yield). HNMR and LCMS showed that desired product was obtained. LCMS (ESI): RT=0.709 min, mass calc. for C$_{16}$H$_{14}$F$_3$N$_5$O$_3$S 413.08, m/z found 413.9 [M+H]$^+$; $^1$H NMR (400 MHz, CDCl$_3$) δ9.79 (s, 1H), 8.07 (d, J=2.8 Hz, 1H), 7.80-7.70 (m, 3H), 7.60-7.50 (m, 5H), 7.50-7.30 (m, 1H), 2.41 (s, 3H).

Example 124: N-methyl-3-(2-methyltetrazol-5-yl)-4-(3-phenoxyanilino)benzenesulfonamide (Compound 134) and N,N-dimethyl-3-(2-methyltetrazol-5-yl)-4-(3-phenoxyanilino)benzenesulfonamide (Compound 135)

Compound 134

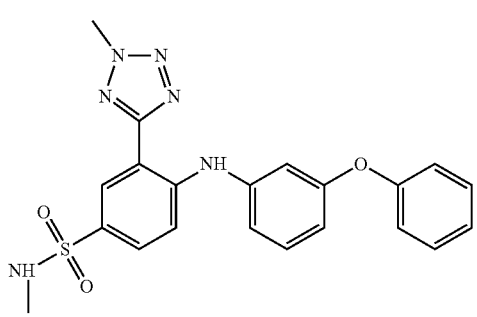

Compound 135

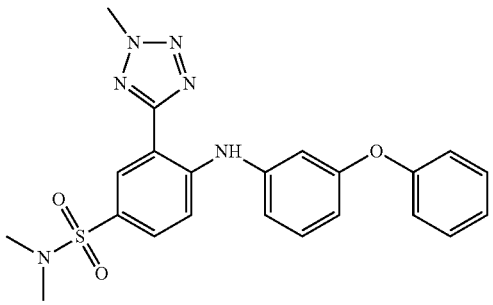

Preparation of Compound 134 and Compound 135:

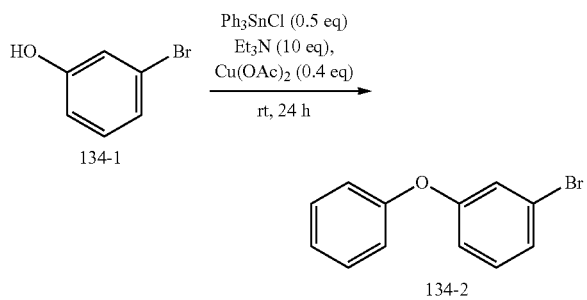

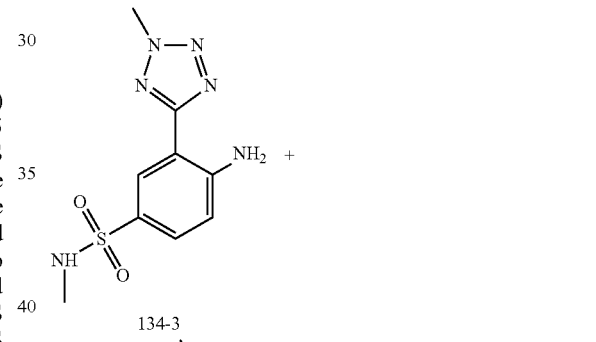

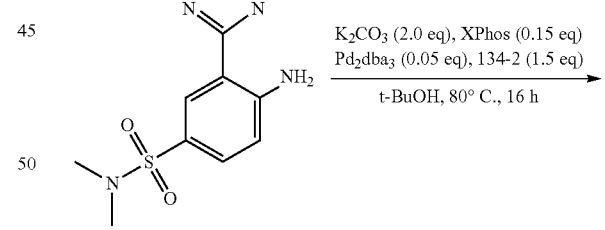

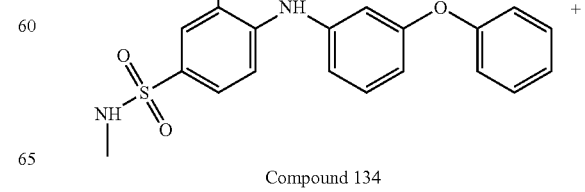

Compound 134

315

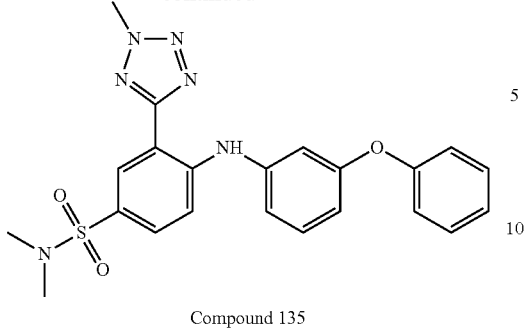

Compound 135

Step 1: 1-bromo-3-phenoxy-benzene

To a Ph₃SnCl (1.11 g, 2.89 mmol, 0.5 eq) and compound 134-1 (1 g, 5.78 mmol, 1 eq) in Et₃N (5.85 g, 57.80 mmol, 8.1 mL, 10 eq) was added Cu(OAc)₂ (419.9 mg, 2.31 mmol, 0.4 eq). The reaction was stirred at 25° C. for 24 hr. TLC (EA:PE=1:3, UV) showed that starting material was detected and a new spot was detected. The reaction was filtered and adjusted pH to 7 with 1N.aq.HCl. The aqueous layer was extracted with EA (3*20 mL). The organic layer was dried over Na₂SO₄ and concentrated. The residue was purified by column chromatography on silica gel (EA:PE=1:15) to give compound 134-2 (0.2 g, crude).

Step 2: N-methyl-3-(2-methyltetrazol-5-yl)-4-(3-phenoxyanilino)benzenesulfonamide and N,N-dimethyl-3-(2-methyltetrazol-5-yl)-4-(3-phenoxyanilino)benzenesulfonamide To a mixture of compound 134-3 and compound 134-3a (50 mg, 0.19 mmol, 1 eq), K₂CO₃ (51.51 mg, 0.37 mmol, 2 eq), 1-bromo-3-phenoxy-benzene (69.6 mg, 0.28 mmol, 1.5 eq) and XPhos (13.3 mg, 27.9 umol, 0.15 eq) in t-BuOH (3 mL) was added Pd₂(dba)₃ (8.5 mg, 9.3 umol, 0.05 eq). The mixture was degassed under vacuum and purged with N₂ 3 times. The mixture was stirred under N₂ at 80° C. for 16 hours. LCMS showed that 35% of P1 and 30% of P2 were detected. The reaction was diluted with EA (30 mL) and washed with water (2*10 mL). The organic layer was dried over Na₂SO₄ and concentrated. The residue was purified by prep-HPLC to give Compound 134 (5.76 mg, 7.1% yield) and Compound 135 (2.12 mg, 2.5% yield). Compound 134: LCMS (ESI): RT=0.798 min, mass calcd. for $C_{21}H_{20}N_6O_3S$, 436.13 m/z found 436.9[M+H]⁺. ¹H NMR (400 MHz, CDCl₃) δ 9.40 (s, 1H), 8.67 (s, 1H), 7.68-7.81 (m, 1H), 7.36 (dd, J=8.41, 4.89 Hz, 4H), 7.13 (br t, J=7.28 Hz, 1H), 7.00-7.10 (m, 3H), 6.96 (s, 1H), 6.82 (d, J=8.03 Hz, 1H), 4.45 (s, 3H), 4.38 (br d, J=5.27 Hz, 1H), 2.68 (d, J=5.27 Hz, 3H). Compound 135: LCMS (ESI): RT=0.842 min, mass calcd. for $C_{22}H_{22}N_6O_3S$, 450.15 m/z found 451.0[M+H]⁺. ¹H NMR (400 MHz, CDCl₃) δ 9.42 (s, 1H), 8.58 (d, J=2.01 Hz, 1H), 7.62 (dd, J=8.91, 2.13 Hz, 1H), 7.32-7.41 (m, 4H), 7.10-7.17 (m, 1H), 7.03-7.09 (m, 3H), 6.97 (s, 1H), 6.82 (br d, J=8.28 Hz, 1H), 4.46 (s, 3H), 2.73 (s, 6H).

316

Example 125:3-[2-[(2-Fluorophenyl)methyl]tetrazol-5-yl]-N-methyl-4-[3-(trifluoromethyl)anilino]benzenesulfonamide (Compound 136)

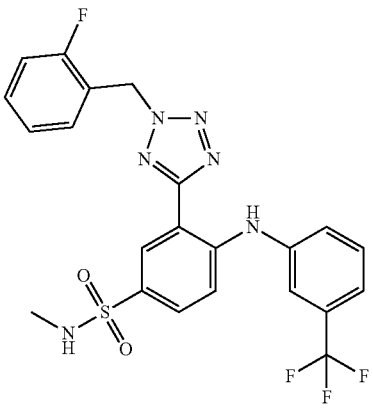 [SMILES: CNS(=O)(=O)c1ccc(Nc2cccc(C(F)(F)F)c2)c(-c2nnn(Cc3ccccc3F)n2)c1]

Preparation of Compound 136:

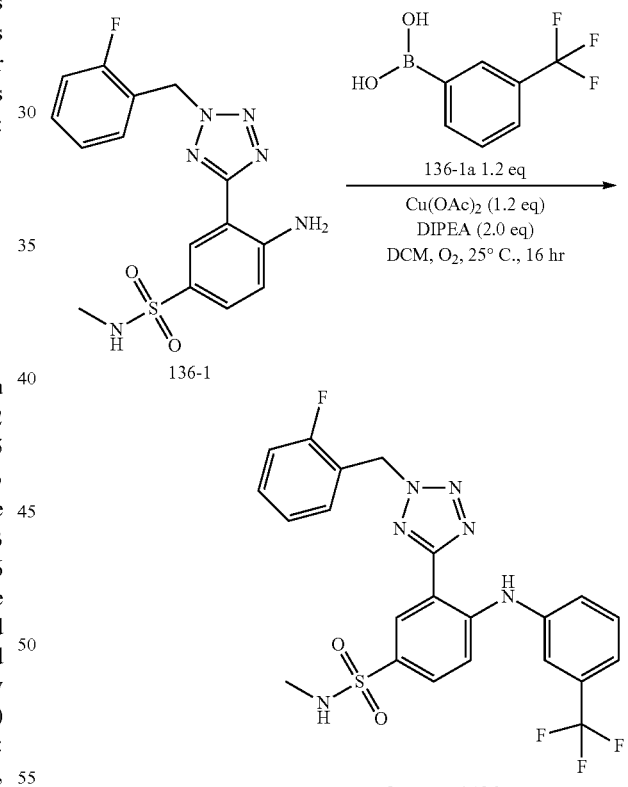

Compound 136

To a solution of compound 136-1 (100 mg, 0.28 mmol, 1.0 eq), compound 136-1a (62.9 mg, 0.33 mmol, 1.2 eq) and Cu(OAc)₂ (60.2 mg, 0.33 mmol, 1.2 eq) in DCM (2 mL) was added DIPEA (71.3 mg, 0.55 mmol, 2.0 eq). The reaction mixture was stirred at 25° C. for 16 hours under O₂. LCMS showed reactant 1 was consumed completely and one main peak with desired MS was detected. The mixture was diluted with water (10 mL) and the resultant mixture was extracted with EA (30 mL*3). The combined organic layers were dried over Na$_2$SO$_4$, filtered and concentrated to dryness under reduced pressure. The residue was purified by prep-HPLC to give Compound 136 (52.54 mg, 37.2% yield). LCMS (ESI): RT=1.045 min, mass calcd. for C$_{22}$H$_{18}$F$_4$N$_6$O$_2$S 506.11, m/z found 507.3 [M+H]$^+$, $^1$H NMR (400 MHz, CDCl$_3$) δ ppm 9.56 (s, 1H), 8.70 (d, J=2.26 Hz, 1H), 7.74 (dd, J=8.78, 2.26 Hz, 1H), 7.54 (s, 1H), 7.50 (m, 3H), 7.44 (d, J=1.76 Hz, 1H), 7.41 (m, 3H), 7.36 (s, 1H), 7.34 (s, 1H), 7.18 (m, 2H), 5.94 (s, 2H), 4.31 (q, J=5.27 Hz, 1H), 2.70 (d, J=5.27 Hz, 3H).

Example 126:3-[2-[(2-Fluorophenyl)methyl]tetrazol-5-yl]-N-methyl-4-[4-(trifluoromethyl)anilino]benzenesulfonamide (Compound 137)

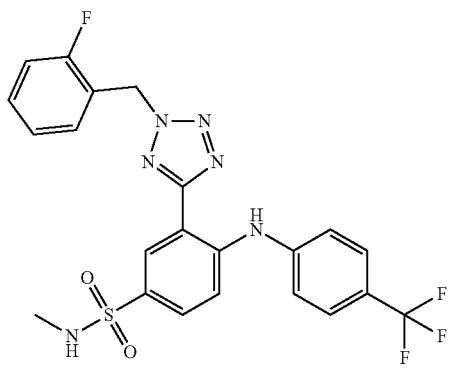 [SMILES: CNS(=O)(=O)c1ccc(Nc2ccc(C(F)(F)F)cc2)c(-c2nnn(Cc3ccccc3F)n2)c1]

Preparation of Compound 137:

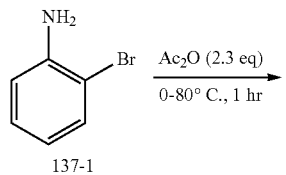

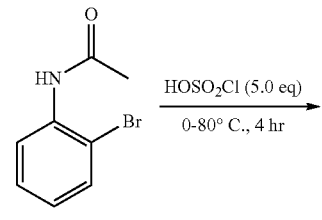

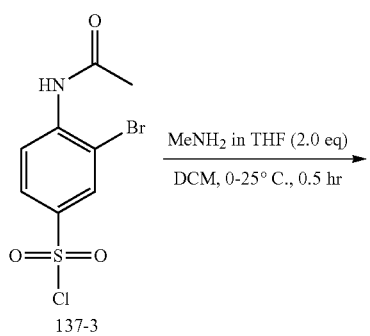

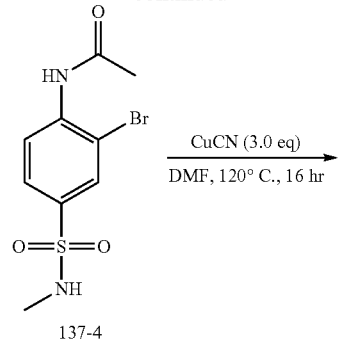

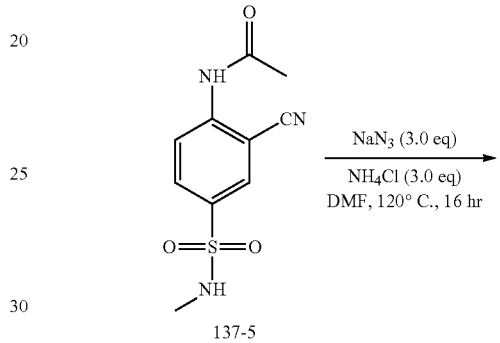

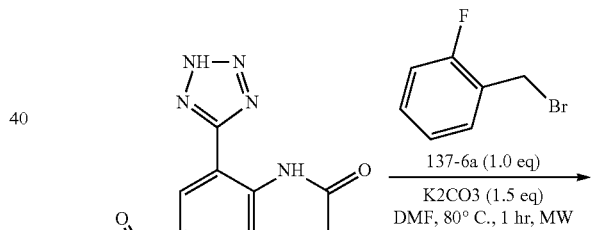

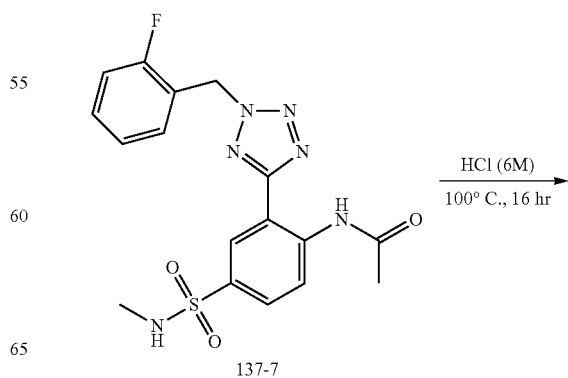

-continued

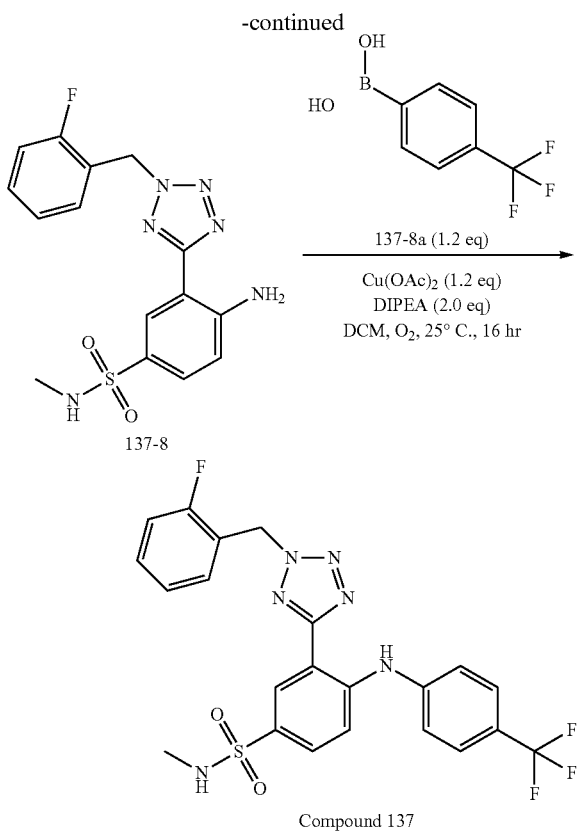

Step 1: N-(2-Bromophenyl)acetamide

To a stirring solution of Ac$_2$O (41.0 g, 401 mmol, 2.3 eq) was added compound 137-1 (30.0 g, 174 mmol, 1.0 eq) at 0° C., and then the reaction mixture was stirred at 80° C. for 1 hour. TLC (Petroleum ether: Ethyl acetate=5:1) indicated reactant 1 was completely, and one major new spot with larger polarity was detected. The reaction mixture was concentrated under reduce pressure to give a residue. The residue was washed with PE (100 mL*2) and dried under reduced pressure to obtain compound 137-2 (34.5 g, 92.4% yield).

Step 2: 4-Acetamido-3-bromo-benzenesulfonyl chloride

To a stirring of HSO$_3$Cl (93.6 g, 803 mmol, 5.0 eq) was added compound 137-2 (34.0 g, 159 mmol, 1.0 eq) at 0° C. After addition, the reaction mixture was stirred at 80° C. for 6 hours. TLC (Petroleum ether:Ethyl acetate=2:1) showed the starting material was consumed and two new spots were formed. The reaction mixture was added to ice (400 g) and then warm up to 25° C. The suspension was extracted with EA (3*400 mL) to obtain compound 137-3 (35 g, crude). $^1$H NMR (400 MHz, DMSO-d$_6$) δ ppm 9.49 (br s, 1H), 7.76 (d, J=1.51 Hz, 1H), 7.54 (m, 1H), 7.32 (dd, J=8.16, 1.88 Hz, 1H), 2.08 (s, 3H).

Step 3: N-[2-Bromo-4-(methylsulfamoyl)phenyl]acetamide

To a solution of compound 137-3 (33.0 g, 106 mmol, 1.0 eq) in DCM (300 mL) was added MeNH$_2$ (2 M, 106 mL, 2.0 eq) at 0° C. The reaction mixture was stirred at 25° C. for 0.5 hour. TLC (Petroleum ether:Ethyl acetate=2:1) showed the starting material was consumed. The reaction mixture was concentrated under reduced pressure. The mixture was diluted with water (100 mL) and the resultant mixture was extracted with EA (300 mL*3). The combined organic layers were dried over Na$_2$SO$_4$, filtered and concentrated to dryness under reduced pressure. EA (30 mL) was added to the crude product, and then the suspension was filtered to obtain compound 137-4 (12.0 g, 37.1% yield).

Step 4: N-[2-Cyano-4-(methylsulfamoyl)phenyl]acetamide

To a solution of compound 137-4 (2.0 g, 6.5 mmol, 1.0 eq) in DMF (20 mL) was added CuCN (1.75 g, 19.5 mmol, 3.0 eq). And then the mixture was stirred at 120° C. for 16 hr. TLC (Petroleum ether:Ethyl acetate=1:1) showed the starting material was consumed. The reaction mixture was concentrated under reduced pressure. The mixture was diluted with EA (50 mL) and the resultant mixture was extracted with water (50 mL*3). The combined organic layers were dried over Na$_2$SO$_4$, and concentrated to dryness under reduced pressure. The residue was purified by column chromatography (SiO$_2$, Petroleum ether/Ethyl acetate=1:0 to 1:1) to obtain compound 137-5 (900 mg, 54.6% yield).

Step 5: N-[4-(Methylsulfamoyl)-2-(2H-tetrazol-5-yl)phenyl]acetamide

To a solution of compound 137-5 (900 mg, 3.55 mmol, 1.0 eq) and NH$_4$Cl (570 mg, 10.7 mmol, 3.0 eq) in DMF (10 mL) was added NaN$_3$ (690 mg, 10.6 mmol, 3.0 eq). The reaction mixture was stirred at 120° C. for 16 hours. LCMS showed reactant 137-5 was consumed completely and one main peak with desired MS was detected. The reaction mixture was dropwise to HCl (15 mL, 1M), and then the suspension was filtered to obtain the title compound 137-6 (750 mg, 71.2% yield).

Step 6: N-[2-[2-[(2-Fluorophenyl)methyl]tetrazol-5-yl]-4-(methylsulfamoyl)phenyl]acetamide Compound 137-6 (500 mg, 1.69 mmol, 1.0 eq), compound 137-6a (319 mg, 1.69 mmol, 1.0 eq) and K$_2$CO$_3$ (350 mg, 2.53 mmol, 1.5 eq) were taken up into a microwave tube in DMF (5 mL). The sealed tube was heated at 80° C. for 1 hr under microwave. LCMS showed reactant 137-6 was consumed completely and one main peak with desired MS was detected. TLC (Petroleum ether: Ethyl acetate=2:1) indicated reactant 137-6 was remained, and one major new spot with lower polarity was detected. The reaction mixture was diluted with H$_2$O (15 mL) and extracted with EA (40 mL). The organic layer was washed with H$_2$O (20 mL*3). The organic layer was dried over Na$_2$SO$_4$, filtered and concentrated to dryness under reduced pressure. The residue was purified by column chromatography (SiO$_2$, Petroleum ether/Ethyl acetate=1:0 to 2:1) to give compound 137-7 (540 mg, 79.1% yield).

Step 7: 4-Amino-3-[2-[(2-fluorophenyl)methyl]tetrazol-5-yl]-N-methyl-benzenesulfonamide To a solution of compound 137-7 (440 mg, 1.09 mmol, 1.0 eq) was added HCl (6 M, 8.8 mL, 48.5 eq). The mixture was stirred at 100° C. for 16 hr. LCMS showed reactant 137-7 was consumed completely and one main peak with desired MS was detected. The mixture was adjusted with NaOH (6M) to pH=8, and then the suspension was extracted with EA (3*50 mL). The combined organic layers were dried over Na$_2$SO$_4$, filtered and concentrated to dryness under reduced pressure to obtain the title compound 137-8 (340 mg, 86.2% yield) was obtained.

Step 8: 3-[2-[(2-Fluorophenyl)methyl]tetrazol-5-yl]-N-methyl-4-[4-(trifluoromethyl)anilino]benzenesulfonamide To a solution of compound 137-8 (100 mg, 0.27 mmol, 1.0 eq) compound 137-8a (62.9 mg, 0.33 mmol, 1.2 eq) and Cu(OAc)$_2$ (60.2 mg, 0.33 mmol, 1.2 eq) in DCM (2 mL) was added DIPEA (71.3 mg, 0.55 mmol, 2.0 eq). The reaction mixture was stirred at 25° C. for 16 hours under O$_2$. LCMS showed reactant 137-8 was consumed completely and one main peak with desired MS was detected. The mixture was diluted with water (10 mL) and the resultant mixture was extracted with EA (30 mL*3). The combined organic layers were dried over Na$_2$SO$_4$, filtered and concentrated to dryness under reduced pressure. The residue was purified by prep-HPLC to give Compound 137 (23.0 mg, 16.3% yield). LCMS (ESI): RT=1.042 min, mass calcd. for C$_{22}$H$_{18}$F$_4$N$_6$O$_2$S 506.11, m/z found 507.3 [M+H]$^+$; $^1$H NMR (400 MHz, CDCl$_3$) δ 9.63 (s, 1H), 8.69 (d, J=2.26 Hz, 1H), 7.77 (d, J=2.26 Hz, 1H), 7.75 (d, J=2.26 Hz, 1H), 7.63 (d, J=8.78 Hz, 2H), 7.48 (d, J=8.78 Hz, 1H), 7.41 (m, 2H), 7.36 (d, J=8.28 Hz, 2H), 7.26 (s, 7H), 7.19 (m, 2H), 5.94 (s, 2H), 4.30 (q, J=5.35 Hz, 1H), 2.70 (d, J=5.27 Hz, 3H), 1.25 (s, 1H).

Example 127: N-(tert-butyl)-3-(2-methyl-2H-tetrazol-5-yl)-4-((4-(trifluoromethyl)phenyl)amino)benzenesulfonamide (Compound 138)

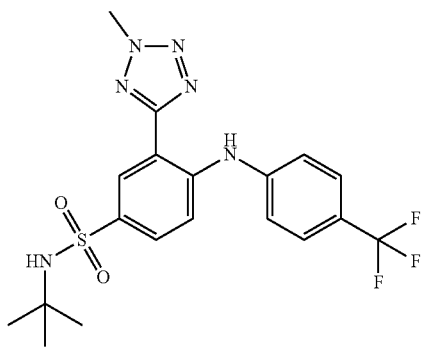 [SMILES: Cn1nnc(-c2cc(S(=O)(=O)NC(C)(C)C)ccc2Nc2ccc(C(F)(F)F)cc2)n1]

Preparation of Compound 138

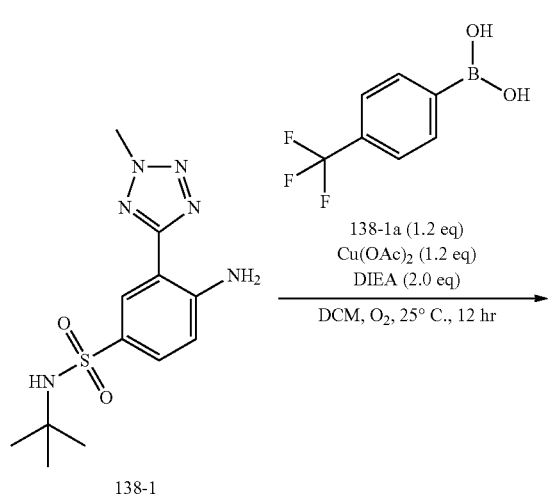

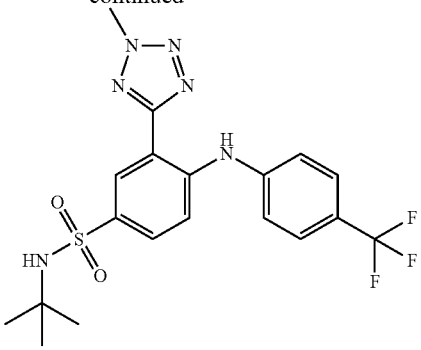

Compound 138

To a solution of compound 138-1 (0.09 g, 0.28 mmol, 1 eq) and compound 138-1a (66.0 mg, 0.34 mmol, 1.2 eq) in DCM (7 mL) was added Cu(OAc)$_2$ (63.2 mg, 0.34 mmol, 1.2 eq) and DIPEA (112.4 mg, 0.86 mmol, 0.2 mL, 3 eq). The mixture was stirred at 25° C. for 16 hr under O$_2$. LCMS showed the starting material was consumed and the desired mass was detected. The reaction mixture was filtered. The filter cake was washed with ethyl acetate (10 ml*3) and the combined organic layers was washed by NaCl (8 mL*3) then concentrated in vacuum to give crude product. The residue was purified by prep-HPLC. Compound 138 (7.88 mg, 5.5% yield, HCl) was obtained. LCMS (ESI): RT=0.833 min, mass calc. for C$_{19}$H$_{21}$F$_3$N$_6$O$_2$S 454.14, m/z found 455.0 [M+H]$^+$; H NMR (400 MHz, DMSO-d$_6$) δ 8.95 (s, 1H), 8.20-8.18 (d, J=8.0 Hz, 1H), 7.89-7.89 (d, J=1.6 Hz, 1H), 7.71 (s, 1H), 7.66-7.64 (d, J=8.8 Hz, 2H), 7.56-7.53 (dd, J$_1$=1.6 Hz, J$_2$=8.0 Hz, 1H), 7.30-7.28 (d, J=8.0 Hz, 2H), 4.46 (s, 3H), 1.38 (s, 9H).

Example 128: 4-(4-chloroanilino)-N-methyl-3-(1-methylimidazol-4-yl)benzenesulfonamide (Compound 139)

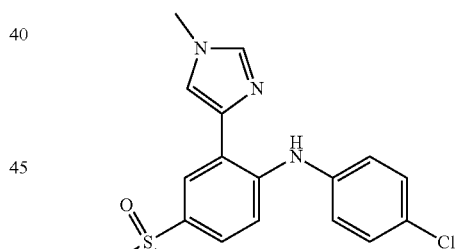

Preparation of Compound 139:

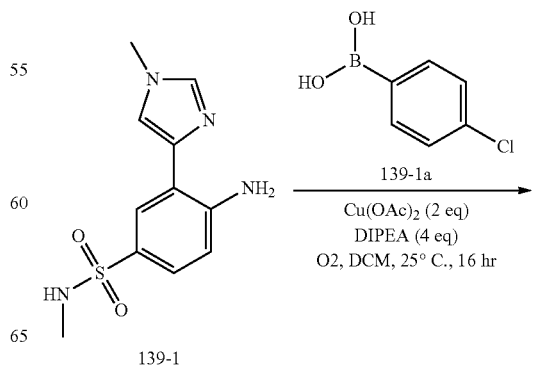

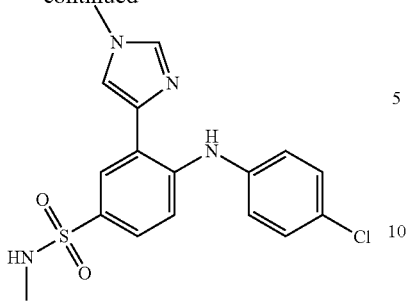

Compound 139

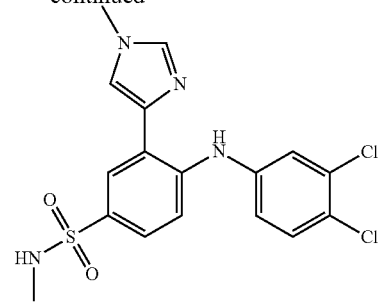

Compound 140

A mixture of compound 139-1 (50 mg, 0.18 mmol, 1 eq), compound 139-1a (58.7 mg, 0.37 mmol, 2 eq), Cu(OAc)$_2$ (68.2 mg, 0.37 mmol, 2 eq) and DIEA (97.0 mg, 0.75 mmol, 0.1 mL, 4 eq) in DCM (3 mL) was degassed and purged with O$_2$ for 3 times, and then the mixture was stirred at 25° C. for 16 hr under 02 atmosphere. LCMS showed the desired compound was detected. The reaction mixture was diluted with H$_2$O (10 mL) and the mixture extracted with EA (15 mL*3). The combined organic phase was washed with brine (10 mL*3), dried with anhydrous Na$_2$SO$_4$, filtered and concentrated in vacuum. The residue was purified by prep-HPLC. Compound 139 (5 mg, 6.9% yield) was obtained and confirmed by LCMS and H NMR. LCMS (ESI): RT=0.657 min, mass calc. for C$_{17}$H$_{17}$ClN$_4$O$_2$S 376.08, m/z found 398.9 [M+Na]$^+$; H NMR (400 MHz, DMSO-d$_6$) δ ppm 2.41 (d, J=5.02 Hz, 3H) 3.83 (s, 3H) 7.18 (d, J=8.78 Hz, 2H) 7.29 (br d, J=5.02 Hz, 1H) 7.31-7.39 (m, 3H) 7.60 (dd, J=8.78, 2.26 Hz, 1H) 7.80 (d, J=2.01 Hz, 1H) 7.88 (s, 1H) 8.68 (br s, 1H).

Example 129: 4-(3,4-dichloroanilino)-N-methyl-3-(1-methylimidazol-4-yl)benzenesulfonamide (Compound 140)

A mixture of compound 140-1 (30 mg, 0.11 mmol, 1 eq), compound 140-1a (42.9 mg, 0.22 mmol, 2 eq), DIEA (58.2 mg, 0.45 mmol, 78 uL, 4 eq) and Cu(OAc)$_2$ (40.9 mg, 0.22 mmol, 2 eq) in DCM (3 mL) was degassed and purged with O$_2$ for 3 times, and then the mixture was stirred at 25° C. for 10 min under 02 atmosphere. LCMS showed the desired compound was detected. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC. Compound 140 (5.8 mg, 12.5% yield) was obtained and confirmed by LCMS and $^1$H NMR. LCMS (ESI): RT=0.657 min, mass calc. for C$_{17}$H$_{16}$Cl$_2$N$_4$O$_2$S 410.04, m/z found 410.9 [M+H]$^+$; $^1$H NMR (400 MHz, DMSO-d$_6$) δ ppm 2.44 (d, J=4.77 Hz, 3H) 3.87 (s, 3H) 7.10-7.16 (m, 1H) 7.34 (d, J=2.51 Hz, 1H) 7.41 (br d, J=5.02 Hz, 1H) 7.50 (dd, J=19.83, 8.78 Hz, 2H) 7.69 (dd, J=8.78, 2.01 Hz, 1H) 7.86 (d, J=2.01 Hz, 1H) 7.98 (s, 1H) 8.89-9.04 (m, 1H) 8.98 (br s, 1H).

Example 130: N-methyl-3-(1-methylimidazol-4-yl)-4-[3-(trifluoromethylsulfanyl)anilino]benzenesulfonamide (Compound 141)

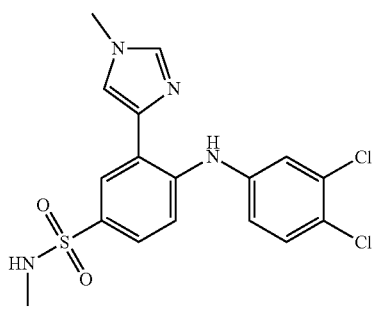 [SMILES: CNS(=O)(=O)c1ccc(Nc2ccc(Cl)c(Cl)c2)c(-c2cn(C)cn2)c1]

Preparation of Compound 140:

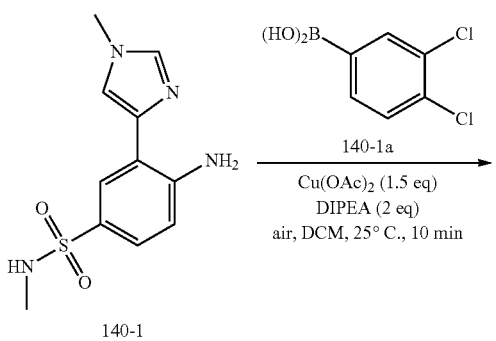

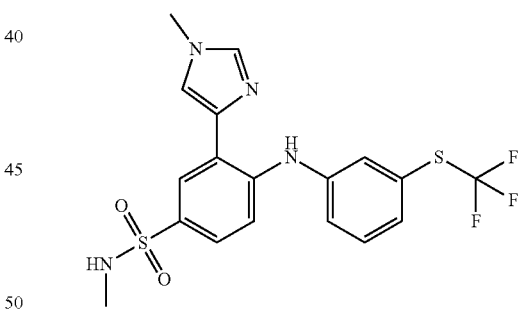

Preparation of Compound 141:

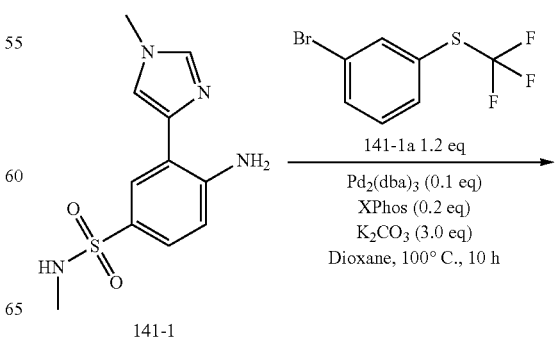

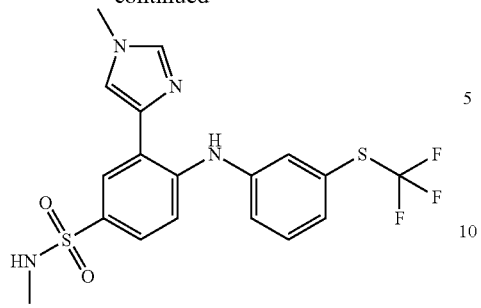

Compound 141

To a mixture of compound 141-1 (0.03 g, 0.11 mmol, 1 eq) and compound 141-1a (34.7 mg, 0.13 mmol, 1.2 eq) in dioxane (2 mL) was added Pd$_2$(dba)$_3$ (10.3 mg, 0.01 mmol, 0.1 eq), XPhos (10.7 mg, 0.02 mmol, 0.2 eq) and K$_2$CO$_3$ (46.7 mg, 0.33 mmol, 3 eq) under N$_2$. The mixture was stirred for 10 h at 100° C. LCMS showed the reaction was complete. The mixture was quenched by EA (30 mL), and the mixture was filtered and the filtered cake was washed with EA (20 mL*3). The combined organic phase was washed with brine (20 mL*3), dried with anhydrous Na$_2$SO$_4$, filtered and concentrated in vacuum. The residue was purified by pre-HPLC was obtained. LCMS (ESI): RT=0.662 min, mass calc. for: C$_{18}$H$_{17}$F$_3$N$_4$O$_2$S$_2$ 442.07, m/z found 442.9 [M+H]$^+$; $^1$H NMR (400 MHz, CD$_3$OD) δ 9.01 (s, 1H), 7.92-7.79 (m, 3H), 7.55-7.42 (m, 3H), 7.38-7.33 (m, 2H), 3.99 (s, 3H), 2.60-2.57 (m, 3H).

Example 131: 4-(3,5-dichloroanilino)-N-methyl-3-(1-methylimidazol-4-yl)benzenesulfonamide (Compound 142)

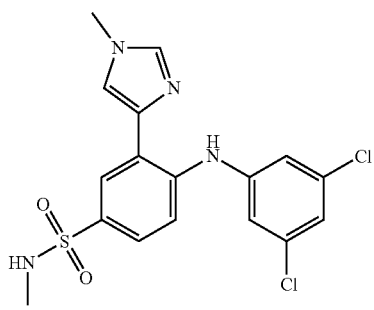 [SMILES: CNS(=O)(=O)c1ccc(Nc2cc(Cl)cc(Cl)c2)c(-c2cn(C)cn2)c1]

Preparation of Compound 142:

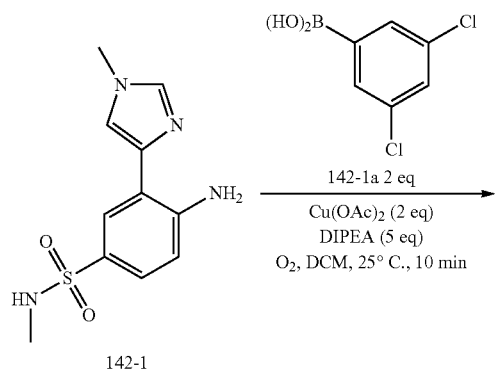

142-1

Compound 142

To a mixture of compound 142-1 (0.05 g, 0.18 mmol, 1 eq) and compound 142-1a (71.6 mg, 0.37 mmol, 2 eq) in DCM (5 mL) was added Cu(OAc)$_2$ (68.2 mg, 0.37 mmol, 2 eq) and DIPEA (121.3 mg, 0.93 mmol, 0.2 mL, 5 eq) in one portion at 25° C. under O$_2$. The mixture was stirred for 10 min under 15 PSI. LCMS showed the reaction was complete. The mixture was quenched by EA (30 mL), and the mixture was filtered and the filtered cake was washed with EA (20 mL*3). The combined organic phase was washed with brine (20 mL*3), dried with anhydrous Na$_2$SO$_4$, filtered and concentrated in vacuum. The residue was purified by pre-HPLC. Compound 142 (12.8 mg, 15.2% yield, HCl) was obtained. LCMS (ESI): RT=0.647 min, mass calc. for: C$_{17}$H$_{16}$Cl$_2$N$_4$O$_2$S 410.04, m/z found 410.9 [M+H]$^+$; $^1$H NMR (400 MHz, CD$_3$OD) δ8.97 (s, 1H), 7.94 (d, J=2.0 Hz, 1H), 7.90-7.83 (m, 2H), 7.53 (d, J=8.5 Hz, 1H), 7.07-7.03 (m, 3H), 3.99 (s, 3H), 2.59 (s, 3H).

Example 132: 4-(3-Chloroanilino)-N-methyl-3-(1-methylimidazol-4-yl)benzenesulfonamide (Compound 143)

Preparation of Compound 143:

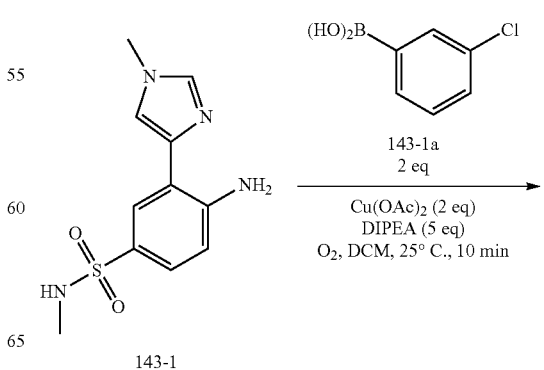

143-1

-continued

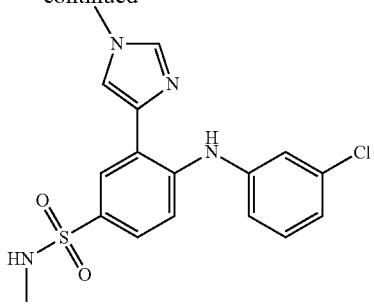

Compound 143

To a mixture of compound 143-1 (0.05 g, 0.18 mmol, 1 eq) and compound 143-1a (58.7 mg, 0.37 mmol, 2 eq) in DCM (20 mL) was added Cu(OAc)$_2$ (68.2 mg, 0.37 mmol, 2 eq) and DIPEA (121.3 mg, 0.93 mmol, 0.2 mL, 5 eq) in one portion at 25° C. under O$_2$. The mixture was stirred for 10 min under 15 psi. LCMS showed the reaction was complete. The mixture was quenched by EA (30 mL), and the mixture was filtered and the filtered cake was washed with EA (20 mL*3). The combined organic phase was washed with brine (20 mL*3), dried with anhydrous Na$_2$SO$_4$, filtered and concentrated in vacuum. The residue was purified by pre-HPLC. Compound 143 (22.02 mg, 28.4% yield, HCl) was obtained. LCMS (ESI): RT=0.616 min, mass calc. for: C$_{17}$H$_{17}$ClN$_4$O$_2$S 376.08, m/z found 376.9 [M+Na]$^+$; $^1$H NMR (400 MHz, DMSO-d$_6$) δ 9.20 (br s, 1H), 8.59 (br s, 1H), 8.02 (s, 1H), 7.83 (d, J=2.3 Hz, 1H), 7.71 (dd, J=2.1, 8.7 Hz, 1H), 7.48-7.39 (m, 2H), 7.32 (t, J=8.0 Hz, 1H), 7.18-7.09 (m, 2H), 7.03 (dd, J=1.3, 7.8 Hz, 1H), 3.90-3.87 (m, 3H), 2.46-2.43 (m, 3H).

Example 133: N-methyl-3-(1-methylimidazol-4-yl)-4-[4-(trifluoromethylsulfanyl)anilino]benzenesulfonamide (Compound 144)

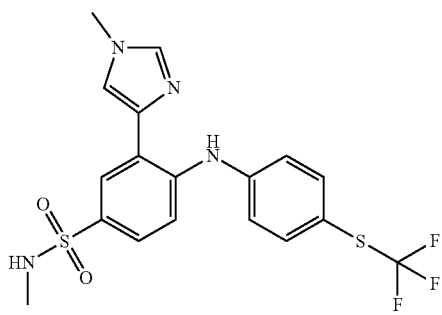 [SMILES: CNS(=O)(=O)c1ccc(Nc2ccc(SC(F)(F)F)cc2)c(-c2cn(C)cn2)c1]

Preparation of Compound 144:

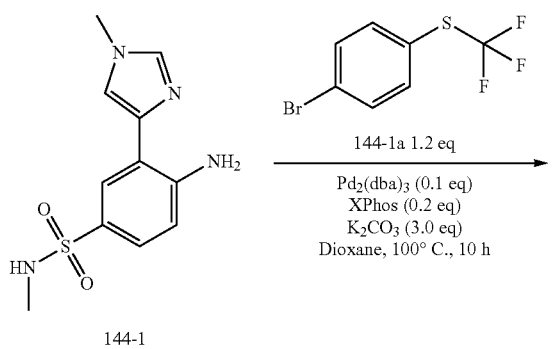

-continued

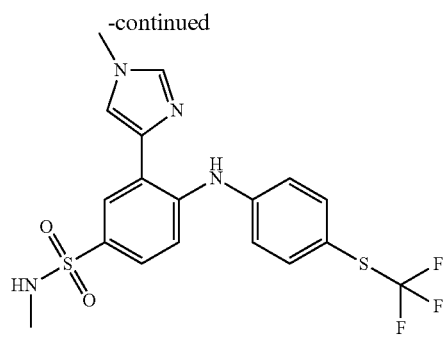

Compound 144

To a mixture of compound 144-1 (0.03 g, 0.11 mmol, 1 eq) and compound 144-1a (34.7 mg, 0.13 mmol, 20 uL, 1.2 eq) in dioxane (2 mL) were added Pd$_2$(dba)$_3$ (10.3 mg, 0.01 mmol, 0.1 eq), XPhos (10.7 mg, 0.02 mmol, 0.2 eq) and K$_2$CO$_3$ (46.7 mg, 0.33 mmol, 3 eq) under N$_2$. The mixture was stirred for 10 h at 100° C. LCMS showed the reaction was complete. The mixture was quenched by EA (30 mL), and the mixture was filtered and the filtered cake was washed with EA (20 mL*3). The combined organic phase was washed with brine (20 mL*3), dried with anhydrous Na$_2$SO$_4$, filtered and concentrated in vacuum. The residue was purified by pre-HPLC. Compound 144 (3.03 mg, 5.6% yield, HCl salt) was obtained. LCMS (ESI): RT=0.672 min, mass calc. for: C$_{18}$H$_{17}$F$_3$N$_4$O$_2$S$_2$ 442.07, m/z found 442.9 [M+H]$^+$; $^1$H NMR (400 MHz, CDOD$_3$) δ 8.99 (s, 1H), 7.93 (d, J=2.0 Hz, 1H), 7.85 (s, 1H), 7.86 (d, J=9.8 Hz, 2H), 7.60 (dd, J=3.0, 8.5 Hz, 3H), 7.19 (d, J=8.8 Hz, 2H), 3.97 (s, 3H), 2.60 (s, 3H).

Example 134: N-methyl-3-(1-methylimidazol-4-yl)-4-(3,4,5-trichloroanilino)benzenesulfonamide (Compound 145)

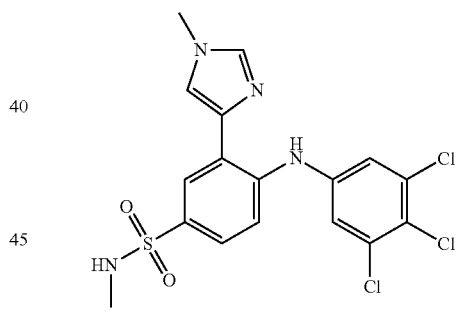

Preparation of Compound 145:

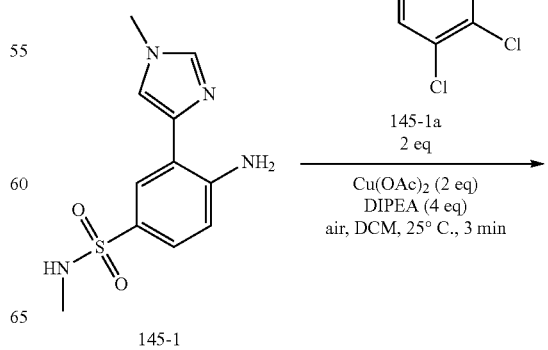

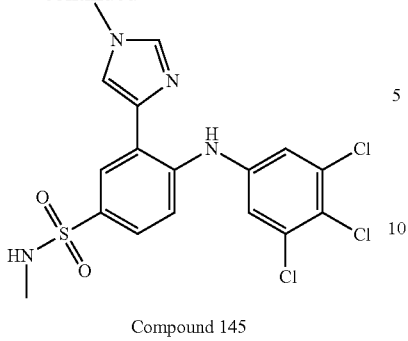

Compound 145

The mixture of compound 145-1 (30 mg, 0.11 mmol, 1 eq), compound 144-1a (50.7 mg, 0.22 mmol, 2 eq), DIEA (58.2 mg, 0.45 mmol, 78.48 uL, 4 eq) and Cu(OAc)$_2$ (40.9 mg, 0.22 mmol, 2 eq) in DCM (5 mL) was stirred at 25° C. for 3 min. LCMS showed the desired compound was detected. The mixture was combined with E7868-127. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC. Compound 145 (5.5 mg, 10.9% yield) was obtained. LCMS (ESI): RT=0.678 min, mass calc. for C$_{17}$H$_{15}$Cl$_3$N$_4$O$_2$S 444.00 found 446.9 [M+H]$^+$; $^1$H NMR (400 MHz, DMSO-d$_6$) δ ppm 2.45 (br d, J=4.52 Hz, 2H) 2.46-2.47 (m, 1H) 3.86 (s, 3H) 7.32 (s, 2H) 7.46 (br d, J=5.02 Hz, 1H) 7.57 (d, J=8.53 Hz, 1H) 7.72 (br d, J=8.28 Hz, 1H) 7.90-8.00 (m, 2H) 8.91 (br s, 1H) 9.23 (br s, 1H).

Example 135: 4-[3,5-Bis(trifluoromethyl)anilino]-N-methyl-3-(1-methylimidazol-4-yl)benzenesulfonamide (Compound 146)

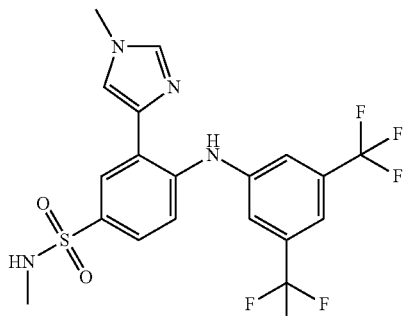

Preparation of Compound 146:

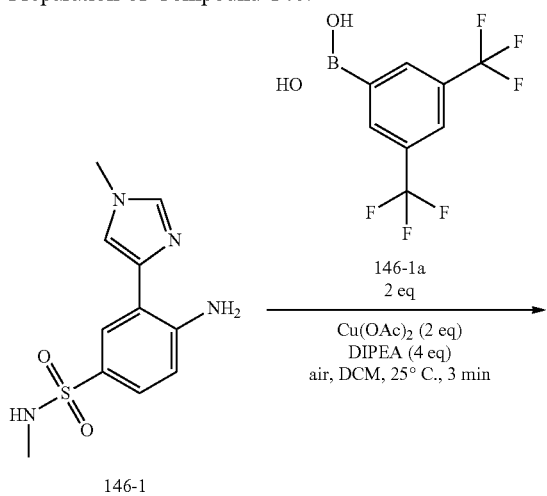

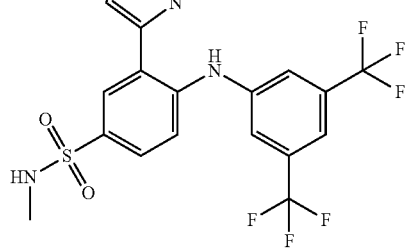

Compound 146

The mixture of compound 146-1 (50 mg, 0.18 mmol, 1 eq), compound 146-1a (96.8 mg, 0.37 mmol, 2 eq), DIEA (97.0 mg, 0.75 mmol, 0.1 mL, 4 eq) and Cu(OAc)$_2$ (68.2 mg, 0.37 mmol, 2 eq) in DCM (5 mL) was stirred at 25° C. for 3 min. LCMS showed the desired compound was detected. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC. Compound 146 (17 mg, 18.1% yield) was obtained. LCMS (ESI): RT=0.728 min, mass calc. for C$_{19}$H$_{16}$F$_6$N$_4$O$_2$S 478.09, m/z found 479.0 [M+H]$^+$; $^1$H NMR (400 MHz, DMSO-d$_6$) δ ppm 2.46 (d, J=5.02 Hz, 3H) 3.84 (s, 3H) 7.45 (br d, J=5.02 Hz, 1H) 7.55 (s, 1H) 7.60 (d, J=8.53 Hz, 1H) 7.58-7.61 (m, 1H) 7.63 (s, 2H) 7.74 (br d, J=7.28 Hz, 1H) 7.97 (br d, J=17.82 Hz, 2H) 8.82 (br s, 1H) 9.25-9.57 (m, 1H).

Example 136: 4-[4-Chloro-3-(trifluoromethyl)anilino]-N-methyl-3-(1-methylimidazol-4-yl)benzenesulfonamide (Compound 147)

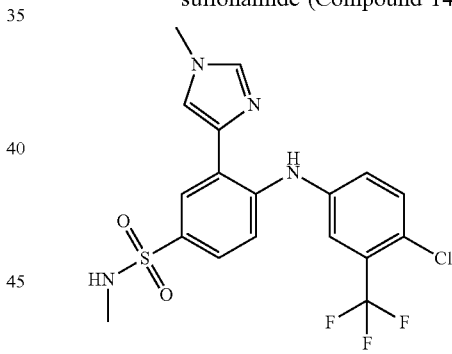

Preparation of Compound 147:

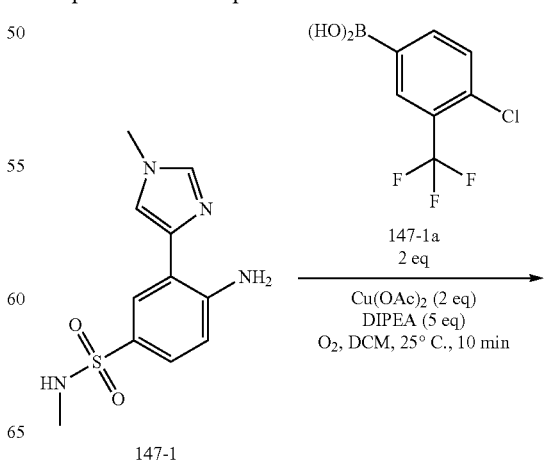

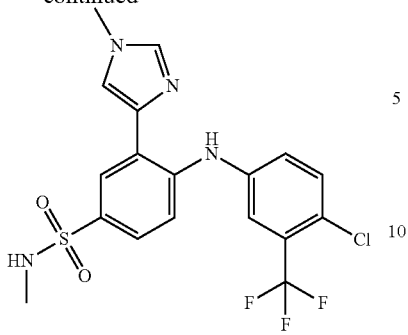

Compound 147

To a mixture of compound 147-1 (0.05 g, 0.18 mmol, 1 eq) and compound 147-1a (84.2 mg, 0.37 mmol, 2 eq) in DCM (20 mL) was added Cu(OAc)$_2$ (68.2 mg, 0.37 mmol, 2 eq) and DIPEA (121.3 mg, 0.93 mmol, 0.2 mL, 5 eq) in one portion at 25° C. under O$_2$. The mixture was stirred for 10 min under 15 Psi. LCMS showed the reaction was complete. The mixture was quenched by EA (30 mL), and the mixture was filtered and the filtered cake was washed with EA (20 mL*3). The combined organic phase was washed with brine (20 mL*3), dried with anhydrous Na$_2$SO$_4$, filtered and concentrated in vacuum. The residue was purified by pre-HPLC. Compound 147 (6.98 mg, 7.7% yield, HCl) was obtained. LCMS (ESI): RT=0.662 min, mass calc. for: C$_{18}$H$_{16}$ClF$_3$N$_4$O$_2$S 444.06, m/z found 444.9 [M+H]$^+$; $^1$H NMR (400 MHz, CD$_3$OD) δ8.98 (s, 1H), 7.93-7.82 (m, 3H), 7.55-7.46 (m, 3H), 7.38 (br d, J=8.8 Hz, 1H), 4.00 (s, 3H), 2.59 (s, 3H).

Example 137: 4-[3-Chloro-4-(trifluoromethyl)anilino]-N-methyl-3-(1-methylimidazol-4-yl)benzenesulfonamide (Compound 148)

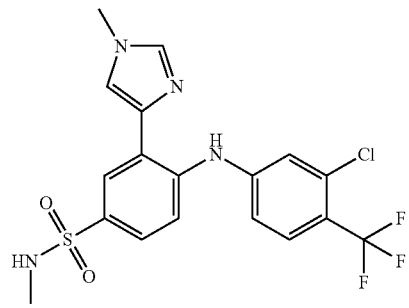 [SMILES: CNS(=O)(=O)c1ccc(Nc2ccc(C(F)(F)F)c(Cl)c2)c(-c2cn(C)cn2)c1]

Preparation of Compound 148:

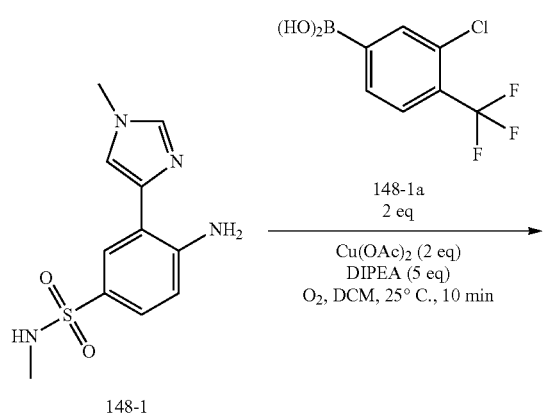

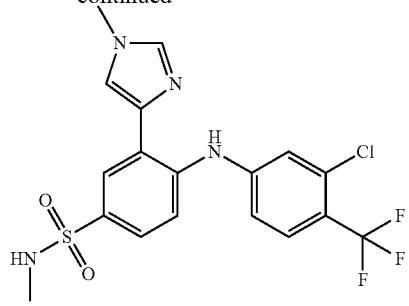

Compound 148

To a mixture of compound 148-1 (0.05 g, 0.18 mmol, 1 eq) and compound 148-1a (84.2 mg, 0.37 mmol, 2 eq) in DCM (20 mL) was added Cu(OAc)$_2$ (68.2 mg, 0.37 mmol, 2 eq) and DIPEA (121.3 mg, 0.93 mmol, 0.2 mL, 5 eq) in one portion at 25° C. under O$_2$. The mixture was stirred for 10 min under 15 Psi. LCMS showed the reaction was complete. The mixture was quenched by EA (30 mL), and the mixture was filtered and the filtered cake was washed with EA (20 mL*3). The combined organic phase was washed with brine (20 mL*3), dried with anhydrous Na$_2$SO$_4$, filtered and concentrated in vacuum. The residue was purified by pre-HPLC. Compound 148 (6.02 mg, 6.7% yield, HCl) was obtained. LCMS (ESI): RT=0.668 min, mass calc. for: C$_{18}$H$_{16}$ClF$_3$N$_4$O$_2$S 444.06, m/z found 444.9 [M+H]$^+$; $^1$H NMR (400 MHz, CD$_3$OD) δ8.97 (s, 1H), 7.99 (d, J=2.3 Hz, 1H), 7.90 (d, J=9.0 Hz, 1H), 7.88-7.86 (m, 1H), 7.64 (dd, J=4.6, 8.7 Hz, 2H), 7.22 (d, J=1.8 Hz, 1H), 7.11 (dd, J=1.9, 8.7 Hz, 1H), 3.99 (s, 3H), 2.61 (s, 3H).

Example 138: 4-((2,6-Difluorophenyl)amino)-N-methyl-3-(1-methyl-1H-imidazol-4-yl)benzenesulfonamide (Compound 149)

Preparation of Compound 149:

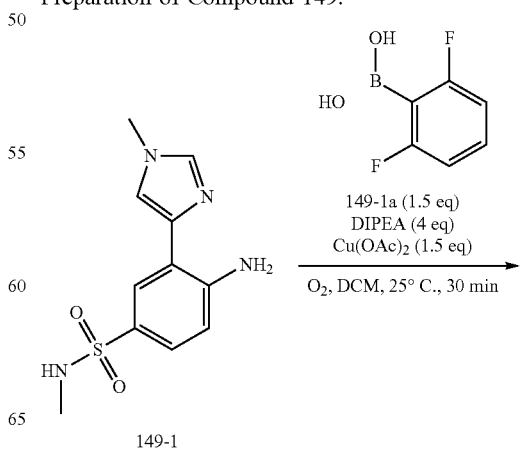

333

-continued

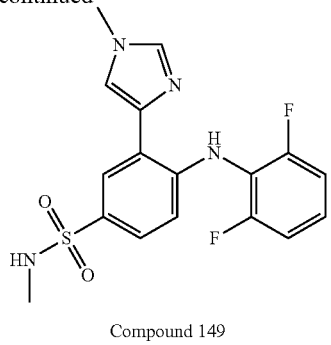

Compound 149

The mixture of compound 149-1 (50 mg, 0.18 mmol, 1 eq), compound 149-1a (44.4 mg, 0.28 mmol, 1.5 eq), Cu(OAc)$_2$ (51.1 mg, 0.28 mmol, 1.5 eq) and DIEA (97.0 mg, 0.75 mmol, 0.1 mL, 4 eq) in DCM (3 mL) was degassed and purged with O$_2$ for 3 times. Then the mixture was stirred at 25° C. for 30 min under O$_2$ atmosphere. LCMS showed the desired compound was detected. The reaction mixture was diluted with H$_2$O (5 mL) and the mixture was extracted with EA (15 mL*3). The combined organic phase was washed with brine (10 mL*3), dried with anhydrous Na$_2$SO$_4$, filtered and concentrated in vacuum. The residue was purified by prep-HPLC. Compound 149 (6 mg, 8.4% yield) was obtained. LCMS (ESI): RT=0.625 min, mass calc. for C$_{17}$H$_{16}$F$_2$N$_4$O$_2$S 378.10, m/z found 400.9 [M+Na]$^+$; $^1$H NMR (400 MHz, DMSO-d$_6$) δ=8.75 (br s, 1H), 8.89-8.57 (m, 1H), 7.91 (s, 1H), 7.79 (s, 1H), 7.58 (br d, J=8.5 Hz, 1H), 7.41-7.31 (m, 1H), 7.31-7.17 (m, 3H), 6.64 (br d, J=8.8 Hz, 1H), 3.85 (s, 3H), 2.41 (d, J=4.0 Hz, 3H).

Example 139: N-methyl-3-(1-methyl-1H-imidazol-4-yl)-4-(((1s,4s)-4-(trifluoromethyl)cyclohexyl)amino)benzenesulfonamide (Compound 150) and N-methyl-3-(1-methyl-1H-imidazol-4-yl)-4-(((1r,4r)-4-(trifluoromethyl)cyclohexyl)amino)benzenesulfonamide (Compound 151)

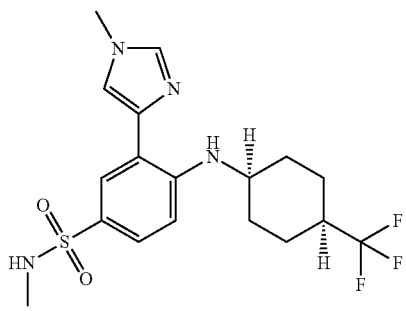

Compound 150

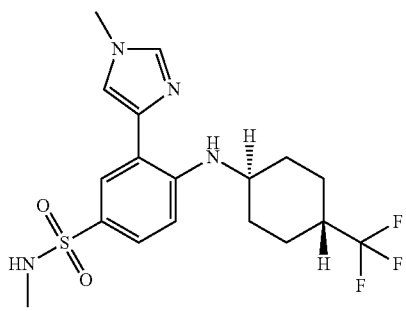

Compound 151

334

Preparation of Compound 150 and Compound 151:

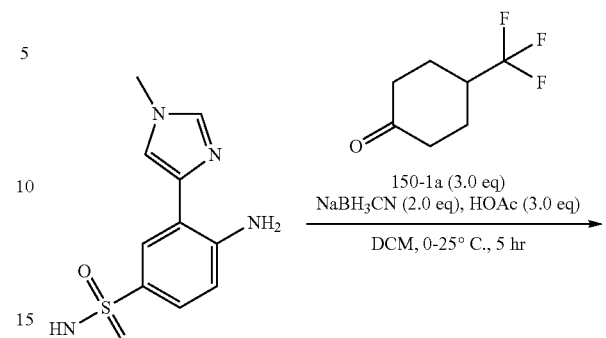

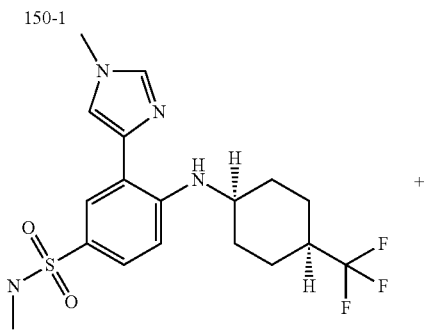

Compound 150

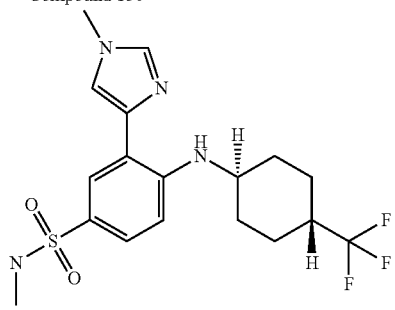

Compound 151

To a solution of compound 150-1 (250 mg, 0.93 mmol, 1 eq) and compound 150-1a (467.8 mg, 2.82 mmol, 3 eq) in DCE (5 mL) was added HOAc (169.1 mg, 2.82 mmol, 0.2 mL, 3 eq) at 25° C. under N$_2$. After addition, the mixture was stirred at 25° C. for 3 hr, and then NaBH$_4$ (106.5 mg, 2.82 mmol, 3 eq) was added at 0° C. The resulting mixture was stirred at 25° C. for 2 hr. TLC (PE/EA=1/1, UV 254) indicated reactant was consumed completely and two new spot formed. LCMS showed reactant was consumed completely and ~83% of desired compound was detected (m/z=439.0; RT: 0.67 min). The residue was poured into H$_2$O (30 mL) and stirred for 5 min. The aqueous phase was extracted with EA (10 mL*3). The combined organic phase was washed with brine (20 mL), dried with anhydrous Na$_2$SO$_4$, filtered and concentrated in vacuum. The residue was purified by flash silica gel chromatography to give Compound 150 (36.7 mg, 9.2% yield). LCMS (ESI): RT=0.814 min, mass calcd for C$_{18}$H$_{23}$F$_3$N$_4$O$_2$S 416.46, m/z found 417.4 [M+H]$^+$, $^1$H NMR (400 MHz, DMSO-d$_6$) δ 9.28 (d, J=8.0 Hz, 1H), 7.82-7.75 (m, 2H), 7.66 (d, J=1.0 Hz, 1H), 7.40 (dd, J=2.1, 8.7 Hz, 1H), 6.98 (q, J=5.0 Hz, 1H), 6.78 (d, J=8.8 Hz, 1H), 3.90 (br d, J=3.8 Hz, 1H), 3.73 (s, 3H), 2.37 (d, J=5.0 Hz, 2H), 2.42-2.31 (m, 1H), 2.42-2.31 (m, 1H), 1.99 (s, 1H), 1.87 (br d, J=12.3 Hz, 2H), 1.77-1.68 (m, 1H), 1.66 (br s, 1H), 1.63 (br s, 1H), 1.60 (br d, J=3.3 Hz, 1H), 1.77-1.54 (m, 1H), 1.56 (br s, 1H). Compound 151 (78.5 mg, 19.8% yield) was obtained. LCMS (ESI): RT=0.815 min, mass calcd for $C_{18}H_{23}F_3N_4O_2S$ 416.46, m/z found 417.4 [M+H]$^+$, $^1$H NMR (400 MHz, DMSO-d$_6$) δ 8.72 (d, J=7.5 Hz, 1H), 7.82-7.71 (m, 2H), 7.62 (s, 1H), 7.39 (dd, J=2.0, 8.8 Hz, 1H), 6.97 (q, J=5.0 Hz, 1H), 6.83 (d, J=9.0 Hz, 1H), 6.87-6.79 (m, 1H), 3.72 (s, 3H), 3.49-3.40 (m, 1H), 2.36 (d, J=5.3 Hz, 2H), 2.33 (br s, 1H), 2.13 (br d, J=11.0 Hz, 2H), 1.92 (br d, J=11.8 Hz, 2H), 1.55-1.40 (m, 2H), 1.34-1.24 (m, 2H).

Example 140: 3-(2-Aminopyridin-4-yl)-N-methyl-4-((3-(trifluoromethyl)phenyl)amino)benzenesulfonamide (Compound 152)

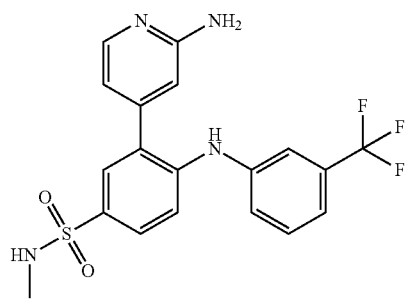 [SMILES: CNS(=O)(=O)c1ccc(Nc2cccc(C(F)(F)F)c2)c(-c2ccnc(N)c2)c1]

Preparation of Compound 152:

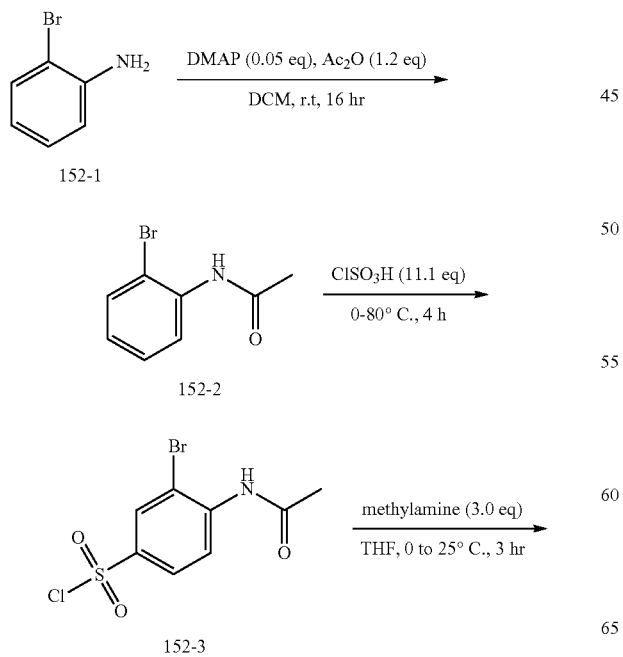

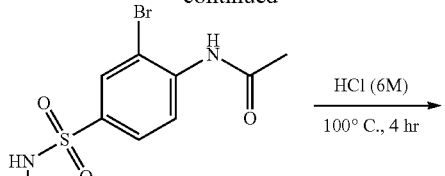

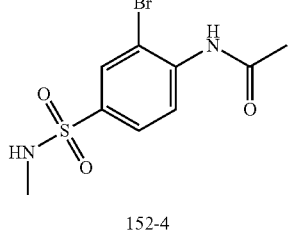

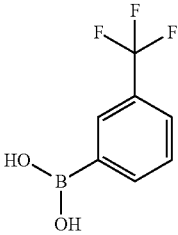

Step 1: N-(2-bromophenyl)acetamide

To a solution of compound 152-1 (20 g, 116.26 mmol, 1.0 eq) in DCM (10 mL) were added Ac₂O (14.24 g, 139.5 mmol, 13.0 mL, 1.2 eq) and DMAP (710.1 mg, 5.81 mmol, 0.05 eq). The mixture was stirred at 25° C. for 16 hr. LCMS showed the reactant was consumed completely and 95% desired MS was detected. The reaction mixture was poured into water (50 mL), and extracted with EA (50 mL*3). The combined organic layers were washed with brine (20 mL), dried over Na₂SO₄, filtered and concentrated under reduced pressure to give a residue. The crude product was used into the next step without further purification. Compound 152-2 (23 g, crude) was obtained. LCMS (ESI): RT=0.713 min, mass calcd. for $C_8H_8BrNO$ 212.98, m/z found 214.2 $[M+H]^+$.

Step 2: 4-acetamido-3-bromobenzene-1-sulfonyl chloride

A mixture of compound 152-2 (23 g, 107.4 mmol, 1.0 eq) in HSO₃Cl (139.8 g, 1.2 mol, 79.9 mL, 11.1 eq) at 0° C. was stirred at 80° C. for 4 hr. LCMS showed the reactant was remained and 30% of desired product was detected. The reaction mixture was poured into ice water (50 mL) and extracted with EA (50 mL*3). The combined organic layers were washed with brine (30 mL), dried over Na₂SO₄, filtered and concentrated under reduced pressure to give a residue. The crude product was used into the next step without further purification. Compound 152-3 (16 g, crude) was obtained. LCMS (ESI): RT=0.703 min, mass calcd. for $C_8H_8BrNO$ 212.98, m/z found 213.3 $[M+H]^+$.

Step 3: N-(2-bromo-4-(N-methylsulfamoyl)phenyl)acetamide

To a solution of compound 152-3 (16 g, 51.1 mmol, 1.0 eq) in THF (5 mL) was added methylamine (2 M, 127.9 mL, 5.0 eq) at 0° C. The mixture was stirred at 25° C. for 3 hr. TLC showed the reactant was consumed completely, and three new spots were detected. 60% of desired product was detected on LCMS. The reaction mixture was concentrated under reduced pressure to remove THF. The residue was purified by flash silica gel chromatography. Compound 152-4 (5 g, 25.4% yield) was obtained. LCMS (ESI): RT=0.568 min, mass calcd. for $C_9H_{11}BrN_2O_3S$ 305.97, m/z found 306.8 $[M+H]^+$.

Step 4: 4-amino-3-bromo-N-methylbenzenesulfonamide

A mixture of compound 152-4 (5 g, 16.3 mmol, 1.0 eq) in HCl (20 mL) was degassed and purged with N₂ for 3 times, and then the mixture was stirred at 100° C. for 3 hr under N₂ atmosphere. LCMS showed the reactant was consumed completely, and ~97% of desired product was detected. The pH of the reaction mixture was adjusted to 9~10 by adding NaHCO₃ solid and then the mixture was filtered and the filter cake was dried in vacuum. The crude product was used into the next step without further purification. Compound 152-5 (4 g, crude) was obtained. LCMS (ESI): RT=0.568 min, mass calcd. for $C_7H_9BrN_2O_2S$ 263.96, m/z found 264.8 $[M+H]^+$; ¹H NMR (400 MHz, CDCl₃) δ 7.93 (d, J=2.0 Hz, 1H), 7.63-7.52 (m, 1H), 6.80 (d, J=8.5 Hz, 1H), 2.65 (d, J=5.4 Hz, 3H).

Step 5: 3-bromo-N-methyl-4-((3-(trifluoromethyl)phenyl)amino)benzenesulfonamide To a solution of compound 152-5 (1 g, 3.7 mmol, 1.0 eq) in DCM (15 mL) were added Cu(OAc)₂ (822.1 mg, 4.5 mmol, 1.2 eq), DIPEA (974.9 mg, 7.5 mmol, 1.3 mL, 2.0 eq) and 5a (859.2 mg, 4.5 mmol, 1.2 eq). The mixture was stirred at 25° C. for 16 hr at O₂ atmosphere. LCMS showed the reactant was remained and ~20% of desired product was detected. TLC showed the reactant was remained and three new spots were detected. The reaction mixture was filtered and the filtrate was concentrated in vacuum. The residue was purified by flash silica gel chromatography. Compound 152-6 (200 mg, 6.5% yield) was obtained. LCMS (ESI): RT=2.210 min, mass calcd. for $C_{14}H_{12}BrF_3N_2O_2S$ 407.98, m/z found 408.9 $[M+H]^+$.

Step 6: N-methyl-3-(4,4,5,5-tetramethyl-1,3,2-dioxaborolan-2-yl)-4-((3-(trifluoromethyl)phenyl)amino)benzenesulfonamide To a solution of compound 152-6 (200 mg, 0.5 mmol, 1.0 eq) in dioxane (10 mL) were added AcOK (95.9 mg, 0.98 mmol, 2.0 eq), Pd(dppf)Cl₂ (17.9 mg, 24.4 umol, 0.05 eq) and compound 152-6a (186.1 mg, 0.73 mmol, 1.5 eq). The mixture was stirred at 90° C. for 16 hr. LCMS showed the reactant was consumed completely and ~40% of desired product was detected. The reaction mixture was filtered and the filtrate was concentrated in vacuum. The crude product was used into the next step without further purification. Compound 152-7 (400 mg, crude) was obtained. LCMS (ESI): RT=0.919 min, mass calcd. for $C_{20}H_{24}BF_3N_2O_4S$ 456.15, m/z found 456.7 $[M+H]^+$.

Step 7: 3-(2-aminopyridin-4-yl)-N-methyl-4-((3-(trifluoromethyl)phenyl)amino)benzenesulfonamide To a solution of compound 152-7 (200 mg, 0.45 mmol, 1.0 eq) in dioxane (15 mL) and H₂O (2 mL) were added Pd(dppf)Cl₂ (16.0 mg, 21.9 umol, 0.05 eq), Cs₂CO₃ (285.6 mg, 0.88 mmol, 2.0 eq) and compound 152-7a (151.6 mg, 0.88 mmol, 2.0 eq). The mixture was stirred at 90° C. for 16 hr. LCMS showed the reactant was consumed completely and 40% of desired product was detected. The reaction mixture was concentrated in vacuum. The residue was purified by prep-HPLC. Compound 152 (1.34 mg, 7.24e-1% yield) was obtained. LCMS (ESI): RT=0.669 min, mass calcd. for $C_{19}H_{17}F_3N_4O_2S$ 422.10, m/z found 423 $[M+H]^+$. ¹H NMR (400 MHz, CDCl₃) δ 8.18 (d, J=5.0 Hz, 1H), 7.77 (d, J=1.8 Hz, 1H), 7.49 (dd, J=1.8, 8.0 Hz, 1H), 7.46-7.41 (m, 1H), 7.38 (d, J=7.9 Hz, 1H), 7.29 (br s, 1H), 7.26 (br s, 1H), 6.72 (dd, J=1.4, 5.3 Hz, 1H), 6.55 (s, 1H), 5.87 (s, 1H), 4.62 (br s, 2H), 4.34 (br d, J=5.3 Hz, 1H), 2.75 (d, J=5.4 Hz, 3H).

Example 141: 3-(2-Aminopyridin-4-yl)-N-methyl-4-((4-(trifluoromethyl)phenyl)amino)benzenesulfonamide (Compound 153)

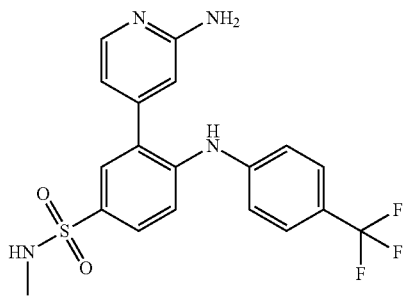 [SMILES: CNS(=O)(=O)c1ccc(Nc2ccc(C(F)(F)F)cc2)c(-c2ccnc(N)c2)c1]

Preparation of Compound 153:

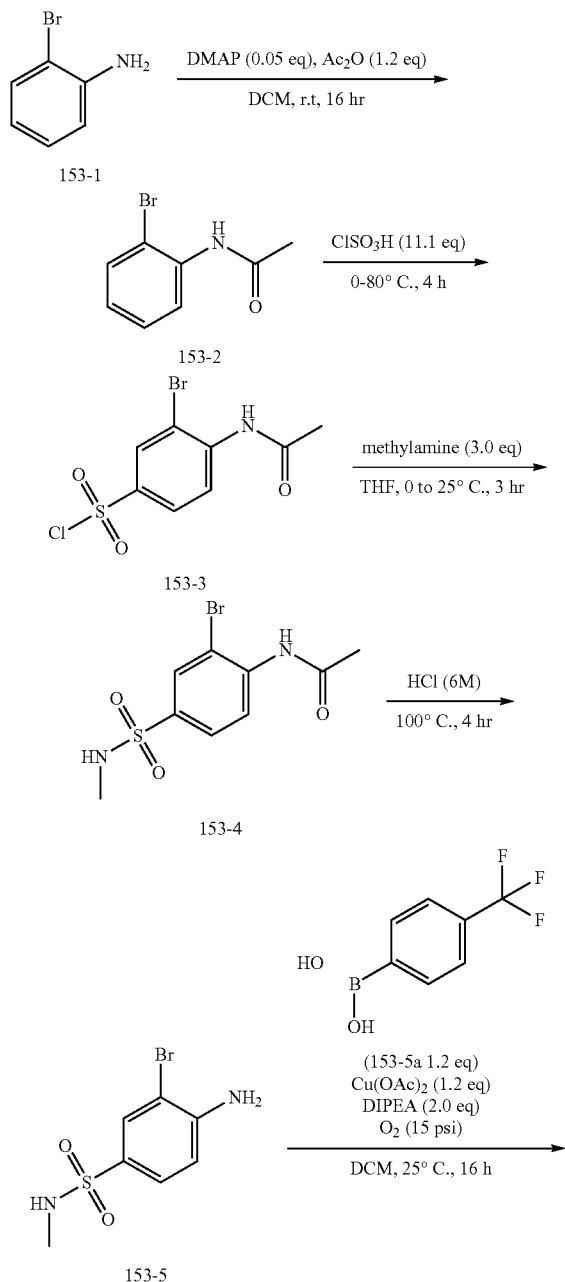

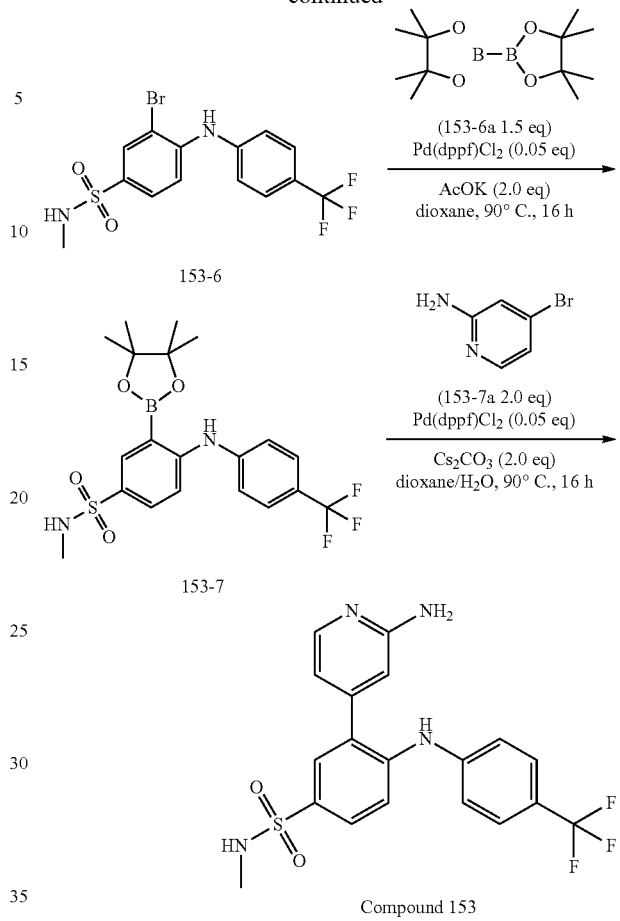

Step 1: N-(2-bromophenyl)acetamide

To a solution of compound 153-1 (20 g, 116.2 mmol, 1.0 eq) in DCM (10 mL) were added Ac$_2$O (14.2 g, 139.5 mmol, 13.0 mL, 1.2 eq) and DMAP (710 mg, 5.81 mmol, 0.05 eq). The mixture was stirred at 25° C. for 16 hr. LCMS showed the reactant was consumed completely and 95% desired MS was detected. The reaction mixture was poured into water (50 mL), and extracted with EA (50 mL*3). The combined organic layers were washed with brine (20 mL), dried over Na$_2$SO$_4$, filtered and concentrated under reduced pressure to give a residue. The crude product was used into the next step without further purification. Compound 153-2 (23 g, crude) was obtained. LCMS (ESI): RT=0.713 min, mass calcd. for C$_8$H$_8$BrNO 212.98, m/z found 214.2 [M+H]$^+$.

Step 2: 4-acetamido-3-bromobenzene-1-sulfonyl chloride

To a solution of compound 153-2 (23 g, 107.4 mmol, 1.0 eq) was added compound 153-2a (139.8 g, 1.2 mol, 79.9 mL, 11.1 eq) at 0° C. The mixture was stirred at 80° C. for 4 hr. LCMS showed the reactant was remained and 30% desired product was detected. The reaction mixture was poured into ice water (50 mL) and extracted with EA (50 mL*3). The combined organic layers were washed with brine (30 mL), dried over Na$_2$SO$_4$, filtered and concentrated under reduced pressure to give a residue. The crude product was used into the next step without further purification. Compound 153-3

(16 g, crude) was obtained. LCMS (ESI): RT=0.703 min, mass calcd. for $C_8H_8BrNO$ 212.98, m/z found 213.3 $[M+H]^+$.

Step 3: N-(2-bromo-4-(N-methylsulfamoyl)phenyl)acetamide

To a solution of compound 153-3 (16 g, 51.1 mmol, 1.0 eq) in THF (5 mL) was added methylamine (2 M, 127.9 mL, 5.0 eq) at 0° C. The mixture was stirred at 25° C. for 3 hr. TLC showed the reactant 153-3 was consumed completely, and three new spots were detected. 60% desired product was detected on LCMS. The reaction mixture was concentrated under reduced pressure to remove THF. The residue was purified by flash silica gel chromatography. Compound 153-4 (5 g, 25.4% yield) was obtained. LCMS (ESI): RT=0.568 min, mass calcd. for $C_9H_{11}BrN_2O_3S$ 305.97, m/z found 306.8 $[M+H]^+$.

Step 4: 4-amino-3-bromo-N-methylbenzenesulfonamide

A mixture of compound 153-4 (5 g, 16.3 mmol, 1.0 eq) in HCl (20 mL) was degassed and purged with $N_2$ for 3 times, and then the mixture was stirred at 100° C. for 3 hr under $N_2$ atmosphere. LCMS showed the reactant was consumed completely, and ~97% desired product was detected. The pH of the reaction mixture was adjusted to 9~10 by adding $NaHCO_3$ solid and then the mixture was filtered and the filter cake was dried in vacuum. The crude product was used into the next step without further purification. Compound 153-5 (4 g, crude) was obtained. LCMS (ESI): RT=0.568 min, mass calcd. for $C_7H_9BrN_2O_2S$ 263.96, m/z found 264.8 $[M+H]^+$; $^1H$ NMR (400 MHz, $CDCl_3$) δ 7.93 (d, J=2.0 Hz, 1H), 7.63-7.52 (m, 1H), 6.80 (d, J=8.5 Hz, 1H), 2.65 (d, J=5.4 Hz, 3H).

Step 5: 3-bromo-N-methyl-4-((4-(trifluoromethyl)phenyl)amino)benzenesulfonamide To a solution of compound 153-5 (1 g, 3.7 mmol, 1.0 eq) in DCM (15 mL) were added $Cu(OAc)_2$ (822.1 mg, 4.5 mmol, 1.2 eq), DIPEA (974.9 mg, 7.5 mmol, 1.3 mL, 2.0 eq) and compound 153-5a (859.6 mg, 4.5 mmol, 1.2 eq). The mixture was stirred at 25° C. for 16 hr at 02 atmosphere. TLC showed the reactant was remained and three new spots were detected. The reaction mixture was filtered and the filtrate was concentrated in vacuum. The residue was purified by flash silica gel chromatography. Compound 153-6 (150 mg, 5.8% yield) was obtained. LCMS (ESI): RT=2.190 min, mass calcd. for $C_{14}H_{12}BrF_3N_2O_2S$ 407.98, m/z found 408.9 $[M+H]^+$.

Step 6: N-methyl-3-(4,4,5,5-tetramethyl-1,3,2-dioxaborolan-2-yl)-4-((4-(trifluoromethyl)phenyl)amino)benzenesulfonamide To a solution of compound 153-6 (150 mg, 0.37 mmol, 1.0 eq) in dioxane (10 mL) were added $Pd(dppf)Cl_2$ (13.4 mg, 18.3 umol, 0.05 eq), AcOK (71.9 mg, 0.73 mmol, 2.0 eq) and compound 153-6a (139.6 mg, 0.55 mmol, 1.5 eq). The mixture was stirred at 90° C. for 6 hr. LCMS showed 40% desired product was detected. The reaction mixture was filtered and the filtrate was concentrated in vacuum. The residue was purified by flash silica gel chromatography. Compound 153-7 (50 mg, 29.9% yield) was obtained. LCMS (ESI): RT=0.907 min, mass calcd. for $C_{20}H_{24}BF_3N_2O_4S$ 456.15, m/z found 457.1 $[M+H]^+$.

Step 7: 3-(2-aminopyridin-4-yl)-N-methyl-4-((4-(trifluoromethyl)phenyl)amino)benzenesulfonamide To a solution of compound 153-7 (50 mg, 0.10 mmol, 1.0 eq) in dioxane (15 mL) and $H_2O$ (2 mL) were added $Pd(dppf)Cl_2$ (4.0 mg, 5.5 umol, 0.05 eq), $Cs_2CO_3$ (71.4 mg, 0.22 mmol, 2.0 eq) and compound 153-7a (37.9 mg, 0.22 mmol, 2.0 eq). The mixture was stirred at 90° C. for 16 hr. LCMS and HPLC showed the reactant was consumed completely and 40% desired product was detected. The reaction mixture was concentrated in vacuum. The residue was purified by prep-HPLC. Compound 153 (5.59 mg, 11.1% yield, HCl) was obtained. LCMS (ESI): RT=0.698 min, mass calcd. for $C_{19}H_{17}F_3N_4O_2S$ 422.10, m/z found 423 $[M+H]^+$; $^1H$ NMR (400 MHz, DMSO-$d_6$) δ 13.86-13.43 (m, 1H), 8.07-7.92 (m, 3H), 7.73 (d, J=8.5 Hz, 2H), 7.41 (d, J=8.5 Hz, 2H), 7.21 (dd, J=2.3, 8.8 Hz, 1H), 7.06-7.04 (m, 1H), 6.95 (s, 1H), 6.80 (d, J=8.8 Hz, 1H), 6.70 (dd, J=1.4, 6.7 Hz, 1H), 6.29 (br s, 2H), 3.13 (s, 3H), 2.53-2.52 (m, 3H).

II. Biological Evaluation

Example A1: YAP Reporter Assay

HEK293T cells stably transfected with 8XTBD luciferase reporter and pRLTK in 384-well plates were treated with the test compounds, starting from 3 μM (final concentration in assay plate), 1:3 dilution, and 10 points in quadruplicates. Post 24-hr incubation with compounds at 37° C. and 5% CO2, cells were lysed and 8XTBD-driven firefly luciferase and control TK-driven renilla luciferase activities were measured using Promega Dual-Luciferase Reporter Assay System.

Reagents: The reagents used for this study are: DMEM: Invitrogen #11960077, Dual-Glo Luciferase Assay System: Promega-E2980, Puromycin Dihydrochloride: Invitrogen-A1113803, 384-well plate: PerkinElmer-6007480, L-GLUTAMINE: Invitrogen-25030164, Hygromycin B: Invitrogen-10687010, and Penicillin-Streptomycin: Merk-TMS-AB2-C Media: The media used for this assay were: Culture Medium: DMEM+1 ug/mL puromycin+200 ug/mL hygromycin (with 10% FBS+1 mM L-glutamine); and Assay Medium: DMEM (with 10% FBS+1 mM L-glutamine+1× P/S).

Cell Plating: The appropriate media was warmed at 37° C. by water bath: Culture Medium, Assay Medium, 1* D-PBS, 0.05% trypsin-EDTA. The cells were trypsinized after removing all media, then washed with 1* sterile D-PBS and then with 2 ml 0.05% trypsin-EDTA. The cells were then incubated at RT for one minute. Then 10 ml/75 cm2 flask Assay Medium was added to each flask. Using a 10 ml pipette, the cells were then gently resuspended in the media, until the clumps completely disappeared. The cells were then transferred into 50 ml centrifuge tubes and were centrifuged at 800 rpm for 5 mins. The medium was removed and the cells were resuspended with Assay Medium. An aliquot of cells was used to count the cell density (cells/ml). The cell suspension was then diluted with Assay Medium to a concentration of 6×104 cells/ml. 50 ul cells suspension was then plated to 384-well plate (PerkinElmer-6007480), 3×103 cells/well and the cells were incubated in an incubator at 37° C., 5% CO2.

Compound Treatment: In the afternoon (incubation of the plate with 3-4 hrs), the test compounds were added by Echo, starting from 3 uM (final concentration in the assay plate), 1:3 dilution, 10 points, quadruplicates. The plate was placed at 37° C., 5% CO2 incubator for 24 hrs.

Detection: The Dual-Glo Luciferase Reagent was prepared by transferring the contents of one bottle of Dual-Glo Luciferase Buffer to one bottle of Dual-Glo Luciferase Substrate to create the Dual-Glo Luciferase Reagent. Mixing was performed by inversion until the substrate was thoroughly dissolved. After mixing, the reagent was aliquoted into 15 ml tubes. In the afternoon (24 hrs post compound treatment), the DMEM+ medium in the 384 well plates were aspirated by Microplate Washer.

Measuring firefly luciferase activity: 20 ul Dual-Glo Luciferase Reagent was added to the 384-well plates. The plates were protected from light to prevent interference with the assay. The plates were shaken for 1 min followed centrifuging plates at 1000 rpm for 30 seconds. After waiting at least 10 minutes, the firefly luminescence was measured by Envision.

Measuring renilla luciferase activity: 20 ul Stop-Glo Reagent was added to the 384-well plates. The plates were shaken for 1 min and then centrifuged at 1000 rpm for 30 seconds. After waiting at least 10 minutes, the renilla luminescence was measured by Envision.

Compound $IC_{50}$ and maximum inhibition on the firefly luciferase and renilla luciferase activities were reported separately. $IC_{50}$ for firefly luciferase activity are shown in the table below.

TABLE 2

| Compound No. | Name | Firefly Luciferase $IC_{50}$ (μM) |
|---|---|---|
| 1 | N-(tert-butyl)-4-(cyclohexylamino)-3-(2H-tetrazol-5-yl)benzenesulfonamide | D |
| 2 | N-(tert-butyl)-4-(cyclohexylamino)-3-(2-(2-hydroxyethyl)-2H-tetrazol-5-yl)benzenesulfonamide | D |
| 3 | N-cyclohexyl-2-(5-methyl-1,2,4-oxadiazol-3-yl)-4-(methylsulfonyl)aniline | A |
| 4 | N-cyclohexyl-4-(methylsulfonyl)-2-(2H-tetrazol-5-yl)aniline | D |
| 5 | N-cyclohexyl-2-(2-methyl-2H-tetrazol-5-yl)-4-(methylsulfonyl)aniline | B |
| 6 | N-cyclohexyl-2-(1-methyl-1H-1,2,3-triazol-4-yl)-4-(methylsulfonyl)aniline | B |
| 7 | N-cyclohexyl-2-(1-methyl-1H-pyrazol-4-yl)-4-(methylsulfonyl)aniline | D |
| 8 | N-cyclohexyl-2-(1-methyl-1H-pyrazol-3-yl)-4-(methylsulfonyl)aniline | B |
| 9 | N-cyclohexyl-4-(methylsulfonyl)-2-(1H-1,2,3-triazol-1-yl)aniline | D |
| 10 | N-cyclohexyl-4-(methylsulfonyl)-2-(1H-pyrazol-1-yl)aniline | C |
| 11 | N-cyclohexyl-2-(1H-imidazol-1-yl)-4-(methylsulfonyl)aniline | D |
| 12 | N-cyclohexyl-4-(methylsulfonyl)-2-(1H-1,2,4-triazol-1-yl)aniline | D |
| 13 | N-cyclohexyl-4-(methylsulfonyl)-2-(2H-1,2,3-triazol-2-yl)aniline | B |
| 14 | 4-(cyclohexylamino)-3-(2-ethyl-2H-tetrazol-5-yl)-N-methylbenzenesulfonamide | A |
| 15 | 4-(cyclohexylamino)-N-methyl-3-(2-propyl-2H-tetrazol-5-yl)benzenesulfonamide | A |
| 16 | 4-(cyclohexylamino)-3-(2-(4-fluorophenyl)-2H-tetrazol-5-yl)-N-methylbenzenesulfonamide | B |
| 17 | 3-(2-cyclobutyl-2H-tetrazol-5-yl)-4-(cyclohexylamino)-N-methylbenzenesulfonamide | A |
| 18 | 4-(cyclohexylamino)-3-(2-cyclopentyl-2H-tetrazol-5-yl)-N-methylbenzenesulfonamide | B |
| 19 | 4-(cyclohexylamino)-3-(2-(2-fluorobenzyl)-2H-tetrazol-5-yl)-N-methylbenzenesulfonamide | A |
| 20 | 3-(2-benzyl-2H-tetrazol-5-yl)-4-(cyclohexylamino)-N-methylbenzenesulfonamide | A |
| 21 | 3-(2-butyltetrazol-5-yl)-4-(cyclohexylamino)-N-methyl-benzenesulfonamide | A |
| 22 | 4-(cyclohexylamino)-N-methyl-3-(2-methyl-2H-tetrazol-5-yl)benzenesulfonamide | A |
| 23 | 4-(cyclohexylamino)-3-(2-(2-fluorophenyl)-2H-tetrazol-5-yl)-N-methylbenzenesulfonamide | B |
| 24 | tert-butyl 3-(5-(2-(cyclohexylamino)-5-(N-methylsulfamoyl)phenyl)-2H-tetrazol-2-yl)pyrrolidine-1-carboxylate | D |
| 25 | tert-butyl 3-(5-(2-(cyclohexylamino)-5-(N-methylsulfamoyl)phenyl)-2H-tetrazol-2-yl)azetidine-1-carboxylate | D |
| 26 | 4-(cyclohexylamino)-3-(2-isopropyl-2H-tetrazol-5-yl)-N-methylbenzenesulfonamide | A |
| 27 | 4-(cyclohexylamino)-3-(2-isobutyl-2H-tetrazol-5-yl)-N-methylbenzenesulfonamide | B |
| 28 | tert-butyl 4-(5-(2-(cyclohexylamino)-5-(N-methylsulfamoyl)phenyl)-2H-tetrazol-2-yl)piperidine-1-carboxylate | D |
| 29 | 4-(cyclohexylamino)-N-methyl-3-(2-(pyridin-3-ylmethyl)-2H-tetrazol-5-yl)benzenesulfonamide | A |
| 30 | 4-(cyclohexylamino)-N-methyl-3-(2-(piperidin-4-yl)-2H-tetrazol-5-yl)benzenesulfonamide | D |
| 31 | 3-(2-(1-acetylpiperidin-4-yl)-2H-tetrazol-5-yl)-4-(cyclohexylamino)-N-methylbenzenesulfonamide | B |
| 32 | 4-(cyclohexylamino)-N-methyl-3-(2-(1-(methylsulfonyl)piperidin-4-yl)-2H-tetrazol-5-yl)benzenesulfonamide | D |
| 33 | 4-(cyclohexylamino)-N-methyl-3-(2-(1-(pyridin-3-yl)piperidin-4-yl)-2H-tetrazol-5-yl)benzenesulfonamide | B |
| 34 | 4-(cyclohexylamino)-N-methyl-3-(2-phenyl-2H-tetrazol-5-yl)benzenesulfonamide | D |
| 35 | 4-(cyclohexylamino)-N-methyl-3-(2-(pyrrolidin-3-yl)-2H-tetrazol-5-yl)benzenesulfonamide | D |
| 36 | 4-(cyclohexylamino)-3-(2-(1-isopropylpyrrolidin-3-yl)-2H-tetrazol-5-yl)-N-methylbenzenesulfonamide | C |
| 37 | 4-(cyclohexylamino)-N-methyl-3-(2-(1-phenylpyrrolidin-3-yl)-2H-tetrazol-5-yl)benzenesulfonamide | D |
| 38 | 4-(cyclohexylamino)-N-methyl-3-(2-(1-phenylpiperidin-4-yl)-2H-tetrazol-5-yl)benzenesulfonamide | D |
| 39 | 4-(cyclohexylamino)-N-methyl-3-(2-(2,2,2-trifluoroethyl)-2H-tetrazol-5-yl)benzenesulfonamide | B |
| 40 | 4-(cyclohexylamino)-3-(2-(2-fluoroethyl)-2H-tetrazol-5-yl)-N-methylbenzenesulfonamide | A |
| 41 | 4-(cyclohexylamino)-3-(2-(4-fluorobenzyl)-2H-tetrazol-5-yl)-N-methylbenzenesulfonamide | B |
| 42 | 3-(2-(1-acetylpyrrolidin-3-yl)-2H-tetrazol-5-yl)-4-(cyclohexylamino)-N-methylbenzenesulfonamide | B |
| 43 | 4-(cyclohexylamino)-N-methyl-3-(2-(1-(methylsulfonyl)pyrrolidin-3-yl)-2H-tetrazol-5-yl)benzenesulfonamide | D |
| 44 | 4-(cyclohexylamino)-3-(2-(2-hydroxyethyl)-2H-tetrazol-5-yl)-N-methylbenzenesulfonamide | B |
| 45 | 4-(cyclohexylamino)-N-methyl-3-(2-(pyridin-3-yl)-2H-tetrazol-5-yl)benzenesulfonamide | A |
| 46 | 4-(cyclohexylamino)-3-(2-(1-isopropylpiperidin-4-yl)-2H-tetrazol-5-yl)-N-methylbenzenesulfonamide | D |

TABLE 2-continued

| Compound No. | Name | Firefly Luciferase IC$_{50}$ (μM) |
|---|---|---|
| 47 | isopropyl 4-(5-(2-(cyclohexylamino)-5-(N-methylsulfamoyl)phenyl)-2H-tetrazol-2-yl)piperidine-1-carboxylate | D |
| 48 | 4-(cyclohexylamino)-N-methyl-3-(5-methyl-1,2,4-oxadiazol-3-yl)benzenesulfonamide | A |
| 49 | 3-(2-(1-acetylazetidin-3-yl)-2H-tetrazol-5-yl)-4-(cyclohexylamino)-N-methylbenzenesulfonamide | B |
| 50 | 4-(cyclohexylamino)-N-methyl-3-(2-(1-(methylsulfonyl)azetidin-3-yl)-2H-tetrazol-5-yl)benzenesulfonamide | D |
| 51 | 4-(cyclohexylamino)-N-methyl-3-(2-(1-phenylazetidin-3-yl)-2H-tetrazol-5-yl)benzenesulfonamide | D |
| 52 | 4-(cyclohexylamino)-3-(2-(1-isopropylazetidin-3-yl)-2H-tetrazol-5-yl)-N-methylbenzenesulfonamide | B |
| 53 | 3-(2-(1-acetylpiperidin-3-yl)-2H-tetrazol-5-yl)-4-(cyclohexylamino)-N-methylbenzenesulfonamide | B |
| 54 | 3-(2-(azetidin-3-yl)-2H-tetrazol-5-yl)-4-(cyclohexylamino)-N-methylbenzenesulfonamide | D |
| 55 | 4-(cyclohexylamino)-N-methyl-3-(pyrimidin-5-yl)benzenesulfonamide | D |
| 56 | 4-(cyclohexylamino)-N-methyl-3-(pyrimidin-2-yl)benzenesulfonamide | A |
| 57 | 4-(cyclohexylamino)-N-methyl-3-(1-methyl-1H-pyrazol-3-yl)benzenesulfonamide | A |
| 58 | 4-(cyclohexylamino)-N-methyl-3-(1-methyl-1H-1,2,3-triazol-4-yl)benzenesulfonamide | A |
| 59 | tert-butyl 3-(5-(2-(cyclohexylamino)-5-(N-methylsulfamoyl)phenyl)-2H-tetrazol-2-yl)piperidine-1-carboxylate | B |
| 60 | tert-butyl 3-(5-(2-(cyclohexylamino)-5-(N-methylsulfamoyl)phenyl)-1H-tetrazol-1-yl)piperidine-1-carboxylate | D |
| 61 | 4-(cyclohexylamino)-3-(2-(1-isopropylpiperidin-3-yl)-2H-tetrazol-5-yl)-N-methylbenzenesulfonamide | D |
| 62 | 4-(cyclohexylamino)-N-methyl-3-(2-(1-(methylsulfonyl)piperidin-3-yl)-2H-tetrazol-5-yl)benzenesulfonamide | D |
| 63 | 4-(cyclohexylamino)-N-methyl-3-(2-(1-phenylpiperidin-3-yl)-2H-tetrazol-5-yl)benzenesulfonamide | D |
| 64 | 4-(cyclohexylamino)-N-methyl-3-(pyridin-2-yl)benzenesulfonamide | A |
| 65 | 4-(cyclohexylamino)-N-methyl-3-(pyridin-4-yl)benzenesulfonamide | D |
| 66 | 4-(cyclohexylamino)-N-methyl-3-(5-methyl-1H-1,2,4-triazol-3-yl)benzenesulfonamide | B |
| 67 | 4-(cyclohexylamino)-3-(1,5-dimethyl-1H-1,2,4-triazol-3-yl)-N-methylbenzenesulfonamide | A |
| 68 | 4-(cyclohexylamino)-N-methyl-3-(2-(1-(pyridin-3-yl)pyrrolidin-3-yl)-2H-tetrazol-5-yl)benzenesulfonamide | B |
| 69 | 4-(cyclohexylamino)-N-methyl-3-(pyrimidin-4-yl)benzenesulfonamide | B |
| 70 | 4-(cyclohexylamino)-N-methyl-3-(2-(1-(pyridin-3-yl)azetidin-3-yl)-2H-tetrazol-5-yl)benzenesulfonamide | B |
| 71 | 4-(cyclohexylamino)-3-(2-cyclopropyl-2H-tetrazol-5-yl)-N-methylbenzenesulfonamide | D |
| 72 | 4-((4,4-difluorocyclohexyl)amino)-N-methyl-3-(2-methyl-2H-tetrazol-5-yl)benzenesulfonamide | A |
| 73 | 4-((3,3-difluorocyclohexyl)amino)-N-methyl-3-((3,3-difluorocyclohexyl)amino)-N-methyl-3-(2-methyl-2H-tetrazol-5-yl)benzenesulfonamide | A |
| 74 | 4-(cyclohexylamino)-N-methyl-3-(2-(piperidin-3-yl)-2H-tetrazol-5-yl)benzenesulfonamide | B |
| 75 | 4-(cyclohexylamino)-N-methyl-3-(1-(piperidin-3-yl)-1H-tetrazol-5-yl)benzenesulfonamide | C |
| 76 | 3-(6-aminopyridin-2-yl)-4-(cyclohexylamino)-N-methylbenzenesulfonamide | B |
| 77 | 4-(cyclohexylamino)-N-methyl-3-(pyridin-3-yl)benzenesulfonamide | D |
| 78 | 4-(cyclohexylamino)-N-methyl-3-(3-methylpyridin-2-yl)benzenesulfonamide | D |
| 79 | 4-(cyclohexylamino)-3-(3-fluoropyridin-2-yl)-N-methylbenzenesulfonamide | A |
| 80 | 4-(cyclohexylamino)-3-(3-methoxypyridin-2-yl)-N-methylbenzenesulfonamide | C |
| 81 | 4-(cyclohexylamino)-N-methyl-3-(2H-1,2,3-triazol-2-yl)benzenesulfonamide | A |
| 82 | 4-(cyclohexylamino)-N-methyl-3-(1-methyl-1H-imidazol-4-yl)benzenesulfonamide | A |
| 83 | 4-(cyclohexylamino)-3-(6-(dimethylamino)pyridin-2-yl)-N-methylbenzenesulfonamide | D |
| 84 | 3-(4-aminopyridin-2-yl)-4-(cyclohexylamino)-N-methylbenzenesulfonamide | B |
| 85 | 4-(cyclohexylamino)-N-methyl-3-(6-(methylamino)pyridin-2-yl)benzenesulfonamide | C |
| 86 | 4-(cyclohexylamino)-N-methyl-3-(2-(1-(pyridin-3-yl)piperidin-3-yl)-2H-tetrazol-5-yl)benzenesulfonamide | B |
| 87 | 4-(cyclohexylamino)-3-(4-(dimethylamino)pyridin-2-yl)-N-methylbenzenesulfonamide | A |
| 88 | 4-(cyclohexylamino)-N-methyl-3-(4-(methylamino)pyridin-2-yl)benzenesulfonamide | A |
| 89 | 4-(cyclohexylamino)-N-methyl-3-(1H-1,2,3-triazol-1-yl)benzenesulfonamide | D |
| 90 | N-methyl-3-(2-methyl-2H-tetrazol-5-yl)-4-(phenylamino)benzenesulfonamide | A |
| 91 | 4-(cyclohexylamino)-N-methyl-3-(3-methyl-1,2,4-oxadiazol-5-yl)benzenesulfonamide | B |
| 92 | N-methyl-3-(2-methyl-2H-tetrazol-5-yl)-4-((3-(trifluoromethyl)phenyl)amino)benzenesulfonamide | A |
| 93 | N-methyl-3-(2-methyl-2H-tetrazol-5-yl)-4-((2-(trifluoromethyl)phenyl)amino)benzenesulfonamide | D |
| 94 | N-methyl-3-(2-methyl-2H-tetrazol-5-yl)-4-((3-(trifluoromethoxy)phenyl)amino)benzenesulfonamide | A |
| 95 | N-methyl-3-(2-methyl-2H-tetrazol-5-yl)-4-((4-(trifluoromethyl)phenyl)amino)benzenesulfonamide | A |
| 96 | N-methyl-3-(1-methyl-1H-tetrazol-5-yl)-4-((4-(trifluoromethyl)phenyl)amino)benzenesulfonamide | D |
| 97 | N-methyl-3-(1-methyl-1H-tetrazol-5-yl)-4-((3-(trifluoromethyl)phenyl)amino)benzenesulfonamide | D |
| 98 | N-methyl-3-(1-methyl-1H-tetrazol-5-yl)-4-((2-(trifluoromethyl)phenyl)amino)benzenesulfonamide | D |
| 99 | N-methyl-3-(1-methyl-1H-tetrazol-5-yl)-4-((4-(trifluoromethoxy)phenyl)amino)benzenesulfonamide | D |
| 100 | N-methyl-3-(1-methyl-1H-tetrazol-5-yl)-4-((3-(trifluoromethoxy)phenyl)amino)benzenesulfonamide | D |
| 101 | N-methyl-3-(1-methyl-1H-tetrazol-5-yl)-4-((2-(trifluoromethoxy)phenyl)amino)benzenesulfonamide | D |
| 102 | N-methyl-3-(2-methyl-2H-tetrazol-5-yl)-4-((2-(trifluoromethoxy)phenyl)amino)benzenesulfonamide | D |
| 103 | N-methyl-3-(2-methyl-2H-tetrazol-5-yl)-4-((4-(trifluoromethoxy)phenyl)amino)benzenesulfonamide | A |
| 104 | 4-((2,3-difluorophenyl)amino)-N-methyl-3-(2-methyl-2H-tetrazol-5-yl)benzenesulfonamide | B |

TABLE 2-continued

| Compound No. | Name | Firefly Luciferase IC$_{50}$ (µM) |
|---|---|---|
| 105 | 4-(cyclohexylamino)-N-methyl-3-(5-methyl-1,3,4-oxadiazol-2-yl)benzenesulfonamide | A |
| 106 | 4-((2,3-difluorophenyl)amino)-N-methyl-3-(1-methyl-1H-tetrazol-5-yl)benzenesulfonamide | D |
| 107 | 4-((3,5-difluorophenyl)amino)-N-methyl-3-(1-methyl-1H-tetrazol-5-yl)benzenesulfonamide | D |
| 108 | 4-((3,5-difluorophenyl)amino)-N-methyl-3-(2-methyl-2H-tetrazol-5-yl)benzenesulfonamide | B |
| 109 | 4-((2,5-difluorophenyl)amino)-N-methyl-3-(1-methyl-1H-tetrazol-5-yl)benzenesulfonamide | D |
| 110 | 4-((2,5-difluorophenyl)amino)-N-methyl-3-(2-methyl-2H-tetrazol-5-yl)benzenesulfonamide | A |
| 111 | 4-(cyclohexylamino)-3-(1-cyclopropyl-1H-imidazol-4-yl)-N-methylbenzenesulfonamide | A |
| 112 | 4-(cyclohexylamino)-3-(1-ethyl-1H-imidazol-4-yl)-N-methylbenzenesulfonamide | A |
| 113 | 4-(cyclohexylamino)-3-(1-isopropyl-1H-imidazol-4-yl)-N-methylbenzenesulfonamide | A |
| 114 | 4-(cyclohexylamino)-3-(1-ethyl-1H-imidazol-5-yl)-N-methylbenzenesulfonamide | D |
| 115 | 3-(2-(2-(benzyloxy)ethyl)-2H-tetrazol-5-yl)-N-methyl-4-((4-(trifluoromethyl)phenyl)amino)benzenesulfonamide | B |
| 116 | 3-(2-(2-hydroxyethyl)-2H-tetrazol-5-yl)-N-methyl-4-((4-(trifluoromethyl)phenyl)amino)benzenesulfonamide | A |
| 117 | 4-((3-fluorophenyl)amino)-N-methyl-3-(2-methyl-2H-tetrazol-5-yl)benzenesulfonamide | B |
| 128 | N-methyl-3-(2-methyltetrazol-5-yl)-4-(4-phenylanilino) benzenesulfonamide | C |
| 130 | N-methyl-3-(2-methyltetrazol-5-yl)-4-(4-phenoxyanilino) benzenesulfonamide | C |
| 131 | N-methyl-3-(2-methyltetrazol-5-yl)-4-(3-phenylanilino) benzenesulfonamide | A |
| 133 | 3-(5-amino-1,3,4-oxadiazol-2-yl)-N-methyl-4-[4-(trifluoromethyl)anilino]benzenesulfonamide | B |
| 134 | N-methyl-3-(2-methyltetrazol-5-yl)-4-(3-phenoxyanilino)benzenesulfonamide | B |
| 136 | 3-[2-[(2-Fluorophenyl)methyl]tetrazol-5-yl]-N-methyl-4-[3-(trifluoromethyl)anilino]benzenesulfonamide | A |
| 137 | 3-[2-[(2-Fluorophenyl)methyl]tetrazol-5-yl]-N-methyl-4-[4-(trifluoromethyl)anilino]benzenesulfonamide | A |
| 139 | 4-(4-chloroanilino)-N-methyl-3-(1-methylimidazol-4-yl)benzenesulfonamide | A |
| 140 | 4-(3,4-dichloroanilino)-N-methyl-3-(1-methylimidazol-4-yl)benzenesulfonamide | A |
| 141 | N-methyl-3-(1-methylimidazol-4-yl)-4-[3-(trifluoromethylsulfanyl)anilino]benzenesulfonamide | A |
| 142 | 4-(3,5-dichloroanilino)-N-methyl-3-(1-methylimidazol-4-yl)benzenesulfonamide | A |
| 143 | 4-(3-Chloroanilino)-N-methyl-3-(1-methylimidazol-4-yl)benzenesulfonamide | A |
| 144 | N-methyl-3-(1-methylimidazol-4-yl)-4-[4-(trifluoromethylsulfanyl)anilino]benzenesulfonamide | A |
| 145 | N-methyl-3-(1-methylimidazol-4-yl)-4-(3,4,5-trichloroanilino)benzenesulfonamide | A |
| 146 | 4-[3,5-Bis(trifluoromethyl)anilino]-N-methyl-3-(1-methylimidazol-4-yl)benzenesulfonamide | B |
| 147 | 4-[4-Chloro-3-(trifluoromethyl)anilino]-N-methyl-3-(1-methylimidazol-4-yl)benzenesulfonamide | A |
| 148 | 4-[3-Chloro-4-(trifluoromethyl)anilino]-N-methyl-3-(1-methylimidazol-4-yl)benzenesulfonamide | A |
| 149 | 4-((2,6-Difluorophenyl)amino)-N-methyl-3-(1-methyl-1H-imidazol-4-yl)benzenesulfonamide | A |
| 150 | N-methyl-3-(1-methyl-1H-imidazol-4-yl)-4-(((1s,4s)-4-(trifluoromethyl)cyclohexyl)amino)benzenesulfonamide | A |
| 151 | N-methyl-3-(1-methyl-1H-imidazol-4-yl)-4-(((1r,4r)-4-(trifluoromethyl)cyclohexyl)amino)benzenesulfonamide | A |
| 152 | 3-(2-Aminopyridin-4-yl)-N-methyl-4-((3-(trifluoromethyl)phenyl)amino)benzenesulfonamide | C |

Note:
Biochemical assay IC$_{50}$ data are designated within the following ranges:
A: ≤0.100 µM
B: >0.100 µM to ≤1.000 µM
C: >1.000 µM to ≤3.000 µM
D: >3.000 µM Example A2: Tumor Suppression Assay The procedures described herein for the tumor suppression assay is as described in PCT/US2013/043752 (WO 2013/188138). Mouse procedures are performed according to the guidelines of approved animal protocol and based on the methods. After the cells are grown to 90%>confluence, these cells are harvested by trypsinization, washed in phosphate-buffered saline (PBS), and resuspended in PBS supplemented with 50% Matrigel (BD Biosciences). An appropriate amount of cells is prepared for administration, such as 200 µL per injection site. Immuno-compromised mice are injected on the dorsolateral sites subcutaneously. Any one of the compounds described herein is formulated accordingly and is then administered at a suitable dose. Control mice received vehicle alone. The average tumor diameter (two perpendicular axes of the tumor are measured) are recorded. The data are expressed in tumor volume estimated by ([width]2×length/2). Paired, two-tailed Student's t-test is performed to access the statistical significance.

Example A3: Cell Proliferation Assay

Cancer cell lines are plated in 384-well plates 24 h before drug treatment. Post incubation for various time periods with the test compounds, starting from 3 µM (final concentration in assay plate), 1:3 dilution, and 10 points in duplicates, the number of viable cells and proliferative cells are determined using CellTiter-Glo® Luminescent Cell Viability Assay Kit (Promega) and Click-iT EdU HCS Assay Kit (Invitrogen) according to the manufacturers' protocols. The IC$_{50}$ values and maximum % inhibition of the test compounds are calculated using the dose response curves.

The examples and embodiments described herein are for illustrative purposes only and various modifications or changes suggested to persons skilled in the art are to be included within the spirit and purview of this application and scope of the appended claims.

What is claimed is:
1. A compound of Formula (I) or a pharmaceutically acceptable salt thereof:

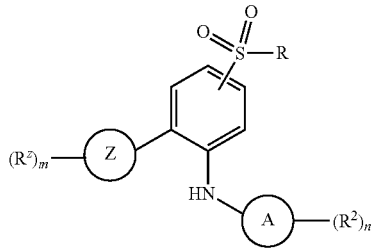

Formula (I)

wherein,

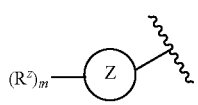

is substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, or substituted or unsubstituted thiadiazolyl;

each $R^z$ is independently H, halogen, —CN, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, substituted or unsubstituted heteroaryl, -$L^1$-$Y^1$, or -$L^2$-$L^3$-$Y^2$;

m is 0, 1, 2, 3, or 4;

$L^1$ is substituted or unsubstituted $C_1$-$C_6$alkylene, substituted or unsubstituted $C_2$-$C_{10}$cyclolkylene, or substituted or unsubstituted $C_2$-$C_{10}$heterocycloalkylene;

$Y^1$ is substituted or unsubstituted $C_3$-$C_{10}$cycloalkyl, substituted or unsubstituted $C_2$-$C_{10}$ heterocycloalkyl, substituted or unsubstituted aryl, or substituted or unsubstituted heteroaryl;

$L^2$ is absent, substituted or unsubstituted $C_1$-$C_6$alkylene, substituted or unsubstituted $C_2$-$C_{10}$cyclolkylene, or substituted or unsubstituted $C_2$-$C_{10}$heterocycloalkylene;

$L^3$ is —O—, —S—, —(S=O)—, —(SO$_2$)—, —NR$^3$—, —(C=O)—, —(C=O)O—, —(C=O)—, —(C=O)NR$^3$—, —(C=O)NR$^3$—O—, —O—NR$^3$(C=O)—, —NR$^3$(C=O)—, —NR$^3$(C=O)NR$^3$—, —O(C=O)NR$^3$—, —NR$^3$(C=O)O—, —NR$^3$(SO$_2$)NR$^3$—, —NR$^3$(SO$_2$)—, —(SO$_2$)NR$^3$—, —(SO$_2$)NR$^3$—(C=O)—, —(C=O)—NR$^3$(SO$_2$)—, —(SO$_2$)NR$^3$—(C=O)O—, —O(C=O)—NR$^3$(SO$_2$)—, —NR$^3$(SO$_2$)NR$^3$—(C=O)—, —(C=O)—NR$^3$(SO$_2$)NR$^3$—, —O(C=O)—NR$^3$(SO$_2$)—NR$^3$—, or —NR$^3$(SO$_2$)NR$^3$—(C=O)O—;

each $R^3$ is independently H or substituted or unsubstituted $C_1$-$C_6$alkyl;

$Y^2$ is H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;

or $R^3$ and $Y^2$ on the same N atom are taken together with the N atom to which they are attached to form a substituted or unsubstituted N-containing heterocycle;

R is $NHR^1$ or $R^1$;

$R^1$ is substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

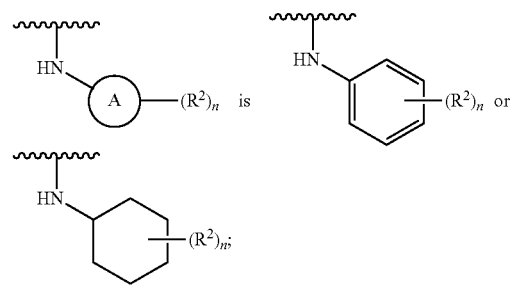

each $R^2$ is independently H, halogen, —$N_3$, —CN, —$OR^4$, —$SR^4$, —$(SO_2)R^4$, —$N(R^4)_2$, —$CO_2R^4$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl substituted or unsubstituted $C_2$-$C_{10}$heterocycloalkyl, substituted or unsubstituted aralkyl, substituted or unsubstituted aryl, substituted or unsubstituted heteroaryl, or

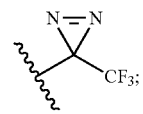

n is 0, 1, 2, 3, 4, or 5; and each $R^4$ is independently H, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

2. The compound or pharmaceutically acceptable salt thereof of claim 1, wherein:

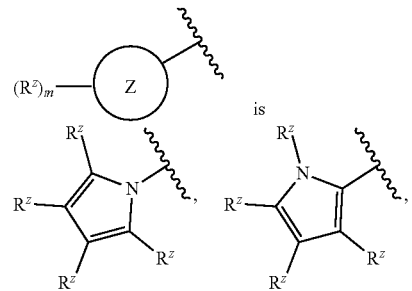

351
-continued
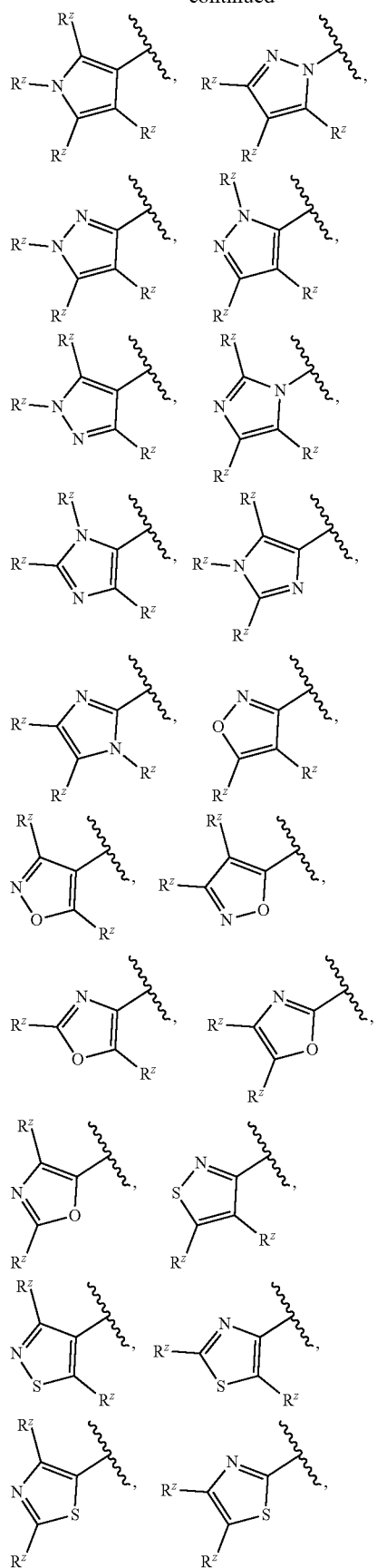
352
-continued
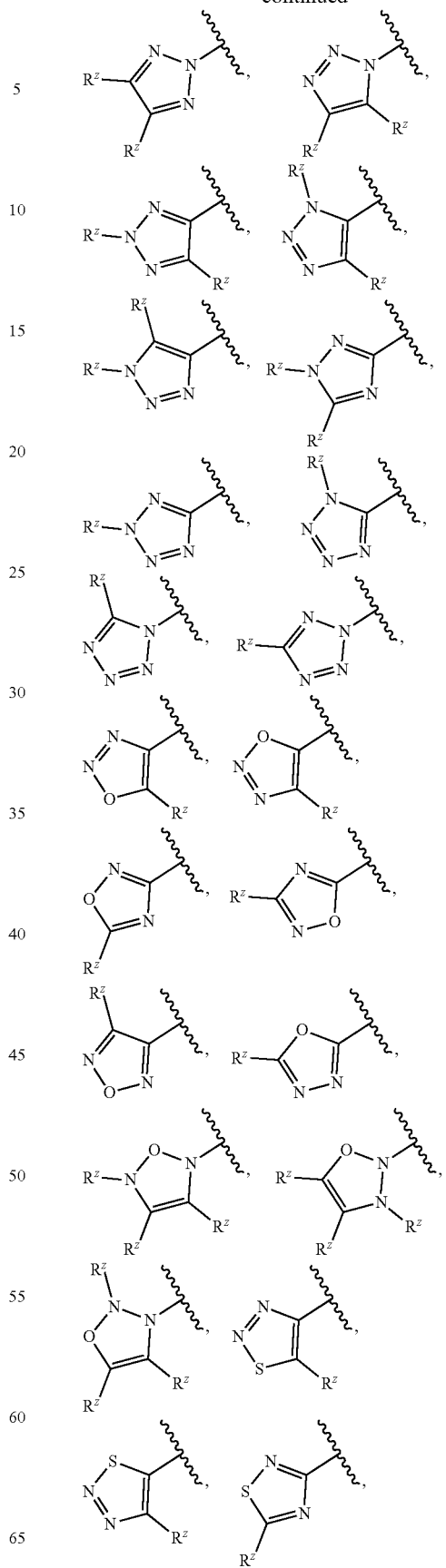

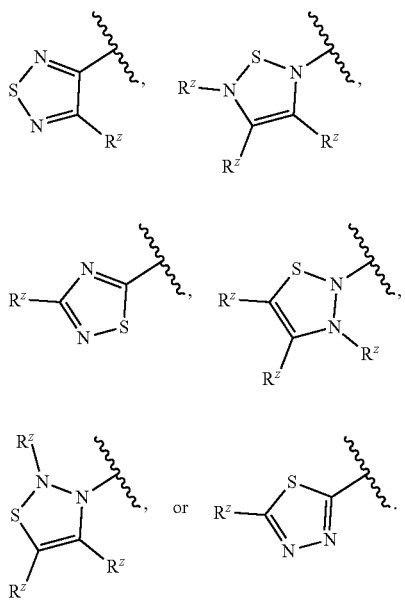

3. The compound or pharmaceutically acceptable salt thereof of claim 1, wherein:

each $R^z$ is independently H, halogen, substituted or unsubstituted $C_1$-$C_6$alkyl, substituted or unsubstituted $C_1$-$C_6$haloalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl.

4. The compound or pharmaceutically acceptable salt thereof of claim 3, wherein:

each $R^z$ is independently H, F, —Cl, —Br, —I, methyl, ethyl, n-propyl, iso-propyl, n-butyl, iso-butyl, tert-butyl, cyclopropyl, cyclobutyl, cyclopentyl, cyclohexyl, or phenyl.

5. The compound or pharmaceutically acceptable salt thereof of claim 1, wherein:

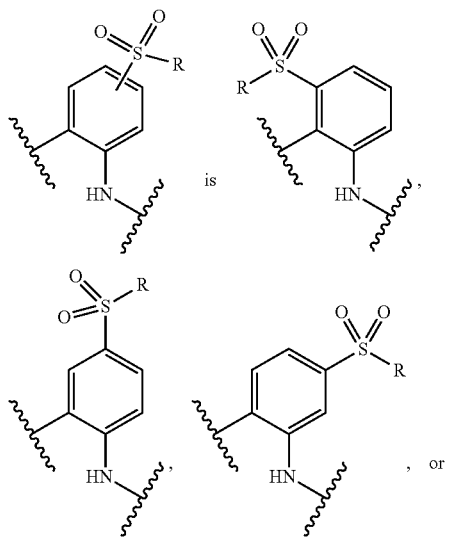

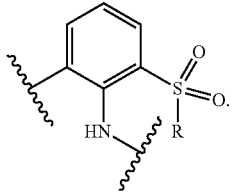

6. The compound or pharmaceutically acceptable salt thereof of claim 1, wherein:

R is $NHR^1$; and $R^1$ is substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl.

7. The compound or pharmaceutically acceptable salt thereof of claim 6, wherein:

$R^1$ is methyl, ethyl, n-propyl, iso-propyl, n-butyl, iso-butyl, tert-butyl, cyclopropyl, cyclobutyl, cyclopentyl, cyclohexyl, or phenyl.

8. The compound or pharmaceutically acceptable salt thereof of claim 1, wherein:

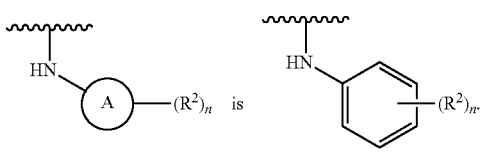

9. The compound or pharmaceutically acceptable salt thereof of claim 8, wherein:

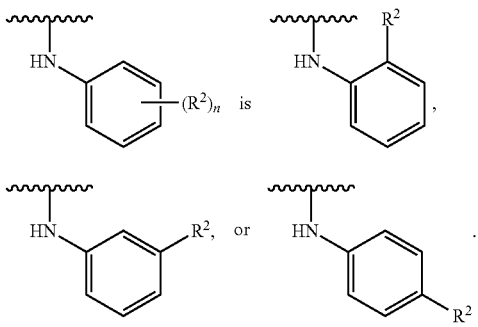

10. The compound or pharmaceutically acceptable salt thereof of claim 1, wherein:

each $R^2$ is independently H, halogen, —$N_3$, —CN, —$OR^4$, —$SR^4$, —$(SO_2)R^4$, —$N(R^4)_2$, —$CH_2R^4$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloakyl, substituted or unsubstituted $C_2$-$C_{10}$heterocycloalkyl, substituted or unsubstituted aralkyl, substituted or unsubstituted aryl, or substituted or unsubstituted heteroaryl.

11. The compound or pharmaceutically acceptable salt thereof of claim 1, wherein the compound has the structure of Formula (Id), or a pharmaceutically acceptable salt thereof:

Formula (Id)

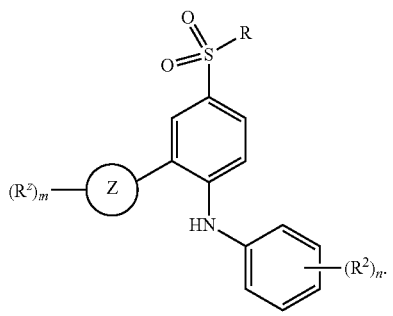

12. The compound or pharmaceutically acceptable salt thereof of claim 1, wherein the compound has the structure of Formula (Ie), or a pharmaceutically acceptable salt thereof:

Formula (Ie)

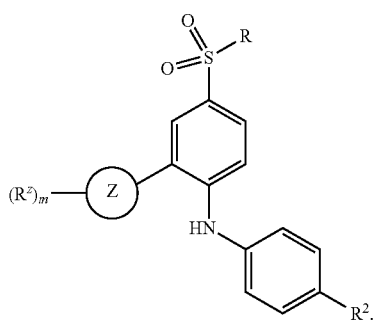

13. The compound or pharmaceutically acceptable salt thereof of claim 1, wherein each $R^2$ is —$CF_3$.

14. A pharmaceutical composition comprising a pharmaceutically acceptable excipient and a compound of claim 1 or a pharmaceutically acceptable salt thereof.

15. A method for treating a cancer in a subject in need thereof comprising administering a therapeutically effective amount of a compound of claim 1 or a pharmaceutically acceptable salt thereof.

16. The method of claim 15, wherein the cancer is selected from mesothelioma, hepatocellular carcinoma, meningioma, malignant peripheral nerve sheath tumor, lung cancer, prostate cancer, pancreatic cancer, adenosquamous carcinoma, thyroid cancer, gastric cancer, esophageal cancer, ovarian cancer, melanoma, and breast cancer.

17. A method of inhibiting one or more of proteins encompassed by, or related to, the Hippo pathway in a subject, comprising administering to a subject a compound of claim 1, or a pharmaceutically acceptable salt thereof.

18. A method of inhibiting transcriptional coactivator with PDZ binding motif/Yes-associated protein transcriptional coactivator (TAZ/YAP) in a subject comprising administering to a subject a compound of claim 1, or a pharmaceutically acceptable salt thereof.

19. A compound that has one of the following structures:

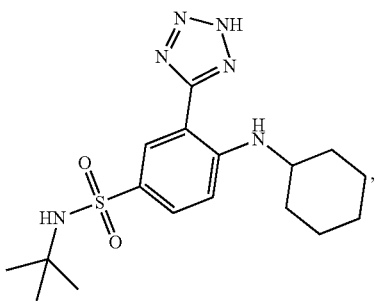

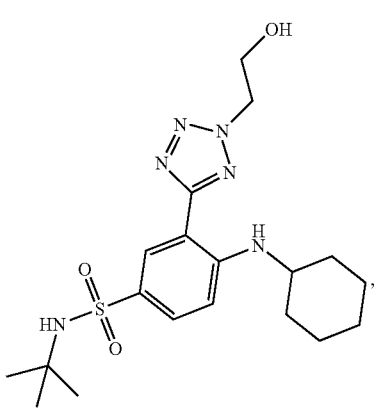

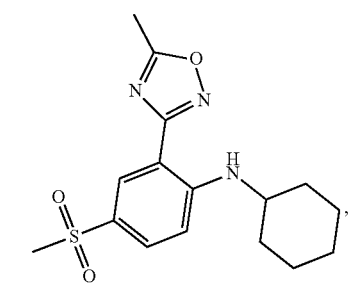

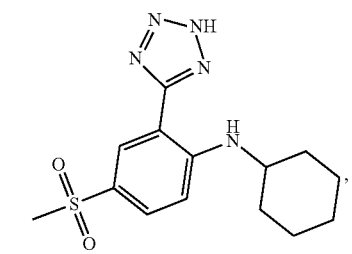

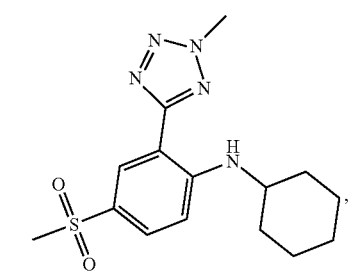

-continued
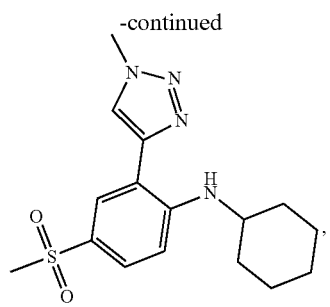
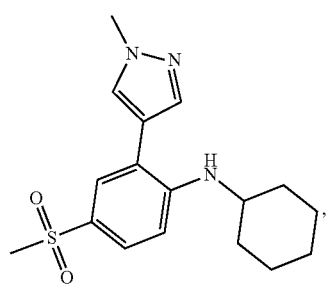
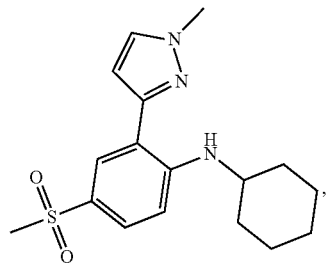
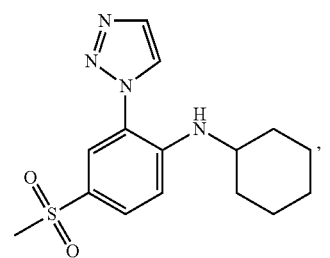
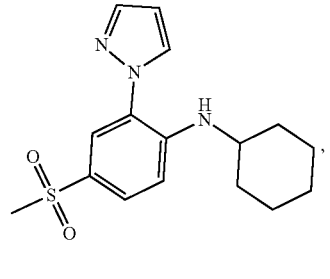
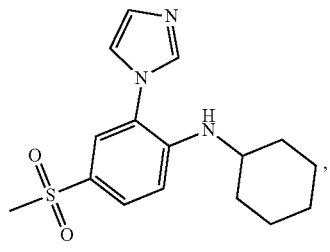
-continued
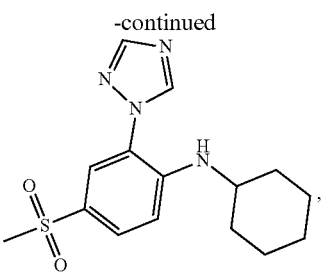
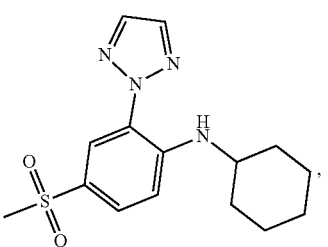
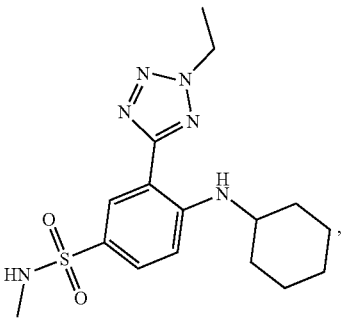
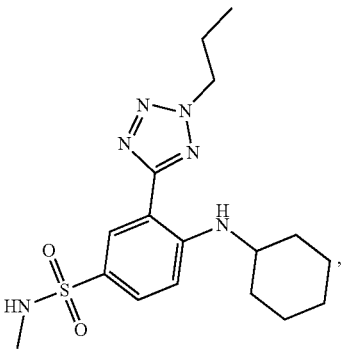
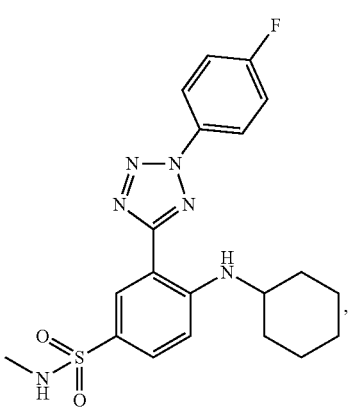

359
-continued
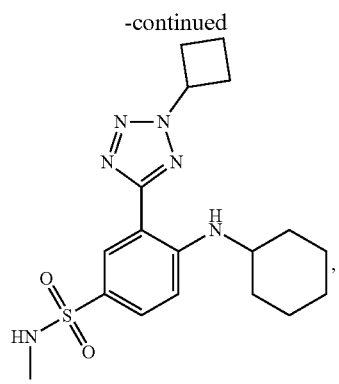
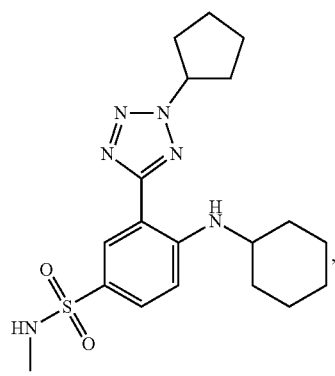
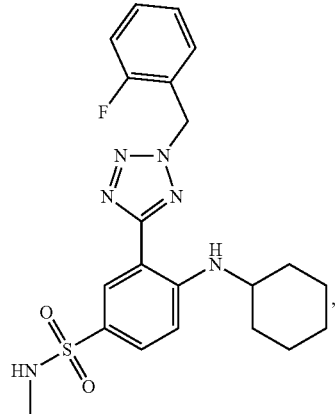
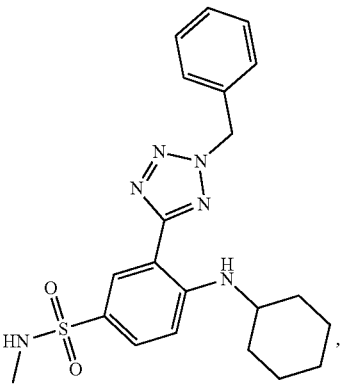
360
-continued
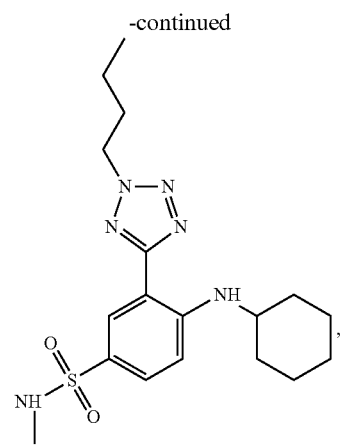
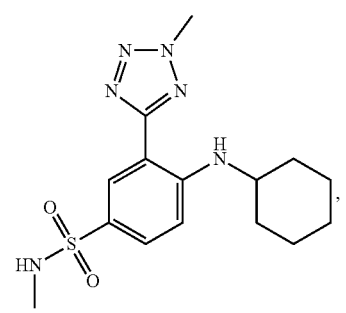
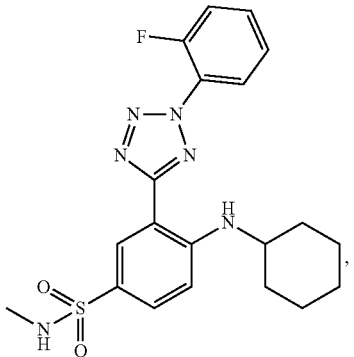
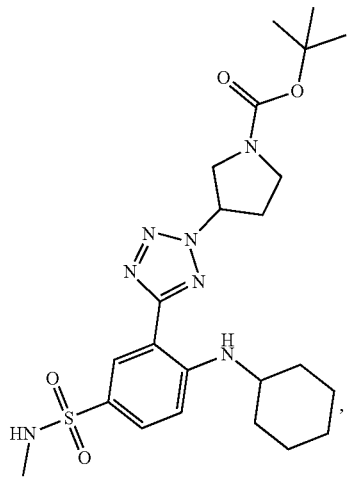

361
-continued
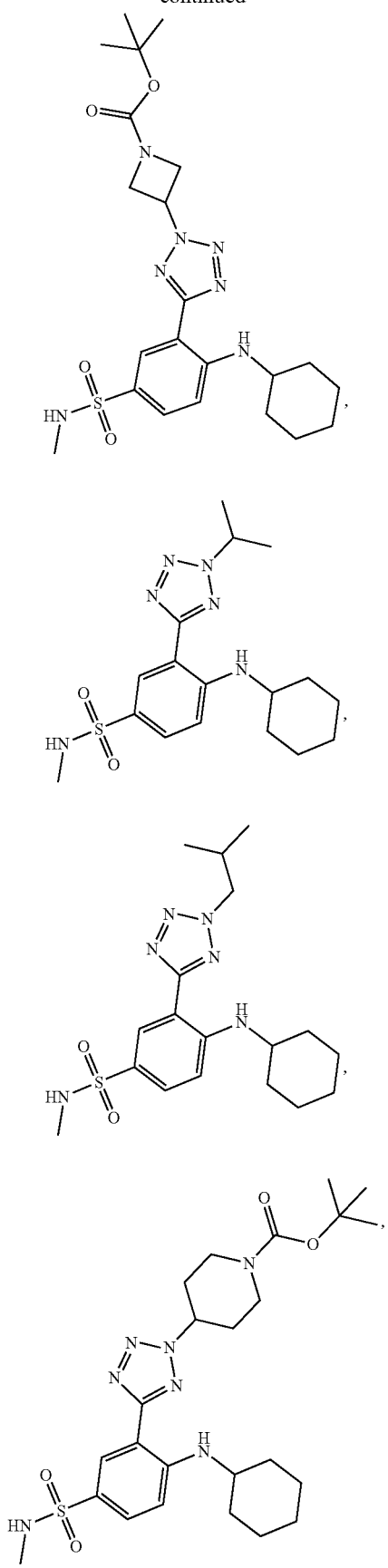
362
-continued
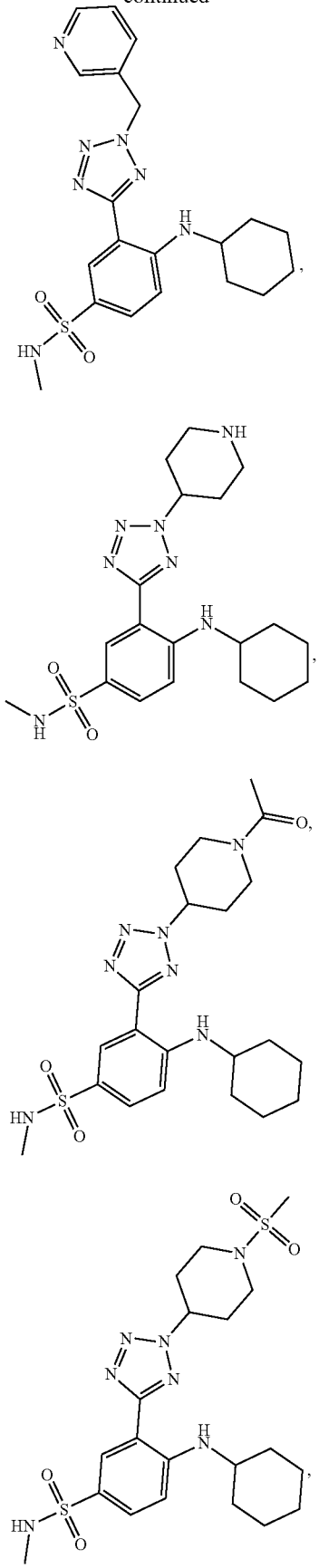

363
-continued
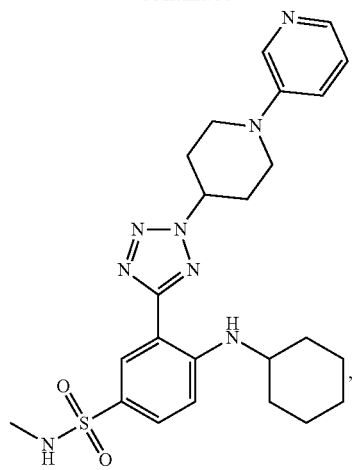
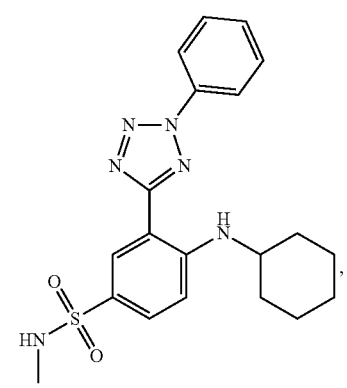
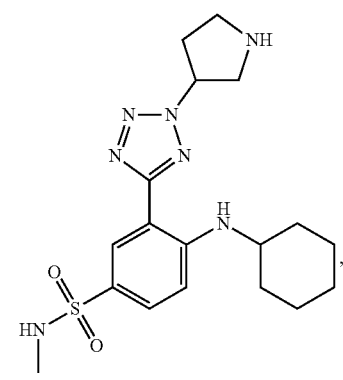
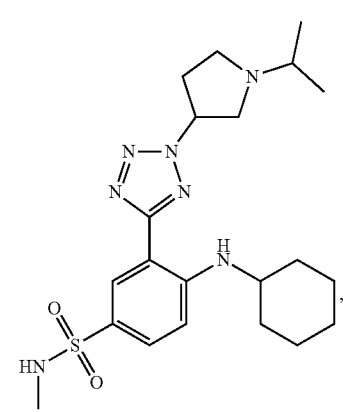
364
-continued
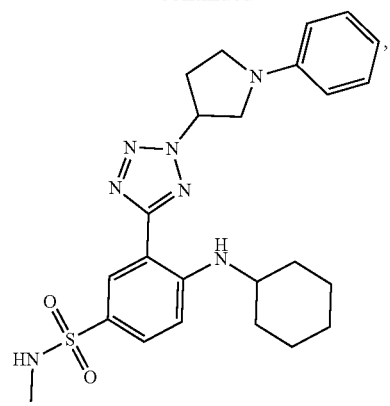
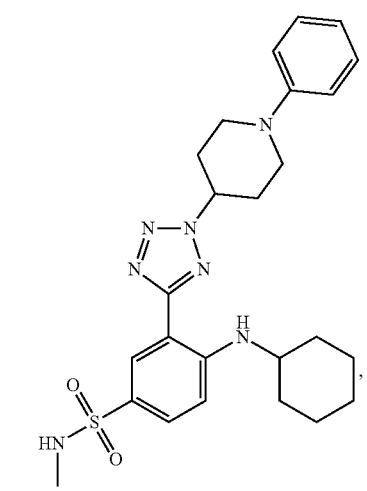
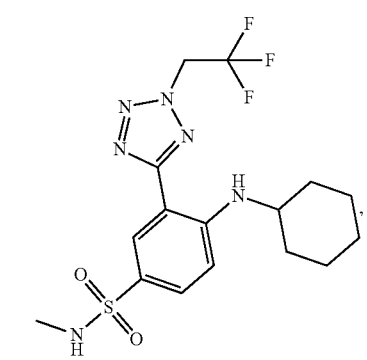
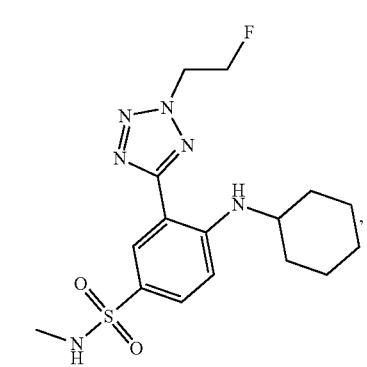

365
-continued
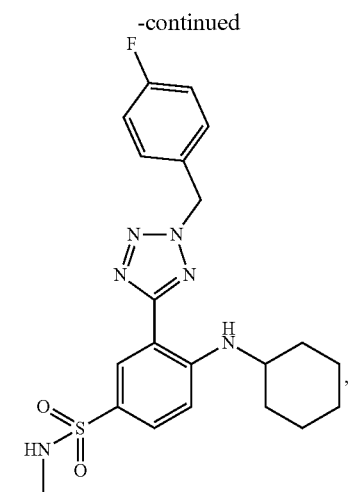
366
-continued
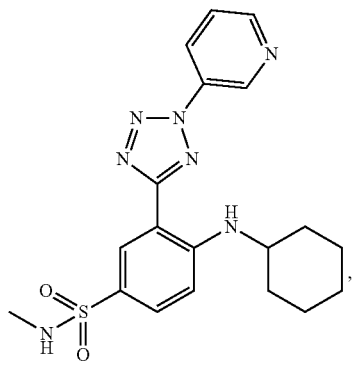
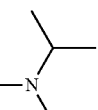
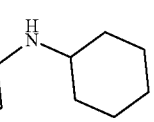
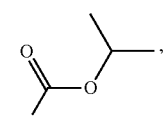

367
-continued
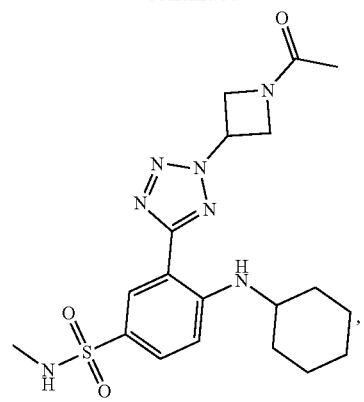
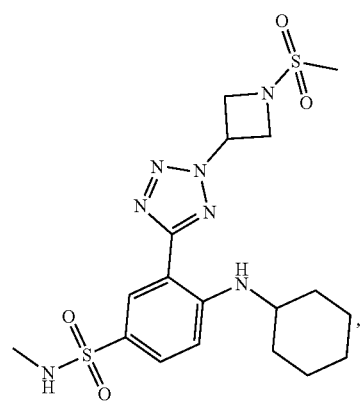
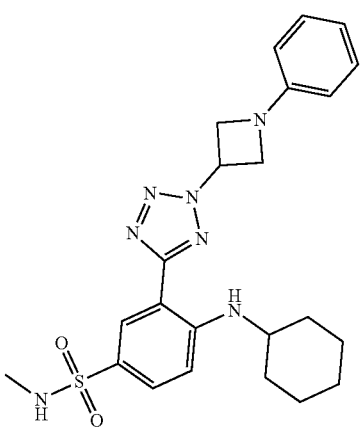
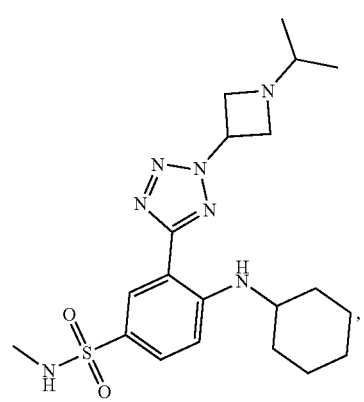
368
-continued
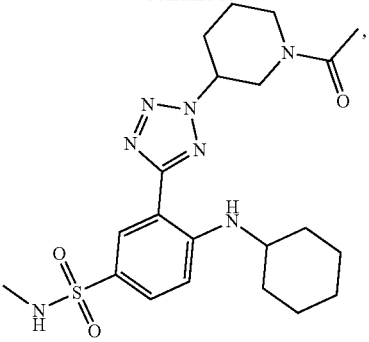
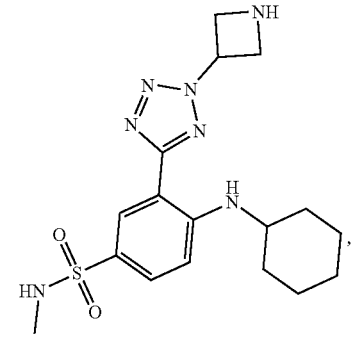
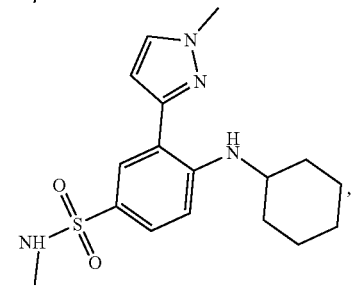
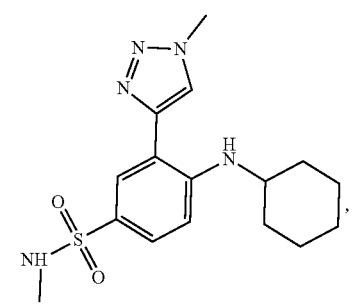
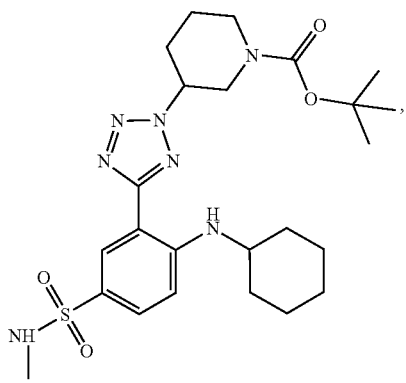

369
-continued
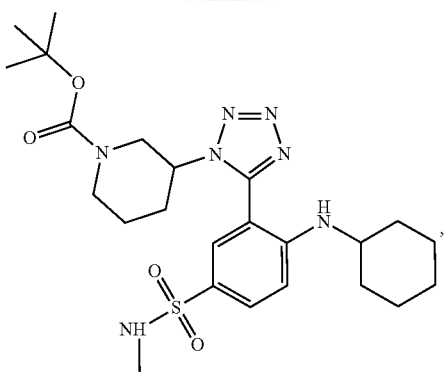
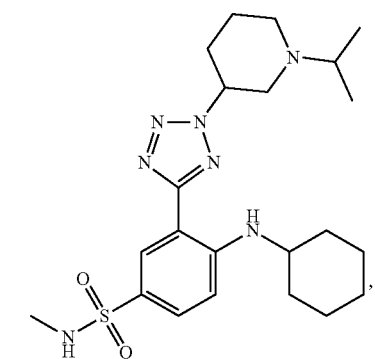
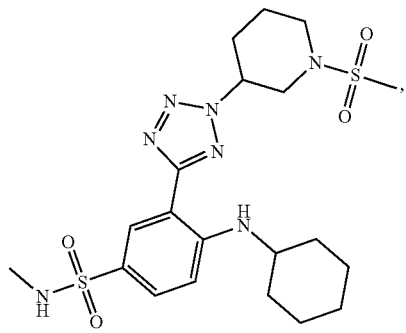
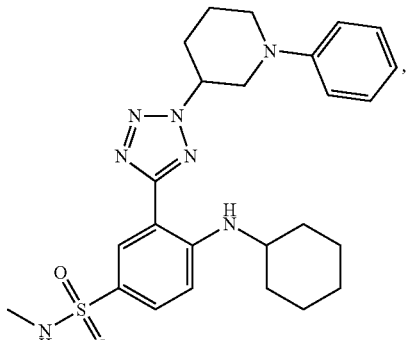
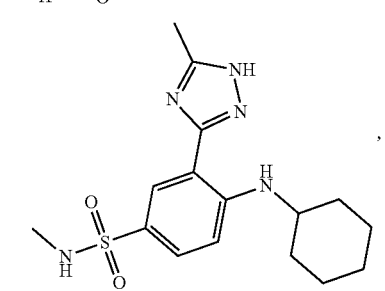
370
-continued
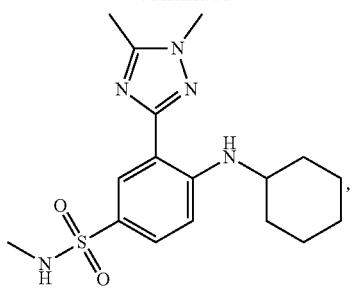
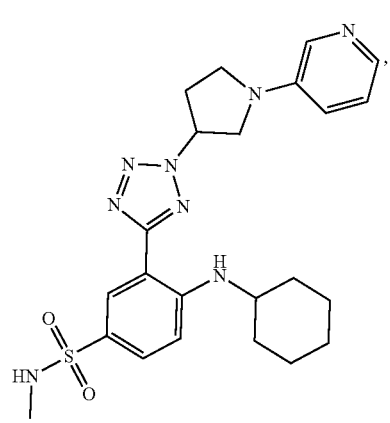
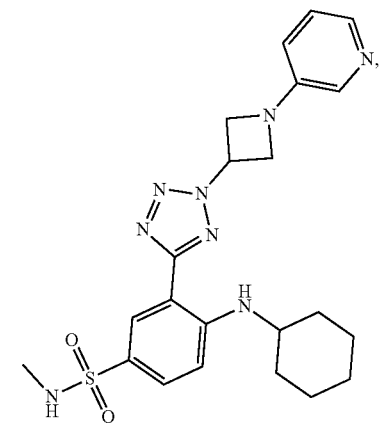
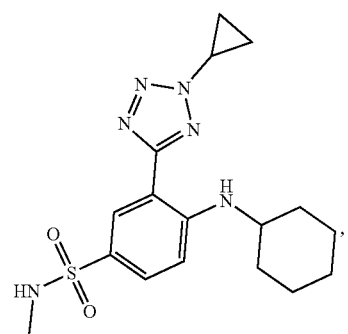

-continued
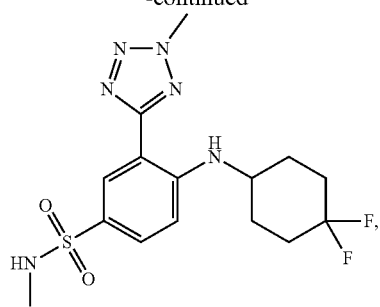
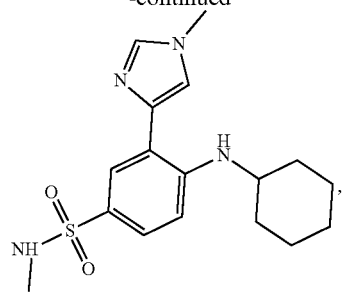
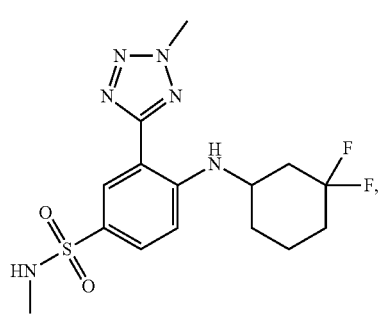
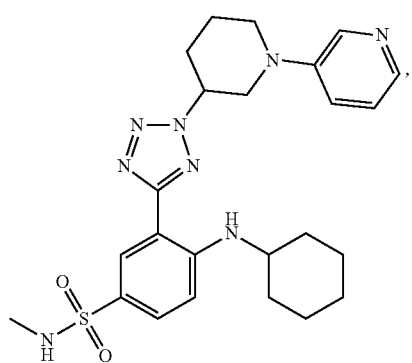
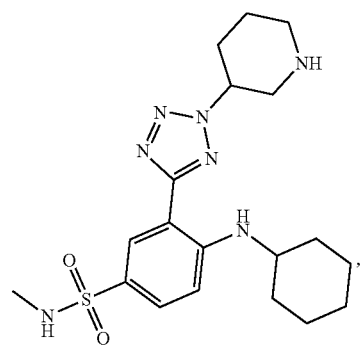
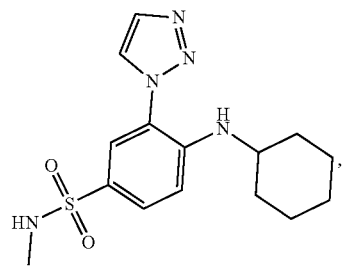
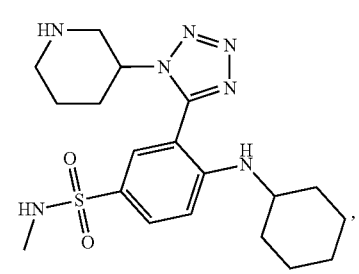
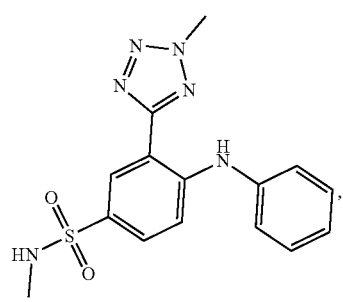
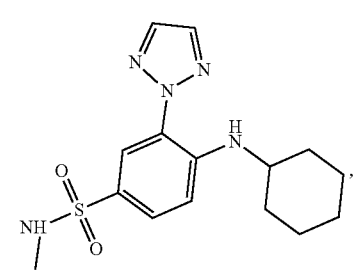
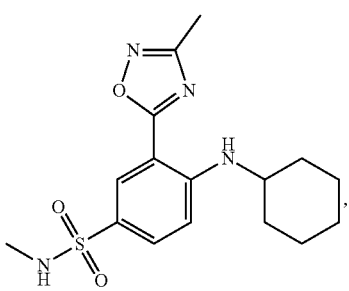

373
-continued
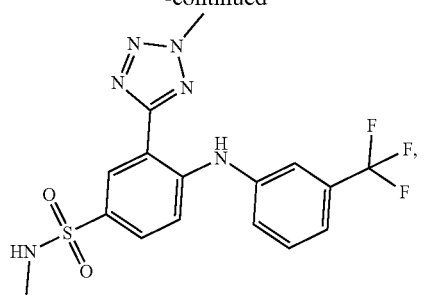
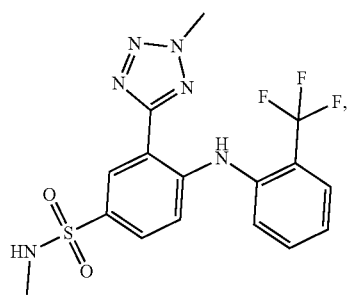
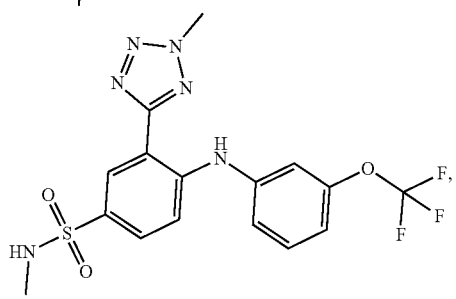
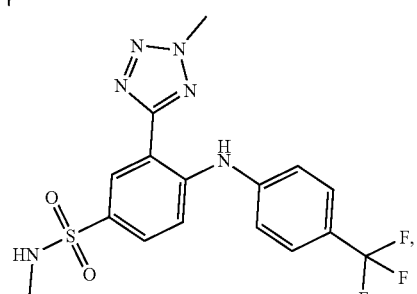
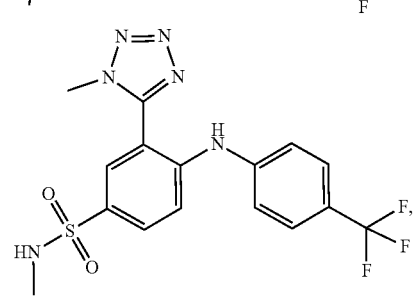
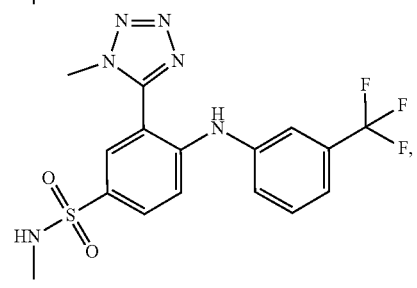
374
-continued
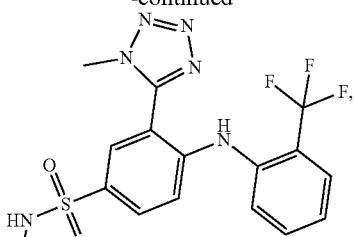
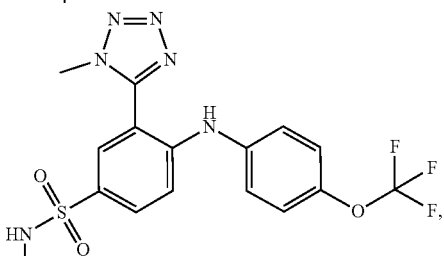
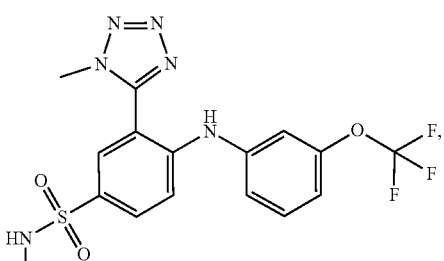
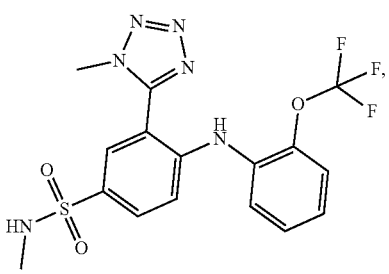
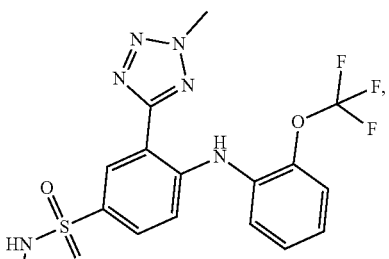
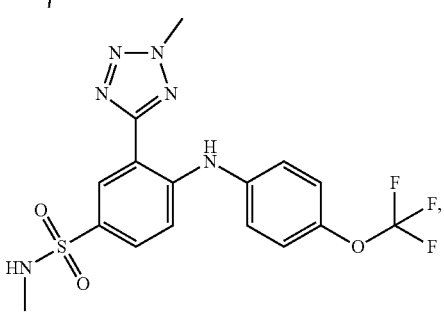

375
-continued
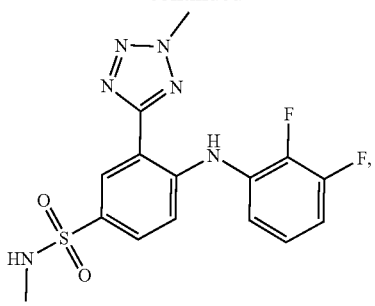
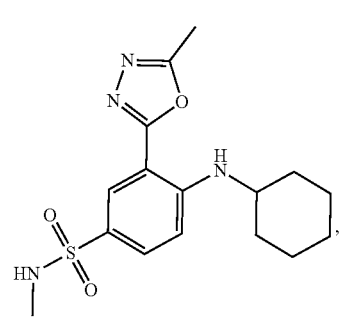
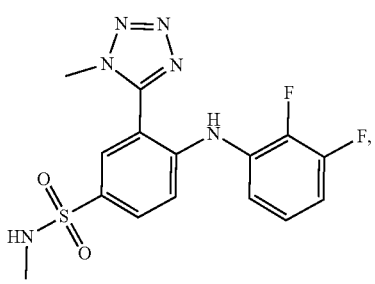
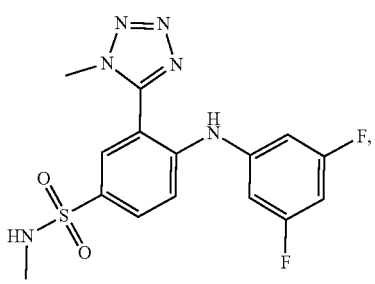
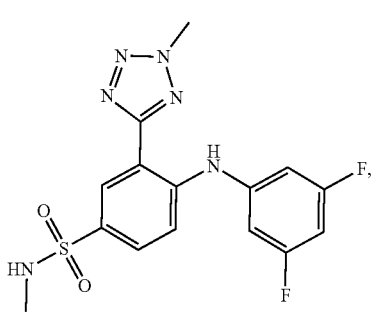
376
-continued
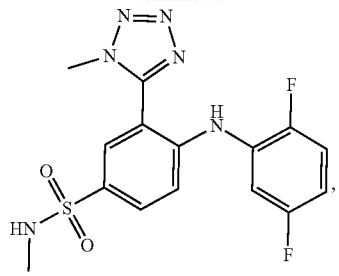
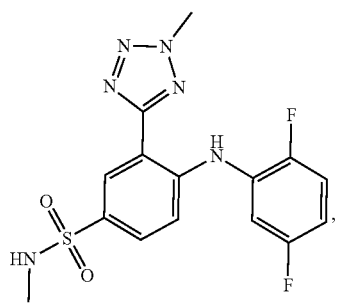
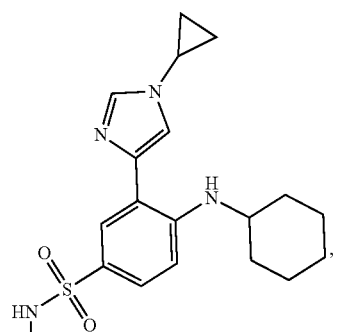
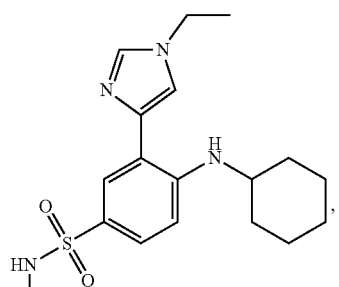
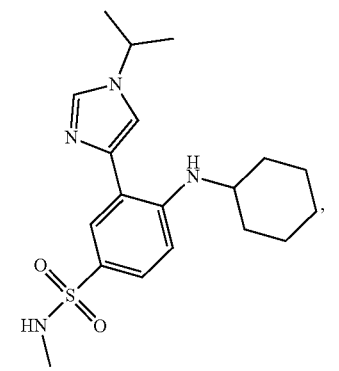

377
-continued
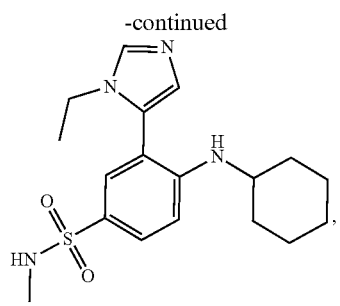
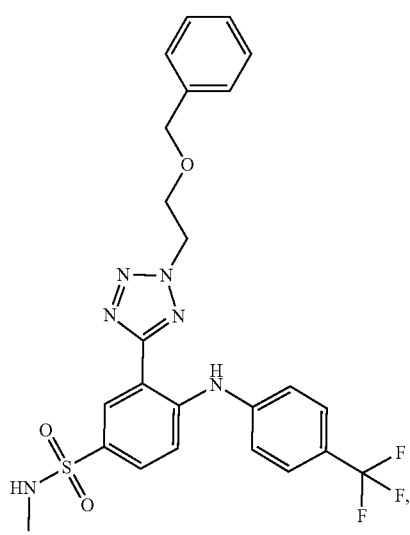
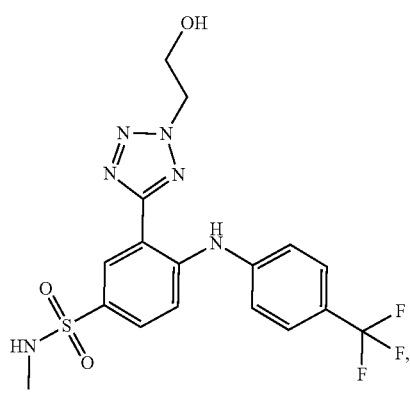
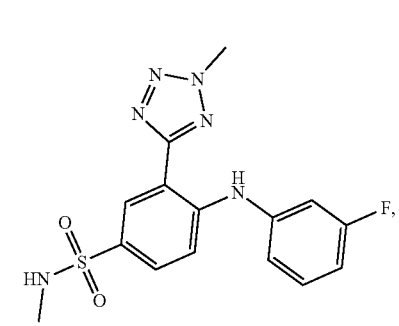
378
-continued
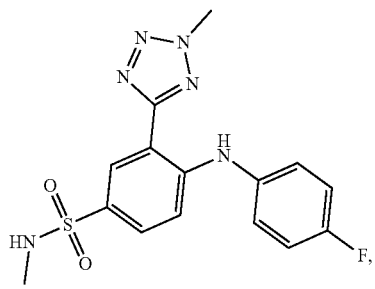
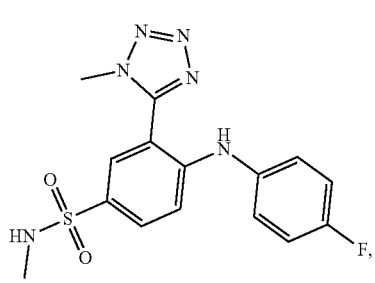
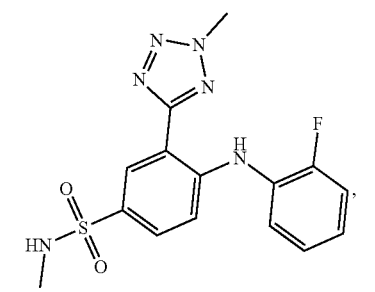
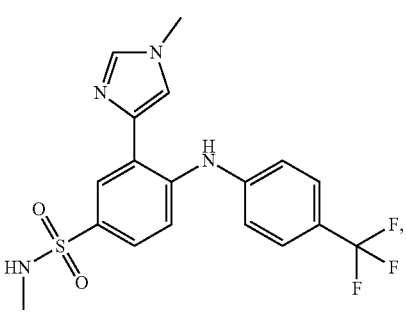
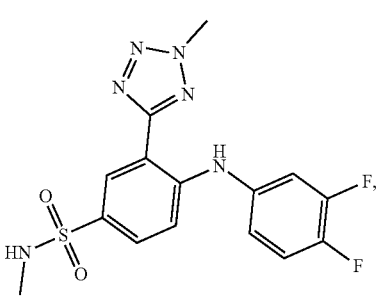

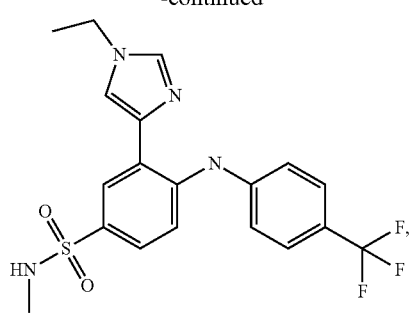
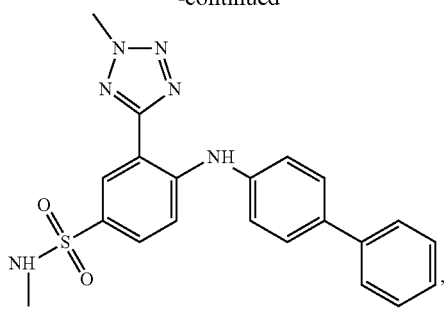
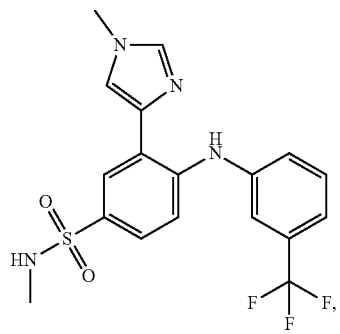
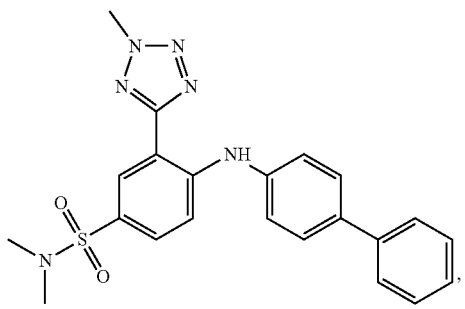
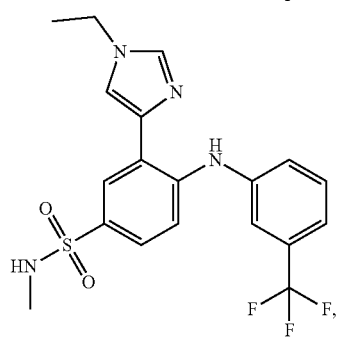
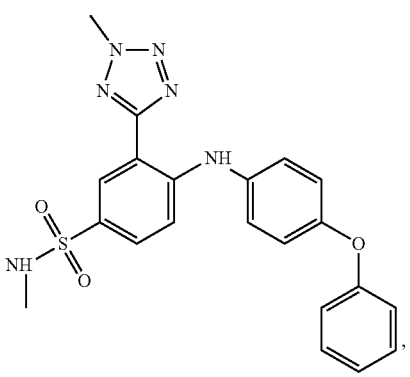
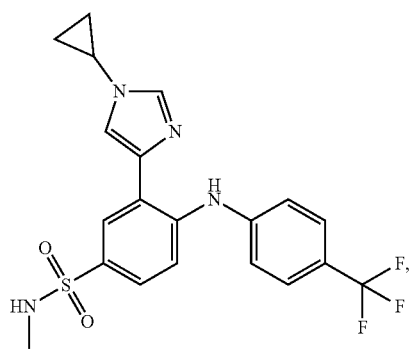
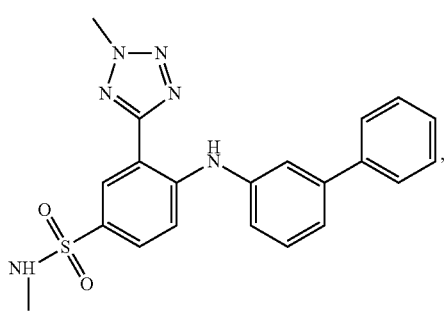
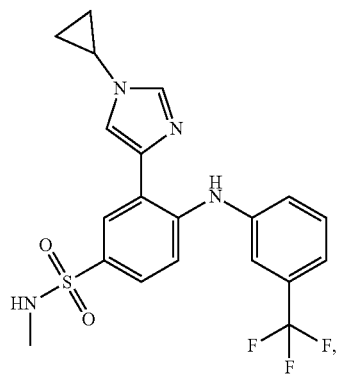
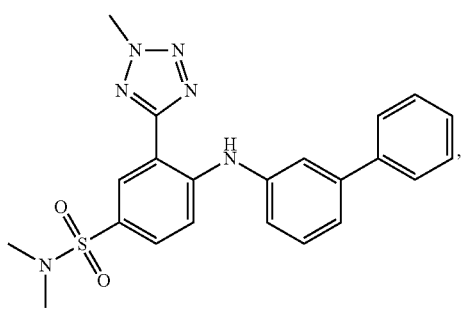

381
-continued
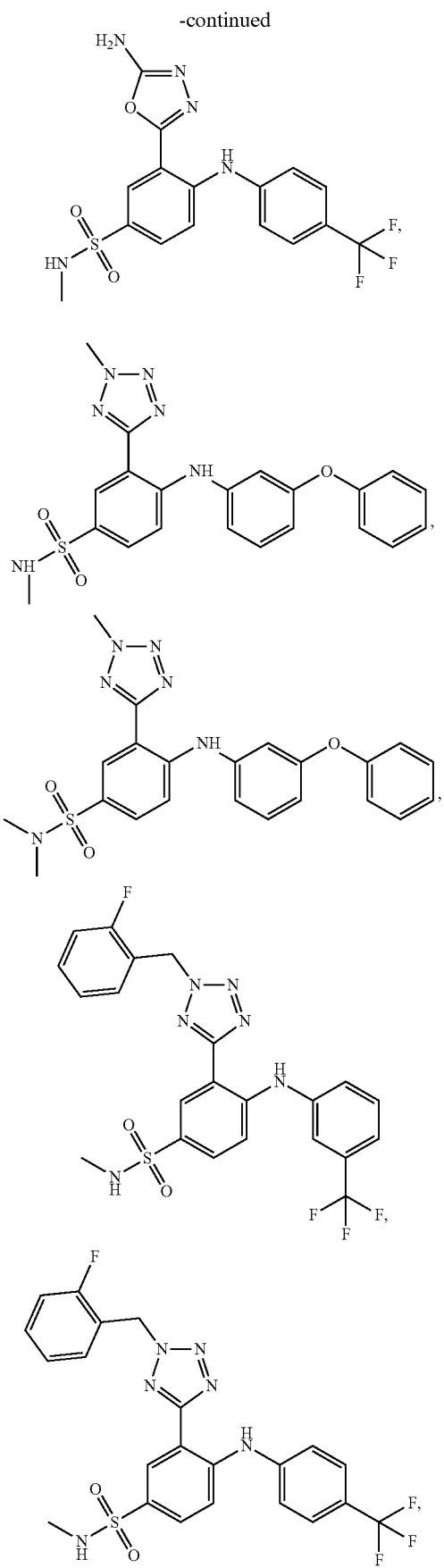
382
-continued
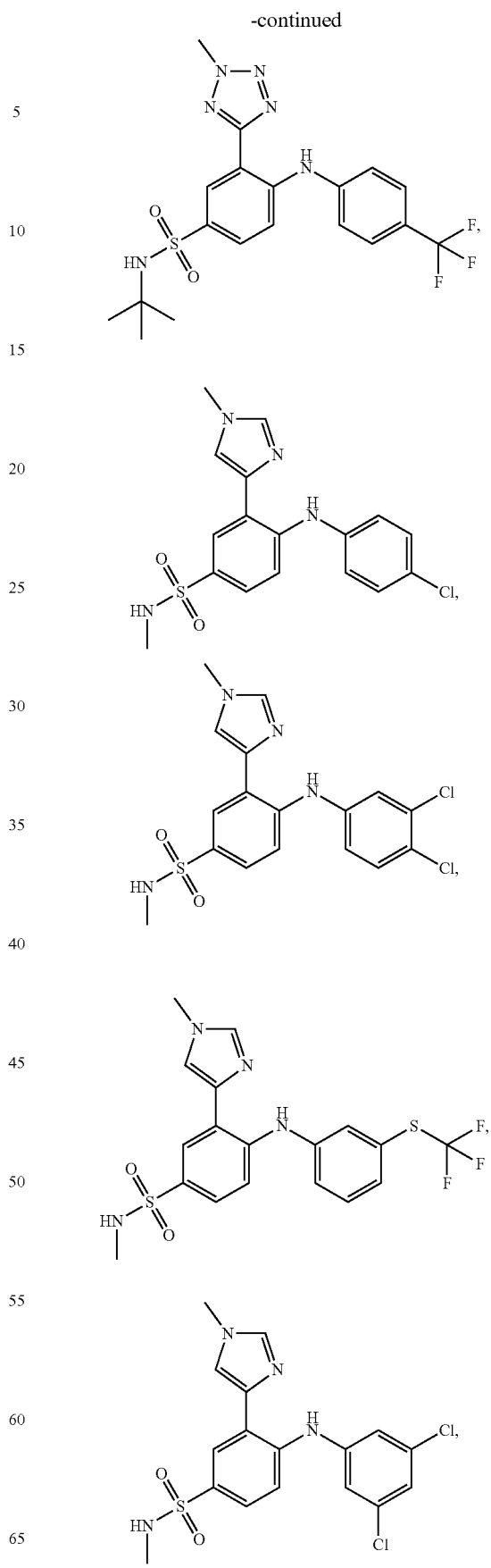

383
-continued
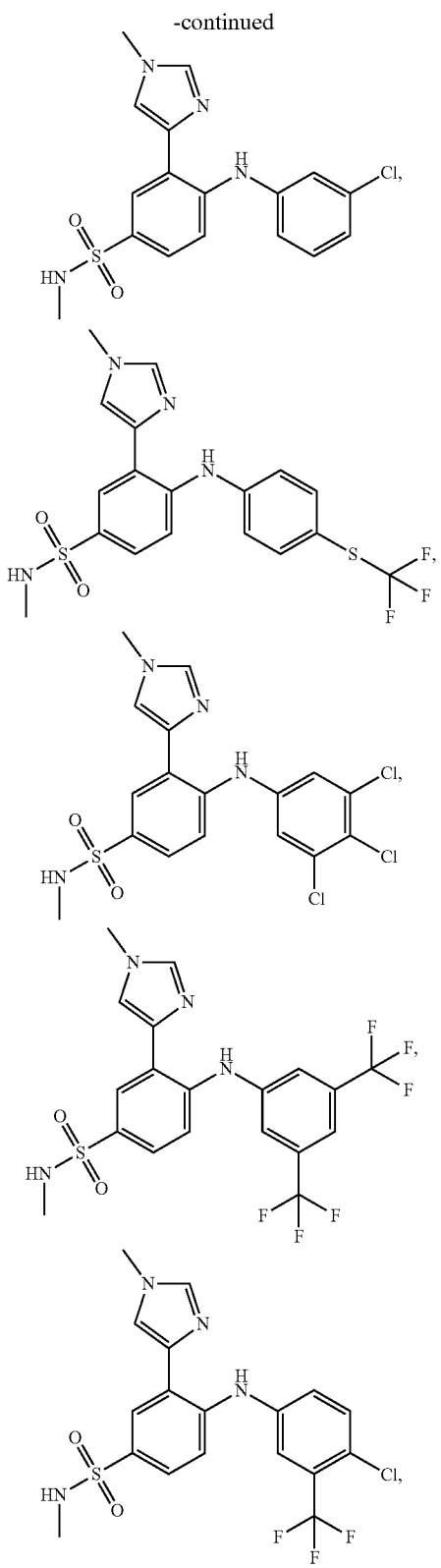
384
-continued
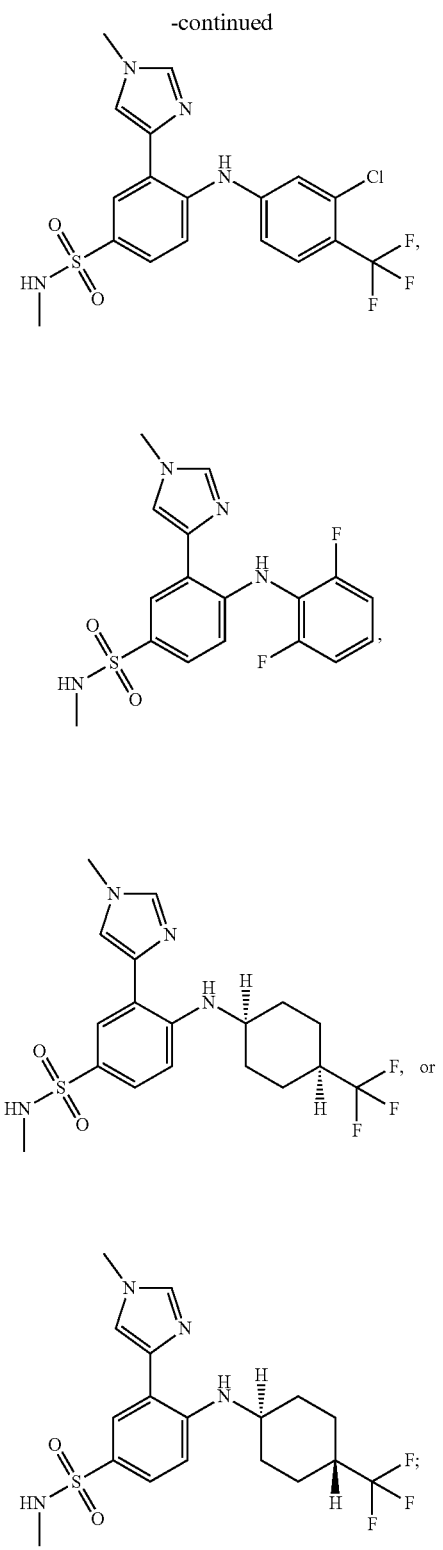
* * * * *